United States Patent [19]
Yanagisawa et al.

[11] Patent Number: 5,616,599
[45] Date of Patent: Apr. 1, 1997

[54] ANGIOTENSIN II ANTAGOSIST 1-BIPHENYLMETHYLIMIDAZOLE COMPOUNDS AND THEIR THERAPEUTIC USE

[75] Inventors: Hiroaki Yanagisawa; Koichi Fujimoto; Yoshiya Amemiya; Yasuo Shimoji; Takuro Kanazaki; Hiroyuki Koike; Toshio Sada, all of Tokyo, Japan

[73] Assignee: Sankyo Company, Limited, Tokyo, Japan

[21] Appl. No.: 378,650

[22] Filed: Jan. 26, 1995

Related U.S. Application Data

[63] Continuation-in-part of Ser. No. 839,482, Feb. 20, 1992, abandoned, and Ser. No. 69,595, Jun. 1, 1993, abandoned.

[30] Foreign Application Priority Data

| | | | |
|---|---|---|---|
| Feb. 21, 1991 | [JP] | Japan | 3-027098 |
| Apr. 26, 1991 | [JP] | Japan | 3-096588 |
| Jun. 6, 1991 | [JP] | Japan | 3-134889 |
| Jul. 8, 1991 | [JP] | Japan | 3-167138 |
| Jul. 15, 1991 | [JP] | Japan | 3-173972 |
| Jul. 24, 1991 | [JP] | Japan | 3-184841 |
| Jun. 2, 1992 | [JP] | Japan | 4-141160 |

[51] Int. Cl.[6] ............ C07D 403/10; C07D 257/04; A61K 31/41; A61K 31/415
[52] U.S. Cl. ............ 514/381; 514/382; 514/396; 514/397; 548/253; 548/315.1; 548/315.4; 548/334.5
[58] Field of Search ............ 548/253, 315.1, 548/315.4, 334.5; 514/381, 382, 396, 397

[56] References Cited

U.S. PATENT DOCUMENTS

| | | | |
|---|---|---|---|
| 4,226,878 | 12/1980 | Iizuka et al. | 424/273 R |
| 4,340,598 | 7/1982 | Furukawa et al. | 424/273 R |
| 4,342,693 | 8/1982 | Sakamoto et al. | 549/229 |

(List continued on next page.)

FOREIGN PATENT DOCUMENTS

| | | |
|---|---|---|
| 78200/91 | 12/1991 | Australia. |
| 80163/91 | 1/1992 | Australia. |
| 028834 | 5/1981 | European Pat. Off.. |

(List continued on next page.)

OTHER PUBLICATIONS

J. Duncia et al, "The Discovery of DUP-753 a Potent, Orally Active Nonpeptide Angiotensin II Receptor Antagonist": *Medical Research Reviews*, 12, 149–191 (1992).

A. Johnson et al, "Nonpeptide Angiotensin II Receptor Antagonists", *Drug News & Perspectives (D N & P)*, 3, 337–351 (1990).

J. Hodges et al, "Angiotensin II Receptor Binding Inhibitors", *Drugs of the Future*, 17, 575–593 (1992).

P. Buhlmayer, "Angiotensin–II Antagonists: Patent Activity Since the Discovery of DUP–753", *Current Opinion in Therapeutic Patents*, 2, 1693–1718 (1992).

Wong et al, "Nonpeptide Angiotensin II Receptor Antagonists, XI, Pharmacology of EXP 3174: An Active Metabolite of DuP 753, An Orally Active Antihypertensive Agent", (1990), 211–217, 255, *The Journal of Pharmacology and Experimental Therapeutics*.

(List continued on next page.)

*Primary Examiner*—David B. Springer
*Attorney, Agent, or Firm*—Frishauf, Holtz, Goodman, Langer & Chick, P.C.

[57] ABSTRACT

Compounds of the following formula (I) or the formula $(I)_p$:

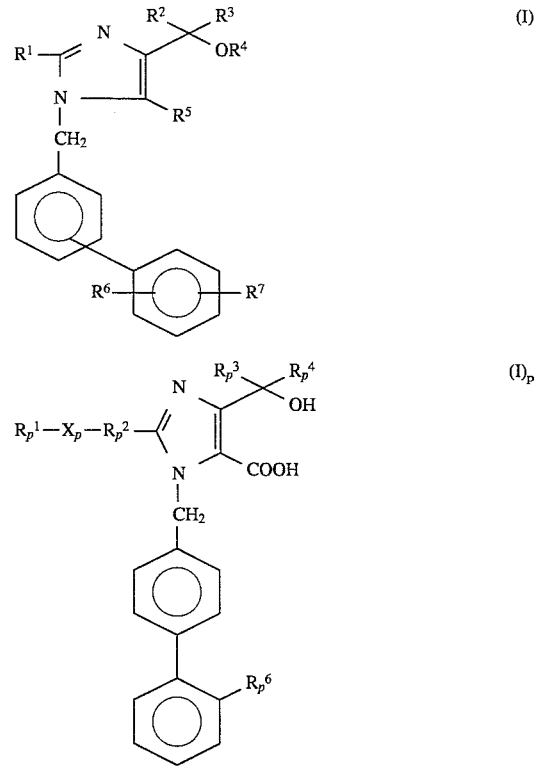

wherein $R^1$ is alkyl or alkenyl; $R^2$ and $R^3$ are hydrogen, alkyl, alkenyl, cycloalkyl, aralkyl, aryl, or aryl fused to cycloalkyl; $R^4$ is hydrogen, alkyl, alkanoyl, alkenoyl, arylcarbonyl, alkoxycarbonyl, tetrahydropyranyl, tetrahydrothiopyranyl, tetrahydrothienyl, tetrahydrofuryl, a group of formula —$SiR^a R^b R^c$, in which $R^a$, $R^b$ and $R^c$ are alkyl or aryl, alkoxymethyl, (alkoxyalkoxy)methyl, haloalkoxymethyl, aralkyl, aryl or alkanoyloxymethoxycarbonyl; $R^5$ is carboxy or —$CONR^8 R^9$, wherein $R^8$ and $R^9$ hydrogens or alkyl, or $R^8$ and $R^9$ together form alkylene; $R^6$ is hydrogen, alkyl, alkoxy or halogen; $R^7$ is carboxy or tetrazol-5-yl; $R_p^1$ is hydrogen, alkyl, cycloalkyl or alkanoyl; $R_p^2$ is a single bond, alkylene or alkylidene; $R_p^3$ and $R_p^4$ are each hydrogen or alkyl; $R_p^6$ is carboxy or tetrazol-5-yl; and $X_p$ is oxygen or sulfur; and pharmaceutically acceptable salts and esters thereof. The compounds are AII receptor antagonists and thus have hypotensive activity and can be used for the treatment and prophylaxis of hypertension. The compounds may be prepared by reacting a biphenylmethyl compound with an imidazole compound.

42 Claims, No Drawings

U.S. PATENT DOCUMENTS

| | | | |
|---|---|---|---|
| 4,355,040 | 10/1992 | Furukawa et al. | 424/273 R |
| 4,555,516 | 11/1985 | Cross et al. | 514/326 |
| 4,812,462 | 3/1989 | Blankley et al. | 514/303 |
| 4,816,463 | 3/1989 | Blankley et al. | 514/293 |
| 4,820,843 | 4/1989 | Aldrich et al. | 548/252 |
| 4,870,186 | 9/1989 | Aldrich et al. | 548/215 |
| 4,874,867 | 10/1989 | Aldrich et al. | 548/101 |
| 4,880,804 | 11/1989 | Carini et al. | 514/234.5 |
| 4,916,129 | 4/1990 | Carini et al. | 514/235.2 |
| 5,015,651 | 5/1991 | Carini et al. | 514/381 |
| 5,039,814 | 8/1991 | Shuman et al. | 548/250 |
| 5,043,349 | 8/1991 | Carini et al. | 514/427 |
| 5,064,825 | 11/1991 | Chakravarty et al. | 514/221 |
| 5,081,127 | 1/1992 | Carini et al. | 514/359 |
| 5,089,626 | 2/1992 | King | 548/253 |
| 5,093,346 | 3/1992 | Carini et al. | 514/381 |
| 5,126,342 | 6/1992 | Chakaravarty et al. | 514/235.8 |
| 5,128,355 | 7/1992 | Carini et al. | 514/381 |
| 5,137,902 | 8/1992 | Carini et al. | 514/381 |
| 5,138,069 | 8/1992 | Carini et al. | 548/253 |
| 5,140,037 | 8/1992 | Chiu et al. | 514/381 |
| 5,153,197 | 10/1992 | Carini et al. | 514/255 |
| 5,155,118 | 10/1992 | Carini et al. | 514/381 |
| 5,171,748 | 12/1992 | Roberts et al. | 514/381 |
| 5,177,097 | 1/1993 | Poss | 514/386 |
| 5,189,048 | 2/1993 | Carini et al. | 514/359 |
| 5,210,079 | 5/1993 | Carini et al. | 514/94 |
| 5,219,856 | 6/1993 | Olson | 514/252 |
| 5,225,414 | 7/1993 | Henning et al. | 514/258 |
| 5,236,928 | 8/1993 | Chakravarty et al. | 514/275 |
| 5,236,943 | 8/1993 | Heitsch et al. | 514/397 |
| 5,252,753 | 11/1993 | Russell et al. | 548/252 |
| 5,254,546 | 10/1993 | Ardecky et al. | 514/225.8 |
| 5,260,322 | 11/1993 | Nakasima et al. | 514/341 |
| 5,266,583 | 11/1993 | Ohtawa | 514/381 |
| 5,294,716 | 3/1994 | Thomas et al. | 546/135 |
| 5,310,928 | 5/1994 | Lo et al. | 548/252 |
| 5,310,929 | 5/1994 | Ardecky et al. | 548/253 |
| 5,312,828 | 5/1994 | Finkelstein et al. | 514/381 |
| 5,354,867 | 10/1994 | Carini et al. | 548/252 |

FOREIGN PATENT DOCUMENTS

| | | |
|---|---|---|
| 028833 | 5/1981 | European Pat. Off. . |
| 245637 | 3/1987 | European Pat. Off. . |
| 253310 | 1/1988 | European Pat. Off. . |
| 323841 | 1/1989 | European Pat. Off. . |
| 324377 | 7/1989 | European Pat. Off. . |
| 437103 | 12/1989 | European Pat. Off. . |
| 392317 | 4/1990 | European Pat. Off. . |
| 400974 | 5/1990 | European Pat. Off. . |
| 380959 | 8/1990 | European Pat. Off. . |
| 485929 | 11/1990 | European Pat. Off. . |
| 399732 | 11/1990 | European Pat. Off. . |
| 399731 | 11/1990 | European Pat. Off. . |
| 400835 | 12/1990 | European Pat. Off. . |
| 401030 | 12/1990 | European Pat. Off. . |
| 505098 | 3/1991 | European Pat. Off. . |
| 461039 | 12/1991 | European Pat. Off. . |
| 468372 | 1/1992 | European Pat. Off. . |
| 465368 | 1/1992 | European Pat. Off. . |
| 470794 | 2/1992 | European Pat. Off. . |
| 475206 | 3/1992 | European Pat. Off. . |
| 480659 | 4/1992 | European Pat. Off. . |
| 492105 | 7/1992 | European Pat. Off. . |
| 503785 | 9/1992 | European Pat. Off. . |
| 503162 | 9/1992 | European Pat. Off. . |
| 550313 | 7/1993 | European Pat. Off. . |
| 4036706A1 | 5/1992 | Germany . |
| 57-98270 | 6/1982 | Japan . |
| 3-58942 | 3/1991 | Japan . |
| 6-73029 | 3/1994 | Japan . |
| 6-87833 | 3/1994 | Japan . |
| WO91/00277 | 1/1991 | WIPO . |
| WO91/00281 | 1/1991 | WIPO . |
| WO91/14367 | 10/1991 | WIPO . |
| WO91/19715 | 12/1991 | WIPO . |
| WO93/04059 | 3/1993 | WIPO . |
| WO94/09778 | 5/1994 | WIPO . |

OTHER PUBLICATIONS

Carini et al., "Nonpeptide Angiotensin II Receptor Antagonists: The Discovery of a Series of N–(Biphenylylmethyl) Imidazoles as a Potent, Orally Active Antihypertensives", (1991), 2525–2547, 34, *J. Med. Chem.*

*Merck Index,* 11th Edition, p. 855, No.5319, Lenampicillin (1989).

*Chem. Abs.* 109:73432w of USP 4,812,462 (1988).

*Chem. Abs.* 114:164233b of EP 399732 (1991).

*Chem. Abs.* 114:228914j of EP 400835 (1991).

ANGIOTENSIN II ANTAGOSIST 1-BIPHENYLMETHYLIMIDAZOLE COMPOUNDS AND THEIR THERAPEUTIC USE

CROSS REFERENCE TO RELATED APPLICATION

This is a continuation-in-part application of application Ser. No. 07/839,482, filed Feb. 20, 1992 and application Ser. No. 08/069,595, filed Jun. 1, 1993, both now abandoned.

BACKGROUND TO THE INVENTION

The present invention provides a series of novel 1-(biphenylmethyl)imidazole compounds which are antagonists to angiotension II (hereinafter referred to as "AII"). These compounds have valuable hypotensive activities, and which may, therefore, be used in the treatment and prophylaxis of hypertension, including diseases of the heart and circulatory system. The invention also provides methods and compositions using these compounds, as well as processes for their preparation.

It is known that the renin-angiotension system provides one of the important mechanisms for maintaining the homeostasis of blood pressure in living animals. When blood pressure is reduced or the sodium ion concentration of the body fluids falls, this system is activated. As a result, the enzyme renin and angiotensin converting enzyme (hereinafter abbreviated, as is conventional, as "ACE") are activated and act on angiotensinogen, which is first decomposed by the renin to produce angiotensin I (hereinafter abbreviated as "AI"). This AI is then converted by ACE to AII. Since AII induces strong contractions of blood vessels and accelerates the secretion of aldosterone (which is a hormone produced by the adrenal glands that controls the excretion of sodium by the kidneys and thereby maintains the balance of salt and water in the body fluids), the activation of the system results in an elevation of blood pressure. Inhibitors or suppressors of the renin-angiotension system, such as renin inhibitors, ACE inhibitors and AII antagonists, dilate blood vessels, cause lower blood pressure and improve the circulatory function, which is the basis for the use of these agents in the treatment of heart diseases.

At present only ACE inhibitors are used clinically, although renin inhibitors and AII antagonists are under investigation for such use. Of these, some peptide type AII antagonists, such as saralasin, have been known for many years, while certain non-peptide type antagonists have recently been discovered (for example, European Patent Publications No. 28 833, 28 834, 245 637, 253 310, 323 841, 324 377, 380 959, 399 732, 399 731, 400 835 and 492 105 and in Japanese Patent Application Kokai No. Sho 57-98270). Close prior art is considered to be European Patent Publications No. 253 310 and 324 377 and German Patent Publication 4 036 706.

European Patent Publication No. 253 310 discloses a series of 1-phenyl, 1-phenethyl or 1-benzyl imidazole derivatives which are said to have the ability to inhibit the activity of AII. Included in the scope of these prior art compounds are a number of 1-biphenylmethylimidazole derivatives, which, however, differ from the compounds of the present invention in the nature of the substituent at the imidazole 4- or 5- position.

European Patent Publication No. 324 377 discloses a series of 1-(substituted phenyl)-, 1-(substituted phenethyl)- or 1-(substituted benzyl)- imidazole derivatives which are said to have the ability to inhibit the activity of AII. Included in the scope of these prior art compounds are a number of 1-biphenylmethylimidazole derivatives, which, however, differ from the compounds of the present invention in the nature of the substituent at the imidazole 4-position.

German Patent Publication No. 4 036 706 also discloses a series of such compounds, differing from the compounds of the present invention in a similar manner. The activities of all of these prior art compounds, however, including those of European Patent Publications No. 253310 and 324 377 and German Patent Publication No. 4 036 706, are not sufficient and more potent AII antagonists are sought for better clinical results.

We have now discovered a limited series of 1-(biphenylmethyl)imidazole-5-carboxylic acid derivatives, including compounds with specific substituents at the imidazole 4-position having an excellent AII receptor antagonist activity, and which are therefore useful as antihypertensive drugs and for the therapy and prophylaxis of heart diseases.

BRIEF SUMMARY OF INVENTION

It is, therefore, an object of the present invention provide a series of new 1-(biphenylmethyl)imidazole-5-carboxylic acid derivatives.

It is a further object of the invention to provide such compounds having AII inhibitory activity.

Other objects and advantages of the present invention will become apparent as the description proceeds.

Thus, the present invention provides compounds of formula (I):

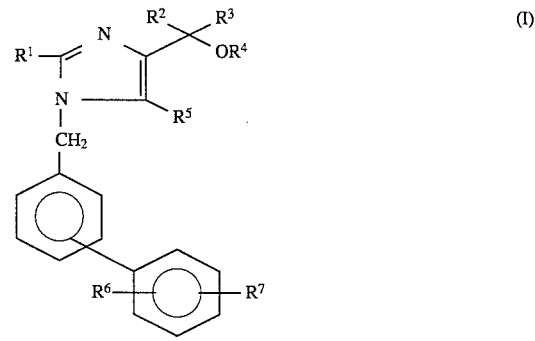

wherein:
R$^1$ represents an alkyl group having from 1 to 6 carbon atoms or an alkenyl group having from 3 to 6 carbon atoms;
R$^2$ and R$^3$ are independently selected from the group consisting of:
  hydrogen atoms:
  alkyl groups having from 1 to 6 carbon atoms;
  alkenyl groups having from 3 to 6 carbon atoms;
  cycloalkyl groups having a total of from 3 to 10 carbon atoms in one or more saturated carbocyclic rings;
  aralkyl groups in which the alkyl part has from 1 to 6 carbon atoms and the aryl part is as defined below;
  aryl groups as defined below; and
  fused ring systems in which an aryl group, as defined below, is fused to a cycloalkyl group having from 3 to 10 carbon atoms;
R$^4$ represents:
  a hydrogen atom;
  an alkyl group having from 1 to 6 carbon atoms;
  an alkanoyl group having from 1 to 6 carbon atoms;

a substituted alkanoyl group having from 2 to 6 carbon atoms and substituted by at least one substituent selected from the group consisting of halogen atoms and alkoxy groups having from 1 to 6 carbon atoms;

an alkenoyl group having from 3 to 6 carbon atoms;

an arylcarbonyl group in which the aryl part is as defined below;

an alkoxycarbonyl group in which the alkyl part has from 1 to 6 carbon atoms;

a tetrahydropyranyl, tetrahydrothiopyranyl, tetrahydrothienyl or tetrahydrofuryl group;

a substituted tetrahydropyranyl, tetrahydrothiopyranyl, tetrahydrothienyl or tetrahydrofuryl group which is substituted by at least one substituent selected from the group consisting of halogen atoms and alkoxy groups having from 1 to 6 carbon atoms; a group of formula —$SiR^aR^bR^c$, in which 1, 2 or 3 of the groups represented by $R^a$, $R^b$ and $R^c$ are independently selected from the group consisting of alkyl groups having from 1 to 6 carbon atoms, and 2, 1 or 0 of the groups represented by $R^a$, $R^b$ and $R^c$ are independently selected from the group consisting of aryl groups, as defined below; alkoxymethyl groups in which the alkoxy part has from 1 to 6 carbon atoms;

(alkoxyalkoxy)methyl groups in which each alkoxy part has from 1 to 6 carbon atoms;

haloalkoxymethyl groups in which the alkoxy part has from 1 to 6 carbon atoms;

aralkyl groups, in which an alkyl group having from 1 to 6 carbon atoms is substituted by at least one aryl group, as defined below; or alkanoyloxymethoxycarbonyl groups in which the alkanoyl part has from 1 to 6 carbon atoms;

$R^5$ represents a carboxy group or a group of formula —$CONR^8R^9$, wherein $R^8$ and $R^9$ are independently selected from the group consisting of hydrogen atoms, unsubstituted alkyl groups having from 1 to 6 carbon atoms, and substituted alkyl groups which have from 1 to 6 carbon atoms and which are substituted by at least one substituent selected from the group consisting of substituents (a), defined below, or $R^8$ and $R^9$ together represent an unsubstituted alkylene group having from 2 to 6 carbon atoms or a substituted alkylene group which has from 2 to 6 carbon atoms and which is substituted by at least one substituent selected from the group consisting of carboxy groups and alkoxycarbonyl groups in which the alkyl part has from 1 to 6 carbon atoms;

$R^6$ represents a hydrogen atom, an alkyl group having from 1 to 6 carbon atoms, an alkoxy group having from 1 to 6 carbon atoms or a halogen atom;

$R^7$ represents a carboxy group or a tetrazol-5-yl group;

said substituents (a) are selected from the group consisting of:

aryl groups as defined below;

heterocyclic groups having 5 or 6 ring atoms, of which from 1 to 4 are hetero-atoms selected from the group consisting of nitrogen, oxygen and sulfur atoms;

halogen atoms;

hydroxy groups;

alkoxy groups having from 1 to 6 carbon atoms;

carboxy groups alkoxycarbonyl groups in which the alkyl part has from 1 to 6 carbon atoms;

amino groups; and acylamino groups, in which the acyl part is an alkanoyl group having from 1 to 6 carbon atoms or an arylcarbonyl group, in which the aryl part is as defined below;

said aryl groups are aromatic carbocyclic groups which have from 6 to 14 ring atoms and which are unsubstituted or are substituted by at least one substituent selected from the group consisting of substituents (b), defined below; and said substituents (b) are selected from the group consisting of nitro groups, cyano groups, halogen atoms, unsubstituted carbocyclic aryl groups having from 6 to 10 ring atoms, alkyl groups having from 1 to 6 carbon atoms, alkoxy groups having from 1 to 6 carbon atoms, carboxy groups, alkoxycarbonyl groups in which the alkoxy part has from 1 to 6 carbon atoms and alkylenedioxy and alkylidene- dioxy groups having from 1 to 3 carbon atoms;

and pharmaceutically acceptable salts and esters thereof.

The invention also provides a pharmaceutical composition for the treatment or prophylaxis of hypertension, which comprises an effective amount of an anti-hypertensive agent in admixture with a pharmaceutically acceptable carrier or diluent, wherein the anti-hypertensive agent is selected from the group consisting of compounds of formula (I) and pharmaceutically acceptable salts and esters thereof.

The invention further provides a method for the treatment or prophylaxis of hypertension in a mammal, e.g. a human being, which comprises administering an effective amount of an anti-hypertensive agent to said mammal, wherein the anti-hypertensive agent is selected from the group consisting of compounds of formula (I) and pharmaceutically acceptable salts and esters thereof.

The invention still further provides processes for the preparation of compounds of formula (I) and pharmaceutically acceptable salts and esters thereof, which are described in more detail hereafter.

In accordance with the present invention, there are also provided compounds of formula $(I)_p$:

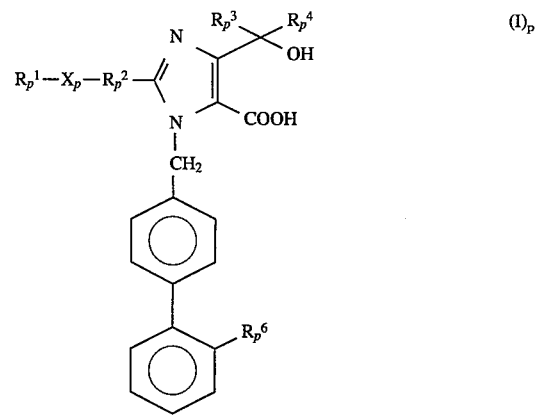

in which:

$R_p^1$ represents a hydrogen atom, an alkyl group having from 1 to 6 carbon atoms, a cycloalkyl group having from 3 to 6 ring carbon atoms or an alkanoyl group having from 1 to 6 carbon atoms;

$R_p^2$ represents a single bond or an alkylene or alkylidene group having from 1 to 4 carbon atoms;

$R_p^3$ $R_p^4$ are independently selected from the group consisting of hydrogen atoms and alkyl groups having from 1 to 6 carbon atoms;

$R_p^6$ represents a carboxy group or a tetrazol-5-yl group; and $X_p$ represents an oxygen or sulfur atom; and pharmaceutically acceptable salts and esters thereof.

The invention also provides a pharmaceutical composition for the treatment or prophylaxis of hypertension or of a cardiovascular disease, which comprises an effective amount of an anti-hypertensive agent in admixture with a pharmaceutically acceptable carrier or diluent, wherein the anti-hypertensive agent is selected from the group consisting of compounds of formula $(I)_p$ and pharmaceutically acceptable salts and esters thereof.

The invention further provides a method for the treatment or prophylaxis of hypertension or of a cardiovascular disease in a mammal, e.g. a human being, which comprises administering an effective amount of an anti-hypertensive agent to said mammal, wherein the anti-hypertensive agent is selected from the group consisting of compounds of formula $(I)_p$ and pharmaceutically acceptable salts and esters thereof.

The invention still further provides processes for the preparation of compounds of formula $(I)_p$ and pharmaceutically acceptable salts and esters thereof, which are described in more detail hereafter.

DETAILED DESCRIPTION OF INVENTION

In the compounds of the present invention, where $R^1$, $R^2$, $R^3$, $R^4$, $R^6$, $R^8$, $R^9$ or substituent (b) is an alkyl group, this is an alkyl group having from 1 to 6 carbon atoms, and may be a straight or branched chain group having from 1 to 6 carbon atoms; examples include the methyl, ethyl, propyl, isopropyl, butyl, isobutyl, sec-butyl, t-butyl, pentyl, t-pentyl, 2-methylbutyl, 3-methylbutyl, 1-ethylpropyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl, hexyl and isohexyl groups. $R^1$ preferably represents a straight or branched chain alkyl group containing from 2 to 5 carbon atoms, and more preferably a straight chain group, i.e. most preferably an ethyl, propyl or butyl group. Each of $R^2$ and $R^3$, which may be the same or different, preferably represents a straight or branched chain alkyl group containing from 1 to 4 carbon atoms, more preferably a methyl, ethyl, propyl, isopropyl or t-butyl group, and most preferably a methyl or ethyl group when $R^5$ represents a carboxy group, or an isopropyl or t-butyl group when $R^5$ represents a group of formula —$CONR^8R^9$. $R^4$ or $R^6$ preferably represents a straight or branched chain alkyl group containing from 1 to 4 carbon atoms, more preferably a methyl or ethyl group. Where $R^8$ and $R^9$ are alkyl groups, these may be the same or different, and each is preferably an alkyl group containing from 1 to 4 carbon atoms, more preferably a methyl, ethyl, propyl or butyl group, and most preferably a methyl or ethyl group. In the case of substituent (b), when this represents an alkyl group, it preferably has from 1 to 4 carbon atoms, and the methyl and ethyl groups are more preferred.

Where $R^1$, $R^2$ and $R^3$ represents an alkenyl group, this may be a straight or branched chain alkenyl group containing from 3 to 6 carbon atoms. Examples of such groups include: the 1-propenyl, 2-propenyl, 1-methyl-2-propenyl, 2-methyl-1-propenyl, 2-methyl-2-propenyl, 2-ethyl-2-propenyl, 1-butenyl, 2-butenyl, 1-methyl-2-butenyl, 2-methyl-2-butenyl, 3-methyl-2-butenyl, 1-ethyl-2-butenyl, 3-butenyl, 1-methyl-3-butenyl, 2-methyl-3-butenyl, 1-ethyl-3-butenyl, 1-pentenyl, 2-pentenyl, 1-methyl-2-pentenyl, 2-methyl-2-pentenyl, 3-pentenyl, 1-methyl-3-pentenyl, 2-methyl-3-pentenyl, 4-pentenyl, 1-methyl-4-pentenyl, 2-methyl-4-pentenyl, 1-hexenyl, 2-hexenyl, 3-hexenyl, 4-hexenyl and 5-hexenyl groups. $R^1$ preferably represents a straight or branched chain alkenyl group containing 3 or 4 carbon atoms, and more preferably a 1-propenyl or 1-butenyl group. Each of $R^2$ and $R^3$, which may be the same or different, preferably represents a straight or branched chain alkenyl group containing 3 or 4 carbon atoms, and more preferably a 2-propenyl or 2-butenyl group.

Where $R^2$ or $R^3$ represents a cycloalkyl group, this has a total of from 3 to 10 carbon atoms in one or more saturated carbocyclic rings, and the or each ring preferably has from 3 to 6 carbon atoms. Where the group is a multiple ring system, this may be a bridged or fused ring system. Examples of such groups include the cyclopropyl, cyclobutyl, cyclopentyl, cyclohexyl, cycloheptyl, norbornyl and adamantyl groups. Of these, we prefer those groups having from 3 to 6 carbon atoms in a single ring, and most prefer the cyclopentyl and cyclohexyl groups.

Alternatively $R^2$, or $R^3$ may represent an aralkyl group, in which the alkyl part has from 1 to 6 (more preferably from 1 to 4, still more preferably 1 or 2, and most preferably 1) carbon atoms and the aryl part is an aromatic carbocyclic groups which has from 6 to 14 (preferably from 6 to 10, and more preferably 6 or 10) ring atoms and which is unsubstituted or is substituted by at least one substituent selected from the group consisting of substituents (b), defined above and exemplified below. Specific examples of alkyl groups which may form the alkyl part are as given above in relation to the alkyl groups which may be represented by $R^2$, and specific examples of the aryl groups which may form the aryl part are as given below in relation to the aryl groups which may be represented by $R^2$. Examples of such aralkyl groups include the benzyl, 1- and 2-naphthylmethyl, indenylmethyl, phenanthrenylmethyl, anthracenylmethyl, diphenylmethyl, triphenylmethyl, 1-phenylethyl, phenethyl, 1-naphthylethyl, 2-naphthylethyl, 1-phenylpropyl, 2-phenylpropyl, 3-phenylpropyl, 1-naphthylpropyl, 2-naphthylpropyl, 3-naphthylpropyl, 1-phenylbutyl, 2-phenylbutyl, 3-phenylbutyl, 4-phenylbutyl, 1-naphthylbutyl, 2-naphthylbutyl, 3-naphthylbutyl, 4-naphthylbutyl, 1-phenylpentyl, 2-phenylpentyl, 3-phenylpentyl, 4-phenylpentyl, 5-phenylpentyl, 1-naphthylpentyl, 2-naphthylpentyl, 3-naphthylpentyl, 4-naphthylpentyl, 5-naphthylpentyl, 1-phenylhexyl, 2-phenylhexyl, 3-phenylhexyl, 4-phenylhexyl, 5-phenylhexyl, 6-phenylhexyl, 1-naphthylhexyl, 2-naphthylhexyl, 3-naphthylhexyl, 4-naphthylhexyl, 5-naphthylhexyl and 6-naphthylhexyl groups. In those cases where the aralkyl group contains a naphthyl group, this may be a 1- or 2-naphthyl group. Of these aralkyl groups, we prefer those groups in which the alkyl part has from 1 to 4 carbon atoms, the benzyl group being most preferred. These groups may be unsubstituted or they may be substituted by one or more of substituents (b), defined above and exemplified below. Examples of the substituted groups include those unsubtituted groups exemplified above but in which the aryl part is replaced by one of the substituted aryl groups given below. However, the unsubtituted groups are preferred.

Where $R^2$ or $R^3$ represents an aryl group, this is an aromatic carbocyclic group which has from 6 to 14 (preferably from 6 to 10, and more preferably 6 or 10) ring atoms and which is unsubstituted or is substituted by at least one substituent selected from the group consisting of substituents (b), defined above and exemplified below. Such groups may be unsubtituted or they may be substituted by at least one, and preferably from 1 to 3, of substituents (b), for example:

nitro groups;

cyano groups;

halogen atoms, such as the fluorine, chlorine, bromine or iodine atoms, of which the fluorine, chlorine and bromine atoms are preferred;

unsubstituted carbocyclic aryl groups, e.g. as exemplified below in relation to $R^2$ and $R^3$;

alkyl groups, as exemplified above, most preferably the methyl group;

alkoxy groups having from 1 to 6, preferably from 1 to 4, carbon atoms, such as the methoxy, ethoxy, propoxy, isopropoxy, butoxy, isobutoxy, sec-butoxy, t-butoxy, pentyloxy, neopentyloxy, 2-methylbutoxy-, 3-methylbutoxy, 1-ethylpropoxy, 4-methylpentyloxy, 3-methylpentyloxy, 2-methylpentyloxy, 1-methylpentyloxy, 3,3-dimethylbutoxy, 2,2-dimethylbutoxy, 1,1-dimethylbutoxy, 1,2-dimethylbutoxy, 1,3-dimethylbutoxy, 2,3-dimethylbutoxy, 2-ethylbutoxy, hexyloxy and isohexyloxy groups, most preferably a methoxy or ethoxy group;

alkoxycarbonyl groups in which the alkoxy part has from 1 to 6, preferably from 1 to 4, carbon atoms, such as the methoxycarbonyl, ethoxycarbonyl, propoxycarbonyl, isopropoxycarbonyl, butoxycarbonyl, isobutoxycarbonyl, t-butoxycarbonyl, pentyloxycarbonyl and hexyloxycarbonyl groups, of which the methoxycarbonyl and ethoxycarbonyl groups are most preferred;

carboxy groups;

alkylenedioxy and alkylidenedioxy groups having from 1 to 3 carbon atoms, for example the methylenedioxy, ethylenedioxy, propylenedioxy, trimethylenedioxy, ethylidenedioxy and isopropylidenedioxy groups, of which the methylenedioxy group is most preferred.

Of these, the alkyl and alkoxy substituents are preferred where $R^2$ or $R^3$ represents a substituted aryl group.

Where the group is substituted, the number of substituents is not critical, and is only limited by the number of substitutable positions, and possibly by steric constraints. However, in practice, we normally prefer 1, 2 or 3 substituents.

Examples of substituted and unsubstituted aryl groups include the phenyl, naphthyl, phenanthrenyl, anthracenyl, 2-methylphenyl, 3-methylphenyl, 4-methylphenyl, 2-ethylphenyl, 3-propylphenyl, 4-ethylphenyl, 2-butylphenyl, 3-pentylphenyl, 4-pentylphenyl, 3,5-dimethylphenyl, 2,5-dimethylphenyl, 2,6-dimethylphenyl, 2,4-dimethylphenyl, 3,5-dibutylphenyl, 2,5-dipentylphenyl, 2,6-dipropyl-4-methylphenyl, 2-methoxyphenyl, 3-methoxyphenyl, 4-methoxyphenyl, 2-ethoxyphenyl, 3-propoxyphenyl, 4-ethoxyphenyl, 2-butoxyphenyl, 3-pentyloxyphenyl and 4-pentyloxyphenyl groups, of which the phenyl, 2-methylphenyl, 3-methylphenyl, 4-methylphenyl, 2-methoxyphenyl, 3-methoxyphenyl and 4-methoxyphenyl groups are the most preferred.

Where $R^2$ or $R^3$ represents a fused ring system in which an aryl group is fused to a cycloalkyl group having from 3 to 10 carbon atoms, the aryl and cycloalkyl parts may be as exemplified above, and preferably the aryl part is a phenyl or naphthyl group, and the cycloalkyl part has 5 or 6 carbon atoms. Examples of such fused ring systems include the indanyl, tetrahydronaphthyl and tetrahydroanthryl groups, of which the indanyl and tetrahydronaphthyl groups are preferred.

$R^4$ can represent an alkanoyl group; such a group may be a straight or branched chain group and has from 1 to 6 carbon atoms. Examples of such groups include the formyl, acetyl, propionyl, butyryl, isobutyryl, pivaloyl, valeryl and isovaleryl groups, of which the formyl and acetyl groups are preferred.

Alternatively, $R^4$ may be a substituted alkanoyl group in which the substituent or substituents is or are selected from the group consisting of the halogen atoms and the alkoxy groups. Examples of such substituted alkanoyl groups include the chloroacetyl, dichloroacetyl, trichloroacetyl, trifluoroacetyl and methoxyacetyl groups, of which the chloroacetyl and trifluoroacetyl groups are preferred.

Where $R^4$ represents an alkenoyl group, this may have from 3 to 6, preferably from 3 to 5, carbon atoms, and examples include the acryloyl, methacryloyl, crotonoyl, 3-methyl-2-butenoyl and 2-methyl-2-butenoyl, especially (E)-2-methyl-2-butenoyl, groups.

Where $R^4$ represents an arylcarbonyl group, the aryl part may be any of those aryl groups exemplified above in relation to $R^2$. However, in this case, if the group is substituted, the substituents are preferably selected from the group consisting of halogen atoms, alkyl groups, alkoxy groups, nitro groups, alkoxycarbonyl groups and unsubstituted aryl groups, more preferably the methyl, methoxy, fluoro and chloro substituents. Examples of the arylcarbonyl groups include the benzoyl, α-naphthoyl, β-naphthoyl, 3-fluorobenzoyl, 2-bromobenzoyl, 4-chlorobenzoyl, 2,4,6-trimethylbenzoyl, 4-toluoyl, 4-anisoyl, 4-nitrobenzoyl, 2-nitrobenzoyl, 2-(methoxycarbonyl)benzoyl and 4-phenylbenzoyl groups, of which the benzoyl, 4-toluoyl, and 4-anisoyl groups are preferred.

Where $R^4$ represents an alkoxycarbonyl group, the alkoxy part has from 1 to 6 carbon atoms, i.e. the group as a whole has from 2 to 7 carbon atoms, and examples of such groups include the methoxycarbonyl, ethoxycarbonyl, propoxycarbonyl, isopropoxycarbonyl, butoxycarbonyl, isobutoxycarbonyl, t-butoxycarbonyl, pentyloxycarbonyl and hexyloxycarbonyl groups, of which the methoxycarbonyl and ethoxycarbonyl groups are preferred.

Where $R^4$ represents a tetrahydropyranyl, tetrahydrothiopyranyl, tetrahydrothienyl or tetrahydrofuryl group, this may be substituted or unsubstituted. If substituted, the substituents are selected from the group consisting of halogen atoms and alkoxy groups having from 1 to 6 carbon atoms, which may be any of those groups and atoms exemplified above in relation to $R^4$, preferably the chloro, bromo and methoxy substituents. Examples of these substituted and unsubstituted groups include the tetrahydropyran-2-yl, 3-chlorotetrahydropyran-2-yl, 3-bromotetrahydropyran-2-yl, 4-methoxytetrahydropyran-2-yl, tetrahydrothiopyran-2-yl, 4-methoxytetrahydrothiopyran-2-yl, tetrahydrofuran-2-yl and tetrahydrothien-2-yl groups, of which the tetrahydropyran-2-yl, 4-methoxytetrahydropyran-2-yl, tetrahydrothiopyran-2-yl and 4-methoxytetrahydrothiopyran-2yl groups are preferred.

Where $R^4$ represents a silyl group of formula —SiR$^a$R$^b$R$^c$ in which 1, 2 or 3 of the groups represented by R$^a$, R$^b$ and R$^c$ are independently selected from the group consisting of alkyl groups having from 1 to 6 carbon atoms, and 2, 1 or 0 of the groups represented by R$^a$, R$^b$ and R$^c$ are independently selected from the group consisting of aryl groups, as defined above, the alkyl and aryl parts may be any of those groups exemplified above in relation to $R^1$ and $R^2$, preferably the methyl, ethyl, t-butyl and phenyl groups. Examples of such silyl groups include the trimethylsilyl, triethylsilyl, isopropyldimethylsilyl, t-butyldimethylsilyl, methyldiisopropylsilyl, methyl-di-t-butylsilyl, triisopropylsilyl, diphenylmethylsily, diphenylbutylsilyl, diphenylisopropylsilyl and phenyldiisopropylsilyl groups, of which the trimethylsilyl, t-butyldimethylsilyl and diphenylmethylsilyl groups are preferred.

Where R⁴ represents an alkoxymethyl group in which the alkoxy part has from 1 to 6 carbon atoms, the alkoxy part may be any of the alkoxy groups exemplified above in relation to substituents (b). Examples of such alkoxymethyl groups include the methoxymethyl, 1,1-dimethyl-1-methoxymethyl, ethoxymethyl, propoxymethyl, isopropoxymethyl, butoxymethyl and t-butoxymethyl groups, of which the methoxymethyl and ethoxymethyl groups are preferred.

Where R⁴ represents an (alkoxyalkoxy)methyl group, each alkoxy part has from 1 to 6 carbon atoms and may be any of the alkoxy groups exemplified above in relation to substituents (b). Examples of such (alkoxyalkoxy)methyl groups include the methoxymethoxymethyl, 2-methoxyethoxymethyl, 2-methoxypropoxymethyl and 2-methoxybutoxymethyl groups, of which the 2-methoxyethoxymethyl group is preferred.

Where R⁴ represents a haloalkoxymethyl group, the alkoxy part has from 1 to 6 carbon atoms and the halogen atoms and alkoxy groups may be any of the atoms and groups exemplified above in relation to substituents (b). Examples of such haloalkoxymethyl groups include the 2,2,2-trichloroethoxymethyl, 2,2,2-tribromoethoxymethyl, bis(2-chloroethoxy)methyl and bis(2-bromoethoxy)methyl groups, of which the 2,2,2-trichloroethoxymethyl and bis(2-chloroethoxy)methyl groups are preferred.

Where R⁴ represents an aralkyl group, in which an alkyl group having from 1 to 6, preferably from 1 to 4, carbon atoms is substituted by at least one aryl group, the alkyl and aryl parts may be any of the alkyl and aryl groups exemplified above in relation to $R^1$ and $R^2$. Examples of such aralkyl groups include the benzyl, α-naphthylmethyl, β-naphthylmethyl, diphenylmethyl(benzhydryl), trityl, α-naphthyldiphenylmethyl, 9-anthrylmethyl, 4-methylbenzyl, 6-phenylhexyl, 2,4,6-trimethylbenzyl, 3,4,5-trimethylbenzyl, 4-methoxybenzyl, 4-methoxyphenyldiphenylmethyl, 2-nitrobenzyl, 4-nitrobenzyl, 4-chlorobenzyl, 4-bromobenzyl and 4-cyanobenzyl groups, of which the benzyl, 4-methylbenzyl, 4-methoxybenzyl, 4-chlorobenzyl and 4-bromobenzyl groups are preferred.

Where R⁴ represents an alkanoyloxymethoxycarbonyl group, the alkanoyl part has from 1 to 6 carbon atoms and may be any of the alkanoyl groups exemplified above in relation to R⁴. Examples of such alkanoyloxymethoxycarbonyl groups include the formyloxymethoxycarbonyl, acetoxymethoxycarbonyl, propionyloxymethoxycarbonyl, butyryloxymethoxycarbonyl and pivaloyloxymethoxycarbonyl groups, of which the pivaloyloxymethoxycarbonyl group is preferred.

R⁵ represents a carboxy group or a group of formula —CONR⁸R⁹. Where it represents a group of formula —CONR⁸R⁹, and R⁸ or R⁹ represents an alkyl group, this may be an unsubstituted alkyl group having from 1 to 6 carbon atoms, such as those groups exemplified above, or a substituted alkyl group, which has from 1 to 6 carbon atoms and which is substituted by at least one substituent selected from the group consisting of substituents (a), defined above and exemplified below.

Where R⁸ and R⁹ together represent an alkylene group, this has from 2 to 6 carbon atoms and may be substituted or unsubstituted; it may also be a straight or branched chain group. Examples of the unsubstituted groups include the ethylene, trimethylene, propylene, ethylethylene, tetramethylene, pentamethylene and hexamethylene groups, of which those groups containing 4 or 5 carbon atoms are preferred. In such cases, the group of formula —NR⁸R⁹ is a nitrogen-containing heterocyclic group having from 3 to 7 ring atoms (one being the nitrogen atom), for example, when the alkylene group contains 4 or 5 carbon atoms, it is a 1-pyrrolidinyl or piperidino group, respectively. Where the group is substituted, there may be one or more substituents selected from the group consisting of carboxy groups and alkoxycarbonyl groups in which the alkoxy part has from 1 to 6 carbon atoms. Examples of such substituents include the carboxy, methoxycarbonyl, ethoxycarbonyl, propoxycarbonyl, butoxycarbonyl, isobutoxycarbonyl, t-butoxycarbonyl, pentyloxycarbonyl and hexyloxycarbonyl groups, of which the carboxy, methoxyarbonyl and ethoxycarbonyl groups are preferred.

Where R⁵ represents a carboxy group, the compound is a carboxylic acid and can, therefore, form esters, in which the carboxy group represented by R⁵ is replaced by a group of formula —COOR⁵ᵃ, in which R⁵ᵃ represents an ester residue (in the case of the carboxylic acid, R⁵ᵃ represents a hydrogen atom). It can also form salts, examples of which are as exemplified below in relation to R⁷. The nature of the ester so formed is not critical to the invention, except where the ester is to be used for pharmaceutical purposes, in which case it should be pharmaceutically acceptable, i.e. it should not have increased, or unacceptably increased, toxicity or reduced, or unacceptably reduced, activity, as compared with the parent acid. However, where the ester is to be used for other purposes, e.g. as intermediates for the preparation of other, and perhaps more active, compounds, even this restriction does not apply, and any ester residue common in the art may be used and may be selected on the basis of its functionality and commercial advantages. However, it is well known in the art that certain ester residues confer advantages on compounds incorporating them, for example easier or better absorption in vivo, and, if desired, such ester residues may be used in the present invention.

Examples of such ester residues include:

alkyl groups having from 1 to 6 carbon atoms, such as those exemplified above in relation to $R^1$;

haloalkyl groups having from 1 to 6, preferably from 1 to 4, carbon atoms, in which the alkyl part may be as exemplified above in relation to $R^1$, for example the trifluoromethyl, 2,2,2-trichloroethyl, 2,2,2-trifluoroethyl, 2-chloroethyl, 2-fluoroethyl, 2-iodoethyl, 4-fluorobutyl, 3-chloropropyl and 6-iodohexyl groups, of which the 2,2,2-trichloroethyl and 2-chloroethyl groups are preferred;

hydroxyalkyl groups having from 1 to 6, preferably from 1 to 4, carbon atoms, in which the alkyl part may be as exemplified above in relation to $R^1$, for example the 2-hydroxyethyl, 2,3-dihydroxypropyl, 3-hydroxypropyl, 3,4-dihydroxybutyl and 4-hydroxybutyl groups, of which the 2-hydroxyethyl group is preferred;

alkoxyalkyl and alkoxyalkoxyalkyl groups in which the alkoxy and the alkyl parts each have from 1 to 6, preferably from 1 to 4, carbon atoms, and may be as exemplified above in relation to substituents (b) and $R^1$, respectively, for example the methoxymethyl, 2-methoxyethyl, 2-ethoxyethyl and 2-methoxyethoxymethyl groups, of which the methoxymethyl group is preferred;

phenacyl groups and phenacyl groups which are substituted by one or more of substituents (b), of which the unsubstituted phenacyl group is preferred;

alkoxycarbonylalkyl groups, such as the methoxycarbonylmethyl group;

cyanoalkyl groups having from 1 to 6, preferably from 1 to 4, carbon atoms, in which the alkyl part may be as exemplified above in relation to $R^1$, for example the 2-cyanoethyl and cyanomethyl groups;

alkylthioalkyl groups in which each alkyl part has from 1 to 6, preferably from 1 to 4, carbon atoms, and may be as exemplified above in relation to $R^1$, for example the methylthiomethyl and ethylthiomethyl;

arylthioalkyl groups in which the alkyl part has from 1 to 6, preferably from 1 to 4, carbon atoms, and may be as exemplified above in relation to $R^1$, and the aryl part may be as defined and exemplified above in relation to $R^2$, for example the phenylthiomethyl group;

alkylsulfonylalkyl groups in which each alkyl part has from 1 to 6, preferably from 1 to 4, carbon atoms, and may be as exemplified above in relation to $R^1$ and may be unsubstituted or substituted by one or more halogen atoms, for example the 2-(methanesulfonyl)ethyl or 2-(trifluoromethanesulfonyl)ethyl groups;

arylsulfonylalkyl groups in which the alkyl part has from 1 to 6, preferably from 1 to 4, carbon atoms, and may be as exemplified above in relation to $R^1$, and the aryl part may be as defined and exemplified above in relation to $R^2$, for example the 2-(benzenesulfonyl) ethyl and 2-(p-toluenesulfonyl)ethyl groups;

aryl groups such as those exemplified above in relation to $R^2$;

aralkyl groups such as those exemplified above in relation to $R^2$, especially the benzyl, p-methoxybenzyl, p-nitrobenzyl and 4-acetoxy-3-methoxybenzyl groups, of which the benzyl group is preferred;

groups of formula —$SiR^dR^eR^f$ (in which $R^d$, $R^e$ and $R^f$ are as defined above in relation to $R^a$, $R^b$ and $R^c$), such as those exemplified above in relation to $R^4$;

alkanoyloxyalkyl groups in which each of the alkanoyl and the alkyl parts has from 1 to 6 carbon atoms and may be as exemplified above in relation to $R^1$ and $R^4$, respectively, and preferably the alkanoyl part has from 1 to 5 carbon atoms and the alkyl part has from 1 to 4 carbon atoms and more preferably the alkanoyl part has from 2 to 5 carbon atoms and alkyl part has from 1 to 2 carbon atoms; examples of such alkanoyloxyalkyl groups include the formyloxymetnyl, acetoxymethyl, propionyloxymethyl, butyryloxymethyl, pivaloyloxymethyl, valeryloxymethyl, isovaleryloxymentyl, hexanoyloxymethyl, 1-(formyloxy)ethyl, 1-(acetoxy) ethyl, 1-(propionyloxy)ethyl, 1-(butyryloxy)ethyl, 1-(pivaloyloxy)ethyl, 1-(valeryloxy)ethyl, 1-(isovaleryloxy)ethyl, 1-(hexanoyloxy)ethyl, 2-(formyloxy) ethyl, 2-(acetoxy)ethyl, 2-(propionyloxy)ethyl, 2-(butyryloxy)ethyl, 2-(pivaloyloxy)ethyl, 2-(valeryloxy) ethyl, 2-(isovaleryloxy)ethyl, 2-(hexanoyloxy)ethyl, 1-(formyloxy)propyl, 1-(acetoxy)propyl, 1-(propionyloxy)propyl, 1-(butyryloxy)propyl, 1-(pivaloyloxy) propyl, 1-(valeryloxy)propyl, 1-(isovaleryloxy)propyl, 1-(hexanoyloxy)propyl, 1-(acetoxy) butyl, 1-(propionyloxy)butyl, 1-(butyryloxy)butyl, 1-(pivaloyloxy)butyl, 1-(acetoxy)pentyl, 1-(propionyloxy) pentyl, 1-(butyryloxy)pentyl, 1-(pivaloyloxy)pentyl and 1-(pivaloyloxy)hexyl groups, preferably the formyloxymethyl, acetoxymethyl, propionyloxymethyl, butyryloxymethyl, pivaloyloxymethyl, 1-(formyloxy) ethyl, 1-(acetoxy)ethyl, 1-(propionyloxy)ethyl, 1-(butyryloxy)ethyl and 1-(pivaloyloxy) ethyl groups, and more preferably the acetoxymethyl, propionyloxymethyl, butyryloxymethyl, pivaloyloxymethyl, 1-(acetoxy)ethyl, 1-(propionyloxy)ethyl, 1-(butyryloxy) ethyl and 1-(pivaloyloxy)ethyl groups and most preferably the pivaloyloxymethyl and 1-(pivaloyloxy) ethyl groups;

cycloalkanoyloxyalkyl groups in which the cycloalkyl part has 5 or 6 carbon atoms and the alkyl parts has from 1 to 6 carbon atoms, each as exemplified above in relation to $R^2$; preferably the alkyl part has from 1 to 4 carbon atoms and more preferably 1 or 2 carbon atoms; examples of such cycloalkanoyloxyalkyl groups include the cyclopentanoyloxymethyl, cyclohexanoyloxymethyl, 1-(cyclopentanoyloxy)ethyl, 1-(cyclohexanoyloxy)ethyl, 1-(cyclopentanoyloxy)propyl, 1-(cyclohexanoyloxy)propyl, 1-(cyclopentanoyloxy)butyl and 1-(cyclohexanoyloxy)butyl, groups, preferably the cyclopentanoyloxymethyl, cyclohexanoyloxymethyl, 1-(cyclopentanoyloxy)ethyl, and 1-(cyclohexanoyloxy)ethyl groups;

alkoxycarbonyloxyalkyl groups in which each of the alkoxy and the alkyl parts has from 1 to 6 carbon atoms as exemplified above in relation to substituents (b) and $R^1$, respectively, and preferably each of the alkoxy and the alkyl parts has from 1 to 4 carbon atoms and more preferably the alkoxy part has from 1 to 4 carbon atoms and alkyl part has from 1 to 2 carbon atoms; examples of such alkoxycarbonyloxyalkyl groups include the methoxycarbonyloxymethyl, ethoxycarbonyloxymethyl, propoxycarbonyloxymethyl, isopropoxycarbonyloxymethyl, butoxycarbonyloxymethyl, isobutoxycarbonyloxymethyl, pentyloxycarbonyloxymethyl, hexyloxycarbonyloxymethyl, 1-(methoxycarbonyloxy) ethyl, 1-(ethoxycarbonyloxy)ethyl, 1-(propoxycarbonyloxy)ethyl, 1-(isopropoxycarbonyloxy)ethyl, 1-(butoxycarbonyloxy)ethyl, 1-(isobutoxycarbonyloxy) ethyl, 1-(pentyloxycarbonyloxy)ethyl, 1-(hexyloxycarbonyloxy)ethyl, 2-(methoxycarbonyloxy)ethyl, 2-(ethoxycarbonyloxy)ethyl, 2-(propoxycarbonyloxy) ethyl, 2-(isopropoxycarbonyloxy)ethyl, 2-(butoxycarbonyloxy)ethyl, 2-(isobutoxycarbonyloxy) ethyl, 2-(pentyloxycarbonyloxy)ethyl, 2-(hexyloxycarbonyloxy)ethyl, 1-(methoxycarbonyloxy)propyl, 1-(ethoxycarbonyloxy)propyl, 1-(propoxycarbonyloxy) propyl, 1-(isopropoxycarbonyloxy)propyl, 1-(butoxycarbonyloxy)propyl, 1-(isobutoxy-carbonyloxy) propyl, 1-(pentyloxycarbonyloxy)propyl, 1-(hexyloxy carbonyloxy)propyl, 1-(methoxycarbonyloxy)butyl, 1-(ethoxycarbonyloxy)butyl, 1-(propoxycarbonyloxy) butyl, 1-(isopropoxycarbonyloxy)butyl, 1-(butoxycarbonyloxy)butyl, 1-(isobutoxycarbonyloxy)butyl, 1-(methoxycarbonyloxy)pentyl, 1-(ethoxycarbonyloxy)pentyl, 1-(methoxycarbonyloxy)hexyl and 1-(ethoxycarbonyloxy)hexyl groups, preferably the methoxycarbonyloxymethyl, ethoxycarbonyloxymethyl, propoxycarbonyloxymethyl, isopropoxycarbonyloxymethyl, butoxycarbonyloxymethyl, isobutoxycarbonyloxymethyl, 1-(methoxycarbonyloxy)ethyl, 1-(ethoxycarbonyloxy)ethyl, 1-(propoxycarbonyloxy) ethyl, 1-(isopropoxycarbonyloxy)ethyl, 1-(butoxycarbonyloxy)ethyl, 1-(isobutoxycarbonyloxy)ethyl, 1-(methoxycarbonyloxy)propyl, 1-(ethoxycarbonyloxy) propyl, 1-(propoxycarbonyloxy)propyl, 1-(isopropoxycarbonyloxy)propyl, 1-(butoxycarbonyloxy) propyl, 1-(isobutoxycarbonyloxy)propyl, 1-(methoxycarbonyloxy)butyl, 1-(ethoxycarbonyloxy) butyl, 1-(propoxycarbonyloxy)butyl, 1-(isopropoxycarbonyloxy)butyl, 1-(butoxycarbonyloxy)butyl, 1-(isobutoxycarbonyloxy)butyl, more preferably methoxycarbonyloxymethyl, ethoxycarbonyloxymethyl, propoxycarbonyloxymethyl, isopropoxycarbonyloxymethyl, butoxycarbonyloxymethyl, isobutoxycarbonyloxymethyl, 1-(methoxycarbonyloxy)ethyl, 1-(ethoxycarbonyloxy)ethyl, 1-(propoxycarbonyloxy)ethyl, 1-(isopropoxycarbonyloxy)ethyl, 1-(butoxycarbonyloxy)ethyl and 1-(isobutoxycarbonyloxy)ethyl groups and most preferably the methoxycarbonyloxymethyl, ethoxycarbonyloxymethyl, isopropoxycarbonyloxymethyl, 1-(methoxycarbonyloxy)ethyl, 1-(ethoxycarbonyloxy)ethyl and 1-(isopropoxycarbonyloxy)ethyl groups;

cycloalkoxycarbonyloxyalkyl groups in which the cycloalkyl part has 5 or 6 carbon atoms and the alkyl parts has from 1 to 6 carbon atoms, each as exemplified above in relation to $R^2$; preferably the alkyl part has from 1 to 4 carbon atoms and more preferably 1 or 2 carbon atoms; examples of such cycloalkoxycarbonyloxyalkyl groups include the cyclopentoxycarbonyloxymethyl, cyclohexyloxycarbonyloxymethyl, 1-(cyclopentyloxycarbonyloxy)ethyl, 1-(cyclohexyloxycarbonyloxy)ethyl, 1-(cyclopentyloxycarbonyloxy)propyl, 1-(cyclohexyloxycarbonyloxy)propyl, 1-(cyclopentyloxycarbonyloxy)butyl and 1-(cyclohexyloxycarbonyloxy)butyl groups, preferably the cyclopentyloxycarbonyloxymethyl, cyclohexyloxycarbonyloxymethyl, 1-(cyclopentoxycarbonyloxy)ethyl and 1-(cyclohexyloxycarbonyloxy)ethyl groups;

[5-(aryl- or alkyl-)-2-oxo-1,3-dioxolen-4-yl]methyl groups in which the alkyl part has from 1 to 6 carbon atoms and may be as exemplified above in relation to $R^1$ and $R^2$, and the aryl part is as defined and exemplified above in relation to $R^2$ (and is preferably a substituted or unsubstituted phenyl group); preferably the alkyl part has from 1 to 4 carbon atoms and more preferably 1 or 2 carbon atoms; examples of such [5-(aryl- or alkyl-)-2-oxo-1,3-dioxolen-4-yl]methyl groups include the (5-phenyl-2-oxo-1,3-dioxolen-4-yl)methyl, [5-(4-methylphenyl)-2-oxo-1,3-dioxolen-4-yl]methyl, [5-(4-methoxyphenyl)-2-oxo-1,3-dioxolen-4-yl]methyl, [5-(4-chlorophenyl)-2-oxo-1,3-dioxolen-4-yl]methyl, [5-(4-fluorophenyl)-2-oxo-1,3-dioxolen-4-yl]methyl, (5-methyl-2-oxo-1,3-dioxolen-4-yl)methyl, (5-ethyl-2-oxo-1,3-dioxolen-4-yl)methyl, (5-propyl-2-oxo-1,3-dioxolen-4-yl)methyl, (5-isopropyl-2-oxo-1,3-dioxolen-4-yl)methyl and (5-butyl-2-oxo-1,3-dioxolen-4-yl)methyl groups, preferably the (5-phenyl-2-oxo-1,3-dioxolen-4-yl)methyl, (5-methyl-2-oxo-1,3-dioxolen-4-yl)methyl and (5-ethyl -2-oxo-1,3-dioxolen-4-yl)methyl groups and more preferably the (5-methyl-2-oxo-1,3-dioxolen-4-yl)methyl group; and phthalidyl groups.

Preferred ester residues are, for example:

$C_1$–$C_4$ alkyl groups phenyl, naphthyl and substituted phenyl groups having one or more, preferably from 1 to 3, methyl, ethyl, methoxy, ethoxy, fluoro and chloro substituents, which, in the case of 2 or 3 substituents, may be the same or different;

benzyl, diphenylmethyl and α- and β-naphthylmethyl groups, and substituted benzyl groups having one or more, preferably from 1 to 3, methyl, ethyl, methoxy, ethoxy, fluoro and chloro substituents, which, in the case of 2 or 3 substituents, may be the same or different;

groups of formula $SiR^dR^eR^f$ in which 1, 2 or 3 of the groups represented by $R^d$, $R^e$ and $R^f$ are independently selected from the group consisting of alkyl groups having from 1 to 4 carbon atoms, and 2, 1 or 0 are phenyl groups;

alkanoyloxyalkyl groups in which the alkanoyl group has from 1 to 5 carbon atoms and the alkyl group has from 1 to 4 carbon atoms;

cycloalkanoyloxyalkyl groups in which the cycloalkyl part has 5 or 6 carbon atoms and the alkyl part has from 1 to 4 carbon atoms;

alkoxycarbonyloxyalkyl groups in which each of the alkoxy part and the alkyl part has from 1 to 4 carbon atoms;

cycloalkoxycarbonyloxyalkyl groups in which the cycloalkyl part has 5 or 6 carbon atoms and the alkyl part has from 1 to 4 carbon atoms;

[5-(phenyl or alkyl-)-2-oxo-1,3-dioxolen-4-yl]methyl groups in which the alkyl part has from 1 to 4 carbon atoms; and phthalidyl groups.

More preferred ester residues are, for example, $C_1$–$C_4$ alkyl groups;

the benzyl group;

alkanoyloxyalkyl groups in which the alkanoyl part has from 1 to 5 carbon atoms and the alkyl part has 1 or 2 carbon atoms;

cycloalkanoyloxyalkyl groups in which the cycloalkyl part has from 5 to 6 carbon atoms and the alkyl part has 1 or 2 carbon atoms;

alkoxycarbonyloxyalkyl groups in which the alkoxy part has from 1 to 4 carbon atoms and alkyl part has 1 or 2 carbon atoms;

cycloalkoxycarbonyloxyalkyl groups in which the cycloalkyl part has 5 or 6 carbon atoms and the alkyl part has 1 or 2 carbon atoms;

[5-(phenyl or alkyl-)-2-oxo-1,3-dioxolen-4-yl]methyl groups in which the alkyl part has 1 or 2 carbon atoms; and phthalidyl groups.

The most preferred ester residues are, for example, pivaloyloxymethyl, ethoxycarbonyloxymethyl, 1-(ethoxycarbonyloxy)ethyl, isopropoxycarbonyloxymethyl, (1-isopropoxycarbonyloxy)ethyl, (5-methyl-2-oxo-1,3-dioxolen-4-yl)methyl and phthalidyl groups.

Examples of the groups and atoms which may form substituents (a) include:

aryl groups, such as those exemplified above in relation to $R^2$;

heterocyclic groups having 5 or 6 ring atoms, of which from 1 to 4 are hetero-atoms selected from the group consisting of nitrogen, oxygen and sulfur atoms, and as exemplified below;

halogen atoms, alkoxy groups and alkoxycarbonyl groups, such as those exemplified in relation to substituents (b);

hydroxy groups, carboxy groups and amino groups; and acylamino groups, in which the acyl part is an alkanoyl group having from 1 to 6 carbon atoms or an arylcarbonyl group, in which the aryl part is as defined above, of which the acyl part is as exemplified above in relation to $R^4$, e.g. a benzamido group, and preferably an alkanoylamino group having from 1 to 4 carbon atoms, and more preferably an acetamido or formamido group.

Where substituent (a) is a heterocyclic group, this has 5 or 6 ring atoms, of which from 1 to 4 are hetero-atoms selected from nitrogen, oxygen and sulfur hetero-atoms. Where there are 4 hetero-atoms, we prefer that all 4 should be nitrogen atoms. Where there are 3 hetero-atoms, we prefer that at least one (more preferably 2) should be a nitrogen atom and one or two should be nitrogen, oxygen or sulfur atoms (and, where there are two, they may be the same or different). Where there are two hereto-atoms, these may be the same or different and they are selected from nitrogen, oxygen and sulfur atoms; however, more preferably one is a nitrogen atom or an oxygen atom and the other is a nitrogen, oxygen or sulfur atom. Examples of such heterocyclic groups include the pyrrolyl, furyl, thienyl, imidazolyl, oxazolyl, thiazolyl, oxadiazoiyl, thiadiazolyl, triazolyl, tetrazolyl and pyridyl groups (preferably a furyl, thienyl, imidazolyl, oxazolyl or thiazolyl group), preferably a furyl or thienyl group.

Preferably the benzene ring for formula (I) which bears the substituents represented by $R^6$ and $R^7$ is at the 3- or 4-position of the benzyl group to which it attaches, more preferably at the 4-position, i.e. the preferred compounds have the formula (Ia):

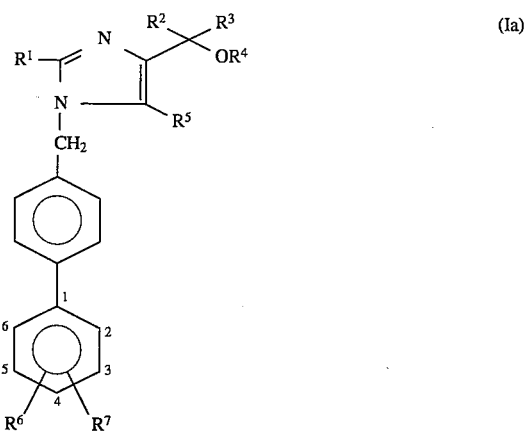

$R^6$ may represent a hydrogen atom, an alkyl group having from 1 to 6 carbon atoms (such as those exemplified above) or an alkoxy group having from 1 to 6 carbon atoms or a halogen atom, both of which are as exemplified above in relation to the same groups or atoms which may be represented by substituents (b). $R^6$ is preferably at the 6-position of the benzene ring.

$R^7$ may represent a carboxy group or a tetrazol-5-yl group. When it represents a carboxy group, or when substituent (a) is a carboxy group, the resulting compounds may form salts or esters. There is no particular restriction on the nature of these salts or esters, provided that, where they are intended for therapeutic use, they are pharmaceutically acceptable. Where they are intended for non-therapeutic uses, e.g. as intermediates in the preparation of other, and possibly more active, compounds, even this restriction does not apply. Examples of such salts include: salts with an alkali metal, such as sodium, potassium or lithium; salts with an alkaline earth metal, such as barium or calcium; salts with another metal, such as magnesium and aluminum; organic base salts, such as a salt with guanidine, triethylamine, dicyclohexylamine; and salts with a basic amino acid, such as lysine or arginine. Examples of ester groups may be as exemplified above in relation to $R^{5a}$.

Preferably $R^7$ represents a carboxy group or a tetrazol-5-yl group, and, where $R^7$ represents a carboxy group, salts of these compounds are also preferred. $R^7$ is preferably at the 2- or 3- position of the phenyl group, and more preferably at the 2-position.

The above compounds of the present invention necessarily contain at least one basic nitrogen atom in the imidazole ring and can therefore form acid addition salts. Examples of such acid addition salts include: addition salts with inorganic acids, such as hydrochloric acid, hydrobromic acid, sulfuric acid or phosphoric acid; and addition salts with organic acids such as maleic acid, fumaric acid, tartaric acid or citric acid.

Preferred classes of compounds of formula (I) (and salts and esters thereof) include:

$R^1$ represents an alkyl group having from 2 to 5 carbon atoms or an alkenyl group having from 3 to 5 carbon atoms;

$R^2$ and $R^3$ are independently selected from the group consisting of:
hydrogen atoms,
alkyl groups having from 1 to 4 carbon atoms,
alkenyl groups having from 3 to 5 carbon atoms,
cycloalkyl groups having 5 or 6 carbon atoms, benzyl, naphthyl and phenyl groups, and
substituted benzyl and phenyl groups which are substituted by at least one substituent selected from the group consisting of substituents (b'), defined below;
substituents (b') are selected from the group consisting of methyl, ethyl, methoxy and ethoxy groups and fluorine and chlorine atoms;

$R^4$ represents:
a hydrogen atom,
an alkyl group having from 1 to 4 carbon atoms,
an alkanoyl group having from 1 to 5 carbon atoms,
a substituted alkanoyl group which has 2 or 3 carbon atoms and which is substituted by at least one substituent selected from the group consisting of fluorine and chlorine atoms and methoxy and ethoxy groups,
an alkenoyl group having from 3 to 5 carbon atoms,
a naphthoyl group,
a benzoyl group,
a substituted benzoyl group which is substituted by at least one substituent selected from the group consisting of substituents (b'), defined below, an alkoxycarbonyl group having from 2 to 5 carbon atoms,
a tetrahydropyranyl, tetrahydrothiopyranyl, tetrahydrothienyl or tetrahydrofuryl group,
a substituted tetrahydropyranyl, tetrahydrothiopyranyl, tetrahydrothienyl or tetrahydrofuryl group which is substituted by at least one substituent selected from the group consisting of chlorine and bromine atoms and methoxy groups,
a group of formula —$SiR^aR^bR^c$, in which 1, 2 or 3 of the groups represented by $R^a$, $R^b$ and $R^c$ are independently selected from the group consisting of alkyl groups having from 1 to 4 carbon atoms, and 2, 1 or 0 of the groups represented by $R^a$, $R^b$ and $R^c$ are phenyl groups,
a methoxymethyl, 2-methoxyethoxymethyl, 2,2,2-trichloroethoxymethyl, bis(2-chloroethoxy)methyl, benzyl, diphenylmethyl or naphthylmethyl group or a substituted benzyl group which is substituted by at least one substituent selected from the group consisting of substituents (b'), defined below, or a pivaloyloxymethoxycarbonyl group;

$R^5$ represents a group of formula —$COOR^{5a}$ or a group of formula —$CONR^8R^9$ in which:
$R^{5a}$ represents
a hydrogen atom,
an alkyl group having from 1 to 4 carbon atoms,
a phenyl, naphthyl, benzyl, diphenylmethyl or naphthylmethyl group,
a substituted phenyl or benzyl group which is substituted by at least one substituent selected from the group consisting of substituents (b'), defined below,
a group of formula —$SiR^aR^bR^c$, in which $R^a$, $R^b$ and $R^c$ are as defined above, an alkanoyloxyalkyl group, in which the alkanoyl part has from 1 to 5 carbon atoms, and the alkyl part has from 1 to 4 carbon atoms, a cycloalkanoyloxyalkyl group, in which the cycloalkanoyl part has 6 or 7 carbon atoms, and the alkyl part has from 1 to 4 carbon atoms, an alkoxycarbonyloxyalkyl group, in which the alkoxy part has from 1 to 4 carbon atoms, and the alkyl part has from 1 to 4 carbon atoms, a cycloalkoxycarbonyloxyalkyl group, in which the cycloalkoxy part has 5 or 6 carbon atoms, and the alkyl part has from 1 to 4 carbon atoms, a [5-(phenyl- or alkyl-)-2-oxo-1,3-dioxolen-4-yl]-methyl group in which the alkyl part has from 1 to 4 carbon atoms, or a phthalidyl group;

$R^8$ and R9 are independently selected from the group consisting of:

hydrogen atoms, alkyl groups having from 1 to 4 carbon atoms, and substituted alkyl groups which have from 1 to 4 carbon atoms and which are substituted by at least one substituent selected from the group consisting of substituents (a'), defined below;

or $R^8$ and $R^9$ together represent an unsubstituted alkylene group which has 4 or 5 carbon atoms or a substituted alkylene group which has 4 or 5 carbon atoms and which is substituted by at least one substituent selected from the group consisting of carboxy groups, methoxycarbonyl groups and ethoxycarbonyl groups;

substituents (a') are selected from the group consisting of phenyl groups, furyl groups, thienyl groups, fluorine atoms, chlorine atoms, hydroxy groups, methoxy groups, ethoxy groups, carboxy groups and alkoxycarbonyl groups having from 2 to 5 carbon atoms;

$R^6$ represents a hydrogen atom, an alkyl group having from 1 to 4 carbon atoms, an alkoxy group having from 1 to 4 carbon atoms, a fluorine atom, a chlorine atom or a bromine atom;

$R^7$ represents a carboxy group or a tetrazol-5-yl group; and the benzene ring which bears the substituents represented by $R^6$ and $R^7$ is at the 3- or 4- position of the benzyl group to which it is attached.

More preferred classes of compounds of formula (I) (and salts and esters) include:

$R^1$ represents an alkyl group having from 2 to 5 carbon atoms or an alkenyl group having from 3 to 5 carbon atoms;

$R^2$ and $R^3$ are independently selected from the group consisting of:

hydrogen atoms, alkyl groups having from 1 to 4 carbon atoms, alkenyl groups having from 3 to 5 carbon atoms, cycloalkyl groups having 5 or 6 carbon atoms, and benzyl and phenyl groups;

$R^4$ represents:

a hydrogen atom, a methyl or ethyl group, an alkanoyl group having from 1 to 5 carbon atoms, an alkenoyl group having from 3 to 5 carbon atoms, a benzoyl group, or an alkoxycarbonyl group having from 2 to 5 carbon atoms;

$R^{5a}$ represents a group of formula —COOR$^{5a}$ or a group of formula —CONR$^8$R$^9$ in which:

$R^{5a}$ represents a hydrogen atom, an alkyl group having from 1 to 4 carbon atoms, a benzyl group, an alkanoyloxyalkyl group, in which the alkanoyl part has from 1 to 5 carbon atoms, and the alkyl part is a methyl or ethyl group, a cycloalkanoyloxyalkyl group, in which the cycloalkanoyl part has 6 or 7 carbon atoms, and the alkyl part is a methyl or ethyl group, an alkoxycarbonyloxyalkyl group, in which the alkoxy part has from 1 to 4 carbon atoms, and the alkyl part is a methyl or ethyl group, a cycloalkoxycarbonyloxyalkyl group, in which the cycloalkoxy part has 5 or 6 carbon atoms, and the alkyl part is a methyl or ethyl group, a [5-(phenyl-, methyl- or ethyl-)-2-oxo-1,3-dioxolen-4-yl]methyl group, or a phthalidyl group;

$R^8$ and $R^9$ are independently selected from the group consisting of:

hydrogen atoms, methyl groups, ethyl groups, and substituted methyl and ethyl groups which are substituted by at least one substituent selected from the group consisting of carboxy groups, methoxycarbonyl groups and ethoxycarbonyl groups;

or $R^8$ and $R^9$ together represent an unsubstituted alkylene group which has 4 or 5 carbon atoms or a substituted alkylene group which has 4 or 5 carbon atoms and which is substituted by at least one substituent selected from the group consisting of carboxy groups, methoxycarbonyl groups and ethoxycarbonyl groups;

$R^6$ represents a hydrogen atom, or it represents a methyl group, an ethyl group, a methoxy group, an ethoxy group, a fluorine atom or a chlorine atom on the 6-position of the benzene ring;

$R^7$ represents a carboxy group or a tetrazol-5-yl group at the 2- or 3- position of the benzene ring; and the benzene ring which bears the substituents represented by $R^6$ and $R^7$ is at the 4-position of the benzyl group to which it is attached.

Still more preferred classes of compounds of formula (I) (and salts and esters thereof) include:

$R^1$ represents an alkyl group having from 2 to 5 carbon atoms;

$R^2$ and $R^3$ are independently selected from the group consisting of hydrogen atoms and alkyl groups having from 1 to 4 carbon atoms;

$R^4$ represents a hydrogen atom, a methyl group, an ethyl group or an alkanoyl group having from 1 to 5 carbon atoms;

$R^5$ represents a group of formula —COOR$^{5a}$ or a group of formula —CONR$^8$R$^9$, in which:

$R^{5a}$ represents a hydrogen atom, a methyl, ethyl or benzyl group, an alkanoyloxymethyl group, in which the alkanoyl part has from 1 to 5 carbon atoms, a 1-(alkanoyloxy)ethyl group, in which the alkanoyl part has from 1 to 5 carbon atoms, an alkoxycarbonyloxymethyl group, in which the alkoxy part has from 1 to 4 carbon atoms, a 1-(alkoxycarbonyloxy)ethyl group, in which the alkoxy part has from 1 to 4 carbon atoms, a [5-(phenyl- or methyl-)-2-oxo-1,3-dioxolen-4yl]
    methyl group, or
a phthalidyl group;

$R^8$ and $R^9$ are independently selected from the group consisting of hydrogen atoms, methyl groups, ethyl groups, methoxycarbonylmethyl groups, ethoxycarbonylmethyl groups and carboxymethyl groups; or $R^8$ and $R^9$ together represent a tetramethylene, pentamethylene, 1-carboxytetramethylene or 1-carboxypentamethylene group;

$R^6$ represents a hydrogen atom, or it represents a methyl group, an methoxy group, a fluorine atom or a chlorine atom at the 6-position of the benzene ring;

$R^7$ represents a carboxy group or a tetrazol-5-yl group at the 2-position of the benzene ring; and the benzene ring which bears the substituents represented by $R^6$ and $R^7$ is at the 4-position of the benzyl group to which it is attached.

Even more preferred classes of compounds of formula (I) (including salts and esters thereof) include:
either $R^1$ represents an ethyl, propyl or butyl group;

$R^2$ and $R^3$ are independently selected from the group consisting of hydrogen atoms and methyl groups;

$R^4$ represents a hydrogen atom or a methyl group;

$R^5$ represents a group of formula —$COOR^{5a}$, in which $R^{5a}$ represents a hydrogen atom, a pivaloyloxymethyl group, an ethoxycarbonyloxymethyl group, a 1-(ethoxycarbonyloxy)ethyl group, an isopropoxycarbonyloxymethyl group, a 1-(isopropoxycarbonyloxy) ethyl group, a (5-methyl-2-oxo-1,3-dioxolen-4-yl)methyl group, or a phthalidyl group;

$R^6$ represents a hydrogen atom;

$R^7$ represents a carboxy group or a tetrazol-5-yl group at the 2-position of the benzene ring; and the benzene ring which bears the substituents represented by $R^6$ and $R^7$ is at the 4-position of the benzyl group to which it is attached.

or $R^1$ represents an ethyl, propyl or butyl group;

$R^2$ represents an isopropyl group or a t-butyl group;

$R^3$ represents a hydrogen atom;

$R^4$ represents a hydrogen atom or a methyl group;

$R^5$ represents a group of formula "$CONR^8R^9$, in which $R^8$ and $R^9$ are independently selected from the group consisting of hydrogen atoms, methyl groups, methoxycarbonylmethyl, ethoxycarbonylmethyl groups, and carboxymethyl groups;

$R^6$ represents a hydrogen atom;

$R^7$ represents a carboxy group or a tetrazol-5-yl group at the 2-position of the benzene ring; and the benzene ring which bears the substituents represented by $R^6$ and $R^7$ is at the 4-position of the benzyl group to which it is attached.

The most preferred classes of compounds of formula (I) (and salts an esters thereof) include:

$R^1$ represents an ethyl, propyl or butyl group;

$R^2$ and $R^3$ both represent methyl groups;

$R^4$ represents a hydrogen atom or a methyl group;

$R^5$ represents a group of formula —$COOR^{5a}$ in which $R^{5a}$ represents a hydrogen atom, a pivaloyloxymethyl group, an ethoxycarbonyloxymethyl group, a 1-(ethoxycarbonyloxy)ethyl group, an isopropoxycarbonyloxymethyl group, a 1-(isopropoxycarbonyloxy) ethyl group, a (5-methyl-2-oxo-1,3-dioxolen-4-yl)methyl group, or a phthalidyl group;

$R^6$ represents a hydrogen atom;

$R^7$ represents a carboxy group or a tetrazol-5-yl group at the 2-position of the benzene ring; and the benzene ring which bears the substituents represented by $R^6$ and $R^7$ is at the 4-position of the benzyl group to which it is attached.

The compounds of the present invention may contain one or more asymmetric carbon atoms in their molecules, and can thus form optical isomers. Although these are all represented herein by a single molecular formula, the present invention includes both the individual, isolated isomers and mixtures, including racemates thereof. Where stereospecific synthesis techniques are employed or optically active compounds are employed as starting materials, individual isomers may be prepared directly; on the other hand, if a mixture of isomers is prepared, the individual isomers may be obtained by conventional resolution techniques.

Where $R_p^1$, $R_p^3$ or $R_p^4$ represents an alkyl group having from 1 to 6 carbon atoms, this may be a straight or branched chain group having from 1 to 6 carbon atoms, and examples include the methyl, ethyl, propyl, isopropyl, butyl, isobutyl, sec-butyl, t-butyl, pentyl, isopentyl, neopentyl, t-pentyl, 2-methylbutyl, 1-ethylpropyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl, hexyl and isohexyl groups. Of these, we prefer those alkyl groups having from 1 to 4 carbon atoms, preferably the methyl, ethyl, propyl, isopropyl, butyl and isobutyl groups, more preferably the methyl and ethyl groups, and most preferably the methyl group.

Where $R_p^1$ represents a cycloalkyl group, this has from 3 to 6 ring carbon atoms, and examples include the cyclopropyl, cyclobutyl, cyclopentyl and cyclohexyl groups, preferably the cyclopropyl group.

Where $R^p$ represents an alkanoyl group having from 1 to 6 carbon atoms, this may be a straight or branched chain group having from 1 to 6 carbon atoms, and examples include the formyl, acetyl, propionyl, butyryl, isobutyryl, pivaloyl, valeryl, isovaleryl and hexanoyl groups, of which we prefer the acetyl and propionyl groups, most preferably the acetyl group.

Where $R_p^2$ represents an alkylene or alkylidene group, this is a bivalent saturated aliphatic hydrocarbon group having from 1 to 4 carbon atoms. Where the two "free" valencies are on the same carbon atom, the group is generally referred to as an "alkylidene" group; where they are on different carbon atoms, it is commonly referred to as an "alkylene" group. The term "alkylene" is also often used to embrace both types of group. Examples of such groups include the methylene, ethylene, trimethylene, propylene, ethylethylene, tetramethylene, ethylidene, propylidene, butylidene and isobutylidene groups, of which those groups having 1 or 2 carbon atoms are preferred, particularly the methylene group.

The compounds of formula $(I)_p$ of the present invention contain a carboxy group at the 5-position of the imidazole group and may contain another carboxy group if this is the meaning of $R_p^6$. These groups can of course, form esters. There is no particular restriction on the nature of the ester group, provided that, where the compound is intended for therapeutic purposes, it is pharmaceutically acceptable (i.e., it is not less active, or unacceptably less active than the free acid, and it is not more toxic, or unacceptably more toxic, than the free acid). Where, however, the compound is intended for non-therapeutic purposes, for example as an intermediate in the preparation of other, and possibly more active, compounds, even this restriction does not apply. In general, however, any protecting group commonly used in the field of synthetic organic chemistry or any ester group capable of conversion to a carboxy group under physiological conditions, to form a pro-drug, may be used.

The compounds of formula $(I)_p$ and their esters may collectively be represented by the formula $(Ia)_p$:

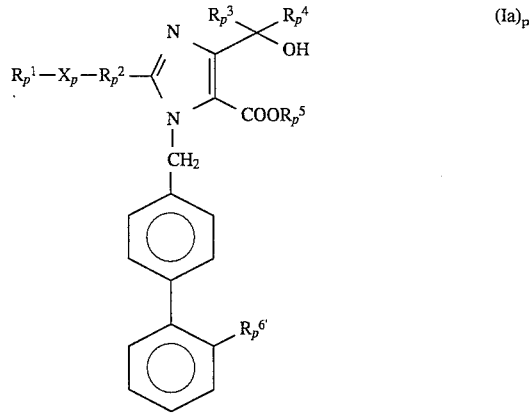

(in which: $R_p^1$, $R_p^2$, $R_p^3$, $R_p^4$ and $X_p$ are as defined above; $R_p^5$ represents a hydrogen atom or an ester group; and $R_p^{6'}$ represents a carboxy group, an esterified carboxy group or a tetrazol-5-yl group).

Examples of such ester groups which may be represented by $R_p^5$ or may be included in the esterified carboxy group represented by $R^{p6'}$ include:

- alkyl groups having from 1 to 6 carbon atoms, such as those exemplified above in relation to $R_p^1$ etc.;
- haloalkyl groups having from 1 to 6 carbon atoms, such as the fluoromethyl, trifluoromethyl, trichloromethyl, 2,2,2-trifluoroethyl, 2,2,2-trichloroethyl, 2-fluoroethyl, 2-chloroethyl, 2-iodoethyl, 3-chloro- propyl, 4-fluorobutyl and 6-iodohexyl groups, of which we prefer the 2,2,2-trichloroethyl and 2-chloroethyl groups;
- hydroxyalkyl groups having from 1 to 6 carbon atoms and having at least one, and preferably 1 or 2, hydroxy groups, such as the 2-hydroxyethyl, 2,3-dihydroxypropyl, 3-hydroxypropyl, 3,4-dihydroxybutyl and 4-hydroxybutyl groups, of which we prefer the 2-hydroxyethyl group;
- alkoxyalkyl and alkoxyalkoxyalkyl groups, in which the or each alkoxy part has from 1 to 6 carbon atoms and the alkyl part has from 1 to 6 carbon atom, for example the methoxymethyl, 2-methoxyethyl, 2-ethoxyethyl, 3-methoxypropyl, 4-methoxybutyl, propoxymethyl, butoxymethyl and 2-methoxyethoxymethyl groups, of which we prefer the methoxymethyl group;
- the phenacyl group;
- alkoxycarbonylalkyl groups, in which the alkoxy part has from 1 to 8 carbon atoms and the alkyl part has from 1 to 6 carbon atoms, such as the methoxycarbonylmethyl, ethoxycarbonylmethyl, propoxycarbonylmethyl, isopropoxycarbonylmethyl, butoxycarbonylmethyl, t-butoxycarbonylmethyl, pentyloxycarbonylmethyl, hexyloxycarbonylmethyl, heptyloxycarbonylmethyl, octyloxycarbonylmethyl, 2-methoxycarbonylethyl, 2-ethoxycarbonylethyl, 2-propoxycarbonylethyl, 2-isopropoxycarbonylethyl, 2-butoxycarbonylethyl, 2-t-butoxycarbonylethyl, 2-pentyloxycarbonylethyl, 2-hexyloxycarbonylethyl, 2-heptyloxycarbonylethyl, 2-octyloxycarbonylethyl, 3-methoxycarbonylpropyl, 3-ethoxycarbonylpropyl, 4-methoxycarbonylbutyl, 4-ethoxycarbonylbutyl, 5-methoxycarbonylpentyl, 5-ethoxycarbonylpentyl, 6-methoxycarbonylhexyl and 6-ethoxycarbonylhexyl groups, of which the methoxycarbonylmethyl group is preferred;
- cyanoalkyl groups, in which the alkyl part has from 1 to 6 carbon atoms, such as the cyanomethyl, 2-cyanoethyl, 3-cyanopropyl, 4-cyanobutyl, 5-cyanopentyl and 6-cyanohexyl groups, of which the cyanomethyl and 2-cyanoethyl groups are preferred;
- alkylthiomethyl groups, in which the alkyl part has from 1 to 6 carbon atoms, such as the methylthiomethyl, ethylthiomethyl, propylthiomethyl, butylthiomethyl, pentylthiomethyl and hexylthiomethyl groups, of which the methylthiomethyl and ethylthiomethyl groups are preferred;
- arylthiomethyl groups, in which the aryl part is a carbocyclic aromatic ring having from 6 to 10 ring carbon atoms and is unsubstituted or substituted, preferably unsubstituted, for example the phenylthiomethyl and naphthylthiomethyl groups; alkanesulfonylalkyl groups, in which each alkyl part (which may be the same as each other or different from each other) has from 1 to 6 carbon atoms and in which the alkane part is unsubstituted or substituted by at least one halogen atom, for example the 2-methanesulfonylethyl and 2-trifluoromethanesulfonylethyl groups;
- arylsulfonylalkyl groups, in which the aryl part has from 6 to 10 ring carbon atoms and the alkyl part has from 1 to 6 carbon atoms, and where the aryl part is unsubstituted or is substituted, preferably by at least one alkyl group, for example the 2-benzenesulfonylethyl, 2-(1-naphthalenesulfonyl)ethyl, 2-p-toluenesulfonylethyl, 3-benzenesulfonylpropyl, 3-(1-naphthalenesulfonyl)propyl, 3-p-toluenesulfonylpropyl, 6-benzenesulfonylhexyl, 6-(1-naphthalenesulfonyl) hexyl, 6-p-toluenesulfonylhexyl, benzenesulfonylmethyl and p-toluenesulfonylmethyl groups, and preferably the 2-benzenesulfonylethyl and 2-p-toluenesulfonylethyl groups;
- aralkyl groups, in which an alkyl group having from 1 to 6 carbon atoms is substituted by at least one (and preferably from 1 to 3) aryl groups which have from 6 to 10 ring carbon atoms and which are unsubstituted or are substituted, preferably unsubstituted; examples include the benzyl, diphenylmethyl, triphenylmethyl, 1-naphthylmethyl, 2-naphthylmethyl, phenethyl, 1-phenylethyl, 3-phenylpropyl, 2-phenylpropyl, 1-phenylpropyl, 4-phenylbutyl, 5-phenylpentyl and 6-phenylhexyl groups, of which the benzyl, diphenylmethyl and 1-naphthylmethyl groups are preferred and the benzyl group is most preferred;
- aryl groups having from 6 to 10, preferably 6 or 10, ring carbon atoms, which may be unsubstituted or substituted (preferably unsubstituted), for example the phenyl and naphthyl groups, of which the phenyl group is preferred;
- alkanoyloxyalkyl groups, in which the alkanoyl and alkyl parts both have from 1 to 6 carbon atoms, for example the formyloxymethyl, acetoxymethyl, propionyloxymethyl, butyryloxymethyl, pivaloyloxymethyl, valeryloxymethyl, isovaleryloxymethyl, hexanoyloxymethyl, 1-formyloxyethyl, 1-acetoxyethyl, 1-propionyloxyethyl, 1-butyryloxyethyl, 1-pivaloyloxyethyl, 1-valeryloxyethyl, 1-isovaleryloxyethyl, 1-hexanoyloxyethyl, 2-formyloxyethyl, 2-acetoxyethyl, 2-propionyloxyethyl, 2-butyryloxyethyl, 2-pivaloyloxyethyl, 2-valeryloxyethyl, 2-isovaleryloxyethyl, 2-hexanoyloxyethyl, 1- formyloxypropyl, 1-acetoxypropyl, 1-propionyloxylpropyl, 1-butyryloxypropyl, 1-pivaloyloxypropyl, 1-valeryoxypropyl, 1-isovaleryloxypropyl, 1-hexanonyloxypropyl, 1-acetoxybutyl, 1-propionyloxybutyl, 1-butyryloxybutyl, 1-pivaloyloxybutyl, 1-acetoxypentyl, 1-propionyloxypentyl, 1-butyryloxypentyl, 1-pivaloyloxypentyl and 1-pivaloyloxyhexyl groups, of which we prefer the formyloxymethyl, acetoxymethyl, propionyloxymethyl, butyryloxymethyl, pivaloyloxymethyl, 1-formyloxyethyl, 1-acetoxyethyl, 1-propionyloxyethyl, 1-butyryloxyethyl and 1-pivaloyloxyethyl groups and more prefer the acetoxymethyl, propionyloxymethyl, butyryloxymethyl, pivaloyloxymethyl, 1-acetoxyethyl, 1-propionyloxyethyl, 1-butyryloxyethyl and 1-pivaloyloxyethyl groups, the pivaloyloxymethyl and 1-pivaloyloxyethyl groups being most preferred;

cycloalkanecarbonyloxyalkyl groups, in which the cycloalkane part has 5 or 6 ring carbon atoms and the alkyl part has from 1 to 6 carbon atoms, for example the cyclopentanecarbonyloxymethyl, cyclohexanecarbonyloxymethyl, 1-cyclopentanecarbonyloxyethyl, 1-cyclohexanecarbonyloxyethyl, 1-cyclopentanecarbonyloxypropyl, 1-cyclohexanecarbonyloxypropyl, 1-cyclopentanecarbonyloxybutyl and 1-cyclohexanecarbonyloxybutyl groups, preferably the cyclopentanecarbonyloxymethyl, cyclohexanecarbonyloxymethyl, 1-cyclopentanecarbonyloxyethyl and 1-cyclohexanecarbonyloxyethyl groups;

alkoxycarbonyloxyalkyl groups, in which the alkoxy and alkyl parts both have from 1 to 6 carbon atoms, for example the methoxycarbonyloxymethyl, ethoxycarbonyloxymethyl, propoxycarbonyloxymethyl, isopropoxycarbonyloxymethyl, butoxycarbonyloxymethyl, isobutoxycarbonyloxymethyl, pentyloxycarbonyloxymethyl, hexyloxycarbonyloxymethyl, 1-methoxycarbonyloxyethyl, 1-ethoxycarbonyloxyethyl, 1-propoxycarbonyloxyethyl, 1-isopropoxycarbonyloxyethyl, 1-butoxycarbonyloxyethyl, 1-isobutoxycarbonyloxyethyl, 1-pentyloxycarbonyloxyethyl, 1-hexyloxycarbonyloxyethyl, 2-methoxycarbonyloxyethyl, 2-ethoxycarbonyloxyethyl, 2-propoxycarbonyloxyethyl, 2-isopropoxycarbonyloxyethyl, 2-butoxycarbonyloxyethyl, 2-isobutoxycarbonyloxyethyl, 2-pentyloxycarbonyloxyethyl, 2-hexyloxycarbonyloxyethyl, 1-methoxycarbonyloxypropyl, 1-ethoxycarbonyloxypropyl, 1-propoxycarbonyloxypropyl, 1-isopropoxycarbonyloxypropyl, 1-butoxycarbonyloxypropyl, 1-isobutoxycarbonyloxypropyl, 1-pentyloxycarbonyloxypropyl, 1-hexyloxycarbonyloxypropyl, 1-methoxycarbonyloxybutyl, 1-ethoxycarbonyloxybutyl, 1-propoxycarbonyloxybutyl, 1-isopropoxycarbonyloxybutyl, 1-butoxycarbonyloxybutyl, 1-isobutoxycarbonyloxybutyl, 1-methoxycarbonyloxypentyl, 1-ethoxycarbonyloxypentyl, 1-methoxycarbonyloxyhexyl and 1-ethoxycarbonyloxyhexyl groups, of which we prefer the methoxycarbonyloxymethyl, ethoxycarbonyloxymethyl, propoxycarbonyloxymethyl, isopropoxycarbonyloxymethyl, butoxycarbonyloxymethyl, isobutoxycarbonyloxymethyl, 1-methoxycarbonyloxyethyl, 1-ethoxycarbonyloxyethyl, 1-propoxycarbonyloxyethyl, 1-isopropoxycarbonyloxyethyl, 1-butoxycarbonyloxypropyl, 1-isobutoxycarbonyloxyethyl, 1-methoxycarbonyloxypropyl, 1-ethoxycarbonyloxypropyl, 1-propoxycarbonyloxypropyl, 1-isopropoxycarbonyloxypropyl, 1-butoxycarbonyloxypropyl, 1-isobutoxycarbonyloxypropyl, 1-methoxycarbonyloxybutyl, 1-ethoxycarbonyloxybutyl, 1-propoxycarbonyloxybutyl, 1-isopropoxycarbonyloxybutyl, 1-butoxycarbonyloxybutyl and 1-isobutoxycarbonyloxybutyl groups, and more prefer the methoxycarbonyloxymethyl, ethoxycarbonyloxymethyl, propoxycarbonyloxymethyl, isopropoxycarbonyloxymethyl, butoxycarbonyloxymethyl, isobutoxycarbonyloxymethyl, 1-methoxycarbonyloxyethyl, 1-ethoxycarbonyloxyethyl, 1-propoxycarbonyloxyethyl, 1-isopropoxycarbonyloxyethyl, 1-butoxycarbonyloxyethyl and 1-isobutoxycarbonyloxyethyl groups, the methoxycarbonyloxymethyl, ethoxycarbonyloxymethyl, isopropoxycarbonyloxymethyl, 1-methoxycarbonyloxyethyl, 1-ethoxycarbonyloxyethyl and 1-isopropoxycarbonyloxyethyl groups being most preferred;

cycloalkyloxycarbonyloxyalkyl groups, in which the cycloalkyl part has 5 or 6 ring carbon atoms and the alkyl part has from 1 to 6 carbon atoms, for example the cyclopentyloxycarbonyloxymethyl, cyclohexyloxycarbonyloxymethyl, 1-cyclopentyloxycarbonyloxyethyl, 1-cyclohexyloxycarbonyloxyethyl, 1-cyclopentyloxycarbonyloxypropyl, 1-cyclohexyloxycarbonyloxypropyl, 1-cyclopentyloxycarbonyloxybutyl and 1-cyclohexyloxycarbonyloxybutyl groups, of which we prefer the cyclopentyloxycarbonyloxymethyl, cyclohexyloxycarbonyloxymethyl, 1-cyclopentyloxycarbonyloxyethyl and 1-cyclohexyloxycarbonyloxyethyl groups;

[5-(aryl or alkyl)-2-oxo-1,3-dioxolen-4-yl]methyl groups, in which the aryl group is a carbocyclic aromatic group having from 6 to 10, preferably 6 or 10, ring carbon atoms (and is substituted, preferably with a halogen atom, an alkyl group or an alkoxy group, or unsubstituted, preferably unsubstituted), and the alkyl group has from 1 to 6 carbon atoms, for example the (5-phenyl-2-oxo-1,3-dioxolen-4-yl)methyl, [5-(4-methylphenyl)-2-oxo-1,3-dioxolen-4-yl]methyl, [5-(4-methoxyphenyl)-2-oxo-1,3-dioxolen-4-yl]methyl, [5-(4-fluorophenyl)-2-oxo-1,3-dioxolen-4-yl]methyl, [5-(4-chlorophenyl)-2-oxo-1,3-dioxolen-4-yl]methyl, (5-methyl-2-oxo-1,3-dioxolen-4-yl)methyl, (5-ethyl-2-oxo-1,3-dioxolen-4-yl)methyl, (5-propyl-2-oxo-1,3-dioxolen-4-yl)methyl, (5-isopropyl-2-oxo-1,3 -dioxolen-4-yl)methyl and (5-butyl-2-oxo-1,3-dioxolen-4-yl)methyl groups, of which we prefer the (5-phenyl-2-oxo-1,3-dioxolen-4-yl)methyl, (5-methyl-2-oxo-1,3-dioxolen-4-yl)methyl and (5-ethyl-2-oxo-1,3-dioxolen-4-yl)methyl groups, and more prefer the (5-methyl-2-oxo-1,3-dioxolen-4-yl)methyl group; and the phthalidyl group.

In the above groups for formula $(I)_p$, where an aryl group is referred to as substituted, examples of suitable substituents include:

alkyl groups having from 1 to 6 carbon atoms, such as those exemplified above in relation to $R_p^1$ etc.;

alkoxy groups having from 1 to 6 carbon atoms, such as the methoxy, ethoxy, propoxy, isopropoxy, t-butoxy, pentyloxy and hexyloxy groups;

halogen atoms, such as the fluorine, chlorine, bromine and iodine atoms;

preferably alkyl groups having from 1 to 4 carbon atoms, alkoxy groups having from 1 to 4 carbon atoms, and florine, chlorine or bromine atoms, most preferably a methyl, ethyl, methoxy or ethoxy group, or a fluorine or chlorine atom.

Examples of such preferred ester groups for formula $(I)_p$ include:

alkyl groups having from 1 to 4 carbon atoms;

phenyl groups which are unsubstituted or are substituted by at least one substituent selected from the group consisting of methyl groups, ethyl groups, methoxy groups, ethoxy groups, fluorine atoms and chlorine atoms;

naphthyl groups;

benzyl groups which are unsubstituted or are substituted by at least one substituent selected from the group consisting of methyl groups, ethyl groups, methoxy groups, ethoxy groups, fluorine atoms and chlorine atoms;

diphenylmethyl groups;

naphthylmethyl groups;

alkanoyloxyalkyl groups in which the alkanoyl part has from 1 to 5 carbon atoms and the alkyl part has from 1 to 4 carbon atoms;

cycloalkanecarbonyloxyalkyl groups in which the cycloalkane part has 5 or 6 ring carbon atoms and the alkyl part has from 1 to 4 carbon atoms;

alkoxycarbonyloxyalkyl groups in which the alkoxy and alkyl parts both have from 1 to 4 carbon atoms;

cycloalkyloxycarbonyloxyalkyl groups in which the cycloalkyl part has 5 or 6 ring carbon atoms and the alkyl part has from 1 to 4 carbon atoms;

[5-phenyl- or 5-alkyl-2-oxo-1,3-dioxolen-4-yl]methyl groups in which the alkyl part has from 1 to 4 carbon atoms; and the phthalidyl group.

Still more preferred ester groups for formula $(I)_p$ include:

alkyl groups having from 1 to 4 carbon atoms;

the benzyl group;

alkanoyloxyalkyl groups in which the alkanoyl part has from 1 to 5 carbon atoms and the alkyl part has 1 or 2 carbon atoms;

cycloalkanecarbonyloxyalkyl groups in which the cycloalkane part has 5 or 6 ring carbon atoms and the alkyl part has 1 or 2 carbon atoms;

alkoxycarbonyloxyalkyl groups in which the alkoxy part has from 1 to 4 carbon atoms and the alkyl part has 1 or 2 carbon atoms;

cycloalkyloxycarbonyloxyalkyl groups in which the cycloalkane part has 5 or 6 ring carbon atoms and the alkyl part has 1 or 2 carbon atoms;

[5-phenyl-, 5-methyl- or 5-ethyl-2-oxo-1,3-dioxolene-4-yl]methyl groups; and the phthalidyl group.

The most preferred ester groups for formula $(I)_p$ include the pivaloyloxymethyl, ethoxycarbonyloxymethyl, 1-(ethoxycarbonyloxy)ethyl, isopropoxycarbonyloxymethyl, 1-(isopropoxycarbonyloxy)ethyl, (5-methyl-2-oxo-1,3-dioxolen-4-yl)methyl and phthalidyl groups.

Preferred compounds of formula $(I)_p$ or $(Ia)_p$ (and salts and (where appropriate) esters thereof) include:

(A) $R_p^1$ represents a hydrogen atom, a methyl group, an ethyl group, a cyclopropyl group or an acetyl group, particularly a methyl or ethyl group;

(B) $R_p^2$ represents a single bond, a methylene group, an ethylene group or an ethylidene group;

(C) $R_p^3$ and $R_p^4$ are the same or different and each represents a hydrogen atom, a methyl group or an ethyl group, particularly a methyl or ethyl group;

(D) $R_p^5$ represents a hydrogen atom, an alkyl group having from 1 to 4 carbon atoms, a phenyl group, a phenyl group substituted by at least one substituent selected from the group consisting of methyl groups, ethyl groups, methoxy groups, ethoxy groups, fluorine atoms and chlorine atoms, a naphthyl group, a benzyl group, a benzyl group substituted by at least one substituent selected from the group consisting of methyl groups, ethyl groups, methoxy groups, ethoxy groups, fluorine atoms and chlorine atoms, a diphenylmethyl group, a naphthylmethyl group, an alkanoyloxyalkyl group in which the alkanoyl part has from 1 to 5 carbon atoms and the alkyl part has from 1 to 4 carbon atoms, a cycloalkanecarbonyloxyalkyl group in which the cycloalkane part has 5 or 6 carbon atoms and the alkyl part has from 1 to 4 carbon atoms, an alkoxycarbonyloxyalkyl group in which the alkoxy and alkyl parts each have from 1 to 4 carbon atoms, a cycloalkyloxycarbonyloxyalkyl group in which the cycloalkyl part has 5 or 6 carbon atoms and the alkyl part has from 1 to 4 carbon atoms, a (5-phenyl-2-oxo-1,3-dioxolen-4-yl)methyl group, a (5-alkyl-2-oxo-1,3-dioxolen-4-yl)methyl group, in which the alkyl part has from 1 to 4 carbon atoms, or a phthalidyl group;

(E) $R_p^{6'}$ represents a carboxy group or a tetrazol-5-yl group.

Of formulas $(I)_p$ and $(Ia)_p$, we particularly prefer those compounds of formula $(Ia)_p$ and salts and esters thereof in which $R_p^1$ is as defined in (A) above, $R_p^2$ is as defined in (B) above, $R_p^3$ and $R_p^4$ are as defined in (C) above, $R_p^5$ is as defined in (D) above and $R_p^{6'}$ is as defined in (E) above.

More preferred compounds of the present invention are those compounds of formula $(I)_p$ or $(Ia)_p$ and salts and (where appropriate) esters thereof, in which:

(F) the group of formula $R_p^1$—$X_p$—$R_p^2$— represents a methoxymethyl group, an ethoxymethyl group, a 1-methoxyethyl group, a 2-methoxyethyl group, a 2-ethoxyethyl group, a methylthiomethyl group, an ethylthiomethyl group, a 1-methylthioethyl group, 2-methylthioethyl, a 2-ethylthioethyl group, a methylthio group or an ethylthio group;

(G) $R_p^3$ and $R_p^4$ are the same or different and each represents a methyl or ethyl group;

(H) $R_p^5$ represents a hydrogen atom, an alkyl group having from 1 to 4 carbon atoms, a benzyl group, an alkanoyloxyalkyl group in which the alkanoyl part has from 1 to 5 carbon atoms and the alkyl part has 1 or 2 carbon atoms, a cycloalkanecarbonyloxyalkyl group in which the cycloalkane part has 5 or 6 carbon atoms and the alkyl part has 1 or 2 carbon atoms, an alkoxycarbonyloxyalkyl group in which the alkoxy part has from 1 to 4 carbon atoms and the alkyl part has 1 or 2 carbon atoms, a cycloalkyloxycarbonyloxyalkyl group in which the cycloalkyl part has 5 or 6 carbon atoms and the alkyl part has 1 or 2 carbon atoms, a (5-phenyl-, 5-methyl- or 5-ethyl- 2-oxo-1,3-dioxolen-4-yl)methyl group, or a phthalidyl group.

Particularly preferred compounds are of formula (Ia)$_p$ and salts and esters thereof in which $R_p^1$—$X_p$—$R_p^2$ is as defined in (F) above, $R_p^3$ and $R_p^4$ are as defined in (G) above, $R_p^5$ is as defined in (H) above and $R_p^{6'}$ is as defined in (E) above.

The most preferred compounds of formula (I)$_p$ or (Ia)$_p$ and salts and (where appropriate) esters thereof, are in which:

(I) the group of formula $R_p^1$—$X_p$—$R_p^2$— represents a methoxymethyl group, an ethoxymethyl group, a methylthiomethyl group, a methylthio group or an ethylthio group;

(J) $R_p^3$ and $R_p^4$ both represent methyl groups; and (K) $R_p^5$ represents a hydrogen atom, a pivaloyloxymethyl group, an ethoxycarbonyloxymethyl group, a 1-(ethoxycarbonyloxy)ethyl group, an isopropoxycarbonyloxymethyl group, a 1-(isopropoxycarbonyloxy)ethyl group, a (5-methyl-2-oxo-1,3-dioxolen-4yl)methyl group or a phthalidyl group.

Particularly preferred compounds of formula (Ia)$_p$ and salts and esters thereof are in which $R_p^1$—$X_p$—$R_p^2$ is as defined in (I) above, $R_p^3$ and $R_p^4$ are as defined in (J) above, $R_p^5$ is as defined in (K) above and $R_p^{6'}$ is as defined in (E) above.

Specific examples of individual compounds of the present invention are shown in the following formulae (I-1), (I-2), (I-3), (I-4), (I-5) and (I-6):

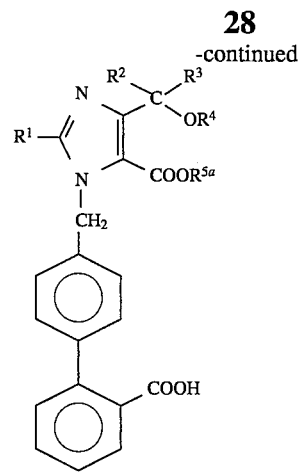
(I-1)

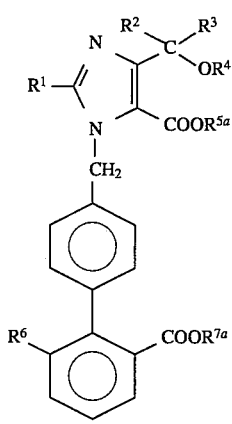
(I-2)

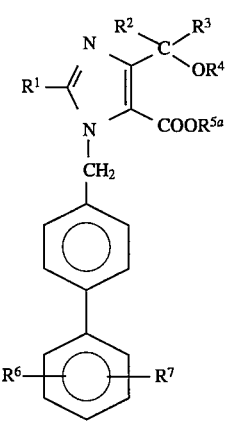

—continued

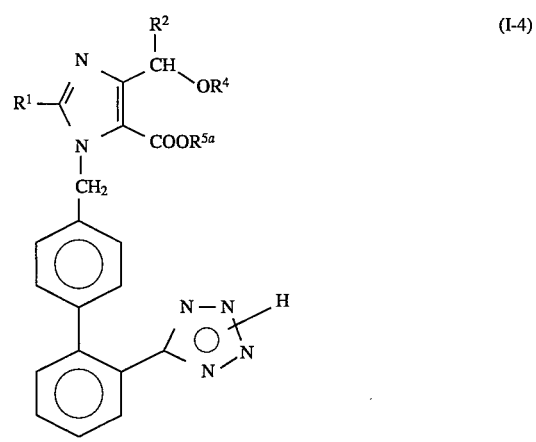
(I-3)

(I-4)

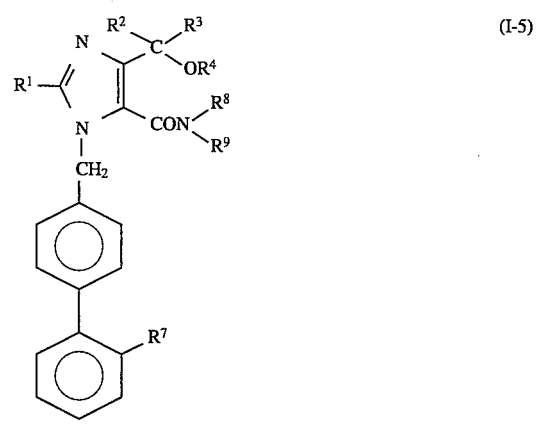
(I-5)

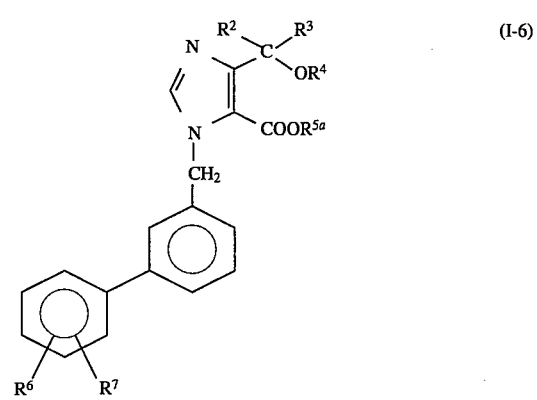
(I-6)

In these formulae, the meanings of the various substituent groups are as given in the following Tables 1 to 6, in which Table 1 relates to formula (I-1), Table 2 relates to formula (I-2), Table 3 relates to formula (I-3), and so on. In the Tables, the following abbreviations are used:

| | |
|---|---|
| Ac | acetyl |
| Boz | benzoyl |
| Bu | butyl |
| iBu | isobutyl |
| tBu | t-butyl |
| Buc | butoxycarbonyl |
| iBuc | isobutoxycarbonyl |
| Bz | benzyl |
| Et | ethyl |
| Etc | ethoxycarbonyl |
| Fo | formyl |
| Fu | 2-furyl |
| cHx | cyclohexyl |
| Im | 4-imidazolyl |
| Me | methyl |
| Mec | methoxycarbonyl |
| Mod | (5-methyl-2-oxo-1,3-dioxolen-4-yl)methyl |
| Ph | phenyl |
| Phth | phthalidyl |
| Piv | pivaloyl |
| Pn | pentyl |
| cPn | cyclopentyl |
| iPn | isopentyl |
| Pr | propyl |
| iPr | isopropyl |
| iPrc | isopropoxycarbonyl |
| Prn | propionyl |
| Tz | tetrazol-5-yl |
| Th | 2-thienyl |

TABLE 1

| Cpd. No. | $R^1$ | $R^2$ | $R^3$ | $R^4$ | $R^{5a}$ | $R^6$ | $R^{7a}$ |
|---|---|---|---|---|---|---|---|
| 1-1 | Pr | H | H | H | H | H | H |
| 1-2 | Bu | H | H | H | H | H | H |
| 1-3 | —CH=CH—Et | N | B | H | H | H | H |
| 1-4 | Pn | H | H | H | H | H | H |
| 1-5 | Bu | H | H | H | Me | H | H |
| 1-6 | Bu | H | H | H | Et | H | H |
| 1-7 | Bu | H | H | H | Bu | H | H |
| 1-8 | Bu | H | H | H | Bz | H | H |
| 1-9 | Bu | H | H | Me | H | H | H |
| 1-10 | Bu | H | H | Et | H | H | H |
| 1-11 | Bu | H | H | Fo | H | H | H |
| 1-12 | Bu | H | H | Ac | H | H | H |
| 1-13 | Bu | H | H | Boz | H | H | H |
| 1-14 | Bu | H | H | Me | Et | H | H |
| 1-15 | Bu | H | H | Me | PivOCH$_2$— | H | H |
| 1-16 | Bu | H | H | H | H | Cl | H |
| 1-17 | Bu | H | H | H | Et | Cl | H |
| 1-18 | Bu | H | H | H | H | OMe | H |
| 1-19 | Bu | H | H | H | Et | OMe | H |
| 1-20 | Bu | H | H | H | H | OEt | H |
| 1-21 | Bu | H | H | H | Et | OEt | H |
| 1-22 | Bu | H | H | H | Mod | H | H |
| 1-23 | Bu | H | H | H | EtcOCH$_2$— | H | H |
| 1-24 | Bu | H | H | H | 1-(EtcO)Et | H | H |
| 1-25 | Bu | Me | H | H | H | H | H |
| 1-26 | Bu | Me | H | H | Et | H | H |
| 1-27 | Bu | Me | H | H | PivOCH$_2$— | H | H |
| 1-28 | Bu | Me | H | H | Mod | H | H |
| 1-29 | Bu | Me | H | Ac | H | H | H |
| 1-30 | Bu | Me | H | Ac | Et | H | H |
| 1-31 | Bu | Me | Me | H | H | H | H |
| 1-32 | Bu | Me | Me | H | Et | H | H |
| 1-33 | Bu | Me | Me | H | Bu | H | H |
| 1-34 | Bu | Me | Me | H | Me | H | H |
| 1-35 | Bu | Me | Me | H | PivOCH$_2$— | H | H |
| 1-36 | Bu | Me | Me | H | Mod | H | H |
| 1-37 | Bu | Me | Me | Me | H | H | H |
| 1-38 | Bu | Me | Me | Me | Et | H | H |
| 1-39 | Bu | Me | Me | Fo | H | H | H |
| 1-40 | Bu | Me | Me | Fo | Et | H | H |
| 1-41 | Bu | Me | Me | Ac | H | H | H |
| 1-42 | Bu | Me | Me | Ac | Et | H | H |
| 1-43 | Bu | Me | Me | Boz | H | H | H |
| 1-44 | Bu | Me | Me | Boz | Et | H | H |
| 1-45 | Bu | Me | Me | H | H | Cl | H |
| 1-46 | Bu | Me | Me | H | Et | Cl | H |
| 1-47 | Bu | Me | Me | H | H | OMe | H |
| 1-48 | Bu | Me | Me | H | Et | OMe | H |
| 1-49 | Pr | Me | Me | H | H | H | H |
| 1-50 | Pr | Me | Me | H | Et | H | H |
| 1-51 | Pr | Me | Me | Ac | Et | H | H |
| 1-52 | Pr | Me | Me | H | H | OMe | H |
| 1-53 | Pr | Me | Me | H | Et | OMe | H |
| 1-54 | Pn | Me | Me | H | H | H | H |
| 1-55 | Pn | Me | Me | H | Et | H | H |

TABLE 1-continued

| Cpd. No. | R¹ | R² | R³ | R⁴ | R⁵ᵃ | R⁶ | R⁷ᵃ |
|---|---|---|---|---|---|---|---|
| 1-56 | Et | Me | H | H | H | H | H |
| 1-57 | Et | Me | H | H | Et | H | H |
| 1-58 | Et | Me | H | H | PivOCH₂— | H | H |
| 1-59 | Et | Me | H | H | Mod | H | H |
| 1-60 | Et | Me | H | H | EtcOCH₂— | H | H |
| 1-61 | Et | Me | H | H | 1-(EtcO)Et | H | H |
| 1-62 | Bu | Et | H | H | H | H | H |
| 1-63 | Bu | Et | H | H | Et | H | H |
| 1-64 | Bu | Et | H | H | H | Cl | H |
| 1-65 | Bu | Et | H | H | Et | Cl | H |
| 1-66 | Bu | Et | H | H | H | OMe | H |
| 1-67 | Bu | Et | H | H | Et | OMe | H |
| 1-68 | Bu | iPr | H | H | H | H | H |
| 1-69 | Bu | iPr | H | H | Et | H | H |
| 1-70 | Bu | iPr | H | H | H | Cl | H |
| 1-71 | Bu | iPr | H | H | Et | Cl | H |
| 1-72 | Bu | iPr | H | H | H | OMe | H |
| 1-73 | Bu | iPr | H | H | Et | OMe | H |
| 1-74 | Bu | tBu | H | H | H | H | |
| 1-75 | Bu | tBu | H | H | Et | H | H |
| 1-76 | Bu | tBu | H | H | H | Cl | H |
| 1-77 | Bu | tBu | H | H | Et | Cl | H |
| 1-78 | Bu | tBu | H | H | H | OMe | H |
| 1-79 | Bu | tBu | H | H | Et | OMe | H |
| 1-80 | Bu | Ph | H | H | H | H | H |
| 1-81 | Bu | Ph | H | H | Et | H | H |
| 1-82 | Bu | Et | Me | H | H | H | H |
| 1-83 | Bu | Et | Me | H | Et | H | H |
| 1-84 | Bu | Et | Et | H | H | H | H |
| 1-85 | Bu | Et | Et | H | Et | H | H |
| 1-86 | Bu | Et | Et | H | H | Cl | H |
| 1-87 | Bu | Et | Et | H | Et | Cl | H |
| 1-88 | Bu | Et | Et | N | H | OMe | H |
| 1-89 | Bu | Et | Et | H | Et | OMe | H |
| 1-90 | Bu | Pr | H | H | H | H | H |
| 1-91 | Bu | Pr | H | H | Et | H | H |
| 1-92 | Pr | Pr | H | H | H | H | H |
| 1-93 | Pr | Pr | H | H | Et | H | H |
| 1-94 | Bu | H | H | H | Me | H | tBu |
| 1-95 | Bu | H | H | H | Et | H | tBu |
| 1-96 | Bu | H | H | H | H | H | tBu |
| 1-97 | Bu | H | H | H | PivOCH₂— | H | tBu |
| 1-98 | Bu | H | H | H | PivOCH₂— | H | H |
| 1-99 | Bu | H | H | Me | Me | H | tBu |
| 1-100 | Pr | H | H | H | Et | H | H |
| 1-101 | Pr | H | H | H | Bu | H | H |
| 1-102 | Pr | H | H | H | PivOCH₂— | H | H |
| 1-103 | Pr | H | H | H | Mod | H | H |
| 1-104 | Pr | H | H | H | H | Cl | H |
| 1-105 | Pr | H | H | H | Et | Cl | H |
| 1-106 | Pr | H | H | H | H | OMe | H |
| 1-107 | Pr | H | H | H | Et | OMe | H |
| 1-108 | Pr | Me | Me | H | H | Cl | H |
| 1-109 | Pr | Me | Me | H | Et | Cl | H |
| 1-110 | Pr | Me | Me | H | H | H | Et |
| 1-111 | Pr | Me | Me | H | H | H | Bu |
| 1-112 | Pr | Me | Me | H | H | H | PivOCH₂— |
| 1-113 | Bu | Me | Me | H | H | H | Et |
| 1-114 | Bu | Me | Me | H | H | H | Bu |
| 1-115 | Bu | Me | Me | H | H | H | PivOCH₂— |
| 1-116 | Bu | Me | Me | Mec | H | H | H |
| 1-117 | Bu | Me | Me | Etc | H | H | H |
| 1-118 | Bu | Me | Me | H | Et | H | tBu |
| 1-119 | Pr | Me | Me | H | Et | H | tBu |
| 1-120 | Bu | Me | Me | H | H | F | H |
| 1-121 | Bu | H | H | Me | Me | H | H |
| 1-122 | Bu | Me | Me | H | H | Cl | tBu |
| 1-123 | Bu | Me | Me | H | Et | Cl | tBu |
| 1-124 | Bu | Me | Me | H | H | OMe | tBu |
| 1-125 | Bu | Me | Me | H | Et | OMe | tBu |
| 1-126 | Pr | Me | Me | H | H | Cl | tBu |
| 1-127 | Pr | Me | Me | H | Et | Cl | tBu |
| 1-128 | Pr | Me | Me | H | H | OMe | tBu |
| 1-129 | Pr | Me | Me | H | Et | OMe | tBu |
| 1-130 | Et | Me | Me | H | Et | H | tBu |
| 1-131 | Et | Me | Me | H | Et | H | H |

TABLE 1-continued

| Cpd. No. | R¹ | R² | R³ | R⁴ | R⁵ᵃ | R⁶ | R⁷ᵃ |
|---|---|---|---|---|---|---|---|
| 1-132 | Et | Me | Me | H | H | H | H |
| 1-133 | Pr | Me | H | H | PivOCH₂— | H | H |
| 1-134 | Pr | Me | H | H | Mod | H | H |
| 1-135 | Pr | Me | H | H | EtcOCH₂— | H | H |
| 1-136 | Pr | Me | H | H | 1-(EtcO)Et | H | H |
| 1-137 | Pr | Me | H | H | Phth | H | H |
| 1-138 | Et | H | H | H | H | H | H |
| 1-139 | Et | H | H | H | PivOCH₂— | H | H |
| 1-140 | Et | H | H | H | Mod | H | H |
| 1-141 | Et | s | H | H | EtcOCH₂— | H | H |
| 1-142 | Et | H | H | H | 1-(EtcO)Et | H | H |
| 1-143 | Et | H | H | H | Phth | H | H |

TABLE 2

| Cpd. No. | R¹ | R² | R³ | R⁴ | R⁵ᵃ | R⁶ | R⁷ |
|---|---|---|---|---|---|---|---|
| 2-1 | Pr | Me | Me | H | H | H | 2-Tz |
| 2-2 | Bu | Me | Me | H | H | H | 2-Tz |
| 2-3 | Pn | Me | Me | H | H | H | 2-Tz |
| 2-4 | —CH=CH—Et | Me | Me | H | H | H | 2-Tz |
| 2-5 | Pr | Me | Me | Me | H | H | 2-Tz |
| 2-6 | Bu | Me | Me | Me | H | H | 2-Tz |
| 2-7 | Pr | Me | Me | H | Et | H | 2-Tz |
| 2-8 | Bu | Me | Me | H | Et | H | 2-Tz |
| 2-9 | Pr | Me | Me | H | Me | H | 2-Tz |
| 2-10 | Bu | Me | Me | H | Me | H | 2-Tz |
| 2-11 | Pr | Me | Me | Me | Me | H | 2-Tz |
| 2-12 | Bu | Me | Me | Me | Me | H | 2-Tz |
| 2-13 | Pr | Me | Me | Me | Et | H | 2-Tz |
| 2-14 | Bu | Me | Me | Me | Et | H | 2-Tz |
| 2-15 | Pr | Me | Me | H | PivOCH₂— | H | 2-Tz |
| 2-16 | Bu | Me | Me | H | PivOCH₂— | H | 2-Tz |
| 2-17 | Pr | Me | Me | H | Mod | H | 2-Tz |
| 2-18 | Bu | Me | Me | H | Mod | H | 2-Tz |
| 2-19 | Pr | Me | M.e | H | EtcOCH₂— | H | 2-Tz |
| 2-20 | Bu | Me | Me | H | EtcOCH₂— | H | 2-Tz |
| 2-21 | Pr | Me | Me | H | iPrcOCH₂— | H | 2-Tz |
| 2-22 | Bu | Me | Me | H | iPrcOCH₂— | H | 2-Tz |
| 2-23 | Pr | Me | Me | H | 1-(EtcO)Et | H | 2-Tz |
| 2-24 | Bu | Me | Me | H | 1-(EtcO)Et | H | 2-Tz |
| 2-25 | Pr | Me | Me | H | 1-(iPrcO)Et | H | 2-Tz |
| 2-26 | Bu | Me | Me | H | 1-(iPrcO)Et | H | 2-Tz |
| 2-27 | Pr | Me | Me | Me | EtcOCH₂— | H | 2-Tz |
| 2-28 | Bu | Me | Me | Me | EtcOCH₂— | H | 2-Tz |
| 2-29 | Pr | Me | Me | Me | iPrcOCH₂— | H | 2-Tz |
| 2-30 | Bu | Me | Me | Me | iPrcOCH₂— | H | 2-Tz |
| 2-31 | Pr | Me | Me | Me | PivOCH₂— | H | 2-Tz |
| 2-32 | Bu | Me | Me | Me | PivOCH₂— | H | 2-Tz |
| 2-33 | Pr | Me | Me | H | H | 6-Cl | 2-Tz |
| 2-34 | Bu | Me | Me | H | H | 6-Cl | 2-Tz |
| 2-35 | Pr | Me | Me | H | H | 6-OMe | 2-Tz |
| 2-36 | Bu | Me | Me | H | H | 6-OMe | 2-Tz |
| 2-37 | Pr | Me | Et | H | H | H | 2-Tz |
| 2-38 | Bu | Me | Et | H | H | H | 2-Tz |
| 2-39 | Pr | Et | Et | H | H | H | 2-Tz |
| 2-40 | Bu | Et | Et | H | H | H | 2-Tz |
| 2-41 | Pr | Me | Me | H | Bz | H | 2-Tz |
| 2-42 | Pr | Me | Me | H | Bu | H | 2-Tz |
| 2-43 | Bu | Me | Me | H | Bz | H | 2-Tz |
| 2-44 | Bu | Me | Me | H | Bu | H | 2-Tz |
| 2-45 | Pr | Et | Et | H | Et | H | 2-Tz |
| 2-46 | Pr | Me | Me | H | H | H | 3-Tz |
| 2-47 | Pr | Me | Me | H | H | H | 4-Tz |
| 2-48 | Pr | Me | Me | H | (4-OAc)-(3-OMe)Bz | H | 2-Tz |
| 2-49 | Pr | Me | Me | H | Fo | H | 2-Tz |
| 2-50 | Pr | Me | Me | H | Ac | H | 2-Tz |
| 2-51 | Pr | Me | Me | H | H | 6-Cl | 3-Tz |
| 2-52 | Bu | Me | Me | H | H | 6-Cl | 3-Tz |
| 2-53 | Pr | Me | Me | H | H | 6-OMe | 3-Tz |
| 2-54 | Bu | Me | Me | H | H | 6-OMe | 3-Tz |
| 2-55 | Pr | Me | Et | H | H | H | 3-Tz |

TABLE 2-continued

| Cpd. No. | R¹ | R² | R³ | R⁴ | R⁵ᵃ | R⁶ | R⁷ |
|---|---|---|---|---|---|---|---|
| 2-56 | Bu |  | Me | Et | H | H | H | 3-Tz |
| 2-57 | Pr |  | Et | Et | H | H | H | 3-Tz |
| 2-58 | Bu |  | Et | Et | H | H | H | 3-Tz |
| 2-59 | Pr |  | Me | Me | Me | Et | H | 3-Tz |
| 2-60 | Pr |  | Me | Me | Me | H | H | 3-Tz |
| 2-61 | Bu |  | Me | Me | Me | Et | H | 3-Tz |
| 2-62 | Bu |  | Me | Me | Me | H | H | 3-Tz |
| 2-63 | Pr |  | Et | Et | H | Et | H | 3-Tz |
| 2-64 | Pr |  | Me | Et | Me | H | H | 2-Tz |
| 2-65 | Pr |  | Me | Me | H | Phth | H | 2-Tz |
| 2-66 | Pr |  | Me | Me | Me | Mod | H | 2-Tz |
| 2-67 | Bu |  | Me | Me | Me | Mod | H | 2-Tz |
| 2-68 | Et |  | Me | Me | H | H | H | 2-Tz |
| 2-69 | Et |  | Me | Me | H | PivOCH₂— | H | 2-Tz |
| 2-70 | Et |  | Me | Me | H | EtcOCH₂— | H | 2-Tz |
| 2-71 | Et |  | Me | Me | H | iPrcOCH₂— | H | 2-Tz |
| 2-72 | Et |  | Me | Me | H | Et | H | 2-Tz |
| 2-73 | Et |  | Me | Me | H | Mod | H | 2-Tz |
| 2-74 | Et |  | Me | Me | H | Phth | H | 2-Tz |
| 2-75 | Et |  | Me | Me | Me | H | H | 2-Tz |
| 2-76 | Et |  | Me | Me | Me | PivOCH₂— | H | 2-Tz |
| 2-77 | Et |  | Me | Me | Me | Mod | H | 2-Tz |

TABLE 3

| Cpd. No. | R¹ | R² | R³ | R⁴ | R⁵ᵃ |
|---|---|---|---|---|---|
| 3-1 | Pr | Me | Me | H | PivOCH₂— |
| 3-2 | Pr | Me | Me | H | AcOCH₂— |
| 3-3 | Pr | Me | Me | H | 1-(PivO)Et |
| 3-4 | Pr | Me | Me | H | 1-(AcO)Et |
| 3-5 | Pr | Me | Me | H | cPnCO.OCH₂— |
| 3-6 | Pr | Me | Me | H | cHxCO.OCH₂— |
| 3-7 | Pr | Me | Me | H | MecOCH₂— |
| 3-8 | Pr | Me | Me | H | 1-(MecO)Et |
| 3-9 | Pr | Me | Me | H | EtcOCH₂— |
| 3-10 | Pr | Me | Me | H | 1-(EtcO)Et |
| 3-11 | Pr | Me | Me | H | 1-(EtcO)-2-MePr |
| 3-12 | Pr | Me | Me | H | 1-(EtcO)Pr |
| 3-13 | Pr | Me | Me | H | iPrcOCH₂— |
| 3-14 | Pr | Me | Me | H | 1-(iPrcO)Et |
| 3-15 | Pr | Me | Me | H | 1-(iPrcO)-2-MePr |
| 3-16 | Pr | Me | Me | H | 1-(iPrcO)Pr |
| 3-17 | Pr | Me | Me | H | cPnO.CO.OCH₂— |
| 3-18 | pr | Me | Me | H | cHxO.CO.OCH₂— |
| 3-19 | Pr | Me | Me | H | BucOCH₂— |
| 3-20 | Pr | Me | Me | H | 1-(BucO)Et |
| 3-21 | Pr | Me | Me | H | iBucOCH₂— |
| 3-22 | Pr | Me | Me | H | 1-(iBucO)Et |
| 3-23 | Pr | Me | Me | H | 1-(iPnO.CO.O)Et |
| 3-24 | Pr | Me | Me | H | 1-(cHxO.CO.O)Et |
| 3-25 | Pr | Me | Me | H | Mod |
| 3-26 | Pr | Me | Me | H | Phth |
| 3-27 | Bu | Et | Et | H | PivOCH₂— |
| 3-28 | Bu | Me | Me | H | AcOCH₂— |
| 3-29 | Bu | Me | Me | H | 1-(PivO)Et |
| 3-30 | Bu | Me | Me | H | 1-(AcO)Et |
| 3-31 | Bu | Me | Me | H | cPnCO.OCH— |
| 3-32 | Eu | Me | Me | H | cHxCO.OCH₂— |
| 3-33 | Bu | Me | Me | H | MecOCH₂— |
| 3-34 | Bu | Me | Me | H | 1-(MecO)Et |
| 3-35 | Bu | Me | Me | H | EtcOCH₂— |
| 3-36 | Bu | Me | Me | H | 1-(EtcO)Et |
| 3-37 | Bu | Me | Me | H | 1-(EtcO)-2-MePr |
| 3-38 | Bu | Me | Me | H | 1-(EtcO)Pr |
| 3-39 | Bu | Me | Me | H | iPrcOCH₂— |
| 3-40 | Bu | Me | Me | H | 1-(iPrcO)Et |
| 3-41 | Bu | Me | Me | H | 1-(iPrcO)-2-MePr |
| 3-42 | Bu | Me | Me | H | 1-(iPrcO)Pr |
| 3-43 | Bu | Me | Me | H | cPnO.CO.OCH₂— |
| 3-44 | Bu | Me | Me | H | cHxO.CO.OCH₂— |
| 3-45 | Bu | Me | Me | H | BucOCH₂— |
| 3-46 | Bu | Me | Me | H | 1-(BucO)Et |
| 3-47 | Bu | Me | Me | H | iBucOCH₂— |
| 3-48 | Bu | Me | Me | H | 1-(iBucO)Et |
| 3-49 | Bu | Me | Me | H | 1-(cPnO.CO.O)Et |
| 3-50 | Bu | Me | Me | H | 1-(cHxO.CO.O)Et |
| 3-51 | Bu | Et | Et | H | Mod |
| 3-52 | Bu | Me | Me | H | Phth |
| 3-53 | Pr | Me | Me | Me | PivOCH₂— |
| 3-54 | Pr | Me | Me | Me | AcOCH₂— |
| 3-55 | Pr | Me | Me | Me | 1-(PivO)Et |
| 3-56 | Pr | Me | Me | Me | 1-(AcO)Et |
| 3-57 | Pr | Me | Me | Me | cPnCO.OCH₂— |
| 3-58 | Pr | Me | Me | Me | cHxCO.OCH₂— |
| 3-59 | Pr | Me | Me | Me | MecOCH₂— |
| 3-60 | Pr | Me | Me | Me | 1-(MecO)Et |
| 3-61 | Pr | Me | Me | Me | EtcOCH₂— |
| 3-62 | Pr | Me | Me | Me | 1-(EtcO)Et |
| 3-63 | Pr | Me | Me | Me | 1-(EtcO)-2-MePr |
| 3-64 | Pr | Me | Me | Me | 1-(EtcO)Pr |
| 3-65 | Pr | Me | Me | Me | iPrcOCH₂— |
| 3-66 | Pr | Me | Me | Me | 1-(iPrcO)Et |
| 3-67 | Pr | Me | Me | Me | 1-(iPrcO)-2-MePr |
| 3-68 | Pr | Me | Me | Me | 1-(iPrcO)Pr |
| 3-69 | Pr | Me | Me | Me | cPnO.CO.OCH₂— |
| 3-70 | Pr | Me | Me | Me | cHxO.CO.OCH₂— |
| 3-71 | Pr | Me | Me | Me | BucOCH₂— |
| 3-72 | Pr | Me | Me | Me | 1-(BucO)Et |
| 3-73 | Pr | Me | Me | Me | iBucOCH₂— |
| 3-74 | Pr | Me | Me | Me | 1-(iBucO)Et |
| 3-75 | Pr | Me | Me | Me | 1-(cPnO.CO.O)Et |
| 3-76 | Pr | Me | Me | Me | 1-(cHxO.CO.O)Et |
| 3-77 | Pr | Me | Me | Me | Mod |
| 3-78 | Pr | Me | Me | Me | Phth |
| 3-79 | Bu | Me | Me | Me | PivOCH₂— |
| 3-80 | Bu | Me | Me | Me | AcOCH₂— |
| 3-81 | Bu | Me | Me | Me | 1-(PivO)Et |
| 3-82 | Bu | Me | Me | Me | 1-(AcO)Et |
| 3-83 | Bu | Me | Me | Me | cPnCO.OCH₂— |
| 3-84 | Bu | Me | Me | Me | cHxCO.OCH₂— |
| 3-85 | Bu | Me | Me | Me | MecOCH₂— |
| 3-86 | Bu | Me | Me | Me | 1-(MecO)Et |
| 3-87 | Bu | Me | Me | Me | EtcOCH₂— |
| 3-88 | Bu | Me | Me | Me | 1-(EtCO)Et |
| 3-89 | Bu | Me | Me | Me | 1-(EtcO)-2-MePr |
| 3-90 | Bu | Me | Me | Me | 1-(EtcO)Pr |

TABLE 3-continued

| Cpd. No. | R¹ | R² | R³ | R⁴ | R⁵ᵃ |
|---|---|---|---|---|---|
| 3-91 | Bu | Me | Me | Me | iPrcOCH₂— |
| 3-92 | Bu | Me | Me | Me | 1-(iPrcO)Et |
| 3-93 | Bu | Me | Me | Me | 1-(iPrcO)-2-MePr |
| 3-94 | Bu | Me | Me | Me | 1-(iPrcO)Pr |
| 3-95 | Bu | Me | Me | Me | cPnO.CO.OCH₂— |
| 3-96 | Bu | Me | Me | Me | cHxO.CO.OCH₂— |
| 3-97 | Bu | Me | He | Me | BucOCH₂— |
| 3-98 | Bu | Me | Me | Me | 1-(BucO)Et |
| 3-99 | Bu | Me | Me | Me | iBucOCH— |
| 3-100 | Bu | Me | Me | Me | 1-(iBucO)Et |
| 3-101 | Bu | Me | Me | Me | 1-(cPnO.CO.O)Et |
| 3-102 | Bu | Me | Me | Me | 1-(cHxO.CO.O)Et |
| 3-103 | Bu | Me | Me | Me | Mod |
| 3-104 | Bu | Me | Me | Me | Phth |
| 3-105 | Et | Me | Me | H | PivOCH₂— |
| 3-106 | Et | Me | Me | H | AcOCH₂— |
| 3-107 | Et | Me | Me | H | EtcOCH₂— |
| 3-108 | Et | Me | Me | H | 1-(EtcO)Et |
| 3-109 | Et | Me | Me | H | iPrcOCH₂— |
| 3-110 | Et | Me | Me | H | 1-(iPrcO)Et |
| 3-111 | Et | Me | Me | H | Mod |
| 3-112 | Et | Me | Me | H | Phth |
| 3-113 | Pn | Me | Me | H | PivOCH₂— |
| 3-114 | Pn | Me | Me | H | AcOCH₂— |
| 3-115 | Pn | Me | Me | H | EtcOCH₂— |
| 3-116 | Pn | Me | Me | H | 1-(EtcO)Et |
| 3-117 | Pn | Me | Me | H | iPrcOCH₂— |
| 3-118 | Pn | Me | Me | H | 1-(iPrcO)Et |
| 3-119 | Pn | Me | Me | H | Mod |
| 3-120 | Pn | Me | Me | H | Phth |
| 3-121 | Pr | Me | Et | H | PivOCH₂— |
| 3-122 | Pr | Me | Et | H | AcOCH₂— |
| 3-123 | Pr | Me | Et | H | EtcOCH₂— |
| 3-124 | Pr | Me | Et | H | 1-(EtcO)Et |
| 3-125 | Pr | Me | Et | H | iPrcOCH₂— |
| 3-126 | Pr | Me | Et | H | 1-(iPrcO)Et |
| 3-127 | Pr | Me | Et | H | Mod |
| 3-128 | Pr | Me | Et | H | Phth |
| 3-129 | Pr | Et | Et | H | PivOCH₂— |
| 3-130 | Pr | Et | Et | H | AcOCH₂— |
| 3-131 | Pr | Et | Et | H | EtcOCH₂— |
| 3-132 | Pr | Et | Et | H | 1-(EtcO)Et |
| 3-133 | Pr | Et | Et | H | iPrcOCH₂— |
| 3-134 | Pr | Et | Et | H | 1-(iPrcO)Et |
| 3-135 | Pr | Et | Et | H | Mod |
| 3-136 | Pr | Et | Et | H | Phth |

TABLE 4

| Cpd. No. | R¹ | R² | R⁴ | R⁵ᵃ |
|---|---|---|---|---|
| 4-1 | Pr | H | H | H |
| 4-2 | Pr | H | H | Me |
| 4-3 | Pr | H | H | Et |
| 4-4 | Pr | H | H | PivOH₂— |
| 4-5 | Pr | H | H | Mod |
| 4-6 | Pr | H | H | EtcOCH₂— |
| 4-7 | Pr | H | H | iPrcOCH₂— |
| 4-8 | Pr | H | H | 1-(EtcO)Et |
| 4-9 | Pr | H | H | 1-(iPrcO)Et |
| 4-10 | Pr | H | H | Phth |
| 4-11 | Pr | H | Me | H |
| 4-12 | Pr | H | Me | Me |
| 4-13 | Pr | H | Me | Et |
| 4-14 | Pr | H | Me | PivOCH₂— |
| 4-15 | Pr | H | Me | Mod |
| 4-16 | Pr | H | Me | EtcOCH₂— |
| 4-17 | Pr | H | Me | iPrcOCH₂— |
| 4-18 | Pr | H | Me | 1-(EtcO)Et |
| 4-19 | Pr | H | Me | 1-(iPrcO)Et |
| 4-20 | Pr | H | Me | Phth |
| 4-21 | Pr | H | Fo | H |
| 4-22 | Pr | H | Fo | PivOCH₂— |
| 4-23 | Pr | H | Fo | Mod |
| 4-24 | Pr | H | Fo | Phth |
| 4-25 | Pr | H | Ac | H |
| 4-26 | Pr | H | Ac | PivOCH₂— |
| 4-27 | Pr | H | Ac | Mod |
| 4-28 | Pr | H | Ac | Phth |
| 4-29 | Pr | Me | H | H |
| 4-30 | Pr | Me | H | Et |
| 4-31 | Pr | Me | H | PivOCH₂— |
| 4-32 | Pr | Me | H | Mod |
| 4-33 | Pr | Me | H | EtcOCH₂— |
| 4-34 | Pr | Me | H | iPrcOCH₂— |
| 4-35 | Pr | Me | H | Phth |
| 4-36 | Pr | Me | Me | H |
| 4-37 | Pr | Me | Me | Et |
| 4-38 | Pr | Me | Me | PivOCH₂— |
| 4-39 | Pr | Me | Me | Mod |
| 4-40 | Pr | Me | Me | Phth |
| 4-41 | Pr | Et | H | H |
| 4-42 | Pr | Et | H | Et |
| 4-43 | Pr | Et | H | PivOCH₂— |
| 4-44 | Pr | Et | H | Mod |
| 4-45 | Pr | Et | H | Phth |
| 4-46 | Bu | H | H | H |
| 4-47 | Bu | H | H | Me |
| 4-48 | Bu | H | H | Et |
| 4-49 | Bu | H | H | PivOCH₂— |
| 4-50 | Bu | H | H | Mod |
| 4-51 | Bu | H | H | EtcOCH₂— |
| 4-52 | Bu | H | H | iPrcOCH₂— |
| 4-53 | Bu | H | H | 1-(EtcO)Et |
| 4-54 | Bu | H | H | 1-(iPrcO)Et |
| 4-55 | Bu | H | H | Phth |
| 4-56 | Bu | H | Me | H |
| 4-57 | Bu | H | Me | Me |
| 4-58 | Bu | H | Me | Et |
| 4-59 | Bu | H | Me | PivOCH₂— |
| 4-60 | Bu | H | Me | Mod |
| 4-61 | Bu | H | Me | EtcOCH₂— |
| 4-62 | Bu | H | Me | iPrcOCH₂— |
| 4-63 | Bu | H | Me | 1-(EtcO)Et |
| 4-64 | Bu | H | Me | 1-(iPrco)Et |
| 4-65 | Bu | H | Me | Phth |
| 4-66 | Bu | H | Fo | H |
| 4-67 | Bu | H | Fo | PivOCH₂— |
| 4-68 | Bu | H | Po | Mod |
| 4-69 | Bu | H | Fo | Phth |
| 4-70 | Bu | H | Ac | H |
| 4-71 | Bu | H | Ac | PivOCH₂— |
| 4-72 | Bu | H | Ac | Mod |
| 4-73 | Bu | H | Ac | Phth |
| 4-74 | Bu | Me | H | H |
| 4-75 | Bu | Me | H | Et |
| 4-76 | Bu | Me | H | PivOCH₂— |
| 4-77 | Bu | Me | H | Mod |
| 4-78 | Bu | Me | H | EtcOCH₂— |
| 4-79 | Bu | Me | H | iPrcOCH₂— |
| 4-80 | Bu | Me | H | Phth |
| 4-81 | Bu | Me | Me | H |
| 4-82 | Bu | Me | Me | Me |
| 4-83 | Bu | Me | Me | PivOCH₂— |
| 4-84 | Bu | Me | Me | Mod |
| 4-85 | Bu | Me | Me | Phth |
| 4-86 | Bu | Et | H | H |
| 4-87 | Bu | Et | H | Me |
| 4-88 | Bu | Et | H | PivOCH₂— |
| 4-89 | Bu | Et | H | Mod |
| 4-90 | Bu | Et | H | Phth |
| 4-91 | Et | H | H | H |
| 4-92 | Et | H | H | Et |
| 4-93 | Et | H | Et | PivOCH₂— |
| 4-94 | Et | H | Et | Mod |
| 4-95 | Et | H | Et | Phth |
| 4-96 | Pn | H | H | H |
| 4-97 | Pn | H | H | Et |
| 4-98 | Pn | H | H | PivOCH₂— |

TABLE 4-continued

| Cpd. No. | R¹ | R² | R⁴ | R⁵ᵃ |
|---|---|---|---|---|
| 4-99 | Pn | H | H | Mod |
| 4-100 | Pn | H | H | Phth |
| 4-101 | Pr | iPr | H | H |
| 4-102 | Pr | iPr | H | PivOCH₂— |
| 4-103 | Pr | iPr | H | Mod |
| 4-104 | Pr | tBu | H | H |
| 4-105 | Pr | tBu | H | PivOCH₂— |
| 4-106 | Pr | tBu | H | Mod |
| 4-107 | Et | Me | H | H |

TABLE 4-continued

| Cpd. No. | R¹ | R² | R⁴ | R⁵ᵃ |
|---|---|---|---|---|
| 4-108 | Et | Me | H | Et |
| 4-109 | Et | Me | H | PivOCH₂— |
| 4-110 | Et | Me | H | Mod |
| 4-111 | Et | Me | H | Phth |
| 4-112 | Et | H | H | PivOCH₂— |
| 4-113 | Et | H | H | Mod |
| 4-114 | Et | Me | H | PivOCH₂— |
| 4-115 | Et | Me | H | Mod |

TABLE 5

| Cpd. No. | R¹ | R² | R³ | R⁴ | R⁷ | R⁸ | R⁹ |
|---|---|---|---|---|---|---|---|
| 5-1 | Pr | H | H | H | COOH | H | H |
| 5-2 | Pr | Me | H | H | COOH | H | H |
| 5-3 | Pr | Et | H | H | COOH | H | H |
| 5-4 | Pr | Pr | H | H | COOH | H | H |
| 5-5 | Pr | iPr | H | H | COOH | H | H |
| 5-6 | Pr | tBu | H | H | COOH | H | H |
| 5-7 | Pr | Me | Me | H | COOH | H | H |
| 5-8 | Pr | Me | Et | H | COOH | H | H |
| 5-9 | Pr | H | H | Me | COOH | H | H |
| 5-10 | Pr | H | H | Et | COOH | H | H |
| 5-11 | Pr | Me | H | Me | COOH | H | H |
| 5-12 | Pr | Et | H | Me | COOH | H | H |
| 5-13 | Pr | iPr | H | Me | COOH | H | H |
| 5-14 | Pr | tBu | H | Me | COOH | H | H |
| 5-15 | Pr | H | H | Fo | COOH | H | H |
| 5-16 | Pr | Me | H | Fo | COOH | H | H |
| 5-17 | Pr | Et | H | Fo | COOH | H | H |
| 5-18 | Pr | iPr | H | Fo | COOH | H | H |
| 5-19 | Pr | tBu | H | Fo | COOH | H | H |
| 5-20 | Pr | H | H | Ac | COOH | H | H |
| 5-21 | Pr | Me | H | Ac | COOH | H | H |
| 5-22 | Pr | Et | H | Ac | COOH | H | H |
| 5-23 | Pr | iPr | H | Ac | COOH | H | H |
| 5-24 | Pr | tBu | H | Ac | COOH | H | H |
| 5-25 | Pr | H | H | H | COOH | H | Me |
| 5-26 | Pr | H | H | H | COOH | H | Et |
| 5-27 | Pr | H | H | H | COOH | H | Pr |
| 5-28 | Pr | H | H | H | COOH | H | iPr |
| 5-29 | Pr | H | H | H | COOH | H | iBu |
| 5-30 | Pr | H | H | H | COOH | H | iPn |
| 5-31 | Pr | H | H | H | COOH | Me | Me |
| 5-32 | Pr | H | H | H | Tz | H | H |
| 5-33 | Pr | Me | H | H | Tz | H | H |
| 5-34 | Pr | Et | H | H | Tz | H | H |
| 5-35 | Pr | Pr | H | H | Tz | H | H |
| 5-36 | Pr | iPr | H | H | Tz | H | H |
| 5-37 | Pr | tBu | H | H | Tz | H | H |
| 5-38 | Pr | Me | Me | H | Tz | H | H |
| 5-39 | Pr | Me | Et | H | Tz | H | H |
| 5-40 | Pr | H | H | Me | Tz | H | H |
| 5-41 | Pr | H | H | Et | Tz | H | H |
| 5-42 | Pr | Me | H | Me | Tz | H | H |
| 5-43 | Pr | Et | H | Me | Tz | H | H |
| 5-44 | Pr | iPr | H | Me | Tz | H | H |
| 5-45 | Pr | tBu | H | Me | Tz | H | H |
| 5-46 | Pr | H | H | Fo | Tz | H | H |
| 5-47 | Pr | Me | H | Fo | Tz | H | H |
| 5-48 | Pr | Et | H | Fo | Tz | H | H |
| 5-49 | Pr | iPr | H | Po | Tz | H | H |
| 5-50 | Pr | tBu | H | Fo | Tz | H | H |
| 5-51 | Pr | H | H | Ac | Tz | H | H |
| 5-52 | Pr | Me | H | Ac | Tz | H | H |
| 5-53 | Pr | Et | H | Ac | Tz | H | H |
| 5-54 | Pr | iPr | H | Ac | Tz | H | H |
| 5-55 | Pr | tBu | H | Ac | Tz | H | H |
| 5-56 | Pr | H | H | H | Tz | H | Me |
| 5-57 | Pr | H | H | H | Tz | H | Et |
| 5-58 | Pr | H | H | H | Tz | H | Pr |
| 5-59 | Pr | H | H | H | Tz | H | iPr |

TABLE 5-continued

| Cpd. No. | $R^1$ | $R^2$ | $R^3$ | $R^4$ | $R^7$ | $R^8$ | $R^9$ |
|---|---|---|---|---|---|---|---|
| 5-60 | Pr | H | H | H | Tz | H | tBu |
| 5-61 | Pr | H | H | H | Tz | H | iPn |
| 5-62 | Pr | H | H | H | Tz | Me | Me |
| 5-63 | Bu | H | H | H | COOH | H | H |
| 5-64 | Bu | Me | H | H | COOH | H | H |
| 5-65 | Bu | Et | H | H | COOH | H | H |
| 5-66 | Bu | Pr | H | H | COOH | H | H |
| 5-67 | Bu | iPr | H | H | COOH | H | H |
| 5-68 | Bu | tBu | H | H | COOH | H | H |
| 5-69 | Bu | Me | Me | H | COOH | H | H |
| 5-70 | Bu | Me | Et | H | COOH | H | H |
| 5-71 | Bu | H | H | Me | COOH | H | H |
| 5-72 | Bu | H | H | Et | COOH | H | H |
| 5-73 | Bu | Me | H | Me | COOH | H | H |
| 5-74 | Bu | Et | H | Me | COOH | H | H |
| 5-75 | Bu | iPr | H | Me | COOH | H | H |
| 5-76 | Bu | tBu | H | Me | COOH | H | H |
| 5-77 | Bu | H | H | Fo | COOH | H | H |
| 5-78 | Bu | Me | H | Fo | COOH | H | H |
| 5-79 | Bu | Et | H | Fo | COOH | H | H |
| 5-80 | Bu | iPr | H | Fo | COOH | H | H |
| 5-81 | Bu | tBu | H | Fo | COOH | H | H |
| 5-82 | Bu | H | H | Ac | COOH | H | H |
| 5-83 | Bu | Me | H | Ac | COOH | H | H |
| 5-84 | Bu | Et | H | Ac | COOH | H | H |
| 5-85 | Bu | iPr | H | Ac | COOH | H | H |
| 5-86 | Bu | tBu | H | Ac | COOH | H | H |
| 5-87 | Bu | H | H | H | COOH | H | Me |
| 5-88 | Bu | H | H | H | COOH | H | Et |
| 5-89 | Bu | H | H | H | COOH | H | Pr |
| 5-90 | Bu | H | H | H | COOH | H | iPr |
| 5-91 | Bu | H | H | H | COOH | H | tBu |
| 5-92 | Bu | H | H | H | COOH | H | iPn |
| 5-93 | Bu | H | H | H | COOH | Me | Me |
| 5-94 | Bu | H | H | H | Tz | H | H |
| 5-95 | Bu | Me | H | H | Tz | H | H |
| 5-96 | Bu | Et | H | H | Tz | H | H |
| 5-97 | Bu | Pr | H | H | Tz | H | H |
| 5-98 | Bu | iPr | H | H | Tz | H | H |
| 5-99 | Bu | tBu | H | H | Tz | H | H |
| 5-100 | Bu | Me | Me | H | Tz | H | H |
| 5-101 | Bu | Me | Et | H | Tz | H | H |
| 5-102 | Bu | H | H | Me | Tz | H | H |
| 5-103 | Bu | H | H | Et | Tz | H | H |
| 5-104 | Bu | Me | H | Me | Tz | H | H |
| 5-105 | Bu | Et | H | Me | Tz | H | H |
| 5-106 | Bu | iPr | H | Me | Tz | H | H |
| 5-107 | Bu | tBu | H | Me | Tz | H | H |
| 5-108 | Bu | H | H | Fo | Tz | H | H |
| 5-109 | Bu | Me | H | Fo | Tz | H | H |
| 5-110 | Bu | Et | H | Fo | Tz | H | H |
| 5-111 | Bu | iPr | H | Fo | Tz | H | H |
| 5-112 | Bu | tBu | H | Fo | Tz | H | H |
| 5-113 | Bu | H | H | Ac | Tz | H | H |
| 5-114 | Bu | Me | H | Ac | Tz | H | H |
| 5-115 | Bu | Et | H | Ac | Tz | H | H |
| 5-116 | Bu | iPr | H | Ac | Tz | H | H |
| 5-117 | Bu | tBu | H | Ac | Tz | H | H |
| 5-118 | Bu | H | H | H | Tz | H | Me |
| 5-119 | Bu | H | H | H | Tz | H | Et |
| 5-120 | Bu | H | H | H | Tz | H | Pr |
| 5-121 | Bu | H | H | H | Tz | H | iPr |
| 5-122 | Bu | H | H | H | Tz | H | iBu |
| 5-123 | Bu | H | H | H | Tz | H | iPn |
| 5-124 | Bu | H | H | H | Tz | Me | Me |
| 5-125 | Bu | H | H | H | COOH | H | $CH_2COOH$ |
| 5-126 | Bu | H | H | H | COOH | H | $CH_2COOEt$ |
| 5-127 | Bu | H | H | H | COOH | H | 1-(HOOC)Et |
| 5-128 | Bu | H | H | H | COOH | H | 1-(Etc)Et |
| 5-129 | Bu | H | H | H | COOH | H | 2-(HOOC)Et |
| 5-130 | Bu | H | H | H | COOH | H | 2-(Etc)Et |
| 5-131 | Bu | H | H | H | COOH | H | α-(HOOC)Bz |
| 5-132 | Bu | H | H | H | COOH | H | 1-(HOOC)-2-(Ph)Et |
| 5-133 | Bu | H | H | H | COOH | H | 1-(HOOC)-2-(Fu)Et |
| 5-134 | Bu | H | H | H | COOH | H | 1-(HOOC)-2-(Th)Et |
| 5-135 | Bu | H | H | H | COOH | H | 1-(HOOC)-2-(Im)Et |

TABLE 5-continued

| Cpd. No. | R¹ | R² | R³ | R⁴ | R⁷ | R⁸ | R⁹ |
|---|---|---|---|---|---|---|---|
| 5-136 | Bu | H | H | H | COOH | H | 1-(HOOC)-2-(HO)Et |
| 5-137 | Bu | H | H | H | COOH | H | 1-(HOOC)-2-(MeO)Et |
| 5-138 | Bu | Me | H | H | COOH | H | CH₂COOH |
| 5-139 | Bu | Me | H | H | COOH | H | CH₂COOEt |
| 5-140 | Bu | Me | H | H | COOH | H | 1-(HOOC)Et |
| 5-141 | Bu | Me | H | H | COOH | H | 1-(Etc)Et |
| 5-142 | Bu | Me | H | H | COOH | H | 2-(HOOC)Et |
| 5-143 | Bu | Me | H | H | COOH | H | 2-(Etc)Et |
| 5-144 | Bu | Me | H | H | COOH | H | α-(HOOC)-Bz |
| 5-145 | Bu | Me | H | H | COOH | H | 1-(HOOC)-2-(Ph)Et |
| 5-146 | Bu | Me | H | H | COOH | H | 1-(HOOC)-2-(Fu)Et |
| 5-147 | Bu | Me | H | H | COOH | H | 1-(HOOC)-2-(Th)Et |
| 5-148 | Bu | Me | H | H | COOH | H | 1-(HOOC)-2-(Im)Et |
| 5-149 | Bu | Me | H | H | COOH | H | 1-(HOOC)-2-(HO)Et |
| 5-150 | Bu | Me | H | H | COOH | H | 1-(HOOC)-2-(MeO)Et |
| 5-151 | Bu | iPr | H | H | COOH | H | CH₂COOH |
| 5-152 | Bu | iPr | H | H | COOH | H | CH₂COOEt |
| 5-153 | Bu | iPr | H | H | COOH | H | 1-(HOOC)Et |
| 5-154 | Bu | iPr | H | H | COOH | H | 1-(Etc)Et |
| 5-155 | Bu | iPr | H | H | COOH | H | 2-(HOOC)Et |
| 5-156 | Bu | iPr | H | H | COOH | H | 2-(Etc)Et |
| 5-157 | Bu | iPr | H | H | COOH | H | α-(HOOC)-Bz |
| 5-158 | Bu | iPr | H | H | COOH | H | 1-(HOOC)-2-(Ph)Et |
| 5-159 | Bu | iPr | H | H | COOH | H | 1-(HOOC)-2-(Fu)Et |
| 5-160 | Bu | iPr | H | H | COOH | H | 1-(HOOC)-2-(Th)Et |
| 5-161 | Bu | iPr | H | H | COOH | H | 1-(HOOC)-2-(Im)Et |
| 5-162 | Bu | iPr | H | H | COOH | H | 1-(HOOC)-2-(HO)Et |
| 5-163 | Bu | iPr | H | H | COOH | H | 1-(HOOC)-2-(MeO)Et |
| 5-164 | Bu | tBu | H | H | COOH | H | CH₂COOH |
| 5-165 | Bu | tBu | H | H | COOH | H | CH₂COOEt |
| 5-166 | Bu | tBu | H | H | COOH | H | 1-(HOOC)Et |
| 5-167 | Bu | tBu | H | H | COOH | H | 1-(Etc)Et |
| 5-168 | Bu | tBu | H | H | COOH | H | 2-(HOOC)Et |
| 5-169 | Bu | tBu | H | H | COOH | H | 2-(Etc)Et |
| 5-170 | Bu | tBu | H | H | COOH | H | α-(HOOC)-Bz |
| 5-171 | Bu | tBu | H | H | COOH | H | 1-(HOOC)-2-(Ph) |
| 5-172 | Bu | tBu | H | H | COOH | H | 1-(HOOC)-2-(Fu |
| 5-173 | Bu | tBu | H | H | COOH | H | 1-(HOOC)-2-(Th)Et |
| 5-174 | Bu | tBu | H | H | COOH | H | 1-(HOOC)-2-(Im)Et |
| 5-175 | Bu | tBu | H | H | COOH | H | 1-(HOOC)-2-(HO)Et |
| 5-176 | Bu | tBu | H | H | COOH | H | 1-(HOOC)-2-(MeO)Et |
| 5-177 | Bu | H | H | H | Tz | H | CH₂COOH |
| 5-178 | Bu | H | H | H | Tz | H | CH₂COOEt |
| 5-179 | Bu | H | H | H | Tz | H | 1-(HOOC)Et |
| 5-180 | Bu | H | H | H | Tz | H | 1-(Etc)Et |
| 5-181 | Bu | H | H | H | Tz | H | 2-(HOOC)Et |
| 5-182 | Bu | H | H | H | Tz | H | 2-(Etc)Et |
| 5-183 | Bu | H | H | H | Tz | H | α-(HOOC)-Bz |
| 5-184 | Bu | H | H | H | Tz | H | 1-(HOOC)-2-(Ph)Et |
| 5-185 | Bu | H | H | H | Tz | H | 1-(HOOC)-2-(Fu)Et |
| 5-186 | Bu | H | H | H | Tz | H | 1-(HOOC)-2-(Th)Et |
| 5-187 | Bu | H | H | H | Tz | H | 1-(HOOC)-2-(Im)Et |
| 5-188 | Bu | H | H | H | Tz | H | 1-(HOOC)-2-(HO)Et |
| 5-189 | Bu | H | H | H | Tz | H | 1-(HOOC)-2-(MeO)Et |
| 5-190 | Bu | Me | H | H | Tz | H | CH₂COOH |
| 5-191 | Bu | Me | H | H | Tz | H | CH₂COOEt |
| 5-192 | Bu | Me | H | H | Tz | H | 1-(HOOC)Et |
| 5-193 | Bu | Me | H | H | Tz | H | 1-(Etc)Et |
| 5-194 | Bu | Me | H | H | Tz | H | 2-(HOOC)Et |
| 5-195 | Bu | Me | H | H | Tz | H | 2-(Etc)Et |
| 5-196 | Bu | Me | H | H | Tz | H | α-(HOOC)-Bz |
| 5-197 | Bu | Me | H | H | Tz | H | 1-(HOOC)-2-(Ph)Et |
| 5-198 | Bu | Me | H | H | Tz | H | 1 (HOOC)-2-(Fu)Et- |
| 5-199 | Bu | Me | H | H | Tz | H | 1-(ROOC)-2-(Th)Et |
| 5-200 | Bu | Me | H | H | Tz | H | 1-(HOOC)-2-(Im)Et |
| 5-201 | Bu | Me | H | H | Tz | H | 1-(HOOC)-2-(HO)Et |
| 5-202 | Bu | Me | H | H | Tz | H | 1-(HOOC)-2-(MeO)Et |
| 5-203 | Bu | iPr | H | H | Tz | H | CH₂COOH |
| 5-204 | Bu | iPr | H | H | Tz | H | CH₂COOEt |
| 5-205 | Bu | iPr | H | H | Tz | H | 1-(HOOC)Et |
| 5-206 | Bu | iPr | H | H | Tz | H | 1-(Etc)Et |
| 5-207 | Bu | iPr | H | H | Tz | H | 2-(HOOC)Et |
| 5-208 | Bu | iPr | H | H | Tz | H | 2-(Etc)Et |
| 5-209 | Bu | iPr | H | H | Tz | H | α-(HOOC)-Bz |
| 5-210 | Bu | iPr | H | H | Tz | H | 1-(HOOC)-2-(Ph)Et |
| 5-211 | Bu | iPr | H | H | Tz | H | 1-(HOOC)-2-(Fu)Et |

TABLE 5-continued

| Cpd. No. | R¹ | R² | R³ | R⁴ | R⁷ | R⁸ | R⁹ |
|---|---|---|---|---|---|---|---|
| 5-212 | Bu | iPr | H | H | Tz | H | 1-(HOOC)-2-(Th)Et |
| 5-213 | Bu | iPr | H | H | Tz | H | 1-(HOOC)-2-(Im)Et |
| 5-214 | Bu | iPr | H | H | Tz | H | 1-(HOOC)-2-(HO)Et |
| 5-215 | Bu | iPr | H | H | Tz | H | 1-(HOOC)-2-(MeO)Et |
| 5-216 | Bu | tBu | H | H | Tz | H | CH₂COOH |
| 5-217 | Bu | tBu | H | H | Tz | H | CH₂COOEt |
| 5-218 | Bu | tBu | H | H | Tz | H | 1-(HOOC)Et |
| 5-219 | Bu | tBu | H | H | Tz | H | 1-(Etc)Et |
| 5-220 | Bu | tBu | H | H | Tz | H | 2-(HOOC)Et |
| 5-221 | Bu | tBu | H | H | Tz | H | 2-(Etc)Et |
| 5-222 | Bu | tBu | H | H | Tz | H | α-(HOOC)-Bz |
| 5-223 | Bu | tBu | H | H | Tz | H | 1-(HOOC)-2-(Ph)Et |
| 5-224 | Bu | tBu | H | H | Tz | H | 1-(HOOC)-2-(Fu)Et |
| 5-225 | Bu | tBu | H | H | Tz | H | 1-(HOOC)-2-(Th)Et |
| 5-226 | Bu | tBu | H | H | Tz | H | 1-(HOOC)-2-(Im)Et |
| 5-227 | Bu | tBu | H | H | Tz | H | 1-(HOOC)-2-(HO)Et |
| 5-228 | Bu | tBu | H | H | Tz | H | 1-(HOOC)-2-(MeO)Et |
| 5-229 | Pr | H | H | H | COOH | H | CH₂COOH |
| 5-230 | Pr | H | H | H | COOH | H | CH₂COOEt |
| 5-231 | Pr | H | H | H | COOH | H | 1-(HOOC)Et |
| 5-232 | Pr | H | H | H | COOH | H | 1-(Etc)Et |
| 5-233 | Pr | H | H | H | COOH | H | 2-(HOOC)Et |
| 5-234 | Pr | H | H | H | COOH | H | 2-(Etc)Et |
| 5-235 | Pr | H | H | H | COOH | H | α-(HOOC)-Bz |
| 5-236 | Pr | H | H | H | COOH | H | 1-(HOOC)-2-(Ph)Et |
| 5-237 | Pr | H | H | H | COOH | H | 1-(HOOC)-2-(Fu)Et |
| 5-238 | Pr | H | H | H | COOH | H | 1-(HOOC)-2-(Th)Et |
| 5-239 | Pr | H | H | H | COOH | H | 1-(HOOC)-2-(Im)Et |
| 5-240 | Pr | H | H | H | COOH | H | 1-(HOOC)-2-(HO)Et |
| 5-241 | Pr | H | H | H | COOH | H | 1-(HOOC)-2-(MeO)Et |
| 5-242 | Pr | Me | H | H | COOH | H | CH₂COOH |
| 5-243 | Pr | Me | H | H | COOH | H | CH₂COOEt |
| 5-244 | Pr | Me | H | H | COOH | H | 1-(HOOC)Et |
| 5-245 | Pr | Me | H | H | COOH | H | 1-(Etc)Et |
| 5-246 | Pr | Me | H | H | COOH | H | 2-(HOOC)Et |
| 5-247 | Pr | Me | H | H | COOH | H | 2-(Etc)Et |
| 5-248 | Pr | Me | H | H | COOH | H | α-(HOOC)-Bz |
| 5-249 | Pr | Me | H | H | COOH | H | 1-(HOOC)-2-(Ph)Et |
| 5-250 | Pr | Me | H | H | COOH | H | 1-(HOOC)-2-(Fu)Et |
| 5-251 | Pr | Me | H | H | COOH | H | 1-(HOOC)-2-(Th)Et |
| 5-252 | Pr | Me | H | H | COOH | H | 1-(HOOC)-2-(Im)Et |
| 5-253 | Pr | Me | H | H | COOH | H | 1-(HOOC)-2-(HO)Et |
| 5-254 | Pr | Me | H | H | COOH | H | 1-(HOOC)-2-(MeO)Et |
| 5-255 | Pr | iPr | H | H | COOH | H | CH₂COOH |
| 5-256 | Pr | iPr | H | H | COOH | H | CH₂COOEt |
| 5-257 | Pr | iPr | H | H | COOH | H | 1-(HOOC)Et |
| 5-258 | Pr | iPr | H | H | COOH | H | 1-(Etc)Et |
| 5-259 | Pr | iPr | H | H | COOH | H | 2-(HOOC)Et |
| 5-260 | Pr | iPr | H | H | COOH | H | 2-(Etc)Et |
| 5-261 | Pr | iPr | H | H | COOH | H | CH₂(Ph)COOH |
| 5-262 | Pr | iPr | H | H | COOH | H | 1-(HOOC)-2-(Ph)Et |
| 5-263 | Pr | iPr | H | H | COOH | H | 1-(HOOC)-2-(FU)Et |
| 5-264 | Pr | iPr | H | H | COOH | H | 1-(HOOC)-2-(Th)Et |
| 5-265 | Pr | iPr | H | H | COOH | H | 1-(HOOC)-2-(Im)Et |
| 5-266 | Pr | iPr | H | H | COOH | H | 1-(HOOC)-2-(HO)Et |
| 5-267 | Pr | iPr | H | H | COOH | H | 1-(HOOC)-2-(MeO)Et |
| 5-268 | Pr | tBu | H | H | COOH | H | CH₂COOH |
| 5-269 | Pr | tBu | H | H | COOH | H | CH₂COOEt |
| 5-270 | Pr | tBu | H | H | COOH | H | 1-(HOOC)Et |
| 5-271 | Pr | tBu | H | H | COOH | H | 1-(Etc)Et |
| 5-272 | Pr | tBu | H | H | COOH | H | 2-(HOOC)Et |
| 5-273 | Pr | tBu | H | H | COOH | H | 2-(Etc)Et |
| 5-274 | Pr | tBu | H | H | COOH | H | α-(HOOC)-Bz |
| 5-275 | Pr | tBu | H | H | COOH | H | 1-(HOOC)-2-(Ph)Et |
| 5-276 | Pr | tBu | H | H | COOH | H | 1-(HOOC)-2-(Fu)Et |
| 5-277 | Pr | tBu | H | H | COOH | H | 1-(HOOC)-2-(Th)Et |
| 5-278 | Pr | tBu | H | H | COOH | H | 1-(HOOC)-2-(Im)Et |
| 5-279 | Pr | tBu | H | H | COOH | H | 1-(HOOC)-2-(HO)Et |
| 5-280 | Pr | tBu | H | H | COOH | H | 1-(HOOC)-2-(MeO)Et |
| 5-281 | Pr | H | H | H | Tz | H | CH₂COOH |
| 5-282 | Pr | H | H | H | Tz | H | CH₂COOEt |
| 5-283 | Pr | H | H | H | Tz | H | 1-(HOOC)Et |
| 5-284 | Pr | H | H | H | Tz | H | 1-(Etc)Et |
| 5-285 | Pr | H | H | H | Tz | H | 2-(HOOC)Et |
| 5-286 | Pr | H | H | H | Tz | H | 2-(Etc)Et |
| 5-287 | Pr | H | H | H | Tz | H | α-(HOOC)-Bz |

TABLE 5-continued

| Cpd. No. | R¹ | R² | R³ | R⁴ | R⁷ | R⁸ | R⁹ |
|---|---|---|---|---|---|---|---|
| 5-288 | Pr | H | H | H | Tz | H | 1-(HOOC)-2-(Ph)Et |
| 5-289 | Pr | H | H | H | Tz | H | 1-(HOOC)-2-(Fu)Et |
| 5-290 | Pr | H | H | H | Tz | H | 1-(HOOC)-2-(Th)Et |
| 5-291 | Pr | H | H | H | Tz | H | 1-(HOOC)-2-(Im)Et |
| 5-292 | Pr | H | H | H | Tz | H | 1-(HOOC)-2-(HO)Et |
| 5-293 | Pr | H | H | H | Tz | H | 1-(HOOC)-2-(MeO)Et |
| 5-294 | Pr | Me | H | H | Tz | H | CH₂COOH |
| 5-295 | Pr | Me | H | H | Tz | H | CH₂COOEt |
| 5-296 | Pr | Me | H | H | Tz | H | 1-(HOOC)Et |
| 5-297 | Pr | Me | H | H | Tz | H | 1-(Etc)Et |
| 5-298 | Pr | Me | H | H | Tz | H | 2-(HOOC)Et |
| 5-299 | Pr | Me | H | H | Tz | H | 2-(Etc)Et |
| 5-300 | Pr | Me | H | H | Tz | H | α-(HOOC)-Bz |
| 5-301 | Pr | Me | H | H | Tz | H | 1-(HOOC)-2-(Ph)Et |
| 5-302 | Pr | Me | H | H | Tz | H | 1-(HOOC)-2-(Fu)Et |
| 5-303 | Pr | Me | H | H | Tz | H | 1-(HOOC)-2-(Th)Et |
| 5-304 | Pr | Me | H | H | Tz | H | 1-(HOOC)-2-(Im)Et |
| 5-305 | Pr | Me | H | H | Tz | H | 1-(HOOC)-2-(HO)Et |
| 5-306 | Pr | Me | H | H | Tz | H | 1-(HOOC)-2-(MeO)Et |
| 5-307 | Pr | iPr | H | H | Tz | H | CH₂COOH |
| 5-308 | Pr | iPr | H | H | Tz | H | CH₂COOEt |
| 5-309 | Pr | iPr | H | H | Tz | H | 1-(HOOC)Et |
| 5-310 | Pr | iPr | H | H | Tz | H | 1-(Etc)Et |
| 5-311 | Pr | iPr | H | H | Tz | H | 2-(HOOC)Et |
| 5-312 | Pr | iPr | H | H | Tz | H | 2-(Etc)Et |
| 5-313 | Pr | iPr | H | H | Tz | H | α-(HOOC)-Bz |
| 5-314 | Pr | iPr | H | H | Tz | H | 1-(HOOC)-2-(Ph)Et |
| 5-315 | Pr | iPr | H | H | Tz | H | 1-(HOOC)-2-(Fu)Et |
| 5-316 | Pr | iPr | H | H | Tz | H | 1-(HOOC)-2-(Th)Et |
| 5-317 | Pr | iPr | H | H | Tz | H | 1-(HOOC)-2-(Im)Et |
| 5-318 | Pr | iPr | H | H | Tz | H | 1-(HOOC)-2-(HO)Et |
| 5-319 | Pr | iPr | H | H | Tz | H | 1-(HOOC)-2-(MeO)Et |
| 5-320 | Pr | tBu | H | H | Tz | H | CH₂COOH |
| 5-321 | Pr | tBu | H | H | Tz | H | CH₂COOEt |
| 5-322 | Pr | tBu | H | H | Tz | H | 1-(HOOC)Et |
| 5-323 | Pr | tBu | H | H | Tz | H | 1-(Etc)Et |
| 5-324 | Pr | tBu | H | H | Tz | H | 2-(HOOC)Et |
| 5-325 | Pr | tBu | H | H | Tz | H | 2-(Etc)Et |
| 5-326 | Pr | tBu | H | H | Tz | H | α-(HOOC)-Bz |
| 5-327 | Pr | tBu | H | H | Tz | H | 1-(HOOC)-2-(Ph)Et |
| 5-328 | Pr | tBu | H | H | Tz | H | 1-(HOOC)-2-(Fu)Et |
| 5-329 | Pr | tBu | H | H | Tz | H | 1-(HOOC)-2-(Th)Et |
| 5-330 | Pr | tBu | H | H | Tz | H | 1-(HOOC)-2-(Im)Et |
| 5-331 | Pr | tBu | H | H | Tz | H | 1-(HOOC)-2-(HO)Et |
| 5-332 | Pr | tBu | H | H | Tz | H | 1-(HOOC)-2-(MeO)Et |
| 5-333 | Bu | iPr | iPr | H | COOH | H | H |
| 5-334 | Bu | H | H | H | COOH | —(CH₂)₃CH(COOH)— | |
| 5-335 | Bu | H | H | H | COOH | —(CH₂)₃CH(COOMe)— | |
| 5-336 | Pr | H | H | H | —COOCH₂—OPiv | H | H |
| 5-337 | Pr | Me | H | H | —COOCH₂OPiv | H | H |
| 5-338 | Pr | Me | Me | H | —COOCH₂OPiv | H | H |
| 5-339 | Pr | H | H | H | —COOMod | H | H |
| 5-340 | Pr | Me | H | H | —COOMod | H | H |
| 5-341 | Pr | Me | Me | H | —COOMod | H | H |
| 5-342 | Bu | H | H | H | —COOCH₂OPiv | H | H |
| 5-343 | Bu | Me | H | H | —COOCH₂OPiv | H | H |
| 5-344 | Bu | Me | Me | H | —COOCH₂OPiv | H | H |
| 5-345 | Bu | H | H | H | —COOMod | H | H |
| 5-346 | Bu | Me | H | H | —COOMod | H | H |
| 5-347 | Bu | Me | Me | H | —COOMod | H | H |
| 5-348 | Et | iPr | H | H | Tz | H | H |
| 5-349 | Et | iPr | H | H | COOH | H | H |
| 5-350 | Et | tBu | H | H | Tz | H | H |
| 5-351 | Et | tBu | H | H | COOH | H | H |

TABLE 6

| Cpd. No. | R¹ | R² | R³ | R⁴ | R⁵ᵃ | R⁶ | R⁷ |
|---|---|---|---|---|---|---|---|
| 6-1 | Pr | Me | Me | H | H | H | 2-Tz |
| 6-2 | Pr | Me | Me | H | H | 6-Cl | 2-Tz |
| 6-3 | Bu | me | Me | H | H | 6-Cl | 2-Tz |
| 6-4 | Pr | Me | Me | H | H | 6-OMe | 2-Tz |

TABLE 6-continued

| Cpd. No. | R¹ | R² | R³ | R⁴ | R⁵ᵃ | R⁶ | R⁷ |
|---|---|---|---|---|---|---|---|
| 6-5 | Bu | Me | Me | H | H | 6-OMe | 2-Tz |
| 6-6 | Pr | Me | Et | H | H | H | 2-Tz |
| 6-7 | Bu | Me | Et | H | H | H | 2-Tz |
| 6-8 | Pr | Et | Et | H | H | H | 2-Tz |
| 6-9 | Bu | Et | Et | H | H | H | 2-Tz |
| 6-10 | Pr | Me | Me | Me | Et | H | 2-Tz |
| 6-11 | Pr | Me | Me | Me | H | H | 2-Tz |
| 6-12 | Bu | Me | Me | Me | Et | H | 2-Tz |
| 6-13 | Bu | Me | Me | Me | H | H | 2-Tz |
| 6-14 | Pr | Et | Et | H | Et | H | 2-Tz |
| 6-15 | Et | Me | Me | H | H | H | 2-Tz |
| 6-16 | Et | Me | Me | H | Et | H | 2-Tz |
| 6-17 | Et | Me | Me | H | iPrcOCH₂— | H | 2-Tz |
| 6-18 | Et | Me | Me | H | PivOCH₂— | H | 2-Tz |
| 6-19 | Et | Me | Me | H | Mod | H | 2-Tz |
| 6-20 | Et | Me | Me | H | Phth | H | 2-Tz |

Of the compounds listed above, the following are preferred, that is to say Compounds No. 1-1, 1-2, 1-3, 1-9, 1-11, 1-12, 1-15, 1-22, 1-23, 1-24, 1-25, 1-27, 1-28, 1-31, 1-35, 1-36, 1-37, 1-39, 1-41, 1-49, 1-54, 1-56, 1-58, 1-59, 1-60, 1-61, 1-62, 1-82, 1-84, 1-98, 1-102, 1-103, 1-132, 1-133, 1-134, 1-138, 1-139, 1-140, 2-1, 2-2, 2-3, 2-4, 2-5, 2-6, 2-15, 2-16, 2-17, 2-18, 2-19, 2-20, 2-21, 2-22, 2-23, 2-24, 2-25, 2-26, 2-27, 2-28, 2-29, 2-30, 2-31, 2-32, 2-37, 2-38, 2-39, 2-40, 2-49, 2-50, 2-64, 2-65, 2-66, 2-67, 2-68, 2-69, 2-70, 2-71, 2-73, 2-74, 2-75, 2-76, 2-77, 3-1, 3-9, 3-10, 3-13, 3-14, 3-25, 3-26, 3-27, 3-35, 3-36, 3-39, 3-40, 3-51, 3-52, 3-53, 3-61, 3-65, 3-77, 3-78, 3-79, 3-87, 3-91, 3-103, 3-104, 3-105, 3-107, 3-109, 3-111, 3-112, 3-121, 3-127, 3-128, 3-129, 3-135, 3-136, 4-1, 4-4, 4-5, 4-6, 4-7, 4-8, 4-9, 4-10, 4-11, 4-14, 4-15, 4-16, 4-17, 4-18, 4-19, 4-20, 4-21, 4-22, 4-23, 4-25, 4-26, 4-27, 4-29, 4-31, 4-32, 4-33, 4-34, 4-35, 4-36, 4-38, 4-39, 4-41, 4-43, 4-44, 4-46, 4-49, 4-50, 4-51, 4-52, 4-53, 4-54, 4-55, 4-56, 4-59, 4-60, 4-61, 4-62, 4-63, 4-64, 4-65, 4-66, 4-67, 4-68, 4-70, 4-71, 4-72, 4-74, 4-76, 4-77, 4-78, 4-79, 4-80, 4-81, 4-83, 4-84, 4-85, 4-91, 4-96, 4-98, 4-99, 4-107, 4-109, 4-110, 4-112, 4-113, 4-114, 4-115, 5-1, 5-2, 5-3 , 5-5, 5-6, 5-13 , 5-14, 5-18, 5-19, 5-23, 5-24, 5-32, 5-33, 5-34, 5-36, 5-37, 5-44, 5-45, 5-49, 5-50, 5-54, 5-55, 5-63, 5-64, 5-65, 5-67, 5-68, 5-75, 5-76, 5-80, 5-81, 5-85, 5-86, 5-94, 5-95, 5-96, 5-98, 5-99, 5-106, 5-107, 5-111, 5-112, 5-116, 5-117, 5-125, 5-138, 5-151, 5-164, 5-177, 5-190, 5-203, 5-216, 5-229, 5-242, 5-255, 5-268, 5-281, 5-294, 5-307, 5-320, 5-348, 5-349, 5-350 and 5-351, of which Compounds No. 1-22, 1-25, 1-27, 1-28, 1-31, 1-35, 1-36, 1-37, 1-49, 1-54, 1-56, 1-58, 1-59, 1-132, 1-133, 1-134, 2-1, 2-2, 2-3, 2-5, 2-6, 2-15, 2-16, 2-17, 2-18, 2-19, 2-20, 2-21, 2-22, 2-23, 2-24, 2-25, 2-26, 2-27, 2-28, 2-29, 2-30, 2-31, 2-32, 2-65, 2-66, 2-67, 2-68, 2-69, 2-70, 2-71, 2-73, 2-74, 2-75, 2-76, 2-77, 3-1, 3-9, 3-10, 3-13, 3-14, 3-25, 3-26, 3-35, 3-39, 3-40, 3-52, 3-53 3-61, 3-65, 3-77, 3-78, 3-79, 3-87, 3-91, 3-103, 3-104, 3-105, 3-107, 3-109, 3-111, 3-112, 4-4, 4-5, 4-6, 4-7, 4-11, 4-14, 4-15, 4-16, 4-17, 4-20, 4-29, 4-31, 4-32, 4-33, 4-34, 4-35, 4-36, 4-38, 4-39, 4-41, 4-43, 4-44, 4-49, 4-50, 4-51, 4-52, 4-55, 4-56, 4-59, 4-60, 4-61, 4-62, 4-65, 4-74, 4-76, 4-77, 4-78, 4-79, 4-80, 4-81, 4-83, 4-84, 4-91, 4-96, 4-107, 4-109, 4-110, 4-114, 4-115, 5-5, 5-6, 5-13, 5-14, 5-32, 5-36, 5-37, 5-44, 5-45, 5-63, 5-67, 5-68, 5-75, 5-76, 5-80, 5-81, 5-94, 5-98, 5-99, 5-106, 5-107, 5-348, 5-349, 5-350 and 5-351 are more preferred, and Compounds No. 1-28, 1-31, 1-35, 1-36, 1-49, 1-56, 1-58, 1-59, 1-132, 1-133, 1-134, 2-1, 2-2, 2-3, 2-5, 2-6, 2-15, 2-16, 2-17, 2-18, 2-19, 2-20, 2-21, 2-22, 2-23, 2-24, 2-25, 2-26, 2-27, 2-28, 2-29, 2-30, 2-31, 2-32, 2-65, 2-66, 2-67, 2-68, 2-69, 2-70, 2-71, 2-73, 2-74, 2-75, 2-76, 2-77, 3-1, 3-9, 3-10, 3-13, 3-14, 3-25, 3-26, 3-53, 3-61, 3-65, 3-77, 3-78, 4-29, 4-31, 4-32, 5-36 and 5-37 are still more preferred. The most preferred compounds are Compounds No.:

1-31. 2-Butyl-1-[(2'-carboxybiphenyl-4-yl)methyl]-4-(1-hydroxy-1-methylethyl)imidazole-5-carboxylic acid;

1-35. Pivaloyloxymethyl 2-butyl-1-[(2'-carboxybiphenyl-4-yl)methyl]-4-(1-hydroxy-1-methylethyl)imidazole-5-carboxylate;

1-36. (5-Methyl-2-oxo-1,3-dioxolen-4-yl)methyl 2-butyl-1-[(2'-carboxybiphenyl-4-yl)methyl]-4-(1-hydroxy-1-methylethyl)imidazole-5-carboxylate;

1-49. 1-[(2'-Carboxybiphenyl-4-yl)methyl]-4-(1-hydroxy-1-methylethyl)-2-propylimidazole-5-carboxylic acid;

1-132. 1-[(2'-Carboxybiphenyl-4-yl)methyl]-2-ethyl-4-(1-hydroxy-1-methylethyl)imidazole-5-carboxylic acid;

2-1. 4-(1-Hydroxy-1-methylethyl)-2-propyl-1-{4-[2-(tetrazol-5-yl)phenyl]phenyl}methylimidazole-5-carboxylic acid;

2-2. 2-Butyl -4-(1-hydroxy-1-methylethyl)-1-{4-[2-(tetrazol-5-yl)phenyl]phenyl}methylimidazole-5carboxylic acid;

2-15. Pivaloyloxymethyl 4-(1-hydroxy-1-methylethyl)-2-propyl-1-{4-[2-(tetrazol-5-yl)phenyl] phenyl}methylimidazole-5-carboxylate;

2-16. Pivaloyloxymethyl 2-butyl-4-(1-hydroxy-1-methylethyl)-1)-1-{4-[2-(tetrazol-5-yl)phenyl] phenyl}methylimidazole-5-carboxylate;

2-17. (5-Methyl-2-oxo-1,3-dioxolen-4-yl)methyl 4-(1-hydroxy-1-methylethyl)-2-propyl-1-{4-[2-(tetrazol-5-yl)phenyl]phenyl}methylimidazole-5-carboxylate;

2-18. (5-Methyl-2-oxo-1,3-dioxolen-4-yl)methyl 2-butyl-4-(1-hydroxy-1-methylethyl)-1-{4-[2-(tetrazol-5-yl)phenyl]phenyl}methylimidazole-5-carboxylate;

2-19. Ethoxycarbonyloxymethyl 4-(1-hydroxy-1-methylethyl)-2-propyl-1-{4-[2-(tetrazol-5-yl)phenyl]phenyl}-methylimidazole-5-carboxylate;

2-21. Isopropoxycarbonyloxymethyl 4-(1-hydroxy-1methylethyl)-2-propyl-1-{4-[2-(tetrazol-5-yl)phenyl] phenyl}methylimidazole-5-carboxylate;

2-23. 1-(Ethoxycarbonyloxy)ethyl 4-(1-hydroxy-1-methylethyl)-2-propyl-1-{4-[2-(tetrazol-5-yl)phenyl]phenyl}-methylimidazole-5-carboxylate;

2-25. 1-(Isopropoxycarbonyloxy)ethyl-(1-hydroxy-1-methylethyl)-2-propyl-1-{4-[2-(tetrazol-5-yl)phenyl] phenyl}methylimidazole-5-carboxylate;

2-69. Pivaloyloxymethyl 2-ethyl-4-(1-hydroxy-1-methylethyl)-1-{4-[2-(tetrazol-5-yl)phenyl] phenyl}methylimidazole-5-carboxylate;

2-73. (5-Methyl-2-oxo-1,3-dioxolen-4-yl)methyl 2-ethyl-4-(1-hydroxy-1-methylethyl)-1-{4-[2-(tetrazol-5-yl)phenyl]phenyl}methylimidazole-5-carboxylate;

3-1. Pivaloyloxymethyl 1-[(2'-carboxybiphenyl-4-yl)methyl]-4-(1-hydroxy-1-methylethyl)-2-propylimidazole-5-carboxylate;

3-25. (5-Methyl -2-oxo-1,3-dioxolen-4-yl)methyl 1-[(2'-carboxybiphenyl-4-yl)methyl]-4-(1-hydroxy-1-methylethyl)-2-propylimidazole-5-carboxylate;

3-26. Phthalidyl 1-[(2'-carboxybiphenyl-4-yl)methyl]-4-(1-hydroxy-1-methylethyl)-2-propylimidazole-5-carboxylate;

4-29. 4-(1-Hydroxyethyl)-2-propyl-1-{4-[2-(tetrazol-5-yl)phenyl]phenyl}methylimidazole-5-carboxylic acid;

4-31. Pivaloyloxymethyl 4-(1-hydroxyethyl)-2-propyl-1-{4-[2-(tetrazol-5-yl)phenyl]phenyl}methylimidazole-5-carboxylate; and 4-32. (5-Methyl-2-oxo-1,3-dioxolen-4-yl)methyl 4-(1-hydroxyethyl)-2-propyl-1-{4-[2-(tetrazol-5-yl)phenyl] phenyl}methylimidazole-5-carboxylate;

and pharmaceutically acceptable salts thereof.

Specific examples of compounds of formula (Ia)$_p$, shown above, in which $R_p^1$—$X_p$—$R_p^2$—, $R_p^3$, $R_p^4$, $R_p^5$ and $R_p^6$ are as defined in the following Table 7. In the Table 7, the following abbreviations are employed:

| | |
|---|---|
| Bu | butyl |
| Et | ethyl |
| Etc | ethoxycarbonyl |
| Me | methyl |
| Mod | (5-methyl-2-oxo-1,3-dioxolen-4-yl)methyl |
| Phth | 3-phthalidyl |
| Pom | pivaloyloxymethyl |
| Pr | Propyl |
| iPr | isopropyl |
| iPrc | isopropoxycarbonyl |
| Tz | tetrazol-5-yl |

TABLE 7

| Compound No. | $R_p^1$-$X_p$-$R_p^2$- | $R_p^3$ | $R_p^4$ | $R_p^5$ | $R_p^{6'}$ |
|---|---|---|---|---|---|
| 1 | MeOCH$_2$— | Me | Me | H | COOH |
| 2 | MeOCH$_2$— | Me | Me | H | Tz |
| 3 | EtOCH$_2$— | Me | Me | H | COOH |
| 4 | EtOCH$_2$— | Me | Me | H | Tz |
| 5 | PrOCH$_2$— | Me | Me | H | COOH |
| 6 | PrOCH$_2$— | Me | Me | H | Tz |
| 7 | BuOCH$_2$— | Me | Me | H | COOH |
| 8 | BuOCH$_2$— | Me | Me | H | Tz |
| 9 | iPrOCH$_2$— | Me | Me | H | COOH |
| 10 | iPrOCH$_2$— | Me | Me | H | Tz |
| 11 | 1-(MeO)Et | Me | Me | H | COOH |
| 12 | 1-(MeO)Et | Me | Me | H | Tz |
| 13 | 2-(MeO)Et | Me | Me | H | COOH |
| 14 | 2-(MeO)Et | Me | Me | H | Tz |
| 15 | 2-(EtO)Et | Me | Me | H | COOH |
| 16 | 2-(EtO)Et | Me | Me | H | Tz |
| 17 | MeSCH$_2$— | Me | Me | H | COOH |
| 18 | MeSCH$_2$— | Me | Me | H | Tz |
| 19 | EtSCH$_2$— | Me | Me | H | COOH |
| 20 | EtSCH$_2$— | Me | Me | H | Tz |
| 21 | 1-(MeS)Et | Me | Me | H | COOH |
| 22 | 1-(MeS)Et | Me | Me | H | Tz |
| 23 | MeS— | Me | Me | H | COOH |
| 24 | MeS— | Me | Me | H | Tz |
| 25 | EtS— | Me | Me | H | COOH |
| 26 | EtS— | Me | Me | H | Tz |
| 27 | PrS— | Me | Me | H | COOH |
| 28 | PrS— | Me | Me | H | Tz |
| 29 | MeOCH$_2$— | Me | Et | H | COOH |
| 30 | MeOCH$_2$— | Me | Et | H | Tz |
| 31 | EtOCH$_2$— | Me | Et | H | COOH |
| 32 | EtOCH$_2$— | Me | Et | H | Tz |
| 33 | PrOCH$_2$— | Me | Et | H | COOH |
| 34 | PrOCH$_2$— | Me | Et | H | Tz |
| 35 | BuOCH$_2$— | Me | Et | H | COOH |
| 36 | BuOCH$_2$— | Me | Et | H | Tz |
| 37 | iPrOCH$_2$— | Me | Et | H | COOH |
| 38 | iPrOCH$_2$— | Me | Et | H | Tz |
| 39 | 1-(MeO)Et | Me | Et | H | COOH |
| 40 | 1-(MeO)Et | Me | Et | H | Tz |
| 41 | 2-(MeO)Et | Me | Et | H | COOH |
| 42 | 2-(MeO)Et | Me | Et | H | Tz |
| 43 | 2-(EtO)Et | Me | Et | H | COOH |
| 44 | 2-(EtO)Et | Me | Et | H | Tz |
| 45 | MeSCH$_2$— | Me | Et | H | COOH |
| 46 | MeSCH$_2$— | Me | Et | H | Tz |
| 47 | EtSCH$_2$— | Me | Et | H | COOH |
| 48 | EtSCH$_2$— | Me | Et | H | Tz |
| 49 | 1-(MeS)Et | Me | Et | H | COOH |
| 50 | 1-(MeS)Et | Me | Et | H | Tz |
| 51 | MeS— | Me | Et | H | COOH |
| 52 | MeS— | Me | Et | H | Tz |
| 53 | EtS— | Me | Et | H | COOH |
| 54 | EtS— | Me | Et | H | Tz |
| 55 | PrS— | Me | Et | H | COOH |
| 56 | PrS— | Me | Et | H | Tz |
| 57 | MeOCH$_2$— | Et | Et | H | COOH |
| 58 | MeOCH$_2$— | Et | Et | H | Tz |
| 59 | EtOCH$_2$— | Et | Et | H | COOH |
| 60 | EtOCH$_2$— | Et | Et | H | Tz |
| 61 | PrOCH$_2$— | Et | Et | H | COOH |
| 62 | PrOCH$_2$— | Et | Et | H | Tz |
| 63 | BuOCH$_2$— | Et | Et | H | COOH |
| 64 | BuOCH$_2$— | Et | Et | H | Tz |
| 65 | iPrOCH$_2$— | Et | Et | H | COOH |
| 66 | iPrOCH$_2$— | Et | Et | H | Tz |
| 67 | 1-(MeO)Et | Et | Et | H | COOH |
| 68 | 1-(MeO)Et | Et | Et | H | Tz |
| 69 | 2-(MeO)Et | Et | Et | H | COOH |
| 70 | 2-(Meo)Et | Et | Et | H | Tz |
| 71 | 2-(EtO)Et | Et | Et | H | COOH |
| 72 | 2-(EtO)Et | Et | Et | H | Tz |
| 73 | MeSCH$_2$— | Et | Et | H | COOH |
| 74 | MeSCH$_2$— | Et | Et | H | Tz |
| 75 | EtSCH$_2$— | Et | Et | H | COOH |
| 76 | EtSCH$_2$— | Et | Et | H | Tz |
| 77 | 1-(MeS)Et | Et | Et | H | COOH |
| 78 | 1-(MeS)Et | Et | Et | H | Tz |
| 79 | MeS— | Et | Et | H | COOH |
| 80 | MeS— | Et | Et | H | Tz |
| 81 | EtS— | Et | Et | H | COOH |
| 82 | EtS— | Et | Et | H | Tz |
| 83 | PrS— | Et | Et | H | COOH |
| 84 | PrS— | Et | Et | H | Tz |
| 85 | MeOCH$_2$— | Me | Me | Pom | COOH |
| 86 | MeOCH$_2$— | Me | Me | Pom | Tz |
| 87 | EtOCH$_2$— | Me | Me | Pom | COOH |
| 88 | EtOCH$_2$— | Me | Me | Pom | Tz |
| 89 | MeSCH$_2$— | Me | Me | Pom | COOH |
| 90 | MeSCH$_2$— | Me | Me | Pom | Tz |
| 91 | MeS— | Me | Me | Pom | COOH |
| 92 | MeS— | Me | Me | Pom | Tz |
| 93 | EtS— | Me | Me | Pom | COOH |
| 94 | EtS— | Me | Me | Pom | Tz |
| 95 | MeOCH$_2$— | Me | Me | Mod | COOH |
| 96 | MeOCH$_2$— | Me | Me | Mod | Tz |
| 97 | EtOCH$_2$— | Me | Me | Mod | COOH |
| 98 | EtOCH$_2$— | Me | Me | Mod | Tz |
| 99 | MeSCH$_2$— | Me | Me | Mod | COOH |
| 100 | MeSCH$_2$— | Me | Me | Mod | Tz |
| 101 | MeS— | Me | Me | Mod | COOH |
| 102 | MeS— | Me | Me | Mod | Tz |
| 103 | EtS— | Me | Me | Mod | COOH |
| 104 | EtS— | Me | Me | Mod | Tz |
| 105 | MeOCH$_2$— | Me | Me | EtcOCH$_2$— | COOH |
| 106 | MeOCH$_2$— | Me | Me | EtcOCH$_2$— | Tz |
| 107 | EtOCH$_2$— | Me | Me | EtcOCH$_2$— | COOH |
| 108 | EtOCH$_2$— | Me | Me | EtcOCH$_2$— | Tz |
| 109 | MeSCH$_2$— | Me | Me | EtcOCH$_2$— | COOH |
| 110 | MeSCH$_2$— | Me | Me | EtcOCH$_2$— | Tz |
| 111 | MeS— | Me | Me | EtcOCH$_2$— | COOH |
| 112 | MeS— | Me | Me | EtcOCH$_2$— | Tz |
| 113 | EtS— | Me | Me | EtcOCH$_2$— | COOH |
| 114 | EtS— | Me | Me | EtcOCH$_2$— | Tz |
| 115 | MeOCH$_2$— | Me | Me | iPrcOCH$_2$— | COOH |
| 116 | MeOCH$_2$— | Me | Me | iPrcOCH$_2$— | Tz |
| 117 | EtOCH$_2$— | Me | Me | iPrcOCH$_2$— | COOH |
| 118 | EtOCH$_2$— | Me | Me | iPrcOCH$_2$— | Tz |
| 119 | MeSCH$_2$— | Me | Me | iPrcOCH$_2$— | COOH |
| 120 | MeSCH$_2$— | Me | Me | iPrcOCH$_2$— | Tz |
| 121 | MeS— | Me | Me | iPrcOCH$_2$— | COOH |
| 122 | MeS— | Me | Me | iPrcOCH$_2$— | Tz |
| 123 | EtS— | Me | Me | iPrcOCH$_2$— | COOH |
| 124 | EtS— | Me | Me | iPrcOCH$_2$— | Tz |
| 125 | MeOCH$_2$— | Me | Me | 1-(EtcO)Et | COOH |
| 126 | MeOCH$_2$— | Me | Me | 1-(EtcO)Et | Tz |
| 127 | EtOCH$_2$— | Me | Me | 1-(EtcO)Et | COOH |
| 128 | EtOCH$_2$— | Me | Me | 1-(EtcO)Et | Tz |
| 129 | MeSCH$_2$— | Me | Me | 1-(EtcO)Et | COOH |
| 130 | MeSCH$_2$— | Me | Me | 1-(EtcO)Et | Tz |
| 131 | MeS— | Me | Me | 1-(EtcO)Et | COOH |
| 132 | MeS— | Me | Me | 1-(EtcO)Et | Tz |
| 133 | EtS— | Me | Me | 1-(EtcO)Et | COCH |
| 134 | EtS— | Me | Me | 1-(EtcO)Et | Tz |

TABLE 7-continued

| Compound No. | $R_p^1$-$X_p$-$R_p^2$- | $R_p^3$ | $R_p^4$ | $R_p^5$ | $R_p^{6'}$ |
|---|---|---|---|---|---|
| 135 | MeOCH$_2$— | Me | Me | 1-(iPrcO)Et | COOH |
| 136 | MeOCH$_2$— | Me | Me | 1-(iPrcO)Et | Tz |
| 137 | EtOCH$_2$— | Me | Me | 1-(iPrcO)Et | COOH |
| 138 | EtOCH$_2$— | Me | Me | 1-(iPrcO)Et | Tz |
| 139 | MeSCH$_2$— | Me | Me | 1-(iPrcO)Et | COOH |
| 140 | MeSCH$_2$— | Me | Me | 1-(iPrcO)Et | Tz |
| 141 | MeS— | Me | Me | 1-(iPrcO)Et | COOH |
| 142 | MeS— | Me | Me | 1-(iPrcO)Et | Tz |
| 143 | EtS— | Me | Me | 1-(iPrcO)Et | COOH |
| 144 | EtS— | Me | Me | 1-(iPrcO)Et | Tz |
| 145 | MeOCH$_2$— | Me | Me | Phth | COOH |
| 146 | MeOCH$_2$— | Me | Me | Phth | Tz |
| 147 | EtOCH$_2$— | Me | Me | Phth | COOH |
| 148 | EtOCH$_2$— | Me | Me | Phth | Tz |
| 149 | MeSCH$_2$— | Me | Me | Phth | COOH |
| 150 | MeS— | Me | Me | Phth | Tz |
| 151 | MeS— | Me | Me | Phth | COOH |
| 152 | MeS— | Me | Me | Phth | Tz |
| 153 | EtS— | Me | Me | Phth | COOH |
| 154 | EtS— | Me | Me | Phth | Tz |
| 155 | MeOCH$_2$— | Me | Me | Me | COOH |
| 156 | MeOCH$_2$— | Me | Me | Me | Tz |
| 157 | EtOCH$_2$— | Me | Me | Et | COOH |
| 158 | EtOCH$_2$— | Me | Me | Et | Tz |
| 159 | PrOCH$_2$— | Me | Me | Pr | COOH |
| 160 | PrOCH$_2$— | Me | Me | Pr | Tz |
| 161 | iPrOCH$_2$— | Me | Me | iPr | COOH |
| 162 | iPrOCH$_2$— | Me | Me | iPr | Tz |
| 163 | 1-(MeO)Et | Me | Me | Me | COOH |
| 164 | 1-(MeO)Et | Me | Me | Me | Tz |
| 165 | MeSCH$_2$— | Me | Me | Et | COOH |
| 166 | MeSCH$_2$— | Me | Me | Et | Tz |
| 167 | MeS— | Me | Me | Et | COOH |
| 168 | MeS— | Me | Me | Et | Tz |
| 169 | EtS— | Me | Me | Et | COOH |
| 170 | EtS— | Me | Me | Et | Tz |
| 171 | PrS— | Me | Me | Et | COOH |
| 172 | PrS— | Me | Me | Et | Tz |
| 173 | 1-(EtO)Et | Me | Me | H | COOH |
| 174 | 1-(EtO)Et | Me | Me | H | Tz |
| 175 | 1-(EtO)Et | Me | Me | Pom | COOH |
| 176 | 1-(EtO)Et | Me | Me | Pom | Tz |
| 177 | 1-(EtO)Et | Me | Me | Mod | COOH |
| 178 | 1-(Eto)Et | Me | Me | Mod | Tz |
| 179 | 1-(EtO)Et | Me | Me | Et | COOH |
| 180 | 1-(EtO)Et | Me | Me | Et | Tz |
| 181 | HOCH$_2$— | Me | Me | H | COOH |
| 182 | HOCH$_2$— | Me | Me | H | Tz |
| 183 | HOCH$_2$— | Me | Me | Et | COOH |
| 184 | HOCH$_2$— | Me | Me | Et | Tz |
| 185 | MeOCH$_2$— | Me | Et | Pom | COOH |
| 186 | MeOCH$_2$— | Me | Et | Pom | Tz |
| 187 | MeSCH$_2$— | Me | Et | Pom | COOH |
| 188 | MeSCH$_2$— | Me | Et | Pom | Tz |
| 189 | MeS— | Me | Et | Pom | COOH |
| 190 | MeS— | Me | Et | Pom | Tz |
| 191 | MeOCH$_2$— | Me | Et | Mod | COOH |
| 192 | MeOCH$_2$— | Me | Et | Mod | Tz |
| 193 | MeSCH$_2$— | Me | Et | Mod | COOH |
| 194 | MeSCH$_2$— | Me | Et | Mod | Tz |
| 195 | MeS— | Me | Et | Mod | COOH |
| 196 | MeS— | Me | Et | Mod | Tz |
| 197 | EtS— | Me | Et | Mod | COOH |
| 198 | EtS— | Me | Et | Mod | Tz |
| 199 | MeOCH$_2$— | Me | Et | EtcOCH$_2$— | COOH |
| 200 | MeOCH$_2$— | Me | Et | EtcOCH$_2$— | Tz |
| 201 | MeSCH$_2$— | Me | Et | EtcOCH$_2$— | COOH |
| 202 | MeSCH$_2$— | Me | Et | EtcOCH$_2$— | Tz |
| 203 | MeS— | Me | Et | EtcOCH$_2$— | COOH |
| 204 | MeS— | Me | Et | EtcOCH$_2$— | Tz |
| 205 | MeOCH$_2$— | Me | Et | iPrcOCH$_2$— | COOH |
| 206 | MeOCH$_2$— | Me | Et | iPrcOCH$_2$— | Tz |
| 207 | MeSCH$_2$— | Me | Et | iPrcOCH$_2$— | COOH |
| 208 | MeSCH$_2$— | Me | Et | iPrcOCH$_2$— | Tz |
| 209 | MeS— | Me | Et | iPrcOCH$_2$— | COOH |
| 210 | MeS— | Me | Et | iPrcOCH$_2$— | Tz |
| 211 | EtS— | Me | Et | iPrcOCH$_2$— | Tz |
| 212 | MeOCH$_2$— | Me | Et | 1-(EtcO)Et | COOH |
| 213 | MeOCH$_2$— | Me | Et | 1-(EtcO)Et | Tz |
| 214 | MeSCH$_2$— | Me | Et | 1-(EtcO)Et | COOH |
| 215 | MeSCH$_2$— | Me | Et | 1-(EtcO)Et | Tz |
| 216 | MeS— | Me | Et | 1-(EtcO)Et | COOH |
| 217 | MeS— | Me | Et | 1-(EtcO)Et | Tz |
| 218 | MeOCH$_2$— | Me | Et | 1-(iPrcO)Et | COOH |
| 219 | MeOCH$_2$— | Me | Et | 1-(iPrcO)Et | Tz |
| 220 | MeSCH$_2$— | Me | Et | 1-(iPrcO)Et | COOH |
| 221 | MeSCH$_2$— | Me | Et | 1-(iPrcO)Et | Tz |
| 222 | MeS— | Me | Et | 1-(iPrcO)Et | COOH |
| 223 | MeS— | Me | Et | 1-(iPrcO)Et | Tz |
| 224 | MeOCH$_2$— | Me | Et | Phth | COOH |
| 225 | MeOCH$_2$— | Me | Et | Phth | Tz |
| 226 | MeSCH$_2$— | Me | Et | Phth | COOH |
| 227 | MeSCH$_2$— | Me | Et | Phth | Tz |
| 228 | MeS— | Me | Et | Phth | COOH |
| 229 | MeS— | Me | Et | Phth | Tz |
| 230 | MeOCH$_2$— | Me | H | H | COOH |
| 231 | MeOCH$_2$— | Me | H | H | Tz |
| 232 | EtOCH$_2$— | Me | H | H | COOH |
| 233 | EtOCH$_2$— | Me | H | H | Tz |
| 234 | 1-(MeO)Et | Me | H | H | COOH |
| 235 | 1-(MeO)Et | Me | H | H | Tz |
| 236 | MeSCH$_2$— | Me | H | H | COOH |
| 237 | MeSCH$_2$— | Me | H | H | Tz |
| 238 | EtSCH$_2$— | Me | H | H | COOH |
| 239 | EtSCH$_2$— | Me | H | H | Tz |
| 240 | 1-(MeS)Et | Me | H | H | COOH |
| 241 | 1-(MeS)Et | Me | H | H | Tz |
| 242 | MeS— | Me | H | H | COOH |
| 243 | MeS— | Me | H | H | Tz |
| 244 | EtS— | Me | H | H | COOH |
| 245 | EtS— | Me | H | H | Tz |
| 246 | MeOCH$_2$— | Me | H | Pom | COOH |
| 247 | MeOCH$_2$— | Me | H | Pom | Tz |
| 248 | MeSCH$_2$— | Me | H | Pom | COOH |
| 249 | MeSCH$_2$— | Me | H | Pom | Tz |
| 250 | MeS— | Me | H | Pom | COOH |
| 251 | MeS— | Me | H | Pom | Tz |
| 252 | MeOCH$_2$— | Me | H | Mod | COOH |
| 253 | MeOCH$_2$— | Me | H | Mod | Tz |
| 254 | MeSCH$_2$— | Me | H | Mod | COOH |
| 255 | MeSCH$_2$— | Me | H | Mod | Tz |
| 256 | MeS— | Me | H | Mod | COOH |
| 257 | MeS— | Me | H | Mod | Tz |
| 258 | EtS— | Me | H | Mod | COOH |
| 259 | EtS— | Me | H | Mod | Tz |
| 260 | MeOCH$_2$— | Me | H | EtcOCH$_2$— | Tz |
| 261 | MeSCH$_2$— | Me | H | EtcOCH$_2$— | COOH |
| 262 | MeSCH$_2$— | Me | H | EtcOCH$_2$— | Tz |
| 263 | MeS— | Me | H | EtcOCH$_2$— | Tz |
| 264 | MeOCH$_2$— | Me | H | iPrcOCH$_2$— | COOH |
| 265 | MeOCH$_2$— | Me | H | iPrcOCH$_2$— | Tz |
| 266 | MeSCH$_2$— | Me | H | iPrcOCH$_2$— | COOH |
| 267 | MeSCH$_2$— | Me | H | iPrcOCH$_2$— | Tz |
| 268 | MeS— | Me | H | iPrcOCH$_2$— | COOH |
| 269 | MeS— | Me | H | iPrcOCH$_2$— | Tz |
| 270 | MeOCH$_2$— | Me | H | 1-(EtcO)Et | Tz |
| 271 | MeSCH$_2$— | Me | H | 1-(EtcO)Et | COOH |
| 272 | MeSCH$_2$— | Me | H | 1-(EtcO)Et | Tz |
| 273 | MeS— | Me | H | 1-(EtcO)Et | COOH |
| 274 | MeS— | Me | H | 1-(EtcO)Et | Tz |
| 275 | MeOCH$_2$— | Me | H | 1-(iPrcO)Et | Tz |
| 276 | MeSCH$_2$— | Me | H | 1-(iPrcO)Et | Tz |
| 277 | MeS— | Me | H | 1-(iPrcO)Et | Tz |
| 278 | MeOCH$_2$— | Me | H | Phth | Tz |
| 279 | MeSCH$_2$— | Me | H | Phth | Tz |
| 280 | MeS— | Me | H | Phth | COOH |
| 281 | MeS— | Me | H | Phth | Tz |
| 282 | MeOCH$_2$— | H | H | H | Tz |
| 283 | EtOCH$_2$— | H | H | H | COOH |
| 284 | EtOCH$_2$— | H | H | H | Tz |
| 285 | 1-(MeO)Et | H | H | H | Tz |
| 286 | MeSCH$_2$— | H | H | H | COOH |

TABLE 7-continued

| Compound No. | $R_p^1$-$X_p$-$R_p^2$- | $R_p^3$ | $R_p^4$ | $R_p^5$ | $R_p^{6'}$ |
|---|---|---|---|---|---|
| 287 | MeSCH$_2$— | H | H | H | Tz |
| 288 | EtSCH$_2$— | H | H | H | COOH |
| 289 | EtSCH$_2$— | H | H | H | Tz |
| 290 | 1-(MeS)Et | H | H | H | COOH |
| 291 | 1-(MeS)Et | H | H | H | Tz |
| 292 | MeS— | H | H | H | COOH |
| 293 | MeS— | H | H | H | Tz |
| 294 | EtS— | H | H | H | COOH |
| 295 | EtS— | H | H | H | Tz |
| 296 | MeOCH$_2$— | H | H | Pom | Tz |
| 297 | MeSCH$_2$— | H | H | Pom | COOH |
| 298 | MeSCH$_2$— | H | H | Pom | Tz |
| 299 | MeS— | H | H | Pom | Tz |
| 300 | MeOCH$_2$— | H | H | Mod | COOH |
| 301 | MeOCH$_2$— | H | H | Mod | Tz |
| 302 | MeSCH$_2$— | H | H | Mod | COOH |
| 303 | MeSCH$_2$— | H | H | Mod | Tz |
| 304 | MeS— | H | H | Mod | COOH |
| 305 | MeS— | H | H | Mod | Tz |
| 306 | EtS— | H | H | Mod | COOH |
| 307 | EtS— | H | H | Mod | Tz |
| 308 | MeOCH$_2$— | H | H | EtcOCH$_2$— | Tz |
| 309 | MeSCH$_2$— | H | H | EtcOCH$_2$— | Tz |
| 310 | MeS— | H | H | EtcOCH$_2$— | Tz |
| 311 | MeOCH$_2$— | H | H | iPrcOCH$_2$— | Tz |
| 312 | MeSCH$_2$— | H | H | iPrcOCH$_2$— | Tz |
| 313 | MeS— | H | H | iPrcOCH$_2$— | Tz |
| 314 | MeOCH$_2$— | H | H | 1-(EtcO)Et | Tz |
| 315 | MeSCH$_2$— | H | H | 1-(EtcO)Et | Tz |
| 316 | MeS— | H | H | 1-(EtcO)Et | Tz |
| 317 | MeOCH$_2$— | H | H | 1-(iPrcO)Et | Tz |
| 318 | MeSCH$_2$— | H | H | 1-(iPrcO)Et | Tz |
| 319 | MeS— | H | H | 1-(iPrcO)Et | Tz |
| 320 | MeOCH$_2$— | H | H | Phth | Tz |
| 321 | MeSCH$_2$— | H | H | Phth | Tz |
| 322 | MeS— | H | H | Phth | COOH |
| 323 | MeS— | H | H | Phth | Tz |
| 324 | EtOCH$_2$— | Me | H | Pom | COOH |
| 325 | EtOCH$_2$— | Me | H | Pom | Tz |
| 326 | EtOCH$_2$— | Me | H | Mod | COOH |
| 327 | EtOCH$_2$— | Me | H | Mod | Tz |
| 328 | EtOCH$_2$— | Me | H | EtcOCH$_2$— | COOH |
| 329 | EtOCH$_2$— | Me | H | EtcOCH$_2$— | Tz |
| 330 | EtOCH$_2$— | Me | H | iPrcOCH$_2$— | COOH |
| 331 | EtOCH$_2$— | Me | H | iPrcOCH$_2$— | Tz |
| 332 | EtOCH$_2$— | Me | H | 1-(iPrcO)Et | COOH |
| 333 | EtOCH$_2$— | Me | H | 1-(iPrcO)Et | Tz |
| 334 | EtOCH$_2$— | Me | H | Phth | COOH |
| 335 | EtOCH$_2$— | Me | H | Phth | Tz |
| 336 | EtOCH$_2$— | H | H | Pom | COOH |
| 337 | EtOCH$_2$— | H | H | EtcOCH$_2$— | Tz |
| 338 | EtOCH$_2$— | H | H | 1-(EtcO)Et | Tz |
| 339 | EtOCH$_2$— | H | H | Phth | Tz |
| 340 | MeOCH$_2$— | H | H | H | COOH |

Of the compounds illustrated above, preferred compounds are Compounds No. 1, 2, 3, 4, 5, 6, 9, 10, 11, 12, 17, 18, 19, 20, 23, 24, 25, 26, 27, 28, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 230, 231, 232, 233, 236, 237, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 286, 287, 288, 289, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339 and 340; and more preferred compounds are Compounds No. 1, 2, 3, 4, 17, 18, 19, 20, 23, 24, 25, 26, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 231, 233, 247, 253, 260, 265, 270, 275, 278, 282, 284, 296, 301, 308, 311, 314, 317, 320, 325, 327, 329, 331, 333, 335, 337, 338 and 339.

The most preferred specific compounds are Compounds No.:

2. 4-(1-hydroxy-1-methylethyl)-2-methoxymethyl-1-{4-[2-(tetrazol-5-yl)phenyl]phenyl}methylimidazole-5-carboxylic acid;

4. 2-ethoxymethyl-4-(1-hydroxy-1-methylethyl)-1-{4-[2-(tetrazol-5-yl)phenyl]phenyl}methylimidazole-5-carboxylic acid;

26. 2-ethylthio-4-(1-hydroxy-1-methylethyl)-1-{4-[2-(tetrazol-5-yl)phenyl]phenyl}methylimidazole-5-carboxylic acid;

86. pivaloyloxymethyl 4-(1-hydroxy-1-methylethyl)-2-methoxymethyl-1-{4-[2-(tetrazol-5-yl)phenyl]phenyl}-methylimidazole-5-carboxylate;

88. pivaloyloxymethyl 2-ethoxymethyl-4-(1-hydroxy-1-methylethyl)-1-{4-[2-(tetrazol-5-yl)phenyl]phenyl}methylimidazole-5-carboxylate;

94. pivaloyloxymethyl 2-ethylthio-4-(1-hydroxy-1-methylethyl)-1-{4-[2-(tetrazol-5-yl)phenyl]phenyl}methylimidazole-5-carboxylate;

96. (5-methyl-2-oxo-1,3-dioxolen-4-yl)methyl 4-(1-hydroxy-1-methylethyl)-2-methoxymethyl-1-{4-[2-(tetrazol-5-yl)phenyl]phenyl}methylimidazole-5-carboxylate;

98. (5-methyl-2-oxo-1,3-dioxolen-4-yl)methyl 2-ethoxymethyl-4-(1-hydroxy-1-methylethyl)-1-{4-[2-(tetrazol-5-yl)phenyl]phenyl}methylimidazole-5-carboxylate;

104. (5-methyl-2-oxo-1,3-dioxolen-4-yl)methyl 2-ethylthio-4-(1-hydroxy-1-methylethyl)-1-{4-[2-(tetrazol-5-yl)phenyl]phenyl}methylimidazole-5-carboxylate;

106. ethoxycarbonyloxymethyl 4-(1-hydroxy-1-methylethyl)-2-methoxymethyl-1-{4-[2-(tetrazol-5-yl)phenyl]phenyl}methylimidazole-5-carboxylate;

108. ethoxycarbonyloxymethyl 2-ethoxymethyl-4-(1-hydroxy-1-methylethyl)-1-{4-[2-(tetrazol-5-yl)phenyl]phenyl}methylimidazole-5-carboxylate;

114. ethoxycarbonyloxymethyl 2-ethylthio-4-(1-hydroxy-1-methylethyl)-1-{4-[2-(tetrazol-5-yl)phenyl]phenyl}methylimidazole-5-carboxylate;

116. isopropoxycarbonylmethyl 4-(1-hydroxy-1-methylethyl)-2-methoxymethyl-1-{4-[2-(tetrazol-5-yl)phenyl]phenyl}methylimidazole-5-carboxylate;

118. isopropoxycarbonyloxxymethyl 2-ethoxymethyl-4-(1-hydroxy-1-methylethyl)-1-{4-[2-(tetrazol-5-yl)phenyl]phenyl}methylimidazole-5-carboxylate and;

124. isopropoxycarbonyloxymethyl 2-ethylthio-4-(1-hydroxy-1-methylethyl)-1-{4- [2-(tetrazol-5-yl)phenyl]phenyl}methylimidazole-5-carboxylate;

and pharmaceutically acceptable salts and esters thereof.

The compounds of formula (I) of the present invention can be prepared by a variety of methods well known in the art for the preparation of compounds of this type.

The example, in general terms, the compounds of formula (I) may be prepared by reacting a compound of formula (II):

in which:

R$^1$ is as defined above and R$^d$ represents a group of formula

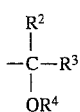

wherein $R^2$, $R^3$ and $R^4$ are as defined above, or $R^d$ represents a group of formula —$COOR^f$ wherein $R^f$ represents a carboxy-protecting group, $R^d$ represents a group of formula —$COR^2$, wherein $R^2$ is as defined above or $R^d$ represents a cyano group; and $R^e$ represents a cyano group, a carboxy group or a group of formula —$COOR^f$, wherein $R^f$ is as defined above, with a compound of formula (III):

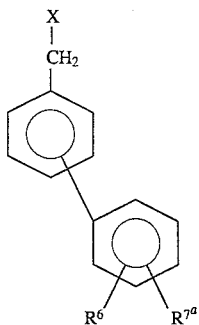

(III)

in which: $R^6$ is as defined above; $R^{7a}$ represents a protected carboxy group, a cyano group, a protected tetrazol-5-yl group, a carbamoyl group or an alkylcarbamoyl group; and X represents a halogen atom; to give a compound of formula (IV):

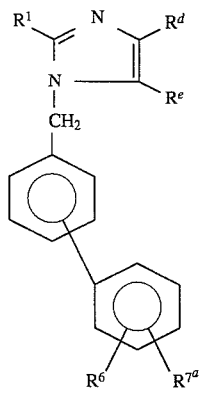

(IV)

wherein $R^d$, $R^e$, $R^1$, $R^6$ and $R^{7a}$ are as defined above; and in any order, removing protecting groups, and, if necessary, converting said group $R^d$ to a group of formula

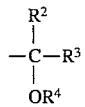

wherein $R^2$, $R^3$ and $R^4$ are as defined above, and, if necessary, converting said group $R^e$ to a group $R^5$, converting said group $R^{7a}$ to a group $R^7$, or alkylating or acylating a hydroxy group in $R^4$, to give a compound of formula (I); and optionally salifying or esterifying the product.

Preferably, $R^e$ represents a protected carboxy group, when $R^{7a}$ represents a protected carboxy group, a cyano group, a protected tetrazolyl group, a carbamoyl group or an alkylcarbamoyl group, and $R^e$ represents a cyano group when $R^{7a}$ represents a protected carboxy group or a protected tetrazolyl group.

In more detail, the compounds of formula (I) of the present invention may be prepared as described below in Reaction Schemes A to F.

Reaction Scheme A:

In this Reaction Scheme, a compound of formula (I) is prepared by reacting an imidazole-5-carboxylic acid or ester thereof of formula (V) with a biphenylmethyl halide of formula (III), and then, if desired, removing protecting groups, converting the group of formula —$COOR^{5a}$ to any other group represented by $R^5$, converting the group represented by $R^{7a}$ to any other group represented by $R^7$ and/or alkylating or acylating a hydroxy group in $R^4$, as shown below:

Reaction Scheme A:

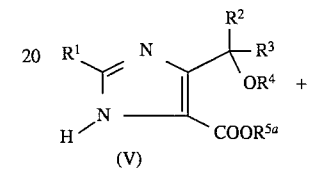

(V)

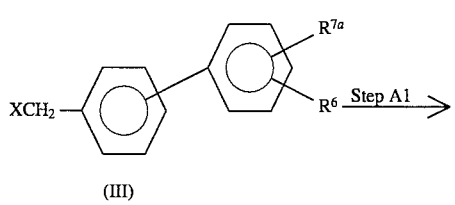

(III)

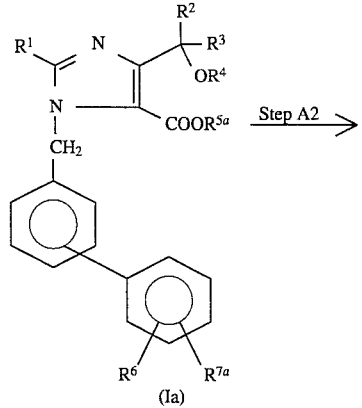

(Ia)

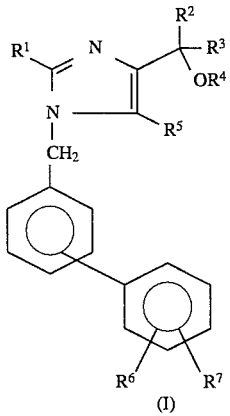

(I)

In the above reaction scheme, $R^1$, $R^2$, $R^3$, $R^4$, $R^5$, $R^{5a}$, $R^6$, $R^7$, $R^{7a}$ and X are as defined above, and $R^{5a}$ preferably represents a group other than a hydrogen atom.

Where $R^{7a}$ represents a protected carboxy group, the protecting group may be any of the ester residues illustrated above in relation to $R^{5a}$. Alternatively, $R^{7a}$ may be a carbamoyl group or a substituted carbamoyl group of formula —CONHR, where R represents a hydrogen atom or an alkyl group having from 1 to 6 carbon atoms, for example any of those illustrated above in relation to $R^1$. Examples of such carbamoyl groups which may be represented by $R^{7a}$ include the carbamoyl, methylcarbamoyl, ethylcarbamoyl, propylcarbamoyl, butylcarbamoyl, t-butylcarbamoyl, pentylcarbamoyl, t-pentylcarbamoyl and hexylcarbamoyl groups, of which the carbamoyl, t-butylcarbamoyl and t-pentylcarbamoyl groups are preferred. Where $R^{7a}$ represents a protected tetrazolyl group, the protecting group may be any protecting group commonly used to protect tetrazolyl groups in conventional compounds of this type. Examples of suitable protecting groups include the aralkyl groups defined and exemplified above in relation to $R^2$, but is preferably a benzyl, diphenylmethyl (benzhydryl) or triphenylmethyl (trityl group), most preferably a trityl group.

X represents a halogen atom, preferably a chlorine, bromine or iodine atom).

In Step A1 of this Reaction Scheme, a compound of formula (Ia) is prepared by reacting an imidazole-5-carboxylate compound of formula (V) with a biphenylmethyl compound of formula (III). The reaction normally and preferably takes place in an inert solvent and preferably in the presence of a base.

The reaction is normally and preferably effected in the presence of a solvent. There is no particular restriction on the nature of the solvent to be employed, provided than it has no adverse effect on the reaction or on the reagents involved and that it can dissolve the reagents, at least to some extent. Examples of suitable solvents include: hydrocarbons, preferably aromatic hydrocarbons, such as benzene or toluene; ethers, such as tetrahydrofuran or dioxane; alcohols, such as methanol, ethanol or t-butanol; amides, such as N,N-dimethylacetamide, N,N-dimethylformamide or N-methyl-2-pyrrolidinone; ketones, such as acetone or methyl ethyl ketone; nitriles, such as acetonitrile; and sulfoxides, such as dimethyl sulfoxide. Of these, we prefer the amides, ketones, nitriles and sulfoxides.

The nature of the base employed in the reaction is likewise not critical, and any base capable of reacting with the acid H-X can be used in this reaction. Preferred examples of bases which may be used include: alkali metal carbonates, such as sodium carbonate or potassium carbonate; alkali metal hydrides, such as sodium hydride, potassium hydride or lithium hydride; alkali metal alkoxides, such as sodium methoxide, sodium ethoxide, potassium t-butoxide or lithium methoxide; and alkali metal bicarbonates, such as sodium bicarbonate or potassium bicarbonate. Of these, we prefer the alkali metal carbonates, alkali metal hydrides or alkali metal alkoxides.

The reaction can take place over a wide range of temperatures, and the precise reaction temperature is not critical to the invention. In general, we find it convenient to carry out the reaction at a temperature of from —10° C. to 100° C., more preferably from 0° C. to 80° C. The time required for the reaction may also vary widely, depending on many factors, notably the reaction temperature and the nature of the reagents and solvent employed. However, provided that the reaction is effected under the preferred conditions outlined above, a period of from 30 minutes to 24 hours, more preferably from 1 to 16 hours, will usually suffice.

After completion of the reaction, the desired compound of formula (Ia) can be recovered from the reaction mixture by conventional means. For example, one suitable recovery procedure comprises: removing the solvent by distillation under reduced pressure; mixing the residue with water; extracted the residue with a water-immiscible solvent, such as ethyl acetate; drying the extract over, for example, anhydrous sodium sulfate; and freeing the product from the solvent by distillation. The resulting product can, if necessary, be purified by conventional means, for example, by recrystallization, or the various chromatography techniques, notably preparative thin layer chromatography or column chromatography.

Step A2 may comprise any one or (if appropriate) more of the following reactions:

(i) removing the carboxy-protecting groups either selectively or non-selectively from the group of formula —COOR$^{5a}$ and/or the group $R^{7a}$, to convert it or them to a free carboxy group as represented by $R^5$ $R^7$;

(ii) esterifying any such free carboxy group to provide an ester of the group, for example as illustrated above in relation to $R^5$;

(iii) converting such a free carboxy group represented by $R^5$ to a group of formula —CONR$^8$R$^9$;

(iv) removing the tetrazolyl-protecting group;

(v) converting a cyano group represented by $R^{7a}$ to a tetrazolyl group;

(vi) converting a monoalkylcarbamoyl group or a carbamoyl group represented by $R^{7a}$ first to a cyano group and then to a tetrazolyl group;

(vii) where $R^4$ represents a tri-substituted silyl group, an aralkyl group, an aliphatic acyl group, an alkoxymethyl group, an alkoxyalkoxymethyl group, a haloalkoxymethyl group, a tetrahydropyranyl group, a tetrahydrothiopyranyl group, a tetrahydrothienyl group, a tetrahydrofuryl group or a substituted tetrahydropyranyl, tetrahydrothiopyranyl, tetrahydrothienyl or tetrahydrofuryl group having a halogen or alkoxy substituent, all of which can be regarded as hydroxy-protecting groups, removing the protecting group to produce a compound in which $R^4$ represents a hydrogen atom; and (viii) where $R^4$ represents a hydroxy group, alkylating or acylating this group.

(i) Removal of carboxy-protecting groups:

The nature of the reaction employed to remove the carboxy-protecting group will, of course, depend on the nature of the group to be removed and are well known in the field of organic synthesis.

For example, where the carboxy-protecting group is an aralkyl group, for example a benzyl or p-nitrobenzyl group, the protecting group may be removed by catalytic reduction, in the presence of hydrogen, which may be under atmospheric pressure or superatmospheric pressure, for example up to 5 atmospheres pressure. The reaction normally and preferably takes place in an inert solvent (preferably an alcohol, such as methanol or ethanol, or a carboxylic acid, such as acetic acid) and in the presence of a catalyst. Any catalyst commonly used for catalytic hydrogenation or reduction may equally be employed here, preferably palladium-on-charcoal or platinum oxide.

Where the carboxy-protecting group is a t-butyl or diphenylmethyl group, it may be removed by reacting the protected compound with an acid (preferably a mineral acid, such as hydrogen chloride or sulfuric acid, or an organic acid, such as trifluoroacetic acid, methanesulfonic acid or p-toluenesulfonic acid) in an inert solvent (preferably an alcohol, such as methanol or ethanol; an ether, such as tetrahydrofuran or dioxane; water; or a mixture of water and one or more of the above organic solvents).

Where the carboxy-protecting group is a silyl group, this may be a group of formula —SiR$^a$R$^b$R$^c$, in which R$^a$, R$^b$ and R$^c$ are as defined above. In this case, the protecting group may be removed by reacting the protected compound with an acid (preferably a mineral acid, such as hydrogen chloride, or an organic acid, such as acetic acid, trifluoroacetic acid, methanesulfonic acid or p-toluenesulfonic acid) or with a fluorine salt, such as tetrabutylammonium fluoride. The reaction normally and preferably takes place in an inert solvent (preferably an ether, such as tetrahydrofuran or dioxane; an alcohol, such as methanol or ethanol; an amide, such as N,N-dimethylformamide or N,N-dimethylacetamide; water; or a mixture of water and one or more of the above organic solvents).

Where the carboxy-protecting group is an ester residue, the protecting group may be removed by hydrolysis using a base (preferably an alkali metal hydroxide, such as lithium hydroxide, sodium hydroxide or potassium hydroxide, or an alkali metal carbonate, such as sodium carbonate or potassium carbonate) in an inert solvent (preferably an alcohol, such as methanol or ethanol; an ether, such as tetrahydrofuran or dioxane; water; or a mixture of water and one or more of the above organic solvents). Where R$^4$ represents an acyl group, it is removed simultaneously in the course of this reaction.

The reaction can take place over a wide range of temperatures, and the precise reaction temperature is not critical to the invention. In general, we find it convenient to carry out the reaction at a temperature of from 0° C. to 100° C., more preferably from about room temperature to 60° C. The time required for the reaction may also vary widely, depending on many factors, notably the reaction temperature and the nature of the reagents and solvent employed. However, provided that the reaction is effected under the preferred conditions outlined above, a period of from 30 minutes to 24 hours, more preferably from 1 to 16 hours, will usually suffice.

After completion of the reaction, the desired compound may be recovered by conventional means, the nature of which will depend on the nature of the reaction. For example, where the deprotection is carried out by catalytic reduction, the desired product can be recovered by filtering off the catalyst and by distilling off the solvent. Where the deprotection is carried out using an acid, the desired product can be recovered by collecting the precipitate in the reaction system by filtration or by concentration of the reaction mixture. Where the deprotection is carried out by alkaline hydrolysis, the desired product can be recovered by distilling off the solvent and then neutralizing the residue with an aqueous acid, after which the precipitate in the aqueous solvent may be collected by filtration; alternatively, it may be recovered by neutralizing the aqueous layer obtained by extracting the reaction mixture with a water-immiscible organic solvent (such as ethyl acetate or diethyl ether), extracting the neutralized solution with a water-immiscible organic solvent (such as ethyl acetate), and then distilling off the solvent. The reaction product may, if necessary, be further purified by conventional means, for example by recrystallization or the various chromatography techniques, notably preparative thin layer chromatography or column chromatography.

Each of the protecting groups represented by R$^{5a}$ and R$^{7a}$ can be selectively eliminated by appropriate choice of the protecting groups and the specific reaction conditions employed to remove them.

(ii) Esterification

Where a compound containing one or more free carboxy groups is produced, this group or these groups may be esterified, by methods well known in organic chemistry. For example, the reaction may be carried out by reacting the corresponding carboxylic acid with a compound of formula, R$^{5b}$-Y [in which R$^{5b}$ may represent any of the groups defined above for R$^{5a}$ other than a hydrogen atom, and Y represents a halogen atom, such as a chlorine, bromine or iodine atom, a group of formula —OSO$_3$R$^{5b}$(in which R$^{5b}$ is as defined above) or a sulfonyloxy group, such as a methanesulfonyloxy or p-toluenesulfonyloxy group]. The reaction is carried out in the presence of a base, for example: an organic amine, such as triethylamine, pyridine or N-methylmorpholine; an alkali metal carbonate, such as sodium carbonate or potassium carbonate; or an alkali metal hydrogencarbonate, such as sodium hydrogencarbonate or potassium hydrogencarbonate. It is also normally and preferably carried out in an inert solvent (preferably an amide, such as N,N-dimethylformamide or N,N-dimethylacetamide; a halogenated hydrocarbon, preferably a halogenated aliphatic hydrocarbon, such as methylene chloride; a ketone, such as acetone or methyl ethyl ketone; or an ether, such as tetrahydrofuran or dioxane). Where the desired ester group is an alkyl group, the reaction is carried out by reacting the carboxylic acid with the corresponding dialkyl sulfate.

The reaction can take place over a wide range of temperatures, and the precise reaction temperature is not critical to the invention. In general, we find it convenient to carry out the reaction at a temperature of from 0° C. to 120° C., more preferably from 20° C. to 80° C. The time required for the reaction may also vary widely, depending on many factors, notably the reaction temperature and the nature of the reagents and solvent employed. However, provided that the reaction is effected under the preferred conditions outlined above, a period of from 30 minutes to 24 hours, more preferably from 1 to 16 hours, will usually suffice.

Where a carboxy-protecting group is a C$_1$–C$_6$ alkyl group, the esterification reaction may be carried out by reacting the corresponding carboxylic acid with a C$_1$–C$_6$ alcohol, such as methanol, ethanol, propanol or hexanol, in the presence of an acid catalyst, such as hydrogen chloride or sulfuric acid, in an inert solvent (for example: one of the C$_1$–C$_6$ alcohols which may be used as the starting material described above; a halogenated hydrocarbon, such as methylene chloride; or an ether, such as tetrahydrofuran or dioxane) at a temperature of from 0° C. to 100° C. for a period of from 1 to 24 hours, or by reacting the corresponding carboxylic acid with a halogenating agent (e.g. phosphorus pentachloride, thionyl chloride or oxalyl chloride) in an inert solvent (for example: a halogenated hydrocarbon, such as methylene chloride; an ether, such as tetrahydrofuran or dioxane; or an aromatic hydrocarbon, such as benzene or toluene) at a temperature of about room temperature for a period of from 30 minutes to 5 hours to yield the corresponding acyl halide, which is then reacted with the corresponding alcohol in an inert solvent (e.g. benzene or methylene chloride) in the presence of a base (for example triethylamine; in case of the t-butyl ester, potassium t-butoxide is used as the preferred base) at a temperature of about room temperature for a period of from 30 minutes to 10 hours. The desired compound can be recovered by conventional means, for example, by a similar method to that described in Step A1.

(iii) Formation of a carbamoyl group

Conversion of a carboxy group represented by R$^5$ to a group of formula —CONR$^8$R$^9$, in which R$^8$ and R$^9$ are as defined above, may be carried out using well known methods, for example by reacting the carboxylic acid compound, in which the group R$^7$ is protected, with a compound of formula (VI):

R⁸R⁹NH   (VI)

wherein $R^8$ and $R^9$ are as defined above).

This reaction consists of the formation of a peptide bond and is generally well known in organic synthetic chemistry. It may be carried out in an inert solvent (preferably a halogenated hydrocarbon, more preferably a halogenated aliphatic hydrocarbon, such as methylene chloride or chloroform; an ester, such as ethyl acetate; an ether, such as tetrahydrofuran or dioxane; or an amide, such as N,N-dimethylacetamide or N,N-dimethylformamide) in the presence of a condensing agent.

Examples of condensing agents which may be used in this reaction include: carbodiimides, such as N,N-dicyclohexylcarbodiimide or 1-(3-dimethylaminopropyl)-3-ethylcarbodiimide hydrochloride; phosphoryl compounds, such as diphenylphosphoryl azide or diethylphosphoryl cyanide; carbonyldiimidazole; and triphenylphosphine-diethyl azodicarboxylate. Of these, we prefer the carbodiimides and diphenylphosphoryl azide. Where a phosphoryl compound is used, the reaction is preferably carried out in the presence of a tertiary amine, such as triethylamine or N-methylmorpholine.

Alternatively, the reaction in this step can be accomplished by reacting the carboxylic acid with a lower alkyl chloroformate, such as ethyl chloroformate or isobutyl chloroformate, in the presence of a tertiary amine, such as triethylamine or N-methylmorpholine, to produce a mixed acid anhydride, or by reacting the carboxylic acid with N-hydroxysuccinimide, N-hydroxybenzotriazole or p-nitrophenol or the like in the presence of a carbodiimide, such as N,N-dicyclohexylcarbodiimide, to produce the corresponding active ester, and subsequently reacting the mixed acid anhydride or the active ester with the amine compound of formula (VI).

As a further alternative, the reaction in this step can be carried out by reacting the carboxylic acid with a halogenating agent, such as phosphorus pentachloride, oxalyl chloride or thionyl chloride, in an inert solvent (for example: a halogenated hydrocarbon, such as methylene chloride; an ether, such as tetrahydrofuran or dioxane; or an aromatic hydrocarbon, such as benzene or toluene) to give the corresponding acyl halide, and then reacting the acyl halide with the amine compound of formula (VI).

All of these reactions can take place over a wide range of temperatures, and the precise reaction temperature is not critical to the invention. In general, we find it convenient to carry out the reaction at a temperature of from −20° C. to 100° C., more preferably from −5° C. to 50° C. The time required for the reaction may also vary widely, depending on many factors, notably the reaction temperature and the nature of the reagents and solvent employed. However, provided that the reaction is effected under the preferred conditions outlined above, a period of from 30 minutes to 24 hours, more preferably from 1 to 16 hours, will usually suffice.

After completion of the reaction, the reaction product can be recovered from the reaction mixture by conventional means. For example, insoluble materials in the reaction system are filtered off; a water-immiscible organic solvent, such as ethyl acetate, and water are added to the filtrate; the organic solvent layer is separated and dried over a drying agent, such as anhydrous magnesium sulfate; and then the solvent is distilled off to leave the desired product. The reaction product may, if necessary, be further purified by conventional means, for example by recrystallization or the various chromatography techniques, notably preparative thin layer chromatography or column chromatography.

(iv) Removal of tetrazolyl-protecting groups

This may be accomplished by reacting the protected compound with an acid. The reaction is normally and preferably effected in an inert solvent.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: water; an organic acid, such as acetic acid; an ether, such as tetrahydrofuran or dioxane; an alcohol, such as methanol, ethanol or t-butanol; a ketone, such as acetone or methyl ethyl ketone; or a mixture of any two or more of these solvents. Of these, we prefer water, an organic acid, an alcohol or a mixture thereof.

There is no particular limitation upon the nature of the acid used in the reaction, provided that it can normally function as a Bronsted acid. Preferred examples of such acids include: organic acids, such as acetic acid, formic acid, oxalic acid, methanesulfonic acid, p-toluenesulfonic acid or trifluoroacetic acid; and inorganic acids, such as hydrochloric acid, hydrobromic acid, sulfuric acid or phosphoric acid. Of these, we prefer acetic acid, formic acid, trifluoroacetic acid or hydrochloric acid.

The reaction can take place over a wide range of temperatures, and the precise reaction temperature is not critical to the invention. In general, we find it convenient to carry out the reaction at a temperature of from −10° C. to 120° C., more preferably from 0° C. to 100° C. The time required for the reaction may also vary widely, depending on many factors, notably the reaction temperature and the nature of the reagents and solvent employed. However, provided that the reaction is effected under the preferred conditions outlined above, a period of from 0.5 to 24 hours, more preferably from 1 to 16 hours, will usually suffice.

After completion of the reaction, the desired product of this reaction can be recovered from the reaction mixture by conventional means. For example, after distilling off the solvent, the residue is dissolved in water and a water-immiscible organic solvent. The organic layer containing the desired compound is separated and dried over anhydrous magnesium sulfate. After distilling off the solvent, the desired compound can be obtained. The reaction product may, if necessary, be further purified by conventional means, for example by recrystallization or the various chromatography techniques, notably preparative thin layer chromatography or column chromatography.

(v) Conversion of a cyano group to a tetrazolyl group

In this step, a cyano group is converted to a tetrazolyl group by reacting the cyano compound with an alkali metal azide.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: amides, such as N,N-dimethylformamide or N,N-dimethylacetamide; ethers, such as dioxane or 1,2-dimethoxyethane; and sulfoxides, such as dimethyl sulfoxide.

Examples of suitable alkali metal azides include lithium azide, sodium azide and potassium azide, of which sodium azide is preferred. There is no particular restriction on the amount of alkali metal azide employed, but we generally prefer to use from 1 to 5 equivalents, more preferably from 1 to 3 equivalents, of the alkali metal azide per equivalent of the cyano compound.

We also prefer to carry out the reaction in the presence of an ammonium halide, for example ammonium fluoride, ammonium chloride or ammonium bromide, of which ammonium chloride is preferred. There is no particular restriction on the amount of ammonium halide employed, but we generally prefer to use from 0.5 to 2 equivalents, more preferably from 1 to 1.2 equivalents, of the ammonium halide per equivalent of the cyano compound.

The reaction can take place over a wide range of temperatures, and the precise reaction temperature is not critical to the invention. In general, we find it convenient to carry out the reaction at a temperature of from 70° to 150° C., more preferably from 80° to 120° C. The time required for the reaction may also vary widely, depending on many factors, notably the reaction temperature and the nature of the reagents and solvent employed. However, provided that the reaction is effected under the preferred conditions outlined above, a period of from 10 hours to 7 days, more preferably from 1 to 5 days, will usually suffice.

Alternatively, the cyano group may be converted to a tetrazolyl group by reacting the cyano compound with a trialkyltin azide or triaryltin azide, and then treating the resulting tin compound with an acid, a base or an alkali metal fluoride.

The reaction of the cyano compound with the trialkyltin azide or triaryltin azide is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: hydrocarbons, which may be aliphatic or aromatic hydrocarbons, such as benzene, toluene, xylene or heptane; halogenated hydrocarbons, especially halogenated aliphatic hydrocarbons, such as 1,2-dichloroethane or chloroform; ethers, such as dioxane or 1,2-dimethoxyethane; amides, such as N,N-dimethylformamide or N,N-dimethylacetamide; and esters, such as ethyl acetate or butyl acetate.

Although there is no particular limitation on the nature of the trialkyltin or triaryl tin azide, and any such compound commonly used in reactions of this type may equally be employed here, we generally prefer to use: a trialkyltin azide in which each of the alkyl groups (which may be the same or different, although they are preferably the same) have from 1 to 4 carbon atoms, for example trimethyltin azide, triethyltin azide or tributyltin azide; or a triaryltin azide in which each of the aryl groups (which may be the same or different, although they are preferably the same) is as defined above in relation to the aryl groups which may be represented by $R^2$, preferably a phenyl or substituted phenyl group, for example triphenyltin azide or tritolyltin azide. The amount of the trialkyltin azide or triaryltin azide employed is not critical, although an amount of from 1 to 3 equivalents per equivalent of cyano compound is preferred, and from 1 to 2 equivalents is more preferred.

The reaction of the cyano compound with the trialkyltin azide or triaryltin azide can take place over a wide range of temperatures, and the precise reaction temperature is not critical to the invention. In general, we find it convenient to carry out the reaction at a temperature of from 60° to 150° C., more preferably from 80° to 120° C. The time required for the reaction may also vary widely, depending on many factors, notably the reaction temperature and the nature of the reagents and solvent employed. However, provided that the reaction is effected under the preferred conditions outlined above, a period of from 8 hours to 7 days, more preferably from 1 to 5 days, will usually suffice.

The tin-containing compound produced by this reaction is then treated with an acid, a base or an alkali metal fluoride, to convert it to the desired tetrazolyl compound. Any acid, base or alkali metal fluoride commonly used for this type of reaction may be used, and examples of suitable compounds include: acids, especially mineral acids, such as hydrochloric acid or sulfuric acid; bases, especially inorganic bases, such as alkali metal carbonates and hydrogencarbonates (for example sodium carbonate, potassium carbonate, sodium hydrogencarbonate or potassium hydrogencarbonate) or alkali metal hydroxides (for example sodium hydroxide or potassium hydroxide); and alkali metal fluorides, such as lithium fluoride, sodium fluoride or potassium fluoride.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include those listed above for the reaction of the cyano compound with the trialkyltin azide or triaryltin azide and other solvents, such as alcohols (for example methanol or ethanol), water or aqueous alcohols. The reaction can take place over a wide range of temperatures, and the precise reaction temperature is not critical to the invention. In general, we find it convenient to carry out the reaction at a temperature of from 0° C. to 100° C., preferably about room temperature. The time required for the reaction may also vary widely, depending on many factors, notably the reaction temperature and the nature of the reagents and solvent employed. However, provided that the reaction is effected under the preferred conditions outlined above, a period of from 30 minutes to 3 days, more preferably from 1 hour to 24 hours, will usually suffice.

A further alternative method of converting a cyano group to a tetrazolyl group is to react the cyano compound with a trialkyltin halide or triaryltin halide, in the presence of an alkali metal azide, and then treating the resulting tin compound with an acid, a base or an alkali metal fluoride.

The reaction of the cyano compound with the trialkyltin halide or triaryltin halide in the presence of an alkali metal azide is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: hydrocarbons, which may be aliphatic or aromatic hydrocarbons, such as benzene, toluene, xylene or heptane; halogenated hydrocarbons, especially halogenated aliphatic hydrocarbons, such as 1,2-dichloroethane or chloroform; ethers, such as dioxane or 1,2-dimethoxyethane; ketones, such as acetone or methyl ethyl ketone; amides, such as N,N-dimethylformamide or N,N-dimethylacetamide; and esters, such as ethyl acetate or butyl acetate.

Although there is no particular limitation on the nature of the trialkyltin or triaryl tin halide, and any such compound commonly used in reactions of this type may equally be employed here, we generally prefer to use: a trialkyltin halide in which each of the alkyl groups (which may be the same or different, although they are preferably the same) have from 1 to 4 carbon atoms, for example trimethyltin chloride, trimethyltin bromide, triethyltin chloride or tributyltin chloride; or a triaryltin halide in which each of the aryl groups (which may be the same or different, although they are preferably the same) is as defined above in relation to the aryl groups which may be represented by $R^2$, preferably a phenyl or substituted phenyl group, for example triphenyltin chloride or tritolyltin chloride. The amount of the trialkyltin halide or triaryltin halide employed is not critical, although an amount of from 1 to 3 equivalents per equivalent of cyano compound is preferred, and from 1 to 2 equivalents is more preferred.

There is no particular restriction on the alkali metal azide which is also employed in this reaction. Examples include lithium azide, sodium azide and potassium azide, of which sodium azide is preferred. The amount of the alkali metal azide employed is not critical, although an amount of from 1 to 3 equivalents per equivalent of cyano compound is preferred, and from 1 to 2 equivalents is more preferred.

The reaction of the cyano compound with the trialkyltin halide or triaryltin halide in the presence of an alkali metal azide can take place over a wide range of temperatures, and the precise reaction temperature is not critical to the invention. In general, we find it convenient to carry out the reaction at a temperature of from 60° to 150° C., more preferably from 80° to 120° C. The time required for the reaction may also vary widely, depending on many factors, notably the reaction temperature and the nature of the reagents and solvent employed. However, provided that the reaction is effected under the preferred conditions outlined above, a period of from 8 hours to 7 days, more preferably from 1 to 5 days, will usually suffice.

The tin-containing compound produced by this reaction is then treated with an acid, a base or an alkali metal fluoride, to convert it to the desired tetrazolyl compound. The reaction is essentially the same as the reaction of the tin-containing compound (produced by reacting the cyano compound with a trialkyltin azide or triaryltin azide) with an acid, a base or an alkali metal fluoride, and may be carried out using the same solvents and reaction conditions.

(vi) Conversion of an alkylcarbamoyl group or a carbamoyl group to a cyano group To convert an alkylcarbamoyl group to a cyano group, the alkylcarbamoyl compound is reacted with a halogen compound capable of acting as a halogenating agent, preferably chlorinating agent, for example oxalyl chloride, phosphorus oxychloride or sulfonyl chloride. There is no particular restriction on the amount of halogen compound employed, although we generally find it convenient to use from 1 to 3 equivalents, more preferably from 1 to 2 equivalents, per equivalent of the carbamoyl compound.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: hydrocarbons, which may be aliphatic or aromatic hydrocarbons, such as benzene, toluene, xylene or heptane; halogenated hydrocarbons, especially halogenated aliphatic hydrocarbons, such as methylene chloride or chloroform; ethers, such as dioxane, tetrahydrofuran or diethyl ether; and esters, such as ethyl acetate or butyl acetate.

The reaction can take place over a wide range of temperatures, and the precise reaction temperature is not critical to the invention. In general, we find it convenient to carry out the reaction at a temperature of from −10° to 100° C., more preferably from 0° to 50° C. The time required for the reaction may also vary widely, depending on many factors, notably the reaction temperature and the nature of the reagents and solvent employed. However, provided that the reaction is effected under the preferred conditions outlined above, a period of from 10 minutes to 16 hours, more preferably from 30 minutes to 6 hours, will usually suffice.

To convert a carbamoyl group to a cyano group, the carbamoyl compound is reacted with a dehydrating agent, for example acetic anhydride, trifluoroacetic anhydride, methanesulfonic anhydride, trifluoromethanesulfonic anhydride, oxalyl chloride or sulfonyl chloride, in the presence of an organic amine, for example triethylamine, pyridine or N-methylmorpholine.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: hydrocarbons, which may be aliphatic or aromatic hydrocarbons, such as benzene, toluene, xylene or heptane; halogenated hydrocarbons, especially halogenated aliphatic hydrocarbons, such as methylene chloride or chloroform; ethers, such as dioxane, tetrahydrofuran or diethyl ether; and esters, such as ethyl acetate or butyl acetate.

The reaction can take place over a wide range of temperatures, and the precise reaction temperature is not critical to the invention. In general, we find it convenient to carry out the reaction at a temperature of from −10° to 100° C., more preferably from 0° to 50° C. The time required for the reaction may also vary widely, depending on many factors, notably the reaction temperature and the nature of the reagents and solvent employed. However, provided that the reaction is effected under the preferred conditions outlined above, a period of from 10 minutes to 16 hours, more preferably from 30 minutes to 6 hours, will usually suffice.

The desired product of these reactions can be recovered from the reaction mixture by conventional means, for example by neutralizing the mixture with a weak base, such as sodium hydrogencarbonate and then working up the product in a similar manner to that described in Step A1 of Reaction Scheme A.

The cyano compound thus obtained may then be converted to the corresponding tetrazolyl compound, using any of the reactions described above.

(vii) Removing hydroxy-protecting groups

Where $R^4$ represents a tri-substituted silyl group, an aralkyl group, an acyl group, alkoxymethyl groups, a tetrahydropyranyl group, a tetrahydrothiopyranyl group, a tetrahydrothienyl group, a tetrahydrofuryl group or a substituted tetrahydropyranyl, tetrahydrothiopyranyl, tetrahydrothienyl or tetrahydrofuryl group, all of which can be regarded as hydroxy-protecting groups, the protecting group is removed, to produce a compound in which $R^4$ represents a hydrogen atom. The nature of the reaction employed to remove the protecting group, will, of course, depend on the nature of the protecting group, as is well known in the art, and any of the many well known reactions used for deprotecting compounds of this type may equally be used here.

Where the hydroxy-protecting group is a silyl group, it can normally be removed by treating the protected compound with a compound capable of forming a fluorine anion, such as tetrabutylammonium fluoride. The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include ethers, such as tetrahydrofuran or dioxane.

The reaction can take place over a wide range of temperatures, and the precise reaction temperature is not critical to the invention. In general, we find it convenient to carry out the reaction at about room temperature. The time required for the reaction may also vary widely, depending on many factors, notably the reaction temperature and the nature of the reagents and solvent employed. However, provided that the reaction is effected under the preferred conditions outlined above, a period of from 10 to 18 hours will usually suffice.

Where the hydroxy-protecting group is an aralkyl group, deprotection can normally be accomplished by catalytic reduction at a temperature of from 0° C. to 80° C., more preferably from 10° C, to 60° C., in a solvent in the presence of hydrogen and of a catalyst.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: alcohols, such as methanol, ethanol or isopropanol; ethers, such as diethyl ether, tetrahydrofuran or dioxane; aromatic hydrocarbons, such as toluene, benzene or xylene; aliphatic hydrocarbons, such as hexane or cyclohexane; esters, such as ethyl acetate or propyl acetate; fatty acids, such as acetic acid; or a mixture of water and any one or more of the above organic solvents.

There is no particular limitation upon the nature of the catalyst used, and any catalyst commonly used for catalytic reduction may also be used here. Preferred examples of such catalysts include palladium on charcoal, Raney nickel, platinum oxide, platinum black, rhodium on aluminum oxide, a complex of triphenylphosphine and rhodium chloride and palladium on barium sulfate.

The hydrogen pressure used is not critical to the reaction and may vary over a wide range, although the reaction is normally carried out at a pressure of from 1 to 3 times atmospheric pressure.

The reaction can take place over a wide range of temperatures, and the precise reaction temperature is not critical to the invention. In general, we find it convenient to carry out the reaction at a temperature of from 0° C. to 100° C., more preferably from 10° C. to 50° C. The time required for the reaction may also vary widely, depending on many factors, notably the reaction temperature and the nature of the reagents, catalyst and solvent employed. However, provided that the reaction is effected under the preferred conditions outlined above, a period of from 5 minutes to 24 hours, more preferably from 30 minutes to 16 hours, will usually suffice.

Where the hydroxy-protecting group is an aliphatic acyl group, an aromatic acyl group or an alkoxycarbonyl group, it can be removed by treating the protected compound with a base.

There is no particular limitation upon the nature of the base used, provided that it does not affect other parts of the compound. Preferred examples of such bases include: metal alkoxides, especially alkali metal alkoxides, such as sodium methoxide; alkali metal carbonates, such as sodium carbonate or potassium carbonate; alkali metal hydroxides, such as sodium hydroxide or potassium hydroxide; and ammonia, which is preferably in the form of aqueous ammonia or a concentrated solution of ammonia in methanol.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: water; organic solvents, such as alcohols (e.g. methanol, ethanol or propanol) or ethers (e.g. tetrahydrofuran or dioxane); or a mixture of water and one or more of these organic solvents.

The reaction can take place over a wide range of temperatures, and the precise reaction temperature is not critical to the invention. In general, we find it convenient to carry out the reaction at a temperature of from 0° C. to 150° C., more preferably from 0° C. to 60° C. The time required for the reaction may also vary widely, depending on many factors, notably the reaction temperature and the nature of the reagents and solvent employed. However, provided that the reaction is effected under the preferred conditions outlined above, a period of from 1 to 20 hours, more preferably from 1 to 16 hours, will usually suffice.

Where the hydroxy-protecting group is an alkoxymethyl group, an alkoxyalkoxymethyl group, a haloalkoxymethyl group, a tetrahydropyranyl group, a tetrahydrothiopyranyl group, a tetrahydrofuranyl group, a tetrahydrothienyl group, or a substituted tetrahydropyranyl, tetrahydrothiopyranyl, tetrahydrofuranyl or tetrahydrothienyl group having at least one halogen or alkoxy substituent, it can normally be removed by treating the protected compound with an acid.

There is no particular limitation upon the nature of the acid used, and any Bronsted acid may be used in this reaction. Preferred examples of such acids include: inorganic acids, especially mineral acids, such as hydrochloric acid or sulfuric acid; and organic acids, including both carboxylic acids and sulfonic acids, such as acetic acid or p-toluenesulfonic acid. Strongly acidic cation exchange resins, such as Dowex 50W (trade mark) can also be used.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: alcohols, such as methanol or ethanol; ethers, such as tetrahydrofuran or dioxane; organic acids, such as formic acid or acetic acid; and mixtures of water and one or more of these solvents.

The reaction can take place over a wide range of temperatures, and the precise reaction temperature is not critical to the invention. In general, we find it convenient to carry out the reaction at a temperature of from 0° C. to 50° C. The time required for the reaction may also vary widely, depending on many factors, notably the reaction temperature and the nature of the reagents and solvent employed. However, provided that the reaction is effected under the preferred conditions outlined above, a period of from 10 minutes to 18 hours will usually suffice.

After completion of any of the above reactions, the desired compound of the invention can be recovered from the reaction mixture by conventional means depending on the nature of the reaction and the reaction medium. An example of one such technique comprises: neutralizing the reaction mixture appropriately; removing any insoluble material which may exist in the mixture, for example by filtration; adding a water-immiscible organic solvent; washing with water; and finally distilling off the solvent. The resulting product can, if necessary, be purified by conventional means, for example, by recrystallization, or by the various chromatography techniques, notably preparative thin layer chromatography or column chromatography.

Under the conditions used for removing the hydroxy-protecting group, simultaneous deprotection of a protected carboxy group may take place occasionally.

(viii) Alkylation and acylation of hydroxy groups

Alkylation of a hydroxy group may be carried out by reacting the hydroxy compound with an alkyl halide in which the alkyl group has from 1 to 6 carbon atoms, preferably methyl iodide, ethyl iodide, ethyl bromide, propyl iodide, propyl bromide or butyl iodide, or a dialkyl sulfate (in which each alkyl group has from 1 to 6 carbon atoms and may be the same or different, although they are preferably the same), such as dimethyl sulfate or diethyl sulfate.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: amides, such as N,N-dimethylformamide, N,N-dimethylacetamide or N-methylpyrrolidinone; ketones, such as acetone or methyl ethyl ketone; or sulfoxides, such as dimethyl sulfoxide.

The reaction is effected in the presence of a base, the nature of which is not critical, provided that it does not damage the reagents or products. Preferred examples of bases which may be used include alkali metal hydrides, such as sodium hydride, potassium hydride or lithium hydride. The reaction can take place over a wide range of temperatures, and the precise reaction temperature is not critical to the invention. In general, we find it convenient to carry out the reaction at a temperature of from 0° C. to 120° C., more preferably from 20° C. to 80° C. The time required for the reaction may also vary widely, depending on many factors, notably the reaction temperature and the nature of the reagents and solvent employed. However, provided that the reaction is effected under the preferred conditions outlined above, a period of from 30 minutes to 24 hours, more preferably from 1 to 16 hours, will usually suffice.

Acylation of a hydroxy group may also be carried out by well known methods commonly used in organic synthetic chemistry. For example, it can be carried out by reacting the hydroxy compound with: an alkanoyl halide, containing from 2 to 6 carbon atoms, such as acetyl chloride, propionyl chloride, butyryl bromide, valeryl chloride or hexanoyl chloride; a carboxylic acid anhydride, in which the group derived from the or each carboxylic acid contains from 1 to 6, preferably from 2 to 6, carbon atoms, such as a mixed anhydride of formic acid and acetic acid, acetic anhydride, propionic anhydride, valeric anhydride or hexanoic anhydride; an alkoxycarbonyl halide, in which the alkoxy group contains from 1 to 6 carbon atoms, such as methoxycarbonyl chloride, methoxycarbonyl bromide, ethoxycarbonyl chloride, propoxycarbonyl chloride, butoxycarbonyl chloride or hexyloxycarbonyl chloride; an arylcarbonyl halide, such as benzoyl chloride, benzoyl bromide or naphthoyl chloride; a halo- or alkoxyalkanoyl halide containing from 2 to 6 carbon atoms, such as chloroacetyl chloride, dichloroacetyl chloride, trichloroacetyl chloride or methoxyacetyl chloride; or an alkenoyl chloride containing from 3 to 6 carbon atoms, such as acryloyl chloride, methacryloyl chloride, crotonoyl chloride, 3-methyl-2-butenoyl chloride or 2-methyl-2-butenoyl chloride.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: halogenated hydrocarbons, especially halogenated aliphatic hydrocarbons, such as methylene chloride or chloroform; esters, such as ethyl acetate; and ethers, such as tetrahydrofuran or dioxane. The reaction is effected in the presence of a base, preferably an organic tertiary amines, such as triethylamine, pyridine, diethylisopropylamine or 4-dimethylaminopyridine. The reaction can take place over a wide range of temperatures, and the precise reaction temperature is not critical to the invention. In general, we find it convenient to carry out the reaction at a temperature of from –10° C. to 120° C., more preferably from 0° C. to 80° C. The time required for the reaction may also vary widely, depending on many factors, notably the reaction temperature and the nature of the reagents and solvent employed. However, provided that the reaction is effected under the preferred conditions outlined above, a period of from 30 minutes to 24 hours, more preferably from 1 to 16 hours, will usually suffice.

After completion of either of the above reactions, the desired product can be recovered from the reaction mixture by conventional means. For example, a recovery method is carried out as already described for recovering the product of Step A1.

Reaction Scheme B:

Compounds of formula (Ia) in which $R^4$ represents a hydrogen atom, that is to say compounds of formula (Ib), may also be prepared as shown in the following Reaction Scheme B:

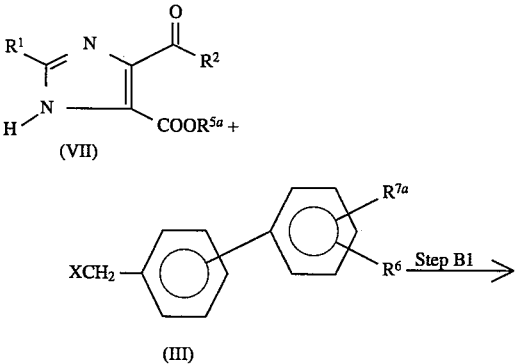

-continued
Reaction Scheme B:

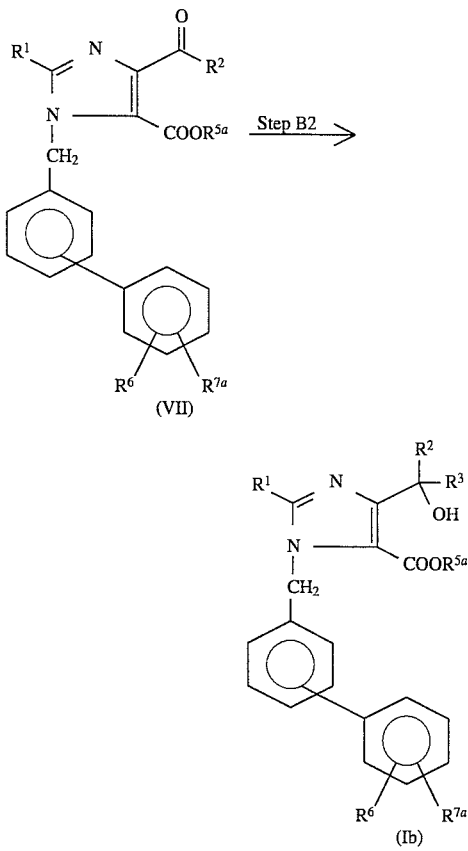

In the above formulae, $R^1$, $R^2$, $R^3$, $R^{5a}$, $R^6$, $R^{7a}$ and X are as defined above and $R^{5a}$ preferably represents a group other than a hydrogen atom.

In Step B1, an imidazole-5-carboxylate compound of formula (VII) is reacted with a biphenylmethyl compound of formula (III), to give a compound of formula (VIII). This reaction is essentially the same as that of Step A1 in Reaction Scheme A, and may be carried out using the same reagents and reaction conditions.

In Step B2, a compound of formula (Ib) is prepared by reacting a compound of formula (VIII) with a reducing agent or with a Grignard reagent of formula, $R^{3a}$—Mg—X (in which $R^{3a}$ represents any of the groups defined above for $R^3$ other than a hydrogen atom, and X is as defined above).

Examples of the reducing agents which may be used include: alkylaluminum hydrides, such as diisobutyl aluminum hydride; and metal, especially alkali metal, borohydrides, such as sodium borohydride or sodium cyanoborohydride. Of these, we prefer diisobutylaluminum hydride and sodium borohydride.

The reaction of the compound of formula (VIII) with the reducing agent is normally and preferably conducted in an inert solvent. There is no particular restriction on the nature of the solvent to be employed, provided that it has no adverse effect on the reaction or on the reagents involved and that it can dissolve the reagents, at least to some extent. Examples of suitable solvents include: hydrocarbons, especially aromatic hydrocarbons, such as toluene or hexane; ethers, such as tetrahydrofuran or dioxane; alcohols, such as methanol or ethanol; water; and mixtures of water with any one or more of the above organic solvents. Preferred solvents vary depending upon the nature of the reducing agent used. For example, where the reducing agent is an alkylaluminum hydride, hydrocarbons or ethers are preferred; alternatively, where it is an alkali metal borohydride, alcohols, water or mixtures of water with an alcohol are preferred.

The reaction can take place over a wide range of temperatures, and the precise reaction temperature is not critical to the invention. In general, we find it convenient to carry out the reaction at a temperature of from −30° C. to 80° C., more preferably from −20° C. to 20° C., when the reducing agent is an alkylaluminum hydride, or at a temperature of from −30° C. to 80° C., more preferably from 0° C. to 50° C., when it is an alkali metal borohydride. The time required for the reaction may also vary widely, depending on many factors, notably the reaction temperature and the nature of the reagents and solvent employed. However, provided that the reaction is effected under the preferred conditions outlined above, a period of from 30 minutes to 24 hours, more preferably from 1 to 16 hours, will usually suffice.

The reaction of the compound of formula (VIII) with a Grignard reagent is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: hydrocarbons, which may be aliphatic or aromatic, such as hexane or toluene; halogenated hydrocarbons, especially halogenated aliphatic hydrocarbons, such as methylene chloride or 1,2-dichloroethane; and ethers, such as tetrahydrofuran or diethyl ether, of which the ethers and halogenated hydrocarbons are preferred.

The reaction can take place over a wide range of temperatures, and the precise reaction temperature is not critical to the invention. In general, we find it convenient to carry out the reaction at a temperature of from −50° C. to 100° C., more preferably from −10° C. to 50° C. The time required for the reaction may also vary widely, depending on many factors, notably the reaction temperature and the nature of the reagents and solvent employed. However, provided that the reaction is effected under the preferred conditions outlined above, a period of from 30 minutes to 24 hours, more preferably from 1 to 16 hours, will usually suffice.

After completion of any of the above the reactions, the desired compounds of each reaction can be recovered from the reaction mixture by conventional means. For example, the reaction mixture is mixed with water or with an aqueous solution of ammonium chloride and stirred at room temperature, after which it is extracted with a water-immiscible solvent, such as ethyl acetate. The extract is washed with water and dried over a drying agent, such as anhydrous magnesium sulfate, and then the solvent is distilled off; if necessary, the product can be further purified by conventional means, for example, by recrystallization, or by the various chromatography techniques, notably preparative thin layer chromatography or column chromatography.

Reaction Scheme C:

Compounds of formula (Ia) in which $R^2$, $R^3$ and $R^4$ all represent hydrogen atoms, that is to say compounds of formula (Ic), and compounds of formula (VIII), which are intermediates in reaction Scheme B, can be prepared as shown in Reaction Scheme C:

Reaction Scheme C:

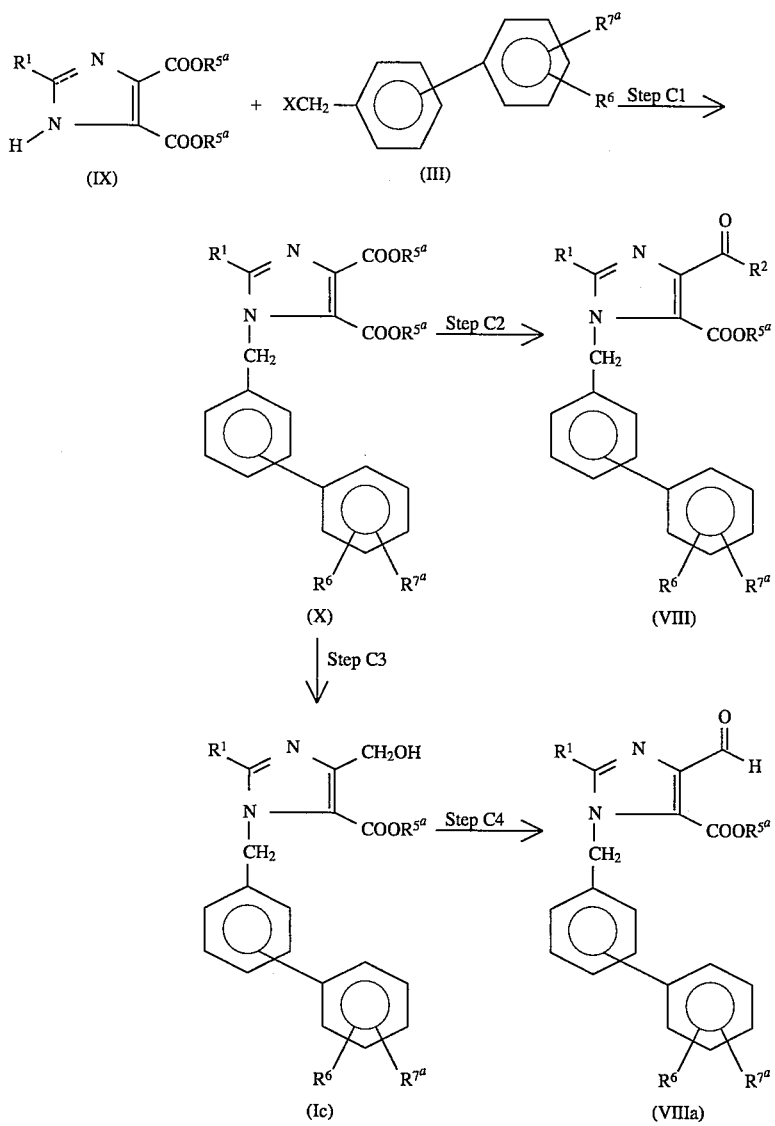

In the above formulae $R^1$, $R^2$, $R^{5a}$, $R^6$, $R^{7a}$ and X are as defined above, and $R^{5a}$ preferably represents a group other than a hydrogen atom.

In Step C1 of this reaction scheme, an imidazole-5-carboxylate compound of formula (IX) is reacted with a biphenylmethyl compound of formula (III), to give a compound of formula (X). This reaction is essentially the same as that described above in Step A1 of Reaction Scheme A, and may be carried out using the same reagents and reaction conditions.

In Step C2 of this reaction scheme, the dicarboxylate compound of formula (X) obtained as shown in Step C1 is reacted with about one equivalent of a Grignard reagent of formula $R^{2a}MgX$ (in which X is as defined above and $R^{2a}$ represents any of the groups defined above for $R^2$ other than a hydrogen atom) and/or with about one equivalent of a reducing agent to give the compound of formula (VIII). These reactions are essentially the same as those described above in Step B2 of Reaction Scheme B, and may be carried out using the same reagents and reaction conditions.

In Step C3 of this reaction scheme, the compound of formula (X) is reacted with two or more molar equivalents of the reducing agent to give the compound of formula (Ic).

The reaction is essentially the same as that described above in Step B2 of Reaction Scheme B, and may be carried out using the same reagents and reaction conditions.

In Step C4, the hydroxymethyl compound of formula (Ic) is oxidized to convert the hydroxymethyl group to a formyl group and prepare a compound of formula (VIIIa).

The oxidization reaction may be carried out by reacting the hydroxymethyl compound with an oxidizing agent, such as magnesium oxide or silver oxide.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: hydrocarbons, which may be aliphatic or aromatic hydrocarbons, such as benzene, toluene, xylene or heptane; halogenated hydrocarbons, especially halogenated aliphatic hydrocarbons, such as methylene chloride or chloroform; ethers, such as diethyl ether, tetrahydrofuran or dioxane; esters, such as ethyl acetate or butyl acetate; and ketones, such as acetone or methyl ethyl ketone.

The reaction can take place over a wide range of temperatures, and the precise reaction temperature is not critical to the invention. In general, we find it convenient to carry out the reaction at a temperature of from 0° to 100° C., more preferably from 10° to 60° C. The time required for the reaction may also vary widely, depending on many factors, notably the reaction temperature and the nature of the reagents and solvent employed. However, provided that the reaction is effected under the preferred conditions outlined above, a period of from 30 minutes to 24 hours, more preferably from 1 to 16 hours, will usually suffice.

Alternatively, the reaction of Step C4 may be carried out by reacting the hydroxymethyl compound of formula (Ic) with dimethyl sulfoxide and with a dehydrating agent in the presence of an organic amine. Suitable dehydrating agents include, for example, sulfur trioxide-dioxane complex, oxalyl chloride and trifluoroacetic anhydride. Suitable organic amines include, for example, triethylamine and pyridine.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: halogenated hydrocarbons, especially halogenated aliphatic hydrocarbons, such as methylene chloride or chloroform; ethers, such as diethyl ether, tetrahydrofuran or dioxane; esters, such as ethyl acetate or butyl acetate; and sulfoxides, such as dimethyl sulfoxide.

The reaction can take place over a wide range of temperatures, and the precise reaction temperature is not critical to the invention. In general, we find it convenient to carry out the reaction at a temperature of from −60° C. to 60° C., more preferably from −50° C. to 30° C. The time required for the reaction may also vary widely, depending on many factors, notably the reaction temperature and the nature of the reagents and solvent employed. However, provided that the reaction is effected under the preferred conditions outlined above, a period of from 10 minutes to 8 hours, more preferably from 30 minutes to 5 hours, will usually suffice.

After completion of any of the above reactions, the desired product of the reaction can be recovered from the reaction mixture by conventional means. For example, the reaction mixture is mixed with water and with a water-immiscible solvent, such as ethyl acetate. The organic layer is separated, washed with water and dried over a drying agent, such as anhydrous magnesium sulfate; the solvent is then removed by distillation, normally under reduced pressure. If necessary, the product can be further purified by conventional means, for example, by recrystallization, or by the various chromatography techniques, notably preparative thin layer chromatography or column chromatography.

The resulting compound of formula (VIII) may then, if desired, be allowed to react with a Grignard reagent of formula $R^{3a}MgX$ (in which $R^{3a}$ and X are as defined above) according to the method described above in Step B2 of Reaction Scheme B, to give the corresponding compound having a group of formula —$CR^2(R^{3a})$—OH (in which $R^2$ and $R^{3a}$ are as described above) at the 4-position of the imidazolyl ring—not shown in the reaction scheme.

Reaction Scheme D:

In this reaction scheme, a cyano compound of formula (XII) is first prepared, and then this is converted to a compound of formula (I):

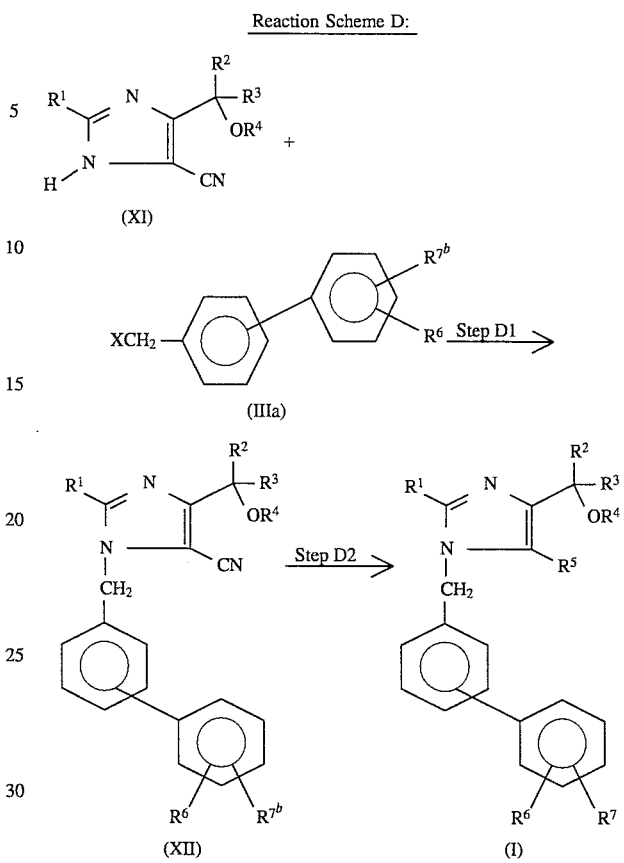

In the above formulae, $R^1$, $R^2$, $R^3$, $R^4$, $R^5$, $R^6$, $R^7$ and X are as defined above, and $R^{7b}$ represents a protected carboxy group or a protected tetrazolyl group, both of which may be as previously exemplified in relation to $R^{7a}$.

In Step D1 of this reaction scheme, an imidazole-5-carbonitrile compound of formula (XI) is reacted with a biphenylmethyl compound of formula (IIIa), to give a compound of formula (XII). This reaction is essentially the same as that described above in Step A1 of Reaction Scheme A, and may be carried out using the same reagents and reaction conditions.

In Step D2, the resulting compound of formula (XII) may be subjected to any one or (in appropriate cases) more of the following reactions:

(ix) converting the cyano group at the 5-position of the imidazole ring to a carboxy group;
(x) converting the cyano group at the 5-position of the imidazole ring to a carbamoyl group;
(xi) removing any carboxy-protecting groups;
(xii) esterifying the carboxy group at the 5-position of the imidazole ring or on the biphenyl group;
(xiii) converting the carboxy group at the 5-position of the imidazole ring to a group of formula —$CONR^8R^9$;
(xiv) removing the tetrazolyl-protecting group;
(xv) where $R^4$ represents a tri-substituted silyl group, an aralkyl group, an aralkyloxycarbonyl group, an aliphatic acyl group, an alkoxymethyl group, an alkoxyalkoxymethyl group, a haloalkoxymethyl group, a tetrahydropyranyl group, a tetrahydrothiopyranyl group, a tetrahydrothienyl group, a tetrahydrofuryl group or a substituted tetrahydropyranyl, tetrahydrothiopyranyl, tetrahydrothienyl or tetrahydrofuryl group having at least one halogen or alkoxy substituent, all of which can be regarded as hydroxy-protecting groups, removing the protecting group to produce a compound in which $R^4$ represents a hydrogen atom; and (xvi) where $R^4$ represents a hydroxy group, alkylating or acylating this group.

(ix) Conversion of a cyano group to a carboxy group

The conversion is effected by hydrolysis of the cyano group in the compound of formula (XII) via a carbamoyl group. This reaction is well known in chemical synthesis generally, and may be carried out using any reagent known for this purpose. For example, alkali metal hydroxides, such as sodium hydroxide, potassium hydroxide or lithium hydroxide.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: water; alcohols, such as methanol or ethanol; ethers, such as tetrahydrofuran or dioxane; or a mixture of any two or more of these solvents; an aqueous solvent is preferred.

The reaction can take place over a wide range of temperatures, and the precise reaction temperature is not critical to the invention. In general, we find it convenient to carry out the reaction at a temperature of from 0° C. to 120° C., more preferably from 20° C. to 100° C. The time required for the reaction may also vary widely, depending on many factors, notably the reaction temperature and the nature of the reagents and solvent employed. However, provided that the reaction is effected under the preferred conditions outlined above, a period of from 30 minutes to 24 hours, more preferably from 1 to 16 hours, will usually suffice.

After completion of the reaction, the desired product can be recovered from the reaction mixture by conventional means. For example, one suitable recovery procedure comprises: neutralizing the reaction mixture by adding a mineral acid, such as hydrochloric acid; if the desired product of formula (I) precipitates, it can then be recovered by filtration; alternatively, after neutralizing the reaction mixture, the solvent is distilled off and the resulting residue is purified by column chromatography to give the desired product; alternatively, the residue is mixed with water and with a water-immiscible solvent, such as ethyl acetate, and the resulting mixture is extracted with an organic solvent, after which the extract is dried over a drying agent, such as anhydrous magnesium sulfate, and freed from the solvent to give the desired product. If necessary, the product can be further purified by conventional means, for example, by recrystallization, or by the various chromatography techniques, notably preparative thin layer chromatography or column chromatography.

In this reaction, where the starting material is a compound in which $R^4$ represents an acyl group and/or $R^{7b}$ represents an ester group of a primary or secondary alcohol (such as methanol, ethanol or isopropanol), the acyl group of $R^4$ and the ester residue of $R^{7b}$ are simultaneously removed.

(x) Conversion of a cyano group to a carbamoyl group

In this reaction, a cyano group in the compound of formula (XII) is converted to a carbamoyl group.

The product of this reaction is an intermediate of the previous reaction (ix). Therefore the reaction is carried out under milder conditions than those employed in reaction (ix).

The reaction is carried out by treating the compound of formula (XII) with an alkali, for example: an alkali metal hydroxide, such as lithium hydroxide, sodium hydroxide or potassium hydroxide; or an alkali metal carbonate, such as sodium carbonate or potassium carbonate. The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: water; a mixture of water and an alcohol, such as methanol or ethanol; or a mixture of water and an ether, such as tetrahydrofuran or dioxane.

The reaction can take place over a wide range of temperatures, and the precise reaction temperature is not critical to the invention. In general, we find it convenient to carry out the reaction at a temperature of from 0° C. to 100° C., more preferably from 10° C. to 80° C. The time required for the reaction may also vary widely, depending on many factors, notably the reaction temperature and the nature of the reagents and solvent employed. However, provided that the reaction is effected under the preferred conditions outlined above, a period of from 0.5 to 24 hours, more preferably from 1 to 8 hours, will usually suffice. The reaction can be accelerated by adding a catalytic amount of hydrogen peroxide.

After completion of the reaction, the reaction product can be recovered from the reaction mixture by conventional means. For example, one suitable recovery procedure comprises: neutralizing the reaction mixture with a mineral acid, such as hydrochloric acid; distilling off the solvent under reduced pressure; adding water to the residue; extracting the mixture with a water-immiscible solvent, such as ethyl acetate; drying the organic extract solution over a drying agent, such as anhydrous magnesium sulfate; and distilling off the solvent. If necessary, the product can be further purified by conventional means, for example, by recrystallization, or by the various chromatography techniques, notably preparative thin layer chromatography or column chromatography.

(xi) Removing carboxy-protecting groups

This is the same reaction as is involved in reaction (i) of Step A2 of Reaction Scheme A, and may be carried out using the same reagents and reaction conditions.

(xii) Esterification

This is the same reaction as is involved in reaction (ii) of Step A2, and may be carried out using the same reagents and reaction conditions.

(xiii) Conversion of a carboxy group to a group of formula —$CONR^8R^9$

This is the same reaction as is involved in reaction (iii) of Step A2, and may be carried out using the same reagents and reaction conditions.

(xiv) Removal of tetrazolyl-protecting groups

This is the same reaction as is involved in reaction (iv) of Step A2, and may be carried out using the same reagents and reaction conditions.

(xv) Removing hydroxy-protecting groups

This is the same reaction as is involved in reaction (vii) of Step A2, and may be carried out using the same reagents and reaction conditions.

(xvi) Alkylation and acylation of hydroxy groups

This is the same reaction as is involved in reaction (viii) of Step A2, and may be carried out using the same reagents and reaction conditions.

Reaction Scheme E:

In this reaction scheme, a compound of formula (XII) in which $R^4$ is hydrogen, that is to say a compound of formula (XV), is prepared from the corresponding compound of formula (XIII) having a ketonic [—$C(O)R^2$] group at the 4-position of the imidazole ring.

Reaction Scheme E:

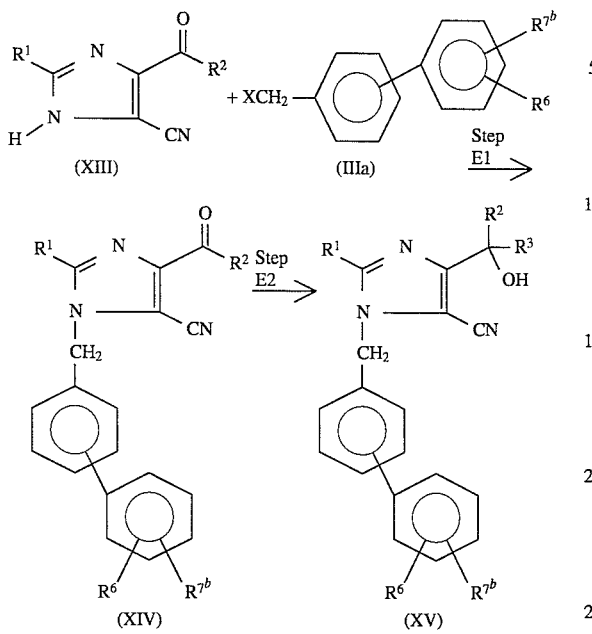

In the above formulae, $R^1$, $R^2$, $R^3$, $R^6$, $R^{7b}$ and X are as defined above.

In Step E1 of this reaction scheme, an imidazole-5-carboxylate compound of formula (XIII) is reacted with a biphenylmethyl compound of formula (IIIa), to give a compound of formula (XIV). This reaction is essentially the same as that described above in Step A1 of Reaction Scheme A, and may be carried out using the same reagents and reaction conditions.

The resulting compound of formula (XIV) is then reacted in Step E2 with a reducing agent or with a Grignard reagent of formula, $R^{3a}$—Mg—X (in which $R^{3a}$ and X are as defined above). This reaction is essentially the same as that described above in Step B2 of Reaction Scheme B, and may be carried out using the same reagents and reaction conditions. The resulting product may then be recovered and, if desired, further purified, as described in Step B2.

Reaction Scheme F:

Certain 5-cyanoimidazole derivatives, for use as intermediates in the foregoing reaction schemes may be prepared as illustrated in the following Reaction Scheme F:

Reaction Scheme F:

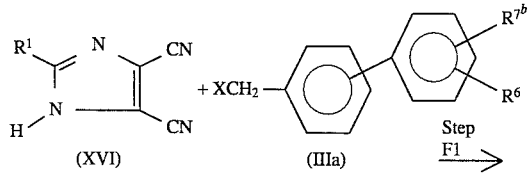

-continued
Reaction Scheme F:

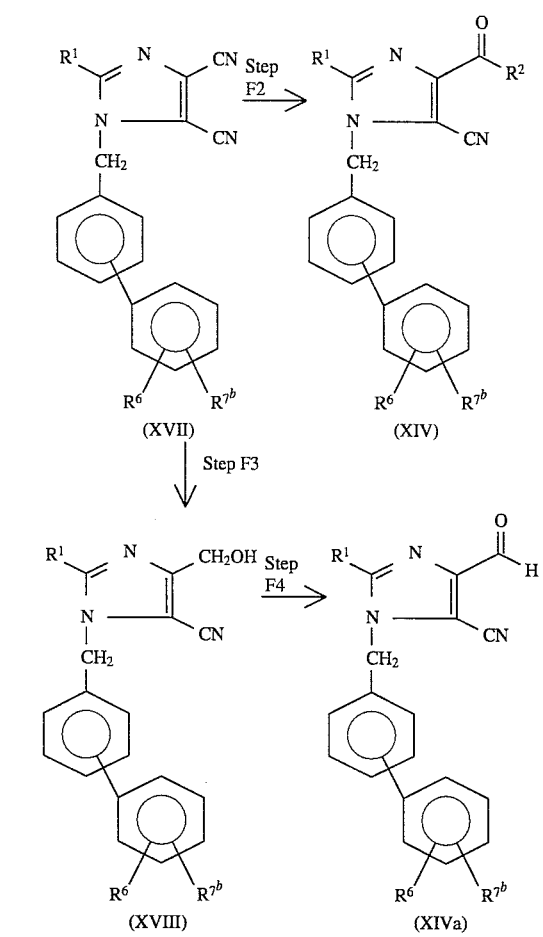

In the above formulae, $R^1$, $R^2$, $R^6$, $R^{7b}$ and X are as defined above.

In Step F1 of this reaction scheme, an imidazole-5-carboxylate compound of formula (XVI) is reacted with a biphenylmethyl compound of formula (IIIa), to give a compound of formula (XVII). This reaction is essentially the same as that described above in Step A1 of Reaction Scheme A, and may be carried out using the same reagents and reaction conditions.

Steps F2, F3 and F4 are essentially the same as Steps C2, C3 and C4, respectively, of Reaction Scheme C, and may be carried out using the same reagents and reaction conditions. The resulting product may then be recovered and, if desired, further purified, as described in Reaction Scheme C.

The preparation of certain of the starting materials used in the above reaction schemes is shown in Reaction Schemes G and H:

Reaction Scheme G:

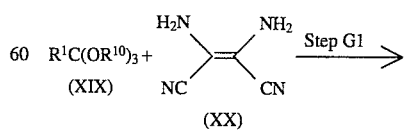

83
-continued
Reaction Scheme G:

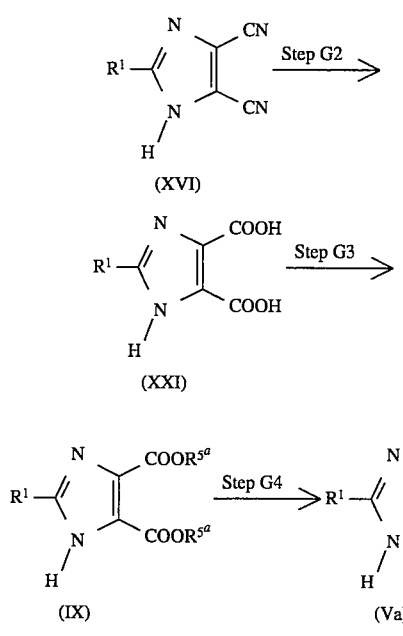

Reaction Scheme H:

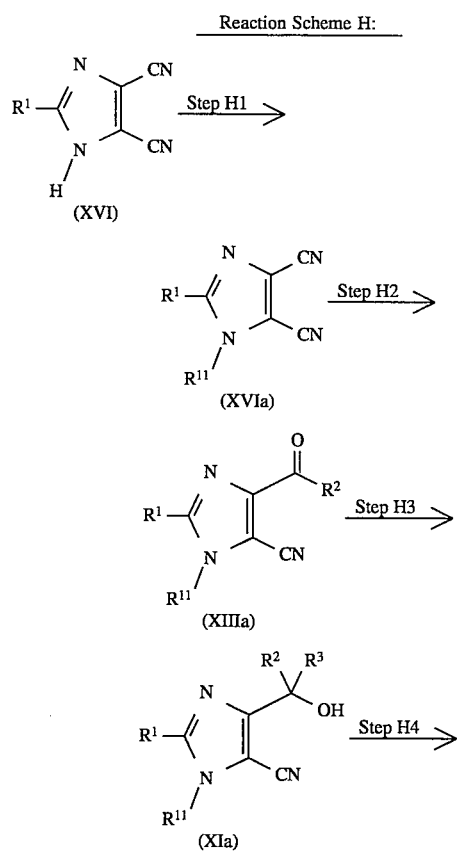

84
-continued
Reaction Scheme H:

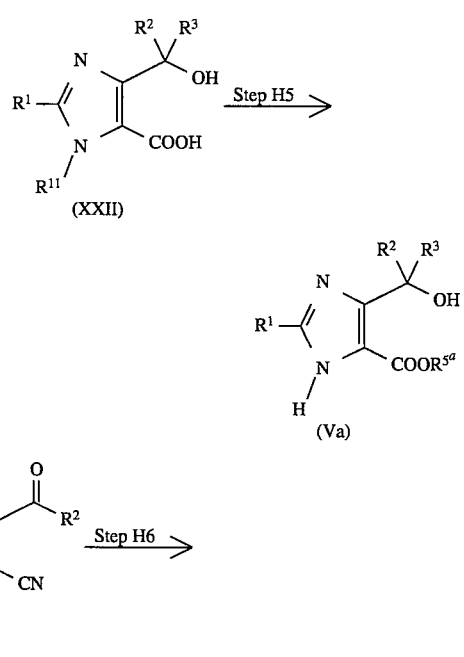

In the above formulae, $R^1$, $R^2$, $R^3$ and $R^{5a}$ are as defined above. $R^{10}$ represents an alkyl group containing from 1 to 6 carbon atoms, such as those illustrated above in respect of $R^1$, and is preferably an alkyl group having from 1 to 4 carbon atoms, and more preferably a methyl or ethyl group. $R^{11}$ represents a hydrogen atom or a imidazolyl-protecting group, for example an aralkyl group, such as a trityl group, a diphenylmethyl group or a benzyl group, or a $C_1$-$C_4$ alkoxymethyl group, such as a methoxymethyl, ethoxymethyl, propoxymethyl or butoxymethyl group, preferably a trityl group, a benzyl group, a methoxymethyl group or an ethoxymethyl group, more preferably a trityl group.

Reaction Scheme G:

In this reaction scheme G, a compound of formula (V) in which $R^4$ represents a hydrogen atom, that is a compound of formula (Va), (IX) or (XVI) (which are starting materials in Reaction Schemes A, C or F, respectively) is prepared. The compound of formula (Va) may then, if desired, be protected, e.g. by alkylation, acylation, formation of a tetrahydropyranyloxy, tetrahydrothiopyranyloxy, tetrahydrothienyloxy or tetrahydrofuryloxy group, a substituted tetrahydropyranyloxy, tetrahydrothiopyranyloxy, tetrahydrothienyloxy or tetrahydrofuryloxy group or a group of formula —$SiR^aR^bR^c$, in which $R^a$, $R^b$ and $R^c$ are as defined above. The these reactions other than formation of an optionally substituted tetrahydropyranyloxy, tetrahydrothiopyranyloxy, tetrahydrothienyloxy or tetrahydrofuryloxy group may be carried out as described in reaction (viii) of Step A2 of Reaction Scheme A, to give the corresponding compound in which $R^4$ represents any of the groups represented by $R^4$ other than a hydrogen atom.

Formation of a tetrahydropyranyloxy, tetrahydrothiopyranyloxy, tetrahydrothienyloxy or tetrahydrofuryloxy group or a substituted tetrahydropyranyloxy, tetrahydrothiopyranyloxy, tetrahydrothienyloxy or tetrahydrofuryloxy group may be carried out by reacting a compound of formula (V) in which $R^4$ represents a hydrogen atom with dihydropyran, dihydrothiopyran, dihydrothiophene or dihydrofuran or a substituted dihydropyran, dihydrothiopyran, dihydrothiophene or dihydrofuran having at least one halogen or $C_1$–$C_6$ alkoxy substituent in the presence of an acid (such as p-toluenesulfonic acid) in an inert solvent (for example a halogenated hydrocarbon, such as methylene chloride) at about room temperature for from 1 to 24 hours.

In Step G1, a compound of formula (XVI) is prepared by reacting an ortho ester compound of formula (XIX) with diaminomaleonitrile of formula (XX). The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aromatic hydrocarbons, such as benzene, toluene or xylene; halogenated hydrocarbons, especially halogenated aliphatic hydrocarbons, such as 1,2-dichloroethane or carbon tetrachloride; ethers, such as tetrahydrofuran or dioxane; and nitriles, such as acetonitrile.

The reaction can take place over a wide range of temperatures, and the precise reaction temperature is not critical to the invention. In general, we find it convenient to carry out the reaction at a temperature of from 50° C. to 180° C., more preferably from 80° C. to 150° C. The time required for the reaction may also vary widely, depending on many factors, notably the reaction temperature and the nature of the reagents and solvent employed. However, provided that the reaction is effected under the preferred conditions outlined above, a period of from 1 to 24 hours, more preferably from 2 to 10 hours, will usually suffice.

The reaction product of formula (XVI) can be recovered by collecting the crystals deposited in the reaction system or by distilling off the solvent. The product can, if necessary, be further purified by conventional means, for example, by recrystallization, or by the various chromatography techniques, notably preparative thin layer chromatography or column chromatography.

Step G2 consists of preparing an imidazole-4,5-dicarboxylic acid compound of formula (XXI) by hydrolyzing the compound of formula (XVI) prepared in Step G1. This reaction may be carried out by heating the compound of formula (XVI) under reflux with an aqueous mineral acid, such as aqueous hydrochloric acid, sulfuric acid or nitric acid, for a period of from 1 to 24 hours (preferably from 3 to 16 hours). The product of formula (XXI) can be recovered by collecting the crystals deposited in the reaction mixture upon cooling, by filtration or by distilling off the solvent.

Step G3, an optional step, consists of preparing a diester compound of formula (IX) by protecting the carboxy group of the imidazole-4,5-dicarboxylic acid compound of formula (XXI) prepared in Step G2. This reaction may be carried out by reacting the compound (XXI) with a compound of formula $R^{5b}$—Y, in which $R^{5b}$ and Y are as defined above.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: hydrocarbons, especially aromatic hydrocarbons, such as benzene or toluene; halogenated hydrocarbons, especially halogenated aliphatic hydrocarbons, such as methylene chloride or chloroform; ethers, such as tetrahydrofuran or dioxane; alcohols, such as methanol, ethanol or t-butanol; amides, such as N,N-dimethylacetamide, N,N-dimethylformamide or N-methyl-2-pyrrolidinone; ketones, such as acetone or methyl ethyl ketone; nitriles, such as acetonitrile; and sulfoxides, such as dimethyl sulfoxide. Of these, we prefer the nitriles, halogenated hydrocarbons or amides.

We also prefer that the reaction should be carried out in the presence of a base, the nature of which is not critical, provided that it does not affect any other parts of the reagents. Preferred examples of bases which may be used include: organic amines, such as triethylamine, N,N-diisopropylethylamine or N-methylmorpholine.

The reaction can take place over a wide range of temperatures, and the precise reaction temperature is not critical to the invention, although the preferred temperature may varies depending upon the nature of the starting material, the solvent and the base. In general, we find it convenient to carry out the reaction at a temperature of from −10° C. to 100° C., more preferably from 0° C. to 80° C. The time required for the reaction may also vary widely, depending on many factors, notably the reaction temperature and the nature of the reagents and solvent employed. However, provided that the reaction is effected under the preferred conditions outlined above, a period of from 0.5 to 24 hours, more preferably from 1 to 16 hours, will usually suffice.

After completion of the reaction, the desired compound can be recovered from the reaction mixture by conventional means. For example, after distilling off the solvent, the residue is mixed with water; the mixture is extracted with a water-immiscible organic solvent, such as ethyl acetate; the extract is dried over a drying agent, such as anhydrous magnesium sulfate; and the solvent is distilled off. The product can, if necessary, be further purified by conventional means, for example, by recrystallization, or by the various chromatography techniques, notably preparative thin layer chromatography or column chromatography.

Alternatively, the dicarboxylic acid compound of formula (XXI) may be esterified, to give the diester of formula (IX). The reaction employed for this will, as is well known in the art, depend on the nature of the ester residue $R^{5b}$.

For example, where the group represented by $R^{5b}$ is a $C_1$–$C_6$ alkyl group or an aralkyl group, such as a benzyl group, the compound of formula (IX) can be prepared by reacting the corresponding dicarboxylic acid with a $C_1$–$C_6$ alcohol, such as methanol, ethanol, propanol or hexanol, or an aralkyl alcohol, such as a benzyl alcohol, in the presence of an acid catalyst, such as hydrogen chloride or sulfuric acid in an inert solvent (for example: one of the $C_1$–$C_6$ alcohols which may be used as the starting material described above; a halogenated hydrocarbon, such as methylene chloride; or an ether, such as tetrahydrofuran or dioxane) at a temperature of from 0° C. to 100° C., preferably from 20° C. to 80° C., for a period of from 1 hour to 3 days, preferably from 16 to 24 hours; or by treating the corresponding dicarboxylic acid with a halogenating agent (e.g. phosphorus pentachloride, thionyl chloride or oxalyl chloride) in an inert solvent (for example: a halogenated hydrocarbon, such as methylene chloride; an ether, such as tetrahydrofuran or dioxane; or an aromatic hydrocarbon, such as benzene or toluene) at about room temperature for a period of from 30 minutes to 5 hours, preferably from 1 to 3 hours, to give the corresponding acyl halide and then reacting this acyl halide with the corresponding alcohol (when the t-butyl ester is prepared, it is desirable to use potassium t-butoxide in place of the alcohol) in an inert solvent (e.g. benzene or methylene chloride) in the presence of a base (e.g. triethylamine) at about room temperature for a period of from 30 minutes to 10 hours.

The desired compound can be recovered from the reaction mixture by conventional means. For example, after distilling off the solvent, the residue is dissolved in water and a water-immiscible organic solvent, such as ethyl acetate, and the resulting solution is neutralized with sodium hydrogencarbonate; the organic layer is then separated and dried over a drying agent, such as anhydrous magnesium sulfate; the solvent is then distilled off to leave the desired product. The product can, if necessary, be further purified by conventional means, for example, by recrystallization, or by the various chromatography techniques, notably preparative thin layer chromatography or column chromatography.

In Step G4, a compound of formula (Va) is prepared by reacting a diester compound of formula (IX) with a Grignard reagent of formula $R^{2a}MgX$ and/or $R^{3a}MgX$ (in which $R^{2a}$, $R^{3a}$ and X are as defined above).

The reaction is essentially the same as that described above in Step B2 of Reaction Scheme B, and may be carried out using the same reagents and reaction conditions.

Reaction Scheme H:

These reactions prepare compounds of formulae (XIIIa), (XIa) and (VIIa), in each of which $R^{11}$ is a hydrogen atom, that is to say compounds of formulae (XIII), (XI) and (VII), and a compound of formula (Va), which are starting materials used in Reaction Schemes E, D, A and B, respectively.

In Step H1, which is an optional step, a compound of formula (XVIa) is prepared by reacting a dinitrile compound of formula (XVI) with a compound of formula $R^{11a}$—X (in which X is as defined above and $R^{11a}$ represents any of the groups defined above for $R^{11}$ other than a hydrogen atom) in the presence of a base.

Examples of suitable bases include: alkali metal hydrides, such as lithium hydride or sodium hydride; alkali metal carbonates, such as sodium carbonate or potassium carbonate; and alkali metal alkoxides, such as sodium methoxide, sodium ethoxide or potassium t-butoxide.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: halogenated hydrocarbons, such as methylene chloride or chloroform; ethers, such as tetrahydrofuran or dioxane; amides, such as dimethylformamide or dimethylacetamide; and ketones, such as acetone or methyl ethyl ketone. The reaction can take place over a wide range of temperatures, and the precise reaction temperature is not critical to the invention. In general, we find it convenient to carry out the reaction at a temperature of from 0° C. to 120° C., more preferably from 20° C. to 80° C. The time required for the reaction may also vary widely, depending on many factors, notably the reaction temperature and the nature of the reagents and solvent employed. However, provided that the reaction is effected under the preferred conditions outlined above, a period of from 1 to 24 hours, more preferably from 3 to 8 hours, will usually suffice.

After completion of the reaction, the desired compound can be recovered from the reaction mixture by conventional means. For example, one suitable recovery procedure comprises: adding water to the reaction mixture: extracting the mixture with a water-miscible organic solvent, such as ethyl acetate; washing the extract with water and drying it over a drying agent, such as anhydrous magnesium sulfate; and finally distilling off the solvent. The product can, if necessary, be further purified by conventional means, for example, by recrystallization, or by the various chromatography techniques, notably preparative thin layer chromatography or column chromatography.

In Step H2, a compound of formula (XIIIa) is prepared by reacting a dinitrile compound of formula (XVIa) with a Grignard reagent of formula $R^{2a}MgX$, in which $R^{2a}$ and X are as defined above, or with a reducing agent. This reaction is essentially the same as that described above in Step B2 of Reaction Scheme B, and may be carried out using the same reagents and reaction conditions.

An imidazolyl-protecting group of a compound of formula (XIIIa) may optionally be removed by treating the compound of formula (XIIIa) in a conventional manner, depending on the nature of the protecting group, to give the compound of formula (XIII).

For example, when the protecting group is a trityl group or an alkoxymethyl group, it may be removed by reacting the protected compound with an acid.

Examples of suitable acids include: inorganic acids, such as hydrochloric acid or sulfuric acid; and organic acids, such as acetic acid, formic acid, trifluoroacetic acid, methanesulfonic acid or p-toluenesulfonic acid.

The reaction is normally and preferably effected in the presence of a solvent. There is no particular restriction on the nature of the solvent to be employed, provided that it has no adverse effect on the reaction or on the reagents involved and that it can dissolve reagents, at least to some extent. Examples of suitable solvents include: ethers, such as tetrahydrofuran or dioxane; alcohols, such as methanol or ethanol; acids, such as acetic acid; water; or a mixture of any two or more of the above solvents.

The reaction can take place over a wide range of temperatures, and the precise reaction temperature is not critical to the invention. In general, we find it convenient to carry out the reaction at a temperature of from 0° C. to 120° C., more preferably from 10° C. to 100° C. The time required for the reaction may also vary widely, depending on many factors, notably the reaction temperature and the nature of the reagents and solvent employed. However, provided that the reaction is effected under the preferred conditions outlined above, a period of from 30 minutes to 24 hours, more preferably from 1 to 16 hours, will usually suffice.

After completion of the reaction, the desired compound can be recovered from the reaction mixture by conventional means. For example, one suitable recovery procedure comprises: evaporating the solvent and purifying the product by recrystallization or chromatography; or neutralizing the reaction mixture with a weak base (such as sodium hydrogencarbonate), extracting with a water-immiscible organic solvent, such as ethyl acetate, and evaporating off the solvent. The product can, if necessary, be further purified by conventional means, for example, by recrystallization, or by the various chromatography techniques, notably preparative thin layer chromatography or column chromatography.

When the imidazolyl-protecting group is an aralkyl group, such as a benzyl or diphenylmethyl group, it can be removed by catalytic hydrogenation. The reaction is essentially the same as that described above in reaction (i) of Step A2 of Reaction Scheme A, in which the carboxy-protecting group is an aralkyl group, and may be carried out using the same reagents and reaction conditions.

In Step H3, the resulting carbonyl compound of formula (XIIIa) is then reacted with a Grignard reagent of formula $R^{3a}MgX$, in which $R^{3a}$ and X are as defined above, or with a reducing agent, to give the compound of formula (XIa). This reaction is essentially the same as that described above in Step B2 of Reaction Scheme B, and may be carried out using the same reagents and reaction conditions.

If desired, the imidazolyl-protecting group of the compound of formula (XIa) can be removed by essentially the same reaction as that optional reaction described above as Step H2 of Reaction Scheme H, which may be carried out using the same reagents and reaction conditions.

In Step H4, a carboxylic acid compound of formula (XXII) is prepared by hydrolyzing the remaining cyano group at the 5-position of the imidazole ring. The reaction may be carried out using an alkali metal hydroxide, such as sodium hydroxide, potassium hydroxide or lithium hydroxide, in an inert solvent (preferably water: an alcohol, such as methanol or ethanol; an ether, such as tetrahydrofuran or dioxane; or a mixture of any two or more of the above solvents). The reaction can take place over a wide range of temperatures, and the precise reaction temperature is not critical to the invention. In general, we find it convenient to carry out the reaction at a temperature of from 0° C. to 120° C., more preferably from 20° C. to 100° C. The time required for the reaction may also vary widely, depending on many factors, notably the reaction temperature and the nature of the reagents and solvent employed. However, provided that the reaction is effected under the preferred conditions outlined above, a period of from 0.5 to 24 hours, more preferably from 1 to 16 hours, will usually suffice. After completion of the reaction, the reaction product can be recovered by conventional means. For example, the reaction mixture is neutralized by adding a mineral acid, such as hydrochloric acid; if the desired compound of formula (XXII) appears as a precipitate in the reaction medium, it can be collected by filtration. Alternatively, the desired compound can be recovered as follows: after neutralizing the reaction mixture, the solvent is distilled off and the residue is subjected to column chromatography; alternatively, the residue may be mixed with water and a water-immiscible organic solvent and extracted with the organic solvent, after which the extract is dried over a drying agent, such as anhydrous magnesium sulfate, and thee solvent is distilled off to leave the desired product. The product can, if necessary, be further purified by conventional means, for example, by recrystallization, or by the various chromatography techniques, notably preparative thin layer chromatography or column chromatography.

In Step H5, an optional step, a compound of formula (Va) is prepared by esterification of the carboxylic acid compound of formula (XXII), optionally followed by deprotection of the imidazolyl group. This esterification reaction is essentially the same as that described above in reaction (ii) of Step A2 of Reaction Scheme A, and the optional deprotection is essentially the same as Step H2 of Reaction Scheme H, and each may be carried out using the same reagents and reaction conditions.

In Step H6, a compound of formula (XXIII) is prepared by hydrolysing a compound of formula (XIII). This reaction is essentially the same as than described above in Step H4 of Reaction Scheme H, and may be carried out using the same reagents and reaction conditions.

In Step H7, a compound of formula (VIIa) is prepared by esterification of the compound of formula (XXIII). This reaction is essentially the same as that described above in Step H5 of Reaction Scheme H, and may be carried out using the same reagents and reaction conditions.

if desired, the imidazolyl-protecting group of the compound of formula (VIIa) can be removed by essentially the same reaction as that optional reaction described above as Step H2 of Reaction Scheme H, which may be carried out using the same reagents and reaction conditions. In Step H8, a compound of formula (Va) is prepared by reacting a compound of formula (VIIa) with a Grignard reagent and/or a reducing agent, and then optionally deprotecting the imidazolyl group. This reaction is essentially the same as that described above in Step B2 of Reaction Scheme B, and the optional deprotection is essentially the same as Step H2 of Reaction Scheme H, and each may be carried out using the same reagents and reaction conditions.

The compounds of formula $(I)_p$ of the present invention can be prepared by a variety of processes well known in the art for the preparation of compounds of this type. For example, they may be prepared by reacting a compound of formula $(II)_p$

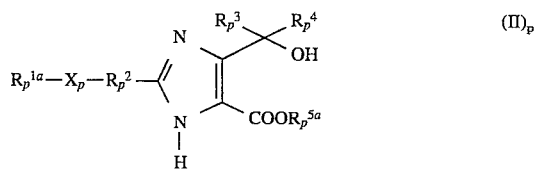

(in which:

$R_p^2$, $R_p^3$, $R_p^4$ and $X_p$ are as defined above;

$R_p^{1a}$ represents when $X_p$ represents an oxygen atom: a hydrogen atom, an alkyl group having from 1 to 6 carbon atoms, a cycloalkyl group having from 3 to 6 carbon atoms or a group of formula $R_p^7CO-$, where $R_p^7$ represents a hydrogen atom, an alkyl group having from 1 to 6 carbon atoms or an aryl group having from 6 to 10 ring carbon atoms; or when $X_p$ represents a sulfur atom: an alkyl group having from 1 to 6 carbon atoms, a cycloalkyl group having from 3 to 6 carbon atoms, a mercapto-protecting group or said group of formula $R_p^7CO-$; and $R_p^{5a}$ represents a carboxy-protecting group) with a compound of formula $(III)_p$:

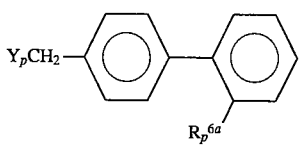 (III)$_p$ (in which $Y_p$ represents a halogen atom; and $R_p^{6a}$ represents a protected carboxy group, a protected tetrazol-5-yl group, a cyano group, a carbamoyl group or an alkylcarbamoyl group in which the alkyl part has from 1 to 6 carbon atoms)

to give a compound of formula (Ib)$_p$:

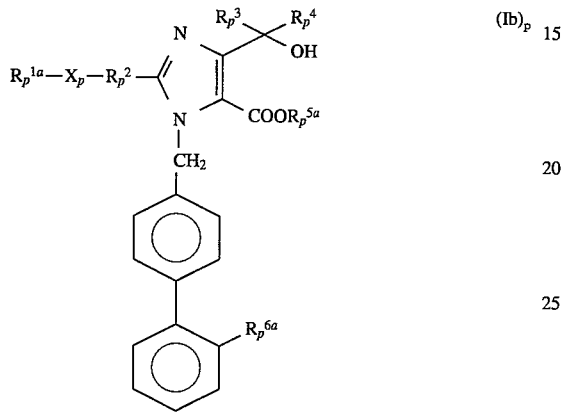

(in which $R_p^{1a}$, $R_p^2$, $R_p^3$, $R_p^4$, $R_p^{5a}$, $R_p^{6a}$ and $X_p$ are as defined above), and, if necessary, converting any group represented by $R_p^{1a}$ or $R_p^{6a}$ to a group represented by $R_p^1$ or $R_p^{6a}$, respectively, and, optionally, removing any carboxy-protecting group, salifying and/or esterifying the resulting compound.

In more detail, the compounds of the present invention may be prepared as shown in the following Reaction Schemes $A_p$, $B_p$ and $C_p$:

Reaction Scheme $A_p$:

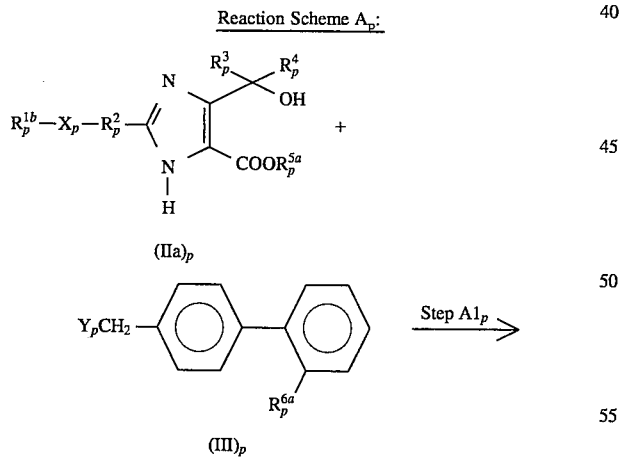

-continued
Reaction Scheme $A_p$:

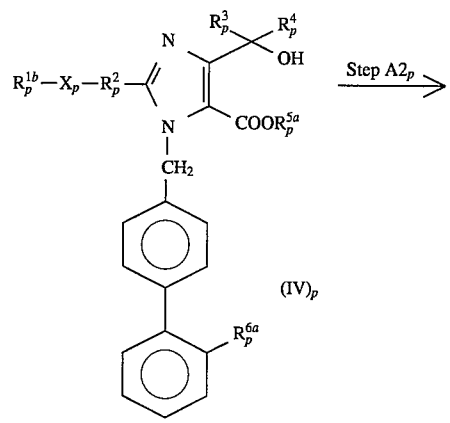

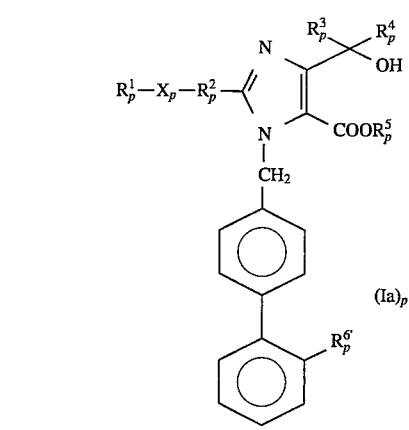

Reaction Scheme $B_p$:

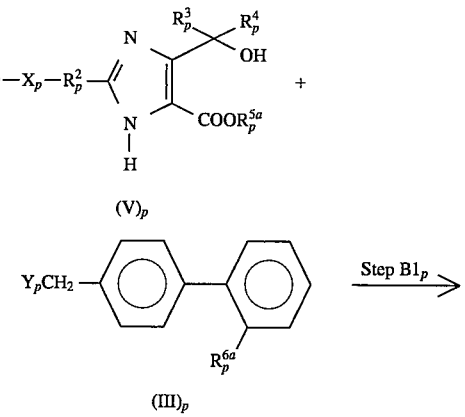

-continued
Reaction Scheme B_p:
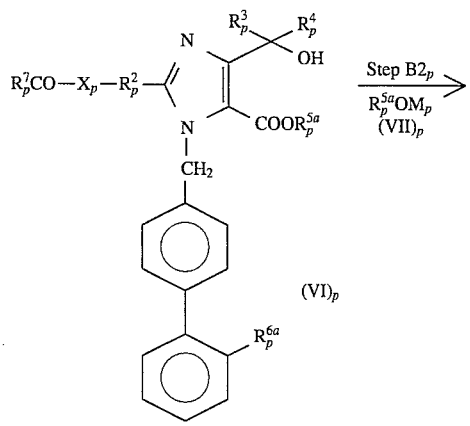
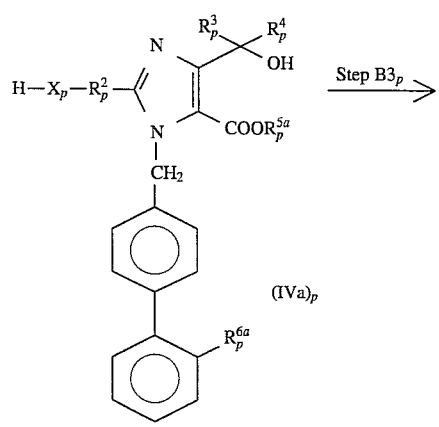
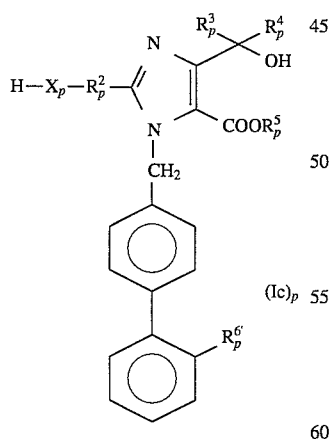
Reaction Scheme C_p:
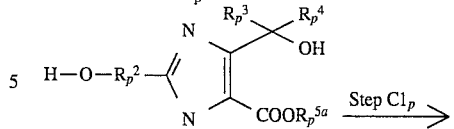
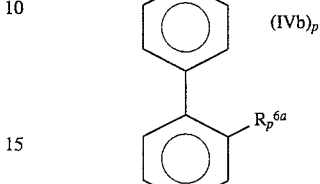
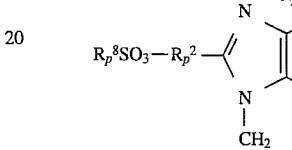
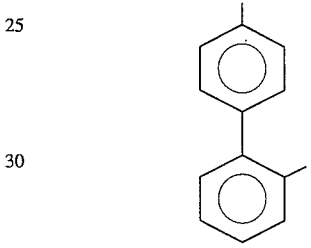
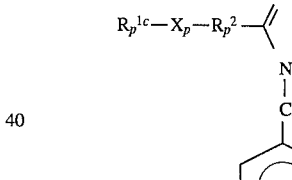

In the above formulae:

$R_p^1$, $R_p^2$, $R_p^3$, $R_p^4$, $R_p^5$, $R_p^{5a}$, $R_p^{6'}$, $R_p^{6a}$, $R_p^7$, $X_p$ and $Y_p$ are as defined above;

$R_p^{1b}$ represents
  when $X_p$ represents an oxygen atom, a hydrogen atom, an alkyl group having from 1 to 6 carbon atoms or a cycloalkyl group having from 3 to 6 carbon atoms, or
  when $X_p$ represents a sulfur atom, an alkyl group having from 1 to 6 carbon atoms group, a cycloalkyl group having from 3 to 6 carbon atoms or a mercapto-protecting group;

$R_p^{1c}$ represents an alkyl group having from 1 to 6 carbon atoms or a cycloalkyl 9group having from 3 to 6 carbon atoms;

$R_p^8$ represents an alkyl group having from 1 to 6 carbon atoms or a haloalkyl group having from 1 to 6 carbon atoms or a phenyl group which is unsubstituted or is substituted by at least one substituent selected from the group consisting of halogen atoms, alkyl groups having from 1 to 6 carbon atoms group and nitro groups;

$M_p$ represents an alkali metal.

Examples of the mercapto-protecting groups which may be represented by $R_p^{1b}$ include: aralkyl groups in which an alkyl group having from 1 to 4 carbon atoms (such as a methyl, ethyl, propyl, isopropyl, butyl, isobutyl or t-butyl group) is substituted by at least one (and preferably from 1 to 3) aryl groups. The aryl groups are aromatic carbocyclic groups having from 6 to 10, preferably 6 or 10, ring carbon atoms, and are unsubstituted or are substituted by at least one substituent selected from the group consisting of halogen atoms, alkyl groups having from 1 to 4 carbon atoms and alkoxy groups having from 1 to 4 carbon atoms. Examples of such aralkyl groups include the diphenylmethyl, bis(4-methylphenyl)methyl, bis(4-methoxyphenyl)methyl and trityl (i.e. triphenylmethyl)groups, preferably the trityl group.

Examples of carboxy-protecting groups which are represented by $R^{5a}$ or included in the protected group represented by $R_p^{6a}$ include the ester groups exemplified above in relation to the groups which may be represented by $R_p^5$.

Examples of the tetrazolyl-protecting groups which may be included in the protected group represented by $R_p^{6a}$ a include aralkyl groups as defined above in relation to the mercapto-protecting groups which may be included in $R_p^{1b}$, such as the benzyl diphenylmethyl and trityl groups, and preferably the trityl group.

The alkyl and cycloalkyl groups which may be represented by $R_p^{1b}$ and $R_p^{1c}$ are as defined and exemplified above in relation to the corresponding groups which may be represented by $R_p^1$.

Examples of alkylcarbamoyl groups which may be represented by $R_p^{6a}$ include methylcarbamoyl, ethylcarbamoyl, propylcarbamoyl, butylcarbamoyl, t-butylcarbamoyl, pentylcarbamoyl, t-pentylcarbamoyl and hexylcarbamoyl groups, preferably the t-butylcarbamoyl and t-pentylcarbamoyl groups.

Where $R_p^7$ represents an alkyl group, this may be, for example, a methyl, ethyl, propyl, butyl, t-butyl, pentyl, t-pentyl or hexyl group, preferably a methyl or ethyl group. Where $R_p^7$ represents an aryl group, this is a carbocyclic aromatic group having from 6 to 10, preferably 6 or 10, ring carbon atoms, which may be unsubstituted or substituted as defined generally above, for example a substituted or unsubstituted phenyl or naphthyl group, preferably a phenyl group.

Where $R_p^8$ represents an alkyl group, this has from 1 to 6 carbon atoms and may be any of those alkyl groups exemplified above in relation to $R_p^1$, and is most preferably a methyl group. Where $R_p^8$ represents a haloalkyl group, this has from 1 to 6 carbon atoms and may be any of those haloalkyl groups exemplified above in relation to $R_p^5$, for example a trifluoromethyl, trichloromethyl or 2,2,2-trichloroethyl group, preferably a trifluoromethyl group. Where $R_p^8$ represents a phenyl group, this may be unsubstituted or it may be substituted by a halogen atom, an alkyl group having from 1 to 6 carbon atoms or a nitro group, and preferred examples of such groups include the phenyl, p-tolyl, p-chlorophenyl, p-bromophenyl and p-nitrophenyl groups.

Examples of the halogen atoms which may be represented by $Y_p$ include the chlorine, bromine and iodine atoms.

Examples of the alkali metals which may be represented by $M_p$ include the lithium, sodium and potassium atoms, of which we prefer the lithium and sodium atoms.

Reaction Scheme $A_p$

This Reaction Scheme illustrates the preparation of compounds of formula $(Ia)_p$.

Step $A1_p$:

In Step $A1_p$, a compound of formula $(IV)_p$ may be prepared by reacting a compound of formula $(IIa)_p$ with a compound of formula $(III)_p$, normally and preferably in an inert solvent and in the presence of a base.

There is no particular restriction on the nature of the solvent to be employed, provided that it has no adverse effect on the reaction or on the reagents involved and that it can dissolve the reagents, at least to some extent. Examples of suitable solvents include: hydrocarbons, especially aromatic hydrocarbons, such as benzene or toluene; ethers, such as tetrahydrofuran or dioxane; alcohols, such as methanol, ethanol or t-butanol; amides, such as N,N-dimethylacetamide, N,N-dimethylformamide or N-methyl-2-pyrrolidinone; ketones, such as acetone or methyl ethyl ketone; nitriles, such as acetonitrile; and sulfoxides, such as dimethyl sulfoxide. Of these, we prefer the amides, ketones, nitriles or sulfoxides.

There is likewise no particular restriction on the nature of the base employed in this reaction, provided that it has no adverse effect on any of the reagents. Preferred examples of bases which may be used include: alkali metal carbonates, such as sodium carbonate or potassium carbonate; alkali metal hydrides, such as sodium hydride, potassium hydride or lithium hydride; alkali metal alkoxides, such as sodium methoxide, sodium ethoxide, potassium t-butoxide or lithium methoxide; and alkali metal hydrogencarbonates, such as sodium hydrogencarbonate or potassium hydrogencarbonate. Of these, we prefer the alkali metal carbonates, alkali metal hydrides or alkali metal alkoxides.

The reaction can take place over a wide range of temperatures, and the precise reaction temperature is not critical to the invention. In general, we find it convenient to carry out the reaction at a temperature of from −10° C. to 100° C., more preferably from 0° C. to 80° C. The time required for the reaction may also vary widely, depending on many factors, notably the reaction temperature and the nature of the reagents, solvent and base employed. However, provided that the reaction is effected under the preferred conditions outlined above, a period of from 30 minutes to 24 hours, more preferably from 1 to 16 hours, will usually suffice.

After completion of the reaction, the desired compound of formula $(IV)_p$ can be recovered from the reaction mixture by conventional means. A suitable recovery procedure comprises: distilling off the solvent under reduced pressure;

adding water to the residue; extracting the mixture with a water-immiscible organic solvent, such as ethyl acetate; drying the extract, for example over anhydrous magnesium sulfate; and then distilling off the solvent. If necessary, the product can be further purified by conventional means, for example, by recrystallization, or by the various chromatography techniques, notably by column chromatography.

Step $A2_p$:

Step $A2_p$ is optional, and comprises a series of reactions any one or more of which may be carried out, if desired:

Reaction $A2(a)_p$: in which the carboxy-protecting groups represented by $R_p^{5a}$ and included in $R_p^{6a}$ may be deprotected selectively or nonselectively;

Reaction $A2(b)_p$: in which the tetrazolyl-protecting groups included in $R_p^{6a}$ may be deprotected;

Reaction $A2(c)_p$: in which a cyano group, a carbamoyl group or an alkylcarbamoyl group having from 1 to 6 carbon atoms in the alkyl part may be converted to a tetrazolyl group;

Reaction $A2(d)_p$: in which the carboxy groups in the compound in which $R_p^5$ represents a hydrogen atom or $R_p^6$ represents a carboxy group may be protected;

Reaction $A2(e)_p$: in which the mercapto-protecting group represented by $R_p^{1b}$ may be deprotected; and Reaction $A2(f)_p$: in those cases where $R_p^{1b}$ represents a hydrogen atom, the resulting hydroxy or mercapto group may be acylated.

These reactions may be carried out in any appropriate order, and are described in more detail below.

Reaction $A2(a)_p$:

The nature of the reaction employed for the deprotection of the carboxy-protecting group in reaction $A2(a)_p$ will, of course, vary depending upon the nature of the protecting group to be removed, as is well known in the art. The reaction can be carried out using procedures well known in the field of organic synthetic chemistry.

For example, where the carboxy-protecting group is an aralkyl group, such as a benzyl group, it can be removed by catalytic reduction in an atmosphere of hydrogen. The pressure of hydrogen is preferably from 1 to 5 atmospheres. The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: alcohols, such as methanol or ethanol; and carboxylic acids, such as acetic acid. Any catalyst commonly used for catalytic reduction may equally be used in this reaction. Examples include palladium-on-charcoal and platinum oxide.

Where the carboxy-protecting group is a t-butyl or diphenylmethyl group, it can be removed by reaction with an acid (preferably a mineral acid, such as hydrogen chloride or sulfuric acid, or an organic acid, such as trifluoroacetic acid, methanesulfonic acid or p-toluenesulfonic acid). The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: alcohols, such as methanol and ethanol; ethers, such as tetrahydrofuran and dioxane; water; or a mixture of water and any one or more of the above organic solvents.

The ester residue can be removed by a conventional hydrolysis reaction, using a base, preferably an alkali metal hydroxide, such as lithium hydroxide, sodium hydroxide or potassium hydroxide; or an alkali metal carbonate, such as sodium carbonate or potassium carbonate. The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: alcohols, such as methanol and ethanol; ethers, such as tetrahydrofuran and dioxane; water; or a mixture of water with any one or more of the above organic solvents.

These reactions can take place over a wide range of temperatures, and the precise reaction temperature is not critical to the invention, although the preferred reaction temperature will vary depending upon the deprotecting method and the nature of the solvent. However, in general, we find it convenient to carry out the reaction at a temperature of from 0° C. to 100° C., more preferably from about room temperature to 60° C. The time required for the reaction may also vary widely, depending on many factors, notably the reaction temperature and the nature of the reagents and solvent employed. However, provided that the reaction is effected under the preferred conditions outlined above, a period of from 30 minutes to 24 hours, more preferably from 1 to 16 hours, will usually suffice.

After completion of the reaction, the desired product can be recovered from the reaction mixture by conventional means, which will depend on the nature of the deprotection reaction. For example, where deprotection is carried out by catalytic reduction, the product can be recovered by filtering off the catalyst and then distilling off the solvent. Where deprotection is carried out using an acid, the product can be recovered by collecting the crystals which appear in the reaction system by filtration or other suitable means, or by distilling off the solvent. Where deprotection is carried out by alkaline hydrolysis, the product can be recovered by distilling off the solvent, neutralizing the residue with an acid, and collecting the crystals which appear in the aqueous solvent; or by neutralizing the mixture with an acid, extracting the product with a water-immiscible organic solvent, such as ethyl acetate, and distilling off the solvent. If necessary, the product can be further purified by conventional means, for example, by recrystallization, or by the various chromatography techniques, notably by column chromatography.

The protecting groups included in $R_p^{5a}$ and $R_p^{6a}$ can be selectively removed by appropriate selection of the reaction conditions.

Reaction $A2(b)_p$:

The nature of the reaction employed for the deprotection of the tetrazolyl-protecting group included in the protected group represented by $R_p^{6a}$ in reaction $A2(b)_p$ will, of course, vary depending upon the nature of the protecting group to be removed, as is well known in the art. The reaction can be carried out using procedures well known in the field of organic synthetic chemistry.

For example, where the protecting group is a trityl group, it may be removed by treating the protected compound with an acid. The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include water and organic solvents, for example: carboxylic acids, such as formic acid and acetic acid; ethers, such as tetrahydrofuran and dioxane; alcohols, such as methanol and ethanol; and mixtures of any two or more of the above solvents.

Examples of acids which may be used in this reaction include: organic carboxylic and sulfonic acids, such as formic acid, acetic acid, oxalic acid, methanesulfonic acid, p-toluenesulfonic acid or trifluoroacetic acid, and inorganic acids, such as hydrochloric acid, hydrobromic acid, sulfuric acid or phosphoric acid. Of these, we prefer acetic acid, trifluoroacetic acid or hydrochloric acid.

The reaction can take place over a wide range of temperatures, and the precise reaction temperature is not critical to the invention. In general, we find it convenient to carry out the reaction at a temperature of from 0° C. to 120° C., more preferably from 10° C. to 100° C. The time required for the reaction may also vary widely, depending on many factors, notably the reaction temperature and the nature of the reagents and solvent employed. However, provided that the reaction is effected under the preferred conditions outlined above, a period of from 30 minutes to 24 hours, more preferably from 1 to 16 hours, will usually suffice.

Where the tetrazolyl-protecting group is a benzyl or diphenylmethyl group, it can be removed by the catalytic reduction method described above in reaction A2(a)$_p$ in relation to the removal of aralkyl groups used as carboxy-protecting groups, using a catalyst such as palladium or platinum oxide.

After completion of the reaction, the desired product of the reaction can be recovered from the reaction mixture by conventional means, for example, in a similar manner to that described in reaction A2(a)$_p$ in Reaction Scheme A$_p$.

Reaction A2(c)$_p$:

The conversion of a cyano group which may be represented by $R_p^{6a}$ to a tetrazolyl group in reaction A2(c)$_p$ may be effected by any of the following three methods.

A2(c-1-1)$_p$ Reaction with an alkali metal azide

The reaction may be carried out by reacting the cyano compound With an alkali metal azide (such as lithium azide, sodium azide or potassium azide, preferably sodium azide). The amount of azide is not critical, although we prefer to use the azide in an amount at least equimolar with respect to the cyano compound. A suitable amount is from 1 to 5 moles (more preferably from 1 to 3 moles) of the azide per mole of the cyano compound. The reaction is normally and preferably effected in the presence of a solvent. There is no particular restriction on the nature of the solvent to be employed, provided that it has no adverse effect on the reaction or on the reagents involved and than it can dissolve the reagents, at least to some extent. Examples of suitable solvents include: ethers, such as dioxane and 1,2-dimethoxyethane; alcohols, such as methanol and ethanol; amides, such as N,N-dimethylformamide and N,N-dimethylacetamide; and sulfoxides, such as dimethyl sulfoxide. The reaction is preferably effected in the presence of an ammonium halide (such as ammonium fluoride, ammonium chloride or ammonium bromide, preferably ammonium chloride). The amount of ammonium halide used is not critical to the invention, although we generally prefer to use from 0.5 to 2 moles, more preferably from 1 to 1.2 moles of ammonium halide per mole of the cyano compound.

The reaction can take place over a wide range of temperatures, and the precise reaction temperature is not critical to the invention. In general, we find it convenient to carry out the reaction at a temperature of from 70° C. to 150° C., more preferably from 90° C. to 120° C. The time required for the reaction may also vary widely, depending on many factors, notably the reaction temperature and the nature of the reagents and solvent employed. However, provided that the reaction is effected under the preferred conditions outlined above, a period of from 10 hours to 7 days, more preferably from 1 day to 5 days will usually suffice.

After completion of the reaction, the product can be recovered by adding water and a water-immiscible organic solvent, such as ethyl acetate, to the reaction mixture, separating the resulting organic solvent layer and distilling off the solvent. If necessary, the product can be further purified by conventional means, for example, by recrystallization, or by the various chromatography techniques, notably by column chromatography.

A2(c-1-2)$_p$ Reaction with a trialkyl- or triaryl- stannic azide

This reaction may be carried out by reacting, in a first step, the corresponding cyano compound with a trialkylstannic azide in which each alkyl group has from 1 to 6 carbon atoms (preferably trimethylstannic azide or tributylstannic azide) or a triarylstannic azide (preferably triphenylstannic azide or tritolylstannic azide) to form a stannic adduct, which is then treated, in a second step, with an acid, a base or an alkali metal fluoride. The amount of the trialkyl- or triarylstannic azide employed is not critical, although we generally find it convenient to use at least an equimolar amount of the trialkyl- or triaryl-stannic azide with respect to the cyano compound, preferably from 1 to 3 moles, more preferably from 1 to 2 moles of the trialkyl- or triaryl-stannic azide per mole of the cyano compound. The reaction is normally and preferably effected in the presence of a solvent. There is no particular restriction on the nature of the solvent no be employed, provided that it has no adverse effect on the reaction or on the reagents involved and that it can dissolve the reagents, at least to some extent. Examples of suitable solvents include: hydrocarbons, such as benzene, toluene, xylene and heptane; halogenated hydrocarbons, especially halogenated aliphatic hydrocarbons, such as methylene chloride and chloroform, ethers; such as dioxane and 1,2 -dimethoxyethane; esters, such as ethyl acetate and butyl acetate; amides, such as N,N-dimethylformamide and N,N-dimethylacetamide; and sulfoxides, such as dimethyl sulfoxide).

The resulting stannic adduct is then treated with an acid (preferably hydrochloric acid or sulfuric acid), a base (preferably an alkali metal hydroxide, such as sodium hydroxide or potassium hydroxide, an alkali metal carbonate, such as sodium carbonate or potassium carbonate, or an alkali metal hydrogencarbonate, such as sodium hydrogencarbonate or potassium hydrogencarbonate) or an alkali metal fluoride (preferably sodium fluoride or potassium fluoride). The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: the solvents listed above for use in the first step; alcohols, such as methanol and ethanol; water; and aqueous alcohols.

These reactions can take place over a wide range of temperatures, and the precise reaction temperature is not critical to the invention. In general, we find it convenient to carry out the reaction of the first step at a temperature of from 0° C. to 150° C., more preferably from 80° C. to 120° C. The time required for each of the reactions may also vary widely, depending on many factors, notably the reaction temperature and the nature of the reagents and solvent employed. However, provided that the reaction is effected under the preferred conditions outlined above, a period of from 8 hours to 7 days, more preferably from 1 day to 5 days, will usually suffice. In the second step of the reaction, a suitable reaction temperature is normally about room temperature, and the reaction will generally be complete within from 30 minutes to 24 hours, more preferably from 1 hour to 6 hours.

After completion of the reaction, the product can be recovered by adding water and a water-immiscible organic solvent (such as ethyl acetate) to the reaction mixture, acidifying the aqueous layer with a mineral acid (such as hydrochloric acid), separating the resulting organic solvent layer and distilling off the solvent. The product may then, if necessary, be further purified by conventional means, for example, by recrystallization, or by the various chromatography techniques, notably by column chromatography.

A2(c-1-3)$_p$ Reaction with a trialkyl- or triaryl-stannic halide and an alkali metal azide This reaction may be conducted by reacting the corresponding cyano compound with a trialkylstannic halide or a triarylstannic halide (preferably trimethylstannic chloride, triethylstannic chloride, tributylstannic chloride or triphenylstannic chloride) and an alkali metal azide, instead of the trialkylstannic azide or triarylstannic azide of reaction A2(c-1-2)$_p$. Examples of suitable alkali metal azides include sodium azide and lithium azide. The amounts of the trialkyl- or triarylstannic halide and the alkali metal azide employed are not critical, although we generally find it convenient to use at least an equimolar amount of the trialkyl- or triarylstannic halide and of the alkali metal azide with respect to the cyano compound, preferably from 1 to 3 moles, more preferably from 1 to 2 moles, of the trialkyl- or triarylstannic halide, and from 1 to 3 moles, more preferably from 1 to 2 moles, of the alkali metal azide per mole of the cyano compound. The reaction is carried out in two steps, each of which may be effected in a similar manner to that described above for reaction A2(c-1-2)$_p$.

The conversion of an alkylcarbamoyl or carbamoyl group represented by $R_p^{6a}$ to a tetrazolyl group may be effected by first converting the alkylcarbamoyl or carbamoyl group to a cyano group, and then converting the cyano group to a tetrazolyl group using the above reactions A2(c-1-1)$_p$, A2(c-1-2)$_p$ and A2(c-1-2)$_p$. The conversion of the alkylcarbamoyl or carbamoyl group to a cyano group may be conducted by either of the following two methods.

A2(c-2-1)$_p$ Reaction with a halogenating agent, to convert an alkylcarbamoyl group to a cyano group This reaction may be conducted by reacting the corresponding alkylcarbamoyl compound with a halogenating agent, preferably oxalyl chloride, phosphorus oxychloride or thionyl chloride. The amount of the halogenating agent employed is not critical, although we generally find it convenient to use at least an equimolar amount of the halogenating agent with respect to the alkylcarbamoyl compound, preferably from 1 to 3 moles, more preferably from 1 to 2 moles, of the halogenating agent per mole of the alkylcarbamoyl compound. The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: hydrocarbons, such as benzene, toluene, xylene and heptane; halogenated hydrocarbons, especially halogenated aliphatic hydrocarbons, such as methylene chloride and chloroform; ethers, such as diethyl ether, tetrahydrofuran and dioxane; and esters, such as ethyl acetate and butyl acetate.

The reaction can take place over a wide range of temperatures, and the precise reaction temperature is not critical to the invention. In general, we find it convenient to carry out the reaction at a temperature of from −10° C. to 100° C., more preferably from 0° C, to 50° C. The time required for the reaction may also vary widely, depending on many factors, notably the reaction temperature and the nature of the reagents and solvent employed. However, provided that the reaction is effected under the preferred conditions outlined above, a period of from 10 minutes to 16 hours, more preferably from 30 minutes to 6 hours, will usually suffice.

After completion of the reaction, the product can be recovered by conventional means. For example, on suitable recovery procedure comprises: adding a weakly basic aqueous solution, for example an aqueous solution of an alkali metal hydrogencarbonate (preferably sodium hydrogencarbonate), and a water-immiscible organic solvent, such as ethyl acetate, to the reaction mixture; separating the resulting organic solvent layer; and distilling off the solvent. The product may then, if necessary, be further purified by conventional means, for example, by recrystallization, or by the various chromatography techniques, notably by column chromatography.

A2(c-2-2)$_p$ Reaction with a dehydrating agent to convert a carbamoyl group to a cyano group This reaction may be conducted by reacting the corresponding carbamoyl compound with a dehydrating agent, preferably an acid anhydride, such as acetic anhydride, trifluoroacetic anhydride, methanesulfonic anhydride or trifluoromethanesulfonic anhydride, or thionyl chloride. The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: hydrocarbons, such as benzene, toluene, xylene and heptane; halogenated hydrocarbons, especially halogenated aliphatic hydrocarbons, such as methylene chloride and chloroform; ethers, such as diethyl ether, tetrahydrofuran and dioxane; and esters, such as ethyl acetate and butyl acetate. The reaction is effected in the presence of an organic amine, preferably triethylamine, pyridine or N-methylmorpholine.

The reaction can take place over a wide range of temperatures, and the precise reaction temperature is not critical to the invention. In general, we find it convenient to carry out the reaction at a temperature of from −10° C. to 100° C., more preferably from 0° C. to 50° C. The time required for the reaction may also vary widely, depending on many factors, notably the reaction temperature and the nature of the reagents and solvent employed. However, provided that the reaction is effected under the preferred conditions outlined above, a period of from 10 minutes to 16 hours, more preferably from 30 minutes to 6 hours, will usually suffice.

After completion of the reaction, the product can be recovered by adding a weakly basic aqueous solution (such as an aqueous solution of sodium hydrogencarbonate) and a water-immiscible organic solvent, such as ethyl acetate, to the reaction mixture, separating the resulting organic solvent layer and distilling off the solvent. The product may then, if necessary, be further purified by conventional means, for example, by recrystallization, or by the various chromatography techniques, notably by column chromatography.

Reaction A2(d)$_p$:

The carboxy-protecting reaction in reaction A2(d)$_p$ may be carried out by conventional means well known in the field of organic synthetic chemistry.

For example, the reaction may be conducted by reacting the corresponding carboxylic acid with a compound of formula $R_p^{5a}$—$Z_p$(IX)$_p$ (in which: $R_p^{5a}$ is as defined above; and $Z_p$ represents a halogen atom, such as a chlorine, bromine or iodine atom, or a group of formula —$OSO_3R_p^{5a}$, in which $R_p^{5a}$ is as defined above), preferably in the presence of a base.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: amides, such as N,N-dimethylformamide or N,N-dimethylacetamide; halogenated hydrocarbons, especially halogenated aliphatic hydrocarbons, such as methylene chloride or 1,2-dichloroethane; ketones, such as acetone or methyl ethyl ketone; and nitriles, such as acetonitrile. Of these, we prefer the amides or the ketones.

Examples of bases which my be used include: alkali metal carbonates, such as sodium carbonate and potassium carbonate; alkali metal hydrogencarbonates, such as sodium hydrogencarbonate and potassium hydrogencarbonate; alkali metal hydrides, such as lithium hydride, sodium hydride and potassium hydride; and tertiary amines, such as triethylamine, N-methylmorpholine and diisopropylethylamine. Of these, we prefer the alkali metal carbonates or the tertiary amines.

The reaction conditions, including the reaction temperature and time, and the recovery procedure are all similar to those described above in step $A1_p$ of Reaction Scheme $A_p$.

Where the carboxy-protecting group to be introduced is an alkyl group having from 1 to 6 carbon atoms, the reaction can be conducted by reacting the corresponding carboxylic acid with an alcohol having from 1 to 6 carbon atoms (such as methanol, ethanol, propanol or hexanol) in the presence of an acid catalyst (such as hydrogen chloride or sulfuric acid), using the alcohol as solvent. The reaction can take place over a wide range of temperatures, and the precise reaction temperature is not critical to the invention. In general, we find it convenient to carry out the reaction at a temperature of from 0° C. to 100° C. The time required for the reaction may also vary widely, depending on many factors, notably the reaction temperature and the nature of the reagents and solvent employed. However, provided that the reaction is effected under the preferred conditions outlined above, a period of from 1 hour to 24 hours will usually suffice. Alternatively, such protecting groups may be introduced by treating the corresponding carboxylic acid with a halogenating agent (such as phosphorus pentachloride, thionyl chloride or oxalyl chloride) in an inert solvent (preferably a halogenated hydrocarbon, such as methylene chloride or chloroform; an ether, such as tetrahydrofuran or dioxane; or an aromatic hydrocarbon, such as benzene or toluene) to give the corresponding acid halide, and then reacting this acid halide with a corresponding alcohol (when preparing the t-butyl ester, potassium t-butoxide is desirable in place of the alcohol) in the presence of a base (for example an organic amine, such as triethylamine). These reactions, likewise, can take place over a wide range of temperatures, and the precise reaction temperature is not critical to the invention. In general, we find it convenient to carry out both reactions at about room temperature. The time required for the reactions may also vary widely, depending on many factors, notably the reaction temperature and the nature of the reagents and solvent employed. However, provided that the reactions are effected under the preferred conditions outlined above, a period of from 30 minutes to 5 hours will usually suffice for the first reaction, whilst a period of from 30 minutes to 10 hours will usually suffice for the second reaction. The desired compound can then be recovered by conventional means, for example, by similar means to those described above in step $A1_p$ of Reaction Scheme $A_p$.

Reaction $A2(e)_p$:

The removal of the mercapto-protecting group represented by $R_p^{1b}$ in reaction $A2(e)_p$ may be effected by treating the protected compound with an acid (such as trifluoroacetic acid or a mixture of hydrobromic acid and acetic acid) and may be conducted in a similar manner to that described above for the deprotection of a carboxy-protecting group with an acid in reaction $A2(a)_p$ described above.

Reaction $A2(f)_p$:

Acylation in reaction $A2(f)_p$ may be conducted by reacting the compound where $R_p^{1b}$ represents a hydrogen atom with: an alkanoyl halide having from 2 to 6 carbon atoms, for example acetyl chloride, propionyl chloride, butyryl bromide, valeryl chloride or hexanoyl chloride; a mixed acid anhydride, such as a mixed acid anhydride between formic acid and acetic acid; or an anhydride of a carboxylic acid having from 2 to 6 carbon atoms, such as acetic anhydride, propionic anhydride, valeric anhydride or hexanoic anhydride. The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: halogenated hydrocarbons, especially halogenated aliphatic hydrocarbons, such as methylene chloride and chloroform; esters, such as ethyl acetate; and ethers, such as tetrahydrofuran and dioxane. The reaction is effected in the presence of a base, for example an organic tertiary amine, such as triethylamine, pyridine, picoline, lutidine or N,N-diethyl-N-isopropylamine.

The reaction can take place over a wide range of temperatures, and the precise reaction temperature is not critical to the invention. In general, we find it convenient to carry out the reaction at a temperature of from 0° C. to 120° C., more preferably from 0° C. to 80° C. The time required for the reaction may also vary widely, depending on many factors, notably the reaction temperature and the nature of the reagents and solvent employed. However, provided that the reaction is effected under the preferred conditions outlined above, a period of from I hour to 24 hours, more preferably from 1 to 16 hours, will usually suffice.

After completion of the reaction, the reaction product can be recovered from the reaction mixture by conventional means, for example, in a similar manner to that described for the recovery of the compound in step $A1_p$ of Reaction Scheme $A_p$, described above.

In this reaction, in order to acylate the group of formula $R_p^{1b}$—$X_p$—$R_p^2$—, where $R_p^{1b}$ represents a hydrogen atom, without affecting the hydroxy group present in the substituent at the 4-position on the imidazole ring [that is in the group of formula —$C(OH)R_p^3R_p^4$], we prefer that the reaction should only be applied to compounds in which the groups represented by $R_p^3$ and $R_p^4$ are alkyl groups and where the hydroxy or mercapto group represented by $R_p^{1b}$—$X_p$— is linked to a primary or secondary carbon atom [such as —$CH_2$— or —$CH(CH_3)$—] in the group represented by $R_p^2$.

However, in the case of those compounds in which the groups represented by $R_p^3$ and $R_p^4$ are hydrogen atoms and the hydroxy or mercapto group represented by $R_p^{1b}$—$X_p$— is linked to a secondary or tertiary carbon atom in the group represented by $R_p^2$, or those compounds in which the group represented by $R_p^3$ is an alkyl group the group represented by $R_p^4$ is a hydrogen atom and the hydroxy or mercapto group represented by $R_p^{1b}$—$X_p$— is linked to a tertiary carbon atom in the group represented by $R_p^2$, we prefer to protect the hydroxy group in the substituent on the 4-position of the imidazole ring by reacting the hydroxy or mercapto compound with a benzyl halide in which the benzene ring is unsubstituted or is substituted by an alkyl or alkoxy group having from 1 to 4 carbon atoms (such as benzyl chloride, benzyl bromide, p-methylbenzyl chloride or p-methoxybenzyl chloride, preferably benzyl chloride or p-methoxybenzyl chloride). The above acylation reaction of the hydroxy or mercapto group represented by $R_p^{1b}$—$X_p$— is then carried out while the hydroxy group in the substituent on the 4-position of the imidazole ring is protected, and then the hydroxy-protecting benzyl or substituted benzyl group is removed. The hydroxyprotecting reaction may be conducted in a similar manner to that described above in step $A1_p$ of Reaction Scheme $A_p$, and the reaction for deprotecting the protected hydroxy group may be conducted in a similar manner to the deprotecting reaction for removing a carboxy-protecting group which is an aralkyl group in reaction $A2(a)_p$, described above.

Reaction Scheme $B_p$

In this Reaction Scheme, a compound of formula $(Ic)_p$, that is a compound of formula $(Ia)_p$ in which the group represented by $R_p^1$ is a hydrogen atom, is prepared.

Step $B1_p$:

In Step $B1_p$, a compound of formula $(VI)_p$ may be prepared by reacting a compound of formula $(III)_p$ with a compound of formula $(V)_p$. This reaction is essentially the same as, and may be carried out using the same reagents and reaction conditions as, that of Step $A1_p$ in Reaction Scheme $A_p$, described above.

Step $B2_p$

In Step $B2_p$, a compound of formula $(IVa)_p$ can be prepared by reacting the compound of formula $(VI)_p$ with a compound of formula $R_p^{5a}OM_p(VII)_p$. The amount of the compound of formula $(VII)_p$ employed in this reaction is not critical, but we generally prefer to employ at least an equimolar amount of the compound of formula $(VII)_p$ with respect to the compound of formula $(VI)_p$. More preferably, we employ from 1 to 3 moles, still more preferably from 1 to 2 moles, of the compound of formula $(VII)_p$ per mole of the compound of formula $(VI)_p$.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: the alcohols represented by the formula $R_p^{5a}OH$ (in which $R_p^{5a}$ is as defined above); ethers, such as tetrahydrofuran and dioxane; and halogenated hydrocarbons, especially halogenated aliphatic hydrocarbons, such as methylene chloride and chloroform. A single one of these organic solvents may be employed, or a mixture of any two or more of them may be employed. Of these solvents, we prefer the alcohols or the ethers.

The reaction can take place over a wide range of temperatures, and the precise reaction temperature is not critical to the invention, although the preferred reaction temperature will depend on the nature of the compounds used as starting materials. In general, we find it convenient to carry out the reaction at a temperature of from −20° C. to 80° C., more preferably from −10° C. to 40° C. The time required for the reaction may also vary widely, depending on many factors, notably the reaction temperature and the nature of the reagents and solvent employed. However, provided that the reaction is effected under the preferred conditions outlined above, a period of from 30 minutes to 24 hours, more preferably from 1 hour to 16 hours, will usually suffice.

After completion of the reaction, the reaction product of formula $(IVa)_p$ can be recovered from the reaction mixture by conventional means. One suitable recovery technique comprises: distilling off the solvent under reduced pressure; adding water and a water-immiscible organic solvent, such as ethyl acetate, to the residue; separating the organic solvent layer containing the desired compound; drying this over a drying agent, such as anhydrous magnesium sulfate; and distilling off the solvent. The product may, if necessary, be further purified by conventional means, for example, by recrystallization, or by the various chromatography techniques, notably by column chromatography.

Step $B3_p$:

In Step $B3_p$, a compound of formula $(Ic)_p$ can be prepared from the compound of formula $(IVa)_p$ in a similar manner to that described above in relation to reactions $A2(a)_p$ to $A2(d)_p$ in step $A2_p$ of Reaction Scheme $A_p$.

Reaction Scheme $C_p$

In this Reaction Scheme, a compound of formula $(Id)_p$, that is a compound of formula $(Ia)_p$ in which $R_p^1$ is an alkyl group having from 1 to 6 carbon atoms or a cycloalkyl group having from 3 to 6 carbon atoms, is prepared.

Step $C1_p$:

In Step $C1_p$, a compound of formula $(IVc)_p$ is prepared by reacting a compound of formula $(IVb)_p$ with a compound of formula $(XI)_p$ or $(XIa)_p$:

$$(R_p^8SO_2)_2O \quad\quad\quad (XI)_p$$

or $$R_p^8SO_2Y_p \quad\quad\quad (XIa)_p$$

(in which $R_p^8$ and $Y_p$ are as defined above) in the presence of a base.

The amount of the compound of formula $(XI)_p$ or $(XIa)_p$ employed in this reaction is not critical, although we prefer to employ at least an equimolar amount of the compound of formula $(XI)_p$ or $(XIa)_p$ with respect to the compound of formula $(IVb)_p$. More preferably, we employ from 1 to 3 moles, still more preferably from 1 to 2 moles, of the compound of formula $(XI)_p$ or $(XIa)_p$ per mole of the compound of formula $(IVb)_p$.

The nature of the base employed in this reaction is also not critical, provided that it has no adverse effect on the reagents, and any base commonly used in a sulfonylation reaction of this type may equally be employed here. Preferred examples of bases which may be used include organic amines, such as triethylamine, N,N-diisopropyl-N-ethylamine, 4-dimethylaminopyridine, 1,5-diazabicyclo[4.3.0]-5-nonene, 1,8-diazabicyclo[5.4.0]- 7-undecene and 1,4-diazabicyclo[2.2.2]octane. Of these, we particularly prefer triethylamine or N,N-diisopropyl-N-ethylamine. The amount of the base employed in this reaction is not critical, although we prefer to employ at least an equimolar amount of the base with respect to the compound of formula $(IVb)_p$. More preferably, we employ from 1 to 3 moles, still more preferably from 1 to 2 moles, of the base per mole of the compound of formula $(IVb)_p$.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent.

Examples of suitable solvents include: hydrocarbons, such as benzene, toluene or hexane; halogenated hydrocarbons, especially halogenated aliphatic hydrocarbons, such as methylene chloride or chloroform; ethers, such as diethyl ether, tetrahydrofuran or dioxane; and esters, such as ethyl acetate. Of these, we prefer the halogenated hydrocarbons or the ethers.

The reaction can take place over a wide range of temperatures, and the precise reaction temperature is not critical to the invention, although the preferred reaction temperature will depend on the nature of the compounds used as starting materials. In general, we find it convenient to carry out the reaction at a temperature of from −10° C. to 80° C., more preferably from 0° C. to 50° C. The time required for the reaction may also vary widely, depending on many factors, notably the reaction temperature and the nature of the reagents and solvent employed. However, provided that the reaction is effected under the preferred conditions outlined above, a period of from 1 to 24 hours, more preferably from 4 to 16 hours, will usually suffice.

After completion of the reaction, the reaction product of formula $(IVc)_p$ can be recovered from the reaction mixture by conventional means. One suitable recovery technique comprises: adding water to the residue; extracting it with a water-immiscible organic solvent, such as ethyl acetate; drying the extract over a drying agent, such as anhydrous magnesium sulfate; and distilling off the solvent. The product may, if necessary, be further purified by conventional means, for example, by recrystallization, or by the various chromatography techniques, notably by column chromatography.

In this reaction, in order to sulfonylate the group of formula $H\text{—}O\text{—}R_p^2\text{—}$ without affecting the hydroxy group present in the substituent at the 4-position on the imidazole ring [that is in the group of formula $\text{—}C(OH)R_p^3R_p^4$], we prefer that the reaction should only be applied to compounds in which the groups represented by $R_p^3$ and $R_p^4$ are alkyl groups and where the hydroxy group is linked to a primary or secondary carbon atom [such as $\text{—}CH_2\text{—}$ or $\text{—}CH(CH_3)\text{—}$] in the group represented by $R_p^2$.

However, in the case of those compounds in which the groups represented by $R_p^3$ and $R_p^4$ are hydrogen atoms and the hydroxy group is linked to a secondary or tertiary carbon atom in the group represented by $R_p^2$, or those compounds in which the group represented by $R_p^3$ is an alkyl group, the group represented by $R_p^4$ is a hydrogen atom and the hydroxy group is linked to a tertiary carbon atom in the group represented by $R_p^2$, we prefer to protect the hydroxy group in the substituent on the 4-position of the imidazole ring by reacting the compound with a benzyl halide in which the benzene ring is unsubstituted or is substituted by an alkyl or alkoxy group having from 1 to 4 carbon atoms (such as benzyl chloride, benzyl bromide, p-methylbenzyl chloride or p-methoxybenzyl chloride, preferably benzyl chloride or p-methoxybenzyl chloride). The above sulfonylation reaction of the hydroxy group in the group represented by the formula $H\text{—}O\text{—}R_p^2\text{—}$ is then carried out while the hydroxy group in the substituent on the 4-position of the imidazole ring is protected, and then the hydroxy-protecting benzyl or substituted benzyl group is removed. The hydroxy-protecting reaction may be conducted in a similar manner to that described above in step $A1_p$ of Reaction Scheme $A_p$, and the reaction for deprotecting the protected hydroxy group may be conducted in a similar manner to the deprotecting reaction for removing a carboxy-protecting group which is an aralkyl group in reaction $A2(a)_p$, described above.

Step $C2_p$:

In Step $C2_p$, a compound of formula $(IVd)_p$ is prepared by reacting the compound $(IVc)_p$ with a compound of formula $R_p^{1c}XM_{pp}(VIII)_p$.

The amount of the compound of formula $(VIII)_p$ employed in this reaction is not critical, although we prefer to employ at least an equimolar amount of the compound of formula $(VIII)_p$ with respect to the compound of formula $(IVc)_p$. More preferably, we employ from 1 to 3 moles, still more preferably from 1 to 2 moles, of the compound of formula $(VIII)_p$ per mole of the compound of formula $(IVc)_p$.

The reaction is normally and preferably effected in the presence of a solvent. There is no particular restriction on the nature of the solvent to be employed, provided that it has no adverse effect on the reaction or on the reagents involved and that in can dissolve the reagents, at least to some extent. Examples of suitable solvents include: hydrocarbons, such as benzene, toluene or hexane; halogenated hydrocarbons, especially halogenated aliphatic hydrocarbons, such as methylene chloride or chloroform; ethers, such as diethyl ether, tetrahydrofuran or dioxane; alcohols, such as methanol, ethanol or t-butanol [preferably, where the compound of formula $(VIII)_p$ is an alkali metal alkoxide, the alcohol corresponding to this alkoxide]; ketones, such as acetone or methyl ethyl ketone; amides, such as N,N-dimethylformamide or N,N-dimethylacetamide; and sulfoxides, such as dimethyl sulfoxide. Of these, we prefer the ethers, alcohols, ketones or amides.

The reaction can take place over a wide range of temperatures, and the precise reaction temperature is not critical to the invention, although the preferred reaction temperature will depend on the nature of the compounds used as starting materials. In general, we find it convenient to carry out the reaction at a temperature of from −10° C. to 120° C., more preferably from 0° C. to 100° C. The time required for the reaction may also vary widely, depending on many factors, notably the reaction temperature and the nature of the reagents and solvent employed. However, provided that the reaction is effected under the preferred conditions outlined above, a period of from 30 minutes to 24 hours, more preferably from 1 to 16 hours, will usually suffice.

After completion of the reaction, the reaction product of formula $(IVd)_p$ can be recovered from the reaction mixture by conventional means, for example, in a similar manner to that described in step $A1_p$ in Reaction Scheme $A_p$.

Step $C3_p$:

In Step $C3_p$, a compound of formula $(Id)_p$ is prepared from the compound of formula $(IVd)_p$ in a similar manner to that described above in relation to reactions $A2(a)_p$ to $A2(d)_p$ in step $A2_p$ of Reaction Scheme $A_p$.

Preparation Of Starting Materials

Many of the starting materials used in these reactions are well known compounds and others can be prepared by well known reactions commonly employed for analogous compounds. The starting materials of formulae $(IIa)_p$ and $(V)_p$ used in Reaction Schemes $A_p$ and $B_p$ may be prepared as illustrated in Reaction Schemes $D_p$ to $G_p$ as follows:

Reaction Scheme $D_p$:

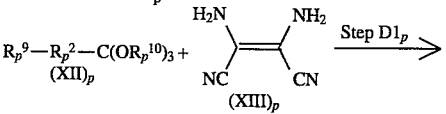

5,616,599
-continued
Reaction Scheme D$_p$:
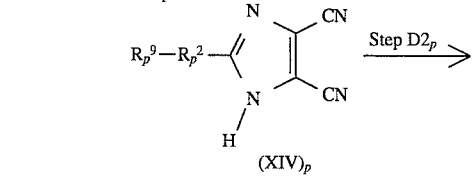 Step D2$_p$ →
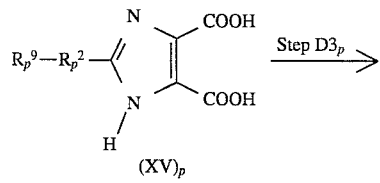 Step D3$_p$ →
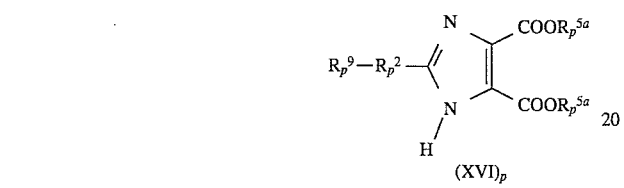 Step D4$_p$ →
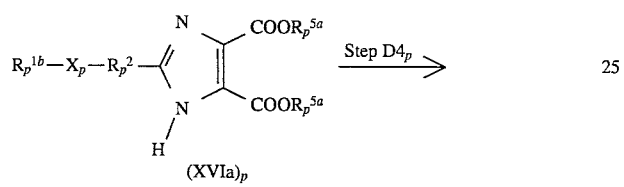
Reaction Scheme E$_p$:
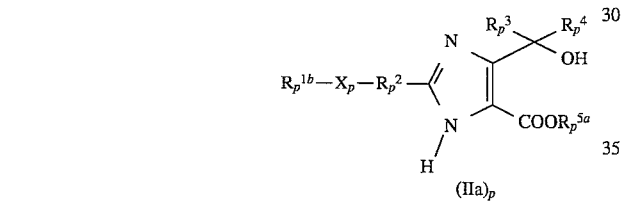 Step E1$_p$ →
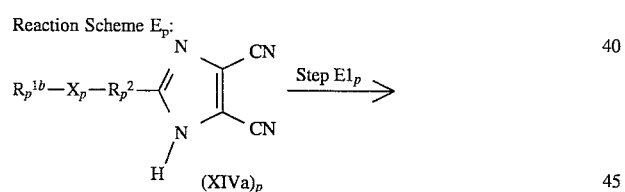 Step E2$_p$ →
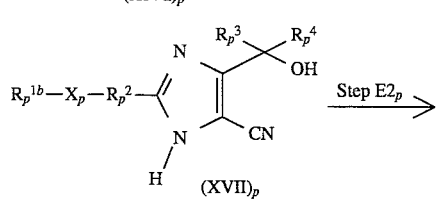 Step E3$_p$ →
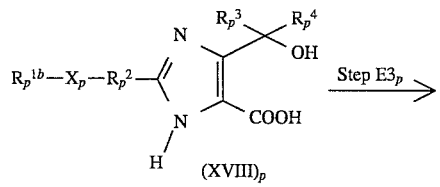
Reaction Scheme E$_p$:
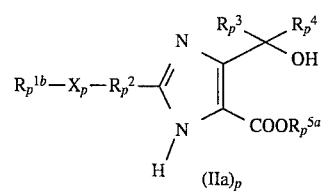
Reaction Scheme F$_p$:
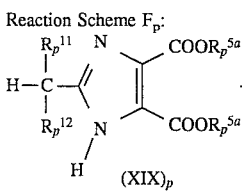 Step F1$_p$ →
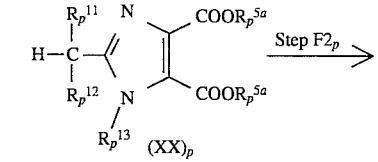 Step F2$_p$ →
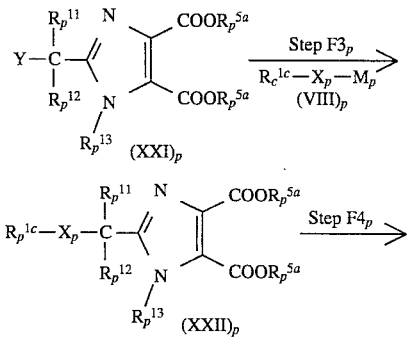 $\xrightarrow[R_c^{1c}-X_p-M_p]{\text{Step F3}_p}$ (VIII)$_p$
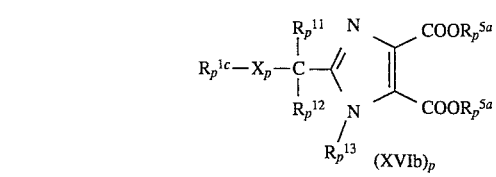 Step F4$_p$ →
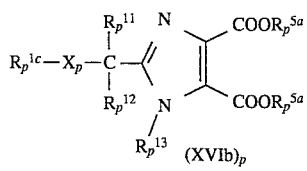
Reaction Scheme G$_p$:
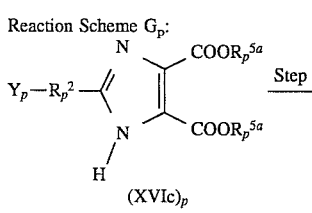 Step G1$_{p7}$ →
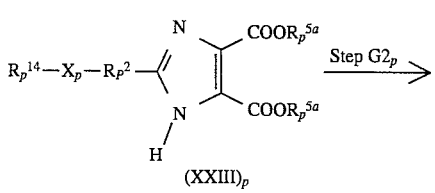 Step G2$_p$ →

Reaction Scheme $G_p$:

-continued

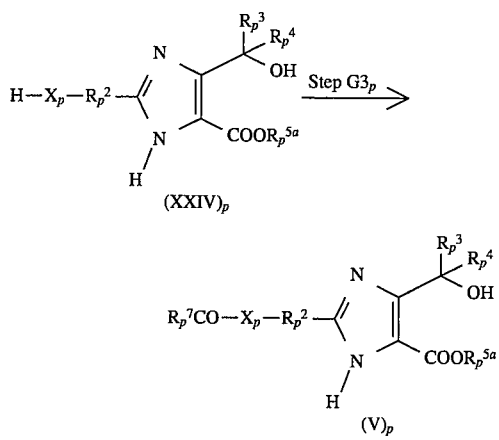

In the above formulae:

$R_p^{1b}$, $R_p^{1c}$, $R_p^2$, $R_p^3$, $R_p^4$, $R_p^{5a}$, $R_p^7$, $X_p$, $Y_p$ and $M_p$ are as defined above;

$R_p^9$ represents a halogen atom, preferably a chlorine, bromine or iodine atom, or a group of formula $R_p^{1b}$—$X_p$— (where $R_p^{1b}$ and $X_p$ are as defined above);

$R_p^{10}$ represents an alkyl group having from 1 to 6 carbon atoms, preferably a methyl or ethyl group;

$R_p^{11}$ and $R_p^{12}$ are the same or different and each represents a hydrogen atom or an alkyl group having from 1 to 3 carbon atoms, provided that the total number of the carbon atoms in the atoms or groups represented by $R_p^{11}$ and $R_p^{12}$ is 3 or less;

$R_p^{13}$ represents an imidazolyl-protecting group; and $R_p^{14}$ represents an alkanoyl group having from 2 to 6 carbon atoms.

Examples of imidazolyl-protecting groups which may be represented by $R_p^{13}$ include: aralkyl groups in which an alkyl group having from 1 to 4 carbon atoms is substituted by at least one (preferably from 1 to 3) aryl groups, which themselves can optionally be substituted by at least one nitro group or alkoxy group having from 1 to 4 carbon atoms, for example the benzyl, p-nitrobenzyl, p-methoxybenzyl, diphenylmethyl and trityl groups; and alkoxymethyl groups, in which the alkoxy part has from 1 to 4 carbon atoms, such as the methoxymethyl, ethoxymethyl, propoxymethyl and butoxymethyl groups. Of these, we prefer the benzyl, p-nitrobenzyl, p-methoxybenzyl, trityl, methoxymethyl and ethoxymethyl groups, more preferably the benzyl or trityl groups.

Reaction Scheme $D_p$

Reaction Scheme $D_p$ consists of the preparation of a compound of formula (IIa)$_p$.

Step D1$_p$:

In Step D1$_p$, an imidazole-4,5-dicarbonitrile of formula (XIV)$_p$ is prepared by reacting an orthoester compound of formula (XII)$_p$ with diaminomaleonitrile of formula (XIII)$_p$, which reaction may be carried out by a conventional method [such as that of R. W. Begland et al., J. Org. Chem., 39, 2341 (1974)]. In this reaction, an orthoester compound of formula (XII)$_p$ is reacted with diaminomaleonitrile in an inert solvent. There is no particular restriction on the nature of the solvent to be employed, provided that it has no adverse effect on the reaction or on the reagents involved and that it can dissolve the reagents, at least to some extent. Examples of suitable solvents include: aromatic hydrocarbons, such as benzene, toluene or xylene; halogenated hydrocarbons, such as 1,2-dichloroethane and carbon tetrachloride; ethers, such as tetrahydrofuran and dioxane; and nitriles, such as acetonitrile.

The reaction can take place over a wide range of temperatures, and the precise reaction temperature is not critical to the invention. In general, we find it convenient to carry out the reaction at a temperature of from 50° C. to 180° C., more preferably from 80° C. to 150° C. The time required for the reaction may also vary widely, depending on many factors, notably the reaction temperature and the nature of the reagents and solvent employed. However, provided that the reaction is effected under the preferred conditions outlined above, a period of from 1 to 24 hours, more preferably from 2 to 10 hours, will usually suffice.

The reaction product of formula (XIV)$_p$ can be recovered from the reaction mixture by collecting by filtration the crystals which appear or by distilling off the solvent. If necessary, the product can be further purified by conventional means, for example, by recrystallization, or by the various chromatography techniques, notably by column chromatography.

Step D2$_p$:

Step D2$_p$ consists of preparing a compound of formula (XV)$_p$ by heating the compound of formula (XIV)$_p$ under reflux for a suitable period, for example from 1 to 20 hours (more preferably from 3 to 17 hours), in the presence of an aqueous mineral acid, such as aqueous hydrochloric acid, aqueous sulfuric acid or aqueous nitric acid. The reaction product of formula (XV)$_p$ can be recovered by collecting the crystals which deposit upon cooling by filtration or by distilling off the solvent.

Step D3$_p$:

Step D3$_p$ consists of preparing a compound of formula (XVI)$_p$ by protecting the carboxy group of the compound of formula (XV)$_p$. This reaction is essentially the same as that of, and may be carried out in a similar manner to that described in, reaction A2(d)$_p$ in step A2$_p$ of Reaction Scheme A$_p$ described above.

Step D4$_p$:

In Step D4$_p$, a compound of formula (IIa)$_p$ is prepared by reacting a compound of formula (XVIa)$_p$, which is a compound of formula (XVI)$_p$ where $R_p^9$ represents a group of formula $R_p^{1b}$—$X_p$— (in which $R_p^{1b}$ and $X_p$ are as defined above), with a reducing agent and/or a Grignard reagent of formula (XXV)$_p$ and/or (XXVa)$_p$:

(in which $Y_p$ is as defined above and $R_p^{3a}$ and $R_p^{4a}$ are the same or different and each represents an alkyl group having from 1 to 6 carbon atoms).

In this reaction, the compound of formula (IIa)$_p$ where $R_p^3$ and $R_p^4$ both represent hydrogen atoms is prepared by reacting the compound of formula (XVIa)$_p$ with 3 or more moles (preferably from 3 to 4 moles) of the reducing agent. The compound of formula (IIa)$_p$ where $R_p^3$ represents an alkyl group having from 1 to 6 carbon atoms and $R_p^4$ represents a hydrogen atom is prepared by reacting the compound of formula (XVIa)$_p$ with approximately 2 moles of the reducing agent and then with the Grignard reagent of formula (XXV)$_p$. The compound of formula (IIa)$_p$ where $R_p^3$ and $R_p^4$ are the same or different and each represents an alkyl group having from 1 to 6 carbon atoms is prepared by reacting the compound of formula (IXVa)$_p$ with approximately 2 moles of the Grignard reagent of formula (XXV)$_p$ and then with the Grignard reagent of formula $(XXVa)_p$. Further, the compound of formula $(IIa)_p$ where $R_p^3$ and $R_{p4}$ are the same alkyl group having from 1 to 6 carbon atoms is prepared by reacting the compound of formula $(XVIa)_p$ with approximately 3 moles or more (preferably from 3 to 4 moles) of the Grignard reagent of formula $(XXV)_p$ or $(XXVa)_p$.

The reaction of the compound of formula $(XVIa)_p$ with a reducing agent is preferably carried out in an inert solvent.

Examples of the reducing agents which may be used include: alkyl aluminum hydrides, such as diisobutyl aluminum hydride; and alkali metal borohydrides, such as sodium borohydride or sodium cyanoborohydride. Of these, we prefer diisobutyl aluminum hydride or sodium borohydride.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: hydrocarbons, such as toluene or hexane; ethers, such as tetrahydrofuran or dioxane; alcohols, such as methanol or ethanol; water; or a mixture of water and any one or more of the above organic solvents. The preferred solvent will vary depending upon the nature of the reducing agent. For example, where the reducing agent is an alkyl aluminum hydride, hydrocarbons and ethers are preferred; and where the reducing agent is an alkali metal borohydride, alcohols, water or aqueous alcohols are preferred.

The reaction can take place over a wide range of temperatures, and the precise reaction temperature is not critical to the invention. In general, we find it convenient to carry out the reaction at a temperature of from $-30°$ C. to $80°$ C. Specifically, when the reducing agent is an alkyl aluminum hydride, the temperature is preferably in the range from $-20°$ C. to $20°$ C. When the reducing agent is an alkali metal borohydride, the temperature is preferably in the range from $0°$ C. to $50°$ C. The time required for the reaction may also vary widely, depending on many factors, notably the reaction temperature and the nature of the reagents and solvent employed. However, provided that the reaction is effected under the preferred conditions outlined above, a period of from 1 to 24 hours, more preferably from 5 to 16 hours, will usually suffice.

The reaction between the compound of formula $(XVIa)_p$ and the Grignard reagent is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: hydrocarbons, such as hexane or toluene; ethers, such as tetrahydrofuran or diethyl ether; and halogenated hydrocarbons, such as methylene chloride. Of these, we prefer the ethers or the halogenated hydrocarbons.

The reaction can take place over a wide range of temperatures, and the precise reaction temperature is not critical to the invention. In general, we find it convenient to carry out the reaction at a temperature of from $-50°$ C. to $100°$ C., more preferably from $-10°$ C. to $50°$ C. The time required for the reaction may also vary widely, depending on many factors, notably the reaction temperature and the nature of the reagents and solvent employed. However, provided that the reaction is effected under the preferred conditions outlined above, a period of from 30 minutes to 24 hours, more preferably from 1 to 16 hours, will usually suffice.

After completion of the reaction, the desired product of each reaction can be recovered from the reaction mixture by conventional means. One suitable recovery technique comprises: adding water or an aqueous ammonium chloride solution to the reaction solution; stirring the resulting mixture at room temperature; filtering off insoluble matter, if present; extracting the mixture with a water-immiscible organic solvent, such as ethyl acetate; washing the extract with water; drying the extract over a drying agent, such as anhydrous magnesium sulfate; and distilling off the solvent. The product may, if necessary, be further purified by conventional means, for example, by recrystallization, or by the various chromatography techniques, notably by column chromatography.

Reaction Scheme $E_p$

Reaction Scheme $E_p$ provides an alternative method of preparing the compound of formula $(IIa)_p$.

Step $E1_p$:

In Step $E1_p$, a compound of formula $(XVII)_p$ is prepared by reacting a compound of formula $(XIVa)_p$, which is a compound of formula $(XIV)_p$ where $R_p^9$ represents a group of formula $R_p^{1b}-X_p-$ (in which $R_p^{1b}$ and $X_p$ are as defined above), with a reducing agent and/or with a Grignard reagent of formula $(XXV)_p$ and/or $(XXVa)_p$. This reaction is essentially the same as that described in, and may be carried out in a similar manner to that described in, step $D4_p$ of Reaction Scheme $D_p$ described above.

In this reaction, the compound of formula $(XVII)_p$ where $R_p^3$ and $R_p^4$ both represent hydrogen atoms is prepared by reacting the compound of formula $(XIVa)_p$ with 2 or more moles of the reducing agent. The compound of formula $(XVII)_p$ where $R_p^3$ represents a hydrogen atom and $R_p^4$ represents an alkyl group having from 1 to 6 carbon atoms is prepared by reacting the compound of formula $(XIVa)_p$ with approximately 2 moles of the reducing agent and then with the Grignard reagent of formula $(XXVa)_p$. The compound of formula $(XVII)_p$ where $R_p^3$ and $R_p^4$ are the same or different and each represents an alkyl group having from 1 to 6 carbon atoms is prepared by reacting the compound of formula $(XIVa)_p$ with approximately 2 moles of the Grignard reagent of formula $(XXV)_p$ and then with the Grignard reagent of formula $(XXVa)_p$. The compound of formula $(XVII)_p$ where $R_p^3$ and $R_p^4$ are the same alkyl group having from 1 to 6 carbon atoms is prepared by reacting the compound of formula $(XVIa)_p$ with approximately 3 or more moles of the Grignard reagent of formula $(XXV)_p$ or $(XXVa)_p$.

Step $E2_p$:

In Step $E2_p$, a compound of formula $(XVIII)_p$ is prepared by hydrolyzing the cyano group of the compound of formula $(XVII)_p$ with an alkali or an acid.

Hydrolysis with an alkali may be carried out by reacting the compound of formula $(XVII)_p$ with a base (preferably an alkali metal hydroxide such as lithium hydroxide, sodium hydroxide or potassium hydroxide) in an inert solvent (preferably an alcohol, such as methanol or ethanol; an ether, such as tetrahydrofuran or dioxane; water; or a mixture of water and any one or more of the above organic solvents).

The reaction can take place over a wide range of temperatures, and the precise reaction temperature is not critical to the invention. In general, we find it convenient to carry out the reaction at a temperature of from $0°$ C. to $120°$ C., more preferably from $20°$ C. to $100°$ C. The time required for the reaction may also vary widely, depending on many factors, notably the reaction temperature and the nature of the reagents and solvent employed. However, provided that the reaction is effected under the preferred conditions outlined above, a period of from 30 minutes to 24 hours, more preferably from 1 hour to 16 hours, will usually suffice.

After completion of the reaction, the product can be recovered a conventional recovery procedure, for example as follows: neutralizing the reaction mixture with a mineral acid, such as hydrochloric acid; collecting the crystals which appear in the reaction system by filtration, or distilling off the solvent. An alternative recovery procedure comprises: adding water and a water-immiscible organic solvent to the neutralized reaction mixture; separating the organic layer; washing the organic layer with water and then drying; and distilling off the solvent. If necessary, the product can be further purified by conventional means, for example, by recrystallization, or by the various chromatography techniques, notably by column chromatography.

Hydrolysis with an acid may be carried out in a similar manner to that described in step $D2_p$ of Reaction Scheme $D_p$ described above.

Step $E3_p$:

In Step $E3_p$, a compound of formula $(IIa)_p$ is prepared by protecting the carboxy group in the compound of formula $(XVIII)_p$. This reaction is essentially the same as that of, and may be carried out in a similar manner to that described in, reaction $A2(d)_p$ in Step $A2_p$ of Reaction Scheme $A_p$ described above.

Reaction Scheme $F_p$

Reaction Scheme $F_p$ consists of an alternative method of preparing a compound of formula $(XVIb)_p$, which is a compound of formula $(XVI)_p$ where $R_p^9$ represents a group of formula $R_p^{1c}$—$X_p$— (in which $R_p^{1c}$ and $X_p$ are as defined above) and $R_p^2$ represents a group of formula —$C(R^{11})_p(R^{12})_p$— (in which $R_p^{11}$ and $R_p^{12}$ are as defined above and preferably $R_p^{11}$ and $R_p^{12}$ are both hydrogen atoms).

Step $F1_p$:

In Step $F1_p$, a compound of formula $(XX)_p$ is prepared by protecting the imidazolyl group of the compound of formula $(XIX)_p$.

This reaction may be carried out by reacting a compound of formula $(XIX)_p$ with a compound of formula $(XXVI)_p$:

$$R_p^{13}-Y_p \qquad (XXVI)_p$$

(in which $R_p^{13}$ and $Y_p$ are as defined above). The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: halogenated hydrocarbons, such as methylene chloride or chloroform; ethers, such as tetrahydrofuran or dioxane; amides, such as N,N-dimethylformamide or N,N-dimethylacetamide; and ketones, such as acetone or methyl ethyl ketone.

The reaction can take place over a wide range of temperatures, and the precise reaction temperature is not critical to the invention. In general, we find it convenient to carry out the reaction at a temperature of from 0° C. to 120° C., more preferably from 20° C. to 80° C. The time required for the reaction may also vary widely, depending on many factors, notably the reaction temperature and the nature of the reagents and solvent employed. However, provided that the reaction is effected under the preferred conditions outlined above, a period of from 1 to 24 hours, more preferably from 3 to 8 hours, will usually suffice.

The reaction product of formula $(XX)_p$ can be recovered by adding water to the reaction mixture, extracting the mixture with a water-immiscible organic solvent, washing the extract with water, drying it, and distilling off the solvent. The product may, if necessary, be further purified by conventional means, for example, by recrystallization, or by the various chromatography techniques, notably by column chromatography.

Step $F2_p$:

In Step $F2_p$, a compound of formula $(XXI)_p$ is prepared by halogenating the compound of formula $(XX)_p$.

This reaction may be carried out by reacting the compound of formula $(XX)_p$ with a halogenating agent (preferably N-chlorosuccinimide, N-bromosuccinimide, N-iodosuccinimide or 1,3-dibromo-5,5-dimethylhydantoin). The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: halogenated hydrocarbons, such as methylene chloride, 1,2-dichloroethane and carbon tetrachloride. The reaction is effected in the presence of a catalyst, preferably benzoyl peroxide or azobisisobutyronitrile.

The reaction can take place over a wide range of temperatures, and the precise reaction temperature is not critical to the invention. In general, we find it convenient to carry out the reaction at a temperature of from 0° C. to 100° C., more preferably from 20° C. to 80° C. The time required for the reaction may also vary widely, depending on many factors, notably the reaction temperature and the nature of the reagents and solvent employed. However, provided that the reaction is effected under the preferred conditions outlined above, a period of from 10 minutes to 24 hours, more preferably from 30 minutes to 16 hours, will usually suffice.

If desired, the reaction may be remarkably accelerated by carrying it out under the irradiation of a tungsten lamp.

The reaction product of formula $(XXI)_p$ can be recovered by washing the reaction mixture with water, drying over a drying agent, such as anhydrous magnesium sulfate, and distilling off the solvent. The product can, if necessary, be further purified by conventional means, for example, by recrystallization, or by the various chromatography techniques, notably by column chromatography.

Step $F3_p$:

In Step $F3_p$, a compound of formula $(XXII)_p$ is prepared by reacting the compound of formula $(XXI)_p$ with a compound of formula $(VIII)_p$. This reaction is essentially the same as that of, and may be carried out in a similar manner to that described in, Step $C2_p$ of Reaction Scheme $C_p$.

Step $F4_p$:

In Step $F4_p$, a compound of formula $(XVIb)_p$ is prepared by deprotecting the imidazolyl-protecting group in the compound of formula $(XXII)_p$. The reaction employed to remove the protecting group will vary depending upon the nature of the protecting group, although all are well-known methods in organic synthetic chemistry.

For example, where the imidazolyl-protecting group is a trityl or alkoxymethyl group, it may be removed by reacting the protected compound with an acid (preferably a mineral acid, such as hydrogen chloride or sulfuric acid, or an organic acid, such as formic acid, acetic acid, trifluoroacetic acid, methanesulfonic acid or p-toluenesulfonic acid). The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: alcohols, such as methanol or ethanol; ethers, such as tetrahydrofuran or dioxane; fatty acids, such as acetic acid; water; or a mixture of water and any one or more of the above organic solvents.

The reaction can take place over a wide range of temperatures, and the precise reaction temperature is not critical to the invention. In general, we find it convenient to carry out the reaction at a temperature of from 0° C. to 120° C., more preferably from 10° C. to 100° C. The time required for the reaction may also vary widely, depending on many factors, notably the reaction temperature and the nature of the reagents and solvent employed. However, provided that the reaction is effected under the preferred conditions outlined above, a period of from 30 minutes to 24 hours, more preferably from 1 hour to 16 hours, will usually suffice.

After completion of the reaction, the product can be recovered by conventional means. For example, one suitable recovery procedure comprises: distilling off the solvent and purifying the product, for example, by recrystallization; or neutralizing the reaction mixture with a weakly basic aqueous solution, such as an aqueous solution of sodium hydrogencarbonate, extracting the mixture with a water-immiscible organic solvent, and distilling off the solvent. If necessary, the product can be further purified by conventional means, for example, by recrystallization, or by the various chromatography techniques, notably by column chromatography.

Where the imidazolyl-protecting group is an aralkyl group, such as a benzyl, p-nitrobenzyl or diphenylmethyl group, it may be removed by reacting a similar reaction to that described in the catalytic reduction reaction of reaction A2(a)$_p$ in Step A2$_p$ of Reaction Scheme A$_p$ described above. In this reaction, the reaction may often be accelerated by adding from 1 to 3 moles of aqueous hydrochloric acid or p-toluenesulfonic acid to the reaction system.

Reaction Scheme G$_p$

In Reaction Scheme G$_p$, a compound of formula (V)$_p$ is prepared.

Step G1$_p$:

In Step G1$_p$, a compound of formula (XXIII)$_p$ is prepared by reacting a compound of formula (XVIc)$_p$, which is a compound of formula (XVI)$_p$ where R$_p^9$ represents a halogen atom, with a compound of formula (XXVII)$_p$:

$$R_p^{14}-X_p-M_p \qquad (XXVII)_p$$

(in which R$_p^{14}$, X$_p$ and M$_p$ are as defined above). The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: amides, such as N,N-dimethylformamide or N,N-dimethylacetamide; and ketones, such as acetone or methyl ethyl ketone.

The reaction can take place over a wide range of temperatures, and the precise reaction temperature is not critical to the invention. In general, we find it convenient to carry out the reaction at a temperature of from 0° C. to 120° C., more preferably from 20° C. to 80° C. The time required for the reaction may also vary widely, depending on many factors, notably the reaction temperature and the nature of the reagents and solvent employed. However, provided that the reaction is effected under the preferred conditions outlined above, a period of from 30 minutes to 24 hours, more preferably from 1 to 16 hours, will usually suffice.

After completion of the reaction, the reaction product of formula (XXIII)$_p$ can be recovered from the reaction mixture by conventional means, for example, in a similar manner to that described in Step A1$_p$ of Reaction Scheme A$_p$ described above.

Step G2$_p$:

Step G2$_p$, a compound of formula (XXIV)$_p$ is prepared by reacting a compound of formula (XXIII)$_p$ with a reducing agent and/or a Grignard reagent of formula (XXV)$_p$ and/or (XXVa)$_p$. This reaction is essentially the same as that of, and may be carried out in a similar manner to that described in, Step D4$_p$ of Reaction Scheme D$_p$ described above.

Step G3$_p$:

In Step G3$_p$, a compound of formula (V)$_p$ is prepared by acylating a compound of formula (XXIV)$_p$. This reaction may be carried out using an arylcarbonyl halide (such as benzoyl chloride, p-methylbenzoyl chloride, p-methoxybenzoyl chloride; p-chlorobenzoyl chloride or naphthoyl chloride) or an alkanoyl halide or an acid anhydride, as described in reaction A2(f)$_p$ in Step A2$_p$ of Reaction Scheme A$_p$ described above.

The product of this reaction may be recovered from the reaction mixture by conventional means, for example as described in Step A2(f)$_p$ of Reaction Scheme A$_p$ above.

The compounds of the present invention can form salts. There is no particular restriction on the nature of these salts, provided that, where they are intended for therapeutic use, they are pharmaceutically acceptable. Where they are intended for non-therapeutic uses, e.g. as intermediates in the preparation of other, and possibly more active, compounds, even this restriction does not apply. The compounds of the present invention can form salts with bases. Examples of such salts include: salts with an alkali metal, such as sodium, potassium or lithium; salts with an alkaline earth metal, such as barium or calcium; salts with another metal, such as magnesium or aluminum; organic base salts, such as a salt with dicyclohexylamine, guanidine or triethylamine; and salts with a basic amino acid, such as lysine or arginine. Also, the compound of the present invention contains a basic group in its molecule and can therefore form acid addition salts. Examples of such acid addition salts include: salts with mineral acids, especially hydrohalic acids (such as hydrofluoric acid, hydrobromic acid, hydroiodic acid or hydrochloric acid), nitric acid, carbonic acid, sulfuric acid or phosphoric acid; salts with lower alkylsulfonic acids, such as methanesulfonic acid, trifluoromethanesulfonic acid or ethanesulfonic acid; salts with arylsulfonic acids, such as benzenesulfonic acid or p-toluenesulfonic acid; salts with organic carboxylic acids, such as acetic acid, fumaric acid, tartaric acid, oxalic acid, maleic acid, malic acid, succinic acid or citric acid; and salts with amino acids, such as glutamic acid or aspartic acid. The compounds of the present invention can be converted to a pharmaceutically acceptable salt by treatment with an acid or a base by conventional means, as is well known in the art.

BIOLOGICAL ACTIVITY

The compounds of the present invention exhibit an excellent inhibitory effect against the elevation of blood pressure induced by angiotensin II and are therefore extremely useful for prevention or treatment of circulatory diseases as a hypotensive drug or a therapeutic drug for heart diseases.

Their biological activity was determined by the following experiment.

Evaluation of AII receptor blocking activity by Inhibition of pressor response to angiotensin II The biological activity of each compound was assessed by determining the dose required to inhibit the pressor response to intravenous angiotensin II by fifty percent ($ID_{50}$) in rats. Male Wister-Imamichi rats, each weighing 300 to 400 g, were anesthesized by intraperitoneal injection of 100 mg/Kg of sodium thiobutabarbital [Inactin (trade name)] and two cannulae were inserted: one into the femoral artery for measuring blood pressure and the other into the femoral vein for injecting drugs. Fifty ng/kg of angiotension II were intravenously administered at intervals of about 10 minutes, and the elevation of blood pressure (normally about 50 mmHg) was observed. After constant pressor responses to angiotensin II were obtained, a test compound was intravenously administered. Two minutes later, angiotension II was again injected, and the inhibitory effect of the test compound was estimated. The percent inhibitions of the pressor response to angiotensin II by progressive increase of the test compound was used to calculate the value of $ID_{50}$. Angiotensin II was used in this test dissolved in 0.5% bovine serum albumin (BSA) and the test compounds were dissolved in 100% dimethyl sulfoxide (DMSO). Tables 8 and 9 show the $ID_{50}$ values thus determined.

In addition to the compounds of the invention (which are identified hereafter by the number of the one of the following Examples which illustrates their preparation), we also carried out the same experiment using a prior art compound (identified in Table 8 as "compound A"), which is 2-[4-(2-butyl-5-chloro-4-hydroxymethylimidazol-1-ylmethyl)phenyl]benzoic acid, which is disclosed in Example 95 of European Patent Publication No. 253 310.

TABLE 8

| Test compound (Compound of Example No.) | ID50 (mg/kg, i.v.) |
| --- | --- |
| 5 | 0.22 |
| 10 | 0.066 |
| 11 | 0.25 |
| 17 | 0.056 |
| 19 | 0.008 |
| 22 | 0.017 |
| 23 | 0.043 |
| 24 | 0.014 |
| 36 | 0.0062 |
| 39 | 0.010 |
| 41 | 0.0063 |
| 44 | 0.0082 |
| 45 | 0.19 |
| 46 | 0.18 |
| 48 | 0.064 |
| 50 | 0.22 |
| 55 | 0.23 |
| 59 | 0.066 |
| 60 | 0.134 |
| 69 | 0.019 |
| 74 | 0.036 |
| 75 | 0.11 |
| 76 | 0.022 |
| A | 3.3 |

TABLE 9

| Test compound (Compound of Example No.) | ID50 (mg/kg, i.v.) |
| --- | --- |
| 83 | 0.0066 |
| 87 | 0.0059 |
| 91 | 0.016 |
| 95 | 0.074 |
| 103 | 0.025 |
| 106 | 0.026 |
| 108 | 0.019 |

The compounds of the present invention can be administered, for example, orally in the form of tablets, capsules, granules, powders, syrups or the like, or parenterally by injection, suppository or the like. These pharmaceutical preparations can be produced in the conventional manner using the adjuvants generally known in the art, such as excipients, binders, disintegrating agents, lubricants, stabilizers, corrigents and the like. Although the dosage may vary depending upon the symptoms and age of the patient, the nature and severity of the disease or disorder and the route and manner of administration, in the case of oral administration to an adult human patient, the compounds of the present invention may normally be administered at a total daily dose of from 1 to 1000 mg, preferably from 5 to 300 mg, either in a single dose, or in divided doses, for example two or three times a day; in the case of intravenous injection, a dose of from 0.1 to 100 mg, preferably from 0.5 to 30 mg, may be administered between one and three times a day.

The invention is further illustrated by the following Examples, which demonstrate the preparation of various of the compounds of the invention. The preparation of certain starting materials used in these Examples is shown in the subsequent Preparations.

EXAMPLE 1

Methyl 1-[(2'-t-butoxycarbonylbiphenyl-4-yl)methyl]-2-butyl-4-hydroxymethylimidazole-5-carboxylate (Compound No. 1-94)

1(a) Dimethyl 1-[(2'-t-butoxycarbonylbiphenyl-4yl)methyl]-2-butylimidazole-4,5-dicarboxylate A sodium methoxide solution prepared from 0.69 g of sodium and 40 ml of methanol was added to a solution of 7.2 g of dimethyl 2-butylimidazole-4,5-dicarboxylate (prepared as described in Preparation 4) in 40 ml of methanol, and the resulting mixture was concentrated by evaporation under reduced pressure. The resulting residue was mixed with benzene, and the mixture was concentrated by distillation under reduced pressure. After this operation had been repeated three times, the solid thus obtained was dissolved in 72 ml of N,N-dimethylacetamide. A solution of 10.41 g of t-butyl 4'-bromomethylbiphenyl-2-carboxylate in 100 ml of N,N-dimethylacetamide was then added dropwise to the resulting solution. The reaction mixture was then stirred at room temperature for 1 hour and at 50°–55° C. for 2 hours. At the end of this time, it was mixed with ethyl acetate and water, and the ethyl acetate layer was separated, and dried over anhydrous magnesium sulfate; the solvent was then removed by distillation under reduced pressure. The residue was purified by column chromatography through silica gel, using a 1:1 by volume mixture of ethyl acetate and hexane as the eluent, to give 15.1 g of the title compound as a gum.

Nuclear Magnetic Resonance Spectrum (CDCl₃) δ ppm:
0.90 (3H, triplet, J=7 Hz);
1.26 (9H, triplet);
1.1–2.0 (4H, multiplet);
2.70 (2H, triplet, J=7 Hz);
3.81 (3H, singlet);
3.90 (3H, singlet);
5.47 (2H, singlet);
6.95–7.85 (8H, multiplet).

1(b) Methyl 1-[(2'-t-butoxycarbonylbiphenyl-4-yl)methyl]-2-butyl-4-hydroxymethylimidazole-5-carboxylate 42 ml of diisobutylaluminum hydride (as a 1.5M solution in toluene) were added dropwise at a temperature between −20° C. and −15° C. to a solution of 16.0 g of dimethyl 1-[(2'-t-butoxycarbonylbiphenyl-4yl)methyl]-2-butylimidazole-4,5-dicarboxylate [prepared as described in step (a) above] in 200 ml of tetrahydrofuran, and the resulting mixture was allowed to stand at 0°–5° C. for 16 hours. At the end of this time, the reaction mixture was mixed with an aqueous solution of ammonium chloride and ethyl acetate and was then stirred for 1 hour. After this, precipitates were removed by filtration. The ethyl acetate layer was then separated and dried over anhydrous magnesium sulfate, and the solvent was removed by distillation under reduced pressure. The residue was then purified by column chromatography through silica gel, using ethyl acetate as the eluent, to give 12.0 g of the title compound as crystals, melting at 99° C.

Nuclear Magnetic Resonance Spectrum (CDCl₃) δ ppm:
0.90 (3H, triplet, J=7 Hz);
1.20 (9H, singlet);
1.1–2.0 (4H, multiplet);
2.69 (2H, triplet, J=7 Hz);
3.55 (1H, broad singlet);
3.78 (3H, singlet);
4.84 (2H, double, J=5 Hz);
5.60 (2H, singlet);
6.95–7.9 (8H, multiplet).

EXAMPLE 2

Ethyl 1-[(2'-t-butoxycarbonylbiphenyl-4-yl)methyl]-2-butyl-4-hydroxymethylimidazole-5-carboxylate (Compound No. 1-95)

2(a) Diethyl 1-[(2'-t-butoxycarbonylbiphenyl-4-yl)methyl]-2-butylimidazole-4,5-dicarboxylate Following a procedure similar to that described in Example 1(a), but using 8.0 g of diethyl 2-butylimidazole-4,5-dicarboxylate (prepared as described in Preparation 3) and 10.41 g of t-butyl 4'-bromomethylbiphenyl-2-carboxylate, 15.4 g of the title compound were obtained as a gum.

Nuclear Magnetic Resonance Spectrum (CDCl₃) δ ppm:
0.90 (3H, triplet, J=7 Hz);
1.1–2.0 (4H, multiplet);
1.24 (9H, singlet);
1.26 (3H, triplet, J=7 Hz);
1.39 (3H, triplet, J=7 Hz);
2.72 (2H, triplet, J=7 Hz);
4.28 (2H, quartet, J=7 Hz);
4.40 (2H, quartet, J=7 Hz);
5.50 (2H, singlet);
7.0–7.9 (8H, multiplet).

2(b) Ethyl 1-[(2'-t-butoxycarbonylbiphenyl-4-yl)methyl]-2-butyl-4-hydroxymethylimidazole-5-carboxylate Following a procedure similar to that described in Example 1(b), but using 1.50 g of diethyl 1-[(2'-t-butoxycarbonylbiphenyl-4-yl)methyl]-2-butylimidazole-4,5-dicarboxylate [prepared as described in step (a) above] and 3.9 ml of diisobutylaluminum hydride (as a 1.5M solution in toluene), 1.1 g of the title compound was obtained as a gum.

Nuclear Magnetic Resonance Spectrum (CDCl₃) δ ppm:
0.90 (3H, triplet, J=7 Hz);
1.24 (9H, singlet);
1.30 (3H, triplet, J=7 Hz);
1.1–2.0 (4H, multiplet);
2.68 (2H, triplet, J=7 Hz);
3.60 (1H, broad singlet);
4.24 (2H, quartet, J=7 Hz);
4.84 (2H, singlet);
5.57 (2H, singlet);
6.9–7.85 (8H, multiplet).

EXAMPLE 3

Methyl 2-butyl-1-[(2'-carboxybiphenyl-4-yl)methyl]-4-hydroxymethylimidazole-5-carboxylate (Compound No. 1-5)

A solution of 0.36 g of methyl 1-[(2'-t-butoxycarbonylbiphenyl-4-yl)methyl]-2-butyl-4-hydroxymethylimidazole-5-carboxylate (prepared as described in Example 1) in 4 ml of a 4N solution of hydrogen chloride in dioxane was allowed to stand at room temperature for 4 hours. At the end of this time, the reaction mixture was concentrated by evaporation under reduced pressure, and the residue was triturated with ethyl acetate, to give crystals, which were collected by filtration to give 0.35 g of the title compound in the form of its hydrochloride, melting at 192°–195° C. (with decomposition).

Nuclear Magnetic Resonance Spectrum (hexadeuterated dimethyl sulfoxide) δ ppm:
0.81 (3H, triplet, J=7 Hz);
1.22–1.35 (2H, multiplet);
1.43–1.56 (2H, multiplet);
3.00 (2H, triplet, J=7 Hz);
3.82 (3H, singlet);
4.81 (2H, singlet);
5.77 (2H, singlet);
7.18–7.75 (8H, multiplet).

EXAMPLE 4

1-[(2'-t-Butoxycarbonylbiphenyl-4-yl)methyl]-2-butyl-4-hydroxymethylimidazole-5-carboxylic acid (Compound No. 1-96)

A solution of 2.01 g of lithium hydroxide monohydrate in 97 ml of water was added to a solution of 4.78 g of methyl 1-[(2'-t-butoxycarbonylbiphenyl-4-yl)methyl]-2-butyl-4-hydroxymethylimidazole-5-carboxylate (prepared as described in Example 1) in 48 ml of dioxane, and the resulting mixture was stirred at room temperature for 18 hours. At the end of this time, the reaction mixture was freed from dioxane by distillation under reduced pressure, and 47.6 ml of 1N aqueous hydrochloric acid were added to the aqueous residue. The crystals which precipitated were collected by filtration and then washed with water and with diethyl ether, in that order, to give 4.26 g of the title compound, melting at 187° C. (with decomposition).

Nuclear Magnetic Resonance Spectrum (CDCl₃) δ ppm:
0.85 (3H, triplet, J=7 Hz);
1.24 (9H, singlet);
1.1–1.9 (4H, multiplet);
2.80 (2H, triplet, J=7 Hz);
5.05 (2H, singlet);
5.93 (2H, singlet);
7.0–7.85 (8H, multiplet).

EXAMPLE 5

2-Butyl-1-[(2'-carboxybiphenyl-4-yl)methyl]-4-hydroxymethylimidazole-5-carboxylic acid (Compound No. 1-2)

A solution of 0.12 g of 1-[(2'-t-butoxycarbonylbiphenyl-4-yl)methyl]-2-butyl-4-hydroxymethylimidazole-5-carboxylic acid (prepared as described in Example 4) in 2 ml of a 4N solution of hydrogen chloride in dioxane was allowed to stand at room temperature for 5 hours and then the solvent was removed by distillation under reduced pressure. The resulting residue was triturated in ethyl acetate, to give 0.11 g of the title compound in the form of its hydrochloride, melting at 130°–140° C. (with softening).

Nuclear Magnetic Resonance Spectrum (hexadeuterated dimethyl sulfoxide) δ ppm:
0.80 (3H, triplet, J=7 Hz);
1.2–1.33 (2H, multiplet);
1.4–1.53 (2H, multiplet);
2.98 (2H, triplet, J=7 Hz);
4.84 (2H, singlet);
5.81 (2H, singlet);
7.17–7.74 (8H, multiplet).

EXAMPLE 6

Pivaloyloxymethyl-1-[(2'-t-butoxycarbonylbiphenyl-4-yl)methyl]-2-butyl-4-hydroxymethylimidazole-5-carboxylate (Compound No. 1-97)

350 mg of potassium carbonate were added to a solution of 552 mg of 1-[(2'-t-butoxycarbonylbiphenyl-4-yl)methyl]-2-butyl-4-hydroxymethylimidazole-5-carboxylic acid (prepared as described in Example 4) and 220 mg of pivaloyloxymethyl chloride in 7 ml of N,N-dimethylacetamide, and the resulting mixture was stirred at room temperature for 5 hours. At the end of this time, the reaction mixture was mixed with ethyl acetate and water, and the ethyl acetate layer was separated and dried over anhydrous magnesium sulfate; the solvent was then removed by distillation under reduced pressure. The resulting residue was purified by column chromatography through silica gel, using ethyl acetate as the eluent, to give 0.62 g of the title compound as a syrup.

Nuclear Magnetic Resonance Spectrum (CDCl₃) δ ppm:
0.91 (3H, triplet, J=7 Hz);
1.18 (9H, singlet);
1.21 (9H, singlet);
1.1–2.0 (4H, multiplet);
2.72 (2H, triplet, J=7 Hz);
3.35 (1H, broad);
4.85 (2H, doublet, J=7 Hz);
5.61 (2H, singlet);
5.90 (2H, singlet);
6.95–7.9 (8H, multiplet).

EXAMPLE 7

Pivaloyloxymethyl 2-butyl-1-[(2'-carboxybiphenyl-4-yl)methyl]-4-hydroxymethylimidazole-5-carboxylate (Compound No. 1-98)

A solution of 0.62 g of pivaloyloxymethyl 1-[(2'-t-butoxycarbonylbiphenyl-4-yl))methyl]-2-butyl-4-hydroxymethylimidazole-5-carboxylate (prepared as described in Example 6) in 10 ml of a 4N solution of hydrogen chloride in dioxane was allowed to stand at room temperature for 4 hours, after which it was concentrated by evaporation under reduced pressure. The syrupy residue was stirred in diethyl ether, and then the solvent was removed by decantation and the residue was dried in vacuo, to give 0.46 g of the hydrochloride of the title compound as a powder.

Nuclear Magnetic Resonance Spectrum (CDCl₃) δ ppm:
0.85 (3H, triplet, J=7 Hz);
1.19 (9H, singlet);
1.25–1.45 (2H, multiplet);
1.65–1.80 (2H, multiplet);
2.99 (2H, triplet, J=7 Hz);
5.01 (2H, singlet);
5.70 (2H, singlet);
5.89 (2H, singlet);
7.05–7.97 (8H, multiplet).

EXAMPLE 8

Methyl 1-[(2'-t-butoxycarbonylbiphenyl-4-yl)methyl]-2-butyl-4-(methoxymethyl)imidazole-5-carboxylate (Compound No. 1-99)

0.057 g of sodium hydride (as a 55% w/w dispersion in mineral oil) was added to a solution of 0.478 g of methyl 1-[(2'-t-butoxycarbonylbiphenyl-4-yl)methyl]-2-butyl-4-hydroxymethylimidazole-5-carboxylate (prepared as described in Example 1) in 5 ml of N,N-dimethylacetamide, and the resulting mixture was stirred at room temperature for 30 minutes. At the end of this time, 0.125 ml of iodomethane were added, and the reaction mixture was stirred at 50° C. for 3 hours. The reaction mixture was then mixed with ethyl acetate and water. The ethyl acetate layer was separated and dried over anhydrous magnesium sulfate; the solvent was then removed by distillation under reduced pressure. The resulting residue was purified by column chromatography through silica gel, using a 1:1 by volume mixture of ethyl acetate and methylene chloride as the eluent, to give 0.30 g of the title compound as a gum.

Nuclear Magnetic Resonance Spectrum (CDCl₃) δ ppm:
0.90 (3H, triplet, J=7 Hz);
1.24 (9H, singlet);
1.1–2.0 (4H, multiplet);
2.71 (2H, triplet, J=7 Hz);
3.46 (3H, singlet);
3.80 (3H, singlet);

4.68 (2H, singlet);
5.60 (2H, singlet);
6.9–7.9 (8H, multiplet).

EXAMPLE 9

Methyl 2-butyl-1-[(2'-carboxybiphenyl-4-yl)methyl]
-4-(methoxymethyl)imidazole-5-carboxylate (Compound No. 1-121)

A solution of 0.30 g of methyl 1-[(2'-t-butoxycarbonyl-biphenyl-4-yl)methyl]-2-butyl-4-(methoxymethyl)imidazole-5-carboxylate (prepared as described in Example 8) in 3 ml of a 4N solution of hydrogen chloride in dioxane was allowed no stand at room temperature for 5 hours, after which the solvent was removed by distillation under reduced pressure. The syrupy residue was triturated in diethyl ether and collected by filtration, to give 0.26 g of the title compound in the form of its hydrochloride, melting at 106°–110° C. (with softening).

Nuclear Magnetic Resonance Spectrum (hexadeuterated dimethyl sulfoxide) δ ppm:

0.81 (3H, triplet, J=7 Hz);
1.2–1.35 (2H, multiplet);
1.45–1.6 (2H, multiplet);
2.97 (2H, triplet, J=7 Hz);
3.39 (3H, singlet);
3.82 (3H, singlet);
4.72 (2H, singlet);
5.75 (2H, singlet);
7.16–7.74 (8H, multiplet).

EXAMPLE 10

2-Butyl-1-[(2'-carboxybiphenyl-4-yl)methyl]-4-[(1-hydroxy-1-methyl)ethyl]imidazole-5-carboxylic acid (Compound No. 1-31)

10(a)  1-[(2'-t-Butoxycarbonylbiphenyl-4-yl)methyl]-2-butyl-5-Cyano-4-[(1-hydroxy-1-methyl)ethyl]imidazole 48 mg of sodium hydride (as a 55% w/w dispersion in mineral oil) were added, at room temperature and under an atmosphere of nitrogen, whilst stirring, to a solution of 207 mg of 2-butyl-5-cyano-4-[(1-hydroxy-1-methyl)ethyl]imidazole (prepared as described in Preparation 7) in 10 ml of N,N-dimethylacetamide, and the resulting mixture was stirred for 30 minutes; at the end of this time, 347 mg of t-butyl 4'-bromomethylbiphenyl-2-carboxylate were added. The reaction mixture was then stirred at room temperature for 2 hours, after which it was poured into a mixture of ice and sodium chloride and extracted with ethyl acetate. The extract was dried over anhydrous magnesium sulfate and concentrated by evaporation under reduced pressure, to give an oily crude product. This was purified by column chromatography through silica gel, using a 1:1 by volume mixture of hexane and ethyl acetate as the eluent, to give 462 mg of the title compound.

Nuclear Magnetic Resonance Spectrum (CDCl$_3$) δ ppm:

0.90 (3H, triplet, J=7 Hz);
1.1–2.1 (4H, multiplet);
1.21 (9H, singlet);
1.61 (6H, singlet);
2.70 (2H, triplet, J=7 Hz);
3.40 (1H, singlet);
5.22 (2H, singlet);
7.0–8.0 (8H, multiplet).

10(b)  2-Butyl-1-[(2'-carboxybiphenyl-4-yl)methyl]-5-cyano-4-[(1-hydroxy-1-methyl)ethyl]imidazole A solution of 462 mg of 1-[(2'-t-butoxycarbonyl-biphenyl-4-yl)methyl]-2-butyl-5-cyano-4-[(1-hydroxy-1-methyl)ethyl]imidazole [prepared as described in step (a) above] in 10 ml of a 4N solution of hydrogen chloride in dioxane was allowed to stand overnight at room temperature. At the end of this time, the reaction mixture was concentrated by evaporation under reduced pressure, and the concentrate was dissolved in methylene chloride. The precipitate which deposited was collected by filtration and dried, to give 457 mg of the hydrochloride of the title compound as a colorless powder, melting at 209°–210° C.

Nuclear Magnetic Resonance Spectrum (hexadeuterated dimethyl sulfoxide) δ ppm:

0.85 (3H, triplet, J=7 Hz);
1.0–1.8 (4H, multiplet);
1.58 (6H, singlet);
3.00 (2H, triplet, J=7 Hz);
5.51 (2H, singlet);
7.1–8.0 (8H, multiplet).

10(c)  2-Butyl-1-[(2'-carboxybiphenyl-4-yl)methyl]-4-[(1-hydroxy-1-methyl)ethyl]imidazole-5-carboxylic acid A solution of 314 mg of 2-butyl-1-[(2'-carboxybiphenyl-4-yl)methyl]-5-cyano-4-[(1-hydroxy-1-methyl)ethyl]imidazole hydrochloride [prepared as described in step (b) above] in an aqueous solution of 460 mg of sodium hydroxide in 5 ml of water was stirred in an oil bath kept at 100° C. for 5 hours. At the end of this time, the reaction mixture was cooled, and its pH was adjusted to a value of 3 to 4 by the addition of 1N aqueous hydrochloric acid. The colorless precipitate which deposited was collected by filtration, washed with water and dried over anhydrous magnesium sulfate, to give 244 mg of the title compound, melting at 139°–141° C.

Nuclear Magnetic Resonance Spectrum (hexadeuterated dimethyl sulfoxide) δ ppm:

0.86 (3H, triplet, J=7 Hz);
1.0–1.9 (4H, multiplet);
1.60 (6H, singlet);
2.66 (2H, triplet, J=7 Hz);
5.70 (2H, singlet);
6.9–7.9 (8H, multiplet).

EXAMPLE 11

2-Butyl-1-[(2'-carboxybiphenyl-4-yl)methyl]-4-(1-hydroxyethyl)imidazole-5-carboxylic acid (Compound No. 1-25)

11(a)  4-Acetyl-1-[(2'-t-butoxycarbonylbiphenyl-4-yl)methyl]-2-butyl-5-cyanoimidazole 0.87 g of potassium carbonate and 2.4 g of t-butyl 4'-bromomethylbiphenyl-2-carboxylate were added to a solution of 1.2 g of 4-acetyl-2-butyl-5-cyanoimidazole (prepared as described in Preparation 5) in 12 ml of N,N-dimethylacetamide, and the resulting mixture was shirred at room temperature for 3 hours. At the end of this time, the reaction mixture was diluted with 100 ml of ethyl acetate and washed with a saturated aqueous solution of sodium chloride. The aqueous layer was once again extracted with 50 ml of ethyl acetate, and the combined extracts were washed with a saturated aqueous solution of sodium chloride. The solvent was removed by distillation under reduced pressure, and the resulting residue was purified by column chromatography through silica gel, using a 3:1 by volume mixture of hexane and ethyl acetate as the eluent, to give 1.31 g of the title compound.

Nuclear Magnetic Resonance Spectrum (CDCl$_3$) δ ppm:

0.93 (3H, triplet, J=7 Hz);

1.1–2.1 (4H, multiplet);

1.23 (9H, singlet);

2.58 (3H, singlet);

2.75 (2H, triplet, J=7 Hz);

5.32 (2H, singlet);

7.0–8.0 (8H, multiplet).

11(b)  4-Acetyl-2-butyl-1-[(2'-carboxybiphenyl-4-yl)methyl]- 5-cyanoimidazole

A solution of 1.3 g of 4-acetyl-1-[(2'-t-butoxycarbonylbiphenyl-4-yl)methyl]-2-butyl-5-cyanoimidazole [prepared as described in step (a) above] in 30 ml of a 4N solution of hydrogen chloride in dioxane was allowed to stand overnight at room temperature, after which it was concentrated by evaporation under reduced pressure. The concentrate was purified by column chromatography through silica gel, using a 10:1 by volume mixture of methylene chloride and methanol as the eluent, to give a colorless amorphous solid. The solid was triturated in hexane, collected by filtration and dried, to give 1.1 g of the title compound, melting at above 55° C. (with softening).

Nuclear Magnetic Resonance Spectrum (CDCl$_3$) δ ppm:

0.84 (3H, triplet, J=7 Hz);

1.0–2.0 (4H, multiplet);

2.54 (3H, singlet);

2.66 (2H, triplet, J=7 Hz);

5.17 (2H, singlet);

6.8–7.0 (8H, multiplet).

11(c)  2-Butyl-1-[(2'-carboxybiphenyl-4-yl)methyl]-5-cyano-4-(1-hydroxyethyl)imidazole 68 mg of sodium borohydride were added to a solution of 718 mg of 4-acetyl-2-butyl-1-[(2'-carboxybiphenyl-4-yl)methyl]-5-cyanoimidazole [prepared as described in step (b) above] in a mixture of 20 ml of isopropanol and 10 ml of ethanol, and the resulting mixture was stirred at room temperature for 3 hours. At the end of this time, the pH of the reaction mixture was adjusted to a value of 3 by the addition of 1N aqueous hydrochloric acid, after which the solvent was distilled off under reduced pressure. The resulting residue was mixed with methylene chloride and water, and the methylene chloride layer was separated. The aqueous layer was extracted three times with methylene chloride, and the combined extracts were dried and concentrated by evaporation under reduced pressure. The resulting residue was dissolved in 10 ml of ethyl acetate and allowed to stand at room temperature. The solid which then deposited was collected by filtration and dried, to give 398 mg of the title compound as a colorless powder, melting at 200°–201° C.

Nuclear Magnetic Resonance Spectrum (hexadeuterated dimethyl sulfoxide) δ ppm:

0.88 (3H, triplet, J=7 Hz);

1.0–2.0 (4H, multiplet);

1.54 (3H, doublet, J=7 Hz);

2.68 (2H, triplet, J=7 Hz);

4.91 (1H, quartet, J=7 Hz);

5.21 (2H, singlet);

7.0–8.0 (8H, multiplet).

11(d) 2-Butyl-1-[(2'-carboxybiphenyl-4-yl)methyl]-4-(1-hydroxyethyl)imidazole-5-carboxylic acid A mixture of 300 mg of 2-butyl-1-[(2'-carboxybiphenyl-4-yl)methyl]-5-cyano-4-(1-hydroxyethyl)imidazole [prepared as described in step (c) above] and 3 ml of a 1N aqueous solution of sodium hydroxide was stirred in an oil bath kept at 80° C. for 3 hours. At the end of this time, the reaction mixture was cooled and then weakly acidified with hydrochloric acid; it was then extracted four times, each time with 30 ml of methylene chloride. The combined extracts were dried and concentrated to dryness by evaporation under reduced pressure, to give an amorphous solid. This solid was purified by column chromatography through silica gel, using mixtures of methylene chloride and methanol ranging from 10:1 to 3:1 by volume as the eluent. A solid obtained from the eluate was triturated in diethyl ether. The resulting powder was collected by filtration and dried, to give 72.3 mg of the title compound as a colorless powder, melting at 168°–170° C. (with softening above 140° C.).

Nuclear Magnetic Resonance Spectrum (hexadeuterated dimethyl sulfoxide) δ ppm:

0.84 (3H, triplet, J=7 Hz);

1.0–2.0 (4H, multiplet);

1.52 (3H, doublet, J=7 Hz);

2.3–2.8 (2H, overlapped with a peak of dimethyl sulfoxide);

4.93 (1H, quartet, J=7 Hz);

5.60 (2H, broad singlet);

6.8–7.8 (8H, multiplet).

EXAMPLE 12

2-Butyl-1-[(2'-carboxybiphenyl-4-yl)methyl]-4-(α-hydroxybenzyl)imidazole-5-carboxylic acid (Compound No. 1-80)

12(a)  4-Benzoyl-1-[(2'-t-butoxycarbonylbiphenyl-4-yl)methyl]-2-butyl-5-cyanoimidazole Following a procedure similar to that described in Example 11(a), but using 1.27 g of 4-benzoyl-2-butyl-5-cyanoimidazole (prepared as described in Preparation 6), 1.74 g of t-butyl 4'-bromomethylbiphenyl-2-carboxylate, 0.69 of potassium carbonate and 20 ml of N,N-dimethylacetamide, and then purifying the product by column chromatography through silica gel, using a 2:1 by volume mixture of hexane and ethyl acetate as the eluent, 2.1 g of the title compound were obtained.

Nuclear Magnetic Resonance Spectrum (CDCl$_3$) δ ppm:

0.93 (3H, triplet, J=7 Hz);

1.0–2.1 (4H, multiplet);

1.23 (9H, singlet);

2.79 (2H, triplet, J=7 Hz);

5.38 (2H, singlet);

7.1–8.0 (11H, multiplet);

8.3–8.7 (2H, multiplet).

12(b)  1-[(2'-t-Butoxycarbonylbiphenyl-4-yl)methyl]-2-butyl-5-cyano-4-(α-hydroxybenzyl)imidazole 50.5 mg of sodium borohydride were added to a solution of 691 mg of 4-benzoyl-1-[(2'-t-butoxycarbonylbiphenyl-4-yl)methyl]-2-butyl-5-cyanoimidazole [prepared as described in step (a) above] in 10 ml of ethanol, and the resulting mixture was stirred at room temperature for 1 hour. The reaction mixture was then neutralized with aqueous hydrochloric acid, after which it was mixed with ethyl acetate and with a saturated aqueous solution of sodium chloride. The ethyl acetate layer was separated, dried over anhydrous magnesium sulfate and concentrated by evaporation under reduced pressure. The residue was purified by column chromatography through silica gel, using a 1:1 by volume mixture of hexane and ethyl acetate as the eluent, to give 589 mg of the title compound as a colorless amorphous solid.

Nuclear Magnetic Resonance Spectrum (CDCl$_3$) δ ppm:
0.89 (3H, triplet, J=7 Hz);
1.0–2.0 (4H, multiplet);
2.68 (2H, triplet, J=7 Hz);
5.18 (2H, singlet);
5.89 (1H, singlet);
7.0–8.0 (13H, multiplet).

12(c) 2-Butyl-1-[(2'-carboxybiphenyl-4-yl)methyl]-5-cyano-4-(α-hydroxybenzyl)imidazole A solution of 589 mg of 1-[(2'-t-butoxycarbonylbiphenyl-4-yl)methyl]-2-butyl-5-cyano-4-(α-hydroxybenzyl)imidazole [prepared as described in step (b) above] in 20 ml of a 4N solution of hydrogen chloride in dioxane was allowed to stand at room temperature overnight and then concentrated by evaporation under reduced pressure. The residue was triturated in hexane and collected by filtration to give 493 mg of the hydrochloride of the title compound as a colorless powder, melting at 95°–97° C. (with softening).

Nuclear Magnetic Resonance Spectrum (hexadeuterated dimethyl sulfoxide) δ ppm:
0.88 (3H, triplet, J=7 Hz);
1.0–2.0 (4H, multiplet);
3.00 (2H, triplet, J=7 Hz);
5.47 (2H, singlet);
6.09 (1H, singlet);
7.0–8.0 (13H, multiplet).

12(d) 2-Butyl-1-[(2'-carboxybiphenyl-4-yl)methyl]-4-(α-hydroxybenzyl)imidazole-5-carboxylic acid A mixture of 450 mg of 2-butyl-1-[(2'-carboxybiphenyl-4-yl)methyl]-5-cyano-4-(α-hydroxybenzyl)imidazole hydrochloride [prepared as described in step (c) above] and 20 ml of a 1N aqueous solution of sodium hydroxide was stirred in an oil bath kept at 100° C. for 7 hours. At the end of this time, the reaction mixture was cooled, and its pH was adjusted to a value of 3 to 4 by the addition of hydrochloric acid. The resulting colorless precipitate was collected by filtration, washed with water and dried to give 331 mg of the title compound as a colorless powder, melting at 192°–194° C.

Nuclear Magnetic Resonance Spectrum (hexadeuterated dimethyl sulfoxide) δ ppm:
0.80 (3H, triplet, J=7 Hz);
1.0–2.0 (4H, multiplet);
2.69 (2H, triplet, J=7 Hz);
5.69 (2H, singlet);
6.32 (1H, singlet);
6.9–7.9 (13H, multiplet).

EXAMPLE 13

Ethyl 1-[(2'-t-butoxycarbonylbiphenyl-4-yl)methyl]-2-butyl-4-(1-hydroxy-1-methylethyl)imidazole-5-carboxylate (Compound No. 1-118)

Following a procedure similar to that described in Example 1(a), but using 0.92 g of ethyl 2-butyl-4-(1-hydroxy-1-methylethyl)imidazole-5-carboxylate (prepared as described in Preparation 8) and 1.28 g of t-butyl 4'-bromomethylbiphenyl-2-carboxylate, 1.23 g of the title compound were obtained as crystals, melting at 92°–93° C.

Nuclear Magnetic Resonance Spectrum (CDCl$_3$) δ ppm:
0.90 (3H, triplet, J=7 Hz);
1.23 (3H, triplet, J=7 Hz);
1.26 (9H, singlet);
1.2–2.05 (4H, multiplet);
1.65 (6H, singlet);
2.69 (2H, triplet, J=7 Hz);
4 (2H, quartet, J=7 Hz);
5.52 (2H, singlet);
5.73 (1H, singlet);
6.88–7.9 (8H, multiplet).

EXAMPLE 14

Ethyl 2-butyl-1-[(2'-carboxybiphenyl-4-yl)methyl]-4-(1-hydroxy-1-methylethyl)imidazole-5-carboxylate (Compound No. 1-32)

Following a procedure similar to that described in Example 7, but using 0.50 g of ethyl 1-[(2'-t-butoxycarbonylbiphenyl-4-yl)methyl]-2-butyl-4-(1-hydroxy-1-methylethyl)imidazole-5-carboxylate (prepared as described in Example 13) and a 4N solution of hydrogen chloride in dioxane, 0.45 g of the hydrochloride of the title compound was obtained as an amorphous powder, melting at above 80° C. (with softening).

Nuclear Magnetic Resonance Spectrum (hexadeuterated dimethyl sulfoxide) δ ppm:
0.8 2 (3H, triplet, J=7 Hz);
1.1 4 (3H, triplet, J=7 Hz);
1.2–1.35 (2H, multiplet);
1.41–1.55 (2H, multiplet);
1.60 (6H, singlet);
3.00 (2H, triplet, J=7 Hz);
4.21 (2H, quartet, J=7 Hz);
5.63 (2H, singlet);
7.14–7.75 (8H, multiplet).

EXAMPLE 15

Ethyl 1-[(2'-t-butoxycarbonylbiphenyl-4-yl)methyl]-4-(1-hydroxy-1-methylethyl)-2-propylimidazole-5-carboxylate (Compound No. 1-119)

Following a procedure similar to that described in Example 1(a), but using 0.845 g of ethyl 4-(1-hydroxy-1-methylethyl)-2-propylimidazole-5-carboxylate (prepared as described in Preparation 9) and 1.22 g of t-butyl 4'-bromomethylbiphenyl-2-carboxylate, 1.31 g of the title compound were obtained as a gum. This compound was allowed to stand at room temperature, which caused it to crystallize. It was then recrystallized from a mixture of diisopropyl ether and hexane, to give pure title compound, melting at 90°–91° C.

Nuclear Magnetic Resonance Spectrum (CDCl$_3$) δ ppm:
0.97 (3H, triplet, J=7 Hz);
1.23 (3H, triplet, J=7 Hz);
1.25 (9H, singlet);
1.60 (6H, singlet);

1.82 (2H, sextet, J=7 Hz);
2.67 (2H, triplet, J=7 Hz);
4.24 (2H, quartet, J=7 Hz);
5.51 (2H, singlet);
5.72 (1H, singlet);
6.87–7.85 (8H, multiplet).

EXAMPLE 16

Ethyl 1-[(2'-carboxybiphenyl-4-yl)methyl]-4-(1-hydroxy-1-methylethyl)-2-propylimidazole-5-carboxylate (Compound No. 1-50)

Following a procedure similar to that described in Example 7, but using 0.80 g of ethyl 1-[(2'-t-butoxycarbonylbiphenyl-4-yl)methyl]-4-(1-hydroxy-1-methylethyl)-2-propylimidazole-5-carboxylate (prepared as described in Example 15) and a 4N solution of hydrogen chloride in dioxane, 0.67 g of the hydrochloride of the title compound was obtained as an amorphous powder.

Nuclear Magnetic Resonance Spectrum (hexadeuterated dimethyl sulfoxide) δ ppm:

0.88 (3H, triplet, J=7 Hz);
1.14 (3H, triplet, J=7 Hz);
1.50–1.65 (2H, multiplet);
1.60 (6H, singlet);
3.00 (2H, triplet, J=7 Hz);
4.20 (2H, quartet, J=7 Hz);
5.63 (2H, singlet);
7.13–7.75 (8H, multiplet).

EXAMPLE 17

1-[(2'-Carboxybiphenyl-4-yl)methyl]-4-(1-hydroxy-1-methylethyl)-2-propylimidazole-5-carboxylic acid (Compound No. 1-49)

A solution of 0.20 g of ethyl 1-[(2'-carboxybiphenyl-4-yl)methyl]-4-(1-hydroxy-1-methylethyl)-2-propylimidazole-5-carboxylate hydrochloride (prepared as described in Example 16) in an aqueous solution of 84 mg of lithium hydroxide monohydrate in 5 ml of water was stirred at room temperature for 6 hours. At the end of this time, 2 ml of 1N aqueous hydrochloric acid were added dropwise to the reaction mixture, and the resulting precipitate was collected by filtration, to give 0.17 g of the title compound, melting at 176°–179° C. (with decomposition).

Nuclear Magnetic Resonance Spectrum (hexadeuterated dimethyl sulfoxide) δ ppm:

0.88 (3H, triplet, J=7 Hz);
1.5–1.65 (2H, multiplet);
1.56 (6H, singlet);
2.66 (2H, triplet, J=7 Hz);
5.69 (2H, singlet);
7.03–7.72 (8H, multiplet).

EXAMPLE 18

Ethyl 4-(1-hydroxy-1-methylethyl)-2-propyl-1-{4-[2-(tetrazol-5-yl)phenyl]phenyl}methylimidazole-5-carboxylate (Compound No. 2-7)

18(a) Ethyl 4-(1-hydroxy-1-methylethyl)-2-propyl-1-{4-[2-(trityltetrazol-5-yl)phenyl]phenyl}methylimidazole-5-carboxylate 48 mg of sodium hydride (as a 55% w/w dispersion in mineral oil) were added to a solution of 0.26 g of ethyl 4-(1-hydroxy-1-methylethyl)-2-propylimidazole-5-carboxylate (prepared as described in Preparation 9) in 5 ml of N,N-dimethylformamide, and the resulting mixture was stirred at room temperature for 30 minutes. A solution of 0.72 g of 4-[2-(trityltetrazol-5-yl)phenyl]benzyl bromide in 5 ml of N,N-dimethylformamide was then added, and the reaction mixture was stirred at room temperature for 2 hours and then at 60° C. for 4 hours. At the end of this time, it was dissolved in ethyl acetate and the solution was washed three times with water. The solution was then dried over anhydrous sodium sulfate, after which it was freed from the solvent by distillation. The residue was purified by column chromatography through silica gel, using a 1:1 by volume mixture of hexane and ethyl acetate as the eluent, to give 0.62 g of the title compound as an amorphous solid. This was crystallized from diisopropyl ether, to give the title compound as crystals, melting at 167°–168° C. (with decomposition).

Nuclear Magnetic Resonance Spectrum (CDCl$_3$) δ ppm:

0.88 (3H, triplet, J=7 Hz);
1.08 (3H, triplet, J=7 Hz);
1.5–1.8 (2H, multiplet);
1.64 (6H, singlet);
2.52 (2H, triplet, J=8 Hz);
4.12 (2H, quartet, J=7 Hz);
5.38 (2H, singlet);
5.78 (1H, singlet);
6.7–7.6 (22H, multiplet);
7.8–8.1 (1H, multiplet).

18(b) Ethyl 4-(1-hydroxy-1-methylethyl)-2-propyl-1-{4-[2-(tetrazol-5-yl)phenyl]phenyl}methylimidazole-5-carboxylate A solution of 0.50 g of ethyl 4-(1-hydroxy-1-methylethyl)-2-propyl-1-{4-[2-(trityltetrazol-5-yl)phenyl]phenyl}methylimidazole-5-carboxylate [prepared as described in Example 18(a)] dissolved in 5 ml of a 4N solution of hydrogen chloride in dioxane was allowed to stand overnight at room temperature, after which the reaction mixture was concentrated by evaporation under reduced pressure. The resulting residue was triturated with diisopropyl ether and then washed with diisopropyl ether, to give 0.34 g of the hydrochloride of the title compound, melting at 100°–103° C.

Nuclear Magnetic Resonance Spectrum (CD$_3$OD) δ ppm:

0.97 (3H, triplet, J=7 Hz);
1.24 (3H, triplet, J=7 Hz);
1.50–1.65 (2H, multiplet);
1.70 (6H, singlet);
3.00 (2H, triplet, J=8 Hz);
4.30 (2H, quartet, J=7 Hz);
5.70 (2H, singlet);
6.9–7.8 (8H, multiplet).

EXAMPLE 19

4-(1-Hydroxy-1-methylethyl)-2-propyl-1-{4-[2-(tetrazol-5-yl)phenyl]phenyl}methylimidazole-5-carboxylic acid (Compound No. 2-1)

3.65 ml of a 1N aqueous solution of sodium hydroxide were added to a solution of 0.31 g of ethyl 4-(1-hydroxy-1-methylethyl)-2-propyl-1-{4-[2-(tetrazol-5-yl)phenyl]

phenyl}methylimidazole-5-carboxylate hydrochloride [prepared as described in Example 18(b)] in 6 ml of methanol, and the resulting mixture was allowed to stand overnight at room temperature. At the end of this time, the reaction mixture was concentrated by evaporation under reduced pressure to remove the methanol. The concentrate was diluted with water and its pH was adjusted to a value of 3 by the addition of dilute hydrochloric acid, after which it was extracted with ethyl acetate. The organic extract was dried over anhydrous sodium sulfate and then concentrated by evaporation under reduced pressure. The resulting residue was triturated with diisopropyl ether, to give 0.15 g of the title compound, melting at 166°–169° C.

Nuclear Magnetic Resonance Spectrum (hexadeuterated dimethyl sulfoxide) δ ppm:

0.85 (3H, triplet, J=7.5 Hz);
1.54 (6H, singlet);
1.4–1.6 (2H, multiplet);
2.58 (2H, triplet, J=8 Hz);
5.64 (2H, singlet);
6.94 (2H, doublet, J=8.5 Hz);
7.06 (2H, doublet, J=8.5 Hz);
7.5–7.7 (4H, multiplet).

EXAMPLE 20

Pivaloyloxymethyl 4-(1-hydroxy-1-methylethyl)-2-propyl-1-{4-[2-(tetrazol-5-yl)phenyl]phenyl}methylimidazole-5-carboxylate (Compound No. 2-15)

20(a) Pivaloyloxymethyl 4-(1-hydroxy-1-methylethyl)-2-propyl-1-{4-[2-(trityltetrazol-5-yl)phenyl]phenyl}methylimidazole-5-carboxylate 5.30 ml of a 1N aqueous solution of sodium hydroxide, followed by 5 ml of tetrahydrofuran, were added to a solution of 0.76 g of ethyl 4-(1-hydroxy-1-methylethyl)-2-propyl-1-{4-[2-(trityltetrazol-5-yl)phenyl]phenyl}methylimidazole-5-carboxylate [prepared as described in Example 18(a)] in 30 ml of methanol, and the resulting mixture was stirred at room temperature for 8 hours. The reaction mixture was then concentrated by evaporation under reduced pressure to remove the methanol and tetrahydrofuran. Water was added to the concentrate, and the pH of the mixture was adjusted to a value of 4 by the addition of dilute hydrochloric acid, whilst ice-cooling. The mixture was when extracted with ethyl acetate. The extract was dried over anhydrous sodium sulfate and concentrated by evaporation to dryness. The residue was dissolved in 10 ml of dimethylacetamide, and 0.23 g of potassium carbonate and 0.13 ml of pivaloyloxymethyl chloride were added to the resulting solution. The mixture was when stirred at 50° C. for 4 hours, after which 0.06 ml of pivaloyloxymethyl chloride was added, and the mixture was shirred for a further 2 hours. The reaction mixture was when diluted with ethyl acetate, and washed three times with water. The organic layer was separated, dried over anhydrous sodium sulfate and concentrated by evaporation under reduced pressure. The concentrate was purified by column chromatography through silica gel, using a 1:1 by volume mixture of hexane and ethyl acetate as the eluent, to give 0.23 g of the title compound as an amorphous solid.

Nuclear Magnetic Resonance Spectrum (CDCl$_3$) δ ppm:

0.86 (3H, triplet, J=7 Hz);
1.12 (9H, singlet);
1.62 (6H, singlet);
1.4–1.9 (2H, multiplet);
2.51 (2H, triplet, J=7 Hz);
5.37 (1H, broad singlet);
5.40 (2H, singlet);
5.72 (2H, singlet);
6.6–8.1 (23H, multiplet).

20(b) Pivaloyloxymethyl 4-(1-hydroxy-1-methylethyl)-2-propyl-1-{4-[2-(tetrazol-5-yl)phenyl]phenyl}methylimidazole-5-carboxylate 5 ml of a 4N solution of hydrogen chloride in dioxane were added to 0.20 g of pivaloyloxymethyl 4-(1-hydroxy-1-methylethyl)-2-propyl-1-{4-[2-(trityltetrazol-5-yl)phenyl]phenyl}methylimidazole-5carboxylate [prepared as described in Example 20(a)], 5-yl)phenyl]phenyl}methylimidazole-5carboxylate temperature overnight. At the end of this time, the reaction mixture was concentrated to dryness by evaporation under reduced pressure. The resulting residue was triturated with diisopropyl ether to induce crystallization and give 0.13 g of the hydrochloride of the title compound as crystals, melting at 104°–107° C.

Nuclear Magnetic Resonance Spectrum (hexadeuterated dimethyl sulfoxide) δ ppm:

0.84 (3H, triplet, J=7.5 Hz);
1.09 (9H, singlet);
1.35–1.50 (2H, multiplet);
1.56 (6H, singlet);
2.88 (2H, triplet, J=8 Hz);
5.58 (2H, singlet);
5.85 (2H, singlet);
7.05 (2H, doublet, J=8.5 Hz);
7.10 (2H, doublet, J=8.5 Hz);
7.5–7.7 (4H, multiplet).

EXAMPLE 21

2-Butyl-4-(1-ethyl-1-hydroxypropyl)-1-{4-[2-(tetrazol-5-yl)phenyl]phenyl}methylimidazole-5-carboxylic acid (Compound No. 2-40)

21(a) Ethyl 2-butyl-4-(1-ethyl-1-hydroxypropyl)-1-{4-[2-(trityltetrazol-5-yl)phenyl]phenyl}methylimidazole-5-carboxylate Following a procedure similar to that described in Example 18(a), but using 0.75 g of ethyl 2-butyl-4-(1-ethyl-1-hydroxypropyl)imidazole-5-carboxylate (prepared as described in Preparation 13), 0.12 g of sodium hydride (as a 55% w/w dispersion in mineral oil) and 1.51 g of 4-[2-(trityltetrazol-5-yl)phenyl]benzyl bromide, there were obtained 1.05 g of the title compound as an amorphous solid.

Nuclear Magnetic Resonance Spectrum (CDCl$_3$) δ ppm:

0.83 (6H, triplet, J=7.5 Hz);
0.85 (3H, triplet, J=6 Hz);
1.11 (3H, triplet, J=7 Hz);
1.23–1.32 (2H, multiplet);
1.56–1.65 (2H, multiplet);
1.80–1.89 (2H, multiplet);
2.03–2.14 (2H, multiplet);
2.55 (2H, triplet, J=8 Hz);
4.12 (2H, quartet, J=7.5 Hz);
5.37 (2H, singlet);

5.64 (1H, broad singlet);
6.70 (2H, doublet, J=8.5 Hz);
6.9–7.0 (6H, multiplet);
7.10 (2H, doublet, J=8.5 Hz);
7.2–7.4 (10H, multiplet);
7.4–7.5 (2H, multiplet);
7.85–7.90 (1H, multiplet).

21(b) 2-Butyl-4-(1-ethyl-1-hydroxypropyl)-1-{4-[2-(tetrazol-5-yl)phenyl]phenyl}methylimidazole-5-carboxylic acid 1.71 ml of 1N aqueous hydrochloric acid were added to a solution of 0.65 g of ethyl 2-butyl-4-(1-ethyl-1-hydroxypropyl)-1-{4-[2-(trityltetrazol-5-yl)phenyl]phenyl}methylimidazole-5-carboxylate [prepared as described in step (a) above] in 10 ml of methanol, and the resulting mixture was allowed to stand overnight at room temperature. At the end of this time, the solvent was removed by distillation under reduced pressure, and the concentrate was again dissolved in 10 ml of methanol. The resulting solution was mixed with 4.28 ml of a 1N aqueous solution of sodium hydroxide and then allowed to stand overnight at room temperature. The reaction mixture was then concentrated by evaporation under reduced pressure to remove the methanol. The pH of the concentrate was adjusted to a value of 3 by the addition of dilute aqueous hydrochloric acid, and the crystals which precipitated were collected by filtration. The crystals thus obtained were suspended in diisopropyl ether and then again collected by filtration and dried to give 0.35 g of the title compound, melting at 181°–183° C.

Nuclear Magnetic Resonance Spectrum (hexadeuterated dimethyl sulfoxide) $\delta$ ppm:

0.74 (6H, triplet, J=7.5 Hz);
0.79 (3H, triplet, J=7.5 HZ);
1.1–1.3 (2H, multiplet);
1.40–1.55 (2H, multiplet);
1.67–1.80 (2H, multiplet);
1.90–2.05 (2H, multiplet)
2.59 triplet, J=7.5 Hz);
5.67 (2H, singlet);
6.88 (2H, doublet, J=8.5 Hz);
7.05 (2H, doublet, J=8.5 Hz);
7.5–7.7 (4H, multiplet).

EXAMPLE 22

2-Butyl-4-(1-hydroxy-1-methylethyl)-1-{4-[2-(tetrazol-5-yl)phenyl]phenyl}methylimidazole-5-carboxylic acid (Compound No. 2-2)

22(a) Ethyl 2-butyl-4-(1-hydroxy-1-methylethyl)-1-{4-[2-(trityltetrazol-5-yl)phenyl]phenyl}methylimidazole-5-carboxylate Following a procedure similar to that described in Example 18(a), but using 0.26 g of ethyl 2-butyl-4-(1-hydroxy-1-methylethyl)imidazole-5-carboxylate (prepared as described in Preparation 8), 45.5 mg of sodium hydride (as a 55% w/w dispersion in mineral oil) and 0.63 g of 4-[2-(trityltetrazol-5-yl)phenyl]benzyl bromide, 0.2 8 g of the title compound were obtained as an oil.

Nuclear Magnetic Resonance Spectrum (CDCl$_3$) $\delta$ ppm:

0.85 (3H, triplet, J=7 Hz);
1.09 (3H, triplet, J=7 Hz);
1.64 (6H, singlet);
1.3–1.8 (4H, multiplet);
2.56 (2H, triplet, J=8 Hz);
4.14 (2H, quartet, J=7 Hz);
5.38 (2H, singlet);
5.78 (1H, singlet);
6.6–7.6 (22H, multiplet);
7.7–8.1 (1H, multiplet).

22(b) 2-Butyl-4-(1-hydroxy-1-methylethyl)-1-{4-[2-(tetrazol-5-yl)phenyl]phenyl}methylimidazole-5-carboxylic acid Following a procedure a similar to that described in Example 21(b), 78 mg of the title compound, melting at 138°–141° C., were obtained by treating 0.28 g of ethyl 2-butyl-4-(1-hydroxy-1-methylethyl)-1-{4-[2-(trityltetrazol-5-yl)phenyl]phenyl}methylimidazole-5carboxylate [prepared as described in step (a) above] with 0.42 ml of 1N aqueous hydrochloric acid and then treating the product with 1.70 ml of a 1N aqueous solution of sodium hydroxide.

Nuclear Magnetic Resonance Spectrum (hexadeuterated dimethyl sulfoxide) $\delta$ ppm:

0.81 (3H, triplet, J=7.5 Hz);
1.15–1.35 (2H, multiplet);
1.4–1.6 (2H, multiplet);
1.53 (6H, singlet);
2.58 (2H, triplet, J=8.5 Hz);
5.64 (2H, singlet);
6.94 (2H, doublet, J=8.5 Hz);
7.06 (2H, doublet, J=8.5 Hz);
7.15–7.70 (4H, multiplet).

EXAMPLE 23

2-Butyl-4-(1-hydroxy-1-methylpropyl)-1-{4-[2-(tetrazol-5-yl)phenyl]phenyl}methylimidazole-5-carboxylic acid (Compound No. 2-38)

23(a) 2-Butyl-5-cyano-4-(1-hydroxy-1-methylpropyl)-1-{4-[2-(trityltetrazol-5-yl)phenyl]phenyl}methylimidazole Following a procedure similar to that described in Example 18(a), but using 465 mg of 2-butyl-5-cyano-4-(1-hydroxy-1-methylpropyl)imidazole (prepared as described in Preparation 19), 92 mg of sodium hydride (as a 55% w/w dispersion in mineral oil) and 1.11 g of 4-[2-(trityltetrazol-5-yl)phenyl]benzyl bromide, 1.00 g of the title compound was obtained as a gum.

Nuclear Magnetic Resonance Spectrum (CDCl$_3$) $\delta$ ppm:

0.86 (3H, triplet, J=7.5 Hz);
0.87 (3H, triplet, J=7 Hz);
1.21–1.34 (2H, multiplet);
1.54–1.66 (2H, multiplet);
1.60 (3H, singlet);
1.82–1.97 (2H, multiplet);
2.51 (2H, triplet, J=7.5 Hz);
3.22 (1H, singlet);
5.04 (2H, singlet);
6.87–7.52 (22H, multiplet);
7.93–7.96 (1H, multiplet).

23(b) 2-Butyl-5-cyano-4-(1-hydroxy-1-methylpropyl)-1-{4-[2-(tetrazol-5-yl)phenyl]phenyl}methylimidazole A mixture of 1.00 g of 2-butyl-5-cyano-4-(1-hydroxy-1-methylpropyl)-1-{4-[2-(trityltetrazol-5-yl)phenyl]phenyl}methylimidazole [prepared as described in step (a) above] and 25 ml of 20% v/v aqueous acetic acid was stirred at 60° C. for 2 hours, and then the solvent was removed by distillation under reduced pressure. The residual water and acetic acid were removed as a toluene azeotrope by distillation under reduced pressure, and the resulting residue was purified by column chromatography through silica gel, using mixtures of methanol and methylene chloride ranging from 1:9 to 1:4 by volume as the eluent, to give 0.65 g of the title compound as a glass.

Nuclear Magnetic Resonance Spectrum (CDCl$_3$) δ ppm:
0.83 (3H, triplet, J=7 Hz);
0.88 (3H, triplet, J=7 Hz);
1.23–1.37 (2H, multiplet);
1.57 (3H, singlet);
1.55–1.70 (2H, multiplet);
1.82–1.89 (2H, multiplet);
2.64 (2H, triplet, J=7 Hz);
5.12 (2H, singlet);
6.9–7.1 (4H, multiplet);
7.29–7.60 (3H, multiplet);
7.87 (1H, doublet, J=7.5 Hz).

23(c) 2-Butyl-4-(1-hydroxy-1-methylpropyl)-1-{4-[2-(tetrazol-5-yl)phenyl]phenyl}methylimidazole-5-carboxylic acid A mixture of 360 mg of 2-butyl-5-cyano-4-(1-hydroxy-1-methylpropyl)-1-{4-[2-(tetrazol-5-yl)phenyl]phenyl}methylimidazole [prepared as described in step (b) above], 266 mg of lithium hydroxide monohydrate and 3.6 ml of water was stirred in an oil bath kept at 115° C. for 16 hours. At the end of this time, the reaction mixture was cooled and 6.4 ml of 1N aqueous hydrochloric acid were added to the mixture, whilst ice-cooling. The crystals which precipitated were collected by filtration, to give 302 mg of the title compound, melting at 152°–154° C.

Nuclear Magnetic Resonance Spectrum (hexadeuterated dimethyl sulfoxide) δ ppm:
0.79 (3H, triplet, J=7 Hz);
0.82 (3H, triplet, J=7 Hz);
1.20–1.34 (2H, multiplet);
1.44–1.55 (2H, multiplet);
1.55 (3H, singlet);
1.71–1.95 (2H, multiplet);
2.62 (2H, triplet, J=7.5 Hz);
5.68 (2H, AB-guartet, Δδ=0.10 ppm, J=17 Hz);
6.86–7.10 (4H, multiplet);
7.53–7.72 (4H, multiplet).

EXAMPLE 24

4-(1-Hydroxy-1-methylpropyl)-2-propyl-1-{4-[2-(tetrazol-5-yl)phenyl]phenyl}methylimidazole-5-carboxylic acid (Compound No. 2-37)

24(a) 5-Cyano-4-(1-hydroxy-1-methylpropyl)-2-propyl-1-{4-[2-(trityltetrazol-5-yl)phenyl]phenyl}methylimidazole Following a procedure a similar to that described in Example 18(a), but using 380 mg of 5-cyano-4-(1-hydroxy-1-methylpropyl)-2-propylimidazole (prepared as described in Preparation 20), 88 mg of sodium hydride (as a 55% w/w dispersion in mineral oil) and 1.07 g of 4-[2-(trityltetrazol-5-yl)phenyl]benzyl bromide, 0.97 g of the title compound were obtained as an amorphous solid.

Nuclear Magnetic Resonance Spectrum (CDCl$_3$) δ ppm:
0.86 (3H, triplet, J=8 Hz);
0.87 (3H, triplet, J=7.5 Hz);
1.60 (3H, singlet);
1.60–1.75 (2H, multiplet);
1.80–2.00 (2H, multiplet);
2.48 (2H, triplet, J=8 Hz);
5.04 (2H, singlet);
6.88 (2H, doublet, J=8.5 Hz);
6.9–7.0 (4H, multiplet);
7.14 (2H, doublet, J=8.5 Hz);
7.2–7.4 (14H, multiplet);
7.45–7.55 (1H, multiplet).

24(b) 5-Cyano-4-(1-hydroxy-1-methylpropyl)-2-propyl-1-{4-[2-(tetrazol-5-yl)phenyl]phenyl}methylimidazole Following a procedure similar to that described in Example 23(b), 0.32 g of the title compound were obtained as crystals, melting at 141°–145° C., by treating 0.51 g of 5-cyano-4-(1-hydroxy-1-methylpropyl)-2-propyl-1-{4-[2-(trityltetrazol-5-yl)phenyl]phenyl}methylimidazole [prepared as described in step (a) above] with 75% v/v aqueous acetic acid.

Nuclear Magnetic Resonance Spectrum (CD$_3$OD) δ ppm:
0.84 (3H, triplet, J=8 Hz);
0.90 (3H, triplet, J=8.5 Hz);
1.52 (3H, singlet);
1.5–1.7 (2H, multiplet);
1.75–1.90 (2H, multiplet);
2.65 (2H, triplet, J=8 Hz);
5.27 (2H, singlet);
7.03 (2H, doublet, J=8.5 Hz);
7.14 (2H, doublet, J=8.5 Hz);
7.45–7.63 (4H, multiplet).

24(c) 4-(1-Hydroxy-1-methylpropyl)-2-propyl-1-{4-[2-(tetrazol-5-yl)phenyl]phenyl}methylimidazole-5-carboxylic acid Following a procedure similar to that described in Example 23(c), 0.14 g of the title compound were obtained as a powder, melting at 174°–177° C., by treating 0.19 g of 5-cyano-4-(1-hydroxy-1-methylpropyl)-2-propyl-1-{4-[2-(tetrazol-5-yl)phenyl]phenyl}methylimidazole [prepared as described in step (b) above] with 0.15 g of lithium hydroxide monohydrate.

Nuclear Magnetic Resonance Spectrum (CD$_3$OD) δ ppm:
0.88 (3H, triplet, J=7.5 Hz);
0.94 (3H, triplet, J=7.5 Hz);
1.50–1.65 (2H, multiplet);
1.63 (3H, singlet);
1.85–2.05 (2H, multiplet);
2.76 (2H, triplet, J=7.5 Hz);
5.80 (2H, AB-quartet, Δδ=0.14 ppm, J=16.5 Hz);
7.01 (2H, doublet, J=8.5 Hz);
7.11 (2H, doublet, J=8.5 Hz);
7.48–7.75 (4H, multiplet).

EXAMPLE 25

Pivaloyloxymethyl-1-[(2'-carboxybiphenyl-4-yl)methyl]-4-(1-hydroxy-1-methylethyl)-2-propylimidazole-5-carboxylate (Compound No. 3-1)butoxycarbonylbiphenyl 25(a) Ethyl 1-[(2'-4-yl)methyl]-4-(1hydroxy-1-methylethyl)-2-propylimidazole-5-carboxylate 3.00 g of potassium t-butoxide were added, whilst ice-cooling, to a solution of 6 g of ethyl 4-(1-hydroxy-1-methylethyl)-2-propylimidazole-5-carboxylate (prepared as described in Preparation 9) in 40 ml of N,N-dimethylacetamide, and the resulting mixture was stirred for 10 minutes, after which a solution of 9.00 g of t-butyl 4'-bromomethylbiphenyl-2-carboxylate in 40 ml of N,N-dimethylacetamide was added. After the reaction mixture had been stirred at room temperature for 1 hour and then at 50° C. for 2 hours, it was mixed with water and extracted with ethyl acetate. The extract was dried over anhydrous magnesium sulfate, and the solvent was removed by distillation under reduced pressure, after which the residue was purified by column chromatography through silica gel, using a 1:1 by volume mixture of hexane and ethyl acetate as the eluent, to give 11.6 g of the title compound as a solid, softening at above 85° C.

Nuclear Magnetic Resonance Spectrum (CDCl$_3$) δ ppm:
0.97 (3H, triplet, J=7 Hz);
1.23 (3H, triplet, J=7 Hz);
1.25 (9H, singlet);
1.60 (6H, singlet);
1.82 (2H, sextet, J=7 Hz);
2.67 (2H, triplet, J=7 Hz);
4.24 (2H, quartet, J=7 Hz);
5.51 (2H, singlet);
5.72 (1H, singlet);
6.87–7.85 (8H, multiplet).

25(b) 1-[(2'-t-Butoxycarbonylbiphenyl-4-yl)methyl]-4-(1-hydroxy-1-methylethyl)-2-propylimidazole-5-carboxylic acid A solution of 4.8 g of lithium hydroxide monohydrate in 100 ml of water was added to a solution of 11.6 g of ethyl 1-[(2'-t-butoxycarbonylbiphenyl-4-yl)methyl]-4-(1-hydroxy-1-methylethyl)-2-propylimidazole-5-carboxylate [prepared as described in step (a) above] in 60 ml of dioxane, and the resulting mixture was stirred at room temperature for 16 hours. The dioxane was removed by distillation under reduced pressure, and then the concentrate was mixed with ice-water and with ethyl acetate, after which 114 ml of 1N aqueous hydrochloric acid were added. The ethyl acetate layer was separated, dried over anhydrous magnesium sulfate and freed from the solvent by distillation under reduced pressure. The crystalline residue was triturated in diisopropyl ether and collected by filtration to give 9.09 g of the title compound, melting at 155°–157° C.

Nuclear Magnetic Resonance Spectrum (CDCl$_3$) δ ppm:
0.85 (3H, triplet, J=7.5 Hz);
1.23 (9H, singlet);
1.53–1.65 (2H, multiplet);
1.65 (6H, singlet);
2.91 (3H, triplet, J=7.5 Hz);
5.90 (2H, singlet);
7.09 (2H, doublet, J=8 Hz);
7.21–7.48 (5H, multiplet);
7.75 (1H, doublet, J=9 Hz).

25(c) Pivaloyloxymethyl 1-[(2'-t-butoxycarbonylbiphenyl-4-yl)methyl]-4-(1-hydroxy-1-methylethyl)-2-propylimidazole-5-carboxylate 2.13 ml of chloromethyl pivalate and 3.99 g of potassium carbonate were added to a solution of 6 g of 1-[(2'-t-butoxycarbonylbiphenyl-4-yl)methyl]-4-(1-hydroxy-1-methylethyl)-2-propylimidazole-5-carboxylic acid [prepared as described in step (b) above] in 70 ml of N,N-dimethylacetamide, and the resulting mixture was stirred at room temperature for 1 hour and then at 50° C. for 2 hours. At the end of this time, the reaction mixture was mixed with ethyl acetate and water. The ethyl acetate layer was separated and dried over anhydrous magnesium sulfate, after which the solvent was removed by distillation under reduced pressure. The resulting residue was purified by column chromatography through silica gel, using a 1:1 by volume mixture of ethyl acetate and hexane as the eluent, to give 6.80 g of the title compound as crystals, melting at 106°–107° C.

Nuclear Magnetic Resonance Spectrum (CDCl$_3$) δ ppm:
1.07 (3H, triplet, J=7 Hz);
1.25 (9H, singlet);
1.32 (9H, singlet);
1.71 (6H, singlet);
1.79–1.90 (2H, multiplet);
2.75 (2H, triplet, J=8 Hz);
5.50 (1H, singlet);
5.59 (2H, singlet);
5.92 (2H, singlet);
7.05 (2H, doublet, J=8 Hz);
7.34–7.56 (5H, multiplet);
7.85 (1H, doublet, J=7 Hz).

25(d) Pivaloyloxymethyl 1-[(2'-carboxybiphenyl-4-yl)methyl]-4-(1-hydroxy-1-methylethyl)-2-propylimidazole-5-carboxylate A mixture of 6.6 g of pivaloyloxymethyl-1-[(2'-t-butoxycarbonylbiphenyl-4-yl)methyl]-4-(1-hydroxy-1-methylethyl)-2-propylimidazole-5-carboxylate [prepared as described in step (c) above] and 57 ml of a 4N solution of hydrogen chloride in dioxane was stirred at room temperature for 4 hours. At the end of this time, the reaction mixture was concentrated by evaporation under reduced pressure, and the residue was triturated with ethyl acetate to crystallize it, giving 6.52 g of the title compound as the hydrochloride, melting at 170°–173° C.

Nuclear Magnetic Resonance Spectrum (hexadeuterated dimethyl sulfoxide) δ ppm:
0.87 (3H, triplet, J=7 Hz);
1.10 (9H, singlet);
1.45–1.60 (2H, multiplet);
1.58 (6H, singlet);
2.96 (2H, triplet, J=7.5 Hz);
5.65 (2H, singlet);
5.87 (2H, singlet);
7.17 (2H, doublet, J=8 Hz);
7.33 (2H, doublet, J=8 Hz);
7.43–7.60 (3H, multiplet);
7.74 (1H, doublet, J=8 Hz).

EXAMPLE 26

Isopropoxycarbonyloxymethyl 1-[(2'-carboxybiphenyl-4-yl)methyl]-4-(1-hydroxy-1-methylethyl)-2-propylimidazole-5-carboxylate (Compound No. 3-13)

26(a) Isopropoxycarbonyloxymethyl 1-[(2'-t-butoxycarbonylbiphenyl-4-yl)methyl]-4-(1-hydroxy-1-methylethyl)-2-propylimidazole-5-carboxylate Following a procedure similar to that described in Example 25(c), 0.58 g of the title compound was obtained as crystals, melting at 85°–87° C., by stirring a mixture comprising 0.50 g of 1-[(2'-t-butoxycarbonylbiphenyl-4-yl)methyl]-4-(1-hydroxy-1-methylethyl)-2-propylimidazole-5-carboxylic acid [prepared as described in Example 25(b)], 0.19 g of isopropoxycarbonyloxymethyl chloride and 0.33 g of potassium carbonate in 6 ml of N,N-dimethylacetamide at room temperature for 3 hours.

Nuclear Magnetic Resonance Spectrum (CDCl$_3$) δ ppm:
0.99 (3H, triplet, J=7 Hz);
1.23 (9H, singlet);
1.29 (6H, doublet, J=6 Hz);
1.63 (6H, singlet);
1.70–1.85 (2H, multiplet);
2.68 (2H, triplet, J=8 Hz);
4.89 (1H, quintet, J=6 Hz);
5.38 (1H, singlet);
5.51 (2H, singlet);
5.82 (2H, singlet);
6.97 (2H, doublet, J=8 Hz);
7.26–7.48 (5H, multiplet);
7.77 (1H, doublet, J=8 Hz).

26(b) Isopropoxycarbonyloxymethyl 1-[(2'-carboxybiphenyl-4-yl)methyl]-4-(1-hydroxy-1-methylethyl)-2-propylimidazole-5-carboxylate Following a procedure similar to that described in Example 25(d), 0.36 g of the hydrochloride of the title compound was obtained as an amorphous powder melting at 153°–155° C., by treating 0.46 g of isopropoxycarbonyloxymethyl 1-[(2'-t-butoxycarbonylbiphenyl-4-yl)methyl]-4-(1-hydroxy-1-methylethyl)-2-propylimidazole-5carboxylate [prepared as described in step (a) above] with a 4N solution o f hydrogen chloride in dioxane.

Nuclear Magnetic Resonance Spectrum (CDCl$_3$) δ ppm:
0.98 (3H, triplet, J=7 Hz);
1.29 (6H, doublet, J=6 Hz);
1.50–1.65 (2H, multiplet);
1.76 (6H, singlet);
3.13 (2H, triplet, J=7 Hz);
4.90 (1H, quintet, J=6 Hz);
5.55 (2H, singlet);
5.82 (2H, singlet);
7.02 (2H, doublet, J=6.5 Hz);
7.21–7.57 (5H, multiplet);
7.96 (1H, doublet, J=8 Hz).

EXAMPLE 27

Ethoxycarbonyloxymethyl 1-[(2'-carboxybiphenyl-4-yl)methyl]-4-(1-hydroxy-1-methylethyl)-2-propylimidazole-5-carboxylate (Compound No. 3-9)

27(a) Ethoxycarbonyloxymethyl 1-[(2'-t-butoxycarbonylbiphenyl-4-yl)methyl]-4-(1-hydroxy-1-methylethyl)-2-propylimidazole-5-carboxylate Following a procedure similar to that described in Example 25(c), 0.69 g of the title compound was obtained as an oil from 0.55 g of 1-[(2'-t-butoxycarbonylbiphenyl-4-yl)methyl]-4-(1-hydroxy-1-methylethyl)-2-propylimidazole-5-carboxylic acid [prepared as described in Example 25(b)], 0.30 g of ethoxycarbonyloxymethyl chloride and 0.50 g of potassium carbonate.

Nuclear Magnetic Resonance Spectrum (CDCl$_3$) δ ppm:
0.99 (3H, triplet, J=7 Hz);
1.23 (9H, singlet);
1.29 (3H, triplet, J=7 Hz);
1.64 (6H, singlet);
1.74–1.85 (2H, multiplet);
2.69 (2H, triplet, J=7.5 Hz);
4.21 (2H, quartet, J=7 Hz);
5.39 (1H, singlet);
5.52 (2H, singlet);
5.83 (2H, singlet);
6.97 (2H, doublet, J=8 Hz);
7.26–7.51 (5H, multiplet);
7.77 (1H, doublet, J=6.5 Hz).

27(b) Ethoxycarbonyloxymethyl 1-[(2'-carboxybiphenyl-4-yl)methyl]-4-(1-hydroxy-1-methylethyl)-2-propylimidazole-5-carboxylate Following a procedure similar to that described in Example 25(d), 0.48 g of the hydrochloride of the title compound was obtained as an amorphous powder, softening at above 70° C., by treating 0.69 g of ethoxycarbonyloxymethyl 1-[(2'-t-butoxycarbonylbiphenyl-4-yl)methyl]-4-(1-hydroxy-1-methylethyl)-2-propylimidazole-5-carboxylate [prepared as described in step (a) above] with a 4N solution of hydrogen chloride in dioxane.

Nuclear Magnetic Resonance Spectrum (hexadeuterated dimethyl sulfoxide) δ ppm:
0.88 (3H, triplet, J=7 Hz);
1.19 triplet, J=7 Hz);
1.5–1.65 (2H, multiplet);
1.59 (6H, singlet);
2.96 triplet, J=7.5 Hz);
4.15 quartet, J=7 Hz);
5.64 (2H, singlet);
5.84 (2H, singlet);
7.18 (2H, doublet, J=8 Hz);
7.32–7.61 (5H, multiplet);
7.74 (1H, doublet, J=7 Hz).

EXAMPLE 28

1-(Isopropoxycarbonyloxy)ethyl 1-[(2'-carboxybiphenyl-4-yl)methyl]-4-(1-hydroxy-1-methylethyl)-2-propylimidazole-5-carboxylate (Compound No. 3-14)

28(a) 1-(Isopropoxycarbonyloxy)ethyl 1-[(2'-t-butoxycarbonylbiphenyl-4-yl)methyl]-4-(1-hydroxy-1-methylethyl)-2-propylimidazole-5-carboxylate Following a procedure similar to that described in Example 25(c), 0.60 g of the title compound was obtained as a gum from 0.50 g of 1-[(2'-t-butoxycarbonylbiphenyl-4-yl)methyl]-4-(1-hydroxy-1-methylethyl)-2-propylimidazole-5-carboxylic acid [prepared as described in Example 25(b)] and 0.21 g of 1-(isopropoxycarbonyloxy)ethyl chloride with a solution of 0.40 g of potassium carbonate in 6 ml of N,N-dimethylacetamide at 60° C. for 16 hours.

Nuclear Magnetic Resonance Spectrum (CDCl$_3$) δ ppm:
0.97 (3H, triplet, J=7.5 Hz);

1.26 (9H, singlet);
1.27 (6H, doublet of doublets, J=4.5 & 6 Hz);
1.42 (3H, doublet, J=5.5 Hz);
1.64 (6H, doublet, J=3 Hz);
1.75–1.80 (2H, multiplet);
2.65 (2H, doublet, J=7.5 Hz);
4.86 (1H, quintet, J=6 Hz);
5.50 (2H, singlet);
6.90 (1H, quartet, J=5.5 Hz);
6.97 (2H, doublet, J=8.5 Hz);
7.26–7.50 (5H, multiplet);
7.78 (1H, doublet, J=8 Hz).

28(b) 1-(Isopropoxycarbonyloxy)ethyl 1-[(2'-carboxybiphenyl-4-yl)methyl]-4-(1-hydroxy-1-methylethyl)-2-propylimidazole-5-carboxylate Following a procedure similar to that described in Example 25(d), 0.41 g of the hydrochloride of the title compound, melting at 94°–96° C. was obtained as an amorphous powder by treating 0.60 g of 1-(isopropoxycarbonyloxy)ethyl 1-[(2'-t-butoxycarbonylbiphenyl-4-yl)methyl]-4-(1-hydroxy-1-methylethyl)-2-propylimidazole-5-carboxylate [prepared as described in step (a) above] with a 4N solution of hydrogen chloride in dioxane.

Nuclear Magnetic Resonance Spectrum (CDCl$_3$) δ ppm:
0.94 (3H, triplet, J=7 Hz);
1.27 (6H, doublet of doublets, J=6.5 & 11 Hz);
1.47 (3H, doublet, J=5.5 Hz);
1.50–1.65 (2H, multiplet);
1.76 (6H, doublet, J=8.5 Hz);
3.08 (2H, broad triplet, J=8 Hz);
4.86 (1H, septet, J=6 Hz);
5.56 (2H, singlet);
6.87 (1H, quartet, J=5.5 Hz);
7.04 (2H, doublet, J=7.5 Hz);
7.27–7.65 (5H, multiplet);
7.97 (1H, doublet, J=8 Hz).

EXAMPLE 29

(5-Methyl-2-oxo-1,3-dioxolen-4-yl)methyl 1-[(2'-carboxybiphenyl-4-yl)methyl]-4-(1-hydroxy-1-methylethyl)-2-propylimidazole-5-carboxylate (Compound No. 3-25)

29(a) (5-Methyl-2-oxo-1,3-dioxolen-4-yl)methyl 1-[(2'-t-butoxycarbonylbiphenyl-4-yl)methyl]-4-(1-hydroxy-1-methylethyl)-2-propylimidazole-5-carboxylate Following a procedure similar to that described in Example 25(c), 0.65 g of the title compound was obtained as a gum from 0.50 g of 1-[(2'-t-butoxycarbonylbiphenyl-4-yl)methyl]-4-(1-hydroxy-1-methylethyl)-2-propylimidazole-5-carboxylic acid [prepared as described in Example 25(b)], 0.27 g of (5-methyl-2-oxo-1,3-dioxolen-4-yl)methyl bromide and 0.3 g of potassium carbonate in 6 ml of N,N-dimethylacetamide.

Nuclear Magnetic Resonance Spectrum (CDCl$_3$) δ ppm:
0.99 (3H, triplet, J=6.5 Hz);
1.28 (9H, singlet);
1.64 (6H, singlet);
1.55–1.90 (2H, multiplet);
2.07 (3H, singlet);
2.70 (2H, triplet, J=7 Hz);
4.90 (2H, singlet);
5.47 (2H, singlet);
5.51 (1H, singlet);
6.91 (2H, doublet, J=8.5 Hz);
7.2–7.9 (6H, multiplet).

29(b) (5-Methyl-2-oxo-1,3-dioxolen-4-yl)methyl 1-[(2'-carboxybiphenyl-4-yl)methyl]-4-(1-hydroxy-1-methylethyl)-2-propylimidazole-5-carboxylate Following a procedure similar to that described in Example 25(d), 0.54 g of the hydrochloride of the title compound was obtained as an amorphous powder, melting at 90°–93° C., by treating 0.65 g of (5-methyl-2-oxo-1,3-dioxolen-4-yl)methyl 1-[(2'-t-butoxycarbonylbiphenyl-4-yl)methyl]-4-(1-hydroxy-1-methylethyl)-2-propylimidazole-5-carboxylate [prepared as described in step (a) above] with a 4N solution of hydrogen chloride in dioxane.

Nuclear Magnetic Resonance Spectrum (hexadeuterated dimethyl sulfoxide) δ ppm;
0.88 (3H, triplet, J=7.5 Hz);
1.5–1.7 (2H, multiplet);
1.59 (6H, singlet);
2.11 (3H, singlet);
3.00 (2H, triplet, J=7.5 Hz);
5.13 (2H, singlet);
5.63 (2H, singlet);
7.13 (2H, doublet, J=8 Hz);
7.26–7.75 (6H, multiplet).

EXAMPLE 30

Pivaloyloxymethyl 1-[(2'-carboxybiphenyl-4-yl)methyl]-4-(1-hydroxy-1-methylethyl)-2-propylimidazole-5-carboxylate (Compound No. 3-1)

30(a) Pivaloyloxymethyl 1-[(2'-t-butoxycarbonylbiphenyl-4-yl)methyl]-4-(1-hydroxy-1-methylethyl)-2-propylimidazole-5-carboxylate Following a procedure similar to that described in Example 25(a), 0.81 g of the title compound was obtained from 500 mg of pivaloyloxymethyl 4-(1-hydroxy-1-methylethyl)-2-propylimidazole-5-carboxylate [prepared as described in Preparation 22(ii)] and 560 mg of t-butyl 4'-bromomethylbiphenyl-2-carboxylate. The melting point and Nuclear Magnetic Resonance Spectrum of the product were identical with those of the compound obtained as described in Example 25(c).

30(b) Pivaloyloxymethyl 1-[(2'-carboxybiphenyl-4-yl)methyl]-4-(1-hydroxy-1-methylethyl)-2-propylimidazole-5-carboxylate Following a procedure similar to that described in Example 25(d), 0.45 g of the hydrochloride of the title compound was obtained as crystals from 0.5 g of pivaloyloxymethyl 1-[(2'-t-butoxycarbonylbiphenyl-4-yl)methyl]-4-(1-hydroxy-1-methylethyl)-2-propylimidazole-5-carboxylate [prepared as described in step (a) above]. The melting point and Nuclear Magnetic Resonance Spectrum of the product were identical with those of the compound prepared as described in Example 25(d).

EXAMPLE 31

Pivaloyloxymethyl 2-butyl-1-[(2'-carboxybiphenyl-4-yl)methyl]-4-(1-hydroxy-1-methylethyl)imidazole-5-carboxylate (Compound No. 3-27)

31(a) Methyl 1-[(2'-t-butoxycarbonylbiphenyl-4-yl)methyl]-2-butyl-4-(1-hydroxy-1-methylethyl)imidazole-5-carboxylate Following a procedure similar to that described in Example 25(a), 3.54 g of the title compound were obtained as a syrup from 2.00 g of methyl 2-butyl-4-(1-hydroxy-1-methylethyl)imidazole-5-carboxylate (prepared as described in Preparation 21) and 3.03 g of t-butyl 4'-bromomethylbiphenyl-2-carboxylate.

Nuclear Magnetic Resonance Spectrum (CDCl$_3$) δ ppm:
0.92 (3H, triplet, J=7.5 Hz);
1.25 (9H, singlet);
1.33–1.46 (2H, multiplet);
1.64 (6H, singlet);
1.68–1.78 (2H, multiplet);
2.70 (2H, triplet, J=8 Hz);
3.78 (3H, singlet);
5.50 (2H, singlet);
5.70 (1H, singlet);
6.97 (2H, doublet, J=8.5 Hz);
7.26–7.33 (3H, multiplet);
7.37–7.54 (2H, multiplet);
7.76–7.81 (1H, multiplet).

31(b) 1-[(2'-t-Butoxycarbonylbiphenyl-4-yl)methyl]-2-butyl-4-(1-hydroxy-1-methylethyl)imidazole-5-carboxylic acid Following a procedure similar to that described in Example 25(b), 2.46 g of the title compound were obtained as crystals, melting at 158°–159° C., by hydrolyzing 3.31 g of methyl 1-[(2'-t-butoxycarbonylbiphenyl-4-yl)methyl]-2-butyl-4-(1-hydroxy-1-methylethyl)imidazole-5-carboxylate [prepared as described in step (a) above] with 1.37 g of lithium hydroxide monohydrate.

Nuclear Magnetic Resonance Spectrum (CDCl$_3$) δ ppm:
0.84 (3H, triplet, J=7.5 Hz);
1.23 (9H, singlet);
1.25–1.38 (2H, multiplet);
1.52–1.65 (2H, multiplet);
1.68 (6H, singlet);
2.83 (2H, triplet, J=6.5 Hz);
5.81 (2H, singlet);
7.07 (2H, doublet, J=8.0 Hz);
7.22–7.28 (3H, multiplet);
7.34–7.50 (2H, multiplet);
7.74–7.78 (1H, multiplet).

31(c) Pivaloyloxymethyl 1-[(2'-t-butoxycarbonylbiphenyl-4-yl)methyl]-2-butyl-4-(1-hydroxy-1-methylethyl)imidazole-5-carboxylate Following a procedure similar to that described in Example 25(c), 0.48 g of the title compound was obtained as a syrup by esterifying 0.40 g of 1-[(2'-t-butoxycarbonylbiphenyl-4-yl)methyl]-2-butyl-4-(1-hydroxy-1-methylethyl)imidazole-5-carboxylic acid [prepared as described in step (b) above] with chloromethyl pivalate and potassium carbonate.

Nuclear Magnetic Resonance Spectrum (CDCl$_3$) δ ppm:
0.92 (3H, triplet, J=7.5 Hz);
1.17 (9H, singlet);
1.24 (9H, singlet);
1.32–1.47 (2H, multiplet);
1.63 (6H, singlet);
1.66–1.79 (2H, multiplet);
2.69 (2H, triplet, J=8 Hz);
5.41 (1H, singlet);
5.51 (2H, singlet);
5.83 (2H, singlet);
6.97 (2H, doublet, J=8 Hz);
7.25–7.28 (3H, multiplet);
7.38–7.51 (2H, multiplet);
7.75–7.79 (1H, multiplet).

31(d) Pivaloyloxymethyl 2-butyl-1-[(2'-carboxybiphenyl-4-yl)methyl]-4-(1-hydroxy-1-methylethyl)imidazole5-carboxylate Following a procedure similar to that described in Example 25(d), 0.45 g of the hydrochloride of the title compound was obtained as an amorphous solid, melting at 139°–144° C. (softening at 127° C.), by treating 0.48 g of pivaloyloxymethyl 1-[(2'-t-butoxycarbonylbiphenyl-4-yl)methyl]-2-butyl-4-(1-hydroxy-1-methylethyl)imidazole-5-carboxylate [prepared as described in step (c) above] with a 4N solution of hydrogen chloride in dioxane.

Nuclear Magnetic Resonance Spectrum (hexadeuterated dimethyl sulfoxide) δ ppm:
0.80 (3H, triplet, J=7.5 Hz);
1.10 (9H, singlet);
1.21–1.35 (2H, multiplet);
1.39–1.50 (2H, multiplet);
1.58 (6H, singlet);
2.96 (2H, triplet, J=7.5 Hz);
5.64 (2H, singlet);
5.88 (2H, singlet);
7.17 (2H, doublet, J=8.5 Hz);
7.32–7.34 (3H, multiplet);
7.43–7.49 (1H, multiplet);
7.55–7.61 (1H, multiplet);
7.73–7.75 (1H, multiplet).

EXAMPLE 32

Isopropoxycarbonyloxymethyl 2-butyl-1-[(2'-carboxybiphenyl-4-yl)methyl]-4-(1-hydroxy-1-methylethyl)imidazole-5-carboxylate (Compound No. 3-39)

32(a) Isopropoxycarbonyloxymethyl 1-[(2'-t-butoxycarbonylbiphenyl-4-yl)methyl]-2-butyl-4-(1-hydroxy-1-methylethyl)imidazole-5-carboxylate Following a procedure similar to that described in Example 25(c). 0.46 g of the title compound was obtained as crystals, melting at 91°–93 ° C., from 0.40 g of 1-[(2'-t-butoxycarbonylbiphenyl-4-yl)methyl]-2-butyl-4-(1-hydroxy-1-methylethyl)imidazole-5-carboxylic acid [prepared as described in Example 31(b)], 0.15 g of isopropoxycarbonyloxymethyl chloride and 0.31 g of potassium carbonate.

Nuclear Magnetic Resonance Spectrum (CDCl$_3$) δ ppm:
0.92 (3H, triplet, J=7.5 Hz);
1.23 (9H, singlet);
1.29 (6H, doublet, J=6 Hz);
1.35–1.45 (2H, multiplet);
1.63 (6H, singlet);
1.65–1.80 (2H, multiplet);
2.71 (2H, triplet, J=7.5 Hz);
4.90 (1H, septet, J=6 Hz);
5.39 (1H, singlet);

5.51 (2H, singlet);
5.82 (2H, singlet);
6.98 (2H, doublet, J=8 Hz);
7.25–7.30 (3H, multiplet);
7.35–7.52 (2H, multiplet);
7.75–7.80 (1H, multiplet).

32(b) Isopropoxycarbonyloxymethyl 2-butyl-1-[(2'-carboxybiphenyl-4-yl)methyl]-4-(1-hydroxy-1-methylethyl)imidazole-5-carboxylate Following a procedure similar to that described in Example 25(d), 0.39 g of the hydrochloride of the title compound was obtained as crystals, melting at 154°–156° C. by treating 0.40 g of isopropoxycarbonyloxymethyl 1-[(2'-t-butoxycarbonylbiphenyl-4-yl)methyl]-2-butyl-4-(1-hydroxy-1-methylethyl)imidazole-5-carboxylate [prepared as described in step (a) above] with a 4N solution of hydrogen chloride in dioxane.

Nuclear Magnetic Resonance Spectrum (hexadeuterated dimethyl sulfoxide) δ ppm:

0.81 (3H, triplet, J=7.5 Hz);
1.21 (6H, doublet, J=6.5 Hz);
1.23–1.36 (2H, multiplet);
1.38–1.52 (2H, multiplet);
1.59 (6H, singlet);
2.98 (2H, triplet, J=6.5 Hz);
4.79 (1H, septet, J=6.5 Hz);
5.65 (2H, singlet);
5.85 (2H, singlet);
7.18 (2H, doublet, J=8 Hz);
7.30–7.38 (3H, multiplet);
7.42–7.62 (2H, multiplet);
7.74 (1H, doublet, J=7.5 Hz).

EXAMPLE 33

(5-Methyl-2-oxo-1,3-dioxolen-4-yl)methyl 2-butyl-1 [(2-carboxybiphenyl-4-yl)methyl]-4-(1-hydroxy-1-methylethyl) imidazole-5-carboxylate (Compound No. 3-51)

33(a) (5-Methyl-2-oxo-1,3-dioxolen-4yl)methyl 1-[(2'-t-butoxycarbonylbiphenyl-4-yl)methyl]-2-butyl-4-(1-hydroxy-1-methylethyl)imidazole-5-carboxylate Following a procedure similar to that described in Example 25(c), 0.43 g of the title compound was obtained as crystals, melting at 156°–157° C., from 0.40 g of 1-[(2'-t-butoxycarbonylbiphenyl-4-yl)methyl]-2-butyl-4-(1-hydroxy-1-methylethyl)imidazole-5-carboxylic acid [prepared as described in Example 31(b)], 0.22 g of (5-methyl-2-oxo-1,3-dioxolen-4-yl)methyl bromide and 0.26 g of potassium carbonate in 5 ml of N,N-dimethylacetamide.

Nuclear Magnetic Resonance Spectrum (CDCl$_3$) δ ppm:

0.92 (3H, triplet, J=7.5 Hz);
1.27 (9H, singlet);
1.30–1.45 (2H, multiplet);
1.62 (6H, singlet);
1.65–1.80 (2H, multiplet);
2.07 (3H, singlet);
2.70 (2H, triplet, J=7.5 Hz);
4.89 (2H, singlet);
5.46 (2H, singlet);
5.55 (1H, singlet);
6.91 (2H, doublet, J=8.5 Hz);
7.26–7.50 (5H, multiplet);
7.76 (1H, doublet, J=6.5 Hz).

33(b) (5-Methyl-2-oxo-1,3-dioxolen-4-yl)methyl 2-butyl-1-[(2'-carboxybiphenyl-4-yl)methyl]-4-(1-hydroxy-1-methylethyl)imidazole-5-carboxylate Following a procedure similar to that described in Example 25(d), 0.26 g of the hydrochloride of the title compound was obtained as a powder, melting at above 70° C. (softening), by treating 0.32 g of (5-methyl-2-oxo-1,3-dioxolen-4-yl)methyl 1-[(2'-t-butoxycarbonylbiphenyl-4-yl)methyl]-4-(1-hydroxy-1-methylethyl)imidazole-5-carboxylate [prepared as described in step (a) above] with a 4N solution of hydrogen chloride in dioxane.

Nuclear Magnetic Resonance Spectrum (hexadeuterated dimethyl sulfoxide) δ ppm:

0.82 (3H, triplet, J=7 Hz);
1.20–1.40 (2H, multiplet);
1.40–1.60 (2H, multiplet);
1.59 (6H, singlet);
2.12 (3H, singlet);
2.98 (2H, triplet, J=7.5 Hz);
5.14 (2H, singlet);
5.63 (2H, singlet);
7.13 (2H, doublet, J=7.5 Hz);
7.30–7.60 (5H, multiplet); 7.74 (1H, doublet, J=7.5 Hz).

EXAMPLE 34

Phthalidyl 1-[(2'-carboxybiphenyl-4-yl)methyl]-4-(1-hydroxy-1-methylethyl)-2-propylimidazole-5-carboxylate (Compound No 3-26)

34(a) Phthalidyl 1-[(2'-t-butoxycarbonylbiphenyl-4yl)methyl]-4-(1-hydroxy-1-methylethyl)-2-propylimidazole-5-carboxylate Following a procedure similar to that described in Example 25(c), 0.62 g of the title compound was obtained as crystals, melting at 144° C., from 0.50 g of 1-[(2'-t-butoxycarbonylbiphenyl)methyl]-4-(1-hydroxy-1-methylethyl)-2-propylimidazole-5-carboxylic acid [prepared as described in Example 25(b)], 0.25 g of 3-bromophthalide and 0.3 g of potassium carbonate in 6 ml of N,N-dimethylacetamide.

Nuclear Magnetic Resonance Spectrum (CDCl$_3$) δ ppm:

0.97 (3H, triplet, J=7.5 Hz);
1.25 (9H, singlet);
1.62 (6H, singlet);
1.75 (2H, sextet, J=7.5 Hz);
2.66 (2H, triplet, J=6.5 Hz);
5.38 (2H, AB-quartet, Δδ=0.10 ppm, J=17 Hz);
5.42 (1H, singlet);
6.69 (2H, doublet, J=7.5 Hz);
7.15 (2H, doublet, J=7.5 Hz);
7.28–7.89 (9H, multiplet).

34(b) Phthalidyl 1-[(2'-carboxybiphenyl-4-yl)methyl]-4-(1-hydroxy-1-methylethyl)-2-propylimidazole-5-carboxylate Following a procedure similar to that described in Example 25(d), 0.37 g of the hydrochloride of the title compound was obtained as an amorphous powder, melting 142°–144° C. by treating 0.45 g of phthalidyl 1-[(2'-butoxycarbonylbiphenyl-4-yl)methyl]-4-(1-hydroxy-1-methylethyl)-2-propylimidazole-5-carboxylate [prepared as described in step (a) above] with a 4N solution of hydrogen chloride in dioxane.

Nuclear Magnetic Resonance Spectrum (hexadeuterated dimethyl sulfoxide) δ ppm:

0.92 (3H, triplet, J=7.5 Hz);
1.50–1.70 (2H, multiplet);
1.59 (6H, singlet);
3.00 (2H, triplet, J=7.5 Hz);
5.65 (2H, singlet);
7.01 (2H, doublet, J=8 Hz);
7.27 (2H, doublet, J=8 Hz);
7.36–7.98 (9H, multiplet).

EXAMPLE 35

Ethyl 4-hydroxymethyl-2-propyl-1-{4-[2-(tetrazol-5-yl)phenyl]phenyl}methylimidazole-5-carboxylate (Compound No. 4-3)

35(a) Diethyl 2-propyl-1-{4-[2-(trityltetrazol-5-yl)phenyl]phenyl}methylimidazole-4,5-dicarboxylate 0.441 g of potassium t-butoxide was added to a solution of 1.00 g of diethyl 2-propylimidazole-4,5-dicarboxylate (prepared as described in Preparation 12) in 15 ml of N,N-dimethylacetamide, and the resulting mixture was stirred at room temperature for 30 minutes. A solution of 2.19 g of 4-[2-(trityltetrazol-5-yl)phenyl]benzyl bromide in 15 ml of N,N-dimethylacetamide was then added dropwise to the reaction mixture at room temperature, and the reaction mixture was stirred at room temperature for 3 hours. At the end of this time, it was diluted with water and then extracting with ethyl acetate. The extract was dried over anhydrous magnesium sulfate and then freed from the solvent by distillation. The residue was purified by column chromatography through silica gel, using a 1:1 by volume mixture of hexane and ethyl acetate as the eluent, to give 2.24 g of the title compound as an amorphous solid.

Nuclear Magnetic Resonance Spectrum (CDCl$_3$) δ ppm:

0.88 (3H, triplet, J=7.5 Hz);
1.20 (3H, triplet, J=7.5 Hz);
1.39 (3H, triplet, J=7.5 Hz);
1.59 (6H, singlet);
1.61–1.72 (2H, multiplet);
2.55 (2H, triplet, J=7.5 Hz);
4.20 (2H, quartet, J=7.5 Hz);
4.39 (2H, quartet, J=7.5 Hz);
5.30 (2H, singlet);
6.78 (2H, doublet, J=8 Hz);
6.92–7.52 (20H, multiplet);
7.90 (1H, doublet, J=7.5 Hz).

35(b) Ethyl 4-hydroxymethyl-2-propyl-1-{4-[2-(trityltetrazol-5-yl)phenyl]phenyl}methylimidazole-5-carboxylate 10 ml of a 1.5M solution of diisobutylaluminum hydride in toluene were added dropwise at −20° C. under an atmosphere of nitrogen to a solution of 4.27 g of diethyl 2-propyl-1-{4-[2-(trityltetrazol-5-yl)phenyl]phenyl}methylimidazole-4,5-dicarboxylate [prepared as described in step (a) above] in 50 ml of tetrahydrofuran. The resulting mixture was allowed to stand at 0° C. for 16 hours and then mixed with ethyl acetate and with a saturated aqueous solution of ammonium chloride; it was then stirred at room temperature for 1 hour. The resulting precipitate was filtered off, and the ethyl acetate layer was separated and dried over anhydrous magnesium sulfate; the solvent was then removed by distillation under reduced pressure. The crystalline residue was washed with diisopropyl ether, to give 4.03 g of the title compound, melting at 135°–138° C.

Nuclear Magnetic Resonance Spectrum (CDCl$_3$) δ ppm:

0.94 (6H, triplet, J=7.5 Hz);
1.29 (3H, triplet, J=7 Hz);
1.67–1.77 (2H, multiplet);
2.56 (2H, triplet, J=7.5 Hz);
3.43 (1H, broad triplet, J=4 Hz);
4.25 (2H, quartet, J=7 Hz);
4.91 (2H, doublet, J=4 Hz);
5.49 (2H, singlet);
6.82 (2H, doublet, J=7.5 Hz);
6.98–7.57 (20H, multiplet);
7.94 (1H, doublet, J=7 Hz).

35(c) Ethyl 4-hydroxymethyl-2-propyl-1-{4-[2-(tetrazol-5-yl)phenyl]phenyl}methylimidazole-5-carboxylate A solution of 0.28 g of ethyl 4-hydroxymethyl-2-propyl-{4-[2-(trityltetrazol-5-yl)phenyl]phenyl}methylimidazole-5-carboxylate [prepared as described in step (b) above] in 4 ml of 75% v/v aqueous acetic acid was stirred at 60° C. for 2 hours. The reaction mixture was then concentrated by evaporation under reduced pressure, and the residue was dissolved in toluene. The resulting solution was again concentrated by evaporation, to remove as much water and acetic acid as possible. The residue was then purified by column chromatography through silica gel, using 9:1 and 4:1 by volume mixtures of methylene chloride and methanol as the eluent, to give 0.20 g of the title compound as an amorphous solid.

Nuclear Magnetic Resonance Spectrum (CDCl$_3$) δ ppm:

0.80 (3H, triplet, J=7.5 Hz);
1.20 (3H, triplet, J=7.5 Hz);
1.45–1.65 (2H, multiplet);
2.44 (2H, triplet, J=7.5 Hz);
4.20 (2H, quartet, J=7.5 Hz);
4.58 (2H, singlet);
5.43 (2H, singlet);
6.78 (2H, doublet, J=7.5 Hz);
6.98 (2H, doublet, J=7.5 Hz);
7.38–7.60 (3H, multiplet);
7.79 (1H, doublet, J=7.5 Hz).

EXAMPLE 36

4-Hydroxymethyl-2-propyl-1-{4-[2-(tetrazol-5-yl)phenyl]phenyl}methylimidazole-5-carboxylic acid (Compound No. 4-1)

A mixture of 0.20 g of ethyl 4-hydroxymethyl-2-propyl-1-{4-[2-(tetrazol-5-yl)phenyl]phenyl}methylimidazole-5-carboxylate [prepared as described in Example 35(c)] and 0.10 g of lithium hydroxide monohydrate in 3 ml of water was stirred at room temperature for 3 hours, after which it was allowed to stand for 16 hours at the same temperature. The reaction mixture was then mixed with 2.38 ml of 1N aqueous hydrochloric acid and the resulting precipitate was collected by filtration, to give 150 mg of the title compound, melting a=233° C. (with decomposition).

Nuclear Magnetic Resonance Spectrum (hexadeuterated dimethyl sulfoxide) δ ppm:

0.88 (3H, triplet, J=7.5 Hz);
1.59 (2H, sextet, J=7.5 Hz);
2.58 (2H, triplet, J=7.5 Hz);
4.64 (2H, singlet);
5.62 (2H, singlet);
6.98 (2H, doublet, J=8 Hz);
7.08 (2H, doublet, J=8 Hz);
7.39–7.69 (4H, multiplet).

EXAMPLE 37

Pivaloyloxymethyl 4-hydroxymethyl-2-propyl-1-{4-[2-(tetrazol-5-yl)phenyl]phenyl}methylimidazole-5-carboxylate (Compound No. 4-4)

37(a) 4-Hydroxymethyl-2-propyl-1-{4-[2-(trityltetrazol-5-yl)phenyl]phenyl}methylimidazole-5-carboxylic acid A solution of 0.66 g of lithium hydroxide monohydrate in 20 ml of water was added to a solution of 1.22 g of ethyl 4-hydroxymethyl-2-propyl-1-{4-[2-(trityltetrazol-5-yl)phenyl]phenyl}methylimidazole-5-carboxylate [prepared as described in Example 35(b)] in 5 ml of dioxane, and the resulting mixture was stirred at 80° C. for 5 hours. At the end of this time, the reaction mixture was freed from dioxane by distillation under reduced pressure, and the aqueous residue was mixed with ice and with ethyl acetate: 15.7 ml of 1N aqueous hydrochloric acid were then added. The title compound precipitated, and was collected by filtration and washed with water. The ethyl acetate layer was then separated from the filtrate and dried over anhydrous magnesium sulfate, and the solvent was removed by distillation under reduced pressure. The resulting residue was washed with diethyl ether, to give more of the title compound as a powder. The two portions of the title compound were combined and together weighed 0.98 g, and this was immediately used in the subsequent esterification reaction without further purification or characterisation.

37(b) Pivaloyloxymethyl 4-hydroxymethyl-2-propyl-1-{4-[2-(trityltetrazol-5-yl)phenyl]phenyl}methylimidazole-5-carboxylate 0.30 g of potassium carbonate and 0.24 g of pivaloyloxymethyl chloride were added to a solution of 0.98 g of 4-hydroxymethyl-2-propyl-1-{4-[2-(trityltetrazol-5-yl)phenyl]phenyl}methylimidazole-5-carboxylic acid [prepared as described in step (a) above] in 10 ml of N,N-dimethylacetamide, and the resulting mixture was stirred at room temperature for 6 hours. At the end of this time, the reaction mixture was mixed with ethyl acetate and water. The ethyl acetate layer was separated and dried over anhydrous magnesium sulfate, and then the solvent was removed by distillation under reduced pressure. The resulting residue was purified by column chromatography through silica gel, using a 2:1 by volume mixture of ethyl acetate and hexane as the eluent, to give 0.91 g of the title compound as a gum.

Nuclear Magnetic Resonance Spectrum (CDCl$_3$) δ ppm:
0.89 (3H, triplet, J=7.5 Hz);
1.18 (9H, singlet);
1.70 (1H, sextet, J=7.5 Hz);
2.52 (2H, triplet, J=8 Hz)
3.35 (1H, broad singlet);
4.83 (2H, singlet);
5.42 (2H, singlet);
5.80 (2H, singlet);
6.76 (2H, doublet, J=8 Hz);
6.92–7.51 (20H, multiplet);
7.90 (1H, doublet, J=7.5 Hz).

37(c) Pivaloyloxymethyl 4-hydroxymethyl-2-propyl-1-{4-[2-(tetrazol-5-yl)phenyl]phenyl}methylimidazole-5-carboxylate Following a procedure similar to that described in Example 35(c), 0.91 g of pivaloyloxymethyl 4-hydroxymethyl-2-propyl-1-{4-[2-(trityltetrazol-5-yl)phenyl]phenyl}methylimidazole [prepared as described in step (b) above] was detritylated by treatment with 75% v/v aqueous acetic acid, to give 0.42 g of the title compound as a powder, melting at above 60° C. (with softening).

Nuclear Magnetic Resonance Spectrum (CDCl$_3$) δ ppm:
0.94 (3H, triplet, J=7.5 Hz);
1.14 (9H, singlet);
1.72 (2H, sextet, J=7.5 Hz);
2.61 (2H, triplet, J=7.5 Hz);
2.90 (2H, broad singlet);
4.77 (2H, singlet);
5.49 (2H, singlet);
5.84 (2H, singlet);
6.94 (2H, doublet, J=8 Hz);
7.15 (2H, doublet, J=8 Hz);
7.26–7.61 (3H, multiplet);
8.07 (1H, doublet, J=7.5 Hz).

EXAMPLE 38

Methyl 2-butyl-4-hydroxymethyl-1-{4-[2-(tetrazol-5-yl)phenyl]phenyl}methylimidazole-5-carboxylate (Compound No. 4-47)

38(a) Dimethyl 2-butyl-1-{4-[2-(trityltetrazol-5-yl)phenyl]phenyl}methylimidazole-4,5-dicarboxylate Following a procedure similar to that described in Example 35(a), but using 0.50 g of dimethyl 2-butylimidazole-4,5-dicarboxylate (prepared as described in Preparation 4) and 1.17 g of 4-[2-(trityltetrazol-5-yl)phenyl]benzyl bromide, 0.51 g of the title compound was obtained as an amorphous solid.

Nuclear Magnetic Resonance Spectrum (CDCl$_3$) δ ppm:
0.85 (3H, triplet, J=7.5 Hz);
1.20–1.80 (4H, multiplet);
2.59 (2H, triplet, J=8.0 Hz);
3.73 (3H, singlet);
3.92 (3H, singlet);
5.30 (2H, singlet);
6.6–7.6 (22H, multiplet);
7.8–8.0 (1H, multiplet).

38 (b) Methyl 2-butyl-4-hydroxymethyl-1-{4-[2-(trityltetrazol-5-yl)phenyl]phenyl}methylimidazole-5-carboxylate Following a procedure similar to that described in Example 35(b), 0.51 g of dimethyl 2-butyl-1-{4-[2-(trityltetrazol-5-yl)phenyl]phenyl}methylimidazole-4,5-dicarboxylate [prepared as described in step (a) above] was reduced using 0.99 ml of a 1.5M solution of diisobutylaluminum hydride in toluene, to give 0.44 g of the title compound as an oil.

Nuclear Magnetic Resonance Spectrum (CDCl$_3$) δ ppm:
0.86 (3H, triplet, J=7.5 Hz);
1.23–1.36 (2H, multiplet);
1.58–1.70 (2H, multiplet);

1.80–1.95 (1H, multiplet);
2.54 (2H, triplet, J=8.0 Hz);
3.72 (3H, singlet);
4.85 (2H, doublet, J=6.0 Hz);
5.43 (2H, singlet);
6.77 (2H, doublet, J=8.5 Hz);
6.92–6.95 (4H, multiplet);
7.08 (2H, doublet, J=8.5 Hz);
7.22–7.51 (14H, multiplet);
7.87–7.90 (1H, multiplet).

38(c) Methyl 2-butyl-4-hydroxymethyl-1-{4-[2-tetrazol-5-yl)phenyl]phenyl}methylimidazole-5-carboxylate A solution of 0.44 g of methyl 2-butyl-4-hydroxymethyl-1-{4-[2-(trityltetrazol-5-yl)phenyl]phenyl}methylimidazole-5-carboxylate [prepared as described in step (b) above] in 10 ml of methanol and 0.70 ml of 1N aqueous hydrochloric acid was allowed to stand overnight at room temperature. At the end of this time, the reaction mixture was concentrated to dryness by distillation under reduced pressure, and the residue was triturated with diethyl ether to give 0.30 g of the hydrochloride of the title compound as a solid.

Nuclear Magnetic Resonance Spectrum (hexadeuterated dimethyl sulfoxide) δ ppm:

0.81 (3H, triplet, J=7.5 Hz);
1.19–1.32 (2H, multiplet);
1.38–1.51 (2H, multiplet);
2.95 (2H, triplet, J=7.5 Hz);
4.80 (2H, singlet);
5.71 (2H, singlet);
7.20–7.75 (8H, multiplet).

EXAMPLE 39

2-Butyl-4-hydroxymethyl-1-{4-[2-(tetrazol-5-yl)phenyl]phenyl}methylimidazole-5-carboxylic acid (Compound No. 4-46)

Following a procedure similar to that described in Example 36, but using 0.30 g of methyl 2-butyl-4-hydroxymethyl-1-{4-[2-(tetrazol-5-yl)phenyl]phenyl}methylimidazole-5-carboxylate [prepared as described in Example 38(c)] and 2.50 ml of a 1N aqueous solution of sodium hydroxide, 95 mg of the title compound were obtained as crystals, melting at 215°–217° C.

Nuclear Magnetic Resonance Spectrum (hexadeuterated dimethyl sulfoxide) δ ppm:

0.82 (3H, triplet, J=7.5 Hz);
1.27 (2H, multiplet);
1.52 (2H, multiplet);
2.56 (2H, triplet, J=7.5 Hz);
4.60 (2H, singlet);
5.58 (2H, singlet);
6.94 (2H, doublet, J=8.5 Hz);
7.06 (2H, doublet, J=8.5 Hz);
7.50–7.70 (4H, multiplet).

EXAMPLE 40

Ethyl 4-(1-hydroxyethyl)-2-propyl-1-{4-[2-(tetrazol-5-yl)phenyl]phenyl}methylimidazole-5-carboxylate (Compound No. 4-30).

40(a) Ethyl 4-formyl-1-propyl-1-{4-[2-(trityltetrazol-5-yl)phenyl]phenyl}methylimidazole-5-carboxylate 6 g of activated manganese dioxide were added to a solution of 2 g of ethyl 4-hydroxymethyl-2-propyl-1-{4-[2-(trityltetrazol-5-yl)phenyl]phenyl}methylimidazole-5-carboxylate [prepared as described in Example 35(b)] in 40 ml of methylene chloride, and the resulting mixture was stirred at room temperature for 2.5 hours. At the end of this time, the manganese dioxide was filtered off and the filtrate was concentrated by evaporation under reduced pressure. The resulting residue was purified by column chromatography through silica gel, using a 1:1 by volume mixture of ethyl acetate and hexane as the eluent, to give 1.45 g of the title compound as crystals, melting at 177°–179° C. (with decomposition).

Nuclear Magnetic Resonance Spectrum (CDCl₃) δ ppm:

0.88 (3H, triplet, J=7.5 Hz);
1.29 (3H, triplet, J=7 Hz);
1.74 (2H, sextet, J=7.5 Hz);
2.57 (2H, triplet, J=7.5 Hz);
4.29 (2H, quartet, J=7 Hz);
5.49 (2H, singlet);
6.76 (2H, doublet, J=8.5 Hz);
6.92–7.88 (20H, multiplet);
7.90 (1H, doublet, J=7.5 Hz);
10.42 (1H, singlet).

40(b) Ethyl 4-(1-hydroxyethyl)-2-propyl-1-{4-[2-(trityltetrazol-5-yl)phenyl]phenyl}methylimidazole-5-carboxylate 4.0 ml of a 1M solution of methylmagnesium bromide tetrahydrofuran were added dropwise at −10° C. to a solution of 1.2 g of ethyl 4-formyl-2-propyl-1-{4-[2-(trityltetrazol-5-yl)phenyl]phenyl}methylimidazole-5-carboxylate [prepared as described in step (a) above] in 5 ml of tetrahydrofuran, and the resulting mixture was stirred at a temperature between −10° C. and 0° C. for 3 hours. At the end of this time, the reaction mixture was mixed with ethyl acetate and with an aqueous solution of ammonium chloride, and the mixture was stirred at room temperature for 20 minutes. The ethyl acetate layer was then separated and dried over anhydrous magnesium sulfate. The solvent was removed by distillation under reduced pressure, and the residue was purified by column chromatography through silica gel, using 1:4 and 1:2 by volume mixtures of ethyl acetate and methylene chloride as the eluent, to give 1.23 g of the title compound as a viscous oil.

Nuclear Magnetic Resonance Spectrum (CDCl₃) δ ppm:

0.87 (3H, triplet, J=7.5 Hz);
0.87 (3H, triplet, J=7.5 Hz);
1.22 (3H, triplet, J=7 Hz);
1.54 (3H, doublet, J=7 Hz);
1.68 (2H, sextet, J=7.5 Hz);
2.50 (2H, triplet, J=7.5 Hz);
3.82 (1H, doublet, J=8 Hz);
4.18 (2H, quartet, J=7 Hz);
5.23 (1H, quintet, J=7 Hz);
6.76 (2H, doublet, J=8 Hz);
6.93–7.52 (20H, multiplet);
7.88 (1H, doublet, J=7.5 Hz).

40(c) Ethyl 4-(1-hydroxyethyl)-2-propyl-1-{4-[2-(tetrazol-5-yl)phenyl]phenyl}methylimidazole-5-carboxylate Following a procedure similar to that described in Example 35(c), 1.23 g of ethyl 4-(1-hydroxyethyl)-2-propyl-1-{4-[2-(trityltetrazol-5-yl)phenyl]phenyl}methylimidazole-5-carboxylate [prepared as described in step (b) above] were treated with 75% v/v aqueous acetic acid, to give 0.82 g of the title compound as an amorphous solid.

Nuclear Magnetic Resonance Spectrum (CDCl$_3$) δ ppm:

0.85 (3H, triplet, J=7.5 Hz);
0.85 (3H, triplet, J=7.5 Hz);
1.42 (3H, doublet, J=6 Hz);
1.42 (3H, doublet, J=6 Hz);
1.59 (2H, sextet, J=7.5 Hz);
2.50 (2H, triplet, J=7 Hz);
4.22 (2H, quartet, J=7 Hz);
5.13–5.20 (1H, multiplet);
5.44 (2H, AB-quartet, Δδ=0.12 ppm, J=16.5 Hz);
6.78 (2H, doublet, J=8 Hz);
6.99 (2H, doublet, J=8 Hz);
7.38–7.59 (3H, multiplet);
7.76 (1H, doublet, J=7.5 Hz).

EXAMPLE 41

4-(1-Hydroxyethyl)-2-propyl-1-{4-[2-(tetrazol-5-yl)phenyl]phenyl}methylimidazole-5-carboxylic acid (Compound No. 4-29)

Following a procedure similar to that described in Example 36, 0.82 g of ethyl 4-(1-hydroxyethyl)-2-propyl-1-{4-[2-(tetrazol-5-yl)phenyl]phenyl}methylimidazole-5-carboxylate [prepared as described in Example 40(c)] was hydrolyzed using 0.43 g of lithium hydroxide monohydrate, to give 0.50 g of the title compound as a powder, melting at 198°–201° C.

Nuclear Magnetic Resonance Spectrum (hexadeuterated dimethyl sulfoxide) δ ppm:

0.86 (3H, triplet, J=7.5 Hz);
1.38 (3H, doublet, J=6.5 Hz);
1.55 (2H, sextet, J=7.5 Hz);
2.58 (2H, triplet, J=8 Hz);
5.21 (1H, quartet, J=6.5 Hz);
5.61 (2H, singlet);
6.95–7.08 (4H, multiplet);
7.51–7.70 (4H, multiplet).

EXAMPLE 42

Ethyl 4-(1-hydroxyethyl)-2-propyl-1-{4-[2-tetrazol-5-yl)phenyl]phenyl}methylimidazole-5-carboxylate (Compound No. 4-30)

42(a) Ethyl 4-(1-hydroxyethyl)-2-propyl-1-{4-[2-(trityltetrazol-5-yl)phenyl]phenyl}methylimidazole-5-carboxylate Following a procedure similar to that described in Example 35(a), but using 113 mg of ethyl 4-(1-hydroxyethyl)-2-propylimidazole-5-carboxylate [prepared as described in Preparation 23(iii)], 280 mg of 4-[2-(trityltetrazol-5-yl)phenyl]benzyl bromide and 60 mg of potassium t-butoxide, 255 mg of the title compound were obtained as a viscous oil. The Nuclear Magnetic Resonance Spectrum of this compound was identical with that of the compound obtained as described in Example 40(b).

42(b) Ethyl 4-(1-hydroxyethyl)-2-propyl-1-{4-[2-(tetrazol-5-yl)phenyl]phenyl}methylimidazole-5-carboxylate Following a procedure similar to that described in Example 35(c), 255 mg of ethyl 4-(1-hydroxyethyl)-2-propyl-1-{4-[2-(trityltetrazol-5-yl)phenyl]phenyl}methylimidazole-5-carboxylate [prepared as described in step (a) above] was detrylated by treatment with 75% v/v aqueous acetic acid, to give 170 mg of the title compound as an amorphous solid. The Nuclear Magnetic Resonance Spectrum of this compound was identical with that of the compound obtained as described in Example 40(c).

EXAMPLE 43

Ethyl 2-butyl-4-(1-hydroxyethyl)-1-{4-[2-(tetrazol-5-yl)phenyl]phenyl}methylimidazole-5-carboxylate (Compound N. 4-75)

43(a) Ethyl 2-butyl-4-(1-hydroxyethyl)-1-{4-[2-(tetrazoltetrazol-5-yl)phenyl]phenyl}methylimidazole-5carboxylate Following a procedure similar to that described in Example 35(a), but using 400 mg of ethyl 2-butyl-4-(1-hydroxyethyl)imidazole-5-carboxylate [prepared as described in Preparation 24(iii)], 1.00 g of 4-[2-(trityltetrazol-5-yl)phenyl]benzyl bromide and 197 mg of potassium t-butoxide, 0.94 g of the title compound was obtained as a viscous oil.

Nuclear Magnetic Resonance Spectrum (CDCl$_3$) δ ppm:

0.87 (3H, triplet, J=7.5 Hz);
1.24 (3H, triplet, J=7 Hz);
1.25–1.38 (2H, multiplet);
1.55 (3H, doublet, J=6.5 Hz);
1.60–1.72 (2H, multiplet);
2.54 (2H, triplet, J=8 Hz);
3.84 (1H, doublet, J=6.5 Hz);
4.20 (4H, quartet, J=7 Hz);
5.25 (1H, quintet, J=6.5 Hz);
5.44 (2H, singlet);
6.78 (2H, doublet, J=8 Hz);
6.94–7.54 (20H, multiplet);
7.90 (1H, doublet, J=7.5 Hz).

43(b) Ethyl 2-butyl-4-(1-hydroxyethyl)-1-{4-[2-(tetrazol-5-yl)phenyl]phenyl}methylimidazole-5-carboxylate Following a procedure similar to that described in Example 40(c), 0.84 g of ethyl 2-butyl-4-(1-hydroxyethyl)-1-{4-[2-(trityltetrazol-5-yl)phenyl]phenyl}methylimidazole-5-carboxylate [prepared as described in step (a) above] was treated with 75% v/v aqueous acetic acid, to give 0.54 g of the title compound as an amorphous solid.

Nuclear Magnetic Resonance Spectrum (CDCl$_3$) δ ppm:

0.78 (3H, triplet, J=7.5 Hz);
1.15–1.30 (2H, multiplet);
1.19 (3H, triplet, J=7 Hz)
1.35 (3H, doublet, J=6.5 Hz);
1.44–1.60 (2H, multiplet);
2.49 (2H, triplet, J=8 Hz);
4.17 (2H, quartet, J=7 Hz);
5.09 (1H, quartet, J=6.5 Hz);
5.35 & 5.45 (each 1H, AB-quartet, J=16.5 Hz);
6.89 (2H, doublet, J=8 Hz);
6.96 (2H, doublet, J=8 Hz);

7.30–7.50 (3H, multiplet);
7.65 (1H, doublet, J=7.5 Hz).

EXAMPLE 44

2-Butyl-4-(1-hydroxyethyl)-1-{4-[2-(tetrazol-5-yl)phenyl]phenyl}methylimidazole-5-carboxylic acid (Compound No. 4-74)

Following a procedure similar to that described in Example 36, 0.54 g of ethyl 2-butyl-4-(1-hydroxyethyl)-1-{4-[2-(tetrazol-5-yl)phenyl]phenyl}methylimidazole-5-carboxylate [prepared as described in Example 43(b)] was hydrolyzed, using 245 mg of lithium hydroxide monohydrate, to give 0.43 g of the title compound as a powder, melting at 214°–217° C.

Nuclear Magnetic Resonance Spectrum (hexadeuterated dimethyl sulfoxide) δ ppm:

0.82 (3H, triplet, J=7.5 Hz);
1.27 (2H, sextet, J=7.5 Hz);
1.37 (3H, doublet, J=6.5 Hz);
1.50 (2H, quintet, J=7.5 Hz);
2.58 (2H, triplet, J=8 Hz);
5.20 (1H, quartet, J=6.5 Hz);
5.61 (2H, singlet);
6.96 (2H, doublet, J=8 Hz);
7.06 (2H, doublet, J=8 Hz);
7.50–7.66 (4H, multiplet).

EXAMPLE 45

2-Butyl-1-[(2'-carboxybiphenyl-4-yl)methyl]-4-(1-hydroxyethyl)imidazol-5-carboxamide (Compound No. 5-64)

45(a) 4-Acetyl-1-[(2'-t-butoxycarbonylbiphenyl-4-yl)methyl]-2-butylimidazole-5-carbonitrile 0.192 g of sodium hydride (as a 55% w/w dispersion in mineral oil) was added to a solution of 0.843 g of 4-acetyl-2-butylimidazole-5-carbonitrile [prepared as described in Preparation 24(i)] in 17 ml of N,N-dimethylacetamide, and the resulting mixture was stirred at room temperature for 20 minutes. 1.68 g of t-butyl 4'-(bromomethyl)biphenyl-2-carboxylate was then added, and the resulting mixture was stirred at 55° C. for 2.5 hours. At the end of this time, an aqueous solution of sodium chloride was added to the mixture, which was then extracted with ethyl acetate. The extract was washed with water and dried over anhydrous magnesium sulfate, and then the solvent was removed by distillation under reduced pressure. The resulting oily residue was purified by column chromatography through silica gel, using 4:1 and 2:1 by volume mixtures of hexane and ethyl acetate as the eluent, to afford 1.14 g of the title compound as a viscous oil.

Nuclear Magnetic Resonance Spectrum (CDCl$_3$) δ ppm:

0.93 (3H, triplet, J=7 Hz);
1.23 (9H, singlet);
1.3–2.1 (4H, multiplet);
2.58 (3H, singlet);
2.75 (2H, triplet, J=7 Hz);
5.32 (2H, singlet);
7.0–8.0 (8H, multiplet).

45(b) 1-[(2'-t-Butoxycarbonylbiphenyl-4-yl)methyl]-2-butyl-4-(1-hydroxyethyl)imidazole-5-carbonitrile 0.098 g of sodium borohydride was added to a solution of 1.18 g of 4-acetyl-1-[(2'-t-butoxycarbonylbiphenyl-4-yl)methyl]-2-butylimidazole-5-carbonitrile [prepared as described in step (a) above] in 30 ml of ethanol, and the resulting mixture was stirred at room temperature for 1 hour. The excess sodium borohydride was decomposed by adding acetone, and then the reaction mixture was concentrated by evaporation under reduced pressure. The residue was diluted with an aqueous solution of sodium chloride and extracted with ethyl acetate. The extract was dried and concentrated by evaporation under reduced pressure. The oily residue was purified by column chromatography through silica gel, using a 3:2 by volume mixture of ethyl acetate and hexane as the eluent, to afford 1.18 g of the title compound as a viscous oil.

Nuclear Magnetic Resonance Spectrum (CDCl$_3$) δ ppm:

0.92 (3H, triplet, J=7.5 Hz);
1.25 (9H, singlet);
1.3–1.5 (2H, multiplet);
1.60 (3H, doublet, J=6.5 Hz);
1.6–1.8 (2H, multiplet);
2.6–2.8 (2H, multiplet);
5.00 (1H, quartet, J=6.5 Hz);
5.22 (2H, singlet);
7.1–7.9 (8H, multiplet).

45(c) 1-[(2'-t-Butoxycarbonylbiphenyl-4-yl)methyl]-2-butyl-4-(1-hydroxyethyl)imidazole-5-carboxamide 12 ml of a 1N aqueous solution of sodium hydroxide were added to a solution of 0.52 g of 1-[(2'-t-butoxycarbonylbiphenyl-4-yl)methyl]-2-butyl-4-(1-hydroxyethyl)imidazole-5-carbonitrile [prepared as described in step (b) above] in 3 ml of ethanol, and the resulting mixture was heated under reflux for 3 hours. At the end of this time, the reaction mixture was neutralized by the addition of dilute aqueous hydrochloric acid and extracted with ethyl acetate. The extract was washed with water and dried over anhydrous magnesium sulfate. The solvent was then removed by distillation under reduced pressure. The resulting residue was purified by column chromatography through silica gel, using a 4:1 by volume mixture of ethyl acetate and hexane, followed by ethyl acetate alone, as the eluent, to afford 0.14 g of the title compound as an amorphous solid.

Nuclear Magnetic Resonance Spectrum (CDCl$_3$) δ ppm:

0.90 (3H, triplet, J=7.5 Hz);
1.23 (9H, singlet);
1.2–1.5 (2H, multiplet);
1.6–1.8 (2H, multiplet);
1.66 (3H, doublet, J=6.5 Hz);
2.63 (2H, triplet, J=8 Hz);
5.11 (1H, quartet, J=6.5 Hz);
5.59 & 5.74 (each 1H, AB-quartet, J=16 Hz);
7.0–7.9 (8H, multiplet).

45(d) 2-Butyl-1-[(2'-carboxybiphenyl-4-yl)methyl]-4-(1-hydroxyethyl)imidazole-5-carboxamide A solution of 0.15 g of 1-[(2'-t-butoxycarbonylbiphenyl-4-yl)methyl]-2-butyl-4-(1-hydroxyethyl)imidazole-5-carboxamide [prepared as described in step (c) above] dissolved in 3 ml of a 4N solution of hydrogen chloride in dioxane was allowed to stand overnight at room temperature. The solution was then concentrated by evaporation under reduced pressure. The resulting residue was triturated in hexane and the powder thus obtained was collected by filtration, to afford 0.105 g of the hydrochloride of the title compound as an amorphous solid, melting at 212°–214° C. (with decomposition).

Nuclear Magnetic Resonance Spectrum (CDCl$_3$) δ ppm:

0.94 (3H, triplet, J=7.5 Hz);
1.3–1.6 (2H, multiplet);
1.59 (3H, doublet, J=6.5 Hz);
1.6–2.0 (2H, multiplet);
3.0–3.4 (2H, multiplet)
5.16 (1H, quartet, J=6.5 Hz);
5.41 & 5.58 teach 1H, AB-quartet, J=15 Hz);
7.1–7.9 (8H, multiplet).

EXAMPLE 46

2-Butyl-1-[(2'-carboxybiphenyl-4-yl)methyl]-4-(1-hydroxypropyl)imidazole-5-carboxamide (Compound No. 5-65)

46(a) 1-[(2'-t-Butoxycarbonylbiphenyl-4-yl)methyl]-2-butyl-4-propionylimidazole-5-carbonitrile Following a procedure similar to that described in Example 45(a) but using 0.923 g of 2-butyl-4-propionylimidazole-5-carbonitrile (prepared as described in Preparation 25), 1.56 g of t-butyl 4'-(bromomethyl)biphenyl-2-carboxylate and 196 mg of sodium hydride (as a 55% w/w dispersion in mineral oil) in 20 ml of N,N-dimethylacetamide, 1.84 g of the title compound were obtained as a viscous oil.

Nuclear Magnetic Resonance Spectrum (CDCl$_3$) δ ppm:

0.91 (3H, triplet, J=7 Hz);
1.0–2.1 (4H, multiplet);
1.25 (9H, singlet);
2.72 (2H, triplet, J=7 Hz);
3.02 (2H, quartet, J=7 Hz);
5.30 (2H, singlet);
7.0–8.0 (8H, multiplet).

46(b) 1-[(2'-t-Butoxycarbonylbiphenyl-4-yl)methyl]2-butyl-4-(1-hydroxypropyl)imidazole-5-carbonitrile Following a procedure similar to that described in Example 45(b), but using 451 mg of 1-[(2'-t-butoxycarbonylbiphenyl-4-yl)methyl]-2-butyl-4-propionylimidazole-5-carbonitrile [prepared as described in step (a) above] and 36 mg of sodium borohydride in 10 ml of ethanol, 369 mg of the title compound were obtained as a viscous oil.

Nuclear Magnetic Resonance Spectrum (CDCl$_3$) δ ppm:

0.91 (3H, triplet, J=7 Hz);
0.99 (3H, triplet, J=7 Hz);
1.0–2.3 (6H, multiplet);
1.25 (9H, singlet);
2.70 (2H, triplet, J=7 Hz);
3.16 (1H, doublet, J=6.5 Hz);
4.74 (1H, quartet, J=7 Hz);
5.21 (2H, singlet);
7.0–8.0 (8H, multiplet).

46(c) 1-[(2'-t-Butoxycarbonylbiphenyl-4-yl)methyl]-2-butyl-4-(1-hydroxypropyl)imidazole-5-carboxamide 20 ml of a 1N aqueous solution of sodium hydroxide were added to a solution of 368 mg of 1-[(2'-t-butoxycarbonylbiphenyl-4-yl)methyl]-2-butyl-4-(1-hydroxypropyl)imidazole-5-carbonitrile [prepared as described in step (b) above] dissolved in 20 ml of ethanol, and the resulting mixture was heated under reflux for 6 hours. At the end of this time, the reaction mixture was worked up in a similar manner to that described in Example 45(c), to afford 316 mg of the title compound as an amorphous solid.

Nuclear Magnetic Resonance Spectrum (CDCl$_3$) δ ppm:

0.89 (6H, triplet, J=7 Hz);
1.0–2.3 (6H, multiplet);
1.24 (9H, singlet);
2.61 (2H, triplet, J=7 Hz);
4.76 (1H, triplet, J=7 Hz);
5.52 & 5.83 (each 1H, AB-quartet, J=17 Hz);
6.9–7.9 (8H, multiplet).

46(d) 2-Butyl-1-[(2'-carboxybiphenyl-4-yl)methyl]-4-(1-hydroxypropyl)imidazole-5-carboxamide Following a procedure similar to that described in Example 45(d), but using 316 mg of 1-[(2'-t-butoxycarbonylbiphenyl4-yl)methyl]-2-butyl-4-(1-hydroxypropyl)imidazole-5-carboxamide [prepared as described in step (c) above] and 10 ml of a 4N solution of hydrogen chloride in dioxane, 148 mg of the hydrochloride of the title compound were obtained as an amorphous powder, melting at above 120° C. (with softening).

Nuclear Magnetic Resonance Spectrum (hexadeuterated dimethyl sulfoxide) δ ppm:

0.80 (3H, triplet, J=7.5 Hz);
0.87 (3H, triplet, J=7.5 Hz);
1.1–2.0 (6H, multiplet);
2.94 (2H, triplet, J=7.5 Hz);
4.85 (1H, triplet, J=7 Hz);
5.68 (2H, singlet);
7.0–7.8 (8H, multiplet).

EXAMPLE 47

2-Butyl-1-[(2'-carboxybiphenyl-4-yl)methyl]-4-(1-hydroxybutyl)imidazole-5-carboxamide (Compound No. 5-66)

47(a) 1-[(2'-t-Butoxycarbonylbiphenyl-4-yl)methyl]-2-butyl-4-butyrylimidazole-5-carbonitrile Following a procedure similar to that described in Example 45(a), but using 0.877 g of 2-butyl-4-butyrylimidazole-5-carbonitrile (prepared as described in Preparation 26), 1.53 g of t-butyl 4'-(bromomethyl)biphenyl-2-carboxylate and 0.175 g of sodium hydride (as a 55% w/w dispersion in mineral oil) in 18 ml of N,N-dimethylacetamide, 0.99 g of the title compound was obtained as a viscous oil.

Nuclear Magnetic Resonance Spectrum (CDCl$_3$) δ ppm:

0.93 (3H, triplet, J=7 Hz);
1.01 (3H, triplet, J=7 Hz);
1.28 (9H, singlet);
1.4–2.1 (6H, multiplet);
2.74 (2H, triplet, J=7 Hz);
3.00 (2H, triplet, J=7 Hz);
5.30 (2H, singlet);
7.0–8.0 (8H, multiplet).

47(b) 1-[(2'-t-Butoxycarboxylbiphenyl-4-yl)methyl]-2-butyl-4-(1-hydroxybutyl)imidazole-5-carbonitrile Following a procedure similar to that described in Example 45(b), but using 0.99 g of 1-[(2'-t-butoxycarbonylbiphenyl-4-yl)methyl-2-butyl-4-butyrylimidazole-5-carbonitrile [prepared as described in step (a) above] and 0.077 g of sodium borohydride in 20 ml of ethanol, 0.88 g of the title compound was obtained as a viscous oil.

Nuclear Magnetic Resonance Spectrum (CDCl$_3$) δ ppm:

0.7–1.2 (6H, multiplet);
1.2–2.1 (8H, multiplet);

1.23 (9H, singlet);

2.71 (2H, triplet, J=7 Hz);

4.28 (1H, doublet, J=6 Hz);

4.82 (1H, quartet, J=6 Hz);

5.28 (2H, singlet);

7.0–8.0 (8H, multiplet).

47(c)  1-[(2'-t-Butoxycarbonylbiphenyl-4-yl)methyl]-2-butyl-4-(1-hydroxybutyl)imidazole-5-carboxamide 14 ml of a 1N aqueous solution of sodium hydroxide were added to a solution of 0.86 g of 1-[(2'-t-butoxycarbonylbiphenyl-4-yl)methyl]-2-butyl-4-(1-hydroxybutyl)imidazole-5-carbonitrile [prepared as described in step (b) above] in 14 ml of ethanol, and the resulting mixture was heated under reflux for 10 hours. At the end of this time, the reaction mixture was worked up in a similar manner to that described in Example 45(c) to afford 0.58 g of the title compound as an amorphous solid.

Nuclear Magnetic Resonance Spectrum (CDCl$_3$) δ ppm:

0.90 (3H, triplet, J=7.5 Hz);

0.94 (3H, triplet, J=7.5 Hz);

1.23 (9H, singlet);

1.3–2.1 (8H, multiplet);

2.63 (2H, triplet, J=8 Hz);

4.91 (1H, triplet, J=7 Hz);

5.56 & 5.7q (each 1H, AB-quartet, J=16 Hz);

7.0–7.8 (8H, multiplet).

47(d)  2-Butyl-1-[(2'-carboxybiphenyl-4-yl)methyl]-4-(1-hydroxybutyl)imidazole-5-carboxamide Following a procedure similar to that described in Example 45(d), but using 0.58 g of 1-[(2'-t-butoxycarbonylbiphenyl-4-yl)methyl]-2-butyl-4-(1-hydroxybutyl)imidazole-5-carboxamide [prepared as described in step (c) above] and 13 ml of a 4N solution of hydrogen chloride in dioxane, 0.55 g of the hydrochloride of the title compound was obtained as an amorphous powder, melting at above 110° C. (with softening).

Nuclear Magnetic Resonance Spectrum (hexadeuterated dimethyl sulfoxide) δ ppm:

0.80 (3H, triplet, J=7.5 Hz);

0.89 (3H, triplet, J=7.5 Hz);

1.1–1.9 (8H, multiplet);

2.96 (2H, triplet, J=7.5 Hz);

4.96 (1H, triplet, J=7.5 Hz);

5.68 (2H, singlet);

7.2–7.8 (8H, multiplet).

EXAMPLE 48

2-Butyl-1-[(2'-carboxybiphenyl-4-yl)methyl]-4-(1-hydroxy-2-methylpropyl)imidazole-5-carboxamide
(Compound No. 5-67)

48(a)  1-[(2'-t-butoxycarbonylbiphenyl-4-yl)methyl]-2-butyl-4-isobutyrylimidazole-5-carbonitrile Following a procedure similar to that described in Example 45(a), but using 0.85 g of 2-butyl-4-isobutyrylimidazole-5-carbonitrile (prepared as described in Preparation 27), 1.34 g of t-butyl 4'-(bromomethyl)biphenyl-2-carboxylate and 170 mg of sodium hydride (as a 55% w/w dispersion in mineral oil) in 15 ml of N,N-dimethylacetamide, 1.62 g of the title compound were obtained as a viscous oil.

Nuclear Magnetic Resonance Spectrum (CDCl$_3$) δ ppm:

0.93 (3H, triplet, J=7 Hz);

1.0–2.1 (4H, multiplet);

1.21 (6H, doublet, J=7 Hz);

1.22 (9H, singlet);

2.73 (2H, triplet, J=7 Hz);

3.66 (1H, septet, J=7 Hz);

5.30 (2H, singlet);

7.0–8.0 (8H, multiplet).

48(b)  1-[(2'-t-Butoxycarbonylbiphenyl-4-yl)methyl]-2-butyl-4-(1-hydroxy-2-methylpropyl)imidazole-5-carbonitrile Following a procedure similar to that described in Example 45(b), but using 500 mg of 1-[(2'-t-butoxycarbonylbiphenyl-4-yl)methyl]-2-butyl-4-isobutyrylimidazole-5-carbonitrile [prepared as described in step (a) above] and 25 mg of sodium borohydride in 10 ml of ethanol, 297 mg of the title compound were obtained as a viscous oil.

Nuclear Magnetic Resonance Spectrum (CDCl$_3$) δ ppm:

0.7–1.2 (9H, multiplet).

1.0–2.5 (5H, multiplet);

1.27 (9H, singlet);

2.70 (2H, doublet, J=7 Hz);

3.01 (1H, doublet, J=7 Hz);

4.54 (1H, triplet, J=7 Hz);

5.23 (2H, singlet);

7.0–8.0 (8H, multiplet).

48(c)  1-[(2'-t-Butoxycarbonylbiphenyl-4-yl)methyl]-2-butyl-4-(1-hydroxy-2-methylpropyl)imidazole-5-carboxamide 20 ml of a 1N aqueous solution of sodium hydroxide were added to a solution of 297 mg of 1-[(2'-t-butoxycarbonylbiphenyl-4-yl)methyl]-2-butyl-4-(1-hydroxy-2-methylpropyl)imidazole-5-carbonitrile [prepared as described in step (b) above] in 20 ml of ethanol, and the resulting mixture was heated under reflux for 8 hours. At the end of this time, the reaction mixture was worked up in a similar manner to that described in Example 45(c), to afford 151 mg of the title compound as an amorphous solid.

Nuclear Magnetic Resonance Spectrum (CDCl$_3$) δ ppm:

0.66 (3H, doublet, J=7 Hz);

0.85 (3H, triplet, J=7 Hz);

1.01 (3H, doublet, J=7 Hz);

1.0–2.4 (5H, multiplet);

1.22 (9H, singlet);

2.59 (2H, triplet, J=7 Hz);

4.40 (1H, doublet, J=7 Hz);

5.53 & 5.83 (each 1H, AB-quartet, J=7Hz);

6.9–7.9 (8H, multiplet).

48(d)  2-Butyl-1-[(2'-carboxybiphenyl-4-yl)methyl]-4-(1-hydroxy-2-methylpropyl)imidazole-5-carboxamide Following a procedure similar to that described in Example 45(d), but using 151 mg of 1-[(2'-t-butoxycarbonylbiphenyl-4-yl)methyl]-2-butyl-4-(1-hydroxy-2-methylpropyl)-5-carboxamide [prepared as described in step (c) above] and 5 ml of a 4N solution of hydrogen chloride in dioxane, 119 mg of the hydrochloride of the title compound were obtained as an amorphous powder, melting at above 131° C. (with softening).

Nuclear Magnetic Resonance Spectrum (hexadeuterated dimethyl sulfoxide) δ ppm:

0.73 (3H, doublet, J=6.5 Hz);

0.79 (3H, triplet, J=7.5 Hz);

0.98 (3H, doublet, J=6.5 Hz);

1.1–1.6 (4H, multiplet);

1.9–2.1 (1H, multiplet);

2.98 (2H, triplet, J=7.5 Hz);
4.65 (1H, doublet, J=8 Hz);
5.69 (2H, singlet);
7.1–7.8 (8H, multiplet).

EXAMPLE 49

1-[2'-Carboxybiphenyl-4-yl)methyl]-4-(1-hydroxybutyl)-2-propylimidazole-5-carboxamide (Compound No. 5-4)

49(a) 1-[(2'-t-Butoxycarbonylbiphenyl-4-yl)methyl]-4-butyryl-2-propylimidazole-5-carbonitrile Following a procedure similar to that described in Example 45(a), but using 1.026 g of 4-butyryl-2-propylimidazole-5-carbonitrile (prepared as described in Preparation 28), 1.91 g of t-butyl 4'-(bromomethyl)biphenyl-2-carboxylate and 0.209 g of sodium hydride (as a 55% w/w dispersion in mineral oil) in 20 ml of N,N-dimethylacetamide, 1.70 g of the title compound were obtained as a viscous oil.

Nuclear Magnetic Resonance Spectrum (CDCl$_3$) δ ppm:
1.00 (6H, triplet, J=7.5 Hz);
1.25 (9H, singlet);
1.7–1.9 (4H, multiplet);
2.70 (2H, triplet, J=7.5 Hz);
2.99 (2H, triplet, J=7.5 Hz);
5.31 (2H, singlet);
7.1–7.9 (8H, multiplet).

49(b) 1-[(2'-t-Butoxycarbonylbiphenyl-4-yl)methyl]-4-(1-hydroxybutyl)-2-propylimidazole-5-carbonitrile Following a procedure similar to that described in Example 45(b), but using 1.13 g of 1-[(2'-t-butoxycarbonylbiphenyl-4-yl)methyl]-4-butyryl-2-propylimidazole-5-carbonitrile [prepared as described in step (a) above] and 0.091 g of sodium borohydride in 23 ml of ethanol, 1.07 g of the title compound were obtained as a viscous oil.

Nuclear Magnetic Resonance Spectrum (hexadeuterated dimethyl sulfoxide) δ ppm:
0.87 (3H, triplet, J=7.5 Hz);
0.90 (3H, triplet, J=7.5 Hz);
1.17 (9H, singlet);
1.2–1.4 (2H, multiplet);
1.5–1.7 (4H, multiplet);
2.67 (2H, triplet, J=7.5 Hz);
4.58 (1H, multiplet);
5.34 (2H, singlet);
5.41 (1H, doublet, J=4.5 Hz);
7.1–7.7 (8H, multiplet).

49(c) 1-[(2'-t-Butoxycarbonylbiphenyl-4-yl)methyl]-4-(1-hydroxybutyl)-2-propylimidazole-5-carboxamide 16 ml of a 1N aqueous solution of sodium hydroxide were added to a solution of 1.07 g of 1-[(2'-t-butoxycarbonylbiphenyl-4-yl)methyl]-4-(1-hydroxybutyl)-2-propylimidazole-5-carbonitrile [prepared as described in step (b) above] in 16 ml of ethanol, and the resulting mixture was worked up in a similar manner to that described in Example 45(c), to afford 0.82 g of the title compound as an amorphous solid.

Nuclear Magnetic Resonance Spectrum (CDCl$_3$) δ ppm:
0.93 (3H, triplet, J=7.5 Hz);
0.95 (3H, triplet, J=7.5 Hz);
1.23 (9H, singlet);
1.2–2.1 (6H, multiplet);
2.60 (2H, triplet, J=8 Hz);
4.89 (1H, triplet, J=7.5 Hz);
5.56 & 5.77 (each 1H, AB-quartet, J=16 Hz);
7.0–7.8 (8H, multiplet).

49(d) 1-[(2'-Carboxybiphenyl-4-yl)methyl]-4-(1-hydroxybutyl)-2-propylimidazole-5-carboxamide Following a procedure similar to that described in Example 45(d), but using a solution of 0.82 g of 1-[(2'-t-butoxycarbonylbiphenyl-4-yl)methyl]-4-(1-hydroxybutyl)-2-propylimidazole-5-carboxamide [prepared as described in step (c) above] in 17 ml of a 4N solution of hydrogen chloride in dioxane, 0.78 g of the hydrochloride of the title compound was obtained as an amorphous powder, melting at 118°–121° C. (with softening).

Nuclear Magnetic Resonance Spectrum (CDCl$_3$) δ ppm:
0.90 (3H, triplet, J=7.5 Hz);
0.93 (3H, triplet, J=7.5 Hz);
1.1–1.5 (2H, multiplet);
1.7–2.1 (4H, multiplet);
2.9–3.1 (2H, multiplet);
5.00 (1H, triplet, J=7.5 Hz);
5.46 & 5.56 (each 1H, AB-quartet, J=15.5 Hz);
7.1–7.9 (89H, multiplet).

EXAMPLE 50

2-Butyl-1-[(2'-carboxybiphenyl-4-yl)methyl]-4-(1-hydroxy-1-methylethyl)imidazole-5-carboxamide (compound No. 5-69)

50(a) 1-[(2'-t-Butoxycarbonylbiphenyl-4-yl)methyl]-2-butyl-4-(1-hydroxy-1-methylethyl)imidazole-5-carboxamide 10 ml of a 1N aqueous solution of sodium hydroxide were added to a solution of 232 mg of 1-[(2'-t-butoxycarbonylbiphenyl-4-yl)methyl]-2-butyl-4-(1-hydroxy-1-methylethyl)imidazole-5-carbonitrile [prepared as described in Example 10(a)] in 10 ml of ethanol, and the resulting mixture was heated under reflux for 3 hours. At the end of this time, the reaction mixture was worked up in a similar manner to that described in Example 45(c), to afford 185 mg of the title compound as an amorphous solid.

Nuclear Magnetic Resonance Spectrum (CDCl$_3$) δ ppm:
0.89 (3H, triplet, J=7 Hz);
1.0–2.0 (4H, multiplet);
1.23 (9H, singlet);
1.68 (6H, singlet);
2.62 (2H, triplet, J=7 Hz);
5.63 (2H, singlet);
6.9–7.9 (8H, multiplet).

50(b) 2-Butyl-1-[(2'-carboxybiphenyl-4-yl)methyl]-4-(1-hydroxy-1-methylethyl)imidazole-5-carboxamide Following a procedure similar to that describe in Example 45(d), but using 185 mg of 1-[(2'-t-butoxycarbonylbiphenyl-4-yl)methyl]-2-butyl-4-(1-hydroxy-1-methylethyl)imidazole-5-carboxamide [prepared as described in step (a) above] and 10 ml of a 4N solution of hydrogen chloride in dioxane, 88 mg of the hydrochloride of the title compound were obtained as an amorphous solid, melting at 130°–138° C. (with softening).

Nuclear Magnetic Resonance Spectrum (hexadeuterated dimethyl sulfoxide) δ ppm:
0.78 (3H, triplet, J=7 Hz);

1.17–1.30 (2H, multiplet);
1.30–1.42 (2H, multiplet);
1.61 (6H, singlet);
2.96 (2H, triplet, J=7.5 Hz);
5.55 (2H, singlet);
7.20–7.75 (8H, multiplet).

EXAMPLE 51

2-Butyl-1-[(2'-carboxybiphenyl-4-yl)methyl]-4-[1-hydroxy-2-methyl-1-(1-methylethyl)propyl]imidazole-5-carboxamide (Compound No. 5-333)

51(a) 1-[(2'-t-Butoxycarbonylbiphenyl-4-yl)methyl]-2-butyl-4-(1-hydroxy-2-methyl-1-(1-methylethyl)propyl]imidazole-5-carbonitrile Following a procedure similar to that described in Example 45(a), but using 282 mg of 2-butyl-4-[1-hydroxy-2-methyl-1-(1-methylethyl)propyl]imidazole-5-carbonitrile (prepared as described in Preparation 30), 409 mg of t-butyl 4'-(bromomethyl)biphenyl-2-carboxylate and 47 mg of sodium hydride (as a 55% w/w dispersion in mineral oil) in 5 ml of N,N-dimethylacetamide, 513 mg of the title compound were obtained as a viscous oil.

Nuclear Magnetic Resonance Spectrum (CDCl$_3$) δ ppm:
0.7–1.1 (15H, multiplet);
1.0–2.0 (4H, multiplet);
1.21 (9H, singlet);
2.15–2.60 (2H, multiplet);
2.68 (2H, triplet, J=7 Hz);
3.20 (1H, singlet);
5.26 (2H, singlet);
6.9–8.0 (8H, multiplet).

51(b) 1-[(2'-t-Butoxycarbonylbiphenyl-4-yl)methyl]-2-butyl-4-[1-hydroxy-2-methyl-1-(1-methylethyl)propyl]imidazole-5-carboxamide 10 ml of a 1N aqueous solution of sodium hydroxide were added to a solution of 500 mg of 1-[(2'-t-butoxycarbonylbiphenyl-4-yl)methyl]-2-butyl-4-[1-hydroxy-2-methyl-1-(1-methylethyl)propyl]imidazole-5-carbonitrile [prepared as described in step (a) above] in 10 ml of ethanol, and the resulting mixture was heated under reflux for 20 hours. At the end of this time, the reaction mixture was worked up in a similar manner to that described in Example 45(c), to give 220 mg of the title compound as an amorphous solid.

Nuclear Magnetic Resonance Spectrum (CDCl$_3$) δ ppm:
0.7–1.1 (15H, multiplet);
1.0–2.1 (4H, multiplet);
1.20 (9H, singlet);
2.2–2.9 (4H, multiplet);
5.59 (2H, singlet);
6.8–7.9 (8H, multiplet).

51(c) 2-Butyl-1-[(2'-carboxybiphenyl-4-yl)methyl]-4-[1-hydroxy-2-methyl-1-(1-methylethyl)propyl]imidazole-5-carboxamide Following a procedure similar to that described in Example 45(d), but using 220 mg of 1-[(2'-t-butoxycarbonylbiphenyl-4-yl)methyl]-2-butyl-4-[1-hydroxy-2-methyl-1-(1-methylethyl)propyl]imidazole-5-carboxamide [prepared as described in step (b) above] and 4.5 ml of a 4N solution of hydrogen chloride in dioxane, 201 mg of the hydrochloride of the title compound were obtained as an amorphous solid, melting at 178°–181° C.

Nuclear Magnetic Resonance Spectrum (hexadeuterated dimethyl sulfoxide) δ ppm:
0.76 (3H, triplet, J=7.5 Hz);
0.8–0.9 (12H, multiplet);
1.1–1.4 (4H, multiplet);
2.2–2.4 (2H, multiplet);
2.8–3.1 (2H, multiplet);
5.51 (2H, singlet);
7.2–7.8 (8H, multiplet).

EXAMPLE 52

2-Butyl-1-[(2'-carboxybiphenyl-4-yl)methyl]-4-hydroxymethylimidazole-5-carboxamide (Compound No. 5-63)

52(a) Succinimido 1-[(2'-t-butoxycarbonylbiphenyl-4-yl)methyl]-2-butyl-4-hydroxymethylimidazole-5-carboxylate 206 mg of N,N-dicyclohexylcarbodiimide were added to a suspension of 464 mg of 1-[(2'-t-butoxycarbonylbiphenyl-4-yl)methyl]-2-butyl-4-hydroxymethylimidazole-5-carboxylic acid (prepared as described in Example 4) and 140 mg of N-hydroxysuccinimide in 10 ml of tetrahydrofuran, and the resulting mixture was stirred at room temperature for 16 hours. At the end of this time, the material which had precipitated was filtered off and the filtrate was concentrated by evaporation under reduced pressure. The concentrate was purified by column chromatography through silica gel, using a 1:15 by volume mixture of methanol and methylene chloride as the eluent, to afford 0.52 g of the title compound as crystals, melting at 107°–109° C.

Nuclear Magnetic Resonance Spectrum (CDCl$_3$) δ ppm:
0.89 (3H, triplet, J=7 Hz);
1.0–2.0 (4H, multiplet);
1.23 (9H, singlet);
2.70 (2H, triplet, J=7.5 Hz);
2.69 (4H, singlet);
4.10 (1H, broad singlet);
4.96 (2H, singlet);
5.56 (2H, singlet);
7.00–7.90 (8H, multiplet).

52(b) 1-[(2'-t-Butoxycarbonylbiphenyl-4-yl)methyl]-2-butyl-4-hydroxymethylimidazole-5-carboxamide 0.5 ml of concentrated aqueous ammonia was added to a solution of 0.60 g of succinimido 1-[(2'-t-butoxycarbonylbiphenyl-4-yl)methyl]-2-butyl-4-hydroxymethylimidazole-5-carboxylate [prepared as described in step (a) above] in 6 ml of tetrahydrofuran, and the title compound started to separate immediately. The solvent was removed by distillation under reduced pressure, and the resulting residue was washed with diethyl ether and with water, to afford 0.38 g of the title compound as a powder, melting at 222°–224° C.

Nuclear Magnetic Resonance Spectrum (hexadeuterated dimethyl sulfoxide) δ ppm:
0.85 (3H, triplet, J=7 Hz);
1.19 (9H, singlet);
1.0–1.9 (4H, multiplet);
2.57 (2H, triplet, J=7.5 Hz);
4.52 (2H, doublet, J=4.5 Hz);
5.63 (2H, singlet);
5.83 (1H, triplet, J=4.5 Hz);
6.95–7.8 (8H, multiplet);

52(c) 2-Butyl-1-[(2'-carboxybiphenyl-4-yl)methyl]-4-hydroxymethylimidazole-5-carboxamide A solution of 0.28 g of 1-[(2'-t-butoxycarbonylbiphenyl-4-yl)methyl]-2-butyl-4-hydroxymethylimidazole-5-carboxamide [prepared as described in step (b) above] in 3 ml of a 4N solution of hydrogen chloride in dioxane was stirred at room temperature for 5 hours and then concentrated by evaporation under reduced pressure. The concentrate was triturated with a mixture of ethyl acetate and diethyl ether, and the solidified material was collected by filtration, to afford 0.26 g of the hydrochloride of the title compound, which softened at above 150° C. and completely decomposed at 235° C.

Nuclear Magnetic Resonance Spectrum (hexadeuterated dimethyl sulfoxide) δ ppm:

0.80 (3H, triplet, J=7.5 Hz);
1.20–1.31 (2H, multiplet);
1.43–1.54 (2H, multiplet);
2.96 (3H, triplet, J=7.5 Hz);
4.68 (2H, singlet);
5.71 (2H, singlet);
7.21–7.75 (8H, multiplet).

EXAMPLE 53

N-Methyl-2-butyl-1-[(2'-carboxybiphenyl-4-yl)methyl]-4-hydroxymethylimidazole-5-carboxamide (Compound No. 5-71)

53(a) N-methyl-1-[(2'-t-butoxycarbonylbiphenyl-4-yl)methyl]-2-butyl-4-hydroxymethylimidazole-5-carboxamide 0.4 ml of a 40% by volume solution of methylamine in water was added at room temperature to a solution of 0.278 g of succinimido 1-[(2'-t-butoxycarbonylbiphenyl-4-yl)methyl]-2-butyl-4-hydroxymethylimidazole-5-carboxylate [prepared as described in Example 52(a)] in a mixture of 3 ml of methylene chloride and 2 ml of methanol, and the resulting mixture was allowed to stand for 16 hours at room temperature. At the end of this time, the solution was concentrated by evaporation under reduced pressure, and the concentrate was dissolved in ethyl acetate. The resulting solution was washed with an aqueous solution of potassium bisulfate and with an aqueous solution of sodium hydrogencarbonate, in that order, after which it was dried over anhydrous magnesium sulfate. The solvent was then removed by distillation under reduced pressure, and the resulting residue was purified by column chromatography through silica gel, using ethyl acetate as the eluent, to give 176 mg of the title compound as a glass.

Nuclear Magnetic Resonance Spectrum (CDCl₃) δ ppm:

0.85 (3H, triplet, J=7 Hz);
1.23 (9H, singlet);
1.0–2.0 (4H, multiplet);
2.54 (2H, triplet, J=7.5 Hz);
2.91 (3H, doublet, J=5 Hz);
4.70 (2H, singlet);
5.62 (2H, singlet);
6.9–7.85 (8H, multiplet);
8.38 (1H, quartet, J=5 Hz).

53(b) N-Methyl-2-butyl-1-[(2'-carboxybiphenyl-4-yl)methyl]-4-hydroxymethylimidazole-5-carboxamide A solution of N-methyl-1-[(2'-t-butoxycarbonylbiphenyl-4-yl)methyl]-2-butyl-4-hydroxymethylimidazole-5-carboxamide [prepared as described in step (a) above] in 2 ml of a 4N solution of hydrogen chloride in hours and then concentrated by evaporation under reduced pressure. The resulting crystalline residue was washed with a mixture of ethyl acetate and diethyl ether, to afford 0.15 g of the hydrochloride of the title compound, melting at 205°–208° C. (with decomposition).

Nuclear Magnetic Resonance Spectrum (hexadeuterated 0.81 (3H, triplet, J=7.5 Hz);
1.25 (2H, sextet, J=7.5 Hz);
1.49 (2H, quintet, J=7.5 Hz);
2.75 (3H, doublet, J=4.5 Hz);
2.96 (2H, triplet, J=8 Hz);
5.64 (2H, singlet);
7.21–7.75 (8H, multiplet);
8.91 (1H, quartet, J=4.5 Hz).

EXAMPLE 54

N-Ethoxycarbonylmethyl-2-butyl-1-[(2'-carboxybiphenyl-4-yl)methyl]-4-hydroxymethylimidazole-5-carboxamide (Compound No. 5-126)

Following a procedure similar to that described in Example 53, but using 0.307 g of succinimido 1-[(2'-t-butoxycarbonylbiphenyl-4-yl)methyl]-2-butyl-4-hydroxymethylimidazole-5-carboxylate [prepared as described in Example 52(a)], 89 mg of ethyl glycinate hydrochloride and 0.089 ml of triethylamine, 0.202 g of the Nuclear Magnetic Resonance Spectrum (hexadeuterated dimethyl sulfoxide) δ ppm:

0.80 (3H, triplet, J=7.5 Hz);
1.18 (3H, triplet, J=7 Hz);
1.20–1.33 (2H, multiplet);
1.47 (2H, quintet, J=7.5 Hz);
2.94 (2H, triplet, J=8 Hz);
4.05 (2H, doublet, J=6 Hz);
4.12 (2H, quartet, J=7 Hz);
4.72 (2H, singlet);
5.63 (2H, singlet);
7.24–7.75 (8H, multiplet);
9.37 (1H, triplet, J=6 Hz).

EXAMPLE 55

N-Carboxymethyl-2-butyl-1-[(2'-carboxybiphenyl-4-yl)methyl]-4-hydroxymethylimidazole-5-carboxamide (Compound No. 5-125)

Following a procedure similar to that described in Example 53, but using 0.32 g of succinimido 1-[(2'-t-butoxycarbonylbiphenyl-4-yl)methyl]-2-butyl-4-hydroxymethylimidazole-5-carboxylate [prepared as described in Example 52(a)], 0.11 g of t-butyl glycinate hydrochloride and 80 mg of 4-dimethylaminopyridine, 0.21 g of the hydrochloride of the title compound was obtained as an amorphous powder melting at above 110° C. (with softening).

Nuclear Magnetic Resonance Spectrum (hexadeuterated dimethyl sulfoxide) δ ppm:

0.81 (3H, triplet, J=7.5 Hz);
1.25 (2H, sextet, J=7.5 Hz);
1.48 (2H, quintet, J=7.5 Hz);
2.95 (2H, triplet, J=8 Hz);

3.98 (2H, doublet, J=6 Hz);
4.71 (2H, singlet);
5.64 (2H, singlet);
7.26–7.75 (8H, multiplet);
9.22 (1H, triplet, J=6 Hz).

EXAMPLE 56

N-[(S)-1-Ethoxycarbonylethyl]-2-butyl-1-[(2'-carboxybiphenyl-4-yl)methyl]-4-hydroxymethylimidazole-5-carboxamide (Compound No. 5-128)

Following a procedure similar to that described in Example 53, but using 0.39 g of succinimido 1-[(2'-t-butoxycarbonylbiphenyl-4-yl)methyl]-2-butyl-4-hydroxymethylimidazole-5-carboxylate [prepared as described in Example 52(a)], 0.13 g of ethyl (S)-alanate hydrochloride and 0.21 ml of triethylamine, 0.27 g of the hydrochloride of the title compound was obtained as an amorphous solid.

Nuclear Magnetic Resonance Spectrum (hexadeuterated dimethyl sulfoxide) δ ppm:

0.82 (3H, triplet, J=7.5 Hz);
1.17 (3H, triplet, J=7 Hz);
1.20–1.35 (2H, multiplet);
1.34 (3H, doublet, J=7 Hz);
1.43–1.58 (2H, multiplet);
2.98 (2H, triplet, J=7.5 Hz);
4.10 (2H, quartet, J=7 Hz);
4.44 (1H, quintet, J=7 Hz);
4.70 (2H, singlet);
5.63 (2H, AB-quartet, Δδ=0.10 ppm, J=16 Hz);
7.24–7.76 (8H, multiplet);
9.39 (1H, doublet, J=7.5 Hz);

EXAMPLE 57

N-(2-Ethoxycarbonylethyl)-2-butyl-1-[(2'-carboxybiphenyl-4-yl)methyl]-4-hydroxymethylimidazole-5-carboxamide (Compound No. 5-130)

Following a procedure similar to that described in Example 53, but using 305 mg of succinimido 1-[(2'-t-butoxycarbonylbiphenyl-4-yl)methyl]-2-butyl-4-hydroxymethylimidazole-5-carboxylate [prepared as described in Example 52(a)], 96 mg of ethyl β-alanate hydrochloride and 0.088 ml of triethylamine, 0.20 g of the hydrochloride of the title compound was obtained as an amorphous solid.

Nuclear Magnetic Resonance Spectrum (hexadeuterated dimethyl sulfoxide) δ ppm:

0.82 (3H, triplet, J=7.5 Hz);
1.16 (3H, triplet, J=7 Hz);
1.20–1.38 (2H, multiplet);
1.42–1.58 (2H, multiplet);
2.97 (2H, triplet, J=7.5 Hz);
3.3–3.6 (4H, multiplet);
4.04 (2H, quartet, J=7 Hz);
4.60 (2H, singlet);
5.63 (2H, singlet);
7.21–7.76 (8H, multiplet);
9.01 (1H, broad triplet).

EXAMPLE 58

Methyl (S)-N-{2-butyl-1-[(2'-carboxybiphenyl-4-yl)methyl]-4-hydroxymethylimidazole-5-carbonyl}prolinate (Compound No. 5-335)

Following a procedure similar to that described in Example 53, but using 529 mg of succinimido 1-[(2'-t-butoxycarbonylbiphenyl-4-yl)methyl]-2-butyl-4-hydroxymethylimidazole-5-carboxylate [prepared as described in Example 52(a)], 180 mg of methyl (S)-prolinate hydrochloride and 0.2 ml of triethylamine, 0.39 g of the hydrochloride of the title compound was obtained as an amorphous powder, melting at above 120° C. (with softening).

Nuclear Magnetic Resonance Spectrum (hexadeuterated dimethyl sulfoxide) δ ppm:

0.88 (3H, triplet, J=7.5 Hz);
1.34 (2H, sextet, J=7.5 Hz);
1.4–2.25 (6H, multiplet);
2.9–3.7 (2H, multiplet);
3.64 (3H, singlet);
4.34 (1H, triplet, J=7.5 Hz);
4.55 (2H, singlet);
5.25 & 5.56 (each 1H, AB-quartet, J=15.5 Hz);
7.26–7.77 (8H, multiplet).

EXAMPLE 59

2-Butyl-1-[(2'-carboxybiphenyl-4-yl)methyl]-4-(1-hydroxy-2,2-dimethylpropyl)imidazole-5-carboxamide (Compound No. 5-68)

59(a) Methyl-[(2'-t-butoxycarbonylbiphenyl-4-yl)methyl]- 2-butyl-4-formylimidazole-5-carboxylate 5.07 ml of triethylamine and 6.0 g of sulfur trioxide/pyridine complex were added, in turn, at a temperature of 10° C. to 15° C. to a solution of 3.0 g of methyl 1-[(2'-t-butoxycarbonylbiphenyl-4-yl)methyl]-2-butyl-4-hydroxymethylimidazole-4-carboxylate [prepared as described in Example 1(b)] in 18 ml of dimethyl sulfoxide, and the resulting mixture was stirred at the same temperature for 45 minutes. At the end of this time, the reaction mixture was mixed with water and extracted with ethyl acetate. The extract was washed with water and with an aqueous solution of sodium hydrogencarbonate, in that order, after which it was dried over anhydrous magnesium sulfate, and the solvent was removed by distillation under reduced pressure. The resulting residue was purified by column chromatography through silica gel, using a 1:1 by volume mixture of hexane and ethyl acetate as the eluent, to afford 2.88 g of the title compound as an amorphous solid.

Nuclear Magnetic Resonance Spectrum (CDCl$_3$) δ ppm:

0.90 (3H, triplet, J=7 Hz);
1.25 (9H, singlet);
1.1–2.1 (4H, multiplet);
2.77 (2H, triplet, J=8 Hz);
3.91 (3H, singlet)
5.65 (2H, singlet);
6.9–7.9 (8H, multiplet);
10.48 (1H, singlet).

59(b) Methyl 1-[(2'-t-butoxycarbonylbiphenyl-4-yl)methyl]- 2-butyl-4-(1-hydroxy-2,2,dimethylpropyl)imidazole-5-carboxylate 2.77 ml of a 2M solution of t-butylmagnesium bromide in tetrahydrofuran were added at −55° C. and under an atmosphere of nitrogen to a solution of 1.32 g of methyl 1-[(2'-t-butoxycarbonylbiphenyl-4-yl)methyl]-2-butyl-4-formylimidazole-5-carboxylate [prepared as described in step (a) above] in 26 ml of tetrahydrofuran, and the resulting mixture was stirred at a temperature of −55° C. to −50° C. for 30 minutes. At the end of this time, the reaction mixture was diluted with 50 ml of ethyl acetate and with a saturated aqueous solution of ammonium chloride. The organic layer was separated and dried over anhydrous magnesium sulfate and the solvent was removed by distillation under reduced pressure. The residue was purified by column chromatography through silica gel, using a 2:1 by volume mixture of hexane and ethyl acetate as the eluent, to afford 0.87 g of the title compound as an amorphous solid.

Nuclear Magnetic Resonance Spectrum (CDCl$_3$) δ ppm:
0.90 (3H, triplet, J=7.5 Hz);
0.93 (9H, singlet);
1.0–2.0 (4H, multiplet);
1.19 (9H, singlet);
2.68 (2H, triplet, J=7.5 Hz);
3.41 (1H, doublet, J=10 Hz);
3.74 (3H, singlet);
4.92 (1H, doublet, J=10 Hz);
5.59 (2H, singlet);
6.9–7.9 (8H, multiplet).

59(c) 1-[(2'-t-Butorycarbonylbiphenyl-4-yl)methyl]-2-butyl-4-(1-hydroxy-2,2-dimethylpropyl)imidazole-5-carboxylic acid Following a procedure similar to that described in Example 4, 0.87 g of methyl 1-[(2'-t-butoxycarbonylbiphenyl-4-yl)methyl]-2-butyl-4-(1-hydroxy-2,2-dimethylpropyl)imidazole-5-carboxylate [prepared as described in step (b) above] was hydrolyzed, using 342 mg of lithium hydroxide monohydrate, to afford 0.73 g of the title compound as crystals, melting at 199°–201° C. (with decomposition).

Nuclear Magnetic Resonance Spectrum (hexadeuterated dimethyl sulfoxide) δ ppm:
0.84 (3H, triplet, J=7.5 Hz);
0.89 (9H, singlet);
1.16 (9H, singlet);
1.22–1.4 (2H, multiplet);
1.58 (2H, quintet, J=7.5 Hz);
2.64 (2H, triplet, J=7.5 Hz);
4.78 (1H, singlet);
5.68 (2H, AB-quartet, Δδ=0.14 ppm, J=17 Hz);
7.02 (2H, doublet, J=8 Hz);
7.22–7.58 (5H, multiplet);
7.65 (1H, doublet, J=7.5 Hz);

59(d) Succinimido 1-[(2'-t-butoxycarbonylbiphenyl-4-yl)methyl]-2-butyl-4-(1-hydroxy-2,2-dimethylpropyl)imidazole-5-carboxylate Following a procedure similar to that described in Example 52(a), but using 600 mg of 1-[(2'-t-butoxycarbonylbiphenyl-4-yl)methyl]-2-butyl-4-(1-hydroxy-2,2-dimethylpropyl)imidazole-5-carboxylic acid [prepared as described in step (c) above], 172 mg of N-hydroxysuccinimide and 250 mg of N,N-dicyclohexylcarbodiimide, 663 mg of the title compound were obtained as an amorphous solid.

Nuclear Magnetic Resonance Spectrum (CDCl$_3$) δ ppm:
0.92 (3H, triplet, J=7.5 Hz);
1.01 (9H, singlet);
1.21 (9H, singlet);
1.38 (2H, sextet, J=7.5 Hz);
1.73 (2H, quintet, J=7.5 Hz);
2.71 (2H, triplet, J=7.5 Hz);
2.84 (4H, singlet);
4.99 (1H, doublet, J=7.5 Hz);
5.53 (2H, singlet);
7.03 (2H, doublet, J=8.5 Hz);
7.26–7.50 (5H, multiplet);
7.77 (1H, doublet, J=8 Hz).

59(e) 1-[(2'-t-Butoxycarbonylbiphenyl-4-yl)methyl]-2-butyl-4-(1-hydroxy-2,2-dimethylpropyl)imidazole-5-carboxamide Following a procedure similar to that described in Example 52(b), but using 0.66 g of succinimido 1-[(2'-t-butoxycarbonylbiphenyl-4-yl)methyl]-2-butyl-4-(1-hydroxy-2,2-dimethylpropyl)imidazole-5-carboxylate [prepared as described in step (d) above], 0.33 g of the title compound was obtained as an amorphous solid.

Nuclear Magnetic Resonance Spectrum (CDCl$_3$) δ ppm:
0.89 (3H, triplet, J=7.5 Hz);
0.96 (9H, singlet);
1.22 (9H, singlet);
1.34 (2H, sextet, J=7.5 Hz);
1.64 (2H, quintet, J=7.5 Hz);
2.62 (2H, triplet, J=7.5 Hz);
4.67 (1H, doublet, J=5.5 Hz);
5.48 & 5.82 (each 1H, AB-quartet, J=16 Hz);
7.02 (2H, doublet, J=8.5 Hz);
7.23–7.50 (5H, multiplet);
7.76 (1H, doublet, J=6.5 Hz);

59(f) 2-Butyl-1-[(2'-carboxybiphenyl-4-yl)methyl]-4-(1-hydroxy-2,2-dimethylpropyl)imidazole-5-carboxamide Following a procedure similar to that described in Example 52(c), but using 326 mg of 1-[(2'-t-butoxycarbonylbiphenyl-4-yl)methyl]-2-butyl-4-(1-hydroxy-2,2-dimethylpropyl)imidazole-5-carboxamide [prepared as described in step (e) above], 228 mg of the hydrochloride of the title compound were obtained as a powdery solid, melting at 150°–154° C. (with softening).

Nuclear Magnetic Resonance Spectrum (hexadeuterated dimethyl sulfoxide) δ ppm:
0.80 (3H, triplet, J=7.5 Hz);
0.91 (9H, singlet);
1.24 (2H, sextet, J=7.5 Hz);
1.45 (2H, quintet, J=7.5 Hz);
2.99 (2H, triplet, J=7.5 Hz);
4.78 (1H, singlet);
5.69 (2H, singlet);
7.21 (2H, doublet, J=8 Hz);
7.33–7.61 (5H, multiplet);
7.75 (1H, doublet, J=8 Hz).

EXAMPLE 60

1-[(2'-Carboxybiphenyl-4-yl)methyl]-4-(1-hydroxy-2,2-dimethylpropyl)-2-propylimidazole-5-carboxamide (Compound No. 5-6)

60(a) Diethyl 1-[(2'-t-butoxycarbonylbiphenyl-4-yl)methyl]-2-propylimidazole-4,5-dicarboxylate Following a procedure similar to that described in Example 1(a), but using 9.0 g of diethyl 2-propylimidazole-4,5-dicarboxylate (prepared as described in Preparation 12), 12.3 g of t-butyl 4'-bromomethylbiphenyl-2-carboxylate and 4.1 g of potassium t-butoxide as a base, 16.47 g of the title compound were obtained as a viscous oil.

Nuclear Magnetic Resonance Spectrum (CDCl$_3$) δ ppm:
0.95 (3H, triplet, J=7.5 Hz);
1.5–2.0 (2H, multiplet);
1.23 (9H, singlet);
1.25 (3H, triplet, J=7 Hz);
1.37 (3H, triplet, J=7 Hz);
2.69 (2H, triplet, J=7 Hz);
4.26 (2H, quartet, J=7 Hz);
4.38 (2H, quartet, J=7 Hz);
5.38 (2H, singlet);
7.0–7.9 (8H, multiplet);

60(b) Ethyl 1-[(2'-t-butoxycarbonylbiphenyl-4-yl)methyl]-4-hydroxymethyl-2-propylimidazole-5-carboxylate Following a procedure similar to that described in Example 1(b), 16.47 g of diethyl 1-[(2'-t-butoxycarbonylbiphenyl-4-yl)methyl]-2-propylimidazole-4,5-dicarboxylate [prepared as described in step (a) above] were reduced, using 44.4 ml of a 1.5M solution of diisobutylaluminum hydride in tetrahydrofuran, to afford 10.83 g of the title compound as crystals, melting at 108°–110° C.

Nuclear Magnetic Resonance Spectrum (CDCl$_3$) δ ppm:
0.98 (3H, triplet, J=7.5 Hz);
1.23 (9H, singlet);
1.31 (3H, triplet, J=7 Hz);
1.79 (2H, sextet, J=7.5 Hz);
2.67 (2H, triplet, J=7.5 Hz);
4.27 (2H, quartet, J=7 Hz);
4.87 (2H, singlet);
5.59 (2H, singlet);
7.00 (2H, doublet, J=8.5 Hz);
7.24–7.75 (5H, multiplet);
7.78 (1H, doublet, J=7 Hz).

60(c) Ethyl 1-[(2'-t-butoxycarbonylbiphenyl-4-yl)methyl]-4-formyl-2-propylimidazole-5-carboxylate Following a procedure similar to that described in Example 59(a), 2.71 g of ethyl 1-[(2'-t-butoxycarbonylbiphenyl-4-yl)methyl]-4-hydroxymethyl-1-propylimidazole-5-carboxylate [prepared as described in step (b) above] were oxidized with 4.6 ml of triethylamine and 5.5 g of sulfur trioxide/pyridine complex in 17 ml of dimethyl sulfoxide, to afford 2.57 g of the title compound as crystals, melting at 117°–119° C.

Nuclear Magnetic Resonance Spectrum (CDCl$_3$) δ ppm:
0.99 (3H, triplet, J=7.5 Hz);
1.26 (9H, singlet);
1.38 (3H, triplet, J=7 Hz);
1.84 (2H, sextet, J=7.5 Hz);
2.73 (2H, triplet, J=7.5 Hz);
4.40 (2H, quartet, J=7 Hz);
5.67 (2H, singlet);
7.02 (2H, doublet, J=8.5 Hz);
7.29–7.54 (5H, multiplet);
7.80 (1H, doublet, J=8 Hz);
10.48 (1H, singlet);

60(d) Ethyl 1-[(2'-t-butoxycarbonylbiphenyl-4-yl)methyl]-4-(1-hydroxy-2,2-dimethylpropyl)-2-propylimidazole-5-carboxylate Following a procedure similar to that described in Example 59(b), 1.14 g of ethyl 1-[(2'-t-butoxycarbonylbiphenyl-4-yl)methyl]-4-formyl-2-propylimidazole-5-carboxylate [prepared as described in step (c) above] was reacted with 2.4 ml of a 2M solution of t-butylmagnesium bromide in tetrahydrofuran, to afford 0.78 g of the title compound as a viscous oil.

Nuclear Magnetic Resonance Spectrum (CDCl$_3$) δ ppm:
0.97 (3H, triplet, J=7.5 Hz);
1.00 (9H, singlet);
1.25 (9H, singlet);
1.35 (3H, triplet, J=7 Hz);
1.77 (2H, sextet, J=7.5 Hz);
2.68 (2H, triplet, J=7.5 Hz);
3.46 (1H, doublet, J=9 Hz);
4.29 (2H, quartet, J=7 Hz);
4.99 (1H, doublet, J=9 Hz);
5.62 (2H, singlet);
7.00 (2H, doublet, J=8 Hz);
7.29–7.54 (5H, multiplet);
7.80 (1H, doublet, J=7.5 Hz).

60(e) 1-[(2'-t-Butoxycarbonylbiphenyl-4-yl)methyl]-4-(1-hydroxy-2,2-dimethylpropyl)-2-propylimidazole-5-carboxylic acid Following a procedure similar to that described in Example 4, 0.78 g of ethyl 1-[(2'-t-butoxycarbonylbiphenyl-1-4-yl)methyl]-4-(1-hydroxy-2,2-dimethylpropyl)-2-propylimidazole-5-carboxylate [prepared as described in step (d) above] was hydrolyzed, using 209 mg of lithium hydroxide monohydrate to afford 0.62 g of the title compound as crystals, melting at 207° C.

Nuclear Magnetic Resonance Spectrum (hexadeuterated dimethyl sulfoxide) δ ppm:
0.88 (3H, triplet, J=7.5 Hz);
0.89 (9H, singlet);
1.15 (9H, singlet);
1.63 (2H, sextet, J=7.5 Hz);
2.63 (2H, triplet, J=7.5 Hz);
4.79 (1H, singlet);
5.63 & 5.76 (each 1H, AB-quartet, J=18.5 Hz);
7.02 (2H, doublet, J=8 Hz);
7.22–7.67 (6H, multiplet);

60(f) Succinimido 1-[(2'-t-Butoxycarbonylbiphenyl-4-yl)methyl)-4-(1-hydroxy-2,2-dimethylpropyl)-2-propylimidazole-5-carboxylate Following a procedure similar to that described in Example 52(a), but using 300 mg of 1-[(2'-t-butoxycarbonylbiphenyl-4-yl)methyl]-4-(1-hydroxy-2,2-dimethylpropyl)-2-propylimidazole-5-carboxylic acid [prepared as described in step (e) above], 110 mg of N-hydroxysuccinimide and 130 mg of N,N-dicyclohexylcarbodiimide, 321 mg of the title compound were obtained as an amorphous solid.

Nuclear Magnetic Resonance Spectrum (CDCl$_3$) δ ppm:
0.94 (3H, triplet, J=7.5 Hz);
0.98 (9H, singlet);
1.18 (9H, singlet);
1.75 (2H, sextet, J=7.5 Hz);
2.64 (2H, triplet, J=7.5 Hz);
3.12 (1H, doublet, J=9.5 Hz);
4.98 (1H, doublet, J=9.5 Hz);

5.52 (2H, singlet);

7.0–7.9 (8H, multiplet).

60(g) 1-[(2'-t-Butoxycarbonylbiphenyl-4-yl)methyl]-4-(1-hydroxy-2,2-dimethylpropyl)-2-propylimidazole-5-carboxamide Following a procedure similar to that described in Example 52(b), but using 0.13 g of succinimido 1-[(2'-t-butoxycarbonylbiphenyl-4-yl)methyl]-4-(1-hydroxy-2,2-dimethylpropylpropyl)-2-propylimidazole-5-carboxylate [prepared as described i n step (f) above], 0.12 g of the title compound was obtained as a glass.

Nuclear Magnetic Resonance Spectrum (CDCl$_3$) δ ppm:

0.88 (3H, triplet, J=7.5 Hz);

0.90 (9H, singlet);

1.24 (9H, singlet);

1.60 (2H, sextet, J=7.5 Hz);

2.58 (2H, triplet, J=7.5 Hz);

4.65 (1H, doublet, J=6 Hz);

5.53 & 5.87 (each 1H, AB-quartet, J=16 Hz);

7.02 (2H, doublet, J=8 Hz);

7.23–7.48 (5H, multiplet);

7.78 (1H, doublet, J=6.5 Hz).

60(h) 1-[(2'-Carboxybiphenyl-4-yl)methyl]-4-(1-hydroxy-2,2-dimethylpropyl)-2-propylimidazole-5-carboxamide Following a procedure similar to that described in Example 52(c), but using 139 mg of 1-[(2'-t-butoxycarbonylbiphenyl-4-yl)methyl]-4-(1-hydroxy-2,2-dimethylpropyl)-2-propylimidazole-5-carboxamide [prepared as described in step (g) above], 96 mg of the hydrochloride of the title compound were obtained as a powder, melting at above 160° C. (with softening).

Nuclear Magnetic Resonance Spectrum (hexadeuterated dimethyl sulfoxide) δ ppm:

0.82 (3H, triplet, J=7.5 Hz);

0.90 (9H, singlet);

1.53 (2H, sextet, J=7.5 );

2.97 (2H, triplet, J=7.5 Hz);

4.79 (1H, singlet);

5.69 (2H, singlet);

7.19–7.75 (8H, multiplet).

EXAMPLE 61

(5-Methyl-2-oxo-1,3-dioxolen-4-yl)methyl 4-(1-hydroxy-1-methylethyl)-2-propyl-1-{4-[2-(tetrazol-5-yl)phenyl]phenyl}methylimidazole-5-carboxylate
(Compound No. 2-17)

61(a) (5-Methyl-2-oxo-1,3-dioxolen-4-yl)methyl 4-(1-hydroxy-1-methylethyl)-2-propyl-1-{4-[2-(trityltetrazol-5-yl)phenyl]phenyl}methylimidazole-5-carboxylate A suspension of 0.97 g of potassium carbonate in 100 ml of N,N-dimethylacetamide was warmed at 60° C., and then a solution of 1.14 g of (5-methyl-2-oxo-1,3-dioxolen-4-yl)methyl 4-(1-hydroxy-1-methylethyl)-2-propylimidazole-5-carboxylate (prepared as described in Preparation 31) and 2.35 g of 4-[2-(trityltetrazol-5-yl)phenyl]benzyl bromide in 50 ml of N,N-dimethylacetamide was added dropwise to the warm suspension, whilst stirring. The reaction mixture was stirred at 60° C. for 3.5 hours, and it was then diluted with ethyl acetate. The ethyl acetate layer was separated, washed with water and dried over anhydrous magnesium sulfate, and then the solvent was removed by distillation under reduced pressure. The resulting residue was purified by column chromatography through silica gel, using a 1:1 by volume mixture of hexane and ethyl acetate as the eluent, to give 1.4 g of the title compound as an amorphous solid. This product was crystallized from diisopropyl ether, to give pure title compound, melting at 98°–99° C. (with decomposition).

Nuclear Magnetic Resonance Spectrum (CDCl$_3$), δ ppm:

0.89 (3H, triplet, J=7.5 Hz);

1.62 (6H, singlet);

1.6–1.75 (2H, multiplet);

1.97 (3H, singlet);

2.54 (2H, triplet, J=8 Hz);

4.70 (2H, singlet);

5.30 (2H, singlet);

5.61 (1H, singlet);

6.68 (2H, doublet, J=7.5 Hz);

6.90–7.52 (20 H, multiplet);

7.87 (1H, doublet, J=7.5 Hz).

61(b) (5-Methyl-2-oxo-1,3-dioxolen-4yl)methyl 4-(1-hydroxy-1-methylethyl)-2-propyl-1-{4-[2-(tetrazol-5-yl)phenyl]phenyl}methylimidazole-5-carboxylate A mixture of 1.4 g of (5-methyl-2-oxo-1,3-dioxolen-4-yl)methyl 4-(1-hydroxy-1-methylethyl)-2-propyl-1-{4-[2-(trityltetrazol-5-yl)phenyl]phenyl}methylimidazole-5-carboxylate [prepared as described in step (a) above] and 48 ml of 75% v/v aqueous acetic acid was stirred at 60° C. for 1 hour, after which it was concentrated by evaporation under reduced pressure. The residue was dissolved in toluene, and the resulting solution was concentrated by distillation under reduced pressure; this was repeated a further time in order to remove the remaining water and acetic acid. The residue thus obtained was purified by column chromatography through silica gel using 1:9 and 1:4 by volume mixtures of methanol and methylene chloride as the eluent, to give 0.73 g of the title compound, melting at 170°–172° C.

Nuclear Magnetic Resonance Spectrum (CDCl$_3$), δ ppm:

0.93 (3H, triplet, J=7.5 Hz);

1.63 (6H, singlet);

1.6–1.8 (2H, multiplet);

2.19 (3H, singlet);

2.70 (2H, triplet, J=7.5 Hz);

5.00 (2H, singlet);

5.45 (2H, singlet);

6.83 (2H, doublet, J=8 Hz);

7.10 (2H, doublet, J=8 Hz);

7.42–7.63 (3H, multiplet);

7.83 (1H, doublet of doublets, J=1 & 7.5 Hz).

EXAMPLE 62

Pivaloyloxymethyl 4-(1-hydroxy-1-methylethyl)-2-propyl-1-{4-[2-(tetrazol-5-yl)phenyl] phenyl}methylimidazole-5-carboxylate (Compound No. 2-15)

62(a) Pivaloyloxymethyl 4-(1-hydroxy-1-methylethyl)-2-propyl-1-{4-[2-(trityltetrazol-5-yl)phenyl] phenyl}methylimidazole-5-carboxylate Following a procedure similar to that described in Example 61(a), but using 0.85 g of pivaloyloxymethyl 4-(1-hydroxy-1-methylethyl)-2-propylimidazole-5-carboxylate [prepared as described in Preparation 22(ii)], 1.52 g of 4-[2-(trityltetrazol-5-yl)phenyl]benzyl bromide and 0.72 g of potassium carbonate, 1.02 g of the title compound were obtained as an amorphous solid.

The Nuclear Magnetic Resonance spectrum of this compound was identical with that of the compound obtained as described in Example 20(a).

62(b) Pivaloyloxymethyl 4-(1-hydroxy-1-methylethyl)-2-propyl-1-{4-[2-(tetrazol-5-yl)phenyl]phenyl}methylimidazole-5-carboxylate The pivaloyloxymethyl 4-(1-hydroxy-1-methylethyl)-2-propyl-1-{4-[2-trityltetrazol-5-yl)phenyl]phenyl}methylimidazole-5-carboxylate prepared as described in step (a) above was detritylated following a procedure similar to that described in Example 20(b), to give the hydrochloride of the title compound in an 80% yield.

The melting point and Nuclear Magnetic Resonance spectrum of this compound were identical with those of the compound obtained as described in Example 20(b).

EXAMPLE 63

Phthalidyl 4-(1-hydroxy-1-methylethyl)-2-propyl-1-{4-[2-(tetrazol-5-yl)phenyl]phenyl}methylimidazole-5-carboxylate (Compound No. 2-65)

63(a) Phthalidyl 4-(1-hydroxy-1-methylethyl)-2-propyl-1-{4-[2-(trityltetrazol-5-yl)phenyl]phenyl}methylimidazole-5-carboxylate Following a procedure similar to that described in Example 61(a), but using 0.456 g of phthalidyl 4-(1-hydroxy-1-methylethyl)-2-propylimidazole-5-carboxylate (prepared as described in Preparation 32), 0.736 g of 4-[2-(trityltetrazol-5-yl)phenyl]benzyl bromide and 0.366 g of potassium carbonate, 0.196 g of the title compound was obtained, melting at 118°–120° C.

Nuclear Magnetic Resonance Spectrum (CDCl$_3$), δ ppm:
0.95 (3H, triplet, J=7.5 Hz);
1.66 (6H, singlet);
1.65–1.80 (2H, multiplet);
2.60 (2H, triplet, J=7.5 Hz);
5.09 (2H, singlet);
6.92–7.56 (27H, multiplet);
7.93 (1H, doublet of doublets, J=1 & 8 Hz).

63(b) Phthalidyl 4-(1-hydroxy-1-methylethyl)-2-propyl-1-{4-[2-(tetrazol-5-yl)phenyl]phenyl}methylimidazole-5-carboxylate Following a procedure similar to that described in Example 61(b), 0.196 g of phthalidyl 4-(1-hydroxy-1-methylethyl)-2-propyl-1-[4-[2-(trityltetrazol-5-yl)phenyl]phenyl}methylimidazole-5-carboxylate [prepared as described in step (a) above] was detritylated by heating it with 75% v/v aqueous acetic acid to give 0.110 g of the title compound, melting at 168°–170° C.

Nuclear Magnetic Resonance Spectrum (CDCl$_3$), δ ppm:
0.92 (3H, triplet, J=7.5 Hz);
1.57 (6H, singlet);
1.60–1.77 (2H, multiplet);
2.65 (2H, triplet, J=7.5 Hz);
5.13 (2H, singlet);
6.91–7.57 (12H, multiplet);
7.80 (1H, doublet, J=7.5 Hz).

EXAMPLE 64

Isopropoxycarbonyloxymethyl 4-(1-hydroxy-1-methylethyl)-2-propyl-1-{4-[2-(tetrazol-5-yl)phenyl]phenyl}methylimidazole-5-carboxylate (Compound No. 2-21)

64(a) Isopropoxycarbonyl 4-(1-hydroxy-1-methylethyl)-2-propyl-1-{4-[2-(trityltetrazol-5-yl)phenyl]phenyl}methylimidazole-5-carboxylate Following a procedure similar to that described in Example 61(a), but using 656 mg of isopropoxycarbonyloxymethyl 4-(1-hydroxy-1-methylethyl)-2-propylimidazole-5-carboxylate (prepared as described in Preparation 33), 1.20 g of 4-[2-(trityltetrazol-5-yl)phenyl]benzyl bromide and 0.51 g of potassium carbonate, 0.78 g of the title compound was obtained as a viscous liquid.

Nuclear Magnetic Resonance Spectrum (CDCl$_3$), δ ppm:
0.87 (3H, triplet, J=7.5 Hz);
1.24 (6H, doublet, J=6 Hz);
1.63 (6H, singlet);
1.65–1.80 (2H, multiplet);
2.52 (2H, triplet, J=7.5 Hz);
4.87 (1H, quintet, J=6 Hz);
5.35 (2H, singlet);
5.42 (1H, singlet);
5.66 (2H, singlet);
6.74–7.87 (22H, multiplet);
7.87–7.96 (1H, multiplet).

64(b) Isopropoxycarbonyloxymethyl 4-(1-hydroxy-1-methylethyl)-2-propyl-1-{4-[2-(tetrazol-5-yl)phenyl]phenyl}methylimidazole-5-carboxylate Following a procedure similar to that described in Example 61(b), 0.78 g of isopropoxycarbonyloxymethyl 4-(1-hydroxy-1-methylethyl)-2-propyl-1-{4-[2-(trityltetrazol-5-yl)phenyl]phenyl}methylimidazole-5-carboxylate [prepared as described in step (a) above] was detritylated by heating it with 75% v/v aqueous acetic acid, to give 0.48 g of the title compound as an amorphous solid.

Nuclear Magnetic Resonance Spectrum (CDCl$_3$), δ ppm:
0.96 (3H, triplet, J=7.5 Hz);
1.21 (6H, doublet, J=6 Hz);
1.63 (6H, singlet);
1.72 (2H, sextet, J=7.5 Hz);
2.60 (2H, triplet, J=7.5 Hz);
4.72 (1H, quintet, J=6.5 Hz);
5.33 (2H, singlet);
5.76 (2H, singlet);
6.77 (2H, doublet, J=7.5 Hz);
6.92 (2H, doublet, J=7.5 Hz);
7.37–7.60 (3H, multiplet);
7.87 (1H, doublet, J=7.5 Hz).

EXAMPLE 65

Ethyl 1-[(2'-t-butoxycarbonylbiphenyl-4yl)methyl]-2-ethyl-4-(1-hydroxy-1-methylethyl)imidazole-5-carboxylate (Compound No. 1-130)

0.337 g of potassium t-butoxide was added to a solution of 0.68 g of ethyl 2-ethyl-4-(1-hydroxy-1-methylethyl)imidazole-5-carboxylate (prepared as described in Preparation 37) in 7 ml of N,N-dimethylacetamide, and the resulting mixture was stirred at room temperature for 10 minutes. 1.04 g of t-butyl 4'-bromomethylbiphenyl-2-carboxylate was then added to the resulting solution, and the reaction mixture was stirred at room temperature for 4 hours. At the end of this time, it was mixed with ethyl acetate and water. The ethyl acetate layer was separated, dried over anhydrous magnesium sulfate and concentrated by evaporation under reduced pressure. The residue was purified by column chromatography through silica gel, using a 1:1 by volume mixture of ethyl acetate and hexane as the eluent, to give 1.32 g of the title compound as a gum.

Nuclear Magnetic Resonance Spectrum (CDCl$_3$) δ ppm:
1.23 (9H, singlet);
1.23 (3H, triplet, J=7.5 Hz);
1.29 (3H, triplet, J=7.5 Hz);
1.63 (6H, singlet);
2.73 (2H, quartet, J=7.5 Hz);
4.26 (2H, quartet, J=7.5 Hz);
5.54 (2H, singlet);
5.73 (1H, singlet);
6.98 (2H, doublet, J=8.5 Hz);
7.5–7.9 (6H, multiplet).

EXAMPLE 66

Ethyl 1-[(2'-carboxybiphenyl-4-yl)methyl]-2-ethyl-4-(1-hydroxy-1-methylethyl)imidazole-5-carboxylate (Compound No. 1-131)

Following a procedure similar to that described in Example 7, but using 1.32 g of ethyl 1-[(2'-t-butoxycarbonylbiphenyl-4-yl)methyl]-2-ethyl-4-(1-hydroxy-1-methylethyl)imidazole-5-carboxylate (prepared as described in Example 65) and a 4N solution of hydrogen chloride in dioxane, 0.94 g of the hydrochloride of the title compound was obtained as an amorphous powder.

Nuclear Magnetic Resonance Spectrum (hexadeuterated dimethyl sulfoxide) δ ppm:
1.09 (3H, triplet, J=7.5 Hz);
1.15 (3H, triplet, J=7.5 Hz);
1.61 (6H, singlet);
3.03 (2H, quartet, J=7.5 Hz);
4.22 (2H, quartet, J=7.5 Hz);
5.64 (2H, singlet);
7.16 (2H, doublet, J=8.5 Hz);
7.32–7.75 (6H, multiplet);

EXAMPLE 67

1-[(2'-Carboxybiphenyl-4-yl)methyl]-2-ethyl-4-(1-hydroxy-1-methylethyl)imidazole-5-carboxylic acid (Compound No. 1-132)

Following a procedure similar to that described in Example 17, but using 0.40 g of the hydrochloride of ethyl 1-[2'-carboxybiphenyl-4-yl)methyl]-2-ethyl-4-(1-hydroxy-1-methylethyl)imidazole-5-carboxylate (prepared as described in Example 66) and 0.18 g of lithium hydroxide monohydrate, 0.25 g of the title compound was obtained as an amorphous powder.

Nuclear Magnetic Resonance Spectrum (hexadeuterated dimethyl sulfoxide) δ ppm:
1.17 (3H, triplet, J=7.5 Hz);
1.64 (6H, singlet);
2.85 (2H, quartet, J=7.5 Hz);
5.74 (2H, singlet);
7.10 (2H, doublet, J=8 Hz);
7.30–7.76 (6H, multiplet);

EXAMPLE 68

Ethyl 2-ethyl-4(1-hydroxy-1-methylethyl)-1-{4-[2-(tetrazol-5-yl)phenyl]phenyl}methylimidazole-5-carboxylate (Compound No. 2-72)

68(a) Ethyl 2-ethyl-4-(1-hydroxy-1-methylethyl)-1-{4-[2-(trityltetrazol-5-yl)phenyl]phenyl}methylimidazole-5-carboxylate 0.52 g of potassium t-butoxide was added to a solution of 1.00 g of ethyl 2-ethyl-4-(1-hydroxy-1-methylethyl)imidazole-5-carboxylate (prepared as described in Preparation 37) in 26 ml of N,N-dimethylacetamide, and the resulting mixture was stirred at room temperature for 10 minutes. A solution of 2.71 g of 4-[2-(trityltetrazol-5-yl)phenyl]benzyl bromide in 35 ml of N,N-dimethylacetamide was then added dropwise to the resulting solution, after which the reaction mixture was stirred at 50° C. for 4 hours. At the end of this time, the reaction mixture was worked up in a similar manner to that described in Example 18(a), to give 2.01 g of the title compound as crystals, melting at 150°–152° C.

Nuclear Magnetic Resonance Spectrum (CDCl$_3$) δ ppm:
1.10 (3H, triplet, J=7.5 Hz);
1.18 (3H, triplet, J=7.5 Hz);
1.65 (6H, singlet);
2.52 (2H, quartet, J=7.5 Hz);
4.14 (2H, quartet, J=7.5 Hz);
5.35 (2H, singlet);
5.80 (1H, singlet);
6.73 (2H, doublet, J=8.5 Hz);
6.93–7.52 (20H, multiplet);
7.87 (1H, doublet, J=7.5 Hz).

68(b) Ethyl 2-ethyl-4-(1-hydroxy-1-methylethyl)-1-{4-[2-(tetrazol-5-yl) phenyl]phenyl}methylimidazole-5-carboxylate A solution of 1.9 g of ethyl 2-ethyl-4-(1-hydroxy-1-methylethyl)-1-{4-[2-(trityltetrazol-5-yl)phenyl] phenyl}methylimidazole-5-carboxylate [prepared as described in step (a) above] in 28 ml of 75% v/v aqueous acetic acid was stirred at 60° C. for 2 hours. At the end of this time, the reaction mixture was diluted with 7 ml of water and cooled to room temperature. Precipitated trityl alcohol was removed by filtration, and the filtrate was concentrated by evaporation under reduced pressure. The syrupy residue was crystallized in diisopropyl ether, to give 1.21 g of the title compound, melting at 166°–167° C.

Nuclear Magnetic Resonance Spectrum (CDCl$_3$) δ ppm:
1.14 (3H, triplet, J=7.5 Hz);
1.20 (3H, triplet, J=7.5 Hz);
1.48 (6H, singlet);
2.52 (2H, quartet, J=7.5 Hz);
4.19 (2H, quartet, J=7.5 Hz);
5.41 (2H, singlet);
6.79 (2H, doublet, J=8.5 Hz);
7.09 (2H, doublet, J=8.5 Hz );

7.41–7.62 (3H, multiplet);
7.85 (1H, doublet, J=7.5 Hz);

EXAMPLE 69

2-Ethyl-4-(1-hydroxy-1-methylethyl)-1-{4-[=-tetrazol-5-yl)phenyl]phenyl}methylimidazole-5-carboxylic acid (Compound No. 2-68)

A solution of 0.54 g of lithium hydroxide monohydrate in 10 ml of water was added to a solution of ethyl 2-ethyl-4-(1-hydroxy-1-methylethyl)-1-{4-[2-(tetrazol-5-yl)phenyl]phenyl}methylimidazole-5-carboxylate [prepared as described in Example 68(b)] in 10 ml of dioxane, and the resulting mixture was stirred at room temperature for 4 hours. At the end of this time, the dioxane was removed by evaporation under reduced pressure, and 12.6 ml of 1N aqueous hydrochloric acid were added to the resulting aqueous residue. Collection of precipitated crystals by filtration gave 0.93 g of the title compound, melting at 179°–181° C.

Nuclear Magnetic Resonance Spectrum (hexadeuterated dimethyl sulfoxide) δ ppm:

1.09 (3H, triplet, J=7.5 Hz);
1.55 (6H, singlet);
2.63 (2H, quartet, J=7.5 Hz);
5.65 (2H, singlet);
6.96 (2H, doublet, J=8.5 Hz);
7.03 (2H, doublet, J=8.5 Hz);
7.08–7.64 (4H, multiplet);

EXAMPLE 70

Ethyl 4-(1-hydroxy-1-methylethyl)-2-propyl-1-{4-[2-(tetrazol-5-yl)phenyl]phenyl}methylimidazole-5-carboxylate (Compound No. 2-7)

70(a) Ethyl 1-(2'-cyanobiphenyl-4-yl)methyl-4-(1-hydroxy-1-methylethyl)-2-propylimidazole-5-carboxylate Following a procedure similar to that as described in Example 68(a), but using 4.01 g of ethyl 4-(1-hydroxy-1-methylethyl)-2-propylimidazole-5-carboxylate (prepared as described in Preparation 9), 5.0 g of 4'-bromomethylbiphenyl-2-carbonitrile and 1.97 g of potassium t-butoxide, 6.86 g of the title compound were obtained as crystals, melting at 92°–93° C.

Nuclear Magnetic Resonance Spectrum (CDCl$_3$) δ ppm:

0.97 (3H, triplet, J=7.5 Hz);
1.16 (3H, triplet, J=7 Hz);
1.65 (6H, singlet);
1.74 (2H, sextet, J=7.5 Hz);
2.67 (2H, triplet, J=7.5 Hz);
4.24 (2H, quartet, J=7 Hz);
5.52 (2H, singlet);
5.77 (1H, singlet);
7.05 (2H, doublet, J=8.5 Hz);
7.42–7.67 (5H, multiplet);
7.76 (1H, doublet, J=8 Hz).

70(b) Ethyl 4-(1-hydroxy-1-methylethyl)-2-propyl-1-{4-[2-(tetrazol-5-yl)phenyl]phenyl}methylimidazole-5-carboxylate A solution of 2.00 g of ethyl 1-(2'-cyanobiphenyl-4-yl)methyl-4-(1-hydroxy-1-methylethyl)-2-propylimidazole-5-carboxylate [prepared as described in step (a) above] and 2.00 g of tributyltin azide in 15 ml of toluene was stirred at 100° C. for 5 days. At the end of this time, the reaction mixture was concentrated by evaporation under reduced pressure, and the residue was dissolved in 30 ml of a 4N solution of hydrogen chloride in dioxane. The solution was allowed to stand at room temperature for 16 hours, after which it was concentrated by evaporation under reduced pressure. The residue was triturated in diisopropyl ether, to give 2.00 g of the hydrochloride of the title compound.

The Nuclear Magnetic Resonance Spectrum of this compound was identical with that of the compound obtained as described in Example 18(b).

EXAMPLE 71

Ethyl 4-(1-hydroxy-1-methylethyl)-2-propyl-1-{4-[2-(tetrazol-5-yl)phenyl]phenyl}methylimidazole-5-carboxylate (Compound No. 2-7)

71(a) Ethyl 1-{4-[2-(t-butylaminocarbonyl)phenyl]phenyl}methyl-4-(1-hydroxy-1-methylethyl)-2-propylimidazole-5-carboxylate Following a procedure similar to that described in Example 68(a), but using 4.16 g of ethyl 4-(1-hydroxy-1-methylethyl)-2-propylimidazole-5-carboxylate (prepared as described in Preparation 9), 6.00 g of N-t-butyl-4-bromomethylbiphenyl-2-carboxamide (prepared as described in Preparation 38) and 2.14 g of potassium t-butoxide, 5.87 g of the title compound was obtained as crystals, melting at 145°–146° C.

Nuclear Magnetic Resonance Spectrum (CDCl$_3$) δ ppm:

0.97 (3H, triplet, J=7.5 Hz);
1.12 (9H, singlet);
1.24 (3H, triplet, J=7 Hz);
1.64 (6H, singlet);
1.75 (2H, sextet, J=7.5 Hz);
2.66 (2H, triplet, J=7.5 Hz);
4.25 (2H, quartet, J=7 Hz);
5.03 (1H, singlet);
5.52 (2H, singlet);
5.69 (1H, singlet);
6.98 (2H, doublet, J=8.5 Hz);
7.28–7.47 (5H, multiplet);
7.65 (1H, doublet, J=7 Hz);

71(b) Ethyl 1-(2'-cyanobiphenyl-4-yl)methyl-4-(1-hydroxy-1-methylethyl)-2-propylimidazole-5-carboxylate 0.345 ml of oxalyl chloride was added dropwise, whilst ice-cooling, to a solution of 1.00 g of ethyl 1-{4-[2-(t-butylaminocarbonyl)phenyl]phenyl}methyl-4-(1-hydroxy-1-methylethyl)-2-propylimidazole-5-carboxylate [prepared as described in step (a) above] in 10 ml of methylene chloride, and the mixture was stirred at the same temperature for 2 hours. At the end of this time, the reaction mixture was diluted with an aqueous solution of sodium hydrogencarbonate and ethyl acetate, and the ethyl acetate layer was separated, dried over anhydrous magnesium sulfate and concentrated by evaporation under reduced pressure. The residue was purified by column chromatography through silica gel, using a 1:1 by volume mixture of ethyl acetate and hexane as the eluent, to give 0.69 g of the title compound as crystals.

The melting point and Nuclear Magnetic Resonance Spectrum of this compound were identical with those of the compound obtained as described in Example 70 (a).

71(c) Ethyl 4-(1-hydroxy-1-methylethyl)-2-propyl-1-{4-[2-(tetrazol-5-yl)phenyl]phenyl}methylimidazole-5-carboxylate Following a procedure similar to that described in Example 70(b), but using ethyl 1-(2'-cyanobiphenyl-4-yl)methyl-4-(1-hydroxy-1-methylethyl)-2-propylimidazole-5-carboxylate [prepared as described in step (b) above], the title compound was obtained in a 91% yield.

The Nuclear Magnetic Resonance Spectrum of this compound was identical with that of the compound obtained as described in Example 18(b).

EXAMPLE 72

Ethyl 4-(1-hydroxy-1-methylethyl)-2-propyl-1-{4-[2-(tetrazol-5-yl)phenyl]phenyl}methylimidazole-5-carboxylate (Compound No. 2-7)

72(a) Ethyl 1-[(2'-t-butoxycarbonylbiphenyl-4-yl)methyl]-4-(1-hydroxy-1-methylethyl)-2-propylimidazole-5-carboxylate Following a procedure similar to that described in Example 68(a), but using 4.80 g of ethyl 4-(1-hydroxy-1-methylethyl)-2-propylimidazole-5-carboxylate (prepared as described in Preparation 9), 6.94 g of t-buryl 4'-bromomethylbiphenyl-2-carboxylate and 2.28 g of potassium t-butoxide, 7.50 g of the title compound were obtained as crystals, melting at 90°–91° C.

Nuclear Magnetic Resonance Spectrum (CDCl$_3$) δ ppm:
0.97 (3H, triplet, J=7 Hz);
1.23 (3H, triplet, J=7 Hz);
1.25 (9H, singlet);
1.60 (6H, singlet);
1.82 (2H, sextet, J=7 Hz);
2.67 (2H, triplet, J=7 Hz);
4.24 (2H, quartet, J=7 Hz);
5.51 (2H, singlet);
5.72 (1H, singlet);
6.87–7.85 (8H, multiplet).

72(b) Ethyl 1-[(2'-carboxybiphenyl-4-yl)methyl]-4-1-hydroxy-1-methylethyl)-2-propylimidazole-5-carboxylate Following a procedure similar to that described in Example 18(b), but using 0.80 g of ethyl 1-[(2'-t-butoxycarbonylbiphenyl-4-yl)methyl]-4-(1-hydroxy-1-methylethyl)-2-propylimidazole-5-carboxylate [prepared as described in step (a) above] and a 4N solution of hydrogen chloride in dioxane, 0.67 g of the hydrochloride of title compound was obtained as an amorphous powder.

Nuclear Magnetic Resonance Spectrum (hexadeuterated dimethyl sulfoxide) δ ppm:
0.88 (3H, triplet, J=7 Hz);
1.14 (3H, triplet, J=7 Hz);
1.50–1.65 (2H, multiplet);
1.60 (6H, singlet);
3.00 (2H, triplet, J=7 Hz);
4.20 (2H, quartet, J=7 Hz);
5.63 (2H, singlet);
7.13–7.75 (8H, multiplet);

72(c) Ethyl 1-[(2'-carbamoylbiphenyl-4-yl)methyl]-4-(1-hydroxy-1-methylethyl)-2-propylimidazole-5-carboxylate 3 ml of oxalyl chloride were added dropwise, whilst ice-cooling, to a solution of 4.00 g of the hydrochloride of ethyl 1-[(2'-carboxybiphenyl-4-yl)methyl]-4-(1-hydroxy-1-methylethyl)-2-propylimidazole-5-carboxylate [prepared as described in step (b) above] in 40 ml of methylene chloride, and the resulting mixture was stirred at room temperature for 2 hours. At the end of this time, the reaction mixture was concentrated by evaporation under reduced pressure. Benzene was then added to the residue, and the mixture was concentrated again by evaporation under reduced pressure, to remove the remaining oxalyl chloride. The crystalline residue was suspended in 100 ml of ethyl acetate and mixed with 15 ml of concentrated aqueous ammonia, whilst ice-cooling, and then the mixture was stirred at room temperature for 10 minutes. The ethyl acetate layer was separated, washed with water, dried over anhydrous magnesium sulfate and concentrated by evaporation under reduced pressure. The crystalline residue was then washed with diisopropyl ether, to give 2.97 g of the title compound, melting at 148°–151° C.

Nuclear Magnetic Resonance Spectrum (CDCl$_3$) δ ppm:
0.96 (3H, triplet, J=7.5 Hz);
1.19 (3H, triplet, J=7 Hz);
1.64 (6H, singlet);
1.73 (2H, sextet, J=7.5 Hz);
2.65 (2H, triplet, J=7.5 Hz);
4.24 (2H, quartet, J=7 Hz);
5.36 (1H, broad singlet);
5.49 (2h, singlet);
5.66 (1H, broad singlet);
5.76 (1H, singlet);
6.99 (2H, doublet, J=8 Hz);
7.32–7.53 (5H, multiplet);
7.71 (1H, doublet, J=6 Hz).

72(d) Ethyl 1-(2'-cyanobiphenyl-4-yl)methyl)-4-(1-hydroxy-1-methylethyl)-2-propylimidazole-5-carboxylate 264 μl of trifluoroacetic anhydride were added, whilst cooling on a bath containing a mixture of ice and sodium chloride, to a solution of 0.70 g of ethyl 1-[(2'-carbamoylbiphenyl-4-yl)methyl]-4-(1-hydroxy-1-methylethyl)-2-propylimidazole-5-carboxylate [prepared as described in step (c) above] and 0.43 ml of triethylamine in 7 ml of methylene chloride, and the resulting mixture was stirred at the same temperature for 30 minutes. At the end of this time, the reaction mixture was diluted with an aqueous solution of sodium hydrogencarbonate and ethyl acetate, and the ethyl acetate layer was separated, dried over anhydrous magnesium sulfate and concentrated by evaporation under reduced pressure. The residue was purified by column chromatography through silica gel, using a 1:1 by volume mixture of ethyl acetate and hexane as the eluent, to give 0.60 g of the title compound as crystals.

The melting point and Nuclear Magnetic Resonance Spectrum of this compound were identical with those of the compound obtained as described in Example 70 (a).

72(e) Ethyl 4-(1-hydroxy-1-methylethyl)-2-propyl-1-{4-[2-(tetrazol-5-yl)phenyl]phenyl}methylimidazole-5-carboxylate Following a procedure similar to that described in Example 70(b), but using ethyl 1-(2'-cyanobiphenyl-4-yl)methyl-4-(1-hydroxy-1-methylethyl)-2-propylimidazole-5-carboxylate [prepared as described in step (d) above] the title compound was obtained in a 90% yield.

The Nuclear Magnetic Resonance Spectrum of this compound was identical with that of the compound obtained as described in Example 18(b).

EXAMPLE 73

Pivaloyloxymethyl 4-(1-hydroxyethyl)-2-propyl-1-{4-[2-tetrazol-5-yl)phenyl]phenyl}methylimidazole-5-carboxylate (Compound No.4-31)

73(a) Pivaloyloxymethyl 4-(hydroxyethyl)-2-propyl-1-{4-[2-(trityltetrazol-5-yl)phenyl]phenyl}methylimidazole-5-carboxylate A solution of 196 mg of lithium hydroxide monohydrate in 15 ml of water was added to a solution of 2.87 g of ethyl 4-(1-hydroxyethyl)-2-propyl-1-{4-[2-(trityltetrazol-5-yl)phenyl]phenyl}methylimidazole-5-carboxylate [prepared as described in Example 42(a)] in 30 ml of dioxane, and the resulting mixture was stirred at room temperature for 16 hours. At the end of this time, small pieces of dry ice were added to the mixture, which was then concentrated by evaporation under reduced pressure to dryness. The residue was dissolved in 40 ml of N,N-dimethylacetamide, and 0.45 g of potassium carbonate and then 1.1 ml of pivaloyloxymethyl chloride were added to the solution. The resulting mixture was stirred at 50° C. for 3 hours. At the end of this time, water and ethyl acetate were added to the reaction mixture, and the ethyl acetate layer was separated, dried over anhydrous magnesium sulfate and concentrated by evaporation under reduced pressure. The residue was purified by column chromatography through silica gel, using a 1:1 by volume mixture of ethyl acetate and hexane as the eluent, to give 2.41 g of the title compound as an amorphous powder.

Nuclear Magnetic Resonance Spectrum (CDCl$_3$) δ ppm:
0.88 (3H, triplet, J=7.5 Hz);
1.17 (9H, singlet);
1.50 (3H, doublet, J=6 Hz);
1.69 sextet, J=7.5 Hz);
2.51 (2H, triplet, J=7.5 Hz);
3.62 (1H, doublet, J=8 Hz);
5.17–5.29 (1H, multiplet);
5.37 (1H, doublet, J=16.5 Hz);
5.46 (1H, doublet, J=16.5 Hz);
5.77 (1H, doublet, J=5.5 Hz);
5.82 (1H, doublet, J=5.5 Hz);
6.75 (2H, doublet, =8.5 Hz);
6.92–7.89 (20H, multiplet);
7.90 (1H, doublet, J=7.5 Hz).

73(b) Pivaloyloxymethyl 4-(1-hydroxyethyl)-2-propyl-1-{4-[2-(tetrazol-5-yl)phenyl]phenyl}methylimidazole-5-carboxylate Following a procedure similar to that described in Example 35(c), but using 2.87 g of pivaloyloxymethyl 4-(1-hydroxyethyl)-2-propyl-1-{4-[2-(trityltetrazol-5-yl)phenyl]phenyl}methylimidazole-5-carboxylate [prepared as described in step (a) above] and 75% v/v aqueous acetic acid, 1.21 g of the title compound was obtained as a powder.

Nuclear Magnetic Resonance Spectrum (CDCl$_3$) δ ppm:
0.90 (3H, triplet, J=7.5 Hz);
1.13 (9H, singlet);
1.43 (3H, doublet, J=6.5 Hz);
1.67 (2H, sextet, J=7.5 Hz);
2.55 (3H, triplet, J=7.5 Hz);
5.16 (1H, quartet, J=6.5 Hz);
5.40 (1H, doublet, J=16.5 Hz);
5.51 (1H, doublet, J=16.5 Hz);
5.80 (1H, doublet, J=6 Hz);
5.85 (1H, doublet, J=6 Hz);
6.86 (2H, doublet, J=8 Hz);
7.08 (2H, doublet, J=8 Hz);
7.40–7.61 (3H, multiplet);
7.92 (1H, doublet, J=7.5 Hz).

EXAMPLE 74

4-(1-Hydroxy-2,2-dimethylpropyl)-2-propyl-1-{4-[2-(tetrazol-5-yl)phenyl]phenyl}methylimidazole-5-carboxamide (Compound No. 5-37)

74(a) 2-Propyl-4-pivaloyl-1-{4-[2-(trityltetrazol-5-yl)phenyl]phenyl}methylimidazole-5-carbonitrile 1.08 g of potassium t-butoxide was added, whilst ice-cooling, to a solution of 2.00 g of 2-propyl-4-pivaloylimidazole-5-carbonitrile (prepared as described in Preparation 41) in 20 ml of N,N-dimethylacetamide, and the resulting mixture was stirred at same temperature for 10 minutes. 6.10 g of 4-[2-(trityltetrazol-5-yl)phenyl]benzyl bromide were then added to the solution, and the resulting mixture was stirred at 50° C. for 4 hours. At the end of this time, ethyl acetate and water were added to the mixture, and the ethyl acetate layer was separated, dried over anhydrous magnesium sulfate and concentrated by evaporation under reduced pressure. The syrupy residue was purified by column chromatography through silica gel, using 1:3 and 1:2 by volume mixtures of ethyl acetate and hexane as the eluent, to give 5.44 g of the title compound as crystals, melting at 107°–110° C.

Nuclear Magnetic Resonance Spectrum (CDCl$_3$) δ ppm:
0.92 (3H, triplet, J=7.5 Hz);
1.42 (9H, singlet);
1.72 (2H, sextet, J=7.5 Hz);
2.50 (2H, triplet, J=7.5 Hz);
5.09 (2H, singlet);
6.92 (2H, doublet, J=8 Hz);
7.13–7.53 (20H, multiplet);
7.95 (1H, doublet, J=7 Hz);

74(b) 4-(1-Hydroxy-2,2-dimethylpropyl)-2-propyl-1-{4-[2-(trityltetrazol-5-yl)phenyl]phenyl}methylimidazole-5-carbonitrile A solution of 108 mg of sodium borohydride in 20 ml of ethanol was added to a solution of 2.00 g of 2-propyl-4-pivaloyl-1-{4-[2-(trityltetrazol-5-yl)phenyl]phenyl}methylimidazole-5-carbonitrile [prepared as described in step (a) above] in 40 ml of tetrahydrofuran, and the mixture was stirred at room temperature for 2.5 hours. At the end of this time, the reaction mixture was concentrated by evaporation under reduced pressure, and the residue was dissolved in a mixture of ethyl acetate and water. The ethyl acetate layer was separated, washed with water, dried over anhydrous magnesium sulfate and concentrated by evaporation under reduced pressure. The syrupy residue was crystallized in a 1:4 by volume mixture of ethyl acetate and hexane, to give 1.93 g of the title compound as crystals, melting at 115°–117° C.

Nuclear Magnetic Resonance Spectrum (CDCl$_3$) δ ppm:
0.87 (3H, triplet, J=7.5 Hz);
0.99 (9H, singlet);
1.64 (2H, sextet, J=7.5 Hz);

2.49 (2H, triplet, J=7.5 Hz);

2.76 (1H, doublet, J=7.5 Hz);

4.46 (1H, doublet, J=7.5 Hz);

5.04 (2H, singlet);

6.85–7.53 (22H, multiplet);

7.95 (1H, doublet, J=7.5 Hz).

74(c) 4-(1-Hydroxy-2,2-dimethylpropyl)-2-propyl-1-{4-[2-(tetrazol-5-yl)phenyl]phenyl}methylimidazole-5-carbonitrile A suspension of 1.65 g of 4-(1-hydroxy-2,2-dimethylpropyl)-2-propyl-1-{4-[2-(trityltetrazol-5-yl)phenyl]phenyl}methylimidazole-5-carbonitrile [prepared as described in step (b) above] in 24 ml of 75% v/v aqueous acetic acid was stirred at 60° C. for 2 hours. At the end of this time, 6 ml of water was added to the reaction mixture, which was then cooled with ice. The trityl alcohol which precipitated was removed by filtration, and the filtrate was concentrated by evaporation under reduced pressure, to give 1.07 g of the title compound as a glass.

Nuclear Magnetic Resonance Spectrum (CDCl$_3$) δ ppm:

0.87 (3H, triplet, J=7.5 Hz);

0.92 (9H, singlet);

1.63 (2H, sextet, J=7.5 Hz);

2.58 (2H, triplet, J=7.5 Hz);

4.36 (1H, singlet);

5.15 (2H, singlet);

7.00 (2H, doublet, J=8 Hz);

7.07 (2H, doublet, J=8 Hz);

7.30–7.61 (3H, multiplet);

7.80 (1H, doublet, J=7.5 Hz).

74(d) 4-(1-Hydroxy-2,2-dimethylpropyl)-2-propyl-1-{4-[2-(tetrazol-5-yl)phenyl]phenyl}methylimidazole-5-carboxamide A mixture of 0.70 g of 4-(1-hydroxy-2,2-dimethylpropyl)-2-propyl-1-{4-[2-(tetrazol-5-yl)phenyl]phenyl}methylimidazole-5-carbonitrile [prepared as described in step (c) above] in 14 ml of 1N aqueous sodium hydroxide and 7 ml of ethanol was heated under reflux for 2 hours. At the end of this time, the ethanol in the reaction mixture was removed by evaporation under reduced pressure, and ethyl acetate and 14 ml of 1N aqueous hydrochloric acid were added to the residue. The ethyl acetate layer was separated, dried over anhydrous magnesium sulfate and concentrated by evaporation under reduced pressure, to give 0.45 g of the title compound as a powder, melting at 174°–176° C.

Nuclear Magnetic Resonance Spectrum (hexadeuterated dimethyl sulfoxide) δ ppm:

0.83 (3H, triplet, J=7.5 Hz);

0.88 (9H, singlet);

1.44–1.63 (2H, multiplet);

2.46 (2H, triplet, J=7.5 Hz);

4.45 (1H, singlet);

5.39 (1H, doublet, J=16 Hz);

5.77 (1H, doublet, J=16 Hz);

6.20 (1H, doublet, J=4.5 Hz);

6.91 (2H, doublet, J=8.5 Hz);

7.04 (2H, doublet, J=8.5 Hz);

7.47–7.63 (4H, multiplet);

EXAMPLE 75

2-Butyl-4-(1-hydroxy-2,2-dimethylpropyl)-1-{4-[2-(tetrazol-5-yl)phenyl]phenyl}methylimidazole-5-carboxamide (Compound No. 5-99)

75(a) 2-Butyl-4-pivaloyl-1-{4-[2-(trityltetrazol-5-yl)phenyl]phenyl}methylimidazole-5-carbonitrile Following a procedure similar to that described in Example 74(a), but using 2.04 g of 2-butyl-4-pivaloylimidazole-5-carbonitrile (prepared as described in Preparation 40), 5.6 g of 4-[2-(trityltetrazol-5-yl)phenyl]benzyl bromide and 1.06 g of potassium t-butoxide, 5.43 g of the title compound were obtained as crystals, melting at 103°–105° C.

Nuclear Magnetic Resonance Spectrum (CDCl$_3$) δ ppm:

0.88 (3H, triplet, J=7.5 Hz);

1.32 (2H, sextet, J=7.5 Hz);

1.41 (9H, singlet);

1.66 (2H, quintet, J=7.5 Hz);

2.53 (2H, triplet, J=7.5 Hz);

5.09 (2H, singlet);

6.91–7.50 (22H, multiplet);

7.96 (1H, doublet, J=7.5 Hz).

75(b) 2-Butyl-4-(1-hydroxy-2,2-dimethylpropyl)-1-{4-[2-(trityltetrazol-5-yl)phenyl]phenyl}methylimidazole-5-carbonitrile Following a procedure similar to that described in Example 74(b), but using 4.03 g of 2-butyl-4-pivaloyl-1-{4-[2-(trityltetrazol-5-yl)phenyl]phenyl}methylimidazole-5-carbonitrile [prepared as described in step (a) above] and 0.22 g of sodium borohydride, 3.79 g of the title compound was obtained as crystals, melting at 134°–135° C.

Nuclear Magnetic Resonance Spectrum (CDCl$_3$) δ ppm:

0.85 (3H, triplet, J=7.5 Hz);

0.99 (9H, singlet);

1.27 (2H, sextet, J=7.5 Hz);

2.52–2.67 (2H, multiplet);

2.51 (2H, triplet, J=7.5 Hz);

2.74 (1H, doublet, J=7.5 Hz);

4.45 (1H, doublet, J=7.5 Hz);

5.04 (2H, singlet);

6.85–7.53 (22H, multiplet);

7.95 (1H, doublet, J=7.5 Hz).

75(c) 2-Butyl-4-(1-Hydroxy-2,2-dimethylpropyl)-1-{4-[2-(tetrazol-5-yl)phenyl]phenyl}methylimidazole-5-carbonitrile Following a procedure similar to that described in Example 74(c), but using 1.00 g of 2-butyl-4-(1-hydroxy-2,2-dimethylpropyl)-1-{4-[2-(trityltetrazol-5-yl)phenyl]phenyl}methylimidazole-5-carbonitrile [prepared as described in step (b) above] in 75% v/v aqueous acetic acid, 0.65 g of the title compound was obtained as a glass.

Nuclear Magnetic Resonance Spectrum (CDCl$_3$) δ ppm:

0.91 (3H, triplet, J=7.5 Hz);

0.96 (3H, singlet);

1.28–1.42 (2H, multiplet);

1.58–1.74 (2H, multiplet);

2.69 (2H, triplet, J=7.5 Hz);

4.40 (1H, singlet);

5.21 (2H, singlet);

7.10–7.32 (4H, multiplet);
7.43–7.65 (3H, multiplet);
8.06 (1H, doublet, J=8 Hz).

75(d) 2-Butyl-4-(1-hydroxy-2,2-dimethylpropyl)-1-{4-[2-(tetrazol-5-yl)phenyl]phenyl}methylimidazole-5-carboxamide Following a procedure similar to that described in Example 74(d), but using 0.34 g of 2-butyl-4-(1-hydroxy-2,2-dimethylpropyl)-1-{4-[2-(tetrazol-5-yl)phenyl]phenyl}methylimidazole-5-carbonitrile [prepared as described in step (c) above] in a 1N aqueous solution of sodium hydroxide, 0.30 g of the title compound was obtained as a powder, melting at 157°–160° C.

Nuclear Magnetic Resonance Spectrum (hexadeuterated dimethyl sulfoxide) δ ppm:

0.79 (3H, triplet, J=7.5 Hz);
0.88 (9H, singlet);
1.16–1.30 (2H, multiplet);
1.39–1.54 (2H, multiplet);
2.59 (2H, triplet, J=7.5 Hz);
4.51 (1H, singlet);
5.46 (1H, doublet, J=16 Hz);
5.73 (1H, doublet, J=16 Hz);
6.21 (1H, doublet, J=4.5 Hz);
6.97 (2H, doublet, J=8.5 Hz);
7.06 (2H, doublet, J=8.5 Hz);
7.51–7.70 (4H, multiplet);

EXAMPLE 76

4-(1-Hydroxy-2-methylpropyl)-2-propyl-1-{4-[2-(tetrazol-5-yl)phenyl]phenyl}methylimidazole-5-carboxamide (Compound No. 5-36)

76(a) 4-Isobutyryl-2-propyl-1-{4-[2-(trityltetrazol-5-yl)phenyl]phenyl}methylimidazole-5-carbonitrile Following a procedure similar to that described in Example 74(a), but using 0.97 g of 4-isobutyryl-2-propylimidazole-5-carbonitrile (prepared as described in Preparation 39), 2.90 g of 4-[2-(trityltetrazol-5-yl)phenyl]benzyl bromide and 0.56 g of potassium t-butoxide, 1.90 g of the title compound was obtained as crystals, melting at 133°–134° C.

Nuclear Magnetic Resonance Spectrum (CDCl$_3$) δ ppm:

0.91 (3H, triplet, J=7.5 Hz);
1.22 (6H, doublet, J=6.5 Hz);
1.69 (2H, sextet, J=7.5 Hz);
2.54 (2H, triplet, J=7.5 Hz);
3.64 (1H, quintet, J=6.5 Hz);
5.12 (2H, singlet);
6.7–8.0 (23H, multiplet).

76(b) 4-(1-Hydroxy-2-methylpropyl)-2-propyl-1-{4-[2-(trityltetrazol-5-yl)phenyl]phenyl}methylimidazole-5-carbonitrile Following a procedure similar to that described in Example 74(b), but using 1.60 g of 4-isobutyryl-2-propyl-1-{4-[2-(trityltetrazol-5-yl)phenyl]phenyl}methylimidazole-5-carbonitrile [prepared as described in step (a) above] and 0.13 g of sodium borohydride, 1.50 g of the title compound was obtained as crystals, melting at 154°–155° C.

Nuclear Magnetic Resonance Spectrum (CDCl$_3$) δ ppm:

0.87 (3H, triplet, J=7.5 Hz);
0.94 (3H, doublet, J=6.5 Hz);
1.00 (3H, doublet, J=6.5 Hz);
1.66 (2H, sextet, J=7.5 Hz);
2.12 (1H, sextet, J=6.5 Hz);
2.50 (2H, triplet, J=7.5 Hz);
4.54 (1H, doublet, J=6 Hz);
5.04 (2H, singlet);
6.85–6.95 (6H, multiplet);
7.14 (2H, doublet, J=8.5 Hz);
7.23–7.53 (14H, multiplet);
7.94 (1H, doublet, J=7.5 Hz);

76(c) 4-(1-Hydroxy-2-methylpropyl)-2-propyl-1-{4-[2-(tetrazol-5-yl)phenyl]phenyl}methylimidazole-5-carbonitrile Following a procedure similar to that described in Example 74(c), but using 1.36 g of 4-(1-hydroxy-2-methylpropyl)-2-propyl-1-{4-[2-(trityltetrazol-5-yl)phenyl]phenyl}methylimidazole-5-carbonitrile [prepared as described in step (b) above] in 75% v/v aqueous acetic acid, 0.87 g of the title compound was obtained as a glass.

Nuclear Magnetic Resonance Spectrum (CDCl$_3$) δ ppm:

0.77 (3H, doublet, J=6.5 Hz);
0.81 (3H, triplet, J=7.5 Hz);
0.93 (3H, doublet, J=6.5 Hz);
1.54 (2H, sextet, J=7.5 Hz);
1.92–2.07 (1H, multiplet);
2.55 (2H, triplet, J=7.5 Hz);
4.33 (1H, doublet, J=7.5 Hz);
5.12 (2H, singlet);
6.96–6.99 (4H, multiplet);
7.35–7.69 (3H, multiplet);
7.71 (1H, doublet, J=7.5 Hz);

76(d) 4-(1-Hydroxy-2-methylpropyl)-2-propyl-1-{4-[2-(tetrazol-5-yl)phenyl]phenyl}methylimidazole-5-carboxamide Following a procedure similar to that described in Example 74(d), but using 0.90 g of 4-(1-hydroxy-2-methylpropyl)-2-propyl-1-{4-[2-(tetrazol-5-yl)phenyl]phenyl}methylimidazole-5-carbonitrile [prepared as described in step (c) above] in a 1N aqueous solution of sodium hydroxide, 0.64 g of the title compound was obtained as a powder, melting at 153°–157° C.

Nuclear Magnetic Resonance Spectrum (hexadeuterated dimethyl sulfoxide) δ ppm:

0.69 (3H, doublet, J=6.5 Hz);
0.81 (3H, triplet, J=6.5 Hz);
0.99 (3H, triplet, J=6.5 Hz);
1.49 (2H, sextet, J=7.5 Hz);
2.05 (1H, quintet, J=6.5 Hz);
2.68 (2H, triplet, J=7.5 Hz);
4.45 (1H, doublet, J=7.5 Hz);
5.55 (1H, doublet, J=16.5 Hz);
5.70 (1H, doublet, J=16.5 Hz);
7.02 (2H, doublet, J=8.5 Hz);
7.08 (2H, doublet, J=8.5 Hz);
7.51–7.71 (4H, multiplet);

EXAMPLE 77

2-Butyl-4-(1-hydroxy-2-methylpropyl)-1-{4-[2-(tetrazol-5-yl)phenyl]phenyl}methylimidazole-5-carboxamide (Compound No. 5-98)

77(a) 2-Butyl-4-isobutyryl-1-{4-[2-(trityltetrazol-5-yl)phenyl]phenyl}methylimidazole-5-carbonitrile Following a procedure similar to that described in Example 74(a), but using 1.42 g of 2-butyl-4-isobutyrylimidazole-5-carbonitrile (prepared as described in Preparation 27), 4.49 g of 4-[2-(trityltetrazol-5-yl)phenyl]benzyl bromide and 0.76 g of potassium t-butoxide, 3.04 g of the title compound was obtained as crystals, melting at 115°–116° C.

Nuclear Magnetic Resonance Spectrum (CDCl₃) δ ppm:

0.87 (3H, triplet, J=7.5 Hz);
1.22 (6H, doublet, J=6.5 Hz);
1.31 (2H, sextet, J=7.5 Hz);
1.63 (2H, quintet, J=7.5 Hz);
2.57 (2H, triplet, J=7.5 Hz);
3.64 (1H, septet, J=7.5 Hz);
5.11 (2H, singlet);
6.90–7.52 (22H, multiplet);
7.96 (1H, doublet, J=9 Hz).

77(b) 2-Butyl-4-(1-hydroxy-2-methylpropyl)-1-{4-[2-(trityltetrazol-5-yl)phenyl]phenyl}methylimidazole-5-carbonitrile Following a procedure similar to that described in Example 74(b), but using 2.00 g of 2-butyl-4-isobutyryl-1-{4-[2-(trityltetrazol-5-yl)phenyl]phenyl}methylimidazole-5-carbonitrile [prepared as described in step (a) above] and 0.22 g of sodium borohydride, 1.68 g of the title compound was obtained as crystals, melting at 127°–128° C.

Nuclear Magnetic Resonance Spectrum (CDCl₃) δ ppm:

0.85 (3H, triplet, J=7.5 Hz);
0.93 (3H, doublet, J=6.5 Hz);
1.00 (3H, doublet, J=6.5 Hz);
1.26 (2H, sextet, J=7.5 Hz);
1.59 (2H, quintet, J=7.5 Hz);
2.13 (1H, sextet, J=6.5 Hz);
2.52 (2H, triplet, J=7.5 Hz);
4.53 (1H, doublet, J=6 Hz);
5.04 (2H, singlet);
6.85–7.52 (2H, multiplet);
7.95 (1H, doublet, J=9 Hz).

77(c) 2-Butyl-4-(1-Hydroxy-2-methylpropyl)-1-{4-[2-(tetrazol-5-yl)phenyl]phenyl}methylimidazole-5-carbonitrile Following a procedure similar to that described in Example 74(c), but using 1.29 g of 2-butyl-4-(1-hydroxy-2-methylpropyl)-1-{4-[2-(trityltetrazol-5-yl)phenyl]phenyl}methylimidazole-5-carbonitrile [prepared as described in step (b) above] in 75% v/v aqueous acetic acid, 0.83 g of the title compound was obtained as a glass.

Nuclear Magnetic Resonance Spectrum (CDCl₃) δ ppm:

0.81 (3H, doublet, J=6.5 Hz);
0.83 (3H, triplet, J=7.5 HZ);
0.95 (3H, doublet, J=6.5 Hz);
1.26 (2H, sextet, J=7.5 Hz);
1.54 (2H, quintet, J=7,5 Hz);
197–2.09 (1H, multiplet);
2.59 (2H, triplet, J=7.5 Hz);
4.37 (1H, doublet, J=6.5 Hz);
5.14 (2H, singlet);
6.98 (2H, doublet, J=8.5 Hz);
7.05 (2H, doublet, J=8.5 Hz);
7.32–7.60 (3H, multiplet);
7.77 (1H, doublet, J=7.5 Hz).

77(d) 2-Butyl-4-(1-hydroxy-2-methylpropyl)-1-{4-[2-(tetrazol-5-yl)phenyl]phenyl}methylimidazole-5-carboxamide Following a procedure similar to that described in Example 74(d), but using 0.34 g of 2-butyl-4-(1-hydroxy-2-methylpropyl)-1-{4-[2-(tetrazol-5-yl)phenyl]phenyl}methylimidazole-5-carbonitrile [prepared as described in step (c) above] in a 1N aqueous solution of sodium hydroxide, 0.24 g of the title compound was obtained as a powder, melting at 155°–157° C.

Nuclear Magnetic Resonance Spectrum (hexadeuterated dimethyl sulfoxide) δ ppm:

0.69 (3H, doublet, J=6.5 Hz);
0.79 (3H, triplet, J=7.5 Hz);
0.93 (3H, doublet, J=6.5 Hz);
1.22 (2H, sextet, J=7.5 Hz);
1.45 (2H, quintet, J=7.5 Hz);
200–2.12 (1H, multiplet);
2.65 (2H, triplet, J=7.5 Hz);
4.41 (2H, doublet, J=8 Hz);
5.53 (1H, doublet, J=16 Hz);
5.71 (1H, doublet, J=16 Hz);
7.00 (2H, doublet, J=8.5 Hz);
7.07 (2H, doublet, J=8.5 Hz);
7.50–7.71 (4H, multiplet).

EXAMPLE 78

(5-Methyl-2-oxo-1,3-dioxolen-4-yl)methyl 4-(1-hydroxy-1-methylethyl)-2-propyl-1-{4-[2-(tetrazol-5-yl)phenyl]phenyl}methylimidazole-5-carboxylate
(Compound No. 2-17)

78(a) (5-Methyl-2-oxo-1,3-dioxolen-4-yl)methyl 4-(1-hydroxy-1-methylethyl)-2-propyl-1-{4-[2-(trityltetrazol-5-yl)phenyl]phenyl}methylimidazole-5-carboxylate A solution of 2.65 g of lithium hydroxide monohydrate in 158 ml of water was added, whilst ice-cooling, to a solution of 30 g of ethyl 4-(1-hydroxy-1-methylethyl)-2-propyl-1-{4-[2-(trityltetrazol-5-yl)phenyl]phenyl}methylimidazole-5-carboxylate [prepared as described in Example 18(a)] in 344 ml of dioxane, and the resulting mixture was stirred at 5°–10° C. for 20 hours. At the end of this time, small pieces of dry ice were added to the mixture, which was then concentrated by evaporation under reduced pressure to a volume of about 100 ml. Ethyl acetate and sodium chloride were added to the concentrate, and the mixture was stirred. The ethyl acetate layer was separated, dried over anhydrous sodium sulfate and concentrated by evaporation under reduced pressure, to give lithium 4-(1-hydroxy-1-methylethyl)-2-propyl-1-{4-[2-(trityltetrazol-5-yl)phenyl]phenyl}methylimidazole-5-carboxylate as a glass. 6.08 g of potassium carbonate were added, whilst ice-cooling, to a solution of whole of this lithium carboxylate in 160 ml of N,N-dimethylacetamide, and then a solution of 11.2 g of 4-chloromethyl-5-methyl-2-oxo-1,3-dioxolene (74% purity) in 26 ml of N,N-dimethylacetamide was added dropwise, whilst ice-cooling, to the mixture. The resulting mixture was stirred at 50° C. for 3 hours. At the end of this time, water and ethyl acetate were added to the reaction mixture, and the ethyl acetate layer was separated, dried over anhydrous magnesium sulfate and concentrated by evaporation under reduced pressure. The residue was crystallized in diisopropyl ether, to give 29.3 g of the title compound as crystals, melting at 98°–100° C. (with decomposition).

The Nuclear Magnetic Resonance Spectrum of this compound was identical with that of the compound obtained as described in Example 61(a).

78(b) (5-Methyl-2-oxo-1,3-dioxolen-4-yl)methyl 4-(1-hydroxy-1-methylethyl)-2-propyl-1-{4-[2-(tetrazol-5-yl)phenyl]phenyl}methylimidazole-5-carboxylate 75 ml of water were added to a suspension of 29.3 g of (5-methyl-2-oxo-1,3-dioxolen-4-yl)methyl 4-(1-hydroxy-1-methylethyl)-2-propyl-1-{4-[2-(trityltetrazol-5-yl)phenyl]phenyl}methylimidazole-5-carboxylate [prepared as described in step (a) above] in 225 ml of acetic acid, and the resulting mixture was stirred at 60° C. for 1.5 hours. At the end of this time, 75 ml of water were added to the mixture, which was then cooled. Precipitated trityl alcohol was removed by filtration, and the filtrate was concentrated by evaporation under reduced pressure. Toluene was added to the residue, and the mixture was again concentrated by evaporation under reduced pressure, to remove the remaining water and acetic acid. The residue was crystallized in ethyl acetate, to give 16.6 g of the title compound as crystals, melting at 177°–180° C. (with decomposition).

The Nuclear Magnetic Resonance Spectrum of this compound was identical with that of the compound obtained as described in Example 61(b).

EXAMPLE 79

(5-Methyl-2-oxo-1,3-dioxolen-4-yl)methyl 4-(1-hydroxy-1-methylethyl)-2-propyl-1-{4-[2-(tetrazol-5-yl)phenyl]phenyl}methylimidazole-5-carboxylate (Compound No. 2-17)

79(a) Ethyl 4-(1-hydroxy-1-methylethyl)-2-propyl-1-{4-[2-(trityltetrazol-5-yl)phenyl]phenyl}methylimidazole-5-carboxylate A solution of 1.00 g of ethyl 1-(2'-cyanobiphenyl-4-yl)methyl-4-(1-hydroxy-1-methylethyl)-2-propylimidazole-5-carboxylate [prepared as described in Example 71(b)] and 100 g of tributyltin azide in 7.5 ml of toluene was stirred at 100° C. for 5 days. 2.5 g of sodium hydrogencarbonate and 20 ml of water were then added to the mixture, and the resulting mixture was stirred at room temperature for 8 hours. At the end of this time, the mixture was diluted with ethyl acetate and acidified with 3N aqueous hydrochloric acid to a pH value of 3. The ethyl acetate layer was separated, dried over anhydrous magnesium sulfate and concentrated by evaporation under reduced pressure, to give ethyl 4-(1-hydroxy-1-methylethyl)-2-propyl-1-{4-[2-(tetrazol-5-yl)phenyl]phenyl}methylimidazole-5-carboxylate as a syrup. 0.80 g of trityl chloride was added to a solution of the whole of this syrup in 15 ml of pyridine, and the mixture was stirred at 60° C. for 4 hours. At the end of this time, the reaction mixture was concentrated by evaporation under reduced pressure, and the residue was purified by column chromatography through silica gel, using a 1:1 by volume mixture of ethyl acetate and hexane as the eluent; it was then crystallized in diisopropyl ether, to give 1.15 g of the title compound as crystals.

The Nuclear Magnetic Resonance Spectrum of this compound was identical with that of the compound obtained as described in Example 18(a).

79(b) (5-Methyl-2-oxo-1,3-dioxolen-4-yl)methyl 4-(1-hydroxy-1-methylethyl)-2-propyl-1-{4-[2-(tetrazol-5-yl)phenyl]phenyl}methylimidazole-5-carboxylate Following-procedures similar to those described in Example 78(a) and 78(b), but using ethyl 4-(1-hydroxy-1-methylethyl)-2-propyl-{4-[2-(trityltetrazol-5-yl)phenyl]phenyl}methylimidazole-5-carboxylate [prepared as described in step (a) above], the title compound was obtained in a 71% yield.

The Nuclear Magnetic Resonance Spectrum of this compound was identical with that of the compound obtained as described in Example 61(b).

EXAMPLE 80

Pivaloyloxymethyl 2-ethyl-4-(1-hydroxy-1-methylethyl)-1-{4-[2-(tetrazole-5-yl)phenyl]phenyl}methylimidazole-5-carboxylate (Compound No. 2-69)

80(a) Pivaloyloxymethyl 2-ethyl-4-(1-hydroxy-1-methylethyl)-1-{4-[2-(trityltetrazole-5-yl)phenyl]phenyl}methylimidazole-5-carboxylate Following a procedure similar to that described in Example 78(a), but using 2.25 g of ethyl 2-ethyl-4-(1-hydroxy-1-methylethyl)-1-{4-[2-(trityltetrazole-5-yl)phenyl]phenyl}methylimidazole-5-carboxylate [prepared as described in Example 68(a)] and using 203 mg of lithium hydroxide monohydrate for hydrolysis and 0.90 g of pivaloyloxymethylchloride for esterification, 2.53 g of the title compound wet obtained as a glass (purified by column chromatography through silica gel using a 1:1 by volume mixture o f ethyl acetate and hexane as the eluent).

Nuclear Magnetic Resonance Spectrum (CDCl$_3$) δ ppm:

1.14 (9H, singlet);

1.19 (3H, triplet, J=7.5 Hz);

1.64 (6H, singlet);

2.50 (2H, quartet, J=7.5 Hz);

5.43 (1H, singlet);

5.43 (1H, singlet);

5.72 (2H, singlet);

6.73 (2H, doublet, J=8 Hz);

6.92–7.49 (20H, multiplet);

7.90 (1H, doublet, J=8.5 Hz).

80(b) Pivaloyloxymethyl 2-ethyl-4-(1-hydroxy-1-methylethyl)-1-{4-[2-(tetrazole-5-yl)phenyl]phenyl}methylimidazole-5-carboxylate Following a procedure similar to that described in Example 78(b), but using 2.53 g of pivaloyloxymethyl 2-ethyl-4-(1-hydroxy-1-methylethyl)-1-}4-[2-(trityltetrazole-5-yl)phenyl]phenyl}methylimidazole-5-carboxylate [prepared as described in step (a) above] and 28 ml of 75% v/v aqueous acetic acid, 1.70 g of the title compound was obtained as a glass.

Nuclear Magnetic Resonance Spectrum (CDCl$_3$) δ ppm:

1.09 (9H, singlet);

1.24 (3H, triplet, J=7.5 Hz);

1.59 (6H, singlet);

2.64 (2H, quartet, J=7.5 Hz);

5.41 (2H, singlet);

5.79 (2H, singlet);

6.86 (2H, doublet, J=8.5 Hz);

7.11 (2H, doublet, J=8.5 Hz);

7.42–7.62 (4H, multiplet).

EXAMPLE 81

(5-Methyl-2-oxo-1,3-dioxolen-4-yl)methyl 2-ethyl-4-(1-hydroxy-1-methylethyl)-1-{4-[2-(tetrazole-5-yl)phenyl]phenyl}methylimidazole-5-carboxylate (Compound No. 2-73)

81(a) (5-Methyl-2-oxo-1,3-dioxolen-4-yl)methyl 2-ethyl-4-(1-hydroxy-1-methylethyl)-1-{4-[2-(trityltetrazole-5- yl)phenyl]phenyl}methylimidazole-5-carboxylate

Following a procedure similar to that described in Example 78(a), but using 2.25 g of ethyl 2-ethyl-4-(1-hydroxy-1-methylethyl)-1-{4-[2-(trityltetrazole-5-yl)phenyl]phenyl}methylimidazole-5-carboxylate [prepared as described in Example 68(a)] and using 203 mg of lithium hydroxide monohydrate for hydrolysis and 0.95 g of 4-chloromethyl-5-methyl-2-oxo-1,3-dioxolene (74% purity) for esterification, 1.23 g of the title compound was obtained as crystals, melting at 145° C.

Nuclear Magnetic Resonance Spectrum (CDCl$_3$) δ ppm:
1.21 (3H, triplet, J=7.5 Hz);
1.63 (6H, singlet);
1.98 (3H, singlet);
2.55 (2H, quartet, J=7.5 Hz);
4.73 (2H, singlet);
5.30 (2H, singlet);
5.59 (1H, singlet);
6.69 (2H, doublet, J=8 Hz);
6.90–7.53 (20H, multiplet);
7.87 (1H, doublet, J=8 Hz).

81(b) (5-Methyl-2-oxo-1,3-dioxolen-4-yl)methyl 2-ethyl-4-(1-hydroxy-1-methylethyl)-1-{4-[2-(tetrazole-5-yl)phenyl]phenyl}methylimidazole-5-carboxylate Following a procedure similar to that described in Example 78(b), but using 1.90 g of (5-methyl-2-oxo-1,3-dioxolen-4-yl)methyl 2-ethyl-4-(1-hydroxy-1-methylethyl)-1-{4-[2-(trityltetrazole-5-yl)phenyl]phenyl}methylimidazole-5-carboxylate [prepared as described in step (a) above] and 20 ml of 75% v/v aqueous acetic acid, 1.23 g of the title compound was obtained as a crystalline powder.

Nuclear Magnetic Resonance Spectrum (CDCl$_3$ and hexadeuterated dimethyl sulfoxide) δ ppm:
1.24 (3H, triplet, J=7.5 Hz);
1.54 (6H, singlet);
2.10 (3H, singlet);
2.69 (2H, quintet, J=7.5 Hz);
4.99 (2H, singlet);
5.44 (2H, singlet);
6.86 (2H, doublet, J=8.5 Hz);
7.08 (2H, doublet, J=8.5 Hz);
7.50–7.65 (4H, multiplet).

EXAMPLE 82

Methyl 4-(1-hydroxy-1-methylethyl)-2-methoxymethyl-1-{4-[2-(tetrazol-5-yl)phenyl]phenyl}methylimidazole-5-carboxylate 82(a) Methyl 4-(1-hydroxy-1-methylethyl)-2-methoxymethyl-1-{4-[2-(trityltetrazol-5-yl)phenyl]phenyl}methylimidazole-5-carboxylate 194 mg of potassium t-butoxide were added, whilst ice-cooling, to a solution of 359 mg of methyl 4-(1-hydroxy-1-methylethyl)-2-methoxymethylimidazole-5-carboxylate [prepared as described in Preparation 42(v)] in 5 ml of N,N-dimethylacetamide, and the resulting mixture was stirred for 15 minutes. An the end of this time, a solution of 1.32 g of 4-[2-(trityltetrazol-5-yl)phenyl]benzyl bromide in 10 ml of N,N-dimethylacetamide was added. The mixture was first stirred at room temperature for 4 hours and then at 50° C. for a further 2 hours. The reaction mixture was then mixed with water and extracted with ethyl acetate. The extract was dried over anhydrous magnesium sulfate, and the solvent was removed by distillation under reduced pressure. The resulting residue was purified by column chromatography through silica gel, using a 1:2 by volume mixture of hexane and ethyl acetate as the eluent, to give 848 mg of the title compound as crystals, melting at 120°–137° C. (with decomposition).

Nuclear Magnetic Resonance Spectrum (CDCl$_3$), δ ppm:
1.64 (6H, singlet);
3.29 (3H, singlet);
3.63 (3H, singlet);
4.36 (2H, singlet);
5.49 (2H, singlet);
5.56 (1H, singlet);
6.76 (2H, doublet, J=8 Hz);
6.95 (6H, doublet, J=7 Hz);
7.09 (2H, doublet, J=8 Hz);
7.23–7.53 (12H, multiplet);
7.89 (1H, doublet, J=7 Hz);

82(b) Methyl 4-(1-hydroxy-1-methylethyl)-2-methoxymethyl-1-{4-[-2-(tetrazol-5-yl)phenyl]phenyl}methylimidazole-5-carboxylate 705 mg of methyl 4-(1-hydroxy-1-methylethyl)-2-methoxymethyl-1-{4-[2-(trityltetrazol-5-yl)phenyl]phenyl}methylimidazole-5-carboxylate [prepared as described in step (a) above] were dissolved in 10 ml of a 25% aqueous solution of acetic acid, and the mixture was stirred at 60° C. for 4 hours. At the end of this time, 10 ml of water were added, whilst ice-cooling, and the trityl alcohol which appeared as crystals was filtered off. The filtrate was concentrated by distillation under reduced pressure, and then acetic acid and water were distilled off as azeotropic mixtures with benzene, to give 460 mg of the title compound as an amorphous powder.

Nuclear Magnetic Resonance Spectrum (CDCl$_3$), δ ppm:
1.54 (6H, singlet);
3.34 (3H, singlet);
3.75 (3H, singlet);
4.45 (2H, singlet);
5.54 (2H, singlet);
6.89 (2H, doublet, J=8 Hz);
7.09 (2H, doublet, J=8 Hz);
7.42–7.62 (3H, multiplet);
7.93 (1H, doublet, J=7 Hz).

EXAMPLE 83

4-(1-Hydroxy-1-methylethyl)-2-methoxymethyl-1-{4-[2-(tetrazol-5-yl)phenyl]phenyl}methylimidazole-5-carboxylic acid A solution of 462 mg of methyl 4-(1-hydroxy-1-methylethyl)-2-methoxymethyl-1-{4-[2-(tetrazol-5-yl)phenyl]phenyl}methylimidazole-5-carboxylate [prepared as described in Example 82(b)] in 4 ml of a 1N aqueous solution of sodium hydroxide was stirred at room temperature for 5 hours. At the end of this time, the insoluble matter was filtered off, and 4 ml of a 1N aqueous solution of hydrochloric acid were added to the filtrate. The resulting crystalline powder was then collected by filtration, to give 338 mg of the title compound, melting at 187° C. (with decomposition at 192°–195° C.).

Nuclear Magnetic Resonance Spectrum (hexadeuterated dimethyl sulfoxide), δ ppm:
1.54 (6H, singlet);
3.20 (3H, singlet);
4.42 (2H, singlet);
5.63 (2H, singlet);
6.96 (2H, doublet, J=8 Hz);
7.05 (2H, doublet, J=8 Hz);
7.52–7.70 (4H, multiplet).

EXAMPLE 84

(5-Methyl-2-oxo-1,3-dioxolen-4-yl)methyl 4-(1-hydroxy-1-methylethyl)-2-methoxymethyl-1-{4-[2-(tetrazol-5-yl)phenyl]phenyl}methylimidazole-5-carboxylate 84(a) (5-Methyl-2-oxo-1,3-dioxolen-4-yl)methyl 4-(1-hydroxy-1-methylethyl)-2-methoxymethyl-1-{4-[2-(trityltetrazol-5-yl)phenyl]phenyl}methylimidazole-5-carboxylate 15 ml of an aqueous solution containing 243 mg of lithium hydroxide monohydrate were added, whilst ice-cooling, to a solution of 2.72 g of methyl 4-(1-hydroxy-1-methylethyl)-2-methoxymethyl-1-{4-[2-(trityltetrazol-5-yl)phenyl]phenyl}methylimidazole-5-carboxylate [prepared as described in Example 82(a)] in 33 ml of dioxane, and the resulting mixture was stirred at 5°–10° C. for 16 hours. At the end of this time, a small piece of dry ice was added to the reaction solution, and the reaction solution was concentrated by distillation under reduced pressure to a volume of about 15 ml. The concentrate was mixed with ethyl acetate and a saturated aqueous solution of sodium chloride and stirred. The resulting reaction mixture was extracted with ethyl acetate, and the extract was dried over anhydrous sodium sulfate. The solvent was then removed by distillation under reduced pressure, to give a glassy salt of lithium 4-(1-hydroxy-1-methylethyl)-2-methoxymethyl-1-{4-[2-(tritylettrazol-5-yl)phenyl]phenyl}methylimidazole-5-carboxylate. The whole of this product was dissolved in 25 ml of N,N-dimethylacetamide, and 533 mg of potassium carbonate were added to the resulting solution, after which a solution of 1.13 g of 4-chloromethyl-5-methyl-2-oxo-1,3-dioxolene (purity degree: 74%) in 5.6 ml of N,N-dimethylacetamide was added dropwise to the mixture, whilst ice-cooling. The mixture was then stirred at 50° C. for 3 hours, after which it was diluted with ethyl acetate and water. The mixture was then extracted with ethyl acetate, and the extract was dried over anhydrous magnesium sulfate and concentrated by distillation under reduced pressure. The resulting crystalline residue was washed with diethyl ether, to give 2.70 g of the title compound, melting at 144°–146° C. (with decomposition).

Nuclear Magnetic-Resonance Spectrum (CDCl$_3$), δ ppm:
1.63 (6H, singlet);
1.98 (3H, singlet);
3.29 (3H, singlet);
4.37 (2H, singlet);
4.72 (2H, singlet);
5.42 (1H, singlet);
5.47 (2H, singlet);
6.70 (2H, doublet, J=8.5 Hz);
6.96 (6H, doublet, J=8.5 Hz);
7.09 (2H, doublet, J=8.5 Hz);
7.24–7.55 (12H, multiplet);
7.88 (1H, doublet, J=7 Hz).

84(b) (5-Methyl-2-oxo-1,3-dioxolen-4-yl)methyl 4-(1-hydroxy-1-methylethyl)-2-methoxymethyl-1-{4-[2-(tetrazol-5-yl)phenyl]phenyl}methylimidazole-5-carboxylate Following a procedure similar to that described in Example 82(b), but detritylating 2.5 g of (5-methyl-2-oxo-1,3-dioxolen-4-yl)methyl 4-(1-hydroxy-1-methylethyl)-2-methoxymethyl-1-{4-[2-(trityltetrazol-5-yl)phenyl]phenyl}methylimidazole-5-carboxylate [prepared as described in step (a) above] with a 25% v/v aqueous solution of acetic acid, 916 mg of the title compound were obtained as crystals, melting at 138°–140° C.

Nuclear Magnetic Resonance Spectrum (CDCl$_3$), δ ppm:
1.64 (6H, singlet);
2.21 (3H, singlet);
3.30 (3H, singlet);
4.44 (2H, singlet);
5.01 (2H, singlet);
5.60 (3H, singlet);
6.83 (2H, doublet, J=8 Hz);
7.11 (2H, doublet, J=8 Hz);
7.43–7.64 (3H, multiplet);
7.89 (1H, doublet, J=8.5 Hz);

EXAMPLE 85

Pivaloyloxymethyl 4-(1-hydroxy-1-methylethyl)-2-methoxymethyl-1-{4-[2-(tetrazol-5-yl)phenyl]phenyl}methylimidazole-5-carboxylate 85(a) Pivaloyloxymethyl 4-(1-hydroxy-1-methylethyl)-2-methoxymethyl-1-{4-[2-(trityltetrazol-5-yl)phenyl]phenyl}methylimidazole-5-carboxylate A solution of 41.9 mg of lithium hydroxide monohydrate in 15 ml of water was added, whilst ice-cooling, to a solution of 0.75 g of methyl 4-(1-hydroxy-1-methylethyl)-2-methoxymethyl-1-{4-[2-(trityltetrazol-5-yl)phenyl]phenyl}methylimidazole-5-carboxylate [prepared as described in Example 82(a)] in 15 ml of dioxane, and the mixture was stirred at room temperature overnight. At the end of this time, a small quantity of dry ice was added to the reaction solution, and the dioxane was removed by distillation under reduced pressure. The residue was then dissolved in a small quantity of an aqueous solution of sodium chloride and ethyl acetate. The ethyl acetate layer was separated, washed with an aqueous solution of sodium chloride and dried over anhydrous sodium sulfate. The solvent was removed by distillation under reduced pressure, and the resulting residue was dried in vacuo at 50° C. for 1 hour. 0.25 g of potassium carbonate were then added to a solution of the resulting residue in 10 ml of N,N-dimethylacetamide, and the mixture was cooled with ice-water. A solution of 0.31 ml of pivaloyloxymethyl chloride in 3 ml of N,N-dimethylacetamide was then added dropwise to the mixture, which was then stirred at 70° C. for 1.5 hours. At the end of this time, water and ethyl acetate were added to the reaction solution. The ethyl acetate layer was separated, washed with water and dried over anhydrous sodium sulfate. The solvent was removed by distillation under reduced pressure, and the resulting residue was purified by column chromatography through silica gel, using a 1:1 by volume mixture of hexane and ethyl acetate as the eluent, to give 0.79 g of the title compound as a foam-like solid.

Nuclear Magnetic Resonance Spectrum (CDCl$_3$), δ ppm:
1.14 (9H, singlet);
1.64 (6H, singlet);
3.28 (3H, singlet);
4.33 (2H, singlet);
5.24 (1H, singlet);
5.50 (2H, singlet);
5.71 (2H, singlet);
6.76 (2H, doublet, J=8 Hz);
6.94 (6H, doublet, J=7.5 Hz);
7.09 (2H, doublet, J=8 Hz);
7.30–7.52 (12H, multiplet);
7.90 (1H, doublet, J=9 Hz).

85(b) Pivaloyloxymethyl 4-(1-hydroxy-1-methylethyl)-2-methoxymethyl-1-{4[2-(tetrazol-5-yl)phenyl]phenyl}methylimidazole-5-carboxylate Following a procedure to that described in Example 82(b), but using a solution of 0.79 g of pivaloyloxymethyl 4-(1-hydroxy-1-ethylmethyl)-2-methoxymethyl-1-{4-[2-(trityltetrazol-5-yl)phenyl]phenyl}methylimidazole-5-carboxylate [prepared as described in step (a) above] as the starting material, 0.44 g of the title compound was obtained as crystals, melting at 71°–72° C.

Nuclear Magnetic Resonance Spectrum (CDCl$_3$), δ ppm:
1.10 (9H, singlet);
1.63 (6H, singlet);
3.33 (3H, singlet);
5.40 (1H, broad singlet);
5.57 (2H, singlet);
5.82 (2H, singlet);
6.91 (2H, doublet, J=8 Hz);
7.14 (2H, doublet, J=8 Hz);
7.28–7.60 (3H, multiplet);
8.08 (1H, doublet, J=8 Hz).

EXAMPLE 86

Ethyl 2-ethoxymethyl-4-(1-hydroxy-1-methylethyl)-1-{4-[2-(tetrazol-5-yl)phenyl]phenyl}methylimidazole-5-carboxylate 86(a) Ethyl 2-ethoxymethyl-4-(1-hydroxy-1-methylethyl)-1-{4-[2-(trityltetrazol-5-yl)phenyl]phenyl}methylimidazole-5-carboxylate 217 mg of potassium t-butoxide were added, whilst ice-cooling, to a solution of 450 mg of ethyl 2-ethoxyethyl-4-(1-hydroxy-1-methylethyl)imidazole-5-carboxylate [prepared as described in Preparation 44(iii)] in 5 ml of N,N-dimethylacetamide, and the mixture was stirred for 30 minutes. At the end of this time, a solution of 1.47 g of 4-[2-(trityltetrazol-5-yl)phenyl]benzyl bromide in 10 ml of N,N-dimethylacetamide was added dropwise to the mixture. The mixture was stirred at room temperature for 2 hours, after which it was mixed with ethyl acetate and water and shaken. The ethyl acetate layer was separated and dried over anhydrous magnesium sulfate. The solvent was removed by distillation under reduced pressure, and the resulting residue was purified by column chromatography through silica gel, using a 1:1 by volume mixture of hexane and ethyl acetate as the eluent, to give 1.2 g of the title compound as an amorphous powder.

Nuclear Magnetic Resonance Spectrum (CDCl$_3$), δ ppm:
1.08 (3H, triplet, J=7 Hz);
1.13 (3H, triplet, J=7 Hz);
1.64 (6H, singlet);
3.44 (2H, quartet, J=7 Hz);
4.14 (2H, quartet, J=7 Hz);
4.39 (2H, singlet);
5.54 (2H, singlet);
5.67 (1H, singlet);
6.75 (2H, doublet, J=8 Hz);
6.96 (6H, doublet, J=7 Hz);
7.09 (2H, doublet, J=8 Hz);
7.23–7.52 (12H, multiplet);
7.88 (1H, doublet, J=7 Hz).

86(b) Ethyl 2-ethoxymethyl-4-(1-hydroxy-1-methylethyl)-1-{4-[2-(tetrazol-5-yl)phenyl]phenyl}methylimidazole-5-carboxylate A solution of 600 mg of ethyl 2-ethoxymethyl-4-(1-hydroxy-1-methylethyl)-1-{4-[2-(trityltetrazol-5-yl)phenyl]phenyl}methylimidazole-5-carboxylate [prepared as described in step (a) above] in 10 ml of a 25% v/v aqueous solution of acetic acid was stirred at 60° C. for 2 hours. 10 ml of water were then added, and the mixture was then cooled with ice. The trityl alcohol which appeared as crystals was filtered off. The filtrate was concentrated by distillation under reduced pressure, and then acetic acid and water were distilled off as azeotropic mixtures with toluene, to give 400 mg of the title compound in an amorphous powder.

Nuclear Magnetic Resonance Spectrum (CDCl$_3$), δ ppm:
1.13 (3H, triplet, J=7 Hz);
1.15 (3H, triplet, J=7 Hz);
3.49 (2H, quartet, J=7 Hz);
4.40 (2H, singlet);
5.57 (2H, singlet);
6.82 (2H, doublet, J=8 Hz);
7.05 (2H, doublet, J=8 Hz);
7.40–7.61 (3H, multiplet);
7.84 (1H, doublet, J=7 Hz).

EXAMPLE 87

2-Ethoxymethyl-4-(1-hydroxy-1-methylethyl)-1-{4-[2-(tetrazol-5-yl)phenyl]phenyl}methylimidazole-5-carboxylic acid A solution of 400 mg of ethyl 2-ethoxymethyl-4-(1-hydroxy-1-methylethyl)-1-{4-[2-(tetrazol-5-yl)phenyl]phenyl}methylimidazole-5-carboxylate [prepared as described in Example 86(b)] in 3.5 ml of a 1N aqueous solution of sodium hydroxide was stirred at room temperature for 1 hour. Insoluble matter was then filtered off, and 3.5 ml of 1N aqueous hydrochloric acid were added to the filtrate. The amorphous powder which precipitated was collected, to give 301 mg of the title compound, melting at 150° C. (with softening).

Nuclear Magnetic Resonance Spectrum (hexadeuterated dimethyl sulfoxide), δ ppm:
0.96 (3H, triplet, J=7 Hz);
1.54 (6H, singlet);
3.40 (2H, quartet, J=7 Hz);
4.45 (2H, singlet);
5.63 (2H, singlet);
6.96 (2H, doublet, J=8 Hz);

7.05 (2H, doublet, J=8 Hz);
7.51–7.70 (4H, multiplet).

EXAMPLE 88

Pivaloyloxymethyl 2-ethoxymethyl-4-(1-hydroxy-1-methylethyl)-1-{4-[2-(tetrazol-5-yl)phenyl]phenyl}methylimidazole-5-carboxylate 88(a) Pivaloyloxymethyl 2-ethoxymethyl-4-(1-hydroxy-1-methylethyl)-1-{4-[2-(trityltetrazol-5-yl)phenyl]phenyl}methylimidazole-5-carboxylate Following a procedure similar to than described in Example 85(a), but using 0.58 g of ethyl 2-ethoxymethyl-4-(1-hydroxy-1-methylethyl)-1-{4-[2-(trityltetrazol-5-yl)phenyl]phenyl}methylimidazole-5-carboxylate [prepared as described in Example 86(a)] as the starting material, 0.45 g of the title compound was obtained as a foam-like solid.

Nuclear Magnetic Resonance Spectrum (CDCl$_3$), δ ppm:
1.14 (9H, singlet);
1.14 (3H, triplet, J=7 Hz);
1.63 (6H, singlet);
3.45 (2H, quartet, J=7 Hz);
4.38 (2H, singlet);
5.25 (1H, singlet);
5.53 (2H, singlet);
5.71 (2H, singlet);
6.77 (2H, doublet, J=8 Hz);
6.95 (6H, doublet, J=7.5 Hz);
7.09 (2H, doublet, J=8 Hz);
7.22–7.36 (10H, multiplet);
7.43–7.49 (2H, multiplet);
7.90 (1H, doublet, J=9 Hz).

88(b) Pivaloyloxymethyl 2-ethoxymethyl-4-(1-hydroxy-1-methylethyl)-1-{4-[2-(tetrazol-5-yl)phenyl]phenyl}methylimidazole-5-carboxylate Following a procedure similar to that described in Example 82(b), but using 0.45 g of pivaloyloxymethyl 2-ethoxymethyl-4-(1-hydroxy-1-methylethyl)-1-{4-[2-(trityltetrazol-5-yl)phenyl]phenyl}methylimidazole-5-carboxylate [prepared as described in step (a) above] as the starting material, 0.28 g of the title compound was obtained as an amorphous powder, melting at 56°–61° C.

Nuclear Magnetic Resonance Spectrum (CDCl$_3$), δ ppm:
1.07 (3H, triplet, J=7 Hz);
1.10 (9H, singlet);
1.61 (6H, singlet);
3.48 (2H, quartet, J=7 Hz);
4.50 (2H, singlet);
5.57 (2H, singlet);
5.80 (2H, singlet);
6.89 (2H, doublet, J=8 Hz);
7.11 (2H, doublet, J=8 Hz);
7.42 (11H, doublet, J=7.5 Hz);
7.52–7.60 (2H, multiplet);
8.01 (1H, doublet, J=7.5 Hz).

EXAMPLE 89

(5-Methyl-2-oxo-1,3-dioxolen-4-yl)methyl 2-ethoxymethyl-4-(1-hydroxy-1-methylethyl)-1-{4-[2-(tetrazol-5-yl)phenyl]phenyl}methylimidazole-5-carboxylate 89(a) (5-Methyl-2-oxo-1,3-dioxolen-4-yl)methyl 2-ethoxymethyl-4-(1-hydroxy-1-methylethyl)-1-{4-[2-(trityltetrazol-5-yl)phenyl]phenyl}methylimidazole-5-carboxylate A solution of 51.5 mg of lithium hydroxide monohydrate in 8 ml of water was added to a solution of 600 mg of ethyl 2-ethoxymethyl-4-(1-hydroxy-1-methylethyl)-1-{4-[2-(trityltetrazol-5-yl)phenyl]phenyl}methylimidazole-5-carboxylate [prepared as described in Example 86(a)] in 19.5 ml of dioxane, whilst ice-cooling, and the mixture was stirred at 5°–10° C. for 16 hours. At the end of this time, a small piece of dry ice was added, and the reaction solution was concentrated by evaporation under reduced pressure down to approximately 8 ml. The concentrate was then mixed with ethyl acetate and sodium chloride and stirred. The ethyl acetate layer was separated and dried over anhydrous sodium sulfate, and the solvent was removed by distillation under reduced pressure, to give lithium 2-ethoxymethyl-4-(1-hydroxyl-methylethyl)-1-{4-[2-(trityltetrazol-5-yl)phenyl]phenyl}methylimidazole-5-carboxylate as an amorphous powder. The whole of this product was dissolved in 6 ml of N,N-dimethylacetamide, and 113 mg of potassium carbonate were added to the resulting solution, after which a solution of 240 mg of 4-chloromethyl-5-methyl-2-oxo-1,3-dioxolene (purity grade: 74%) in 2 ml of N,N-dimethylacetamide was added dropwise to the mixture. The mixture was then stirred at 50° C. for 1 hour, after which it was mixed with ethyl acetate and water. The ethyl acetate layer was separated and dried over anhydrous magnesium sulfate, and then the solvent was removed by distillation under reduced pressure. The resulting residue was purified by column chromatography through silica gel, using a 3:1 by volume mixture of methylene chloride and ethyl acetate as the eluent, to give 548 mg of the title compound as crystals, melting at 129°–130.5° C.

Nuclear Magnetic Resonance Spectrum (CDCl$_3$), δ ppm:
1.14 (3H, triplet, J=7 Hz);
1.64 (6H, singlet);
1.99 (3H, singlet);
3.46 (2H, quartet, J=7 Hz);
4.43 (2H, singlet);
4.73 (2H, singlet);
5.44 (1H, singlet);
5.51 (2H, singlet);
6.72 (2H, doublet, J=8 Hz);
6.98 (6H, doublet, J=7 Hz);
7.10 (2H, doublet, J=8 Hz);
7.25–7.55 (12H, multiplet);
7.88 (1H, doublet, J=8 Hz).

89(b) (5-Methyl-2-oxo-1,3-dioxolen-4-yl)methyl 2-ethoxymethyl-4-(1-hydroxy-1-methylethyl)-1-{4-[2-(tetrazol-5-yl)phenyl]phenyl}methylimidazole-5-carboxylate Following a procedure similar to that described in Example 82(b), but detritylating 456 mg of (5-methyl-2-oxo-1,3-dioxolen-4-yl)methyl 2-ethoxymethyl-4-(1-hydroxy-1-methylethyl)-1-{4-[2-(trityltetrazol-5-yl)phenyl]phenyl}methylimidazole-5-carboxylate [prepared as described in step (a) above] with a 25% v/v aqueous solution of acetic acid, 286 mg of the title compound were obtained as crystals, melting at 166°–167.5° C.

Nuclear Magnetic Resonance Spectrum (CDCl$_3$), δ ppm:
1.03 (3H, triplet, J=7 Hz);
1.64 (6H, singlet);
2.22 (3H, singlet);
3.44 (2H, quartet, J=7 Hz);
4.48 (2H, singlet);

5.01 (2H, singlet);
5.62 (3H, singlet);
6.84 (2H, doublet, J=8 Hz);
7.11 (2H, doublet, J=8 Hz);
7.42–7.61 (3H, multiplet);
7.89 (1H, doublet, J=8.5 Hz).

EXAMPLE 90

Propyl 4-(1-hydroxy-1-methylethyl)-2-propoxymethyl-1-{4-[2-(tetrazol-5-yl)phenyl]phenyl}methylimidazole-5-carboxylate 90(a) Propyl 4-(1-hydroxy-1-methylethyl)-2-propoxymethyl-1-{4-[2-(trityltetrazol-5-yl)phenyl]phenyl}methylimidazole-5-carboxylate Following a procedure similar to that described in Example 82(a), but using 189 mg of propyl 4-(1-hydroxy-1-methylethyl)-2-propoxymethylimidazble-5-carboxylate [prepared as described in Preparation 45(iii)], 78 mg of potassium t-butoxide and 445 mg of 4-[2-(trityltetrazol-5-yl)phenyl]benzyl bromide as starting materials and then purifying the product by column chromatography through silica gel using a 1:1 mixture of hexane and ethyl acetate as the eluent, 395 mg of the title compound were obtained as a foam-like solid.

Nuclear Magnetic Resonance Spectrum (CDCl$_3$), δ ppm:
0.76 (3H, triplet, J=7.5 Hz);
0.86 (3H, triplet, J=7.5 Hz);
1.49 (2H, sextet, J=7.5 Hz);
1.52 (2H, sextet. J=7.5 Hz);
1.66 (6H, singlet);
3.34 (2H, triplet, J=7.5 Hz);
4.06 (2H, triplet, J=7.5 Hz);
4.37 (2H, singlet);
5.56 (2H, singlet);
5.70 (1H, singlet);
6.74 (2H, doublet, J=8.5 Hz);
6.96 (6H, doublet, J=7.5 Hz);
7.09 (2H, doublet, J=8.5 Hz);
6.22–7.51 (12H, multiplet);
7.88 (1H, doublet, J=8 Hz);

90(b) Propyl 4-(1-hydroxy-1-methylethyl)-2-propoxymethyl-1-{4-[2-(tetrazol-5-yl)phenyl]phenyl}methylimidazole-5-carboxylate Following a procedure similar to that described in Example 82(b), but using 394 mg of propyl 4-(1-hydroxy-1-methylethyl)-2-propoxymethyl-1-{4-[2-(trityltetrazol-5-yl)phenyl]phenyl}methylimidazole-5-carboxylate [prepared as described in step (a) above], 259 mg of the title compound were obtained as a foam-like solid.

Nuclear Magnetic Resonance Spectrum (CDCl$_3$), δ ppm:
0.83 (3H, triplet, J=7 Hz);
0.85 (3H, triplet, J=7 Hz);
1.45–1.60 (4H, multiplet);
1.50 (6H, singlet);
3.38 (2H, triplet, J=6.5 Hz);
4.11 (2H, triplet, J=7 Hz);
4.37 (2H, singlet);
5.58 (2H, singlet);
6.79 (2H, doublet, J=8 Hz);
7.04 (2H, doublet, J=8 Hz);
7.39 (1H, doublet, J=8 Hz);
7.46–7.60 (2H, multiplet);
7.78 (1H, doublet, J=7.5 Hz).

EXAMPLE 91

4-(1-hydroxy-1-methylethyl)-2-propoxymethyl-1-{4-[2-(tetrazol-5-yl)phenyl]phenyl}methylimidazole-5-carboxylate 394 mg of propyl 4-(1-hydroxy-1-methylethyl)-2-propoxymethyl-1-{4-[2-(tetrazol-5-yl)phenyl]phenyl}methylimidazole-5-carboxylate [prepared as described in Example 90(b)] were dissolved in a solution of 88 mg of lithium hydroxide monohydrate in 10 ml of a 50% v/v aqueous solution of dioxane, and the mixture was stirred at room temperature for 3 hours. At the end of this time, the reaction solution was concentrated by distillation under reduced pressure, and the dioxane was removed by distillation under reduced pressure. The concentrate was then cooled with ice, and 2.1 ml of 1N aqueous hydrochloric acid were added. The crystals which precipitated were collected by filtration, to give 235 mg of the title compound, melting at 166°–168° C.

Nuclear Magnetic Resonance Spectrum (hexadeuterated dimethyl sulfoxide), δ ppm:
0.75 (3H, triplet, J=7.5 Hz);
1.36 (2H, sextet, J=7.5 Hz);
1.54 (6H, singlet);
3.32 (2H, triplet, J=7.5 Hz);
4.46 (2H, singlet);
5.63 (2H, singlet);
6.96 (2H, doublet, J=8 Hz);
7.05 (2H, doublet, J=8 Hz);
7.50–7.70 (4H, multiplet).

EXAMPLE 92

Isopropyl 4-(1-hydroxy-1-methylethyl)-2-isopropoxymethyl-1-{4-[2-(tetrazol-5-yl)phenyl]phenyl}methylimidazole-5-carboxylate 92(a) Isopropyl 4-(1-hydroxy-1-methylethyl)-2-isopropoxymethyl-1-{4-[2-(trityltetrazol-5-yl)phenyl]phenyl}methylimidazole-5-carboxylate 239 mg of potassium t-butoxide were added, whilst ice-cooling, to a solution of 550 mg of isopropyl 4-(1-hydroxy-1-methylethyl)-2-isopropoxymethylimidazole-5-carboxylate [prepared as described in Preparation 46(iii)] in 6 ml of N,N-dimethylacetamide, and the resulting mixture was stirred for 30 minutes. A solution of 1.62 g of 4-[2-(trityltetrazol-5-yl)phenyl]benzyl bromide in 10 ml of N,N-dimethylacetamide was then added dropwise, and the mixture was stirred at room temperature for 2 hours. At the end of this time, the reaction mixture was mixed with water and ethyl acetate and shaken. The ethyl acetate layer was separated and dried over anhydrous magnesium sulfate, and the solvent was removed by distillation under reduced pressure. The resulting residue was purified by column chromatography through silica gel, using a 1:1 by volume mixture of hexane and ethyl acetate as the eluent, to give 1.47 g of the title compound as an amorphous powder.

Nuclear Magnetic Resonance Spectrum (CDCl$_3$), δ ppm:
1.06 (6H, doublet, J=6.5 Hz);

1.10 (6H, doublet, J=6 Hz);
3.57 (1H, septet, J=6 Hz);
4.38 (2H, singlet);
5.07 (1H, septet, J=6.5 Hz);
5.56 (2H, singlet);
5.80 (1H, singlet);
6.73 (2H, doublet, J=8 Hz);
6.96 (6H, doublet, J=7 Hz);
7.10 (2H, doublet, J=8 Hz);
7.23–7.52 (12H, multiplet);
7.86 (1H, doublet, J=7 Hz).

92(b) Isopropyl 4-(1-hydroxy-1-methylethyl)-2-isopropoxymethyl-1-{4-[2-(tetrazol-5-yl)phenyl]phenyl}methylimidazole-5-carboxylate A solution of 609 mg of isopropyl 4-(1-hydroxy-1-methylethyl)-2-isopropoxymethyl-1-{4-[2-(trityltetrazol-5-yl)phenyl]phenyl}methylimidazole-5-carboxylate [prepared as described in step (a) above] in 10 ml of a 25% v/v aqueous solution of acetic acid was stirred at 60° C. for 2.5 hours. 10 ml of water were then added, after which the mixture was cooled with ice. The trityl alcohol which appeared as crystals was filtered off. The filtrate was concentrated by distillation under reduced pressure, and then acetic acid and water were distilled off as azeotropic mixtures with benzene, to give 398 mg of the title compound as an amorphous powder.

Nuclear Magnetic Resonance Spectrum (CDCl$_3$), δ ppm:
 1.13 (12H, doublet, J=6 Hz);
 1.51 (6H, singlet);
 3.63–3.72 (1H, septet, J=6 Hz);
 4.37 (2H, singlet);
 5.09–5.18 (1H, septet, J=6 Hz);
 5.62 (2H, singlet);
 6.20 (1H, broad singlet);
 6.85 (2H, doublet, J=8 Hz);
 7.12 (2H, doublet, J=8 Hz);
 7.39 (1H, doublet, J=7.5 Hz);
 7.51–7.63 (2H, multiplet);
 7.92 (1H, doublet, J=6.5 Hz);

EXAMPLE 93

4-(1-Hydroxy-1-methylethyl)-2-isopropoxymethyl-1-{4-[2-(tetrazol-5-yl)phenyl]phenyl}methylimidazole-5-carboxylic acid A solution of 393 mg of isopropyl 4-(1-hydroxy-1-methylethyl)-2-isopropoxymethyl-1-{4-[2-(tetrazol-5-yl)phenyl]phenyl}methylimidazole-5-carboxylate [prepared as described in Example 92(b)] in 3 ml of a 1N aqueous solution of sodium hydroxide was stirred at room temperature for 2 hours, and then insoluble matter was filtered off. 3 ml of 1N aqueous hydrochloric acid were added to the filtrate, and the precipitated amorphous powder was collected by filtration, to give 325 mg of the title compound, melting at 153°–161° C. (with softening).

Nuclear Magnetic Resonance Spectrum (hexadeuterated dimethyl sulfoxide), δ ppm:
 1.00 (6H, doublet, J=6 Hz);
 1.54 (6H, singlet);
 3.58 (1H, septet, J=6 Hz);
 4.43 (2H, singlet);
 5.64 (2H, singlet);
 6.96 (2H, doublet, J=8.5 Hz);
 7.05 (2H, doublet, J=8.5 Hz);
 7.50–7.69 (4H, multiplet).

EXAMPLE 94

Methyl 4-(1-hydroxy-1-methylethyl)-2-(1-methoxyethyl)-1-{4-[2-(tetrazol-5-yl)phenyl]phenyl}methylimidazole-5-carboxylate 94(a) Methyl 4-(1-hydroxy-1-methylethyl)-2-(1-methoxyethyl)-1-{4-[2-(trityltetrazol-5-yl)phenyl]phenyl}methylimidazole-5-carboxylate 570 mg of potassium t-butoxide were added, whilst ice-cooling, to a solution of 1.12 g of methyl 4-(1-hydroxy-1-methylethyl)-2-(1-methoxyethyl)imidazole-5-carboxylate [prepared as described in Preparation 47(v)] in 11 ml N,N-dimethylacetamide, and the mixture was stirred for 20 minutes, after which a solution of 3.86 g of 4-[2-trityltetrazol-5-yl)phenyl]benzyl bromide in 20 ml of N,N-dimethylacetamide was added dropwise to the reaction mixture. The reaction mixture was then stirred at room temperature for 2.5 hours and then mixed with ethyl acetate and water. The ethyl acetate layer was separated and dried over anhydrous magnesium sulfate, and the solvent was removed by distillation under reduced pressure. The resulting residue was purified by column chromatography through silica gel, using a 1:1 by volume mixture of hexane and ethyl acetate as the eluent, to give 1.69 g of the title compound as crystals, melting at 131°–133° C.

Nuclear Magnetic Resonance Spectrum (CDCl$_3$), δ ppm:
 1.44 (3H, doublet, J=6.5 Hz);
 1.63 (6H, singlet);
 3.18 (3H, singlet);
 3.57 (3H, singlet);
 4.54 (1H, quartet, J=6.5 Hz);
 5.56 (2H, AB-quartet, Δδ=0.17 ppm, J=16.5 Hz);
 5.59 (1H, singlet);
 6.75 (2H, doublet, J=8 Hz);
 6.97 (6H, doublet, J=7 Hz);
 7.09 (2H, doublet, J=8 Hz);
 7.24–7.52 (12H, multiplet);
 7.83 (1H, doublet, J=7 Hz).

94(b) Methyl 4-(1-hydroxy-1-methylethyl)-2-(1-methoxyethyl)-1-{4-[2-(tetrazol-5-yl)phenyl]phenyl}methylimidazole-5-carboxylate A solution of 600 mg of methyl 4-(1-hydroxy-1-methylethyl)-2-(1-methoxyethyl)-1-{4-[2-(trityltetrazol-5-yl)phenyl]phenyl}methylimidazole-5-carboxylate [prepared as described in step (a) above] in 10 ml of a 25% v/v aqueous solution of acetic acid was stirred at 60° C. for 1.5 hours. The solution was then mixed with 10 ml of water and cooled with ice. The trityl alcohol which appeared as crystals was filtered off. The filtrate was concentrated by distillation under reduced pressure, and then acetic acid and water were distilled off as azeotropic mixtures with toluene, to give 331 mg of the title compound as an amorphous powder.

Nuclear Magnetic Resonance Spectrum (CDCl$_3$), δ ppm:
 1.51 (3H, doublet, J=6.5 Hz);
 1.56 (6H, singlet);
 3.23 (3H, singlet);
 3.71 (3H, singlet);
 4.63 (1H, quartet, J=6.5 Hz);

5.61 (2H, AB-quartet, Δδ=0.10 ppm, J=16.5 Hz);
6.87 (2H, doublet, J=8 Hz);
7.09 (2H, doublet, J=8 Hz);
7.27–7.58 (3H, multiplet);
7.89 (1H, doublet, J=7 Hz).

EXAMPLE 95

4-(1-Hydroxy-1-methylethyl)-2-(1-methoxyethyl)-1-{4-[2-(tetrazol-5-yl)phenyl]phenyl}methylimidazole-5-carboxylate acid A solution of 331 mg of methyl 4-(1-hydroxy-1-methylethyl)-2-(1-methoxyethyl)-1-{4-[2-(tetrazol-5-yl)phenyl]phenyl}methylimidazole-5-carboxylate [prepared as described in Example 94(b)] in 3 ml of a 1N aqueous solution of sodium hydroxide was stirred at room temperature for 2.5 hours. At the end of this time, insoluble matter was filtered off and 3 ml of 1N aqueous hydrochloric acid was added to the filtrate. The amorphous powder which precipitated was collected by filtration, to give 209 mg of the title compound, melting at 174°–85° C. (with softening).

Nuclear Magnetic Resonance Spectrum (hexadeuterated dimethyl sulfoxide), δ ppm:
1.35 (3H, doublet, J=6.5 Hz);
1.55 (6H, singlet);
3.02 (3H, singlet);
4.54 (1H, quartet, J=6.5 Hz);
5.70 (2H, AB-quartet, Δδ=0.14 ppm, J=16.5 Hz);
6.93 (2H, doublet, J=8 Hz);
7.05 (2H, doublet, J=8 Hz);
7.52–7.70 (4H, multiplet).

EXAMPLE 96

Methyl 1-[4-(2-carboxyphenyl)phenyl]methyl-4-(1-hydroxy-1-methylethyl)-2-methoxymethylimidazole-5-carboxylate 96(a) Methyl 1-{4-[2-(t-butoxycarbonyl)phenyl]phenyl}methyl-4-(1-hydroxy-1-methylethyl)-2-methoxymethylimidazole-5-carboxylate Following a procedure similar to that described in Example 82(a), but using 230 mg of methyl 4-(1-hydroxy-1-methylethyl)-2-methoxymethylimidazole-5-carboxylate [prepared as described in Preparation 42(v)], 119 mg of potassium t-butoxide and 420 mg of 4-[2-(t-butoxycarbonyl)phenyl]benzyl bromide and then purifying the product by column chromatography through silica gel using a 1:2 by volume mixture of hexane and ethyl acetate as the eluent, 468 mg of the title compound were obtained as a syrup.

Nuclear Magnetic Resonance Spectrum (CDCl$_3$), δ ppm:
1.24 (9H, singlet);
1.63 (6H, singlet);
3.38 (3H, singlet);
3.79 (3H, singlet);
4.54 (2H, singlet);
5.54 (1H, singlet);
5.62 (2H, singlet);
6.99 (2H, doublet, J=8 Hz);
7.26–7.48 (5H, multiplet);
7.77 (1H, doublet, J=7.5 Hz).

96(b) Methyl 1-[4-(2-carboxyphenyl)phenyl]methyl-4-(1-hydroxy-1-methylethyl)-2-methoxymethylimidazole-5-carboxylate 468 mg of methyl 1-{4-[2-(t-butoxycarbonyl)phenyl]phenyl}methyl-4-(1-hydroxy-1-methylethyl)-2-methoxymethylimidazole-5-carboxylate [prepared as described in step (a) above] were dissolved in 10 ml of a 4N solution of hydrogen chloride in dioxane, and the mixture was left at room temperature for 2 hours. At the end of this time, the reaction solution was concentrated and dried by evaporation under reduced pressure, to give 445 mg of the hydrochloride of the title compound as a foam-like solid.

Nuclear Magnetic Resonance Spectrum (CDCl$_3$), δ ppm:
1.72 (6H, singlet);
3.41 (3H, singlet);
3.80 (3H, singlet);
4.93 (2H, singlet);
5.65 (2H, singlet);
7.04 (2H, doublet, J=8.5 Hz);
7.32 (3H, doublet, J=8.5 Hz);
7.39–7.56 (2H, multiplet);
7.93 (1H, doublet, J=6.5 Hz).

EXAMPLE 97

1-[4-(2-Carboxyphenyl)phenyl]methyl-4-(1-hydroxy-1-methylethyl)-2-methoxymethylimidazole-5-carboxylic acid A procedure similar to that described in Example 91 was repeated, except that 445 mg of methyl 1-[4-(2-carboxyphenyl)phenyl]methyl-4-(1-hydroxy-1-methylethyl)-2-methoxymethylimidazole-5-carboxylate hydrochloride [prepared as described in Example 96(b)] were employed, to obtain 250 mg of the title compound as crystals, melting at 164°–165° C.

Nuclear Magnetic Resonance Spectrum (hexadeuterated dimethyl sulfoxide), δ ppm:
1.55 (6H, singlet);
3.25 (3H, singlet);
4.47 (2H, singlet);
5.67 (2H, singlet);
7.06 (2H, doublet, J=8 Hz);
7.28 (2H, doublet, J=8 Hz);
7.36 (1H, doublet, J=7.5 Hz);
7.40–7.58 (2H, multiplet);
7.70 (1H, doublet, J=8.5 Hz).

EXAMPLE 98

Ethyl 1-[4-(2-carboxyphenyl)phenyl]methyl-2-ethoxymethyl-4-(1-hydroxy-1-methylethyl)imidazole-5-carboxylate 98(a) Ethyl 1-{4-[2-(t-butoxycarbonyl)phenyl]phenyl}methyl-2-ethoxymethyl-4-(1-hydroxy-1-methylethyl)imidazole-5-carboxylate A procedure similar to that described in Example 82(a) was repeated, except that 315 mg of ethyl 4-(1-hydroxy-1-methylethyl)-2-ethoxymethylimidazole-5-carboxylate [prepared as described in Preparation 44(iii)], 145 mg of potassium t-butoxide and 510 mg of 4-[2-(t-butoxycarbonyl)phenyl]benzyl bromide were employed and the product was purified by column chromatography through silica gel using a 1:1 by volume mixture of hexane and ethyl acetate as the eluent, to obtain 600 mg of the title compound as a syrup.

Nuclear Magnetic Resonance Spectrum (CDCl$_3$), δ ppm:
1.18 (3H, triplet, J=7 Hz);
1.26 (9H, singlet);
1.26 (3H, triplet, J=7 Hz);
1.64 (6H, singlet);
3.54 (2H, quartet, J=7 Hz);
4.27 (2H, quartet, J=7 Hz);
4.57 (2H, singlet);
5.65 (1H, singlet);
5.67 (2H, singlet);
6.99 (2H, doublet, J=8 Hz);
7.25–7.29 (3H, multiplet);
7.38–7.47 (2H, multiplet);
7.76 (1H, doublet, J=7.5 Hz).

98(b) Ethyl 1-[4-(2-carboxyphenyl)phenyl]methyl-2-ethoxymethyl-4-(1-hydroxy-1-methylethyl)imidazole-5-carboxylate Following a procedure similar to that described in Example 96(b), but using 600 mg of ethyl 1-{4-[2-(t-butoxycarbonyl)phenyl]phenyl}methyl-2-ethoxymethyl-4-(1-hydroxy-1-methylethyl)imidazole-5-carboxylate [prepared as described in step (a) above], 585 mg of the hydrochloride of the title compound were obtained as a foam-like solid.

Nuclear Magnetic Resonance Spectrum (CD$_3$OD), δ ppm:
1.15 (3H, triplet, J=7 Hz);
1.23 (3H, triplet, J=7 Hz);
1.69 (6H, singlet);
3.61 (2H, quartet, J=7 Hz);
4.30 (2H, quartet, J=7 Hz);
5.78 (2H, singlet);
5.80 (2H, singlet);
7.18 (2H, doublet, J=8 Hz);
7.29–7.58 (5H, multiplet);
7.82 (1H, doublet, J=8 Hz).

EXAMPLE 99

1-[4-(2-Carboxyphenyl)phenyl]methyl-2-ethoxymethyl-4-(1-hydroxy-1-methylethyl)imidazole-5-carboxylic acid A procedure similar to that described in Example 91 was repeated, except that 585 mg of ethyl 1-[4-(2-carboxyphenyl)phenyl]methyl-2-ethoxymethyl-4-(1-hydroxy-1-methylethyl)imidazole-5-carboxylate hydrochloride [prepared as described in Example 98(b)] were employed, to obtain 465 mg of the title compound as a crystalline powder, melting at 166°–169° C.

Nuclear Magnetic Resonance Spectrum (hexadeuterated dimethyl sulfoxide), δ ppm:
1.01 (3H, triplet, J=7 Hz);
1.55 (6H, singlet);
3.44 (2H, quartet, J=7 Hz);
4.50 (2H, singlet);
5.68 (2H, singlet);
7.06 (2H, doublet, J=8 Hz);
7.28 (2H, doublet, J=8 Hz);
7.35 (1H, doublet, J=7 Hz);
7.41–7.58 (2H, multiplet);
7.70 (1H, doublet, J=8.5 Hz).

EXAMPLE 100

Propyl 1-[4-(2-carboxyphenyl)phenyl]methyl-4-(1-hydroxy-1-methylethyl)-2-propoxymethylimidazole-5-carboxylate 100(a) Propyl 1-{4-[2-(t-butoxycarbonyl)phenyl]phenyl}methyl-4-(1-hydroxy-1-methylethyl)-2-propoxymethylimidazole-5-carboxylate Following a procedure similar to that described in Example 82(a), but using 0.20 g of propyl 4-(1-hydroxy-1-methylethyl)-2-propoxymethylimidazole-5-carboxylate [prepared as described in Preparation 45(iii)], 82 mg of potassium t-butoxide and 290 mg of 4-[2-(t-butoxycarbonyl)phenyl]benzyl bromide and then purifying the product by column chromatography through silica gel using a 1:1 by volume mixture of hexane and ethyl acetate as the eluent, 293 mg of the title compound were obtained as a syrup.

Nuclear Magnetic Resonance Spectrum (CDCl$_3$), δ ppm:
0.89 (6H, triplet, J=7.5 Hz);
1.26 (9H, singlet);
1.53–2.59 (4H, multiplet);
1.64 (6H, singlet);
3.44 (2H, triplet, J=7.5 Hz);
4.17 (2H, triplet, J=7.5 Hz);
4.56 (2H, singlet);
5.67 (1H, singlet);
5.69 (2H, singlet);
6.98 (2H, doublet, J=8.5 Hz);
7.27 (3H, doublet, J=8.5 Hz);
7.38–7.47 (2H, multiplet);
7.76 (1H, doublet, J=6.5 Hz).

100(b) Propyl 1-[4-(2-carboxyphenyl)phenyl]methyl-4-(1-hydroxy-1-methylethyl)-2-propoxymethylimidazole-5-carboxylate A procedure similar to that described in Example 96(b) was repeated, except that 293 mg of propyl 1-[4-(2-carboxyphenyl)phenyl]methyl-4-(1-hydroxy-1-methylethyl)-2-propoxymethylimidazole-5-carboxylate [prepared as described in step (a) above] were employed, to obtain 281 mg of the hydrochloride of the title compound as a foam-like solid.

Nuclear Magnetic Resonance Spectrum (CDCl$_3$), δ ppm:
0.85 (3H, triplet, J=7.5 Hz);
0.88 (3H, triplet, J=7.5 Hz);
1.53–1.65 (4H, multiplet);
1.75 (6H, singlet);
3.54 (2H, doublet, J=6.5 Hz);
4.19 (2H, triplet, J=6.5 Hz);
4.98 (2H, singlet);
5.70 (2H, singlet);
7.01 (2H, doublet, J=8 Hz);
7.24–7.39 (3H, multiplet);
7.41–7.56 (2H, multiplet);
7.92 (1H, doublet, J=7.5 Hz).

EXAMPLE 101

1-[4-(2-Carboxyphenyl)phenyl]methyl-4-(1-hydroxy-1-methylethyl)-2-propoxymethylimidazole-5-carboxylic acid A procedure similar to that described in Example 10 was repeated, except that 281 mg of propyl 1-[4-(2-carboxyphenyl)phenyl]methyl-4-(1-hydroxy-1-methylethyl)-2-propoxymethylimidazole-5-carboxylate hydrochloride [prepared as described in Example 100(b)] were employed, to obtain 212 mg of the title compound as a crystalline powder, melting at 109°–111° C.

Nuclear Magnetic Resonance Spectrum (hexadeuterated dimethyl sulfoxide), δ ppm:

0.78 (3H, triplet, J=7.5 Hz);
1.41 (2H, sextet, J=7.5 Hz);
1.56 (6H, singlet);
3.36 (2H, triplet, J=7.5 Hz);
4.51 (2H, singlet);
5.69 (2H, singlet);
7.06 (2H, doublet, J=8 Hz);
7.28 (2H, doublet, J=8 Hz);
7.34 (1H, doublet, J=7.5 Hz);
7.41–7.58 (2H, multiplet);
7.70 (1H, doublet, J=6,5 Hz).

EXAMPLE 102

Ethyl 4-(1-hydroxy-1-methylethyl)-2-methylthiomethyl-1-{4-[2-(tetrazol-5-yl)phenyl]phenyl}methylimidazole-5-carboxylate 102(a) Ethyl 2-acetoxymethyl-4-(1-hydroxy-1-methylethyl]-1-{4-[2-(trityltetrazol-5-yl)phenyl]phenyl}methylimidazole-5-carboxylate Following a procedure similar to that described in Example 82(a), but using 730 mg of ethyl 2-acetoxymethyl-4-(1-hydroxy-1-methylethyl)imidazole-5-carboxylate [prepared as described in Preparation 48(iii)], 320 mg of potassium t-butoxide and 2.11 g of 4-[2-(trityltetrazol-5-yl)phenyl]benzyl bromide and then purifying the product by column chromatography through silica gel using a 2:1 by volume mixture of hexane and ethyl acetate, 1.23 g of the title compound were obtained as a foam-like solid.

Nuclear Magnetic Resonance Spectrum (CDCl$_3$), δ ppm:

1.08 (3H, triplet, J=7 Hz);
1.66 (6H, singlet);
1.84 (3H, singlet);
4.15 (2H, quartet, J=7 Hz);
5.04 (2H, singlet).
5.49 (2H, singlet);
5.58 (1H, singlet);
6.76 (2H, doublet, J=8.5 Hz);
6.98 (6H, doublet, J=7.5 Hz);
7.11 (2H, doublet, J=8.5 Hz);
7.23–7.37 (10H, multiplet);
7.41–7.53 (2H, multiplet);
7.84 (1H, doublet, J=8 Hz).

102(b) Ethyl 2-hydroxymethyl-4-(1-hydroxy-1-methylethyl)-1-{4-[2-(trityltetrazol-5-yl)phenyl]phenyl}methylimidazole-5-carboxylate 0.75 ml of a 0.15N solution of sodium ethoxide in ethanol was added to a solution of 1.69 g of ethyl 2-acetoxymethyl-4-(1-hydroxy-1-methylethyl)-1-{4-[2-(trityltetrazol-5-yl)phenyl]phenyl}methylimidazole-5-carboxylate [prepared as described in Example 102(a)] in 15 ml of ethanol, and the mixture was stirred at room temperature for 5 minutes. The reaction solution was then concentrated by evaporation under reduced pressure, ethyl acetate and water were added to the residue, and the ethyl acetate layer was separated. This ethyl acetate layer was washed with an aqueous solution of sodium chloride and then dried over anhydrous sodium sulfate, after which it was concentrated by evaporation under reduced pressure. The resulting residue was purified by recrystallization from a mixture of diethyl ether and diisopropyl ether, to give 1.47 g of the title compound as crystals, melting at 151°–152° C.

Nuclear Magnetic Resonance Spectrum (CDCl$_3$), δ ppm:

1.09 (3H, triplet, J=7 Hz);
1.62 (6H, singlet);
4.17 (2H, quartet, J=7 Hz);
4.48 (2H, singlet);
5.46 (2H, singlet);
5.66 (1H, singlet);
6.74 (2H, doublet, J=8.5 Hz);
6.94 (6H, doublet, J=8 Hz);
7.10 (2H, doublet, J=8.5 Hz);
7.22–7.53 (12H, multiplet);
7.91 (1H, doublet, J=9 Hz).

102(c) Ethyl 4-(1-hydroxy-1-methylethyl)-2-methanesulfonyloxymethyl-1-{4-[2-(trityltetrazol-5-yl)phenyl]phenyl}methylimidazole-5-carboxylate 0.371 ml of N,N-diisopropyl-N-ethylamine and then 0.371 g of methanesulfonic anhydride were added, under a nitrogen atmosphere, to a solution of 500 mg of ethyl 2-hydroxymethyl-4-(1-hydroxy-1-methylethyl)-1-{4-[2-(trityltetrazol-5-yl)phenyl]phenyl}methylimidazole-5-carboxylate [prepared as described in step (b) above] in 10 ml of tetrahydrofuran. The mixture was then stirred at room temperature for 1.5 hours, after which it was mixed with ethyl acetate and an aqueous solution of sodium hydrogencarbonate. The ethyl acetate layer was separated, dried over anhydrous magnesium sulfate and concentrated by evaporation under reduced pressure, to give 610 mg of the title compound as an amorphous powder. The compound was employed in the subsequent reactions without any further purification.

Nuclear Magnetic Resonance Spectrtun (CDCl$_3$), δ ppm:

1.11 (3H, triplet, J=7 Hz);
1.65 (6H, singlet);
2.83 (3H, singlet);
4.20 (2H, quartet, J=7 Hz);
5.09 (2H, singlet);
5.47 (1H, broad singlet);
5.53 (2H, singlet);
6.77 (2H, doublet, J=8 Hz);
6.97 (6H, doublet, J=7 Hz);
7.12 (2H, doublet, J=8 Hz);
7.24–7.52 (12H, multiplet);
7.87 (1H, doublet, J=7 Hz).

102(d) Ethyl 4-(1-hydroxy-1-methylethyl)-2-methylthiomethyl-1-{4-[2-(trityltetrazol-5-yl)phenyl]phenyl}methylimidazole-5-carboxylate 50.3 ml of sodium methanethiolate were added to a solution of 610 mg of ethyl 4-(1-hydroxy-1-methylethyl)-

2-methanesulfonyloxymethyl-1-{4-[2-(trityltetrazol-5-yl)phenyl]phenyl}methylimidazole-5-carboxylate [prepared as described in step (c) above] in 6 ml of N,N-dimethylformamide. The mixture was stirred at room temperature for 45 minutes, after which it was mixed with ethyl acetate and water. The ethyl acetate layer was separated, dried over anhydrous magnesium sulfate and then concentrated by evaporation under reduced pressure, after which the residue was purified by column chromatography through silica gel, using a 10:1 by volume mixture of methylene chloride and ethyl acetate as the eluent, to give 338 mg of the title compound as crystals, melting at 174.5°–176.5° C. (with decomposition).

Nuclear Magnetic Resonance Spectrum (CDCl$_3$), δ ppm:
1.10 (3H, triplet, J=7 Hz);
1.65 (6H, singlet);
2.06 (3H, singlet);
3.46 (2H, singlet);
4.17 (2H, quartet, J=7 Hz);
5.49 (2H, singlet);
5.72 (1H, singlet);
6.73 (2H, doublet, J=8 Hz);
6.93 (6H, doublet, J=7 Hz);
7.10 (2H, doublet, J=8 Hz);
7.23–7.52 (12H, multiplet);
7.92 (1H, doublet, J=7 Hz).

102(e) Ethyl 4-(1-hydroxy-1-methylethyl)-2-methylthiomethyl-1-{4-[2-(tetrazol-5-yl)phenyl]phenyl}methylimidazole-5-carboxylate A mixture of 300 mg of ethyl 4-(1-hydroxy-1-methylethyl)-2-methylthiomethyl-1-{4-[2-(trityltetrazol-5-yl)phenyl]phenyl}methylimidazole-5-carboxylate [prepared as described in step (d) above] and 5 ml of a 25% v/v aqueous solution of acetic acid was stirred at 60° C. for 1 hour. At the end of this time, the resulting solution was mixed with 5 ml of water and cooled with ice. The trityl alcohol which appeared as crystals was filtered off, and the filtrate was concentrated by evaporation under reduced pressure. Acetic acid and water in the residue were removed by distillation as azeotropic mixtures with toluene, to give 217 mg of the title compound as an amorphous powder.

Nuclear Magnetic Resonance Spectrum (CDCl$_3$), δ ppm:
1.18 (3H, triplet, J=7.5 Hz);
1.55 (6H, singlet);
2.09 (3H, singlet);
3.63 (2H, singlet);
4.24 (2H, quartet, J=7.5 Hz);
5.58 (2H, singlet);
6.89 (2H, doublet, J=8 Hz);
7.12 (2H, doublet, J=8 Hz);
7.41–7.62 (3H, multiplet);
7.95 (1H, doublet, J=7 Hz).

EXAMPLE 103

4-(1-Hydroxy-1-methylethyl)-2-methylthiomethyl-1-{4-[2-(tetrazol-5-yl)phenyl]phenyl}methylimidazole-5-carboxylic acid A mixture of 217 mg of ethyl 4-(1-hydroxy-1-methylethyl)-2-methylthiomethyl-1-{4-[2-(tetrazol-5-yl)phenyl]phenyl}methylimidazole-5-carboxylate [prepared as described in Example 102(e)] and 3.2 ml of a 0.5N aqueous solution of sodium hydroxide was stirred at room temperature for 1 hour. At the end of this time, the insoluble matter was filtered off, and the filtrate was mixed with 1.6 ml of a 1N aqueous solution of hydrochloric acid. The amorphous powder which had precipitated was collected by filtration, to give 155 mg of the title compound, melting at 172°–181° C. (with softening).

Nuclear Magnetic Resonance Spectrum (hexadeuterated dimethyl sulfoxide), δ ppm:
1.54 (6H, singlet);
2.05 (3H, singlet);
3.73 (2H, singlet);
5.66 (2H, singlet);
6.96 (2H, doublet, J=8 Hz);
7.06 (2H, doublet, J=8 Hz);
7.51–7.69 (4H, multiplet).

EXAMPLE 104

Pivaloyloxymethyl 1-[4-(2-carboxyphenyl)phenyl]methyl-2-ethoxymethyl-4-(1-hydroxy-1-methylethyl)imidazole-5-carboxylate 104(a) Pivaloyloxymethyl 1-{4-[2-(t-butoxycarbonyl)phenyl]phenyl}methyl-2-ethoxymethyl-4-(1-hydroxy-1-methylethyl)imidazole-5-carboxylate A procedure similar to that described in Example 85(a) was repeated, except that 374 mg of ethyl 1-{4-[2-(t-butoxycarbonyl)phenyl]phenyl}methyl-2-ethoxymethyl-4-(1-hydroxy-1-methylethyl)imidazole-5-carboxylate [prepared as described in Example 98(a)] were employed, to obtain 396 mg of the title compound as a syrup.

Nuclear Magnetic Resonance Spectrum (CDCl$_3$), δ ppm:
1.18 (9H, singlet);
1.20 (3H, triplet, J=7.5 Hz);
1.24 (9H, singlet);
1.63 (6H, singlet);
3.56 (2H, quartet, J=7.5 Hz);
4.58 (2H, singlet);
5.24 (1H, singlet);
5.67 (2H, singlet);
5.84 (2H, singlet);
7.03 (2H, doublet, J=8 Hz);
7.25–7.29 (3H, multiplet);
7.38–7.48 (2H, multiplet);
7.77 (1H, doublet, J=6 Hz).

104(b) Pivaloyloxymethyl 1-[4-(2-carboxyphenyl)phenyl]methyl-2-ethoxymethyl-4-(1-hydroxy-1-methylethyl)imidazole-5-carboxylate Following a procedure similar to that described in Example 96(b) but using 396 mg of pivaloyloxymethyl 1-{4-[2-(t-butoxycarbonyl)phenyl]phenyl}methyl-2-ethoxymethyl-4-(1-hydroxy-1-methylethyl)imidazole-5-carboxylate [prepared as described in step (a) above], 312 mg of the hydrochloride of the title compound were obtained as an amorphous powder, melting at 65° C. (with softening).

Nuclear Magnetic Resonance Spectrum (hexadeuterated dimethyl sulfoxide), δ ppm:
1.02 (3H, triplet, J=7 Hz);
1.09 (9H, singlet);
1.55 (6H, singlet);
3.48 (2H, quartet, J=7 Hz);

4.71 (2H, singlet);
5.62 (2H, singlet);
5.85 (2H, singlet);
7.15 (2H, doublet, J=8 Hz);
7.29–7.35 (3H, multiplet);
7.43–7.59 (2H, multiplet);
7.73 (1H, doublet, J=6.5 Hz).

EXAMPLE 105

Ethyl 4-(1-hydroxy-1-methylethyl)-2-methylthio-1-{4-[2-(tetrazol-5-yl)phenyl]phenyl}methylimidazole-5-carboxylate 105(a) Ethyl 4-(1-hydroxy-1-methylethyl)-2-methylthio-1-{4-[2-(tetrazol-5-yl)phenyl]phenyl}methylimidazole-5-carboxylate 242 mg of potassium t-butoxide were added, whilst ice-cooling, to a solution of 500 mg of ethyl 4-(1-hydroxy-1-methylethyl)-2-methylthioimidazole-5-carboxylate [prepared as described in Preparation 49(ii)] in 10 ml of N,N-dimethylacetamide and stirred for 30 minutes. 1.26 g of 4-[2-(trityltetrazol-5-yl)phenyl]benzyl bromide were then added in portions to the resulting solution, and the mixture was stirred at room temperature for 4 hours. An the end of this time, the reaction mixture was mixed with ethyl acetate and water and shaken. The ethyl acetate layer was separated, washed with water and then with a saturated aqueous solution of sodium chloride and dried over anhydrous magnesium sulfate. The solvent was removed by distillation under reduced pressure, and the resulting residue was purified by column chromatography through silica gel, using a 1:5 by volume mixture of ethyl acetate and hexane as the eluent, to give 940 mg of the title compound as colorless crystals, melting at 125°–127° C.

Nuclear Magnetic Resonance Spectrum (CDCl$_3$), δ ppm:

1.11 (3H, triplet, J=7.5 Hz);
1.63 (6H, singlet);
2.61 (3H, singlet);
4.16 (2H, quartet, J=7.5 Hz);
5.34 (2H, singlet);
5.75 (1H, singlet).
6.80–7.90 (23H, multiplet).

105(b) Ethyl 4-(1-hydroxy-1-methylethyl)-2-methylthio-1-{4-[2-(tetrazol-5-yl)phenyl]phenyl}methylimidazole-5-carboxylate 900 mg of ethyl 4-(1-hydroxy-1-methylethyl)-2-methylthio-1-{4-[2-(trityltetrazol-5-yl)phenyl]phenyl}metylimidazole-5-carboxylate [prepared as described in step (a) above] were added to 10 ml of a 25% v/v aqueous solution of acetic acid, and the mixture was stirred at 60° C. for 1 hour. At the end of this time, the reaction mixture was cooled, and the crystals of trityl alcohol which appeared were filtered off. These crystals were washed with a 50% v/v aqueous solution of acetic acid, and the filtrate and the washings were mixed. The resulting mixture was concentrated by evaporation under reduced pressure, and the resulting residue was crystallized from ethyl acetate, to give 529 mg of the title compound as crystals, melting at 209°–210° C.

Nuclear Magnetic Resonance Spectrum (hexadeuterated dimethyl sulfoxide), δ ppm:

1.07 (3H, triplet, J=7.5 Hz);
1.49 (6H, singlet);
2.62 (3H, singlet);
4.16 (2H, quartet, J=7.5 Hz);
5.37 (2H, singlet);
5.41 (1H, singlet);
6.95 (2H, doublet, J=8 Hz);
7.08 (2H, doublet, J=8 Hz);
7.50–7.72 (4H, multiplet).

EXAMPLE 106

4-(1-Hydroxy-1-methylethyl)-2-methylthio-1-{4-[2-(tetrazol-5-yl)phenyl]phenyl}methylimidazole-5-carboxylic acid 500 mg of ethyl 4-(1-hydroxy-1-methylethyl)-2-methylthio-1-{4-[2-(tetrazol-5-yl)phenyl]phenyl}methylimidazole-5-carboxylate [prepared as described in Example 105(b)] and 131 mg of lithium hydroxide monohydrate were added to a mixture of 5 ml of water and 5 ml of dioxane, and the resulting mixture was stirred at room temperature for 24 hours. At the end of this time, the reaction mixture was concentrated by evaporation under reduced pressure, and the resulting residue was dissolved in water. 3.1 ml of 1N aqueous hydrochloric acid were then added, and the crystals which appeared were collected by filtration. These crystals were dissolved in ethyl acetate, and water was added to induce crystallization. The crystals which appeared were collected by filtration and washed with ethyl acetate and water, to give 290 mg of the title compound as crystals, melting at 169°–171° C. (with decomposition).

Nuclear Magnetic Resonance Spectrum (hexadeuterated dimethyl sulfoxide), δ ppm:

1.55 (6H, singlet);
2.59 (3H, singlet);
5.51 (2H, singlet);
7.01 (2H, doublet, J=8 Hz);
7.07 (2H, doublet, J=8 Hz);
7.47–7.75 (4H, multiplet).

EXAMPLE 107

Ethyl 2-ethylthio-4-(1-hydroxy-1-methylethyl)-1-{4-[2-(tetrazol-5-yl)phenyl]phenyl}methylimidazole-5-carboxylate 107(a) Ethyl 2-ethylthio-4-(1-hydroxy-1-methylethyl)-1-{4-[2-(trityltetrazol-5-yl)phenyl]phenyl}methylimidazole-5-carboxylate 478 mg of potassium t-butoxide were added to a solution of 1.00 g of ethyl 2-ethylthio-4-(1-hydroxy-1-methylethyl)imidazole-5-carboxylate [prepared as described in Preparation 50(ii)] in 20 ml of N,N-dimethylacetamide, whilst ice-cooling, and the mixture was stirred for 30 minutes. At the end of this time, 2.59 g of 4-[2-(trityltetrazol-5-yl)phenyl]benzyl bromide were added in portions to the mixture. Following a procedure similar to that described in Example 105(a) and purifying the residue by column chromatography through silica gel using a 1:5 by volume mixture of ethyl acetate and hexane as the eluent, 2.22 g of the title compound were obtained as an amorphous powder.

Nuclear Magnetic Resonance Spectrum (CDCl$_3$), δ ppm:

1.10 (3H, triplet, J=7.5 Hz);
1.34 (3H, triplet, J=7.5 Hz);

1.63 (6H, singlet);

3.19 (2H, quartet, J=7.5 Hz);

4.17 (2H, quartet, J=7.5 Hz);

5.35 (2H, singlet);

5.78 (1H, singlet);

6.78–7.88 (23H, multiplet).

107(b) Ethyl 2-ethylthio-4-(1-hydroxy-1-methylethyl)-1-{4-[2-(tetrazol-5-yl)phenyl]phenyl}methylimidazole-5-carboxylate 2.22 g of ethyl 2-ethylthio-4-(1-hydroxy-1-methylethyl)-1-{4-[2-(trityltetrazol-5-yl)phenyl]phenyl}methylimidazole-5-carboxylate [prepared as described in step (a) above] were added to 20 ml of a 25% v/v aqueous solution of acetic acid, and the mixture was stirred at 60° C. for 2 hours. The reaction mixture was then concentrated by evaporation under reduced pressure, and the resulting residue was crystallized by the addition of ethyl acetate, to give 1.22 g of the title compound as crystals, melting at 185°–188° C.

Nuclear Magnetic Resonance Spectrum (hexadeuterated dimethyl sulfoxide), δ ppm:

1.06 (3H, triplet, J=7.5 Hz);

1.30 (3H, triplet, J=7.5 Hz);

1.49 (6H, singlet);

3.17 (2H, quartet, J=7.5 Hz);

4.16 (2H, quartet, J=7.5 Hz);

5.38 (2H, singlet);

6.95 (2H, doublet, J=8.5 Hz);

7.08 (2H, doublet, J=8.5 Hz);

7.50–7.74 (4H, multiplet).

EXAMPLE 108

2-Ethylthio-4-(1-hydroxy-1-methylethyl)-1-{4-[2-(tetrazol-5-yl)phenyl]phenyl}methylimidazole-5-carboxylate 1.00 g of ethyl 2-ethylthio-4-(1-hydroxy-1-methylethyl)-1-{4-[2-(tetrazol-5-yl)phenyl]phenyl}methylimidazole-5-carboxylate [prepared as described in Example 107(b)] and 256 mg of lithium hydroxide monohydrate were added to a mixture of 10 ml of water and 10 ml of dioxane. The mixture was then stirred at room temperature for 24 hours after which it was concentrated by evaporation under reduced pressure. The resulting residue was dissolved in water, and then 6.1 ml of 1N aqueous hydrochloric acid were added. The oily matter which appeared was extracted with ethyl acetate. The extract was washed with a saturated aqueous solution of sodium chloride, dried over anhydrous magnesium sulfate and concentrated by evaporation under reduced pressure, to give 955 mg of the title compound as an amorphous powder.

Nuclear Magnetic Resonance Spectrum (CDCl$_3$), δ ppm:

1.29 (3H, triplet, J=7.5 Hz);

1.60 (6H, singlet);

3.11 (2H, quartet, J=5 Hz);

5.55 (2H, singlet);

6.92 (2H, doublet, J=8.5 Hz);

6.98 (2H, doublet, J=8.5 Hz);

7.36–7.60 (3H, multiplet);

7.81 (1H, doublet, J=7.5 Hz).

EXAMPLE 109

Ethyl 2-hydroxymethyl-4-(1-hydroxy-1-methylethyl)-1-{4-[2-(tetrazol-5-yl)phenyl]phenyl}methylimidazole-5-carboxylate A procedure similar to that described in Example 82(b) was repeated, except that 400 mg of ethyl 2-hydroxymethyl-4-(1-hydroxy-1-methylethyl)-1-{4-[2-(trityltetrazol-5-yl)phenyl]phenyl}methylimidazole-5-carboxylate [prepared as described in Example 102(b)] were used as a starting material, to obtain 264 mg of the title compound as crystals, melting at 98°–99° C.

Nuclear Magnetic Resonance Spectrum (CDCl$_3$), δ ppm:

1.14 (3H, triplet, J=7.5 Hz);

1.48 (6H, singlet);

4.20 (2H, quartet, J=7.5 Hz);

4.55 (2H, singlet);

5.57 (2H, singlet);

6.77 (2H, doublet, J=8 Hz);

6.99 (2H, doublet, J=8 Hz);

7.28–7.59 (3H, multiplet);

7.83 (1H, doublet, J=7.5 Hz).

EXAMPLE 110

2-Hydroxymethyl-4-(1-hydroxy-1-methylethyl)-1-{4-[2-(tetrazol-5-yl)phenyl]phenyl}methylimidazole-5-carboxylic acid Following a procedure similar to that described in Example 91, but using 200 mg of ethyl 2-hydroxymethyl-4-(1-hydroxy-1-methylethyl)-1-{4-[2-(tetrazol-5-yl)phenyl]phenyl}methylimidazole-5-carboxylate (prepared as described in Example 109)], 169 mg of the title compound were obtained as crystals, melting at 201°–202° C.

Nuclear Magnetic Resonance Spectrum (hexadeuterated dimethyl sulfoxide), δ ppm:

1.54 (6H, singlet);

4.46 (2H, singlet);

5.69 (2H, singlet);

6.98 (2H, doublet, J=9 Hz);

7.05 (2H, doublet, J=9 Hz);

7.52–7.70 (4H, multiplet).

PREPARATION 1

2-Butylimidazole-4,5-dicarbonitrile

A suspension of 51.4 g of diaminomaleonitrile and 85.6 g of trimethyl orthovalerate in 300 ml of acetonitrile was stirred in an oil bath kept at 85° C. for 6 hours. At the end of this time, the reaction mixture was concentrated by evaporation under reduced pressure, and the concentrate was purified by short column chromatography through silica gel, using a 1:1 by volume mixture of ethyl acetate and hexane as the eluent, to give 99 g of 1-amino-2-N-(1-methoxypentylidene)aminosuccinonitrile. The whole of this compound was dissolved in 300 ml of xylene, and the resulting solution was stirred in an oil bath kept at 150° C. for 8 hours, after which the reaction mixture was concentrated to half its original volume and allowed to stand at room temperature. The crystals which precipitated were collected by filtration and washed with a small amount of xylene, to give 55.2 g of the title compound, melting at 109°–111° C.

PREPARATION 2

2-Butylimidazole-4,5-dicarboxylic acid

A solution of 100 g of 2-butylimidazole-4,5-dicarbonitrile (prepared as described in Preparation 1) in 1 liter of 6N aqueous hydrochloric acid was heated under reflux for 7 hours, and then the reaction mixture was allowed to stand overnight at room temperature. At the end of this time, the crystals which precipitated were collected by filtration and washed with water and with a small amount of acetone, to give 84 g of the title compound, melting at 261°–263° C.

PREPARATION 3

Diethyl 2-butylimidazole-4,5-dicarboxylate

Dry hydrogen chloride was bubbled through a suspension of 40 g of 2-butylimidazole-4,5-dicarboxylic acid (prepared as described in Preparation 2) in 600 ml of ethanol at room temperature, whilst stirring, for 2 hours to yield a solution. This solution was allowed to stand at room temperature for 18 hours, after which the reaction mixture was concentrated by evaporation under reduced pressure. The concentrate was then mixed with ethyl acetate and with an aqueous solution of sodium hydrogencarbonate and neutralized by adding powdery sodium hydrogencarbonate. The ethyl acetate layer was separated and dried over anhydrous magnesium sulfate, and the solvent was removed by distillation under reduced pressure. The resulting crystalline residue was triturated with a mixture of diisopropyl ether and hexane, and collected by filtration, to give 43 g of the title compound, melting at 82°–84° C.

PREPARATION 4

Dimethyl 2-butylimidazole-4,5-dicarboxylate

A procedure similar to that described in Preparation 3 was repeated, using 40 g of 2-butylimidazole-4,5-dicarboxylic acid, and except that methanol was used instead of ethanol, to give 41.6 g of the title compound as crystals, melting at 88° C.

PREPARATION 5

4-Acetyl-2-butyl-5-cyanoimidazole

5(i) 2-Butyl-1-tritylimidazole-4,5-dicarbonitrile 1.25 g of sodium hydride (as a 55% w/w dispersion in mineral oil) were added, whilst ice-cooling, to a solution of 5 g of 2-butylimidazole-4,5-dicarbonitrile (prepared as described in Preparation 1) in 50 ml of N,N-dimethylformamide, and the resulting mixture was stirred for 15 minutes. 10 g of trityl chloride were then added, and the reaction mixture was stirred at 50° C. for 6 hours. At the end of this time, it was mixed with ethyl acetate and water, and the product was extracted with ethyl acetate. The extract was dried over anhydrous magnesium sulfate, and the solvent was removed by distillation under reduced pressure. The resulting residue was purified by column chromatography through silica gel, using a 1:5 by volume mixture of ethyl acetate and hexane as the eluent, to give 9.83 g of the title compound as a syrup, which solidified on being allowed to stand. The solid melted at 144°–147° C. (with decomposition and coloration at 94°–98° C.).

Nuclear Magnetic Resonance Spectrum (CDCl$_3$), δ ppm:

0.60 (3H, triplet, J=7 Hz);

0.5–1.4 (4H, multiplet);

2.03 (2H, triplet, J=7 Hz);

7.0–7.6 (15H, multiplet).

5(ii) 4-Acetyl-2-butyl-5-cyano-1-tritylimidazole 11.1 ml of a 2M solution of methylmagnesium iodide in diethyl ether was slowly added dropwise at room temperature, in an atmosphere of nitrogen, to a solution of 4.5 g of 2-butyl-1-tritylimidazole-4,5-dicarbonitrile [prepared as described in step (i) above] in 45 ml of tetrahydrofuran, and the resulting mixture was stirred at room temperature for 3 hours. At the end of this time, a saturated aqueous solution of ammonium chloride was added dropwise, whilst ice-cooling, to the mixture. The tetrahydofuran layer was separated, washed with a saturated aqueous solution of sodium chloride and concentrated by evaporation under reduced pressure to give a concentrate. The aqueous layer was once again extracted with a small amount of ethyl acetate. The extract was washed with a saturated aqueous solution of sodium chloride, dried and concentrated by evaporation under reduced pressure. The resulting extract was combined with the above concentrate, and the resulting crude product was purified by column chromatography through silica gel, using a 3:1 by volume mixture of hexane and ethyl acetate as the eluent, and the product was crystallized from a mixture of ethyl acetate and hexane, to give 1.46 g of the title compound, melting at 159°–160° C. (with decomposition).

Nuclear Magnetic Resonance Spectrum (CDCl$_3$), δ ppm:

0.60 (3H, triplet, J=7 Hz);

0.5–1.5 (4H, multiplet);

2.08 (2H, triplet, J=7 Hz);

2.58 (3H, singlet);

7.1–7.6 (15H, multiplet).

5(iii) 4-Acetyl-2-butyl-5-cyanoimidazole

A suspension of 1.78 g of 4-acetyl-2-butyl-5-cyano-1-tritylimidazole [prepared as described in step (ii) above] in 80% v/v aqueous acetic acid was stirred at 60° C. for 1 hour. The solution thus obtained was concentrated to dryness by evaporation under reduced pressure. The resulting residue was purified by column chromatography through silica gel, using a 3:1 by volume mixture of hexane and ethyl acetate as the eluent, to give 0.66 g of the title compound as a colorless solid, melting at 77°–78° C.

Nuclear Magnetic Resonance Spectrum (CDCl$_3$), δ ppm:

0.93 (3H, triplet, J=7 Hz);

1.0–2.1 (4H, multiplet);

2.72 (3H, singlet);

2.89 (2H, triplet, J=7 Hz).

PREPARATION 6

4-Benzoyl-2-butyl-5-cyanoimidazole

6(i) 4-Benzoyl-2-butyl-5-cyano-1-tritylimidazole

Following a procedure similar to that described in Preparation 5(ii), 10.3 g of the title compound were obtained as an amorphous solid by reacting a solution of 10 g of 2-butyl-1-tritylimidazole-4,5-dinitrile [prepared as described in Preparation 5(i)] in 100 ml of tetrahydrofuran with 25 ml of a 2M solution of phenylmagnesium iodide in diethyl ether.

Nuclear Magnetic Resonance Spectrum (CDCl$_3$), δ ppm:

0.67 (3H, triplet, J=7 Hz);

0.5–1.5 (4H, multiplet);

2.11 (2H, triplet, J=7 Hz);

7.1–8.0 (20H, multiplet).

6(ii) 4-Benzoyl-2-butyl-5-cyanoimidazole

A suspension of 10.3 g of 4-benzoyl-2-butyl-5-cyano-1-tritylimidazole [prepared as described in step (i) above] in 80% v/v aqueous acetic acid was stirred at 60° C. for 5 hours. At the end of this time, the solution thus obtained was concentrated by evaporation under reduced pressure, and the concentrate was purified by column chromatography through silica gel, using a 2:1 by volume mixture of hexane and ethyl acetate as the eluent. The resulting oily product was dissolved in carbon tetrachloride and the solution was allowed to stand at room temperature, to precipitate crystals, which were collected by filtration to give 4.46 g of the title compound, melting at 121°–122° C.

Nuclear Magnetic Resonance Spectrum (CDCl$_3$), δ ppm:
0.90 (3H, triplet, J=7 Hz);
1.0–2.3 (4H, multiplet);
2.85 (2H, triplet, J=7 Hz);
7.2–8.0 (5H, multiplet);
11.0–12.1 (1H, broad).

PREPARATION 7

2-Butyl-5-cyano-4-(1-hydroxy-1-methylethyl)imidazole

7(i) 2-Butyl-5-cyano-4-(1-hydroxy-1-methylethyl)-1-tritylimidazole 1 ml of a 2M solution of methylmagnesium iodide in tetrahydrofuran was added dropwise at room temperature, whilst stirring, to a solution of 840 mg of 4-acetyl-2-butyl-5-cyano-1-tritylimidazole [prepared as described in Preparation 5(ii)] in 15 ml of tetrahydrofuran, and the resulting mixture was stirred at 40° C. for 1 hour. The mixture was cooled, and then a saturated aqueous solution of ammonium chloride was added to it dropwise. The tetrahydrofuran layer was separated and concentrated by evaporation under reduced pressure. The concentrate was purified by column chromatography through silica gel, using a 2:1 by volume mixture of hexane and ethyl acetate as the eluent, to give 539 mg of the title compound as a colorless solid, melting at 151°–152° C.

Nuclear Magnetic Resonance Spectrum (CDCl$_3$), δ ppm:
0.60 (3H, triplet, J=7 Hz);
0.6–1.5 (4H, multiplet);
1.59 (6H, singlet);
2.01 (2H, triplet, J=7 Hz);
3.78 (1H, singlet);
7.0–7.6 (15H, multiplet).

7(ii) 2-Butyl-5-cyano-4-(1-hydroxy-1-methylethyl)imidazole

A mixture of 1.3 g of 2-butyl-5-cyano-4-(1-hydroxy-1-methylethyl)-1-tritylimidazole [prepared as described in step (i) above] and 26 ml of 75% v/v aqueous acetic acid was stirred at 50° C. for 3 hours, and then the solvent was removed by distillation under reduced pressure. The resulting residue was washed with carbon tetrachloride and purified by column chromatography through silica gel, using a 10:1 by volume mixture of methylene chloride and methanol as the eluent, and the product was crystallized in carbon tetrachloride, to give 0.6 g of the title compound as colorless crystals, melting at 171°–172° C.

Nuclear Magnetic Resonance Spectrum (CDCl$_3$+ CD$_3$OD), δ ppm:
0.90 (3H, triplet, J=7 Hz);
1.0–2.0 (4H, multiplet);
1.62 (6H, singlet);
2.68 (2H, triplet, J=7 Hz).

PREPARATION 8

Ethyl 2-butyl-4-(1-hydroxy-1-methylethyl)imidazole-5-carboxylate

A solution of 5.36 g of diethyl 2-butylimidazole-4,5-dicarboxylate (prepared as described in Preparation 3) in 100 ml of tetrahydrofuran was cooled to −30° C. in an atmosphere of nitrogen, and 32 ml of a methylmagnesium bromide solution (2.5M in tetrahydrofuran) were added dropwise at −30° to −20° C. to the cooled solution. The reaction mixture was then stirred at 0° C. for 1.5 hours and subsequently mixed with ethyl acetate and with an aqueous solution of ammonium chloride. The ethyl acetate layer was separated and dried over anhydrous magnesium sulfate, and the solvent was removed by distillation under reduced pressure. The residue was purified by column chromatography through silica gel, using a 1:20 by volume mixture of methanol and methylene chloride as the eluent, to give 5.01 g of the title compound as an oil.

Nuclear Magnetic Resonance Spectrum (CDCl$_3$), δ ppm:
0.90 (3H, triplet, J=7 Hz);
1.32 (3H, triplet, J=7 Hz);
1.2–2.0 (4H, multiplet);
1.64 (6H, singlet);
2.70 (2H, triplet, J=7 Hz);
4.33 (2H, quartet, J=7 Hz);
5.97 (1H, broad singlet);
10.2 (1H, broad singlet).

PREPARATION 9

Ethyl 4-(1-hydroxy-1-methylethyl)-2-propylimidazole-5-carboxylate

Following a procedure similar to that described in Preparation 8, 2.34 g of the title compound were obtained as an oil by reacting 3.01 g of diethyl 2-propylimidazole-4,5-dicarboxylate (prepared as described in Preparation 12) with 16 ml of a 2.5M solution of methylmagnesium bromide in tetrahydrofuran. The compound was crystallized by allowing it to stand at room temperature, to give a product melting at 69°–71° C., and was then recrystallized from diisopropyl ether, to give a product melting at 101°–102° C.

Nuclear Magnetic Resonance Spectrum (CDCl$_3$), δ ppm:
0.96 (3H, triplet, J=7 Hz);
1.35 (3H, triplet, J=7 Hz);
1.64 (6H, singlet);
1.81 (2H, sextet, J=7 Hz);
2.68 (2H, triplet, J=7 Hz);
4.35 (2H, quartet, J=7 Hz);
5.81 (1H, singlet);
9.9 (1H, broad singlet).

PREPARATION 10

2-Propylimidazole-4,5-dicarbonitrile

Following a procedure similar to that described in Preparation 1, but using 16.0 g of diaminomaleonitrile and 24 g of trimethyl orthobutyrate, 18.7 g of the title compound were obtained as crystals, melting at 141°–144° C.

PREPARATION 11

2-Propylimidazole-4,5-dicarboxylic acid

Following a procedure similar to that described in Preparation 2, but using 18.2 g of 2-propylimidazole-4,5-dicarbonitrile (prepared as described in Preparation 10), 9.95 g of the title compound were obtained as crystals, melting at 261°–263° C.

PREPARATION 12

Diethyl 2-propylimidazole-4,5-dicarboxylate

Following a procedure similar to that described in Preparation 3, but using 10.0 g of 2-propylimidazole-4,5-dicarboxylic acid (prepared as described in Preparation 11), 9.55 g of the title compound were obtained as crystals, melting at 81°–83° C.

PREPARATION 13

Ethyl 2-butyl-4-(1-ethyl-1-hydroxypropyl)imidazole-5-carboxylate

Following a procedure similar to that described in Preparation 8, 2.68 g of the title compound, melting at 63°–64° C., were obtained as crystals by reacting 2.68 g of diethyl 2-butylimidazole-4,5-dicarboxylate (prepared as described in Preparation 3) with a 3.0M solution of ethylmagnesium bromide in diethyl ether.

Nuclear Magnetic Resonance Spectrum (CDCl$_3$), δ ppm:
0.82 (6H, triplet, J=7 Hz);
0.93 (3H, triplet, J=7 Hz);
1.38 (3H, triplet, J=7 Hz);
1.31–1.45 (2H, multiplet);
1.65–1.76 (2H, multiplet);
1.79–1.89 (2H, multiplet);
1.97–2.11 (2H, multiplet);
2.76 (2H, triplet, J=7.5 Hz);
4.36 (2H, quartet, J=7 Hz);
5.70 (1H, broad singlet).

PREPARATION 14

2-Propyl-1-tritylimidazole-4,5-dicarbonitrile

Following a procedure similar to that described in Preparation 5(i), but using 7.8 g of 2-propylimidazole-4,5-dicarbonitrile (prepared as described in Preparation 10), 2.14 g of sodium hydride (as a 55% w/w dispersion in mineral oil) and 17.1 g of trityl chloride, 14.6 g of the title compound were obtained as crystals, melting at 107° C. (with decomposition and with a yellow coloration at 102° C.).

Nuclear Magnetic Resonance Spectrum (CDCl$_3$), δ ppm:
0.52 (3H, triplet, J=7 Hz);
1.07–1.21 (2H, multiplet);
2.03 (2H, triplet, J=8 Hz);
7.19–7.48 (15H, multiplet).

PREPARATION 15

2-Butyl-5-cyano-4-propionyl-1-tritylimidazole 14 ml of a 3M solution of ethylmagnesium bromide in diethyl ether were added dropwise at 10° C. under an atmosphere of nitrogen to a solution of 8.33 g of 2-butyl-1-tritylimidazole-4,5-dicarbonitrile [prepared as described in Preparation 5(i)] in 83 ml of tetrahydrofuran, and the resulting mixture was stirred at room temperature for 3 hours. At the end of this time, a mixture of a saturated aqueous solution of ammonium chloride and ethyl acetate was added to the reaction mixture, whilst ice-cooling. The ethyl acetate layer was separated, washed with water and dried over anhydrous magnesium sulfate. The solvent was then removed by distillation under reduced pressure. The crystalline product thus obtained was washed with diisopropyl ether, to give 4.56 g of the title compound, melting at 140°–143° C. (softening at 83° C.).

Nuclear Magnetic Resonance Spectrum (CDCl$_3$), δ ppm:
0.61 (3H, triplet, J=7 Hz);
0.84–1.14 (4H, multiplet);
1.18 (3H, triplet, J=8 Hz);
2.08 (2H, triplet, J=7 Hz);
3.03 (2H, quartet, J=7 Hz);
7.22–7.42 (15H, multiplet).

PREPARATION 16

5-Cyano-4-Propionyl-2-propyl-1-tritylimidazole

Following a procedure similar to that described in Preparation 15, but using 8.05 g of 2-propyl-1-tritylimidazole-4,5-dicarbonitrile (prepared as described in Preparation 14) and 14 ml of a 3M solution of ethylmagnesium bromide in diethyl ether, 7.03 g of the title compound were obtained as crystals, melting at 96° C. (softening at 87° C.).

Nuclear Magnetic Resonance Spectrum (CDCl$_3$). δ ppm:
0.52 (3H, triplet, J=7 Hz);
1.05–1.3 (2H, multiplet);
1.18 (3H, triplet, J=7 Hz);
2.05 (2H, triplet, J=7 Hz);
3.03 (2H, quartet, J=7 Hz);
7.20–7.40 (15H, multiplet).

PREPARATION 17

2-Butyl-5-cyano-4-(1-hydroxy-1-methylpropyl)-1-tritylimidazole 5 ml of a 1M solution of methylmagnesium bromide in tetrahydrofuran were added dropwise at 10° C. under an atmosphere of nitrogen to a solution of 2 g of 2-butyl-5-cyano-4-propionyl-1-tritylimidazole (prepared as described in Preparation 15) in 36 ml of tetrahydrofuran, and the resulting mixture was stirred at 20° C. for 1 hour and subsequently at 30° C. for a further 1 hour. At the end of this time, a mixture of a saturated aqueous solution of ammonium chloride and ethyl acetate was added to the reaction mixture, which was then well shaken. The ethyl acetate layer was separated and dried over anhydrous magnesium sulfate. After the drying agent had been removed by filtration, the solvent was distilled off under reduced pressure. The residue was purified by column chromatography through silica gel, using a 1:2 by volume mixture of ethyl acetate and hexane as the eluent, to give 1.29 g of the title compound as crystals, melting at 90°–93° C.

Nuclear Magnetic Resonance Spectrum (CDCl$_3$), δ ppm:
0.60 (3H, triplet, J=7 Hz);
0.80 (3H, triplet, J=7 Hz);
0.80–1.00 (2H, multiplet);
1.00–1.13 (2H, multiplet);
1.58 (3H, singlet);
1.75–2.05 (4H, multiplet);
3.90 (1H, broad singlet);
7.23–7.43 (15H, multiplet).

PREPARATION 18

5-Cyano-4-(1-hydroxy-1-methylpropyl)-2-propyl-1-tritylimidazole

Following the procedure described in Preparation 17, but using 5.00 g of 5-cyano-4-propionyl-2-propyl-1-tritylimidazole (prepared as described in Preparation 16) and 12.5 ml of a 1M solution of methylmagnesium bromide in tetrahydrofuran, 3.32 g of the title compound were obtained as a crystalline powder, melting at above 120° C. (softening at 110° C.).

Nuclear Magnetic Resonance Spectrum (CDCl$_3$), δ ppm:
0.50 (3H, triplet, J=7 Hz);
0.80 (3H, triplet, J=7 Hz);
1.07–1.12 (2H, multiplet);
1.58 (3H, singlet);
1.74–2.00 (4H, multiplet);
3.90 (1H, broad singlet);
7.24–7.37 (15H, multiplet).

PREPARATION 19

2-Butyl-5-cyano4-(1-hydroxy-1-methylpropyl)imidazole

A mixture of 1.21 g of 2-butyl-5-cyano-4-(1-hydroxy-1-methylpropyl)-1-trirtylimidazole (prepared as described in Preparation 17) and 20 ml of 75% v/v aqueous acetic acid was stirred at 50° C. for 1 hour, after which the mixture was cooled, and the deposited crystals of trityl alcohol were removed by filtration. The filtrate was concentrated by evaporation under reduced pressure, and the remaining water and acetic acid were distilled off as a toluene azeotrope under reduced pressure. The residue was purified by column chromatography through silica gel, using a 9:1 by volume mixture of methylene chloride and methanol as the eluent, to give 0.47 g of the title compound as a crystalline powder, melting at 139°–142° C.

Nuclear Magnetic Resonance Spectrum (hexadeuterated dimethyl sulfoxide), δ ppm:
0.74 (3H, triplet, J=7 Hz);
0.87 (3H, triplet, J=7 Hz);
1.21–1.34 (2H, multiplet);
1.49 (3H, singlet);
1.53–1.64 (2H, multiplet);
1.72 (2H, quartet, J=7.5 Hz);
2.56 (2H, triplet, J=7 Hz);
5.45 (1H, singlet).

PREPARATION 20

5-Cyano-4-(1-hydroxy-1-methylpropyl)-2-propylimidazole

Following the procedure described in Preparation 19, but using 1.20 g of 5-cyano-4-(1-hydroxy-1-methylpropyl)-2-propyl-1-tritylimidazole (prepared as described in Preparation 18), 0.48 g of the title compound was obtained as a crystalline powder, melting at 157°–159° C.

Nuclear Magnetic Resonance Spectrum (CDCl$_3$), δ ppm:
0.89 (3H, triplet, J=7.5 Hz);
0.98 (3H, triplet, J=7.5 Hz);
1.57 (3H, singlet);
1.76 (2H, quartet, J=7.5 Hz);
1.83–2.08 (2H, multiplet);
2.00 (1H, singlet);
2.67 (2H, triplet, J=7.5 Hz).

PREPARATION 21

Methyl 2-butyl-4-(1-hydroxy-1-methylethyl)imidazole-5-carboxylate

A solution of 9.73 g of dimethyl 2-butylimidazole-4,5-dicarboxylate (prepared as described in Preparation 4) in 100 ml of tetrahydrofuran was cooled to −30° C. under an atmosphere of nitrogen, and 162 ml of a 1M solution of methylmagnesium bromide in tetrahydrofuran were added dropwise to this solution at a temperature of −30° C. to −20° C. The resulting mixture was stirred at 0° C. for 2.5 hours, and then ethyl acetate and an aqueous solution of ammonium chloride were added to it. The ethyl acetate layer was separated and dried over anhydrous magnesium sulfate, after which the solvent was removed by distillation under reduced pressure. The resulting residue was purified by column chromatography through silica gel, using a 1:20 by volume mixture of methanol and methylene chloride as the eluent, to give 7.15 g of the title compound as an oil. The compound was crystallized by allowing it to stand at room temperature, to give a product melting at 60°–65° C.

Nuclear Magnetic Resonance Spectrum (CDCl$_3$), δ ppm:
0.88 (3H, triplet, J=7 Hz);
1.0–2.0 (4H, multiplet);
1.64 (6H, singlet);
2.69 (2H, triplet, J=7.5 Hz);
3.84 (3H, singlet);
7.35 (2H, broad singlet).

PREPARATION 22

Pivaloyloxymethyl 4-(1-hydroxy-1-methylethyl)-2-propylimidazole-5-carboxylate

22(i) 4-Hydroxy-1-methylethyl)-2-propylimidazole-5-carboxylic acid

A solution of 0.28 g of lithium hydroxide monohydrate in 5 ml of water was added to a solution of 0.48 g of ethyl 4-(1-hydroxy-1-methylethyl)-2-propylimidazole-5-carboxylate (prepared as described in Preparation 9) in 5 ml of methanol, and the resulting mixture was stirred at room temperature for 18 hours. At the end of this time, the pH of the reaction mixture was adjusted to a value of 2.3 by adding 6.67 ml of 1N aqueous hydrochloric acid, and the mixture was concentrated by evaporation under reduced pressure to a volume of about 2 ml. The crystals which precipitated were collected by filtration to give 0.20 g of the title compound, melting at 232° C. (with decomposition).

Nuclear Magnetic Resonance Spectrum (hexadeuterated dimethyl sulfoxide). δ ppm:

0.87 (3H, triplet, J=7.5 Hz);
1.48 (6H, singlet);
1.65 (2H, sextet, J=7.5 Hz);
2.62 (2H, triplet, J=7.5 Hz).

22(ii) Pivaloyloxymethyl 4-(1-hydroxy-1-methylethyl)-2-propylimidazole-5-carboxylate 1.76 ml of N,N-diisopropylethylamine were added to a suspension of 1.14 g of 4-(1-hydroxy-1-methylethyl)-2-propylimidazole-5-carboxylic acid [prepared as described in step (i) above] in 12 ml of N,N-dimethylacetamide, and the resulting mixture was stirred at room temperature for 10 minutes; 1.36 ml of pivaloyloxymethyl chloride was then added. The reaction mixture was stirred at 60° C. for 4 hours, after which it was mixed with ethyl acetate and water. The ethyl acetate layer was separated and concentrated by evaporation under reduced pressure. The crystals which precipitated were triturated with diisopropyl ether and collected by filtration to give 1.53 g of the title compound, melting at 177° C.

Nuclear Magnetic Resonance Spectrum (CDCl$_3$) δ ppm:

0.99 (3H, triplet, J=7.5 Hz);
1.22 (9H, singlet);
1.62 (6H, singlet);
1.76 (2H, sextet, J=7.5 Hz);
2.70 (2H, triplet, J=7.5 Hz);
5.15 (1H, broad singlet);
5.95 (2H, singlet).

PREPARATION 23

Ethyl 4-(1-hydroxyethyl)-2-propylimidazole-5-carboxylate

23(i) 4-Acetyl-2-propylimidazole-5-carbonitrile 194 ml of a 1M solution of methylmagnesium bromide in tetrahydrofuran were added dropwise at a temperature of 10° C. to 15° C. and under an atmosphere of nitrogen to a solution of 10 g of 2-propylimidazole-4,5-dicarbonitrile (prepared as described in Preparation 10) in 100 ml of tetrahydrofuran, and the resulting mixture was stirred at a temperature of 10° C. to 15° C. for 30 minutes. The reaction mixture was then cooled, and 200 ml of ethyl acetate and 100 ml of a saturated aqueous solution of ammonium chloride were added to it. The mixture was then acidified by adding an aqueous solution of potassium bisulfate. The organic layer was separated and dried over anhydrous magnesium sulfate, and the solvent was removed by distillation under reduced pressure. The residue was subjected to column chromatography through silica gel, using a 1:1 by volume mixture of ethyl acetate and hexane as the eluent, to give 9.18 g of the title compound as crystals, melting at 93°–95° C.

Nuclear Magnetic Resonance Spectrum (CDCl$_3$), δ ppm:

0199 (3H, triplet, J=7.5 Hz);
1.83 (2H, sextet, 7.5 Hz);
2.71 (3H, singlet);
2.82 (2H, triplet, J=8 Hz).

23(ii) Ethyl 4-acetyl-2-propylimidazole-5-carboxylate

A mixture of 4.0 g of 4-acetyl-2-propylimidazole-5-carbonitrile [prepared as described in step (i) above] and 60 ml of 6N aqueous hydrochloric acid was heated under reflux, with stirring, for 8 hours. The reaction mixture was then concentrated by evaporation under reduced pressure, and the concentrate was dissolved in ethanol, after which it was again concentrated in the same way. The residue was dissolved in ethanol and the solvent was again distilled off. After this sequence of dissolution and concentration had been carried out for a total of five times, the residue was dissolved in 60 ml of ethanol. A stream of hydrogen chloride was bubbled through the resulting solution at room temperature for 20 minutes, and then the solution was allowed to stand at room temperature for 16 hours. It was then concentrated by evaporation under reduced pressure. The concentrate was dissolved in a mixture of ethyl acetate and an aqueous solution of sodium hydrogencarbonate, and the solution was neutralized by adding sodium hydrogencarbonate. The ethyl acetate layer was separated and dried over anhydrous magnesium sulfate. The solvent was removed by distillation under reduced pressure, and the resulting residue was purified by column chromatography through silica gel, using a 1:1 by volume mixture of ethyl acetate and hexane as the eluent, to give 3.07 g of the title compound as crystals, melting at 76°–78° C.

Nuclear Magnetic Resonance Spectrum (CDCl$_3$), δ ppm:

0.96 (3H, triplet, J=7.5 Hz);
1.39 (3H, triplet, J=7 Hz);
1.82 (2H, sextet, J=7.5 Hz);
2.75 (3H, singlet);
2.80 (2H, triplet, J=7.5 Hz);
4.44 (2H, quartet, J=7 Hz).

23(iii) Ethyl 4-(1-hydroxyethyl)-2-propylimidazole-5-carboxylate 125 mg of sodium borohydride were added to a solution of 1.50 g of ethyl 4-acetyl-2-propylimidazole-5-carboxylate [prepared as described in step (ii) above] in 15 ml of ethanol, and the resulting mixture was stirred at room temperature for 30 minutes. 2 ml of acetone were added, and the mixture was stirred for a further 10 minutes. The reaction mixture was then concentrated by evaporation under reduced pressure, and the concentrate was dissolved in methanol. The solution was again concentrated by evaporation under reduced pressure, and the residue was purified by column chromatography through silica gel, using 1:20 and 1:10 by volume mixtures of methylene chloride and methanol as the eluent, to give 1.32 g of the title compound as crystals, melting at 151°–153° C.

Nuclear Magnetic Resonance Spectrum (CDCl$_3$+hexadeuterated dimethyl sulfoxide), δ ppm:

0.95 (3H, triplet, J=7.5 Hz);
1.38 (3H, triplet, J=7 Hz);
1.48 (3H, doublet, J=6.5 Hz);
1.74 (2H, sextet, J=7.5 Hz);
2.67 (2H, triplet, J=8 Hz);
4.34 (2H, quartet, J=7 Hz);
5.28 (1H, quartet, J=6.5 Hz).

PREPARATION 24

Ethyl 2-butyl-4-(1-hydroxyethyl)imidazole-5-carboxylate

24(i) 4-Acetyl-2-butylimidazole-5-carbonitrile

Following a procedure similar to that described in Preparation 23(i), but using 10 g of 2-butylimidazole-4,5-dicarbonitrile (prepared as described in Preparation 1), 9.15 g of the title compound were obtained as crystals, melting at 77°–78° C.

Nuclear Magnetic Resonance Spectrum (CDCl₃), δ ppm:
0.93 (3H, triplet, J=7 Hz);
1.0–2.1 (4H, multiplet);
2.72 (3H, singlet);
2.89 (2H, triplet, J=7 Hz).

24(ii) Ethyl 4-acetyl-2-butylimidazole-5-carboxylate

Following a procedure similar to that described in Preparation 23(ii), but using 1.00 g of 4-acetyl-2-butylimidazole-5-carbonitrile [prepared as described in step (i) above], 0.92 g of the title compound was obtained as a viscous oil.

Nuclear Magnetic Resonance Spectrum (CDCl₃), δ ppm:
0.88 (3H, triplet, J=7 Hz);
1.1–2.1 (4H, multiplet);
1.33 (3H, triplet, J=7 Hz);
2.74 (3H, singlet);
2.82 (2H, triplet, J=7.5 Hz);
4.38 (2H, quartet, J=7 Hz).

24(iii) Ethyl 2-butyl-4-(1-hydroxyethyl)imidazole-5-carboxylate

Following a procedure similar to that described in Preparation 23(iii), but using 0.64 g of ethyl 4-acetyl-2-butylimidazole-5-carboxylate [prepared as described in step (ii) above]. 0.55 g of the title compound was obtained as crystals, melting at 149° C.

Nuclear Magnetic Resonance Spectrum (CDCl₃+hexadeuterated dimethyl sulfoxide), δ ppm:
0.91 (3H, triplet, J=7.5 Hz);
1.37 (3H, triplet, J=7 Hz);
1.3–1.42 (2H, multiplet);
1.50 (3H, doublet, J=6.5 Hz);
1.69 (2H, quintet, J=7.5 Hz);
2.69 (2H, triplet, J=8 Hz);
4.34 (2H, quartet, J=7 Hz);
5.26 (1H, quartet, J=6.5 Hz).

PREPARATION 25

2-Butyl-4-propionylimidazole-5-carbonitrile

Following a procedure similar to that described in Preparation 24(i), but using ethylmagnesium bromide instead of methylmagnesium bromide, the title compound, melting at 84°–85° C, was obtained in a 51.9% yield.

Nuclear Magnetic Resonance Spectrum (CDCl₃), δ ppm:
0.95 (3H, triplet, J=7 Hz);
1.0–2.2 (4H, multiplet);
1.28 (3H, triplet, J=7.0 Hz);
2.88 (2H, triplet, J=7 Hz);
3.15 (2H, quartet, J=7 Hz).

PREPARATION 26

2-Butyl-4-butyrylimidazole-5-carbonitrile

Following a procedure similar to that described in Preparation 24(i), but using propylmagnesium bromide instead of methylmagnesium bromide, the title compound, melting at 91°–92° C., was obtained in a 57.2% yield.

Nuclear Magnetic Resonance Spectrum (CDCl₃), δ ppm:
1.02 (3H, triplet, J=7.5 Hz);
1.11 (3H, triplet, J=7.5 Hz);
1.3–1.6 (2H, multiplet);
1.7–2.0 (4H, multiplet);
2.88 (2H, triplet, J=8 Hz);
3.13 (2H, triplet, J=7.5 Hz).

PREPARATION 27

2-Butyl-4-isobutyrylimidazole-5-carbonitrile

Following a procedure similar to that described in Preparation 24(i), but using isopropylmagnesium bromide instead of methylmagnesium bromide, the title compound, melting at 88°–89° C., was obtained in a 36.2% yield.

Nuclear Magnetic Resonance Spectrum (CDCl₃), δ ppm:
0.94 (3H, triplet, J=7 Hz);
1.0–2.1 (4H, multiplet);
1.30 (6H, doublet, J=7 Hz);
2.91 (2H, triplet, J=7 Hz);
3.71 (1H, septet, J=7 Hz).

PREPARATION 28

4-Butyryl-2-propylimidazole-5-carbonitrile

Following a procedure similar to that described in Preparation 24(i), but using 2-propylimidazole-4,5-dicarbonitrile (prepared as described in Preparation 10) and propylmagnesium bromide, the title compound, melting at 94°–95° C., was obtained in a 49.8% yield.

Nuclear Magnetic Resonance Spectrum (CDCl₃), δ ppm:
1.00 (3H, triplet, J=7.5 Hz);
1.04 (3H, triplet, J=7.5 Hz);
1.7–1.9 (4H, multiplet);
2.79 (2H, triplet, J=7.5 Hz);
3.06 (2H, triplet, J=7.5 Hz).

PREPARATION 29

2-Butyl-4-(hydroxy-1-methylethyl)imidazole-5-carbonitrile

Following a procedure similar to that described in Preparation 23(i), but using 4-acetyl-2-butylimidazole-5-carbonitrile [prepared as described in Preparation 24(i)] and a solution of methylmagnesium bromide in tetrahydrofuran, the title compound, melting at 171°–172° C., was obtained in a 66.3% yield.

Nuclear Magnetic Resonance Spectrum (CDCl₃+CD₃OD), δ ppm:
0.91 (3H, triplet, J=7 Hz);
1.0–2.1 (4H, multiplet);
1.62 (6H, singlet);
2.69 (2H, triplet, J=7 Hz).

PREPARATION 30

2-Butyl-4-[1-hydroxy-2-methyl-1-(1-methylethyl)propyl]imidazole-5-carbonitrile

Following a procedure similar to that described in Preparation 23(i), but using 2-butyl-4-isobutyrylimidazole-5-carbonitrile (prepared as described in Preparation 27) and a solution of isopropyl-magnesium bromide in tetrahydrofuran, the title compound, melting at 63°–65° C. was obtained in a 87% yield.

Nuclear Magnetic Resonance Spectrum (CDCl$_3$), δ ppm:
0.7–1.0 (3H, multiplet);
0.87 (6H, doublet, J=7 Hz);
0.91 (6H, doublet, J=7 Hz);
1.0–2.1 (4H, multiplet);
2.0–2.9 (2H, multiplet);
2.71 (2H, triplet, J=7 Hz).

PREPARATION 31

(5-Methyl-2-oxo-1,3-dioxolen-4-yl)methyl 4-(1-hydroxy-1-methylethyl)-2-propylimidazole-5-carboxylate 1.76 ml of N,N-diisopropylethylamine were added to a suspension of 1.06 g of 4-(1-hydroxy-1-methylethyl)-2-propylimidazole-5-carboxylic acid [prepared as described in Preparation 22(i)] in 10 ml of N,N-dimethylacetamide, and the resulting mixture was stirred at room temperature for 10 minutes, after which 1.12 g of (5-methyl-2-oxo-1,3-dioxolen-4-yl)methyl chloride was added, and the mixture was stirred at 60° C. for 4 hours. At the end of this time, the reaction mixture was mixed with ethyl acetate and water. The ethyl acetate layer was separated and concentrated by evaporation under reduced pressure, and the concentrate was purified by column chromatography through silica gel, using a 1:15 by volume mixture of methanol and methylene chloride as the eluent, to give 1.14 g of the title compound as a viscous oil.

Nuclear Magnetic Resonance Spectrum (CDCl$_3$), δ ppm:
0.94 (3H, triplet, J=7.5 Hz);
1.62 (6H, singlet);
1.6–1.8 (2H, multiplet);
2.19 (3H, singlet);
2.67 (2H, triplet. J=8 Hz);
5.03 (2H, singlet).

PREPARATION 32

Phthalidyl 4-(1-hydroxy-1-methylethyl)-2-propylimidazole-5-carboxylate

Following a procedure similar to that described in Preparation 31, but using 1.06 g of 4-(1-hydroxy-1-methylethyl)-2-propylimidazole-5-carboxylic acid [prepared as described in Preparation 22(i)] and 1.15 g of 3-bromophthalide, 1.63 g of the title compound were obtained as an amorphous solid.

Nuclear Magnetic Resonance Spectrum (CDCl$_3$), δ ppm:
0.92 (3H, triplet, J=7.5 Hz);
1.64 (6H, singlet);
1.6–1.75 (2H, multiplet);
2.63 (2H, triplet, J=7.5 Hz);
7.63–7.79 (4H, multiplet);
7.91 (1H, doublet. J=8.5 Hz).

PREPARATION 33

Isopropoxycarbonyloxymethyl 4-(1-hydroxy-1-methylethyl)-2-propylimidazole-5-carboxylate Following a procedure similar to that described in Preparation 22(ii), but using 1.06 g of 4-(1-hydroxy-1-methylethyl)-2-propylimidazole-5-carboxylic acid [prepared as described in Preparation 22(i)] and 0.83 g of isopropoxycarbonyloxymethyl chloride, 1.22 g of the title compound, melting at 144°–146° C., were obtained.

Nuclear Magnetic Resonance Spectrum (CDCl$_3$), δ ppm:
0.98 (3H, triplet, J=7.5 Hz);
1.32 (6H, doublet, J=6.5 Hz);
1.62 (6H, singlet);
1.76 (2H, sextet, J=7.5 Hz);
2.69 (2H, triplet, J=7.5 Hz);
4.93 (1H, quintet, J=6.5 Hz);
5.95 (2H, singlet).

PREPARATION 34

2-Ethylimidazole-4,5-dicarbonitrile

Following a procedure similar to that described in Preparation 1, but using 53.3 g of diaminomaleonitrile and 91.3 g of triethyl orthopropionate, 59.5 g of the title compound were obtained as crystals, melting at 179°–181° C.

PREPARATION 35

2-Ethylimidazole-4,5-dicarboxylic acid

Following a procedure similar to that described Preparation 2, but using 45.0 g of 2-ethylimidazole-4,5-dicarbonitrile (prepared as described in Preparation 34), 31.2 g of the title compound were obtained as crystals, melting at 265°–268° C.

PREPARATION 36

Diethyl 2-ethylimidazole-4,5-dicarboxylate

Following a procedure similar to that described in Preparation 3, but using 35.0 g of 2-ethylimidazole-4,5-dicarboxylic acid (prepared as described in Preparation 35), 38.7 g of the title compound were obtained as crystals, melting at 83°–84° C.

PREPARATION 37

Ethyl 2-ethyl-4-(1-hydroxy-1-methylethyl)imidazole-5-carboxylate

Following a procedure similar to that described in Preparation 8, but using 3.60 g of diethyl 2-ethylimidazole-4,5-dicarboxylate (prepared as described in Preparation 36) and 60 ml of a 1M solution of methylmagnesium bromide in tetrahydrofuran, 2.05 g of the title compound were obtained as crystals, melting 181°–184° C.

Nuclear Magnetic Resonance Spectrum (hexadeuterated dimethyl sulfoxide) δ ppm:
1.22 (3H, triplet, J=7 Hz);
1.33 (3H, triplet, J=7.5 Hz);

1.50 (6H, singlet);
2.65 (2H, quartet, J=7.5 Hz);
3.30 (1H, broad singlet);
4.31 (2H, quartet, J=7.5 Hz).

PREPARATION 38

N-t-Butyl-4'-bromomethylbiphenyl-2-carboxamide

38(i) N-t-Butyl-4'-methylbiphenyl-2-carboxamide 5.7 ml of oxalyl chloride were added dropwise, whilst ice-cooling, to a solution of 6.91 g of 4'-methylbiphenyl-2-carboxylic acid in 70 ml of methylene chloride, and the mixture was stirred at room temperature for 2 hours. The mixture was then concentrated by evaporation under reduced pressure, and the residue was dissolved in 70 ml of tetrahydrofuran. A solution of 7.5 ml of t-butylamine in 50 ml of tetrahydrofuran was added dropwise, whilst ice-cooling to the solution, and the mixture was stirred at room temperature for 10 minutes. At the end of this time, the reaction mixture was diluted with water and ethyl acetate. The ethyl acetate layer was separated, washed with aqueous sodium hydrogencarbonate and then with aqueous sodium chloride, dried over anhydrous sodium sulfate and concentrated by evaporation under reduced pressure, to give 7.48 g of the title compound as crystals, melting at 105°–106.5° C. (after recrystallization from ethyl acetate and hexane).

Nuclear Magnetic Resonance Spectrum (CDCl$_3$) δ ppm:
1.12 (9H, singlet);
2.41 (3H, singlet);
5.04 (1H, broad singlet);
7.2–7.5 (7H, multiplet);
7.71 (1H, doublet, J=8 Hz).

38(ii) N-t-Butyl-4'-bromomethylbiphenyl-2-carboxamide 4.39 g of N-bromosuccinimide and 50 mg of benzoyl peroxide were added to a solution of 6.00 g of N-t-butyl-4'-methylbiphenyl-2-carboxamide [prepared as described in Preparation 38(i)] in 90 ml of carbon tetrachloride, and the mixture was heated under reflux for 4 hours. At the end of this time, the reaction mixture was cooled to room temperature, washed with water, dried over anhydrous magnesium sulfate and concentrated by evaporation under reduced pressure. The residue was purified by column chromatography through silica gel, using a 1:4 by volume mixture of ethyl acetate and hexane as the eluent, to give 7.04 g of the title compound as crystals, melting at 124°–126° C.

Nuclear Magnetic Resonance Spectrum (CDCl$_3$) δ ppm:
1.14 (9H, singlet);
4.55 (2H, singlet);
4.99 (1H, broad singlet);
7.30–7.72 (8H, multiplet).

PREPARATION 39

4-Isobutyryl-2-propylimidazole-5-carbonitrile

Following a procedure similar to that described in Preparation 23(i), but using 8.24 g of 2-propylimidazole-4,5-dicarbonitrile (prepared as described in Preparation 10) and 103 ml of a 2M solution of isopropylmagnesium iodide in diethyl ether, 45.0 g of the title compound were obtained as crystals, melting at 90.5°–91° C.

Nuclear Magnetic Resonance Spectrum (CDCl$_3$) δ ppm:
1.01 (3H, triplet, J=7.5 Hz);
1.29 (6H, doublet, J=6.5 Hz);
1.82 (2H, sextet, J=7.5 Hz);
2.81 (2H, triplet, J=7.5 Hz);
3.66 (1H, septet, J=6.5 Hz).

PREPARATION 40

2-Butyl-4-pivaloylimidazole-5-carbonitrile

A solution of 10.4 g of 2-butylimidazole-4,5-dicarbonitrile (prepared as described in Preparation 1) in 150 ml of methylene chloride was added dropwise in an atmosphere of nitrogen at 10°–15° C. to 100 ml of a 2M solution of t-butylmagnesium chloride in diethyl ether, and the mixture was stirred at the same temperature for 1 hour. 200 ml of ethyl acetate and 100 ml of aqueous potassium hydrogensulfate were then added dropwise to the reaction mixture, and the mixture was stirred at room temperature for 20 minutes. At end of this time, insoluble materials were removed by filtration, and the organic layer was separated, dried over anhydrous magnesium sulfate and concentrated by evaporation under reduced pressure. The residue was purified by column chromatography through silica gel, using a 1:3 by volume mixture of ethyl acetate and hexane as the eluent, to give 7.95 g of the title compound as crystals, melting at 135°–137° C.

Nuclear Magnetic Resonance Spectrum (CDCl$_3$) δ ppm:
0.95 (3H, triplet, J=7.5 Hz);
1.42 (2H, septet, J=7.5 Hz);
1.46 (9H, singlet);
1.75 (2H, quintet, J=7.5 Hz);
2.79 (2H, triplet, J=7.5 Hz).

PREPARATION 41

2-Propyl-4-pivaloylimidazole-5-carbonitrile

Following a procedure similar to that described in Preparation 40, but using 3.2 g of 2-propylimidazole-4,5-dicarbonitrile (prepared as described in Preparation 10) and 33 ml of a 2M solution of t-butylmagnesium chloride in diethyl ether, 2.35 g of the title compound were obtained as crystals, melting at 176°–178° C.

Nuclear Magnetic Resonance Spectrum (CDCl$_3$) δ ppm:
0.93 (3H, triplet, J=7.5 Hz);
1.36 (9H, singlet);
1.75 (2H, sextet, J=7.5 Hz);
2.68 (2H, triplet, J=7.5 Hz).

PREPARATION 42

Ethyl 4-(1-hydroxy-1-methylethyl)-2-methoxymethylimidazole-5-carboxylate

42(i) Diethyl 1-benzyl-2-methylimidazole-4,5-carboxylate 5.21 g of potassium t-butoxide were added to a solution of 10.0 g of diethyl 2-methylimidazole-4,5-dicarboxylate in 100 ml of N,N-dimethylacetamide, whilst ice-cooling and under a nitrogen atmosphere. The mixture was stirred for 30 minutes, until a homogeneous solution was obtained, and then 5.78 ml of benzyl bromide were added dropwise to this solution, whilst ice-cooling. The resulting mixture was stirred at room temperature for 1 hour, after which it was mixed with ethyl acetate and water and shaken. The ethyl acetate layer was separated, washed with an aqueous solution of sodium chloride and then dried over anhydrous magnesium sulfate. The solvent was removed by distillation under reduced pressure, and the resulting residue was purified by column chromatography through silica gel, using a 3:1 by volume mixture of hexane and ethyl acetate as the eluent, to give 12.38 g of the title compound as a syrup.

Nuclear Magnetic Resonance Spectrum (CDCl$_3$) δ ppm:
1.26 (3H, triplet, J=7.5 Hz);
1.39 (3H, triplet, J=7.5 Hz);
2.39 (3H, singlet);
4.28 (2H, quartet, J=7.5 Hz);
4.39 (3H, quartet, J=7.5 Hz);
5.39 (2H, singlet);
7.01 (2H, doublet, J=6 Hz);
7.24–7.34 (3H, multiplet).

42(ii) Diethyl 1-benzyl-2-bromomethylimidazole-4,5-dicarboxylate 2.52 g of N-bromosuccinimide and 0.42 of benzoyl peroxide were added to a solution of 4.07 g of diethyl 1-benzyl-2-methylimidazole-4,5-dicarboxylate [prepared as described in step (i) above] in 80 ml of carbon tetrachloride, and the mixture was irradiated by a 375 W tungsten lamp for 50 minutes, whilst stirring. At the end of this time, the reaction solution was washed with a 5% w/v aqueous solution of sodium thiosulfate and with a saturated aqueous solution of sodium hydrogencarbonate, in that order, after which it was concentrated by evaporation under reduced pressure. The resulting residue was purified by column chromatography through silica gel, using a 3:2 by volume mixture of hexane and ethyl acetate as the eluent, to give 3.81 g of the title compound as a syrup.

Nuclear Magnetic Resonance Spectrum (CDCl$_3$), δ ppm:
1.25 (3H, triplet, J=7.5 Hz);
1.39 (3H, triplet, J=7.5 Hz);
4.28 (2H, quartet, J=7.5 Hz);
4.39 (2H, singlet);
4.40 (2H, quartet, J=7.5 Hz);
5.52 (2H, singlet);
7.10 (2H, doublet, J=5.5 Hz);
7.27–7.39 (3H, multiplet).

42(iii) Dimethyl 1-benzyl-2-methoxymethylimidazole-4,5-dicarboxylate 492 mg of a 28% w/v solution of sodium methoxide in methanol were added to a solution of 655 mg of diethyl 1-benzyl-2-bromomethylimidazole-4,5-dicarboxylate [prepared as described in step (ii) above] in 7 ml of methanol, and the mixture was allowed to stand at room temperature for 13 hours. At the end of this time, 2.5 ml of 1N aqueous hydrochloric acid were added to the reaction solution, and the methanol was removed by distillation under reduced pressure. The concentrate was mixed with ethyl acetate and water and then shaken. The ethyl acetate layer was separated, washed with a saturated aqueous solution of sodium hydrogencarbonate and with a saturated aqueous solution of sodium chloride, in that order, and dried over anhydrous magnesium sulfate. The solvent was removed by distillation under reduced pressure, and then the residue was purified by column chromatography through silica gel, using a 5:1 by volume mixture of methylene chloride and ethyl acetate as the eluent, to give 391 mg of the title compound as a syrup.

Nuclear Magnetic Resonance Spectrum (CDCl$_3$), δ ppm:
3.34 (3H, singlet);
3.81 (3H, singlet);
3.92 (3H, singlet);
4.51 (2H, singlet);
5.52 (2H, singlet);
7.05 (2H, doublet, J=8 Hz);
7.25–7.34 (3H, multiplet).

42(iv) Dimethyl 2-methoxymethylimidazole-4,5-dicarboxylate 650 mg of 10% w/w palladium-on-carbon and 6.1 ml of a 4N solution of hydrogen chloride in dioxane were added to a solution of 6.5 g of dimethyl 1-benzyl-2-methoxymethylimidazole-4,5-dicarboxylate [prepared as described in step (iii) above] in 65 ml of methanol. The mixture was then stirred at room temperature for 1.5 hours under a hydrogen atmosphere. At the end of this time, the catalyst was filtered off and the filtrate was concentrated by evaporation under reduced pressure, to give a crystalline compound. This crystalline compound was washed with ethyl acetate, to give 5.13 g of the hydrochloride of the title compound, melting at 108°–111° C.

Nuclear Magnetic Resonance Spectrum (hexadeuterated dimethyl sulfoxide), δ ppm:
3.29 (3H, singlet);
3.82 (6H, singlet);
4.43 (2H, singlet);
7.28 (2H, broad singlet).

42(v) Methyl 4-(1-hydroxy-1-methylethyl)-2-methoxymethylimidazole-5-carboxylate 8.87 ml of a 0.98M solution of methylmagnesium iodide in diethyl ether were added dropwise at 4°–6° C. to a solution of 575 mg of dimethyl 2-methoxymethylimidazole-4,5-carboxylate hydrochloride [prepared as described in step (iv) above] in 40 ml of methylene chloride, under a-nitrogen atmosphere. The mixture was then stirred at room temperature for 1 hour, after which it was mixed with ethyl acetate and then with an aqueous solution of ammonium chloride, whilst ice-cooling. Sodium chloride was added no the aqueous layer until it was saturated, and then the mixture was further shaken. The ethyl acetate layer was separated and dried over anhydrous magnesium sulfate. The solvent was removed by distillation under reduced pressure, and the resulting residue was purified by column chromatography through silica gel, using a 1:20 by volume mixture of methanol and methylene chloride as the eluent, to give 391 mg of the title compound as crystals, melting at 94.5°–96.0° C.

Nuclear Magnetic Resonance Spectrum (CDCl$_3$), δ ppm:
1.63 (6H, singlet);
3.46 (3H, singlet);
3.92 (3H, singlet);
4.55 (2H, singlet).

PREPARATION 43

Dimethyl 2-methoxymethylimidazole-4,5-dicarboxylate

43(i) Diethyl 2-methyl-1-(4-nitrobenzyl)imidazole-4,5-dicarboxylate

Following a procedure similar to that described in Preparation 42(i), but using 6.65 g of diethyl 2-methylimidazole-4,5-dicarboxylate and 6.35 g of p-nitrobenzyl bromide as starting materials, 8.57 g of the title compound were obtained as crystals, melting at 109° C.

Nuclear Magnetic Resonance Spectrum (CDCl$_3$), δ ppm:
1.28 (3H, triplet, J=7.5 Hz);

1.41 (3H, triplet, J=7.5 Hz);
2.40 (3H, singlet);
4.28 (2H, quartet, J=7.5 Hz);
4.41 (2H, quartet, J=7.5 Hz);
5.53 (2H, singlet);
7.19 (2H, doublet, J=9 Hz);
8.21 (2H, doublet, J=9 Hz);

43(ii) Diethyl 2-bromomethyl-1-(4-nitrobenzyl)imidazole-4,5-dicarboxylate

Following a procedure similar to that described in Preparation 42(ii), but brominating 6.6 g of diethyl 2-methyl-1-(4-nitrobenzyl)imidazole-4,5-dicarboxylate [prepared as described in step (i) above] with 3.9 g of N-bromosuccinimide, 5.75 g of the title compound were obtained as a syrup.

Nuclear Magnetic Resonance Spectrum (CDCl$_3$), δ ppm:
1.26 (3H, triplet, J=7.5 Hz);
1.41 (3H, triplet, J=7.5 Hz);
4.27 (2H, quartet, J=7.5 Hz);
4.42 (2H, quartet, J=7.5 Hz);
5.66 (2H, singlet);
7.27 (2H, doublet, J=8.5 Hz);
8.22 (2H, doublet, J=8.5 Hz).

43(iii) Dimethyl 2-methoxymethyl-1-(4-nitrobenzyl)imidazole-4,5-dicarboxylate

Following a procedure similar to that described in Preparation 42(iii), but using 2.63 g of diethyl 2-bromomethyl-1-(4-nitrobenzyl)imidazole-4,5-dicarboxylate [prepared as described in step (ii) above], 1.38 g of the title compound were obtained as crystals, melting at 107°–110° C.

Nuclear Magnetic Resonance Spectrum (CDCl$_3$), δ ppm:
3.82 (3H, singlet);
3.94 (3H, singlet);
4.28 (3H, singlet);
4.54 (2H, singlet);
5.56 (2H, singlet);
7.23 (2H, doublet, J=8.5 Hz);
8.19 (2H, doublet, J=8.5 Hz).

43(iv) Dimethyl 2-methoxymethylimidazole-4,5-dicarboxylate

Following a procedure similar to that described in Preparation 42(iv), but catalytically reducing 1.25 g of dimethyl 2-methoxymethyl-1-(4-nitrobenzyl)imidazole-4,5-dicarboxylate [prepared as described in step (iii) above], a mixture of the hydrochlorides of the title compound and of p-toluidine was obtained. This was mixed with ethyl acetate and with a saturated aqueous solution of sodium hydrogencarbonate to neutralize it, and then the ethyl acetate layer was separated. This layer was dried over anhydrous magnesium sulfate, and the solvent was removed by distillation under reduced pressure. The resulting syrup was left in diisopropyl ether and the crystals which appeared were collected by filtration, to give 563 mg of the title compound, melting at 93°–95° C.

Nuclear Magnetic Resonance Spectrum (CDCl$_3$), δ ppm:
3.43 (3H, singlet);
3.93 (6H, singlet);
4.59 (2H, singlet).

PREPARATION 44

Ethyl 2-ethoxymethyl-4-(1-hydroxy-1-methylethyl)imidazole-5-carboxylate

44(i) Diethyl 1-benzyl-2-ethoxymethylimidazole-4,5-dicarboxylate

A solution of 1.80 g of diethyl 1-benzyl-2-bromomethylimidazole-4,5-dicarboxylate [prepared as described in Preparation 42(ii)] in 50 ml of ethanol was added dropwise to a solution of sodium ethoxide in ethanol (prepared from 0.18 g of sodium and 50 ml of ethanol), and the resulting mixture was left at room temperature for 13 hours. At the end of this time, a procedure similar to that described in preparation 42(iii) was repeated, and the residue was purified by column chromatography through silica gel, using a 1:1 by volume mixture of hexane and ethyl acetate as the eluent, to give 1.14 g of the title compound as a syrup.

Nuclear Magnetic Resonance Spectrum (CDCl$_3$), δ ppm:
1.13 (3H, triplet, J=7 Hz);
1.22 (3H, triplet, J=7 Hz);
1.38 (3H, triplet, J=7 Hz);
3.50 (2H, quartet, J=7 Hz);
4.25 (2H, quartet, J=7 Hz);
4.38 (2H, quartet, J=7 Hz);
4.56 (2H, singlet);
5.53 (2H, singlet);
7.06 (2H, doublet, J=6 Hz);
7.26–7.39 (3H, multiplet).

44(ii) Diethyl 2-ethoxymethylimidazole-4,5-dicarboxylate

Following a procedure similar to that described in Preparation 42(iv), but using 4.37 g of diethyl benzyl-2-ethoxymethylimidazole-4,5-dicarboxylate [prepared as described in step (i) above], 3.49 g of the hydrochloride of the title compound were obtained as crystals, melting at 60°–61° C.

Nuclear Magnetic Resonance Spectrum (CDCl$_3$), δ ppm:
1.16 (3H, triplet, J=7 Hz);
1.38 (6H, triplet, J=7 Hz);
3.65 (2H, quartet, J=7 Hz);
4.40 (4H, quartet, J=7 Hz);
4.96 (2H, singlet).

A solution of the diethyl 2-ethoxymethylimidazole-4,5-dicarboxylate hydrochloride thus obtained in ethyl acetate was neutralized by the addition of a saturated aqueous solution of sodium hydrocarbonate. The ethyl acetate layer was separated, dried over anhydrous magnesium sulfate and concentrated by evaporation under reduced pressure, to give the title compound as crystals, melting at 71°–74° C.

Nuclear Magnetic Resonance Spectrum (CDCl$_3$), δ ppm:
1.26 (3H, triplet, J=7 Hz);
1.39 (4H, triplet, J=7 Hz);
3.63 (2H, quartet, J=7 Hz);
4.41 (4H, quartet, J=7 Hz);
4.64 (2H, singlet).

44(iii) Ethyl 2-methoxymethyl-4-(1-hydroxy-1-methylethyl)imidazole-5-carboxylate A solution of 800 mg of diethyl 2-ethoxymethylimidazole-4,5-dicarboxylate hydrochloride [prepared as described in step (ii) above] in 20 ml of methylene chloride were added dropwise at 4°–8° C. to 8.6 ml of a solution of methylmagnesium iodide in diethyl ether (prepared from 285 mg of magnesium and 0.731 ml of methyl iodide), under a nitrogen atmosphere. The reaction solution -was then stirred at room temperature for 1.5 hours, after which it was concentrated by evaporation under reduced pressure. The resulting residue was dissolved in ethyl acetate, and a saturated aqueous solution of ammonium chloride was added, whilst ice-cooling. The mixture was stirred for 30 minutes, and then the ethyl acetate layer was separated and dried over anhydrous magnesium sulfate. It was then concentrated by evaporation under reduced pressure, and the residue was purified by column chromatography through silica gel, using a 20:1 by volume mixture of methylene chloride and methanol as the eluent, to give 495 mg of the title compound as crystals, melting at 112°–113° C.

Nuclear Magnetic Resonance Spectrum (hexadeuterated dimethyl sulfoxide), δ ppm:

1.12 (3H, triplet, J=7 Hz);
1.29 (3H, triplet, J=7 Hz);
1.52 (6H, singlet);
3.48 (2H, quartet, J=7 Hz);
4.25 (2H, quartet, J=7 Hz);
5.79 (1H, broad singlet).

PREPARATION 45

Propyl 4-(1-hydroxy-1-methylethyl)-2-propoxymethylimidiazole-5-carboxylate

45(i) Dipropyl 1-benzyl-2-propoxymethylimidazole-4,5-dicarboxylate

A solution of 2.59 g of diethyl 1-benzyl-2-bromomethylimidazole-4,5-dicarboxylate (prepared as described in Preparation 42(ii)] in 10 ml of propanol and 5 ml of tetrahydrofuran was added dropwise to a solution of sodium propoxide in propanol (prepared from 0.23 g of sodium and 20 ml of propanol), and the resulting mixture was left at room temperature for 3 hours. At the end of this time, following a procedure similar to that described in Preparation 42(iii), the residue was purified by column chromatography through silica gel, using a 3:1 by volume mixture of hexane and ethyl acetate as the eluent, to give 0.99 g of the title compound as a syrup.

Nuclear Magnetic Resonance Spectrum (CDCl$_3$), δ ppm:

0.87 (6H, triplet, J=7 Hz);
0.98 (3H, triplet, J=7 Hz);
1.53 (2H, quartet, J=7 Hz);
1.60 (2H, quartet, J=7 Hz);
1.77 (2H, quartet, J=7 Hz);
3.40 (2H, triplet, J=7 Hz);
4.14 (2H, triplet, J=7 Hz);
4.28 (2H, triplet, J=7 Hz);
4.56 (2H, singlet);
5.53 (2H, singlet);
7.06 (2H, doublet, J=7 Hz);
7.23–7.39 (3H, multiplet).

45(ii) Dipropyl 2-propoxymethylimidazole-4,5-dicarboxylate

Following a procedure similar to that described in Preparation42(iv), but using 0.99 g of dipropyl 1-benzyl-2-propoxymethylimidazole-4,5-dicarboxylate [prepared as described in step (i) above] as the starting material, 0.83 g of the hydrochloride of the title compound was obtained as a syrup.

Nuclear Magnetic Resonance Spectrum (CDCl$_3$), δ ppm:

0.85 (3H, triplet, J=7 Hz);
0.98 (6H, triplet, J=7 Hz);
1.57 (2H, sextet, J=7 Hz);
1.79 (4H, sextet, J=7 Hz);
3.59 (2H, triplet, J=7 Hz);
4.30 (4H, triplet, J=7 Hz);
5.11 (2H, singlet).

45(iii) Propyl 4-(1-hydroxy-1-methylethyl)-2-propoxymethylimidazole-5-carboxylate Following a procedure similar to that described in Preparation44(iii), but using 0.83 g of dipropyl 2-propoxymethylimidazole-4,5-dicarboxylate hydrochloride [prepared as described in step (ii) above] and then purifying the product by column chromatography through silica gel using a 1:20 by volume mixture of methanol and methylene chloride as the eluent, 0.63 g of the title compound was obtained as crystals, melting at 72°–73° C.

Nuclear Magnetic Resonance Spectrum (CDCl$_3$), δ ppm:

0.94 (3H, triplet, J=7 Hz);
0.94 (3H, triplet, J=7 Hz);
0.99 (3H, triplet, J=7 Hz);
1.54–1.68 (2H, multiplet);
1.62 (6H, singlet);
1.78 (2H, sextet, J=7 Hz);
3.50 (2H, triplet, J=7 Hz);
4.28 (2H, doublet, J=7 Hz);
4.58, (2H, singlet);
5.74 (1H, singlet).

PREPARATION 46

Isopropyl 4-(1-hydroxy-1-methylethyl)-2-isopropoxymethylimidazole-5-carboxylate

46(i) Diisopropyl 1-benzyl-2-isopropoxymethylimidazole-4,5-dicarboxylate

A solution of 5.19 g of diethyl 1-benzyl-2-bromomethylimidazole-4,5-dicarboxylate [prepared as described in Preparation 42(ii)] in 20 ml of isopropanol and 25 ml of tetrahydrofuran was added dropwise to a solution of sodium isopropoxide in isopropanol (prepared from 0.77 g of sodium and 100 ml of isopropanol), and then, the resulting mixture was heated under reflux for 5 hours. The reaction solution was then treated following a procedure similar to that described in Preparation 42(iii). The residue was purified by column chromatography through silica gel, using a 3:2 by volume mixture of hexane and ethyl acetate as the eluent, to give 1.47 g of the title compound as a syrup.

Nuclear Magnetic Resonance Spectrum (CDCl$_3$), δ ppm:

1.13 (6H, doublet, J=6 Hz);
1.19 (6H, doublet, J=6.5 Hz);
1.38 (6H, doublet, J=6.5 Hz);
3.65 (1H, septet, J=6 Hz);
4.54 (2H, singlet);
5.08 (2H, septet, J=6.5 Hz);
5.25 (2H, septet, J=6.5 Hz);
5.52 (2H, singlet);
7.06 (2H, doublet, J=6 Hz);
7.25–7.33 (3H, multiplet).

46(ii) Diisopropyl 2-isopropoxymethylimidazole-4,5-dicarboxylate

Following a procedure similar to that described in Preparation 42(iv), but using 1.47 g of diisopropyl 1-benzyl-2-isopropoxymethylimidazole-4,5-dicarboxylate [prepared as described in step (i) above] and then crystallizing the product from diisopropyl ether, 1.0 g of the hydrochloride of the title compound was obtained as crystals, melting at 85°–89° C.

Nuclear Magnetic Resonance Spectrum (CDCl$_3$), δ ppm:

1.20 (3H, doublet, J=6 Hz);

1.40 (6H, doublet, J=6.5 Hz);

3.91 (1H, septet, J=6 Hz);

5.09 (2H, singlet);

5.24 (2H, doublet, J=6.5 Hz).

46(iii) Isopropyl 4-(1-hydroxy-1-methylethyl)-2-isopropoxymethylimidazole-5-carboxylate 950 mg of diisopropyl 2-isopropoxymethylimidazole-4,5-dicarboxylate hydrochloride [prepared as described in step (ii) above] in 10 ml of methylene chloride were added dropwise, whilst keeping the temperature at 7° C. or less, to a solution of 4.5 ml of methylmagnesium iodide in diethyl ether (prepared from 298 mg of magnesium and 0.763 ml of methyl iodide) under a nitrogen atmosphere. the resulting mixture was stirred at room temperature for 2 hours, and then the reaction solution was concentrated by evaporation under reduced pressure. The resulting residue was dissolved in ethyl acetate, and a saturated aqueous solution of ammonium chloride was added, whilst ice-cooling. The mixture was stirred for 30 minutes, and then the ethyl acetate layer was separated. The extract was dried over anhydrous magnesium sulfate, after which it was concentrated by evaporation under reduced pressure. The resulting residue was purified by column chromatography through silica gel, using a 20:1 by volume mixture of methylene chloride and methanol as the eluent, to give 603 mg of the title compound as crystals, melting at 153.5°–155° C.

Nuclear Magnetic Resonance Spectrum (CDCl$_3$), δ ppm:

1.24 (6H, doublet, J=6 Hz);

1.38 (6H, doublet, J=6 Hz);

1.60 (6H, singlet);

3.75 (1H, septet, J=6 Hz);

4.61 (2H, singlet);

5.26 (1H, septet, J=6 Hz);

5.71 (1H, singlet).

PREPARATION 47

Methyl 4-(1-hydroxy-1-methylethyl)-2-(1-methoxyethyl)imidazole-5-carboxylate

47(i) Diethyl 1-benzyl-2-ethylimidazole-4,5-dicarboxylate

Following a procedure similar to that described in Preparation42(i), 4.00 g of diethyl 2-ethylimidazole-4,5-dicarboxylate were benzylated, using 2.20 ml of benzyl bromide. The product was purified by column chromatography through silica gel, using a 1:1 by volume mixture of methylene chloride and ethyl acetate as the eluent, to give 5.19 g of the title compound as a syrup.

Nuclear Magnetic Resonance Spectrum (CDCl$_3$), δ ppm:

1.24 (3H, triplet, J=7 Hz);

1.28 (3H, triplet, J=7 Hz);

1.40 (3H, triplet, J=7 Hz);

2.70 (2H, quartet, J=7 Hz);

4.26 (2H, quartet, J=7 Hz);

4.40 (2H, quartet, J=7 Hz);

5.41 (2H, singlet);

7.01 (2H, doublet, J=6 Hz);

7.27–7.35 (3H, multiplet).

47(ii) Diethyl 1-benzyl-2-(1-bromoethyl)imidazole-4,5-dicarboxylate 3.08 g of N-bromosuccinimide and 0.51 g of benzoyl peroxide were added to a solution of 5.19 g of diethyl 1-benzyl-2-ethylimidazole-4,5-dicarboxylate [prepared as described in step (i) above] in 100 ml of carbon tetrachloride, and the resulting mixture was heated under reflux for 1 hour. Following a procedure similar to that described in Preparation 42(ii), 6.29 g of the title compound were obtained as a syrup from the resulting reaction solution.

Nuclear Magnetic Resonance Spectrum (CDCl$_3$), δ ppm:

1.24 (3H, triplet, J=7 Hz);

1.38 (3H, triplet, J=7 Hz);

2.12 (3H, doublet, J=6.5 Hz);

4.26 (2H, quartet, J=7 Hz);

4.40 (2H, quartet, J=7 Hz);

4.92 (1H, quartet, J=6.5 Hz);

5.35 (1H, doublet, J=16 Hz);

5.74 (1H, doublet, J=16 Hz);

7.06 (2H, doublet, J=6 Hz);

7.26–7.50 (3H, multiplet).

47(iii) Dimethyl 1-benzyl-2-(1-methoxyethyl)imidazole-4,5-dicarboxylate

Following a procedure similar to that described in Preparation42(iii), but using 7.60 g of diethyl 1-benzyl-2-(1-bromoethyl)imidazole-4,5-dicarboxylate [prepared as described in step (ii) above] and purifying 1-benzyl-2-(1-bromoethyl)imidazole-4,5-dicarboxylate using a 3:2 by volume mixture of hexane and ethyl acetate as the eluent, 4.36 g of the title compound were obtained as a syrup.

Nuclear Magnetic Resonance Spectrum (CDCl$_3$), δ ppm:

1.51 (3H, doublet, J=7 Hz);

3.23 (3H, singlet);

3.73 (3H, singlet);

3.83 (3H, singlet);

4.68 (1H, quartet, J=7 Hz);

5.56 (1H, doublet, J=16 Hz);

5.65 (1H, doublet, J=16 Hz);

7.00 (2H, doublet, J=7 Hz);

7.23–7.33 (3H, multiplet).

47(iv) Dimethyl 2-(1-methoxyethyl)imidazole-4,5-dicarboxylate

Following a procedure similar to that described in Preparation 42(iv), but using 3.30 g of dimethyl 1-benzyl-2-(1-methoxyethyl)imidazole-4,5-dicarboxylate [prepared as described in step (iii) above], 2.02 g of the hydrochloride of the title compound were obtained as a syrup.

Nuclear Magnetic Resonance Spectrum (CDCl$_3$), δ ppm:

1.74 (3H, doublet, J=6.5 Hz);

3.42 (3H, singlet);

3.52 (3H, singlet);

4.00 (3H, singlet);

5.31 (1H, quartet, J=6.5 Hz).

47(v) Methyl 2-(1-methoxyethyl)-4-(1-hydroxy-1-methylethyl)imidazole-5-carboxylate A suspension of 1.9 g of dimethyl 2-(1-methoxyethyl)imidazole-4,5-dicarboxylate hydrochloride [prepared as described in step (iv) above] in 30 ml of methylene chloride was added dropwise, whilst keeping the temperature at 5° C. or less, to a solution of 30 ml of methylmagnesium iodide in diethyl ether (prepared from 746 mg of magnesium and 1.91 ml of methyl iodide), under a nitrogen atmosphere. The resulting mixture was stirred at room temperature for I hour, after which it was concentrated by evaporation under reduced pressure. The residue was dissolved in ethyl acetate, and a saturated aqueous solution of ammonium chloride solution was added, whilst ice-cooling. The mixture was stirred for 30 minutes, and then the ethyl acetate layer was separated. The extract was dried over anhydrous magnesium sulfate, and then concentrated by evaporation under reduced pressure. The residue was purified by column chromatography through silica gel, using a 20:1 by volume mixture of methylene chloride and methanol as the eluent, to give 1.12 g of the title compound as a syrup.

Nuclear Magnetic Resonance Spectrum (CDCl$_3$), δ ppm:

1.52 (3H, doublet, J=6 Hz);

1.61 & 1.67 (total 6H, each singlet);

3.36 & 3.40 (total 3H, each singlet);

3.92 & 3.94 (total 3H, each singlet);

4.53 (1H, quartet, J=6 Hz);

5.51 & 5.62 (total 1H, each singlet).

PREPARATION 48

Ethyl 2-acetoxymethyl-4-(1-hydroxy-1-methylethyl)imidazole-5-carboxylate

48(i) Diethyl 2-acetoxymethyl-1-benzylimidazole-4,5-dicarboxylate 1.11 g of sodium acetate were added to a solution of 2.67 g of diethyl11-benzyl-2-bromomethylimidazole-4,5-dicarboxylate [prepared as described in Preparation 42(ii)] in 30 ml of dimethylformamide, and the resulting mixture was heated at 40° C. for 5 hours. At the end of this time, the reaction solution was mixed with ethyl acetate and water, and then the ethyl acetate layer was separated. The resulting ethyl acetate extract was washed with an aqueous solution of sodium chloride and then dried over anhydrous sodium sulfate. The solvent was then removed by distillation under reduced pressure. The residue was purified by column chromatography through silica gel, using a 1:1 by volume mixture of hexane and ethyl acetate as the eluent, to give 1.52 g of the title compound as a syrup.

Nuclear Magnetic Resonance Spectrum (CDCl$_3$), δ ppm:

1.23 (3H, triplet, J=7 Hz);

1.39 (3H, triplet, J=7 Hz);

1.89 (3H, singlet);

4.27 (2H, quartet, J=7 Hz);

4.40 (2H, quartet, J=7 Hz);

5.15 (2H, singlet);

5.47 (2H, singlet);

7.01 (2H, doublet, J=6 Hz);

7.29–7.34 (3H, multiplet).

48(ii) Diethyl 2-acetoxymethylimidazole-4,5-dicarboxylate

Following a procedure similar to that described in Preparation 42(iv), but using 2.00 g of diethyl 2-acetoxymethyl-1-benzylimidazole-4,5-dicarboxylate [prepared as described in step (i) above] as a starting material, 1.70 g of the hydrochloride of the title compound were obtained as a syrup.

Nuclear Magnetic Resonance Spectrum (CDCl$_3$), δ ppm:

1.39 (6H, triplet, J=7 Hz);

2.12 (3H, singlet);

4.40 (4H, quartet, J=7 Hz);

5.64 (2H, singlet);

13.1 (3H, broad singlet).

1.70 g of the hydrochloride of the title compound prepared as described above were dissolved in a mixture of ethyl acetate and water, and the resulting solution was mixed with 0.47 g of sodium hydrogencarbonate. The ethyl acetate layer was then separated, washed with an aqueous solution of sodium chloride and dried over anhydrous sodium sulfate, after which the solvent was removed by distillation under reduced pressure, to give 1.49 g of the title compound as a syrup.

Nuclear Magnetic Resonance Spectrum (CDCl$_3$), δ ppm:

1.34 (6H, doublet, J=7 Hz);

2.06 (3H, singlet);

4.36 (4H, quartet, J=7 Hz);

5.20 (2H, singlet).

48(iii) Ethyl 2-acetoxymethyl-4-(1-hydroxy-1-methylethyl)imidazole-5-carboxylate Following a procedure similar to that described in Preparation 44(iii), 1.54 g of diethyl 2-acetoxymethylimidazole-4,5-dicarboxylate were reacted with 6.5 equivalents of methylmagnesium iodide. Ethyl acetate was then added to the reaction solution, whilst ice-cooling, and the reaction solution was concentrated by evaporation under reduced pressure. The resulting residue was mixed with 50 ml of pyridine and 25 ml of acetic anhydride, and left at room temperature overnight. At the end of this time, 10 ml of methanol were added to the reaction solution, which was then stirred for 30 minutes. The solution was then concentrated by evaporation under reduced pressure. The residue was mixed with water and ethyl acetate, and the ethyl acetate layer was separated, washed twice with a saturated aqueous solution of sodium hydrogencarbonate and then once with an aqueous solution of sodium chloride, and then dried over anhydrous sodium sulfate. The solvent was removed by distillation under reduced pressure, and the resulting residue was purified by column chromatography through silica gel, using a 1:4 by volume mixture of hexane and ethyl acetate as the eluent, to give 1.46 g of the title compound as a syrup.

Nuclear Magnetic Resonance Spectrum (CDCl$_3$), δ ppm:

1.33 (3H, triplet, J=6.5 Hz);

1.64 (6H, singlet);

2.06 (3H, singlet);

4.37 (2H, quartet, J=6.5 Hz);

5.10 (2H, singlet);

5.83 (1H, broad singlet).

PREPARATION 49

Ethyl 4-(1-hydroxy-1-methylethyl)-2-methylthioimidazole-5-carboxylate

49(i) Diethyl 2-methylthioimidazole-4,5-dicarboxylate 1.14 g of potassium carbonate and 1.17 g of methyl iodide were added to a solution of 2.00 g of diethyl 2-mercaptoimidazole-4,5-dicarboxylate in 100 ml of acetone, and the mixture was heated under reflux, whilst stirring, for 30 minutes. At the end of this time, the insoluble matter was removed from the reaction mixture by filtration, and the filtrate was concentrated by evaporation under reduced pressure. The residue was purified by column chromatography through silica gel, using ethyl acetate as the eluent, to give 1.72 g of the title compound as crystals, melting at 119°–121° C.

Nuclear Magnetic Resonance Spectrum (CDCl$_3$), δ ppm:

1.37 (6H, triplet, J=7.5 Hz);

2.67 (3H, singlet);

4.39 (4H, quartet, J=7.5 Hz).

49(ii) Ethyl 4-(1-hydroxy-1-methylethyl)-2-methylthioimidazole-5-carboxylate

A solution of 3.30 g of methyl iodide in 5 ml of diethyl ether was added dropwise to a mixture of 565 mg of magnesium in 30 ml of diethyl ether, under a nitrogen atmosphere, and the resulting solution was heated under reflux, whilst stirring, for 30 minutes. At the end of this time, a solution of 1.50 g of diethyl 2-methylthioimidazole-4,5-dicarboxylate [prepared as described in step (i) above] in 10 ml of methylene chloride was added dropwise to the reaction solution, and then the solution was stirred at room temperature for 1 hour. 50 ml of a saturated aqueous solution of ammonium chloride were then added to the reaction mixture, after which the mixture was stirred, and then the product was extracted with ethyl acetate. The extract was washed with a saturated aqueous solution of sodium chloride and then dried over anhydrous magnesium sulfate. The solvent was removed by distillation under reduced pressure, and the resulting crystalline residue was washed with hexane, to give 1.00 g of the title compound, melting at 128°–129° C.

Nuclear Magnetic Resonance Spectrum (CDCl$_3$), δ ppm:
1.36 (3H, triplet, J=7.5 Hz);
1.62 (6H, singlet);
2.62 (3H, singlet);
4.35 (2H, quartet, J=7.5 Hz);
5.74 (1H, singlet).

PREPARATION 50

Ethyl 2-ethylthio-4-(1-hydroxy-1-methylethyl)imidazole-5-carboxylate

50(i) Diethyl 2-ethylthioimidazole-4,5-dicarboxylate 1.19 g of potassium carbonate and 1.34 g of ethyl iodide were added to a solution of 2.00 g of diethyl 2-mercaptoimidazole-4,5-dicarboxylate in 40 ml of acetone, and the resulting mixture was heated under reflux, whilst stirring, for 2 hours. At the end of this time, the mixture was treated in a similar manner to that described in Preparation 49(i). The residue was purified by column chromatography through silica gel, using ethyl acetate as the eluent, to give 2.03 g of the title compound as an oil.

Nuclear Magnetic Resonance Spectrum (CDCl$_3$), δ ppm:
1.30–1.40 (9H, multiplet);
3.20 (2H, quartet, J=7.5 Hz);
4.39 (4H, quartet, J=7.5 Hz).

50(ii) Ethyl 2-ethylthio-4-(1-hydroxy-1-methylethyl)imidazole-5-carboxylate 4.20 g of methyl iodide were added dropwise to a mixture of 714 mg of magnesium in 30 ml of diethyl ether, under a nitrogen atmosphere, and the resulting solution was heated under reflux, whilst stirring, for 30 minutes. At the end of this time, a solution of 2.00 g of diethyl 2-ethylthioimidazole-4,5-dicarboxylate [prepared as described in step (i) above] in 20 ml of methylene chloride was added dropwise to the reaction solution, and the mixture was treated in a similar manner to that described in Preparation 49(ii). The resulting crystalline residue was washed with a mixture of hexane and diisopropyl ether, to give 1.32 g of the title compound, melting at 82°–85° C.

Nuclear Magnetic Resonance Spectrum (CDCl$_3$), δ ppm:
1.30–1.42 (6H, multiplet);
1.62 (6H, singlet);
3.14 (2H, quartet, J=7.5 Hz);
4.37 (2H, quartet, J=7.5 Hz);
5.64 (1H, singlet).

We claim:
1. A compound of formula (I):

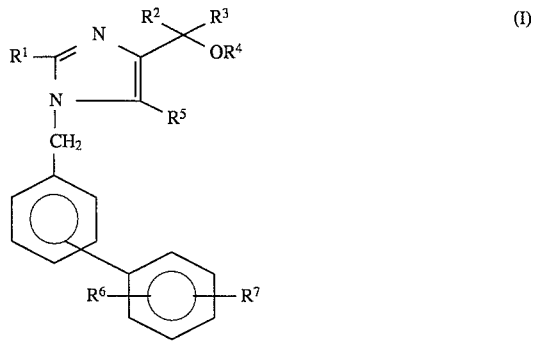

wherein:
$R^1$ represents an alkyl group having from 2 to 5 carbon atoms or an alkenyl group having from 3 to 5 carbon atoms;
$R^2$ and $R^3$ are independently selected from the group consisting of:
alkyl groups having from 1 to 4 carbon atoms;
$R^4$ represents:
a hydrogen atom; a methyl group; an ethyl group; or an alkanoyl group having from 1 to 5 carbon atoms;
$R^5$ represents a group of formula —COOR$^{5a}$ or a group of formula —CONR$^8$R$^9$,
$R^{5a}$ represents
a hydrogen atom,
an alkyl group having from 1 to 4 carbon atoms,
a benzyl group,
an alkanoyloxyalkyl group, in which the alkanoyl part has from 1 to 5 carbon atoms, and the alkyl part is a methyl or ethyl group,
a cycloalkanoyloxyalkyl group, in which the cycloalkanoyl part has 6 or 7 carbon atoms, and the alkyl part is a methyl or ethyl group,
an alkoxycarbonyloxyalkyl group, in which the alkoxy part has from 1 to 4 carbon atoms, and the alkyl part is a methyl or ethyl group,
a cycloalkoxycarbonyloxyalkyl group, in which the cycloalkoxy part has 5 or 6 carbon atoms, and the alkyl part is a methyl or ethyl group,
a (5-phenyl-2-oxo-1,3-dioxolen-4-yl)methyl group, a (5-methyl-2-oxo-1,3-dioxolen-4-yl)methyl group, a (5-ethyl-2-oxo-1,3dioxolen-4-yl)methyl group or a phthalidyl group;
$R^8$ and $R^9$ are independently selected from the group consisting of hydrogen atoms,
methyl groups, ethyl groups, methoxycarbonylmethyl groups, ethoxycarbonylmethyl groups and carboxymethyl groups; or $R^8$ and $R^9$ together represent
a tetramethylene, pentamethylene, 1-carboxytetramethylene or 1-carboxypentamethylene group;
$R^6$ represents a hydrogen atom,
a methyl group, a methoxy group or a fluorine atom or a chlorine atom at the 6-position of the benzene ring; $R^7$ represents a carboxy group or a tetrazol-5-yl group at the 2-position of the benzene ring;
the benzyl ring which bears the substituents represented by $R^6$ and $R^7$ is at the 4-position of the benzyl group to which it is attached;
and pharmaceutically acceptable salts and esters thereof.
2. The compound of claim 1, wherein $R^{5a}$ represents a pivaloyloxymethyl, ethoxycarbonyloxymethyl, 1-(ethoxycarbonyloxy)ethyl, isopropoxycarbonyloxymethyl, (1-isopropoxycarbonyloxy)ethyl, (5-methyl-2-oxo-1,3-dioxolen-4-yl)methyl or phthalidyl group.

3. The compound of claim 1, wherein:

$R^1$ represents an ethyl, propyl or butyl group;

$R^2$ and $R^3$ are methyl groups;

$R^4$ represents a hydrogen atom or a methyl group;

$R^5$ represents a group of formula —COOR$^{5a}$, in which $R^{5a}$ represents a hydrogen atom, a pivaloyloxymethyl group, an ethoxycarbonyloxymethyl group, a 1-(ethoxycarbonyloxy)ethyl group, an isopropoxycarbonyloxymethyl group, a 1-(isopropoxycarbonyloxy)ethyl group, a (5-methyl-2-oxo-1,3-dioxolen-4-yl)methyl group, or a phthalidyl group; and $R^6$ represents a hydrogen atom.

4. The compound of claim 1, selected from the group consisting of 2-butyl-1-[(2'-carboxybiphenyl-4-yl)methyl]-4-(1-hydroxy-1-methylethyl)imidazole-5-carboxylic acid and pharmaceutically acceptable salts thereof.

5. The compound of claim 1, selected from the group consisting of pivaloyloxymethyl 2-butyl-1-[(2'-carboxybiphenyl-4-yl)methyl]-4-(1-hydroxy-1-methylethyl)imidazole-5-carboxylate and pharmaceutically acceptable salts thereof.

6. The compound of claim 1, selected from the group consisting of (5-methyl-2-oxo-1,3-dioxolen-4-yl)methyl 2-butyl-1-[(2'-carboxybiphenyl-4-yl)methyl]-4-(1-hydroxy-1-methylethyl)imidazole-5-carboxylate and pharmaceutically acceptable salts thereof.

7. The compound of claim 1, selected from the group consisting of 1-[(2'-carboxybiphenyl-4-yl)methyl]-4-(1-hydroxy-1-methylethyl)-2-propylimidazole-5-carboxylic acid and pharmaceutically acceptable salts thereof.

8. The compound of claim 1, selected from the group consisting of 1-[(2'-carboxybiphenyl-4-yl)methyl]-2-ethyl-4-(1-hydroxy-1-methylethyl)imidazole-5-carboxylic acid and pharmaceutically acceptable salts thereof.

9. The compound of claim 1, selected from the group consisting of 4-(1-hydroxy-1-methylethyl)-2-propyl-1-{4-[2-(tetrazol-5-yl)phenyl]phenyl}methylimidazole-5-carboxylic acid and pharmaceutically acceptable salts thereof.

10. The compound of claim 1, selected from the group consisting of 2-butyl-4-(1-hydroxy-1-methylethyl)-1-{4-[2-(tetrazol-5-yl)phenyl]phenyl}methylimidazole-5-carboxylic acid and pharmaceutically acceptable salts thereof.

11. The compound of claim 1, selected from the group consisting of pivaloyloxymethyl 4-(1-hydroxy-1-methylethyl)-2-propyl-1-{4-[2-(tetrazol-5-yl)phenyl]phenyl}-methylimidazole-5-carboxylate and pharmaceutically acceptable salts thereof.

12. The compound of claim 1, selected from the group consisting of pivaloyloxymethyl 2-butyl-4-(1-hydroxy-1-methylethyl)-1-{4-[2-(tetrazol-5-yl)phenyl]phenyl}-methylimidazole-5-carboxylate and pharmaceutically acceptable salts thereof.

13. The compound of claim 1, selected from the group consisting of (5-methyl-2-oxo-1,3-dioxolen-4-yl)methyl 4-(1-hydroxy-1-methylethyl)-2-propyl-1-{4-[2-(tetrazol-5-yl)phenyl]phenyl}methylimidazole-5-carboxylate and pharmaceutically acceptable salts thereof.

14. The compound of claim 1, selected from the group consisting of (5-methyl-2-oxo-1,3-dioxolen-4-yl)methyl 2-butyl-4-(1-hydroxy-1-methylethyl)-1-{4-[2-(tetrazol-5-yl)phenyl]phenyl}methylimidazole-5-carboxylate and pharmaceutically acceptable salts thereof.

15. The compound of claim 1, selected from the group consisting of ethoxycarbonyloxymethyl 4-(1-hydroxy-1-methylethyl)-2-propyl-1-{4-[2-(tetrazol-5-yl)phenyl]phenyl}methylimidazole-5-carboxylate and pharmaceutically acceptable salts thereof.

16. The compound of claim 1, selected from the group consisting of isopropoxycarbonyloxymethyl 4-(1-hydroxy-1-methylethyl)-2-propyl-1-{4-[2-(tetrazol-5-yl)phenyl]phenyl}methylimidazole-5-carboxylate and pharmaceutically acceptable salts thereof.

17. The compound of claim 1, selected from the group consisting of 1-(ethoxycarbonyloxy)ethyl 4-(1-hydroxy-1-methylethyl)-2-propyl-1-{4-[2-(tetrazol-5-yl)phenyl]phenyl}methylimidazole-5-carboxylate and pharmaceutically acceptable salts thereof.

18. The compound of claim 1, selected from the group consisting of 1-(isopropoxycarbonyloxy)ethyl 4-(1-hydroxy-1-methylethyl)-2-propyl-1-{4-[2-(tetrazol-5-yl)phenyl]phenyl}methylimidazole-5-carboxylate and pharmaceutically acceptable salts thereof.

19. The compound of claim 1, selected from the group consisting of pivaloyloxymethyl 2-ethyl-4-(1-hydroxy-1-methylethyl)-1-{4-[2-(tetrazol-5-yl)phenyl]phenyl}-methylimidazole-5-carboxylate and pharmaceutically acceptable salts thereof.

20. The compound of claim 1, selected from the group consisting of (5-methyl-2-oxo-1,3-dioxolen-4-yl)methyl 2-ethyl-4-(1-hydroxy-1-methylethyl)-1-{4-[2-(tetrazol-5-yl)phenyl]phenyl}methylimidazole-5-carboxylate and pharmaceutically acceptable salts thereof.

21. The compound of claim 1, selected from the group consisting of pivaloyloxymethyl 1-[(2'-carboxybiphenyl-4-yl)methyl]-4-(1-hydroxy-1-methylethyl)-2-propylimidazole-5-carboxylate and pharmaceutically acceptable salts thereof.

22. The compound of claim 1, selected from the group consisting of (5-methyl-2-oxo-1,3-dioxolen-4-yl)methyl 1-[(2'-carboxybiphenyl-4-yl)methyl]-4-(1-hydroxy-1-methylethyl)-2-propylimidazole-5-carboxylate and pharmaceutically acceptable salts thereof.

23. The compound of claim 1, selected from the group consisting of phthalidyl 1-[(2'-carboxybiphenyl-4-yl)methyl]-4-(1-hydroxy-1-methylethyl)-2-propylimidazole-5-carboxylate and pharmaceutically acceptable salts thereof.

24. A pharmaceutical composition for the treatment or prophylaxis of hypertension, which comprises an effective amount of an anti-hypertensive agent in admixture with a pharmaceutically acceptable carrier or diluent, wherein the anti-hypertensive agent is selected from the group consisting of compounds of formula (I) and pharmaceutically acceptable salts thereof, as claimed in claim 1.

25. The composition of claim 24, wherein said anti-hypertensive agent is selected from the group consisting of:

2-butyl-1-[(2'-carboxybiphenyl-4-yl)methyl]-4-(1-hydroxy-1-methylethyl)imidazole-5-carboxylic acid;

pivaloyloxymethyl 2-butyl-1-[(2'-carboxybiphenyl-4-yl)methyl]-4-(1-hydroxy-1-methylethyl)imidazole-5-carboxylate;

(5-methyl-2-oxo-1,3-dioxolen-4-yl)methyl 2-butyl-1-[(2'-carboxybiphenyl-4-yl)methyl]-4-(1-hydroxy-1-methylethyl)imidazole-5-carboxylate;

1-[(2'-carboxybiphenyl-4-yl)methyl]-4-(1-hydroxy-1-methylethyl)-2-propylimidazole-5-carboxylic acid;

1-[(2'-carboxybiphenyl-4-yl)methyl]-2-ethyl-4-(1-hydroxy-1-methylethyl)imidazole-5-carboxylic acid;

4-(1-hydroxy-1-methylethyl)-2-propyl-1-{4-[2-(tetrazol-5-yl)phenyl]phenyl}methylimidazole-5-carboxylic acid;

2-butyl-4-(1-hydroxy-1-methylethyl)-1-{4-[2-(tetrazol-5-yl)phenyl]phenyl}methylimidazole-5-carboxylic acid;

pivaloyloxymethyl 4-(1-hydroxy-1-methylethyl)-2-propyl-1-{4-[2-(tetrazol-5-yl)phenyl]phenyl}methylimidazole-5-carboxylate;

pivaloyloxymethyl 2-butyl-4-(1-hydroxy-1-methylethyl)-1-{4-[2-(tetrazol-5-yl)phenyl]phenyl}methylimidazole-5-carboxylate;

(5-methyl-2-oxo-1,3-dioxolen-4-yl)methyl 4-(1-hydroxy-1-methylethyl)-2propyl-1-{4-[2-(tetrazol-5-yl)phenyl]phenyl}methylimidazole-5-carboxylate;

(5-methyl-2-oxo-1,3-idoxolen-4-yl)methyl 2-butyl-4-(1-hydroxy-1-methylethyl)-1-{4-[2-(tetrazol-5-yl)phenyl]phenyl}methylimidazole-5-carboxylate;

ethoxycarbonyloxymethyl 4-(1-hydroxy-1-methylethyl)-2-propyl-1-{4-[2-(tetrazol-5-yl)phenyl]phenyl}methylimidazole-5-carboxylate;

isopropoxycarbonyloxymethyl 4-(1-hydroxy-1-methylethyl)-2-propyl-1-{4-[2-(tetrazol-5-yl)phenyl]phenyl}methylimidazole-5-carboxylate;

1-(ethoxycarbonyloxy)ethyl 4-(1-hydroxy-1-methylethyl)-2-propyl-1-{4-[2-(tetrazol-5-yl)phenyl]phenyl}methylimidazole-5-carboxylate;

1-(isopropoxycarbonyloxy)ethyl 4-(1-hydroxy-1-methylethyl)-2-propyl-1-{4-[2-(tetrazol-5-yl)phenyl]phenyl}methylimidazole-5-carboxylate;

pivaloyloxymethyl 2-ethyl-4-(1-hydroxy-1-methylethyl)-1-{4-[2-(tetrazol-5-yl)phenyl]phenyl}methylimidazole-5-carboxylate;

(5-methyl-2-oxo-1,3-dioxolen-4-yl)methyl 2-ethyl-4-(-1-hydroxy-1-methylethyl)-1-{4-[2-(tetrazol-5-yl-phenyl]phenyl}methylimidazole-5-carboxylate;

pivaloyloxymethyl 1-[(2'-carboxybiphenyl-4-yl)methyl]-4-(1-hydroxy-1-methylethyl)-2-propylimidazole-5-carboxylate;

(5-methyl-2-oxo-1,3-dioxolen-4-yl)methyl 1-[(2'-carboxybiphenyl-4-yl)methyl]-4-(1-hydroxy-1-methylethyl)-2-propylimidazole-5-carboxylate;

phthalidyl 1-[(2'-carboxybiphenyl-4-yl)methyl]-4-(1-hydroxy-1-methylethyl)-2-propylimidazole-5-carboxylate;

and pharmaceutically acceptable salts thereof.

26. A method for the treatment of prophylaxis of hypertension in a mammal which comprises administering an effective amount of an anti-hypertensive agent to said mammal, wherein the anti-hypertensive agent is selected from the group consisting of compounds of formula (I) and pharmaceutically acceptable salts thereof, as claimed in claim 1.

27. The method of claim 26, wherein said anti-hypertensive agent is selected from the group consisting of:

2-butyl-1-[(2'-carboxybiphenyl-4-yl)methyl]-4-(1-hydroxy-1-methylethyl)imidazole-5-carboxylic acid;

pivaloyloxymethyl 2-butyl-1-[(2'-carboxybiphenyl-4-yl)methyl]-4-(1-hydroxy-1-methylethyl)imidazole-5-carboxylate;

(5-methyl-2-oxo-1,3-dioxolen-4-yl)methyl 2-butyl-1-[(2'-carboxybiphenyl-4-yl)methyl]-4-(1-hydroxy-1-methylethyl)imidazole-5-carboxylate;

1-[(2'-carboxybiphenyl-4-yl)methyl]-4-(1-hydroxy-1-methylethyl)-2-propylimidazole-5-carboxylic acid;

1-[(2'-carboxybiphenyl-4-yl)methyl]-2-ethyl-4-(1-hydroxy-1-methylethyl)imidazole-5-carboxylic acid;

4-(1-hydroxy-1-methylethyl)-2-propyl-1-{4-[2-(tetrazol-5-yl)phenyl]phenyl}methylimidazole-5-carboxylic acid;

2-butyl-4-(1-hydroxy-1-methylethyl)-1-{4-[2-(tetrazol-5-yl)phenyl]phenyl}methylimidazole-5-carboxylic acid;

pivaloyloxymethyl 4-(1-hydroxy-1-methylethyl)-2-propyl-1-{4-[2-(tetrazol-5-yl)phenyl]phenyl}methylimidazole-5-carboxylate;

pivaloyloxymethyl 2-butyl-4-(1-hydroxy-1-methylethyl)-1-{4-[2-(tetrazol-5-yl)phenyl]phenyl}methylimidazole-5-carboxylate;

(5-methyl-2-oxo-1,3-dioxolen-4-yl)methyl 4-(1-hydroxy-1-methylethyl)-2-propyl-1-{4-[2-(tetrazol-5-yl)phenyl]phenyl}methylimidazole-5-carboxylate;

(5-methyl-2-oxo-1,3-dioxolen-4-yl)methyl 2-butyl-4-(1-hydroxy-1-methylethyl)-1-{4-[2-(tetrazol-5-yl)phenyl]phenyl}methylimidazole-5-carboxylate;

ethoxycarbonyloxymethyl 4-(1-hydroxy-1-methylethyl)-2-propyl-1-{4-[2-(tetrazol-5-yl)phenyl]phenyl}methylimidazole-5-carboxylate;

isopropoxycarbonyloxymethtyl 4-(1-hydroxy-1-methylethyl)-2-propyl-1-{4-[2-(tetrazol-5-yl)phenyl]phenyl}methylimidazole-5-carboxylate;

1-(ethoxycarbonyloxy)ethyl 4-(1-hydroxy-1-methylethyl)-2-propyl-1-{4-[2-(tetrazol-5-yl)phenyl]phenyl}methylimidazole-5-carboxylate;

1-(isopropoxycarbonyloxy)ethyl 4-(1-hydroxy-1-methylethyl)-2-propyl-1-{4-[2-(tetrazol-5-yl)phenyl]phenyl}methylimidazole-5-carboxylate;

pivaloyloxymethyl 2-ethyl-4-(1-hydroxy-1-methylethyl)-1-{4-[2-(tetrazol-5-yl)phenyl]phenyl}methylimidazole-5-carboxylate;

(5-methyl-2-oxo-1,3-dioxolen-4-yl)methyl 2-ethyl-4-(1-hydroxy-1-methylethyl)-1-{4-[2-(tetrazol-5-yl)phenyl]phenyl}methylimidazole-5-carboxylate;

pivaloyloxymethyl 1-[(2'-carboxybiphenyl-4-yl)methyl]-4-(1-hydroxy-1-methylethyl)-2-propylimidazole-5-carboxylate;

(5-methyl-2-oxo-1,3-dioxolen-4-yl)methyl 1-[(2'-carboxybiphenyl-4-yl)methyl]-4-(1-hydroxy-1-methylethyl)-2-propylimidazole-5-carboxylate;

phthalidyl 1-[(2'-carboxybiphenyl-4-yl)methyl]-4-(1-hydroxy-1-methylethyl)-2-propylimidazole-5-carboxylate;

and pharmaceutically acceptable salts thereof.

28. The compound of claim 1, wherein $R^2$ and $R^3$ are both methyl groups.

29. The compound of claim 1, wherein both of $R^2$ and $R^3$ are ethyl groups.

30. The compound of claim 1, wherein one of $R^2$ and $R^3$ is a methyl group and the other of $R^2$ and $R^3$ is an ethyl group.

31. The compound of claim 1, wherein $R^5$ is

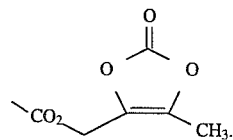

32. The composition of claim 21, wherein $R^2$ and $R^3$ are both methyl groups.

33. The method of claim 26, wherein $R^2$ and $R^3$ are both methyl groups.

34. A compound of formula (I):

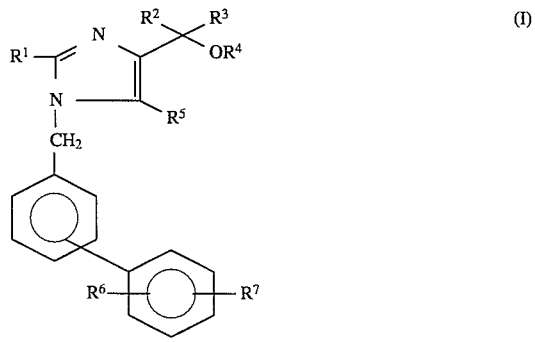

wherein:

$R^1$ represents an alkyl group having from 1 to 6 carbon atoms or an alkenyl group having from 3 to 6 carbon atoms;

$R^2$ and $R^3$ are independently alkyl groups having from 1 to 6 carbon atoms;

$R^4$ represents:
  a hydrogen atom;
  an alkyl group having from 1 to 6 carbon atoms;
  an alkanoyl group having from 1 to 6 carbon atoms;
  a substituted alkanoyl group having from 2 to 6 carbon atoms and substituted by at least one substituent selected from the group consisting of halogen atoms and alkoxy groups having from 1 to 6 carbon atoms;
  an alkenoyl group having from 3 to 6 carbon atoms;
  an arylcarbonyl group in which the aryl part is as defined below;
  an alkoxycarbonyl group in which the alkyl part has from 1 to 6 carbon atoms;
  a tetrahydropyranyl, tetrahydrothiopyranyl, tetrahydrothienyl or tetrahydrofuryl group;
  a substituted tetrahydropyranyl, tetrahydrofuryl group which is substituted by at least one substituent selected from the group consisting of halogen atoms and alkoxy groups having from 1 to 6 carbon atoms;
  alkoxymethyl groups in which the alkoxy part has from 1 to 6 carbon atoms;
  (alkoxyalkoxy)methyl groups in which each alkoxy part has from 1 to 6 carbon atoms;
  haloalkoxymethyl groups in which the alkoxy part has from 1 to 6 carbon atoms;
  aralkyl groups, in which an alkyl group having from 1 to 6 carbon atoms is substituted by at least one aryl group, as defined below; or
  alkanoyloxymethoxycarbonyl groups in which the alkanoyl part has from 1 to 6 carbon atoms;

$R^5$ represents a carboxy group or a group of formula —$CONR^8R^9$, wherein $R^8$ and $R^9$ are independently selected from the group consisting of
  hydrogen atoms,
  unsubstituted alkyl groups having from 1 to 6 carbon atoms, and
  substituted alkyl groups which have from 1 to 6 carbon atoms and which are substituted by at least one substituent selected from the group consisting of substituents (a), defined below, or
$R^8$ and $R^9$ together represent an unsubstituted alkylene group having from 2 to 6 carbon atoms or a substituted alkylene group which has from 2 to 6 carbon atoms and which is substituted by at least one substituent selected from the group consisting of carboxy groups and alkoxycarbonyl groups in which the alkyl part has from 1 to 6 carbon atoms;

$R^6$ represents a hydrogen atom, an alkyl group having from 1 to 6 carbon atoms, an alkoxy group having from 1 to 6 carbon atoms or a halogen atom;

$R^7$ represents a carboxy group or a tetrazol-5-yl group;

said substituents (a) are selected from the group consisting of:
  aryl groups as defined below;
  heterocyclic groups having 5 or 6 ring atoms, of which from 1 to 4 are hetero-atoms selected from the group consisting of nitrogen, oxygen and sulfur atoms;
  halogen atoms;
  hydroxy groups;
  alkoxy groups having from 1 to 6 carbon atoms;
  carboxy groups
  alkoxycarbonyl groups in which the alkyl part has from 1 to 6 carbon atoms;
  amino groups; and
  acylamino groups, in which the acyl part is an alkanoyl group having from 1 to 6 carbon atoms or an arylcarbonyl group, in which the aryl part is as defined below;

said aryl groups are aromatic carbocyclic groups which have from 6 to 14 ring atoms and which are unsubstituted or are substituted by at least one substituent selected from the group consisting of substituents (b), defined below; and said substituents (b) are selected from the group consisting of nitro groups, cyano groups, halogen atoms, unsubstituted carbocyclic aryl groups having from 6 to 10 ring atoms, alkyl groups having from 1 to 6 carbon atoms, alkoxy groups having from 1 to 6 carbon atoms, carboxy groups, alkoxycarbonyl groups in which the alkoxy part has from 1 to 6 carbon atoms and alkylenedioxy and alkylidene-dioxy groups having from 1 to 3 carbon atoms;

and pharmaceutically acceptable salts thereof.

35. The compound of claim 1, wherein $R^2$ and $R^3$ are methyl and $R^4$ is hydrogen.

36. The compound of claim 1, wherein said $R^5$ is the group of the formula —$COOR^{5a}$.

37. The composition of claim 24, wherein said $R^5$ is the group of the formula —$COOR^{5a}$.

38. The method of claim 26, wherein said $R^5$ is the group of the formula —$COOR^{5a}$.

39. The compound of claim 1, wherein:
  $R^1$ represents an alkyl group having from 2 to 5 carbon atoms; and
  $R^{5a}$ represents
    a hydrogen atom,
    a methyl, ethyl or benzyl group,
    an alkanoyloxymethyl group, in which the alkanoyl part has from 1 to 5 carbon atoms,
    a 1-(alkanoyloxy)ethyl group, in which the alkanoyl part has from 1 to 5 carbon atoms,
    an alkoxycarbonyloxymethyl group, in which the alkoxy part has from 1 to 4 carbon atoms,
    a 1-(alkoxycarbonyloxy)ethyl group, in which the alkoxy part has from 1 to 4 carbon atoms,
    a (5-phenyl-2-oxo-1,3-dioxolen-4-yl)methyl group, a (5-methyl-2-oxo-1,3-dioxolen-4-yl)methyl group or a phthalidyl group.

40. The compound of claim 39, wherein $R^2$ and $R^3$ are both methyl groups.

41. The composition of claim 24, wherein:
  $R^1$ represents an alkyl group having from 2 to 5 carbon atoms; and
  $R^{5a}$ represents
    a hydrogen atom,
    a methyl, ethyl or benzyl group,
    an alkanoyloxymethyl group, in which the alkanoyl part has from 1 to 5 carbon atoms,
    a 1-(alkanoyloxy)ethyl group, in which the alkanoyl part has from 1 to 5 carbon atoms,
    an alkoxycarbonyloxymethyl group, in which the alkoxy part has from 1 to 4 carbon atoms,
    a 1-(alkoxycarbonyloxy)ethyl group, in which the alkoxy part has from 1 to 4 carbon atoms,
    a (5-phenyl-2-oxo-1,3-dioxolen-4-yl)methyl group, a (5-methyl-2-oxo-1,3-dioxolen-4-yl)methyl group or a phthalidyl group.

42. The method of claim 26, wherein:
  $R^1$ represents an alkyl group having from 2 to 5 carbon atoms; and $R^{5a}$ represents
- a hydrogen atom,
- a methyl, ethyl or benzyl group,
- an alkanoyloxymethyl group, in which the alkanoyl part has from 1 to 5 carbon atoms,
- a 1-(alkanoyloxy)ethyl group, in which the alkanoyl part has from 1 to 5 carbon atoms,
- an alkoxycarbonyloxymethyl group, in which the alkoxy part has from 1 to 4 carbon atoms,
- a 1-(alkoxycarbonyloxy)ethyl group, in which the alkoxy part has from 1 to 4 carbon atoms,
- a (5-phenyl-2-oxo-1,3-dioxolen-4-yl)methyl group,
- a (5-methyl-2-oxo-1,3-dioxolen-4-yl)methyl group or a phthalidyl group.

* * * * *

UNITED STATES PATENT AND TRADEMARK OFFICE
CERTIFICATE OF CORRECTION

PATENT NO. : 5,616,599
DATED : April 1, 1997
INVENTOR(S) : YANAGISAWA et al

It is certified that error appears in the above-identified patent and that said Letters Patent is hereby corrected as shown below:

Column 246, line 62 (Claim 1): delete "and esters".

Column 250, line 45 (Claim 32): delete "claim 21" and insert --claim 24--.

Signed and Sealed this

Thirteenth Day of April, 1999

Q. TODD DICKINSON

Attest:

Attesting Officer

Acting Commissioner of Patents and Trademarks

UNITED STATES PATENT AND TRADEMARK OFFICE
CERTIFICATE OF CORRECTION

PATENT NO.    : 5,616,599
DATED         : April 1, 1997
INVENTOR(S)   : Yanagisawa et al.

Page 1 of 1

It is certified that error appears in the above-identified patent and that said Letters Patent is hereby corrected as shown below:

<u>Title page,</u>
Item [54], title replace "ANTAGOSIST" with -- ANTAGONIST --.

<u>Column 249,</u>
Line 7, replace "3-idoxolen" with -- 3-dioxolen --.

Signed and Sealed this

Fifteenth Day of October, 2002

Attest:

Attesting Officer

JAMES E. ROGAN
*Director of the United States Patent and Trademark Office*

UNITED STATES PATENT AND TRADEMARK OFFICE

(12)      CERTIFICATE EXTENDING PATENT TERM
UNDER 35 U.S.C. § 156

(68) PATENT NO. : 5,616,599

(45) ISSUED : April 1, 1997

(75) INVENTOR : Hiroaki Yanagisawa, et al.

(73) PATENT OWNER : Sankyo Company, Limited

(95) PRODUCT : BENICAR® (olmesartan medoxomil)

This is to certify that an application under 35 U.S.C. § 156 has been filed in the United States Patent and Trademark Office, requesting extension of the term of U.S. Patent No. 5,616,599 based upon the regulatory review of the product BENICAR® (olmesartan medoxomil) by the Food and Drug Administration. Since it appears that the requirements of the law have been met, this certificate extends the term of the patent for the period of

(94)                 755 days from April 1, 2014, the original expiration date of the patent, subject to the payment of maintenance fees as provided by law, with all rights pertaining thereto as provided by 35 U.S.C. § 156(b).

I have caused the seal of the United States Patent and Trademark Office to be affixed this 17th day of November 2004.

Jon W. Dudas
Under Secretary of Commerce for Intellectual Property and
Director of the United States Patent and Trademark Office

UNITED STATES PATENT AND TRADEMARK OFFICE
CERTIFICATE OF CORRECTION

PATENT NO. : 5,616,599
DATED : April 1, 1997
INVENTOR(S) : Yanagisawa et al.

It is certified that error appears in the above-identified patent and that said Letters Patent is hereby corrected as shown below:

<u>Column 249,</u>
Line 35, after "treatment" replace "of" with -- or --.

Signed and Sealed this

Third Day of May, 2005

JON W. DUDAS
*Director of the United States Patent and Trademark Office*